United States Patent
Stahl et al.

(10) Patent No.: US 7,033,772 B1
(45) Date of Patent: Apr. 25, 2006

(54) METHODS OF IDENTIFYING INHIBITORS OF FATTY ACID TRANSPORT PROTEINS (FATP)

(75) Inventors: Andreas Stahl, Allston, MA (US); David J. Hirsch, Brookline, MA (US); Harvey F. Lodish, Brookline, MA (US); Ruth E. Gimeno, Wellesley, MA (US); Louis A. Tartaglia, Newton, MA (US)

(73) Assignees: Millennium Pharmaceuticals, Inc., Cambridge, MA (US); Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/405,504

(22) Filed: Sep. 23, 1999

Related U.S. Application Data

(63) Continuation-in-part of application No. 09/232,201, filed on Jan. 14, 1999, now Pat. No. 6,348,321.
(60) Provisional application No. 60/110,941, filed on Dec. 4, 1998, provisional application No. 60/093,491, filed on Jul. 20, 1998, and provisional application No. 60/071,374, filed on Jan. 15, 1998.

(51) Int. Cl.
*G01N 33/53* (2006.01)
*C12P 21/06* (2006.01)
*C07K 1/00* (2006.01)

(52) U.S. Cl. .................. 435/7.21; 435/7.1; 435/7.2; 435/7.37; 435/69.1; 435/71.2; 435/71.1; 435/252.3; 435/252.8; 435/325; 530/350

(58) Field of Classification Search .............. 435/320.1, 435/325, 252.3, 69.1, 284.11, 410, 252.1, 435/183, 7.1, 7.2, 7.37, 7.21, 71.1, 71.2, 435/471, 252.8; 530/350; 536/23.5
See application file for complete search history.

(56) References Cited

U.S. PATENT DOCUMENTS

| | | | |
|---|---|---|---|
| 4,935,450 A | 6/1990 | Cone, Jr. .................. 514/728 |
| 6,284,487 B1 | 9/2001 | Stahl et al. | |
| 6,288,213 B1 | 9/2001 | Stahl et al. | |
| 6,300,096 B1 | 10/2001 | Stahl et al. | |
| 6,348,321 B1 | 2/2002 | Stahl et al. | |

FOREIGN PATENT DOCUMENTS

| | | |
|---|---|---|
| WO | WO 99/36537 | 7/1999 |
| WO | WO 99/46281 | 9/1999 |
| WO | WO 99/51740 | 10/1999 |
| WO | WO 00/26245 | 5/2000 |
| WO | WO 00/58473 | 10/2000 |
| WO | WO 01/21795 | 3/2001 |

OTHER PUBLICATIONS

Atsushi, et al, 1996, J. Biol. Chem. 271(48): 30360–30365, esp. Fig. 8.*
Smith et al., 1997 Nature Biotechnology 15:1222–1223.*
Brenner, S.E., 1999, Trends in Genetics 15:132–133.*
Bisson, et al, 1993, Crit Rev Biochem Mol Biol, 28(4):259–308.*
Abumrad, N., et al., "Membrane Proteins Implicated in Long–Chain Fatty Acid Uptake by Mammalian Cells: CD36, FATP and FABPm," *Biochimica et Biophysica Acta* 1441: 4–13 (1999).
Berk, P.D. and Stump D.D., "Mechanisms of Cellular Uptake of Long–Chain Free Fatty Acids," *Molecular and Cellular Biochem.* 192:17–31 (1999).
Berk, P.D., et al., "Characterization of Membrane Transport Processes: Lessons from the Study of BSP, Bilirubin, and Fatty Acid Uptake," *Seminars In Liver Disease* 16(2):107–120 (1996).
Boisclair, Y.R., et al., "Three Clustered Sp1 Sites Are Required for Efficient Transcription of the TATA–Less Promoter of the Gene for Insulin–Like Growth Factor–binding Protein–2 from the Rat," *American Society Biochem.* 268(33):24892–24901 (1993).
De Simone, V. and Cortese, R., "Transcription Factors and Liver–Specific Genes," *Biochimica et Biophysica Acta* 1132:119–126 (1992).
Fitscher, B.A., et al., "Protein–Mediated Facilitated Uptake Processes for Fatty Acids, Bilirubin, and Other Amphipathic Compounds (43987)," *Proc Soc Exp Biol Med* 212:15–23 (1996).
Frohnert, B.I., et al., "Identification of a Functional Peroxisome Proliferator–Responsive Element in the Murine Fatty Acid Transport Protein Gene," *J. of Biological Chem.* 274(7):3970–3977 (1999).

(Continued)

*Primary Examiner*—Elizabeth Kemmerer
*Assistant Examiner*—Sandra Wegert
(74) *Attorney, Agent, or Firm*—Hamilton, Brook, Smith & Reynolds, P.C.

(57) ABSTRACT

A family of fatty acid transport proteins (FATPs) mediate transport of long chain fatty acids (LCFAs) across cell membranes into cells. These proteins exhibit different expression patterns among the organs of mammals. Nucleic acids encoding FATPs of this family, vectors comprising these nucleic acids, as well as the production of FATP proteins in host cells are described. Also described are methods to test FATPs for fatty acid transport function, and methods to identify inhibitors or enhancers of transport function. The altering of LCFA uptake by administering to the mammal an inhibitor or enhancer of FATP transport function of a FATP in the small intestine can decrease or increase calories available as fats, and can decrease or increase circulating fatty acids. The organ specificity of FATP distribution can be exploited in methods to direct drugs, diagnostic indicators and so forth to an organ such as the heart.

23 Claims, 175 Drawing Sheets

OTHER PUBLICATIONS

Glatz, J.F.C., et al., "Molecular Mechanism of Cellular Uptake and Intracellular Translocation of Fatty Acids," *Prostaglandins, Leukotrienes and Essential Fatty Acids* 57(1):3–9 (1997).

Göttlicher, M., et al., "Fatty Acids Activate a Chimera of the Clofibric Acid–Activated Receptor and the Glucocorticoid Receptor," *Proc. Natl. Acad. Sci. USA* 89:4653–4657 (1992).

Grimaldi, P.A., et al., "Long Chain Fatty Acids as Modulators of Gene Transcription in Preadipose Cells," *Molecular and Cellular Biochem.* 192:63–68 (1999).

Hamilton, J.A., "Fatty Acid Transport: Difficult or Easy?," *J. Lipid Res.* 39:467–481 (1998).

Hanson, R.W. "Regulation of Phosphoenolpyruvate Carboxykinase (GTP) Gene Expression" *Annu. Rev. Biochem.* 66:581–611 (1997).

Heinemeyer, T., et al., "Databases on Transcriptional Regulation: TRANSFAC, TRRD and COMPEL," *Nucleic Acids Res.* 26(1):362–367 (1998).

Heinemeyer, T. et al., "Expanding the TRANSFAC Database Towards an Expert System of Regulatory Molecular Mechanisms," *Nucleic Acids Res.* 27(1):318–322 (1999).

Hillier, L. et. al.; Data Submission; zu10c01.r2 *Soares testis NHT Homo sapiens* cDNA clone 731426 5', *Homo sapiens*(human);EMBL Accession No. AA469992; (1997).

Hillier, L., et al.; Data Submission; zc44h06.r1 /Soares senescent fibroblasts NbHSF *Homo spiens* cDNA clone 325211 5' similar to PIR:A55093 A55093 fatty acid transport protein precursor—mouse, *Homo sapiens*(human); EMBL Accession No. W48808; (1996).

Hua, X., et al., "Synergistic Cooperation of TFE3 and Smad Proteins in TGF–β–Induced Transcription of the Plasminogen Activator Inhibitor–1 Gene," *Genes & Development* 12: 3084–3095 (1998).

Lai, E., "Regulation of Hepatic Gene Expression and Development," *Seminars in Liver Disease* 12(3):246–251 (1992).

Lee, Y.H., et al., "A Novel cis–Acting Element Controlling the Rat CYP2D5 Gene and Requiring Cooperativity between C/EBPβ and an SP1 Factor," *Molecular and Cellular Biology*, 14(2):1383–1394 (1994).

Martin, G., et al., "Coordinate Regulation of the Expression of the Fatty Acid Transport Protein and Acyl–CoA Synthetase Genes by PPARα and PPARγ Activators," *J. Biological Chem.* 272(45):28210–28217 (1997).

Memon, R.A., et al., "Regulation of Putative Fatty Acid Transporters and Acyl–CoA Synthetase in Liver and Adipose Tissue in ob/ob Mice," *Diabetes* 48:121–127 (1999).

Motojima, K., et al., "Expression of Putative Fatty Acid Transporter Genes Are Regulated by Peroxisome Proliferator–Activated Receptor α and γ Activators in a Tissue– and Inducer–Specific Manner," *J. Biol. Chem.* 273(27):16710–16714 (1998).

Rodenburg, R.J.T., et al., "A Functional Sp1 Binding Site Is Essential for the Activity of the Adult Liver–Specific Human Insulin–Like Growth Factor II Promoter," *Molecular Endocrinology* 11:237–250 (1997).

Rongnoparut, P., et al., "Isolation and Characterization of the Transcriptionally Regulated Mouse Liver (B–type) Phosphofructokinase Gene and Its Promoter," *J. Biological Chem.* 266(13):8086–8091 (1991).

Ryu, S., et al., "The Transcriptional Cofactor Complex CRSP is Required for Activity of the Enhancer–Binding Protein Sp1," *Nature* 397:446–450 (1999).

Schaffer, J.E. and Lodish, H.F., "Molecular Mechanism of Long–Chain Fatty Acid Uptake," *TCM* 5(6):218–224 (1995).

Schoonjans, K., et al., "The Peroxisome Proliferator Activated Receptors (PPARs) and Their Effects of Lipid Metabolism and Adipocyte Differentiation," *Biochem. Biophys. Acta* 1302:93–109 (1996).

Sorensen, P. and Wintersberger, E., "Sp1 and NF–Y Are Necessary and Sufficient for Growth–Dependent Regulation of the Hamster Thymidine Kinase Promoter*," *J. Biological Chem.* 274(43):30943–30949 (1999).

Stahl, et al.; Data Submission; *Mus musculus* fatty acid transport protein 2 mRNA, complete cds.; *Mus musculus;* GenBank Accession No. AF072757; (1998).

Strausberg, R.; Data Submission; nc84e10.s1 NCI_CGAP_GC1 *Homo sapiens* cDNA clone IMAGE:797514, *Homo sapiens*(human); EMBL Accession No. Aa581592; (1997).

Strausberg, R.; Data Submission; no82f09.s1 NCI_CGAP_AA1 *Homo sapiens* cDNA clone IMAGE:1113353 similar to TR:G563829 G563829 Fatty Acid Transport Protein, *Homo sapiens*(human); EMBL Accession No. Aa614135; (1997).

Strausberg, R.; Data Submission; nn89d05.s1 NCI_CGAP_Br2 *Homo sapiens* cDNA clone IMAGE:1098345 similar to TR:G563829 Fatty Acid Transport Protein, *Homo sapiens*(human); EMBL Accession No. AA614445; (1997).

Strausberg, R.; Data Submission; ne19b11.s1 NCI_CGAP_Co3 *Homo sapiens* cDNA clone IMAGE:881661, *Homo sapiens*(human); EMBL Accession No. AA470762; (1997).

Stremmel, W., "Mechanism of Hepatic Fatty Acid Uptake," *J. Hepatology* 9:374–382 (1989).

Uchiyama, A. et al., "Molecular Cloning of cDNA Encoding Rat Very Long–chain Acyl–CoA Synthetase," *J. Biol. Chem.* 271(48):30360–30365 (1996).

Stuhlsatz–Krouper, S.M. et al., "Substitution of Alanine for Serine 250 in the Murine Fatty Acid Transport Protein Inhibits Long Chain Fatty Acid Transport," *J. Biol. Chem.* 273(44):2862–28650 (1998).

Watkins, P.A. et al., "Disruption of the *Saccharomyces cerevisiae* FAT1 Gene Decreases Very Long–chain Fatty Acyl–CoA Synthetase Activity and Elevates Intracellular Very Long–chain Fatty Acid Concentrations," *J. Biol. Chem.* 273(29):18210–18219 (1998).

Hirsch, D. et al., "A family of fatty acid transporters conserved from mycobacterium to man," *Proc. Natl. Acad. Sci.* 95:8625–8629 (1998).

Berger, J. et al., "A Novel Relative of the Very–Long–Chain Acyl–CoA Synthetase and Fatty Acid Transporter Protein Genes with a Distinct Expression Pattern," *Biochem. Biophys. Res. Commun.* 247:255–260 (1998).

Hui, T.Y. et al., "Characterization of the Murine Fatty Acid Transport Protein Gene and Its Insulin Response Sequence," *J. Biol. Chem.* 273(42):27420–27429 (1998).

Faergeman, N.J. et al., "Disruption of the *Saccharomyces cerevisiae* Homologue to the Murine Fatty Acid Transport Protein Impairs Uptake and Growth on Long–chain Fatty Acids," *J. Biol. Chem.* 272(13):8531–8538 (1997).

Schaap, F.G. et al., "Molecular cloning of fatty acid–transport protein cDNA from rat," *Biochem. Biophys. Acta* 1354:29–34 (1997).

Schaffer, J.E. and Lodish, H.F., "Expression Cloning and Characterization of a Novel Adipocyte Long Chain Fatty Acid Transport Protein," *Cell* (79):427–436 (1994).

Bonaldo, M.F. et al.; Data Submission; *Rattus norvegicus* cDNA clone; *Rattus norvegicus*; GenBank Accession No. AA817672; (1996).

Schaap, F.G. et al.; Data Submission; *Rattus norvegicus* fatty acid transport protein mRNA, complete cds.; *Rattus norvegicus;* GenBank Accession No. U89529; (1997).

Lee, N.H. et al.; Data Submission; Normalized rat heart, Bento Soares *Rattus sp.* cDNA clone; *Rattus sp.;* GenBank Accession No. AA799326; (1998).

Hui, T.Y. et al.; Data Submission; *Mus musculus* fatty acid transport protein (FATP) gene, exons 1–3; *Mus musculus;* GenBank Accession No. AF023256; (1997).

Schaffer, J.E. and Lodish, H.F.; Data Submission; *Mus musculus* fatty acid transport protein (FATP) mRNA, complete cds.; *Mus musculus*; GenBank Accession No. U15976; (1994).

Stahl, A. et al.; Data Submission; *Mus musculus* fatty acid transport protein 5 mRNA, complete cds.; *Mus musculus*; GenBank Accession No. AF072760; (1998).

Stahl, A. et al.; Data Submission; *Mus musculus* fatty acid transport protein 4 mRNA, partial cds.; *Mus musculus*; GenBank Accession No. AF072759; (1998).

Stahl, A. et al.; Data Submission; *Mus musculus* fatty acid transport protein 3 mRNA, partial cds.; *Mus musculus;* GenBank Accession No. AF072758; (1998).

Stahl, A. et al.; Data Submission; *Mus musculus* fatty acid transport protein 2 mRNA, complete cds.; *Mus musculus;* GenBank Accession No. AF072757; (1998).

Hui, T.Y. et al.; Data Submission; *Mus musculus* fatty acid transport protein (FATP) gene, exons 1–3; *Mus musculus;* GenBank Accession No. AF023256; (1997).

Hui, T.Y. et al.; Data Submission; *Mus musculus* fatty acid transport protein (FATP) gene, exons 4–7; *Mus musculus;* GenBank Accession No. AF023257; (1997).

Hui, T.Y. et al.; Data Submission; *Mus musculus* fatty acid transport protein (FATP) gene, exons 8–13 and complete cds.; *Mus musculus;* GenBank Accession No. AF023258; (1997).

Kamijo, K.; Data Submission; *Homo sapiens* mRNA for very–long–chain acyl–CoA synthetase, complete cds.; *Homo sapiens* (human); EMBL Accession No. D88308; (1996).

Harmon, C.M. et al., "Labelling of an 88 kDa adipocyte membrane protein by sulpho–N–succinimidyl long–chain fatty acids: inhibition of fatty acid transport," *Biochemical Society Transactions* 20(4):811–813 (1992).

Schaffer, J.E. et al., "Cloning and Structure–Function Analysis of Human Heart Fatty Acid Transport Protein," *Circulation* 96(8):2031 (1997).

Ghosh, B. et al., "Molecular cloning and sequencing of human palmitoyl–CoA ligase and its tissue specific expression," *Mol. Cell. Biochem.* 151:77–81 (1995).

Fitscher, B.A. et al., "Tissue distribution and cDNA cloning of a human fatty acid transport protein (hsFATP4)," *Biochimica et Biophysica Acta* 1443:381–385 (1998).

Banaszak, L., et al., "Lipid–Binding Proteins: A Family of Fatty Acid And Retinoid Transport Proteins," Advances in Protein Chemistry 45:89–151 (1994).

Binas, B., et al., "Requirement for the Heart–Type Fatty Acid Binding Protein in Cardiac Fatty Acid Utilization," FASEB Journal, Fed. of American Soc. for Experimental Biology, 13:805–812 (1999).

Flower, D.R., "The Lipocalin Protein Family: Structure and Function," Biochem J., 318:1–14 (1996).

Flower, D.R., "Multiple Molecular Recognition Properties of the Lipocalin Protein Family," Journal of Molecular Recognition, 8:185–195 (1995).

Flower, D.R., "Structural Relationship of Streptavidin to the Calycin Protein Superfamily," Fed. OfEur. Biochemical Soc., 333(12):99–102 (1993).

Hillier, L., et al.; Data Submission; zu10c02.sl/*Soares testis* NHT *Homo sapiens* cDAN clone IMAGE: 731426 3', mRNA sequence.*Homo sapiens*(human); GenBank Accession No. AA412064 (1997).

Hui, T.Y. and Bernlohr, D.A., "Fatty Acid Transporters in Animal Cells," Frontiers in Bioscience 2, d222–231 (1997).

Hui, T.Y., et al.; Data Submission; *Mus musculus* fatty acid transport protein (FATP) gene, exons 8–13 and complete cds.; *Mus musculus;* GenBank Accession No. AF023258; (1997).

Hui, T.Y., et al.; Data Submission; *Mus musculus* fatty acid transport protein (FATP) gene, exons 4–7; *Mus musculus;* GenBank Accession No. AF023257; (1997).

Liu, Y.Q., et al., "Fatty Acid–induced cell Hypersensitivity to Glucose," J. Clin. Invest., 101(9):1870–1875 (1998).

Stahl, A., et al., "Identification of the Major Intestinal Fatty Acid Transport Protein," Molecular Cell 4:299–308 (1999).

Strausberg, R., ov56b02.x1 *Soares testis* NHT *Homo sapiens* cDNA clone Image:1641291 3', *Homo Sapiens* (human) EMBL Accession No. AI041230 (1998).

Tartaglia, L.A., et al., "Identification and Expression cloning of a Leptin Receptor, OB–R," Cell 83:1263–1271 (1995).

\* cited by examiner

```
mmFATP1  64  VRLELRRHRRAGDTIPCIFQAVARRQPERLAALYDAS
mmFATP2  41  RRVRSYRQRRPVRTILRAFLEQARKTPHKPFLLFR-
mmFATP3  35  QRFSYAEAERESNRIARAELR--ARGWTGGRRGSGR-
mmFATP4   1  ----------------------------------------
mmFATP5  74  LKFRRRLNKHPPETFVDALERQALWPDRVALVCTG
ceFATPa  63  VKIDLWWRLHQNKGIHELFLDIVKKNPAMIDL
scFATP   64  VFCYIDVRRHRFQNWYLFIKQVQNGDHLAISYTR
mtFATP   35  AMTQLLARPNSKABIGTVFQDRIAARYQDRVFLKFG-
```

FIG. 1C

```
          S--QICWTFFAQLDTYSNAVANLFRQLGF---------
          ----DETLLYAQVLDRRSNQVARALHDQLG------
          GE-QSTEEGARVAPPAGDAAARGTTAPP--------
          ET---ITNSOLDARSCQAAWVLKAKLKDAV-------
MAEKGEFQL-----NTETYAEFNAHCNRYANYFQGLGY---
PMAEKGEFQL-----ETFTYIETYNIVLRLSHILHFDYN-
          ----DQQLTYRDANATANRYAAVLAARG-
```

| | | | |
|---|---|---|---|
| mmFATP1 | 265 | RYYRIAAFGHHSYSMRA- | ADVLYDCLPLYHSAQN |
| mmFATP2 | 241 | RLRYGTG-LAMSGITA- | QDVIYTTMPLYHSAAL |
| mmFATP3 | 234 | KVLQCQG-FYHLCGYHQ- | EDVIYLALPLYHMSQS |
| mmFATP4 | 125 | RYYRMASLVYYG-FRMRP- | DDICLPLYHSSRK |
| mmFATP5 | 283 | RVIQVGN-VLSLCQCRA- | DDYVLPLYHTIQL |
| ceFATPa | 264 | RYYSIAVGAAKSFGIRP- | SDRMYVSMPIYHTAAG |
| scFATP | 273 | KSSVGCQVFQHVLHMTN- | ESTVFTAMPLFHSTAA |
| mtFATP | 223 | RWLRALA-VFGGMGLRLKQ | SDTLYSCLPLYHNNAL |

FIG. 1I

| | | |
|---|---|---|
| IMGVGQCVIYG | LTVYLRKKFSASRFWDDCVKYNCTVVQ |
| MIGLHGCIVV | AAKKLCDKFSASGQFWDDCRKINVTVIQ |
| LLGIVGCLGI | IGATVVLKPKFSASNFWDDCQKHRVTVFQ |
| HRGDWQCLLHQ | MTVGATCVLAPKFSASRFWAECROHGVTVIL |
| VLGFLQCLQV | GATSGSCVIRKKFSASRFWRDCVKYDCTVSJQ |
| ILGVGQALLGG | HQGCLALSHKFSASTFWKQVYLTGATHIQ |
| LLQACAILSHG | ATLALGIKSFSASRFWDEVIANRATAFV |
| TVAVSSVIINSQ | |

FIG. 6 mmFATP3 DNA sequence

```
ACGACTCACTATAGGGCACAGCTATGACGTCGCATGGAC  40
GGCTAACGTTGGGGGCTGACCGATCCTCTAGAGGGCCC   80
CGGGACGGGGAAGCTCTAGAGCGGCCGCAGTCTGCGGT  120
GCGGTCTGGCTAGTTCGGGCCAGCGGCACACAC       160
CTTGCTCATGCAGCGCGCAGCGCTTTAGCTAGCGGCAG  200
GCTGACGGGACAGCAAGGCATTGCTGCGGCCTTTCTGC  240
CGCCAGGGCCTGAGGGCGGGCGGCAGCCTGGGCAG     280
GGGACCACTGAGGAAGCGCAGCGCTGCGCCTTGGCCT   320
CGACATGCGCCTGCTACGGACGACGCGCGGGCTCTGG   360
CAGGCGGCGGAGGTGCGGCCTGCTGCTGGACGCCCCC   400
```

FIG. 8A

FIG. 8B mmFATP3 protein sequence

AADPESSESGCSLAWRLAYLAREQPIHIFLIHGAQRFSYAEAERESNRIA 50
RAFLRARGWIGGRRGSGRGSIEEGARVAPPAGDAAARGITAPPLAPGATV 100
ALLLPAGPDFLWIWFGLAKAGLRIAFVPTALRRGPLLHCLRSCGASALVL 150
ATEFLESLEPDLPALRAMGLHLWATGPEINVAGLSNLLSEAADQVDEPVP 200
GYLSAPQNIMDICLYIFTSGTTGLPKAARISHLKVLQQGFYHLGVHQE 250
DVTYLALPLYHMSGSLLGIVGCLGIGATVVLKPKFSASQFWDDQKHRVL 300
VFQYIGELCRYLVNQPPSKAEFDHKVRLAVGSGLRPDIWERFLRRFGPLQ 350
ILETYGMTEGNVATFNYTGRQGAVGRASWLYKHIFPFSLIRYDVMTGEPI 400
RNAQGHQMTISPGEPGLLVAPVSQQSPFLGYAGAPELAKDKLLKDVFWSG 450
DVFFNTGDLLVCDEQGFLHFHDRTGDTLRWKGENVATTEVAEVLETLDFL 500
QEVNIYGVTVPGHEGRAGMAALAIRPPQAINLVQLYSHVSENLPPYARPR 550
FLRLQESLATTETFKQQKVRMANEGFDPSVLSDPLYVLDQDIGAYLPLTP 600
APYSALLSGDLRI 613

FIG. 9 mmFATP4 DNA sequence

CCCACGCGTCCGCCCAGCGCGTCGGCATGCCAAGCTGCG 40
CGTCCAGGCGGCTCTCATCAACACCAACCTTAGCGCGCAT 80
GCCCTGCGCCACTGTCTTGACAGCTCAAAGGACGAGCTC 120
TCATCTTTGGCAGTCAGATGGCCTCAGCTATCTGTCAGAT 160
CCATGCTAGCCTGGAGGCCACACTCAGCCTCTTCTGCTCT 200
GGATCCTGGCAGCCCAGCACAGTGCGGGTCAGCACAGAGC 240
ATCTGGACCCTCTTCTGGAAGATGCCCCGAGCACCTGCC 280
CAGTCACCCAGACAAGGGTTTTACAGATAAGCTCTTCTAC 320
ATCTACACATGGGCACCACGGGCTACCCAAAGCTGCCA 360
TTGTCGTGCACAGCAGGTATTATCGTATGCCTTCCCTGGT 400
CTACTATGCATTCCGCATCCGGCCTCATCACATTGTCTAT 440
GACTGCCTTCCCCTCTACCACTCAAGCAGCAAACATGGTG 480
GCGATTGCCAGTGCTTACTCCACGGCATCACTGTGGTCAT 520
CCGGAAGAAGTTCTCAGCCTCCCGGTTCTGGCATGATTGT 560
ATCAAGTACAACTGCACAGTCGTACAGTACATTCGCGACC 600
TCTGCCGGCTACCTCCTCAACAGCCACCCGTGAGGCTCA 640
GTCTCGGCCACAAGGTCGGCATGCACTGGGCAAGGTCTC 680
CGGCAGTCCATCTGCACGGACTTCTCCAGCCGTTTCCACA 720

FIG. 10A

```
TCCCCCAGGTGCCTCAGTTCTATCGGCCACTCAATGCAA 760
CTGTAGCCTGGGCAACTTTCACAGCGGGTCGGGCCCTGT 800
CGCTTCAATAGCGGCATCCTGTCCTTTGTGTACCCTATCC 840
GTTTCGTAGGTGTCAATCACCTACCATCCAACTCATCCG 880
CCCACCCCATCCAGTCTGCATTCCCTGTCAACCAGGTCAG 920
CCAGCCCAGCTGGTCGGTGGCATCATCCACCAGCCCCTC 960
TCGCCCGTTTCACGGGTACCTCAACCACGGTGCCAACAA 1000
CAACAACATTGCTAATCATGTCTTCAACAAGGGCCACCAA 1040
GCCTACCTCACTGGTCACGTCCTGGTCATGCATCAGCCTGG 1080
GTTACCTGTACTTCCGACATCCACTCGGGACACGTTCCG 1120
CTCCAAACGGCACAATCTATCTACCACTCAGGTCCACGGC 1160
ACACTCACCCGCCTGCTTCATATGCCACATGTCGCCAGTTT 1200
ATCGTCTTCAGGTCCAGCAACTCAACGCCCACCAGCAAT 1240
GCCTGCCGTTGCAAGTCCATCAGCAACTGTCACCTGCAG 1280
AGCTTTGCACACACCTTCAAAAGGAGCTGCCTCTGTATC 1320
CCCGCCCCATCTTCCTGGCTTCTTCCCTCAGCTGCACAA 1360
CACAGGCACCTTCAAGTTCCACAACACAGTTGCGGAAG 1400
CACCCCTTTCACCCATCTGTTGTCAAACACCCCTGTTCT 1440
ATCTGCATCCTCCAAGCCCTCCTACGTTGCACTGCACCA 1480
CCAGCCCTATACCGCATCCAGCCACCCAGCACAAGCTG 1520
TCATTTCCCCCTACATCCCTCTCAGCCCACAACATGCTG 1560
CATTCAGCGCCTACCGTCCACCCCACAGGTCCTGGGCA 1600
ATGCCACACCCAAAGCTACCAGGGCCCGCACCTCCCCCT 1640
AGGTCCTCCATCTCCCCTCTCCAAACTGCCAAGTCACTCA 1680
CTGCCCGCTTCCCCCACCCTCCACAGCCTTTCTGTCAAGT 1720
CTCATCCAAGCCTGTGTCTTCTCGTCCAGGCGTGCCCCTG 1760
GCCCCAGGGTTTCTCATACCCTCCTTTACCATCCTATCTT 1800
CCGTCCAGCCCGGCACGGTGTCCACAGCAGTCACTAACA 1840
TCCCTCCAATCACAAGCCACCTTACAAAGCAACCAAGCCA 1880
AAGCCTGTACACTCAGCAAGCTAAGTGGGCACACACTATA 1920
GTGGCCAGTCATCCATGTCCACACAGCATCTTGGTCCAG 1960
AGCTCGCAAAGTGTCACCTCTCCCTGCCTCCACCTCTGGG 2000
CAAAACACCAGCATGTGGCCACTGCCCACCTGTCTCAA 2040
CAAGTCAGCATCACACTCAGTCCTTGTTTCTCCAGGTT 2080
CCCTTCTTCTTGTCTCGGCAGGAGCCACGTCTCCTG 2120
TCTGTCCTTCCTGCCTGTCTCTCAGTCTCTGTTGCTTCTC 2160
CATCTGTCCTAGCCTCAGTGTCGGTCCACAGGCATCAGG 2200
ACAGTGTCGCTCAGGGCCAATAAACTCTGCCTTCACTCC 2240
TCTTAAAAAAAAAAAAAAAAAAAAAAAAAAAAAAAAAAAA 2280
AAAAAAAAAAAAAAAAAAAAA 2301
```

FIG. 10B mmFATP4 protein sequence

HASAHASGMAKLGVEAALININLRRDALRHCLDISKARAL 40
IFGSEMASAICEIHASLEPILSLFCSGSWEPSIVPVSIEH 80
LDPLLEDAPKHLPSHPDKGFIDKLFYIYTSGTTGLPKAAI 120
VVHSRYYRMASLVYYGFRMRPDDIVYDCLPLYHSSRKHRG 160
DWQCLLHGMTVVIRKKFSASRFWDDCIKYNCIVVQYIGEL 200
CRYLINQPPREAESRHKVRMALGNGLRQSIWIDFSSRFHI 240
PQVAEFYGATECNCSLGNFDSRVGACGFNSRILSFVYPIR 280
LVRVNEDIMELIRGPDGVCIPCQFGQPGQLVGRIIQQDPL 320
RRFDGYLNQGANNKKIANDVFKKGDQAYLIGDVLVMDELG 360
YLYFRDRIGDIFRWKGENVSTIEVEGILSRLLHMADVAVY 400
GVEVPGIEGRAGMAAVASPISNCDLESFAQILKKELPLYA 440
RPIFLRFLPELHKTGIFKFQKIELRKEGFDPSVVKDPLFY 480
LDARKGCYVALDQEAYIRIQAGEEKL 506

FIG. 11 mmFATP5 DNA sequence

CACTCATCAGAGCTAAGAGAGACTACAGGCTCTCATCTAC 40
TTCAGAAAGAGCCAATGCCATGGGTATTTGCAAGAAACTA 80
ACCTTACTGCTGTTGCTGCTTCTGCTGGTTGCCCTGGGGC 120
AGCCCCCATGGCCAGCAGCTATGCCTCTGCCCTGCAGTTG 160
GTTCCTGGCAGACCCACATGCCTTGTGCTGCTTGGCTTG 200
GCATTGCTGGGCAGACCCTGGATCAGCTCCTGCATGCCCC 240
ACTGGCTGAGCCTGGTAGGAGCAGCTCTTACCTTATTCCT 280
ATTGCCCTCTACAGCCACCCCAGGGCTAGGCTGGCTGCAT 320
AAACATGTGGCTTTCACCTTCAAGATGCTTTTCTATGGCC 360
TAAAGTTCAGGGCAGGCCTTAACAAACATGCTGCAGAC 400
CTTTGTGCATGCTTTACAGCGGCAAGCACTGGCATGGCT 440
CACGCGGTGGCCTTGGTGTGTACTGGGTCTGAGGGCTCCT 480
CAATCACAAATAGCCAGCTGGATGCCAGGTCCTGTCAGGC 520
AGCATGGGTCCTGAAAGCAAAGCTGAAGCATGCCGTAATC 560
CAGAACAACAAGAGATGCTGCTGCTATCTTAGTTCTGCCGT 600
CCAAGACCATTTCTGCTTTCAGTGTGTTTCTCGGGTTGCC 640
CAAGTTGGGCTGCCCTGTGCCCTGCATCAATCCACACAGC 680
CCAGGGATGCCCTTCCTACACTCTGTACGAGCTCTGGGG 720
CCAGTGTGCTCATTGTGGATCACAGCCTCCAGGAGAACCT 760
GGAACAAGTCCTTCCCAAGCTGCTAGCTGAACATTCAC 800

FIG. 12A

```
TGCTTCTACCTTGCCCACAGCTCACCACCCCGGAGTAG  840
AGCCTCTGCCAGCTTCCCTGCATCCTGCACTTCTCACCC  880
AGTACCTGCCAGCCTTCAGCTACCATTAAGTGGAAATCT  920
CCTGCCATATTCATCTTTACTTCAGCACCACTGCACTCC  960
CAAAGCCAGCCATCTTATCACATCAGCGGTCATACAAGT 1000
CACCAACGTCCTCTTCTTCTGTCCATCCAGACCTCATCAT 1040
GTCGTCTATCACGTCCTACCTCTGTACCATACATAGGGC 1080
TTGTCCTTGCATTCCTTGCCTGCTACAAGTTGCAGCCAC 1120
CTGTCTCCTGGCGCCAAGTTCTCTGCCTCCCGATTCTGG 1160
GCTCAGTGCCGCCACCATGCGTAACACTCATCTTCTATG 1200
TGGCTCAATCCTGCGGTACTTCTGTAAGTCCCTCAGCA  1240
ACCACAACAAGATACATACAGTGCGCTTCGCCATGGCA  1280
ACTGCACTTGCGCAAATGTGTCCAAAACTTCCAGCAAC  1320
GCTTTCCTGCCATTGCATCTGCCAATTCTACGCATCCAC 1360
AGAGGGCAATGTCGGCTTAATCAACTATGTCGGGCACTGC 1400
GGGGCTCTCCAAGCACCAGCTGCATCCTTCAATGCTCA  1440
CTCCCTTTCAGCTTGTACAGTTGCACATAGACAGCACA  1480
GCCTCTCAGGACAAACAGGGTTTTTGCATTGCTGTGGAG 1520
CCAGGAAAGCAGCACTTCTTTTGACCAAGGTTGCAAACA 1560
AGGAAGCCTTCCTGCGCTACGTGCTTCCAGGCCGAGTC  1600
CAATGGGAAACTTGTTGCGAATGTACGACGCGTAGCAGAC 1640
CTGTACTTCAACACTGGGACGTGCTCAACTTGCACCAGG 1680
AAGGCTTCTTCTACTTTCAAGACGGCCTTGCTCACACCTT 1720
CCGGTGCAACGGCCAAAACGTATCTACTGCAGACGTCAG 1760
TCTGTTTTGTCTAGCCTACACTTCCTACAGCAAGTCAATG 1800
TCTATGCTGCTCCCTGCTGCCAGCGTGTCAGCGTAAGGTTGG 1840
CATGCCTGCCTGTAAACTGGCTCCTGCCAACACTTTCAT 1880
GCCCACAAGCTATACCAGCATGTGCCCTCCTGCCTCCCTG 1920
CCTATGCCACAGGTCATTTCATCGGTATCCAGCATTCCT 1960
GCACATCACAAATACCTACAAGCTGCTAAAGTCACGGCTG 2000
GTGGCTCAGCGTTTTCATCTGCCCATCATTGCTCACCCC 2040
TCTACATACTGCACAACAAGGGCACACCTTCCGCAGTCT 2080
CATCCCTACATCTGCTACCAGGCTCTCTGTCAAGCAACCTGG 2120
AATGTGTCACCACCTAGCCAACTGCAGCCAATCCAAAG 2160
TGTACAGTTCACACTAGTCAGCTTCACAAAGTTGTCCGG 2200
GTTCCAGATGCCCATCCCCAGTAGTACTTACAGAATAAA 2240
CTTCAATGTGTATACAAAAAAAAAAAAAAAAAAAAAA  2277
```

FIG. 12B mmFATP5 protein sequence

```
MALALRWFLGDPTCLVLLGLALLGRFWISSWMPHWLSLVG 40
AALTTFLLPLQPPPGLFWLHKDVAFTFKMLFYGLKFRRRL 80
NKHPPETFVDALERQALAWPDRVALVCIGSEGSSTTNSQL 120
DARSCQAAWWLKAKLKDAVIQNIRDAAAILVLPSKTISAL 160
SVFLGLAKLGCPVAWINPHSRGMPLLHSVRSSGASVLIVD 200
PDLQENLEEVLPKLIAENIHCFYLGHSSPTPGVEALGASL 240
DAAPSDPVPASLRATIKWKSPAIFIFTSGTTGLPKPAILS 280
HERVIQVSNVLSFCGRADDVVYDVLPLYHTIGLVLGFLG 320
CLQVGATCVLAPKFSASRFWABCRQHGVIVILYVGEILRY 360
LCNVPEQPEDKIHIVRLAMGTGLRANVWKNFQQRFGPIRI 400
WEFYGSTEGNVGLMNYVGHGAVGRTSCILRMLTPFELVQ 440
FDIETAEPLRDKQGFCIPVEFGKPGLLLIKVRKNQPFLGY 480
RGSQAESNRKLVANVRRVGDLYFNIGDVLITLDQEGFFYFQ 520
DRLGDIFRWKGENVSIGEVECVLSSLDFLEEVNVYGVPVP 560
GCEGKVGMAAVKLAPGKIFDGQKLYQHVRSWLPAYATEHF 600
TRIQDSLETTNTYKLVKSRLVREGFDVGLIADPLYILLNK 640
AQIFRSIMPDVYQAVCEGIWNL 662
```

FIG. 13 hsFATP2 DNA sequence

```
ATGGCATTGACTCTTTCCTGGACAAAGTGGATGAAGTATC 40
AACTGAACCTATCCACAGTCATGGGTCTGAAGTCACT 80
TTTTCCACTCCTGCCTTATACATTTATACTTCTGGAACCA 120
CAGGTCTTCCAAAAGCAGCCATGATCACTCATCAGCGGCAT 160
ATGGTATGCAACTGCCCTCACTTTTGTAAGCGGATTGAAG 200
GCAGATGATGTCATCTATATCACTCTGCCCTTTTACCACA 240
GTGCTGCACTACTGATTGGCATTCAGGATGTATTGTCGC 280
TGGTGCCTACTCTTGCCTTGCGCACTAAATTTTCAGCCAGC 320
CAGTTTTGGATCACTGCAGAAATACAAGGTCACTGTCA 360
TTCAGTATATCGGTGAACTGCTTGGTATTTATGCAACTC 400
ACCACACAAACCAAATGACGGTCATCATAAAGTCAGACTG 440
GCACTGCGAAATGGCTTACGAGGATGTGTGGAGACAAT 480
TTGTCAAGGATTTGGGGACATATGGATCTATCAGTTCTA 520
TGCTGCCACTCAAGGCAATATTGCATTTATGAATTATGCG 560
AGAAAAGTTGGTGCTGTTGCAAGAGTAAACTACCTACAGA 600
AAAAAATCATAACTTATCACCTCATTAAATATCATGTCCA 640
GAAAGATGAACCTGTCCGTCATCAAAATGGATATTGGGTC 680
AGAGTTCCCAAAGGTCAAGTTGCACTTCTGGTTTGCAAAA 720
TCACAACTTACACCATTTAATGGCTATGCTGCAGCCAAA 760
GGCTCAGCACAGAACAAAAACTCAGAGTGTCTTTAAG 800
```

FIG. 14A

```
AAAGCAGACCTCTATTTCAACAGTGGAGATCTCTTAATGG 840
TTCACCATGAAAATTTCATCTATTTGCAGGACAGAGTTGG 880
AGATACATTCGCGTGGAAAGCGGAAAATGTCGCCACCACT 920
GAAGTTGCTGATATAGTTGGACTGGTTGATTTTTTTTCAA 960
GGAAGTAAAATGTTTATGGCAGTCCATCGGCAAGATNAT 1000
GGAGGTTGGAATTGGCATGGCNTTCCNTTCAAAATGGAAA 1040
GAAAACCATGGAATTGATGGAAAGAAATTTTTTCAGNAC 1080
ATTGCTGATAACCNACCTAGTTATCCAAGGCGGGCGTTT 1120
NTAAGAANACAGCACACCATTGAGATCACTGGAATTTTA 1160
AACAGGGCAAAATGACCTTTGGCTGGAGGACGGGCTTTAACC 1200
CNGCTGTCATCAAACAATGCCTTGTATTTTCTTGGATGACA 1240
CAGCCAAAAATGTATCTGCCCTATGACTGAGGACATNTATAA 1280
TGGCATAAGTGNTAAAACCCTGAAATTNTGAATATTCCCA 1320
GGAGGATAATTCAACATTTCCAGAAACAAACTGAATGGAC 1360
AGCCACTTGATATAATCCAACTTTAATTTGATTGAAGATT 1400
GTGCCGAAATTTGTAGGAAATTGCATACCCGTAAAGGG 1440
AGACTTTTTAAATAACAGTTGAGTCTTTGCAAGTAAAAA 1480
GATTTAGAGATTATTATTTTCAGTGTGCACCTACTGTTT 1520
GTATTTGCAAACTGAGCTTGTTGGAGGGAAGCCATTATTT 1560
TTTAAATACTTAGTAAATTAAAGAACACCAACATGTGAA 1600
AAAAAAAAAAAAAAAAAAAAA 1622 hsFATP2 protein sequence

YTYTSGTTCLPKAAMITHQRIWYGTGLIFVSGLKADDVIY 40
ITLPFYHSAALLIGTHGCTVAGATLALRIKFSASQFWDDC 80
RKYNVTVIQYIGELLRYLCNSPQKPNDRDHKVRLAIGNGL 120
RGDVWRQFVKRFGDICIYEFYAATEGNIGFMNYARKVGAV 160
GRVNYLQKKITTYDLIKVDVEKDEPVRDENGYCVRVPKGE 200
VGLLVCKITQLTPFNGYAGAKAQTEKKKLRDVFKKGDLYF 240
NSGDLLMVIHENFTYFHDRVGDIFRWKGENVATIEVADIV 280
GLVDFF 286 hsFATP3 DNA sequence

CAATTGGCACCCCAGGGGCACTGTATGGCACATCTCC 40
AGGTCAGCCAGCGGAAGTTGCTAAAGCATGTCTTCCGGCC 80
TGGCGATGTTTTCTTCAACACTGGGACCTGCTGGTCTGC 120
GATGCCAAGGTTTTCTCGGCTTGCATCGATGTACTGGAG 160
```

```
ACACCTTCAGGTCCAAAGGGACAATGTCGCCACAACCGA 200
CGTCGCACAGGTCTTCGAGGGCTAGATTTCTTCAGCAG 240
GTGAACGTCTATGAGTCACTGTGCCACGGCATCAAGGCA 280
GGGCTCCAATGGAGGGCTAGTTCTCGGTCCGCCCACGC 320
TTTCCACCTTATGCAGCTCTACACGCACGTGTCTGAGAAC 360
TTGCCACCTTATGCGGCGCGGATTCCTCAGGCTCCAGG 400
AGTCTTTCGCCACCACAGACCTTCAAACAGCACAAAGT 440
TGCATGGCAAATGAGGGCTTGCACGGAGCACGGGTGTCT 480
GACCCACTGTACGTTCTGGACCAGGCTGTAGGTGCCTACC 520
TGCCCGCTCACAACTGGCCGGCTACAGCGCCTGCTGGCAGG 560
AAACCTTCCAATCTCAGAACTTCCACACCTGAGCCACCTG 600
ACAGACGAACTCTGTGCCGTGGGCGGGGTTGCAGGTGTAC 640
TGCGCTGTCAGGATCTTTTCTATAGCAGAACTGCGGTCA 680
CTATTTGTAATAAATGTGCCTGCAGCTGATCCAGCTGTC 720
TCTGACCTACAAAAAAAAAAAAAAAAAAAAAAAAA 753 hsFATP3 protein sequence

QFGTPRGTVWPHLQVSQEKLLKDVFRPGDVFFNTGDLLVC 40
DDQGFLRFHDRTGDIFRWKGENVATTEVAEVFEALDFLQE 80
VNVYGVTVPGHEGRAGMAALVLRPPHALDLMQLYTHVSEN 120
LPPYARPRFLRLQESLATTETFKQQKVRMANEGFDPSTLS 160
DPLYVLDQAVGAYLPLTTARYSALLAGNLRI 191 hsFATP4 DNA sequence

TCAAGTACAACTGCACGATTGTCATANCATTCGTGAACTG 40
TGCCGNTACCTCCTGAACCAGCCACGGCGGAGGCACAAA 80
ACCACCACCAGGTTGCCATGGCACTAGCAATGGCCTCCG 120
GCAGTCCATCTGACCAACTTTTCAGCGGCTTCCACATA 160
CCCCAGGTGCCTGAGTTYTACGGGCCACACAGTGCAACT 200
GTAGCCTGGGCAACTTCACAGCCAGGTGGCCCCTGTGG 240
TTTCAATAGCGGCATCCTGTCCTTCGTGACCCGCATCGG 280
TTCGTACGTGTCAAGAGCACACCATCGAGCTCATCCGGG 320
GGCCGGACGGCGTCTTGCATTCCTTGCCAGCCAGGTCAGCC 360
GGGCCAGCTCCGTTCCGCGCATCATCCAGAAACCGGGCTG 400
CGGCCTTCGATGCCTACTCAACCAGGGCGCCAACAACA 440
AGAAGATTGCCAAGCATGTCTTCAAGAAGGCGCACCAGGC 480
CTACCTTACTGGTCATGTGCCTCCGATCCACCAGCTGGGC 520
```

```
TACCTGTACTTCGGCGACACGGCACTGGCGCAAGGTTCGGCT 560
CGAAAGCTGACAAGGTGTCCACCACGCAGGTGCAAGGCAC   600
ACTCAGCGGCCTCCTGCACATCGCTCAGGTGCGGGTGTAT   640
CGTGTCGACGTGCCAGCAACGCAGGCGCCGGCGCGAATCG   680
CTGCTGTCCGCAGCGCCACTGGCAACTGTCACCTGCCACC   720
GCTTTCCTCAGGTC 734
``` hsFATP4 protein sequence

```
IGELCRYLLNQPPREAENQHQVRMALGNGLRQSIWINFSS   40
RFHIPQVAEFYGATECNCSLGNFDSQVCACGENSRILSFV   80
YPIRLVRVNEDIMELIRGPDGVCIPCQPGEPGQLVGRIIQ  120
KDPLRRFDGYLNQCANNKKTAKDVFKKGDQAYLIGEVLVM  160
DELGYLYFRDFIGDIFRWKGENVSITEVEGILSRLLDMAD  200
VAVYGVEVPGIEG 213
``` hsFATP5 DNA sequence

```
CNTGCCTCTTGTACCACGTCATGGCACTTTGTCGTTCGCA   40
TCCTCGCCTGCTTACATCTGCAGCCACCTGTGTTCTCGCC   80
CCCCAAGTTCTCTACTTCCTCCTTCTCGGCATCACTGTCGG  120
CAGCCATGCCGTCACAGTCATCCTGTATGTCGGCAGCTCC  160
TGCCNTACTTGTGTAACATTGGCCAGCAACCACAGCACCG  200
CACACATACAGTCGGCCTGGCAATGGCAATCGACTACGG   240
GCTCATGTGTCGGCAGACCTTCCAGCAGCGCTTTCCGTCCT  280
ATTTGGCATCTNGGCAAGTCTTACGGGCTTCCACACAAGG  320
GCAACATGGGCTTTAGTTCAACTATTGTTCGGGGCGCTG   360
GGGCGGCCTGCGGCAAAGATGGAGCTTGCCTCCTCCGAA   400
TGCTGTCCGGCTTTGACGTGGTCCAGTTGACATCGAGGC   440
CGGCCAGCCTGTCAGGCACAATCAGGGCTTCTGCATCGCT  480
GTACGGCTACGGCACGGCGGCTCCTGTTGACCAAGGTGG   520
TAACCACCAACCTTCGTGCCCTACGGCGCCCCCGACA    560
CGTGTCCCAACCGAAGCTCGTCGCCAAGCTCGGCAATCG   600
CGGCAGCTTACTACAACACGGCACGTACTGCCCATGG    640
ACCGCTAAGGCTTCCTCTACTTCGGCACCACTGGGCA    680
CACCTTCGGATCCAAGGGCGACAACGTGTCCACGCACCAG  720
GTGCAGCGCGTGTTGTCCAGGTGCACTTCTTGCAACAGG  760
TTAACGTGTATGGCGTGTCGGTGCCAGGTTGTCAGGGGTAA  800
CGTGCCCATGCCTGCTGGTGGCATTAGCGCGGGCCAGACT  840
```

```
TTCACCGCCACAAGTTGTACCAGCACGTTGCGCGTTGGC  880
TCCCTGCCTACCCTACCGGGCATTTCATGGCCATCCAGGA 920
CGCCATGCAGGTCACCAGCACGTTCAAACTCATCAACACC 960
CGGTTGGTGCGGTCAGGGCTTCAATGTGGGCATCGTCGTTG 1000
ACCCTCTGTTTGTACTGCACAACGGCCCCAGTCCTTCCG  1040
CCCCCTCACGGCACAAATGTACCAGGCTGTGTGTCAGGCA 1080
ACCTGCAGGCTCTCATCACCTGGGCAACCCACTGGCGTAG 1120
GCATCAAAGCCAGCCACCCCACCCCAACACACTGGTGT   1160
CCCTTTCATCCTGGGCCTGTGTCAATCCCAGCCTGGCCAT 1200
ACCCTCAACCTCAGTCGGCCTGGAAATCACAGTGGCCCCTG 1240
TACCAGTCGCCAGAATAAACTCAGTTGYGTTCACAGAAA  1278
``` hsFATP5 protein sequence

```
EGQHGALVQLLLGALRGFGCKDGACLLRMLSPFELVQFTM  40
FAAEPVRINQGFCIPVGLGFPGLLLTKVVSQQPFVGYRGP  80
RELSERKLVRNVRQSGDVYYNIGDVLAMDREGFLYFRDRL 120
GDTFRWKGENVSIHEVEGVLSQVDFLQQVNVYGVCVPGCE 160
GKVGMAAVALAPGQIFDGEKLYQHVRAWLPAYATPHFIR  199
``` hsFATP6 DNA sequence

```
CCCTTGTCTGTTAAACAAGAATTTTCAGCAAGCCAGTTT   40
TCCAGTCACTGCAACAAGTATGATGTCACTGTGTTTCAGT  80
ATATTGGACAAACTTTGTGCTACCTTTGCAAACAATCTAA 120
CACAAGCAGAAAGGATCATAAGGTGCGTTTGGCAATT    160
GGAAATCGCATACGCAGTCATGTATGCACAGAATTTTTAG 200
ACAGATTTGCAAATATAAAGGTGTGTGAACTTTATGCAGC 240
TACCAATCAAGCATATCTTTCATGAACTACACTGGCAGA  280
ATTGCAGCCAATTGGCAGAACAAATTGTTTTACAAACTTC 320
TTTCCACTTTTCACTTAATAAGTATGACTTTCAGAAACA  360
TCAACCCATCGCAAATCAGCACCGGTTGGGTATTCATCAG 400
AAAAGCAGCCTGCACTTCTCATTTCTCCAGTCAATGCAA  440
AAAATCGCTTCTTTCGGCTATGCCTGGCCCTTATAGCACAC 480
AAAACACAAATTGCTTGTCATGTTTTTAAGAAGGCAT    520
GTTTACCTTAATACTGCCACTTAATAGTCCAGCATCAGG  560
ACAATTGCTTTATTTTTGGCACCGTACTGCCACACTTT   600
CACATGCAAAGCGAAATGTGGCAACCACTCACGTTGCT   640
GATGTTATTGCAATGTTGCTTTCATACAGCAGCAAACG   680
TCTATGGTGTGGCTATATCAGGTTATCAGCAAGCAGG    720
```

```
AATGGCTTCTATTATTTTAAAAGCAAATACATCTTTACAT 760
TTGCAAAAGTTTATGAACAAGTTGTAACATTTCTACCAG  800
CTTATGCTTGTCCACGATTTTAAGAATTCAGGAAAAAAT  840
GGAAGCAACAGGAACATTCAAACTATTGAAGCATCAGTTG 880
GTGGAAGATGGATTTAATCCACTGAAAATTTCTGAACCAC 920
TTTACTTCATGGATAACTTGAAAAGTCTTATGTTCTACT  960
GACCAGGGAACTTTATGATCAAATAATGTTAGGGAAATA  1000
AAACTTTAAGATTTTTATATCTAGAACTTTCATATGCTTT 1040
CTTAGGAAGAGTGAGAGGGGGTATATCATTCTTTATGAA  1080
ATGGCGAAGCCAGCTAACATTAATTATGCATGTACTATA  1120
TTTCCTTAATATGAGAATAATTTTTTAATTGCATAAGAA  1160
TTTTAATTTCTTTTAATTGATATAAACAGAGTTGATTATT 1200
CTTTTTATCTATTTGGAGATTCAGTGCATAACTAAGTATT 1240
TTCCTTAATACTAAAGATTTTAAATAATAAATAGTGGCTA 1280
GGGGTTTGGACAATCACTAAAAATGTACTTTCTAATAAGT 1320
AAAATTTCTAATTTTGAATAAAGATTAAATTTTACTGAA  1360
A 1361
```

FIG. 22B hsFATP6 protein sequence

```
ACVLKKKFSASQFWSDCKKYDVIVFQYIGELCRYLCKQSKREGEKDHKVR 50
LAIGNGIRSDWWREFLDRFGNIKVCELYAATESSISFMNYTGRIGAIGRT 100
NLFYKLLSTFDLIKYDFQKDEPMRNEGGWVFMRKRRPGLLISRVNAKNPF 150
FGYAGPYKHIKDKLLCDVFKKGDVYLNIGDLIVQDQINFLYFWDRIGDIF 200
RWKGENVATTEVADLVIGMLDFIQEFANVYGVAISGYEGRAGMASIILKENT 250
SLDLEKVYEQVVIFLPAYACPRFLRIQEKMEATGIFKLLKHQLVEDGFNP 300
LKISEPLYFMDNLKKSYVLLIRELYDQIMLGEIKL 335
```

FIG. 23 mtFATP DNA sequence

```
TAGTCCATAACGTCAAGCACGCTCTGCGGCCCTGCGCACC 40
TTCCTGAGGTTCGTCGACAACCAATTCGACATTTCGCAAA 80
CGAATCGAGGGCTTACGTGTGCGATTACTAGGCGGGGCA  120
CACACAACGGTCAGGCTGATCGACTGGCAACTGGCATGC  160
GCGCAGTGTTCGCGGACAGCCGGTGATTGTCCGTGGGGC  200
AATGACGGGCTGCTGGCGGGGCAATTCAAGGCGCTCG    240
ATGGCACGGTGTTCCAGCACGGCGGCTGCCTACGGTG    280
ACCAGTCTTCCTGAATTGGCGCATCAGCAGCTGACCTA   320
CGGCCAGGCTAACGCCACGCCAACGGTACGCGGGGTG    360
```

FIG. 24A

```
TTCCCCGCCCCGCGCGTGCGCGGGCGCAGCTCGTTCCCA 400
TCATGTTGCGTAACTCAGCCAGCACAGTCTTCCCCATGCT 440
CCCCAGCGTCAAGTGCGGCGCTATGCGGCCATGCTCAAC 480
TACCACCAGCGCGGCGAGGTGTTCGCGCACAGCCTCGGTC 520
TGCTCCACGGCAAGGTACTCATCGCACAGTCCGACTTCGT 560
CAGCCGGTCGGCAATCGGCGCGTGCACGCGCCCGTA 600
CGGCGGGCAGCGTCCTCACGTGCAGCAGGTGCAGCCATTCG 640
CCACAAGGCGCGGGCGACCAACGGCGTGCCGTGCGC 680
CGTGCAAGGCAAACAGGCGGTTCTACATCTTCACCTCG 720
CCACCAAGGCATTTCGGAAGGCAGTGTCATCAGGCATC 760
ATGGCTGGCTGCGGCGGCTGGCGGTGTTGCCACGGCATGCG 800
GGTCAGCGCTCAAGGGTTGGCACAGCCTCTACAGCTCGCTG 840
CGGCCTGTACCAACAACGGCGTAACGGTGCGCGCGTGCT 880
CGGCTCATCAATTCTGCGGGCACGCCTGGCGCTGGGTAAGTC 920
GTTTTCGCGTGCGCGTTCTGCCATCAGGCTATTGCCAAC 960
CGGGCCAGCGCGTTCGTCTACATGGCGAAATCTGCCGGTT 1000
ATCTGCTCAACCAGCGGCGCAAGCCGACCGACCGTGCCCA 1040
CCAGGTCGGCGTCATCGTCGCGTAACGGGCTCCGGCCGCAG 1080
ATCTGCGATCAGTTCAGCAGGGCCTTGCGCGTGCAGCGGC 1120
TGTGCGAGTTCTACGGCGGCAGCGAAGGCAACTGGCCTT 1160
TATCAACATCTTCAAGGTCGCCAGCAGCCGCGGGTATCG 1200
CCGATCGGGCTTCGCCTTTCTCGAATACCAACCTCGACACCG 1240
CGCATCGCCTCGCGGCATGGCAGCGCGCAGTCGTGCGGT 1280
ACGCCAGCGTCAAGCGGCGCTGTTGCTTAGCCGGGTCAAC 1320
CCGCTCCAGCGGTTCCAGCGCTACAGCCAACCCGGTTGCCA 1360
GCGAAAACAAGTTGCTGCGCCAAGCCTTTTCCAGATCCCGA 1400
CTGTTCGTTCAACAGCGGTCAGGTCATCAGCCCGCAGGGC 1440
ATGGCGCATGGCGCGTTCGTCGATGCGCTGGGCACAGCCT 1480
TGGCCTCCAAGGCGCAATGTCGCCACCACTCAGGTCA 1520
ACGGCCACTGGCTGGCACGAGGGTCCAGCAGTGCAGG 1560
GTCTAGGCGCTCCACATTCGCGCCACGCGCGGCGCGCGCGG 1600
CAATGCGGCGCATCACACTCGCGCGCTGCGCGGCAATTCA 1640
CCGCCAGCGGCCTGCGGCAAGGGTTACGGTCACTTGCCC 1680
CCGTATCCACTTGCCGTCTTTGTTCGCGCTAGCGGGGTGCC 1720
TGGCGCACCACCGACGGTTCAACAGTGGCCAACGTGCAGTT 1760
GCCGAGCAGGCGCTATGGCGGCCATGCAGCATCGCCTG 1800
TAGGGTACTGGCGGCGGCGACGAAGCATATGCGGCGTACT 1840
AGGGGCAATACGGGTCAGCAGGCTTGGCCTGGAAGGCCACC 1880
CCAGGGCTACGGCATTCGGCGCGCAGTCTCCATACGGGCA 1920
CTGCACGCTCACGGTAACCACGGCACTATGCATGCGTGCC 1960
TTCAACACGGCGGCCCTCACGCGGCCTCGTTCAACACGGCCCG 2000
GGGTTAG 2007
```

FIG. 24B mtFATP protein sequence

```
msdyyggahttvrlidlatmprvladtpvivrgamtgll   40
arpnskasigtvfqdraarygdrvflkfgdqgltyrdana  80
tanryaavlaargvgpgdvvgimlmspstvlamlatvkc  120
gaiagmlnyhqrgevlahslglldakvliaesdlvsavae 160
cgasrgrvagdvltvedverfattapatmpasasavqakd 200
tafyiftsgttgfpkasvmthhrwlralavfggmglrlkg 240
sdtlysclplyhmaltvavssvinsgatlalgksfsasr  280
fwdevianratafvyigeicryllnqpakptdrahqvrvi 320
cgnglrpeiwdefttrfgvarvcefyaasegnsafinifn 360
vprtagvsqmplafveydldtgdplrdasgrvnrvpdgep 400
glllsrvnrlqpfdqytdpvasekklvmafrdgdcwfnt  440
gdvmspqgmghaafvdrlgdtfrwkgenvattqveaalas 480
dgtveectvygvqiprtggragmaaitlragaefdgqala 520
rtvyghlpgyalplfvrvvgslahtttfksrkvelmqay  560
gadiedplyvlagpdegyvpyyaeypeevslgmpqg     597
```

FIG. 25 hsFATP1

```
  1  tcg acc cac ggc gtc cgg gac ccc aaa gca gaa gcc cgc aca gta ggc aca gcg cac cca
 61  aga agg gtc cag gag tct gca gaa acg gaa agg tcc ccg gcc tca gcc tcc tag tcc ctg
                                                                                 M  R
121  cct gcc tcc tgc ctg agc ttc tgg gag act gaa ggc acg gct tgc agc ttc agg atg cgg
181  gct ccg ggt gcg ggc gcc gcc tcg gtg gtc tcg ctg gcg ctg ttg tgg ctg ctg ggg ctg
      A   P   G   A   G   A   A   S   V   V   S   L   A   L   L   W   L   L   G   L
241  ccg tgg acc tgg agc gcg gca gcg ctc ggc gtg tac gtg ggc agc ggc ggc tgg cgc
      P   W   T   W   S   A   A   A   L   G   V   Y   V   G   S   G   G   W   R
301  ttc ctg cgc atc gtc tgc aag acc gcg agg cga gac ctc ttc ggt ctc tct gtg ctg atc
      F   L   R   I   V   C   K   T   A   R   R   D   L   F   G   L   S   V   L   I
361  cgc gtg cgc ctg gag ctg cag cag cgg cgg cac cag cgt gcc cac atc ccg cgc atc ttt
      R   V   R   L   E   L   Q   Q   R   R   H   Q   R   A   H   I   P   R   I   F
421  cag gcg gta gtg cag cag cga cag ccc gag cgc ctg gcg ctg gat gcc ggg acc ggc gag
      Q   A   V   V   Q   Q   R   Q   P   E   R   L   A   L   D   A   G   T   G   E
481  tgc tgg acc ttc gcg ccg cag ctg gac gcc gtg gtg gcc atc ttc ctg gag ggc cgg cag
      C   W   T   F   A   Q   L   D   A   V   V   A   I   F   L   E   G   R   Q
541  ctg ggc ttc gcg ccg ggc gac gtg gtg gcc atc ttc ctg gag gcc cgg cgg ccc gag ttc gtg
      L   G   F   A   P   G   D   V   V   A   I   F   L   E   G   R   P   E   F   V
601  ggg ctg tgg ctg ggc ctg gcc aag gcg atg gag gcg ggc atg gag gcc gcg ctc ctc aac gtg aac ctg
      G   L   W   L   G   L   A   K   A   G   M   E   A   A   L   L   N   V   N   L
```

FIG. 26A

```
 661  cgg cgc gag ccc ctg gcc ttc tgc ctg ggc acc tcg ggc gct aag gcc ctg atc ttt gga
       R   R   E   P   L   A   F   C   L   G   T   S   G   A   K   A   L   I   F   G 721  gga gaa atg gtg gcg gcg gtg gcc gaa gtg agc ggg cat ctg ggg aaa agt ttg atc aag
       G   E   M   V   A   A   V   A   E   V   S   G   H   L   G   K   S   L   I   K 781  ttc tgc tct gga gac ttg ggg ccc gag ggc atc ttg ccg gac acc ctc ctg gac ccg
       F   C   S   G   D   L   G   P   E   G   I   L   P   D   T   H   L   L   D   P 841  ctg ctg aag gag gcc tct act gcc ccc ttg gca cag atc ccc agc aag ggc atg gac gat
       L   L   K   E   A   S   T   A   P   L   A   Q   I   P   S   K   G   M   D   D 901  cgt ctt ttc tac atc tac acg ggg acc acc ccc aag cct gcc att gtc gtg
       R   L   F   Y   I   Y   T   G   T   T   G   L   P   K   A   I   V   V 961  cac agc agg tac tac cgc atg gca gcc ttc ggc cac cac tac cgc atg cag gcg gct
       H   S   R   Y   Y   R   M   A   A   F   G   H   H   Y   R   M   Q   A   A 1021  gac gtg ctc atc tat gac tgc ctg ccc ctg tac cac tcg gcc atc atc ggc gtg ggg
       D   V   L   I   Y   D   C   L   P   L   Y   H   S   A   I   I   G   V   G 1081  cag tgt ctc atc aag tac gtg aca gtc ctc cgc aag aaa ttc tcg gcc agc cgc ttc
       Q   C   L   I   K   Y   V   T   V   L   R   K   K   F   S   A   S   R   F 1141  tgg gac gac tgc atc aag tac aac tgc acg gtg gtt cag tac atc ggg gag atc tgc cgc
       W   D   D   C   I   K   Y   N   C   T   V   V   Q   Y   I   G   E   I   C   R 1201  tac ctg ctg aag cag ccg gtg cgc gag agg cga cac cgc gtg cgc ctg gcg gtg
       Y   L   L   K   Q   P   V   R   E   A   E   R   R   H   R   V   R   L   A   V
```

FIG. 26B

```
1261  ggg aac ggg ctg cgt cct gcc atc tgg gag gag ttc acg gag cgc ttc ggc gta cgc caa
      G   N   G   L   R   P   A   I   W   E   E   F   T   E   R   F   G   V   R   Q 1321  atc ggg gag ttc tac ggc gcc acc gag tgc aac tgc agc att gcc aac atg gac ggc aag
      I   G   E   F   Y   G   A   T   E   C   N   C   S   I   A   N   M   D   G   K 1381  gtc ggc tcc tgt ggt ttc aac agc cgc atc ctg ccc cac gtg tac ccc, atc cgg ctg gtg
      V   G   S   C   G   F   N   S   R   I   L   P   H   V   Y   P   I   R   L   V 1441  aag gtc aat gag gac aca atg gag ctg cgg gat gcc cag ggc ctc tgc atc ccc tgc
      K   V   N   E   D   T   M   E   L   R   D   A   Q   G   L   C   I   P   C 1501  cag gcc ggg gag cct gtc agc gag agc gcc acc agc atc aag aag atc gcc cac gtc ttc agc
      Q   A   G   E   P   V   S   E   S   A   T   S   I   K   K   I   A   H   S   V   F   S 1561  ttc gat ggc tat gtc agc gcc tac ctc tca ggt gac gtg cta gtg atg gat gag ctg ggc tac atg
      F   D   G   Y   V   S   A   Y   L   S   G   D   V   L   V   M   D   E   L   G   Y   M 1621  aag ggc gac agc gcc cgt agc ggg gac acc ttc cgc tgg cga aca gag gag aac gtc tcc acc acc
      K   G   D   S   A   R   S   G   D   T   F   R   W   R   G   E   N   V   S   T   T 1681  tac ttc cgg gac cgt gtc ctg agc cgc ctg ctg gga atg gcg gcc gtc gca gac ccc cac agc ctg
      Y   F   R   D   R   V   L   S   R   L   L   G   M   A   A   V   A   D   P   H   S   L 1741  gag gtg gag ggc gtg gag ctg aag gca ggg gtt cag gag ctg gcc gtc gtc tat ggg gtg
      E   V   E   G   V   E   L   K   A   G   V   Q   E   L   A   V   V   Y   G   V 1801  gct gtt cca gga gtg gag gtg gag aag gca ggg aag gca gag ctg gca gtg ctg gca ccc tat gcc cac agc ctg
      A   V   P   G   V   E   V   E   K   A   G   K   A   E   L   A   V   L   A   P   Y   A   H   S   L 1861  ctg gac ccc aac gcg ata tac cag gag ctg cag aag gtg ctg gca ccc tat gcc cgg ccc
      L   D   P   N   A   I   Y   Q   E   L   Q   K   V   L   A   P   Y   A   R   P
```

FIG. 26C

```
1921 atc ttc ctg cgc ctc ctg ccc cag gtg gac acc aca ggc acc ttc aag atc cag aag acg
      I   F   L   R   L   L   P   Q   V   D   T   T   G   T   F   K   I   Q   K   T
1981 agg ctg cag cga gag ggc ttt gac cca cgc cag acc tca gac cgg ctc ttc ctg gac
      R   L   Q   R   E   G   F   D   P   R   Q   T   S   D   R   L   F   L   D
2041 ctg aag cag ggc cac tac ctg ccc tta aat gag gca gtc tac act cgc atc tgc tcg ggc
      L   K   Q   G   H   Y   L   P   L   N   E   A   V   Y   T   R   I   C   S   G
2101 gcc ttc gcc ctc tga agc tgt tcc tct act ggc cac aaa ctc tgg gcc tgg gag agg
      A   F   A   L   *
2161 cca gct tga gcc aga cag cgc cca tgc cca ggg gtg gcc tag tac aca ccc acc tgg ccg
2221 agc tgt acc tgg cac ggc cca tcc tgg act gag aaa ctg gaa cct cag agg aac ccg tgc
2281 ctc tct gct gcc ttg gtg ccc ctg tgt cct ctg cct gct ctc cct ttt cag cct ctg tct
2341 cct tcc atc cct gtc cct gtc tgg cct gtc ctc ttc cct ctc ttt ctt ctt
2401 ttc ttt ttt aag ata gag tct cac tct gcc cgg gct aga gtg cag tgg cag tgg tgg gat
2461 ctc ggc tca ctg caa cct ctg cct ccc ggg gtt caa gtg atc ctc cca cag cct cct
```

FIG. 26D

```
2521        gag tag ctg gga tta cag gca ccc gcc acc acg tcc agc taa ttt tta tat ttt tag tag
2581        aga cgg ggt ttc acc atg ttg gtc agg ctg gtc ttg aac tcc tga cct cag gtg atc cgc
2641        tgg cct cgg cct ccc aga gtg ctg gga tta tag gcg tga gcc tct ggc ccg gcc ttt cct
2701        ttt tcc tct cct ctg ccg aga gtg gaa cac acg tgt cct ggg agc tgc atc ttg tgt
2761        agg gtc cag ctg ctt ttg ggg act gca gga atc atc tcc cct ggg ccc tgg act cgg act
2821        ggg gcc tcc cca cct ccc tct cgg ctg tgc ctt acg gag ccc caa tcc agg cct cct gtg
2881        gct gtt ggg ttc cag atg ctg cag ctc cat gtg act tcc aag cag gcc ctc cgc cct ccc
2941        tga atg gag gag ccg ggg gtc ccc cag gcc aac atc tcc tgg aaa atc tcc cag gct agg cca
3001        att gcc ttt tgc act tcc ccg ttc tca cat ttc ctg tca ctt ccc agc ccc acc ttc ccc tcc tga
3061        tgc cct gaa agc ttc cgg aat tga ctg tga cca ctt gga tgt cac cac tgt cag ccc ctg
3121        cct tga tgt ccc cat tta gcc atc tcc atg gag ctc ctg gag ggc cct gaa ccc tgc
3181        act gcg tgg ctg ccc agc cag ctg cct cct gtc ctg gga gga ggc ctc ctg ggt gtc ctc
3241        atc tgg tgt gtc tac tgg agg gtc cca cag gag agg cag agg ggt cag ggg agg tct
3301        cct gcc ggg ggt tgg ccg ctc aag cct ctc ggg ttc tag cct gtt cac cgt gtt ggt ggc gat gtc
3361        ggt ggg tgg ccc ctc cga tgt ccc cac tga ctc tga cgt gtt ggt ctg gtg gct cat ctc
3421        cca gac aat ccc acc agg acg gcc cag gcc cca ccc agg ccg cct tcg ctg gct ctg tcc tcc
3481        gaa cat cca cgc cag cct ttc tgg ggc cct gga gtg gtg ggg cca tgg caa gag aca ccg tgg cgt
3541        ctc cag cac cgc cag cac ccc cct gcc cct gga gtg gtg ggg cca tgg caa gag aca ccg tgg cgt
3601        ctc atg tga act ttc ctg ggc act gtg gtt tta ttt cct aat tga ttt aag aaa taa acc
3661        tga aga ccg tct ggt gaa aaa aaa aaa aaa agg gcg gcc gc
```

FIG. 26E hsFATP4

```
  1  cga ccc acg cgt ccg ggc ggg cgg ggc ggc ggg gct ggc ggg gcg gcc ggg
 61  cca tgc agg gcg cag agc cgg cta aac cct gct gag acc cgg ctc cgt agg ggc
121  ggc taa tgc ccc tca cgc tgt cta cgc tgc tgc aac cgg gcc gca tct gga cgg ggc gcc
181  gcg cgg cgg agc cga cgc cgg gcc aca atg ctg gga gcc ctt gga gcc tct ctg gtg ggg gtg ctg
                                     M   L   G   A   S   L   V   G   V   L
241  ctg ttc tcc aag ctg gtg ctg aaa ctg ccc tgg acc cag gtg gga ttc tcc ctg ttg ttc
      L   F   S   K   L   V   L   K   L   P   W   T   Q   V   G   F   S   L   L   F
301  ctc tac ttg gga tct ggc ggc gtc atc cgg ttc atc gtc ttc atc aag acc atc agg cgc
      L   Y   L   G   S   G   G   V   I   R   F   I   V   F   I   K   T   I   R   R
361  gat atc ttt ggc gga ctg gtc ctc att ttg ttt gcc tct acc gtt cgg cgc cac ccc gac aag acg
      D   I   F   G   G   L   V   L   I   L   F   A   S   T   V   R   R   H   P   D   K   T
421  gag cgg cgg aca gtg gag ggc aca gat acc cac tgg acc ttc cgc cag ctg gat gag tac tca
      E   R   R   T   V   E   G   T   D   T   H   W   T   F   R   Q   L   D   E   Y   S
481  gcc ctg atc ttc gag aac ttc ctg cag gcc cgg ggc ctg gcc tcg gcc gat gtg gct gcc atc
      A   L   I   F   E   N   F   L   Q   A   R   G   L   A   S   G   D   V   A   A   I
541  agc agt gta gcc aac cgc aat gag ttc gtg ggc cta tgg ctg ggc atg gcc aag ctc ggt gtg
      S   S   V   A   N   R   N   E   F   V   G   L   W   L   G   M   A   K   L   G   V
601  ttc atg gag aac cgc aat gag ttc gtg ggc cta tgg ctg ggc atg gcc aag ctc ggt gtg
      F   M   E   N   R   N   E   F   V   G   L   W   L   G   M   A   K   L   G   V
```

FIG. 27A

```
 661  gag gca gcc ctc atc aac acc aac ctg cgg cgg gat gct ctg ctc cac tgc ctc acc acc
      E   A   A   L   I   N   T   N   L   R   R   D   A   L   L   H   C   L   T   T 721  tcg cgc gca cgg gcc ctt gtc ttt ggc agc gaa atg gcc tca gcc atc tgt gag gtc cat
      S   R   A   R   A   L   V   F   G   S   E   M   A   S   A   I   C   E   V   H 781  gcc agc ctg gac ccc tcg ctc agc ctg ttc tgc tct ggc tcc tgg gag ccc ggt gcg gtg
      A   S   L   D   P   S   L   S   L   F   C   S   G   S   W   E   P   G   A   V 841  cct cca agc aca gaa cac ctg aaa cct ctg ctg aaa gat gct ccc aag cac ctt ccc agt
      P   P   S   T   E   H   L   K   P   L   L   K   D   A   P   K   H   L   P   S 901  tgc cct gac aag ggc ttc aca gat aaa ctg ttc tac atc tac aca tcc ggc acc aca ggg
      C   P   D   K   G   F   T   D   K   L   F   Y   I   Y   T   S   G   T   T   G 961  ctg ccc aag gcc gcc atc gtg gta cac ccc aac gac gtc tat gac tgc ctg ccc ctg tac
      L   P   K   A   A   I   V   V   H   S   R   Y   Y   D   C   L   P   L   Y 1021  tat gga ttc cgc atg cgg ccc aac atc gtc gat ggc cag tgc ctg ctg cat ggc atg acg gtg gtg att cgg
      Y   G   F   R   M   R   P   N   D   I   V   D   C   L   L   H   G   M   T   V   I   R 1081  gca gga aac atc gtg gga ttc tca gcc tcc cgg ttc tgg gac gat tgt atc aag tac aac tgc acg att gtg
      A   G   N   I   V   G   F   S   A   S   R   F   W   D   D   C   I   K   Y   N   C   T   I   V 1141  aag aag ttc tca gcc tca gcc tgg gac tgc aag ggc cag gag gca gaa aac
      K   K   F   S   A                                                  E   A   E   N 1201  cag tac att ggt gaa ctg tgc cgc tac ctc ctg aac cag cca ccg cgg gag gca gaa aac
      Q   Y   I   G   E   L   C   R   Y   L   L   N   Q   P   P   R   E   A   E   N
```

FIG. 27B

```
1261  cag cac cag gtt cgc atg gca cta ggc aat ggc ctc cgg cag tcc atc tgg acc aac ttt
       Q   H   Q   V   R   M   A   L   G   N   G   L   R   Q   S   I   W   T   N   F 1321  tcc agc cgc ttc cac ata ccc cag gtg gct gag ttc tac ggg gcc aca gag tgc aac tgt
       S   S   R   F   H   I   P   Q   V   A   E   F   Y   G   A   T   E   C   N   C 1381  agc ctg ggc aac ttc gac agc cag agc cag gtg gtg ggg gcc tgt ggt ttc aat agc cgc atc tcc
       S   L   G   N   F   D   S   Q   V   G   A   C   G   F   N   S   R   I   L   S 1441  ttc gtg tac ccc atc cgg ttg gta cgt gtc aac gag gac atg gag ctg atc cgg ggg
       F   V   Y   P   I   R   L   V   R   V   N   E   D   M   E   L   I   R   G 1501  ccc gac ggc gtc att ccc tgc cag gtt gag cca ccg ggc cag ctg gtg ggc cgc atc
       P   D   G   V   I   P   C   Q   V   E   P   P   G   Q   L   V   G   R   I 1561  atc cag aaa gac ccc ctg cgc cgc ttc gat ggc tac ctc aac cag ggc gcc aac aag
       I   Q   K   D   P   L   R   R   F   D   G   Y   L   N   Q   G   A   N   K 1621  aag att gcc aag gat gtc ttc aag aag ggg gac cag gcc tac ctt act ggt gat gtg ctg
       K   I   A   K   D   V   F   K   K   G   D   Q   A   Y   L   T   G   D   V   L 1681  gtg atg gac gag ctg ggc tac acc ctg ttc cga gac cgc aca ctc agc cgc ctg gac ttc cgc tgg
       V   M   D   E   L   G   Y   T   L   F   R   D   R   T   L   S   R   L   D   F   R   W 1741  aaa ggt gag aac gtg tcc acc acc gag gtg gag gtg cca gag gtg gaa ggc acg gag ctg gac atg
       K   G   E   N   V   S   T   T   E   V   E   V   P   E   V   E   G   T   E   L   D   M 1801  gct gac gtg gcc gtg tat ggt gtc gtg gag gtc cca gga acc gag ggc cgg gcc gga atg gct
       A   D   V   A   V   Y   G   V   V   E   V   P   G   T   E   G   R   A   G   M   A 1861  gct gtg gcc agc ccc act ggc aac tgt gat ctg gag cgc ttt gct cag gtc ttg gag aag
       A   V   A   S   P   T   G   N   C   D   L   E   R   F   A   Q   V   L   E   K
```

FIG. 27C

```
1921 gaa ctg ccc ctg tat gcg cgc ccc atc ttc ctg cgc ctc ctg cct gag ctg cac aaa aca
      E   L   P   L   Y   A   R   P   I   F   L   R   L   L   P   E   L   H   K   T
1981 gga acc tac aag ttc cag aag aca gag cta cgg aag gag ggc ttt gac ccg gct att gtg
      G   T   Y   K   F   Q   K   T   E   L   R   K   E   G   F   D   P   A   I   V
2041 aaa gac ccg ctg ttc tat cta gat gcc cag aag ggc cgc tac gtc ccg ctg gac caa gag
      K   D   P   L   F   Y   L   D   A   Q   K   G   R   Y   V   P   L   D   Q   E
2101 gcc tac agc cgc atc cag gca ggc gag gag aag ctg tga ttc ccc cca tcc ctc tga ggg
      A   Y   S   R   I   Q   A   G   E   E   K   L   *
2161 ccg gcg gat gct gga tcc gga gcc gcc cca ggt tcc gcc cca gag cgg tcc tgg aca agg cca
2221 gac caa agc agg cag ggc ctg gca cct cca gct gcc cct cca tcc aaa act
2281 gcc aag tga ctc att gcc ttc cca acc ctt cca gag gct ttc tgt gaa agt ctc atg tcc
2341 aag ttc cgt ctt ctg ggc tgg gca ggc cct ctg gtt ccc agg ctg aga ctg acg ggt ttt
2401 ctc agg atg agg tct tgg gtg agg gta aga gga caa ggg gtc acc gag ccc ttc cca
2461 gag agc agg gag ctt ata aat gga acc aga gca gaa gtc ccc aga ctc agg aag tca aca
2521 gag tgg gca ggg aca gtg gta gca ctc cac ccc atc tgg tgg cca aag aga gga gga cct gac atc
2581 ctg ccc aag ttc act ggg ctc cac ccc cag ctc cag cag gag gtc agg acc acg ccc gcc tct
2641 tgt agg tgg ccc ctg atg ccc cat cta cag gag gtc cct gat tat ccc tca ggc agg gcc tct
2701 ccc cac tcc ccc atc ctc cct ggg tgg ctg cct ggc agt gcc ttg gcc tgg cta tga ggg ccg
2761 cag tcc ttg tgg gtc tgt gtc acc tcc atc gtc ttg gcc tgg cta tga ggg ccg
2821 gaa tgg gag agg ggg ctc agg ggc caa taa act ctg cct tga gtc cct ctc cta aaa aaa aaa
2881 aaa aaa aaa aaa aaa aaa aaa aaa ggg cgg ccg c
```

FIG. 27D

Protein Sequence 646 a.a. MRAPGAGAASVV....VYTRICSGAFAL
646 Amino Acids  MW: 71062 Dalton

|   |   | n | n% | MW | MW% |
|---|---|---|---|---|---|
| A ala | Alanine | 64 | 9.9 | 4546 | 6.4 |
| C cys | cysteine | 15 | 2.3 | 1545 | 2.2 |
| D asp | aspartic acid | 30 | 4.6 | 3450 | 4.9 |
| E glu | glutamic acid | 31 | 4.8 | 4000 | 5.6 |
| F phe | phenylalanine | 29 | 4.5 | 4264 | 6.0 |
| G gly | glycine | 63 | 9.8 | 3592 | 5.1 |
| H his | histidine | 13 | 2.0 | 1781 | 2.5 |
| I ile | isoleucine | 29 | 4.5 | 3279 | 4.6 |
| K lys | lysine | 22 | 3.4 | 2818 | 4.0 |
| L leu | leucine | 77 | 11.9 | 8707 | 12.3 |
| M met | methionine | 11 | 1.7 | 1441 | 2.0 |
| N asn | asparagine | 15 | 2.3 | 1710 | 2.4 |
| P pro | proline | 29 | 4.5 | 2814 | 4.0 |
| Q gln | glutamine | 25 | 3.9 | 3201 | 4.5 |
| R arg | arginine | 49 | 7.6 | 7648 | 10.8 |
| S ser | serine | 33 | 5.1 | 2872 | 4.0 |
| T thr | threonine | 27 | 4.2 | 2728 | 3.8 |
| V val | valine | 51 | 7.9 | 5052 | 7.1 |
| W trp | tryptophan | 9 | 1.4 | 1674 | 2.4 |
| X ukw | unknown | -- | -- |   |   |
| Y tyr | tyrosine | 24 | 3.7 | 3913 | 5.5 |
| Z --- STOP |   |   |   |   |   |

FIG. 28B hs FATP4. pep-> A.A. Usage

Protein Sequence 643 a.a. MLLGASLVGVLL....AYSRIQAGEEKL
643 Amino Acids MW: 72018 Dalton

|   |   | n | n% | MW | MW% |
|---|---|---|---|---|---|
| A ala | alanine | 46 | 7.2 | 3267 | 4.5 |
| C cys | cysteine | 16 | 2.5 | 1648 | 2.3 |
| D asp | aspartic acid | 33 | 5.1 | 3795 | 5.3 |
| E glu | glutamic acid | 33 | 5.1 | 4258 | 5.9 |
| F phe | phenylalanine | 34 | 5.3 | 5000 | 6.9 |
| G gly | glycine | 54 | 8.4 | 3079 | 4.3 |
| H his | histidine | 12 | 1.9 | 1644 | 2.3 |
| I ile | isoleucine | 30 | 4.7 | 3392 | 4.7 |
| K lys | lysine | 31 | 4.8 | 3970 | 5.5 |
| L leu | leucine | 76 | 11.8 | 8594 | 11.9 |
| M met | methionine | 12 | 1.9 | 1572 | 2.2 |
| N asn | asparagine | 21 | 3.3 | 2394 | 3.3 |
| P pro | proline | 31 | 4.8 | 3008 | 4.2 |
| Q gln | glutamine | 23 | 3.6 | 2945 | 4.1 |
| R arg | arginine | 45 | 7.0 | 7024 | 9.8 |
| S ser | serine | 35 | 5.4 | 3046 | 4.2 |
| T thr | threonine | 32 | 5.0 | 3233 | 4.5 |
| V val | valine | 46 | 7.2 | 4557 | 6.3 |
| W trp | tryptophan | 8 | 1.2 | 1488 | 2.1 |
| X ukw | unknown | -- | -- |   |   |
| Y tyr | tyrosine | 25 | 3.9 | 4076 | 5.7 |
| Z --- STOP |   |   |   |   |   |

FIG. 29B

```
  1  A T G C G G G C T C C G G G T G C G G G  hFATP1con.seq ORF
  1  A T G C G G G C T C C T G G A G C A G G  mFATP1.seq ORF (from genomic)

21  C G C G G C C T C G G T G G T C T C G C  hFATP1con.seq ORF
 21  A A C A G C C T C T G T G G C C T C A C  mFATP1.seq ORF (from genomic)

41  T G G C G C T G T T G T G G C T G C T G  hFATP1con.seq ORF
 41  T G G C G C T G C T T T G G T T T C T G  mFATP1.seq ORF (from genomic)

61  G G G C T G C C G T G G A C C T G G A G  hFATP1con.seq ORF
 61  G G A C T T C C G T G G A C C T G G A G  mFATP1.seq ORF (from genomic)

81  C G C G G C A G C G G C G C T C G G C G  hFATP1con.seq ORF
 81  C G C G G C G G C G G C G T C T G T G   mFATP1.seq ORF (from genomic)

101  T G T A C G T G G G C A G C G G C G G C  hFATP1con.seq ORF
101  T G T A C G T G G G T G G C G G C G G C  mFATP1.seq ORF (from genomic)

121  T G G C G C T T C C T G C G C A T C G T  hFATP1con.seq ORF
121  T G G C G C T T T C T G C G T A T C G T  mFATP1.seq ORF (from genomic)

141  C T G C A A G A C C G C G A G G C G A G  hFATP1con.seq ORF
141  C T G C A A G A C G G C G A G G C G A G  mFATP1.seq ORF (from genomic)

161  A C C T C T T C G G T C T C T C T G T G  hFATP1con.seq ORF
161  A C C T C T T T G G C C T C T C T G T T  mFATP1.seq ORF (from genomic)

181  C T G A T C C G C G T G C G C C T G G A  hFATP1con.seq ORF
181  C T G A T T C G T G T T C G G C T A G A  mFATP1.seq ORF (from genomic)

201  G C T G C G G C G G C A C C A G C G T G  hFATP1con.seq ORF
201  G C T G C G A C G A C A C C G G C G A G  mFATP1.seq ORF (from genomic)

221  C C G G C C A C A C C A T C C C G C G C  hFATP1con.seq ORF
221  C A G G A G A C A C G A T C C C G T G C  mFATP1.seq ORF (from genomic)

241  A T C T T T C A G G C G G T A G T G C A  hFATP1con.seq ORF
241  A T C T T C C A G G C T G T G G C C C G  mFATP1.seq ORF (from genomic)

261  G C G A C A G C C C G A G C G C C T G G  hFATP1con.seq ORF
261  G C G A C A A C C A G A G C G C C T G G  mFATP1.seq ORF (from genomic)

281  C G C T G G T G G A T G C C G G G A C C  hFATP1con.seq ORF
281  C A C T G G T G G A C G C C A G T A G T  mFATP1.seq ORF (from genomic)

301  G G C G A G T G C T G G A C C T T T G C  hFATP1con.seq ORF
301  G G T A T A T G C T G G A C C T T C G C  mFATP1.seq ORF (from genomic)

321  G C A G C T G G A C G C C T A C T C C A  hFATP1con.seq ORF
321  A C A G C T G G A C A C C T A C T C C A  mFATP1.seq ORF (from genomic)

341  A T G C G G T A G C C A A C C T C T T C  hFATP1con.seq ORF
341  A T G C T G T A G C C A A C C T G T T C  mFATP1.seq ORF (from genomic)
```

FIG. 30A

```
361  C G C C A G C T G G G C T T C G C G C C   hFATP1con.seq ORF
361  C G C C A G C T G G G C T T T G C A C C   mFATP1.seq ORF (from genomic)

381  G G G C G A C G T G G T G G C C A T C T   hFATP1con.seq ORF
381  A G G C G A T G T G G T G G C T G T G T   mFATP1.seq ORF (from genomic)

401  T C C T G G A G G G C C G G C C G G A G   hFATP1con.seq ORF
401  T C C T G G A G G G C C G G C C G G A G   mFATP1.seq ORF (from genomic)

421  T T C G T G G G G C T G T G G C T G G G   hFATP1con.seq ORF
421  T T C G T G G G A C T G T G G C T G G G   mFATP1.seq ORF (from genomic)

441  C C T G G C C A A G G C G G G C A T G G   hFATP1con.seq ORF
441  C C T G G C C A A G G C C G G T G T G G   mFATP1.seq ORF (from genomic)

461  A G G C C G C G C T G C T C A A C G T G   hFATP1con.seq ORF
461  T G G C T G C T C T T C T C A A T G T C   mFATP1.seq ORF (from genomic)

481  A A C C T G C G G C G C G A G C C C T    hFATP1con.seq ORF
481  A A C C T G A G G C G G G A G C C C T    mFATP1.seq ORF (from genomic)

501  G G C C T T C T G C C T G G G C A C C T   hFATP1con.seq ORF
501  G G C C T T C T G C C T G G G C A C A T   mFATP1.seq ORF (from genomic)

521  C G G C G C T A A G G C C C T G A T C    hFATP1con.seq ORF
521  C A G C T G C C A A G G C C C T C A T T   mFATP1.seq ORF (from genomic)

541  T T T G G A G G A G A A A T G G T G G C   hFATP1con.seq ORF
541  T A T G G C G G G G A G A T G G C A G C   mFATP1.seq ORF (from genomic)

561  G G C G G T G G C C G A A G T G A G C G   hFATP1con.seq ORF
561  G G C G G T G G C G G A G G T G A G C G   mFATP1.seq ORF (from genomic)

581  G C A T C T G G G G A A A A G T T T G    hFATP1con.seq ORF
581  A G C A G C T G G G G A A G A G C C T C   mFATP1.seq ORF (from genomic)

601  A T C A A G T T C T G C T C T G G A G A   hFATP1con.seq ORF
601  C T C A A G T T C T G C T C T G G A G A   mFATP1.seq ORF (from genomic)

621  C T T G G G G C C C G A G G G C A T C T   hFATP1con.seq ORF
621  T C T G G G G C C T G A G A G C A T C C   mFATP1.seq ORF (from genomic)

641  T G C C G G A C A C C C A C C T C C T G   hFATP1con.seq ORF
641  T G C C T G A C A C G C A G C T C C T G   mFATP1.seq ORF (from genomic)

661  G A C C C G C T G C T G A A G G A G G C   hFATP1con.seq ORF
661  G A C C C A T G C T T G C T G A G G C    mFATP1.seq ORF (from genomic)

681  C T C T A C T G C C C C T T G G C A C    hFATP1con.seq ORF
681  G C C C A C C A C A C C C C T G G C A C   mFATP1.seq ORF (from genomic)

701  A G A T C C C C A G C A A G G G C A T G   hFATP1con.seq ORF
701  A A G C C C C A G C A A G G G C A T G    mFATP1.seq ORF (from genomic)
```

FIG. 30B

```
721  G A C G A T C G T C T T T C T A C A T    hFATP1con.seq ORF
721  G A T G A T C G G C T G T T T A C A T    mFATP1.seq ORF (from genomic 741  C T A C A C G T C G G G A C C A C C G    hFATP1con.seq ORF
741  C T A T A C T T C T G G G A C C A C C G  mFATP1.seq ORF (from genomic 761  G G C T G C C C A A G G C T G C C A T T  hFATP1con.seq ORF
761  G G C T T C C T A A G G C T G C C A T T  mFATP1.seq ORF (from genomic 781  G T C G T G C A C A G C A G G T A C T A  hFATP1con.seq ORF
781  G T G G T G C A C A G C A G G T A C T A  mFATP1.seq ORF (from genomic 801  C C G C A T G G C A G C C T T C G G C C  hFATP1con.seq ORF
801  C C G C A T T G C T G C C T T T G G C C  mFATP1.seq ORF (from genomic 821  A C C A C G C C T A C C G C A T G C A G  hFATP1con.seq ORF
821  A C C A T T C C T A C A G C A T G C G T  mFATP1.seq ORF (from genomic 841  G C G G C T G A C G T G C T C T A T G A  hFATP1con.seq ORF
841  G C C G C C G A T G T G C T C T A T G A  mFATP1.seq ORF (from genomic 861  C T G C C T G C C C C T G T A C C A C T  hFATP1con.seq ORF
861  C T G C C T G C C A C T C T A C C A C T  mFATP1.seq ORF (from genomic 881  C G G C A G G A A A C A T C A T C G G C  hFATP1con.seq ORF
881  C T G C A G G G A A C A T C A T G G G T  mFATP1.seq ORF (from genomic 901  G T G G G C A G T G T C T C A T C T A    hFATP1con.seq ORF
901  G T G G G C A G T G C G T C A T C T A    mFATP1.seq ORF (from genomic 921  T G G G C T G A C A G T C G T C C T C C  hFATP1con.seq ORF
921  C G G G T T G A C G G T G G T A C T G C  mFATP1.seq ORF (from genomic 941  G C A A G A A A T T C T C G G C C A G C  hFATP1con.seq ORF
941  G C A A G A A G T T C T C C G C C A G C  mFATP1.seq ORF (from genomic 961  C G C T T C T G G G A C G A C T G C A T  hFATP1con.seq ORF
961  C G C T T C T G G G A T G A C T G T G T  mFATP1.seq ORF (from genomic 981  C A A G T A C A A C T G C A C G G T G G  hFATP1con.seq ORF
981  C A A G T A C A A T T G C A C G G T A G  mFATP1.seq ORF (from genomic 1001 T T C A G T A C A T C G G G G A G A T C  hFATP1con.seq ORF
1001 T G C A G T A C A T A G G T G A A A T C  mFATP1.seq ORF (from genomic 1021 T G C C G C T A C C T G C T G A A G C A  hFATP1con.seq ORF
1021 T G C C G C T A C C T G C T G A G G C A  mFATP1.seq ORF (from genomic 1041 G C C G G T G C G C G A G G C G G A G A  hFATP1con.seq ORF
1041 G C C G G T T C G C G A C G T G G A G C  mFATP1.seq ORF (from genomic 1061 G G C G A C A C C G C G T G C G C C T G  hFATP1con.seq ORF
1061 A G C G A C A C C G C G T G C G C C T G  mFATP1.seq ORF (from genomic
```

FIG. 30C

```
1081  G C G G T G G G G A A C G G G C T G C G    hFATP1con.seq ORF
1081  G C C G T G G G T A A T G G G C T G C G    mFATP1.seq ORF (from genomic)

1101  T C C T G C C A T C T G G G A G G A G T    hFATP1con.seq ORF
1101  G C C A G C C A T C T G G G A G G A G T    mFATP1.seq ORF (from genomic)

1121  T C A C G G A G C G C T T C G G C G T A    hFATP1con.seq ORF
1121  T C A C G C A G C G C T T C G G T G T G    mFATP1.seq ORF (from genomic)

1141  C G C C A A T C G G G G A G T T C T A    hFATP1con.seq ORF
1141  C C A C A G A T C G G C G A G T T C T A    mFATP1.seq ORF (from genomic)

1161  C G G C G C C A C C G A G T G C A A C T    hFATP1con.seq ORF
1161  C G G C G C T A C C G A G T G C A A C T    mFATP1.seq ORF (from genomic)

1181  G C A G C A T T G C C A A C A T G G A C    hFATP1con.seq ORF
1181  G C A G C A T T G C C A A C A T G G A C    mFATP1.seq ORF (from genomic)

1201  G G C A A G G T C G G C T C C T G T G G    hFATP1con.seq ORF
1201  G G C A A G G T C G G C T C C T G C G G    mFATP1.seq ORF (from genomic)

1221  T T T C A A C A G C C G C A T C C T G C    hFATP1con.seq ORF
1221  C T T C A A C A G C C G T A T C C T C A    mFATP1.seq ORF (from genomic)

1241  C C C A C G T G T A C C C C A T C C G G    hFATP1con.seq ORF
1241  C G C A T G T G T A C C C C A T C C G T    mFATP1.seq ORF (from genomic)

1261  C T G G T G A A G G T C A A T G A G G A    hFATP1con.seq ORF
1261  C T G G T C A A G G T C A A T G A G G A    mFATP1.seq ORF (from genomic)

1281  C A C A A T G G A G C T G C T G C G G G    hFATP1con.seq ORF
1281  C A C G A T G G A G C C A C T G C G G G    mFATP1.seq ORF (from genomic)

1301  A T G C C C A G G G C C T C T G C A T C    hFATP1con.seq ORF
1301  A C T C C G A G G G C C T C T G C A T C    mFATP1.seq ORF (from genomic)

1321  C C C T G C C A G G C C G G G G A G C C    hFATP1con.seq ORF
1321  C C G T G C C A G C C C G G G G A A C C    mFATP1.seq ORF (from genomic)

1341  T G G C C T C C T T G T G G G T C A G A    hFATP1con.seq ORF
1341  C G G C C T T C T C G T G G G C C A G A    mFATP1.seq ORF (from genomic)

1361  T C A A C C A A C A G G A C C C G C T G    hFATP1con.seq ORF
1361  T C A A C C A G C A G G A C C C T C T G    mFATP1.seq ORF (from genomic)

1381  C G C G C T T C G A T G G C T A T G T    hFATP1con.seq ORF
1381  C G G C G T T T C G A T G G T T A T G T    mFATP1.seq ORF (from genomic)

1401  C A G C G A G A G C G C C A C C A G C A    hFATP1con.seq ORF
1401  T A G T G A C A G T G C C A C C A A C A    mFATP1.seq ORF (from genomic)

1421  A G A A G A T C G C C C A C A G C G T C    hFATP1con.seq ORF
1421  A G A A G A T T G C C C A C A G C G T T    mFATP1.seq ORF (from genomic)
```

FIG. 30D

```
1441  T T C A G C A A G G G C G A C A G C G C   hFATP1con.seq ORF
1441  T T C C G A A A G G G C G A T A G C G C   mFATP1.seq ORF (from genomic)

1461  C T A C C T C T C A G G T G A C G T G C   hFATP1con.seq ORF
1461  C T A C C T C T C A G G T G A C G T G C   mFATP1.seq ORF (from genomic)

1481  T A G T G A T G G A T G A G C T G G G C   hFATP1con.seq ORF
1481  T A G T G A T G G A C G A G C T G G G C   mFATP1.seq ORF (from genomic)

1501  T A C A T G T A C T T C C G G G A C C G   hFATP1con.seq ORF
1501  T A C A T G T A T T T C C G T G A C C G   mFATP1.seq ORF (from genomic)

1521  T A G C G G G G A C A C C T T C C G C T   hFATP1con.seq ORF
1521  C A G C G G G G A C A C C T T C C G C T   mFATP1.seq ORF (from genomic)

1541  G G C G A G G G G A G A A C G T C T C C   hFATP1con.seq ORF
1541  G G C G C G G G G A G A A C G T G T C C   mFATP1.seq ORF (from genomic)

1561  A C C A C C G A G G T G G A G G C G T    hFATP1con.seq ORF
1561  A C C A C G G A G G T G G A A G C C G T   mFATP1.seq ORF (from genomic)

1581  G C T G A G C C G C C T G C T G G G C C   hFATP1con.seq ORF
1581  G C T G A G C C G C C T A C T G G C C   mFATP1.seq ORF (from genomic)

1601  A G A C A G A C G T G G C C G T C T A T   hFATP1con.seq ORF
1601  A G A C G G A C G T G G C T G T G T A T   mFATP1.seq ORF (from genomic)

1621  G G G G T G G C T G T T C C A G G A G T   hFATP1con.seq ORF
1621  G G G G T G G C T G T G C C A G G A G T   mFATP1.seq ORF (from genomic)

1641  G G A G G G T A A G C A G G G A T G G   hFATP1con.seq ORF
1641  G G A G G G G A A A G C T G G C A T G G   mFATP1.seq ORF (from genomic)

1661  C G G C C G T C G C A G A C C C C C A C   hFATP1con.seq ORF
1661  C A G C C A T C G C A G A T C C C C A C   mFATP1.seq ORF (from genomic)

1681  A G C C T G C T G G A C C C C A A C G C   hFATP1con.seq ORF
1681  A G C C A G T T G G A C C C T A A C T C   mFATP1.seq ORF (from genomic)

1701  G A T A T A C C A G G A G C T G C A G A   hFATP1con.seq ORF
1701  A A T G T A C C A G G A A T T A C A G A   mFATP1.seq ORF (from genomic)

1721  A G G T G C T G G C A C C C T A T G C C   hFATP1con.seq ORF
1721  A G G T T C T T G C A T C C T A T G C T   mFATP1.seq ORF (from genomic)

1741  C G G C C C A T C T T C C T G C G C C T   hFATP1con.seq ORF
1741  C G G C C C A T C T T C C T G C G T C T   mFATP1.seq ORF (from genomic)

1761  C C T G C C C C A G G T G G A C A C C A   hFATP1con.seq ORF
1761  T C T G C C C C A G G T G G A T A C C A   mFATP1.seq ORF (from genomic)

1781  C A G G C A C C T T C A A G A T C C A G   hFATP1con.seq ORF
1781  C A G G C A C C T T C A A G A T C C A G   mFATP1.seq ORF (from genomic)
```

FIG. 30E

```
1801  A A G A C  G A G G C T G C A G C G A G A   hFATP1con.seq ORF
1801  A A G A C  C C G G C T G C A G C G T G A   mFATP1.seq ORF (from genomic)

1821  G G G C T T T G A C C C A C G C C A G A   hFATP1con.seq ORF
1821  A G G C T T T G A C C C C C G T C A G A   mFATP1.seq ORF (from genomic)

1841  C C T C A G A C C G G C T C T T C T T C   hFATP1con.seq ORF
1841  C C T C A G A C A G G C T C T T C T T T   mFATP1.seq ORF (from genomic)

1861  C T G G A C C T G A A G C A G G G C C A   hFATP1con.seq ORF
1861  C T A G A C C T G A A G C A G G G A C G   mFATP1.seq ORF (from genomic)

1881  C T A C C T G C C C T T A A A T G A G G   hFATP1con.seq ORF
1881  C T A T G T A C C C C T G G A T G A G A   mFATP1.seq ORF (from genomic)

1901  C A G T C T A C A C T C G C A T C T G C   hFATP1con.seq ORF
1901  G A G T C C A T G C C C G C A T T T G T   mFATP1.seq ORF (from genomic)

1921  T C G G C G C C T T C G C C C T C T G    hFATP1con.seq ORF
1921  G C A G G C G A C T T C T C A C T C      mFATP1.seq ORF (from genomic)

1941  A                                        hFATP1con.seq ORF
1938                                           mFATP1.seq ORF (from genomic)
```

Decoration 'Decoration #2': Box residues that match the consensus named 'Consensus #1' exactly.

| | | | | | | |
|---|---|---|---|---|---|---|
| 211 | TCT | ACCGTT | CG | GCGCCACCC | C | GACAAGACG | hsFATP4 |
| 211 | TCA | ATGGTA | CG | AGCGCCACCC | G | GACAAGACA | mmFATP4 |
| 241 | GCCCTGAT | C | TTCGAGGGCACAGA | T | ACCAC | hsFATP4 |
| 241 | GCCCTGAT | T | TTCGAGGGCACAGA | C | ACTCAC | mmFATP4 |
| 271 | TGGACCTTCCGCCAGCTGGATGAGTACTC | A | hsFATP4 |
| 271 | TGGACCTTCCGCCAGCTGGATGAGTACTC | C | mmFATP4 |
| 301 | A | GCAGTGT | AGCCAACTTCCTGCAGGCCCGG | hsFATP4 |
| 301 | A | GTAGTGT | GGCCAACTTCCTGCAGGCCCGG | mmFATP4 |
| 331 | GCCCTGGCC | CGG | GATGTG | GCCA | TC | hsFATP4 |
| 331 | GCCCTGGCC | CTC | AGGCAATGTA | GTTGCC | TC | mmFATP4 |
| 361 | TT | CATGGAGA | AACCCGCCAATGAGTT | CGTGGGC | hsFATP4 |
| 361 | TT | TATGGAA | AAACCCGCCAATGAGTT | TGTGGGT | mmFATP4 |
| 391 | C | TATGGCTGGGCATGGCCAAGCT | C | GGTGTG | hsFATP4 |
| 391 | C | TGGGCTAGGCATGGCCAAGCT | G | GGCGTG | mmFATP4 |

```
631  CTG AAAGATGCT CCAAGCACCT TCCCAGT  hsFATP4
631  CTG GAAGATGCC CGAAGCACCT GCCCAGT  mmFATP4

661  TGCCCT GACAAGGG CTTCACAGATAAA CTG  hsFATP4
661  CACCCA GACAAGGG TTTACAGATAAG CTC  mmFATP4

691  TTCTACATCTACACA TCCGGCACCACA GGG  hsFATP4
691  TTCTACATCTACACA TCGGGCACCACG GGG  mmFATP4

721  CTG CCAAG GC CGCCATT CGTGGTGCACAGC  hsFATP4
721  CTA CCCAA AG CTGCCATT GTGGTGCACAGC  mmFATP4

751  AGGTATTAC CGCATGGCTG CCCTGGTGTAC  hsFATP4
751  AGGTATTAT CGTATGGCTT CCCTGGTGTAC  mmFATP4

781  TATGGATTCCGCATGGCGCC CAAC GACATC  hsFATP4
781  TATGGATTCCGCATGGCGCC CTGAT GACATT  mmFATP4

811  GTCTATGACTGCCCTCCCTCTACCACTCA  hsFATP4
811  GTCTATGACTGCCCTCCCTCTACCACTCA  mmFATP4
```

FIG. 31D

```
841  -GCAGGAAACATCGTGGGAATCGGCCAGTG  hsFATP4
841  AGCAGGAAACATCGTGGGGATTGGC-AGTG  mmFATP4

870  CCTGCTGCATGGCATGACGGTGGTGATTCG  hsFATP4
870  CTTACTCCACGGCATGACTGTGGTGATCCG  mmFATP4

900  GAAGAAGTTCTCAGCCCTCCCGGTTCTGGGA  hsFATP4
900  GAAGAAGTTCTCAGCCCTCCCGGTTCTGGGA  mmFATP4

930  CGATTGTATCAAGTACAACTGCACGATTGT  hsFATP4
930  TGATTGTATCAAGTACAACTGCACAGTGGT  mmFATP4

960  GCAGTACATTGGTGAACTGTGCCCGCTACCT  hsFATP4
960  ACAGTACATTGGCGAGCTCTGCCGCTACCT  mmFATP4

990  CCTGAACCAGCCACCGCGGAGGCAGAAAA   hsFATP4
990  CCTGAACCAGCCACCCCGTGAGGCTGAGTC  mmFATP4

1020 CCAGCACCAGGTTCGCATGGCACTAGGCAA  hsFATP4
1020 TCGGCACAAGGTGCGCATGGCACTGGGCAA  mmFATP4
```

FIG. 31E

```
1050  TGG CTCCGGCAGTCCATCTGGACC A ACTT  hsFATP4
1050  CGG TCTCCGGCAGTCCATCTGGACC G ACTT  mmFATP4

1080  T TCCAGCCCG CTTCCACATA CCCCAGGTGGC  hsFATP4
1080  C TCCAGCCCG TTTCCACATC CCCCAGGTGGC  mmFATP4

1110  TGAGTTCTA CGGGGCCACA AGA GTGCAACTG  hsFATP4
1110  TGAGTTCTA TGGGGCCACT GAA TGCAACTG  mmFATP4

1140  TAGCCTGGG CAACTT C GACAGCCA GGTGGG  hsFATP4
1140  TAGCCTGGG CAACTT T GACAGCC GGGTGGG  mmFATP4

1170  GGCCTGTGG TTTCAATAGCCCGCATCCTGTC  hsFATP4
1170  GGCCTGTGG CTTCAATAGCCCGCATCCTGTC  mmFATP4

1200  CTT CGTGTACCC C ATCCGG TTGGTACGTGT  hsFATP4
1200  CTT TGTGTACCC T ATCCGT TTGGTACGTGT  mmFATP4

1230  CAAC GAGGA CACCATGGAGCTGATCCGGGG  hsFATP4
1230  CAAT GAGGA TACCATGGAACTGATCCGGGG  mmFATP4
```

FIG. 31F

```
1260  g C C C G A  C G G  C G T C T G C A T T C C C T G C  C A G C C   hsFATP4
1260  a C C C G A  T G G  a G T C T G C A T T C C C T G T  T C A A C C  mmFATP4

1290  A G G T G  A G C C C G  G G C C A G C T G G T G G G  C C G C A T  hsFATP4
1290  A G G T C  A G C C A G C  a G C C A G C T G G T G G G T  C G C A T  mmFATP4

1320  C A T C C A G A  A A  A G A C C C C  C T G C G C C C G  T T T C G A  hsFATP4
1320  C A T C C A G C  A  G A C C C T  C T G C G C C G  T T T C G A   mmFATP4

1350  T G G C  T A C C T C A A C C A G G G  C G C C A A C A A C A A  hsFATP4
1350  C G G  T A C C T C A A C C A G G G T  G C C A A C A A C A A  mmFATP4

1380  G A A G A T T G C C  A A G  G A T G T C T T C A A G A A G G G  T G T G C T  hsFATP4
1380  G A A G A T T G C C  A A G  T A A T  G A T G T C T T C A A G A A G G G  A C G T C C T  mmFATP4

1410  G G A C C A G G  C C T A C C T  T A C T G G T G A T G T G C T  hsFATP4
1410  G G A C C A A G C C T A C C T  C A C T G G T G A C G T C C T  mmFATP4

1440  G G T G A T G G A  C G A G C T G G G  C T A C C T G T A C T T  hsFATP4
1440  G G T G A T G G A T G A G C T G G G T  T A C C T G T A C T T  mmFATP4
```

FIG. 31G

| | | |
|---|---|---|
| 1470 | CCGAGAC CGCACTGGGGACACGTTCCGCTG | hsFATP4 |
| 1470 | CCGAGATCGCACTGGGGACACGTTCCGCTG | mmFATP4 |
| 1500 | GAAAGGTGAGAACGTGTCCACCACCGAGGT | hsFATP4 |
| 1500 | GAAAGGGGAGAATGTATCTACCACTGAGGT | mmFATP4 |
| 1530 | GGAAGGCACACTCAGCCCGCCTGCTGGACAT | hsFATP4 |
| 1530 | GGAGGGGCACACTCAGCCCGCCTGCTTCATAT | mmFATP4 |
| 1560 | GGCTGACGTGGCCGTGTATGGTGTCGAGGT | hsFATP4 |
| 1560 | GGCAGATGTGGCCAGTTTATGGTGTTGAGGT | mmFATP4 |
| 1590 | GCCAGGAACCGAGGCCGGAATGGC | hsFATP4 |
| 1590 | GCCAGGAACTGAAGGCCGAGGAATGGC | mmFATP4 |
| 1620 | TGCTGTTGGCCAGCCCCACTGGCAACTGTGA | hsFATP4 |
| 1620 | TGCCGTTGCAAGTCCCATCCAGCAACTGTGA | mmFATP4 |
| 1650 | CCTGGAGCGCTTTGCTCAGGTCTTTGGAGAA | hsFATP4 |
| 1650 | CCTGGAGAGCTTTGCACAGACCTTGAAAAA | mmFATP4 |

FIG. 31H

| | | | | | | | | | | | |
|---|---|---|---|---|---|---|---|---|---|---|---|
|1680|GGA|ACTGCC|CCTGTATGCG|CGCCCCATCTT|hsFATP4|
|1680|GGA|GCTGCC|TCTGTATGCC|CCGCCCCATCTT|mmFATP4|
|1710|CCTGCGC|CCT|CCT|TGCCCTGAGCTGCACAAAAC|hsFATP4|
|1710|CCTGCGC|TT|TCT|TGCCCTGAGCTGCACAAGAC|mmFATP4|
|1740|AGG|AACCTA|CAAGTTCCAGAAGACAGAGCT|hsFATP4|
|1740|AGG|GACCTT|CAAGTTCCAGAAGACAGAGT|T|mmFATP4|
|1770|A|CGGAAGGAGGGCTTTGACCCGG|CTATTGT|hsFATP4|
|1770|GC|GGAAGGAGGGCTTTGACCCC|ATCTGTTGT|mmFATP4|
|1800|GAAAGACCCCGCTGTTCTATCTA|GATGCC|CA|hsFATP4|
|1800|GAAAGACCCCGCTGTTCTATCT|GGATGCT|CG|mmFATP4|
|1830|GAAGGGCC|GCTGACCAAGA|hsFATP4|
|1830|GAAGGGCT|TGCACTGGACCAGGA|mmFATP4|
|1860|GGCCTAC|AGCCCGCATCCAGGCAGGCGAGGA|hsFATP4|
|1860|GGCCTAT|ACCCGCATCCAGGCAGGCGAGGA|mmFATP4|
|1890|GAAGCTG|hsFATP4|
|1890|GAAGCTG|mmFATP4|

FIG. 311

```
1    M R A P G A G A A S V V S L A L L W L L    hFATP1.
1    M R A P G A G T A S V A S L A L L W F L    mmFATP1

21   G L P W T W S A A A A L G V Y V G S G G    hFATP1.
21   G L P W T W S A A A A F C V Y V G G G G    mmFATP1

41   W R F L R I V C K T A R R D L F G L S V    hFATP1.
41   W R F L R I V C K T A R R D L F G L S V    mmFATP1

61   L I R V R L E L R R H Q R A G H T I P R    hFATP1.
61   L I R V R L E L R R H R R A G D T I P C    mmFATP1

81   I F Q A V V Q R Q P E R L A L V D A G T    hFATP1.
81   I F Q A V A R R Q P E R L A L V D A S S    mmFATP1

101  G E C W T F A Q L D A Y S N A V A N L F    hFATP1.
101  G I C W T F A Q L D T Y S N A V A N L F    mmFATP1

121  R Q L G F A P G D V V A I F L E G R P E    hFATP1.
121  R Q L G F A P G D V V A V F L E G R P E    mmFATP1

141  F V G L W L G L A K A G M E A A L L N V    hFATP1.
141  F V G L W L G L A K A G V V A A L L N V    mmFATP1

161  N L R R E P L A F C L G T S G A K A L I    hFATP1.
161  N L R R E P L A F C L G T S A A K A L I    mmFATP1

181  F G G E M V A A V A E V S G H L G K S L    hFATP1.
181  Y G G E M A A A V A E V S E Q L G K S L    mmFATP1

201  I K F C S G D L G P E G I L P D T H L L    hFATP1.
201  L K F C S G D L G P E S I L P D T Q L L    mmFATP1

221  D P L L K E A S T A P L A Q I P S K G M    hFATP1.
221  D P M L A E A P T T P L A Q A P G K G M    mmFATP1

241  D D R L F Y I Y T S G T T G L P K A A I    hFATP1.
241  D D R L F Y I Y T S G T T G L P K A A I    mmFATP1

261  V V H S R Y Y R M A A F G H H A Y R M Q    hFATP1.
261  V V H S R Y Y R I A A F G H H S Y S M R    mmFATP1
```

FIG. 32A

```
281  A A D V L Y D C L P L Y H S A G N I I G   hFATP1.
281  A A D V L Y D C L P L Y H S A G N I M G   mmFATP1

301  V G Q C L I Y G L T V V L R K K F S A S   hFATP1.
301  V G Q C V I Y G L T V V L R K K F S A S   mmFATP1

321  R F W D D C I K Y N C T V V Q Y I G E I   hFATP1.
321  R F W D D C V K Y N C T V V Q Y I G E I   mmFATP1

341  C R Y L L K Q P V R E A E R H R V R L     hFATP1.
341  C R Y L L R Q P V R D V E Q R H R V R L   mmFATP1

361  A V G N G L R P A I W E E F T E R F G V   hFATP1.
361  A V G N G L R P A I W E E F T Q R F G V   mmFATP1

381  R Q I G E F Y G A T E C N C S I A N M D   hFATP1.
381  P Q I G E F Y G A T E C N C S I A N M D   mmFATP1

401  G K V G S C G F N S R I L P H V Y P I R   hFATP1.
401  G K V G S C G F N S R I L T H V Y P I R   mmFATP1

421  L V K V N E D T M E L L R D A Q G L C I   hFATP1.
421  L V K V N E D T M E P L R D S E G L C I   mmFATP1

441  P C Q A G E P G L L V G Q I N Q Q D P L   hFATP1.
441  P C Q P G E P G L L V G Q I N Q Q D P L   mmFATP1

461  R R F D G Y V S E S A T S K K I A H S V   hFATP1.
461  R R F D G Y V S D S A T N K K I A H S V   mmFATP1

481  F S K G D S A Y L S G D V L V M D E L G   hFATP1.
481  F R K G D S A Y L S G D V L V M D E L G   mmFATP1

501  Y M Y F R D R S G D T F R W R G E N V S   hFATP1.
501  Y M Y F R D R S G D T F R W R G E N V S   mmFATP1

521  T T E V E G V L S R L L G Q T D V A V Y   hFATP1.
521  T T E V E A V L S R L L G Q T D V A V Y   mmFATP1

541  G V A V P G V E G K A G M A A V A D P H   hFATP1.
541  G V A V P G V E G K A G M A A I A D P H   mmFATP1
```

FIG. 32B

```
561  S L D P N A I Y Q E L Q K V L A P Y A   hFATP1.
561  S Q L D P N S M Y Q E L Q K V L A S Y A  mmFATP1

581  R P I F L R L L P Q V D T T G T F K I Q  hFATP1.
581  R P I F L R L L P Q V D T T G T F K I Q  mmFATP1

601  K T R L Q R E G F D P R Q T S D R L F F  hFATP1.
601  K T R L Q R E G F D P R Q T S D R L F F  mmFATP1

621  L D L K Q G H Y L P N E A V Y T R I C    hFATP1.
621  L D L K Q G R Y V P L D E R V H A R I C  mmFATP1

641  S G A F A L                              hFATP1.
641  A G D F S L                              mmFATP1
```

```
VPPSTEHLDPLLKDAPKHLPSCPDKGFTDK   hsFATP4pep
VPVSTEHLDPLLEDAPKHLPSHPDKGFTDK   mmFATP4pep LFYIYTSGTTGLPKAAIVVHSRYYRMAALV   hsFATP4pep
LFYIYTSGTTGLPKAAIVVHSRYYRMASLV   mmFATP4pep YYGFRMRPNDIVYDCLPLYHSAGNIVGIGQ   hsFATP4pep
YYGFRMRPDDIVYDCLPLYHSSRKHRGDWQ   mmFATP4pep CLLHGMTVVIRKKFSASRFWDDCIKYNCTI   hsFATP4pep
CLLHGMTVVIRKKFSASRFWDDCIKYNCTV   mmFATP4pep VQYIGELCRYLLNQPPREAENQHQVRMALG   hsFATP4pep
VQYIGELCRYLLNQPPREAESRHKVRMALG   mmFATP4pep NGLRQSIWTNFSSRFHIPQVAEFYGATECN   hsFATP4pep
NGLRQSIWTDFSSRFHIPQVAEFYGATECN   mmFATP4pep CSLGNFDSQVGACGFNSRILSFVYPIRLVR   hsFATP4pep
CSLGNFDSRVGACGFNSRILSFVYPIRLVR   mmFATP4pep
```

FIG. 33B

```
V N E D T M E L I R G P D G V C I P C Q P G E P G Q L V G R    hsFATP4pep
V N E D T M E L I R G P D G V C I P C Q P G Q P G Q L V G R    mmFATP4pep I I Q K D P L R R F D G Y L N Q G A N N K K I A K D V F K K   hsFATP4pep
I I Q Q D P L R R F D G Y L N Q G A N N K K I A N D V F K K   mmFATP4pep G D Q A Y L T G D V L V M D E L G Y L Y F R D R T G D T F R   hsFATP4pep
G D Q A Y L T G D V L V M D E L G Y L Y F R D R T G D T F R   mmFATP4pep W K G E N V S T T E V E G T L S R L L D M A D V A V Y G V E   hsFATP4pep
W K G E N V S T T E V E G T L S R L L H M A D V A V Y G V E   mmFATP4pep V P G T E G R A G M A A V A S P T G N C D L E R F A Q V L E   hsFATP4pep
V P G T E G R A G M A A V A S P I S N C D L E S F A Q T L K   mmFATP4pep K E L P L Y A R P I F L R L L P E L H K T G T Y K F Q K T E   hsFATP4pep
K E L P L Y A R P I F L R F L P E L H K T G T F K F Q K T E   mmFATP4pep L R K E G F D P A I V K D P L F Y L D A Q K G R Y V P L D Q   hsFATP4pep
L R K E G F D P S V V K D P L F Y L D A R K G C Y V A L D Q   mmFATP4pep E A Y S R I Q A G E E K L    hsFATP4pep
E A Y T R I Q A G E E K L    mmFATP4pep
```

FIG. 33C hsFATP6

```
  1  aac ggc aag taa gcg caa cgc aat taa tgt gag tag ctc act cat tag gca ccc cag gct
 61  tta cac ttt atg cag ctt ccg ggc tcg tat gtt gtg aat tgt gag cgg ata cca att tca
121  cac agg aac cag cta cat gat tac gaa ttt aat acg act gag tac tat agg gaa ttt ggc
181  cct cga ggc caa gaa ttc ggc acg agg ggt gct gag ccc ctg cgc cgt ggt ttc tgc gta
241  gag act gta aat cgc tgc gct tct cag tca tca ttc cag ctt ttc ccg gct cga att
301  cag cct cca act caa gct cgc ggg aaa gac tac ctg aga gga gaa aag ctt ctg tcc ctg
361  gac ctt ctt ctg agg gtg gag tcg gag gct ccc ttt cca gcc gcc tga ccc aag
421  ctt aat ctt cag cac cac ttg ggg cga cct ttt cgg tgc aaa cct acg att ctg ttt ctc
481  agg att cct ccc cat ccc gct ccc cgg tcg ccc aaa agc tga caa gaa ctt cag gtg taa gcc
541  ctg agt agt gag gat ctg cgg tct ccg tgg aga gct gtg cct gga aga gga cga cgc tgg
601  tgg ggg ctg aga tca gag ctg tct tct ggc cca gtt gcc ccc atg ctt ctg tca tgg cta
                                                         M   L   L   S   W   L
661  aca gtt cta ggg gct gga atg gtc ctg gtc ctg cac ttc ttg cag aaa ctc ctg ttc cct tac
      T   V   L   G   A   G   M   V   L   V   L   H   F   L   Q   K   L   L   F   P   Y
721  ttt tgg gat gac ttc tgg ttc gtg ttg aag gtg gtg ctc att ata att cgg ctg aag aag
      F   W   D   D   F   W   F   V   L   K   V   V   L   I   I   I   R   L   K   K
781  tat gaa aag aga ggg gag ctg gag ctg gtg act gtg ctg gat aaa ttc ttg agt cat gcc aaa aga
      Y   E   K   R   G   E   L   V   L   T   V   L   D   K   F   L   S   H   A   K   R
```

FIG. 34A

```
841   caa cct cgg aaa cct ttc atc atc tat gag gga gac atc tac acc tat cag gat gta gac
      Q   P   R   K   P   F   I   I   Y   E   G   D   I   Y   T   Y   Q   D   V   D 901   aaa agg agc agc aga gtg gcc cat gtc ctg ttc aac cat tcc tct ctg aaa aag ggg gac
      K   R   S   S   R   V   A   H   V   L   F   N   H   S   S   L   K   K   G   D 961   acg gtg gct ctg ctg atg agc aat gag ccg gac ttc gtt cac gtg ttc ggc ctc gcc
      T   V   A   L   L   M   S   N   E   P   D   F   V   H   V   F   G   L   A 1021  aag ctg ggc tgc gtg gtg gcc ttt ctc aac acc aac att cgc tcc aac tcc ctc aat
      K   L   G   C   V   V   A   F   L   N   T   N   I   R   S   N   S   L   N 1081  tgc atc cgc gcc tgt ggg ccc aga gcc cta gtg gtg ggc gca gat ttg ctt gga acg gta
      C   I   R   A   C   G   P   R   A   L   V   V   G   A   D   L   L   G   T   V 1141  gaa gaa atc ctt cca agc ctc tca gaa aat atc agt gtt tgg ggg atg aaa gat tct gtt
      E   E   I   L   P   S   L   S   E   N   I   S   V   W   G   M   K   D   S   V 1201  cca caa ggt gta att tca ctc aaa gaa ctc tca agc acc tca cct gat ccc gtg cca
      P   Q   G   V   I   S   L   K   E   L   S   S   T   S   P   D   E   P   V   P 1261  cgc agc cac cat gtt gtc tca aag tct act act tgt ctt tac att ttt acc tct gga
      R   S   H   H   V   V   S   L   K   S   T   T   C   L   Y   I   F   T   S   G 1321  aca aca ggt cta cca aaa gca gct gtg att agt cag ctg cag gtt tta agg ggt tct gct
      T   T   G   L   P   K   A   A   V   I   S   Q   L   Q   V   L   R   G   S   A 1381  gtc ctg tgg gct ttt ggt tgt act gct cat gct gtt tat ata acc ctt cct ctg tat
      V   L   W   A   F   G   C   T   A   H   A   V   Y   I   T   L   P   L   Y
```

FIG. 34B

```
1441  cat agt tca gca gct atc ctg gga att tct gga tgt gtt gag ttg ggt gcc act tgt gtg
      H   S   S   A   A   I   L   G   I   S   G   C   V   E   L   G   A   T   C   V 1501  tta aag aaa ttt tca gca agc cag ttt tgg agt gac tgc aag tat gat gtg act
      L   K   K   F   S   A   S   Q   F   W   S   D   C   K   Y   D   V   T 1561  gtg ttt cag tat att gga gaa ctt tgt cgc tac ctt tgc aaa caa tct aag aga gaa gga
      V   F   Q   Y   I   G   E   L   C   R   Y   L   C   K   Q   S   K   R   E   G 1621  gaa aag gat cat aag gtg cgt ttg gca att gga aat ggc ata cgg agt gat gta tgg aga
      E   K   D   H   K   V   R   L   A   I   G   N   G   I   R   S   D   V   W   R 1681  gaa ttt tta gac aga ttt gga aat ata aag gtg tgt gaa ctt tat gca gct acc gaa tca
      E   F   L   D   R   F   G   N   I   K   V   C   E   L   Y   A   A   T   E   S 1741  agc ata tct ttc atg aac tac act ggg aga att gca ttt aga aca aat ttg ttt
      S   I   S   F   M   N   Y   T   G   R   I   G   A   I   R   T   N   L   F 1801  tac aaa ctt tcc act ttt gac tta ata aag tat ttt cag aaa gat gaa ccc atg
      Y   K   L   S   T   F   D   L   I   K   Y   F   Q   K   D   E   P   M 1861  aga aat gag ctt ctt cat gtg aaa gga gaa cct gga ctt ctc att tct
      R   N   E   L   L   H   V   K   G   E   P   G   L   L   I   S 1921  cga gtg aat gca aat ccc ttt ggc tat gct ggg tat aag cac aca aaa gac
      R   V   N   A   N   P   F   G   Y   A   G   Y   K   H   T   K   D 1981  aaa ttg ctt gat gtt ttt aag aag gga gat gtt tac ctt aat act gga gac tta ata
      K   L   L   D   V   F   K   K   G   D   V   Y   L   N   T   G   D   L   I 2041  gtc cag gat cag gac aat ttc ctt tat tgg gac cgt act act ttc aga tgg
      V   Q   D   Q   D   N   F   L   Y   W   D   R   T   G   D   T   F   R   W 2101  aaa gga gaa aat gtc gca acc act gag gtt gct gat gtt att gga atg ttg gat ttc ata
      K   G   E   N   V   A   T   T   E   V   A   D   V   I   G   M   L   D   F   I
```

FIG. 34C

```
2161  cag gaa gca aac gtc tat ggt gtg gct ata tca ggt gct ata gca gga atg gct
       Q   E   A   N   V   Y   G   V   A   I   S   G   A   I   A   G   M   A
2221  tct att att tta aaa cca aat aca tct tta gat ttg aaa gtt tat gaa caa gtt gta
       S   I   I   L   K   P   N   T   S   L   D   L   K   V   Y   E   Q   V   V
2281  aca ttt cta cca gct tat gct cca cga ttt tta aga att cag gaa aaa atg gaa gca
       T   F   L   P   A   Y   A   P   R   F   L   R   I   Q   E   K   M   E   A
2341  aca gga aca ttc aaa cta ttg aag cat cag gat gga aaa ttt aat cca ctg aaa
       T   G   T   F   K   L   L   K   H   Q   D   G   K   F   N   P   L   K
2401  att tct gaa cca ctt tac ttc atg atg aag tct taa aag ctt tat atc tag aac
       I   S   E   P   L   Y   F   M   M   K   S   *   K   L   Y   L   T   R
2461  gaa ctt tat gat caa ata atg tta ggg gaa ata aaa ctt   
       E   L   Y   D   Q   I   M   L   G   E   I   K   L
2521  ttt cat atg ctt tct tag gaa gag tga ttt ggt ata tga ttc ttt atg aaa tgg gga
2581  aag gga gct aac att aat aat gca tgt act gca ttt cct taa tat gag aga taa ttt
2641  aat tgc ata aga att tta att tct aat tga tat ttt aaa cat tag ttg att att ctt ttt
2701  atc tat ttg gag att cag att tgc ata act aag tat cct taa atg tac taa ata
2761  ata aat agt ggc tag cgg ttt gga caa tca cta ttt cta ata agt aaa att
2821  tct aat ttt gaa taa aag att aaa ttt tac tga aaa aaa aaa aaa ttg aca
2881  gcc gc
```

FIG. 34D

Protein Sequence 619 a.a. MLLSWLTVLGAG....LYDQIMLGEIKL
619 Amino Acids MW: 70066 Dalton

|   |   | n | n% | MW | MW% |
|---|---|---|---|---|---|
| A ala | alanine | 33 | 5.3 | 2344 | 3.3 |
| C cys | cysteine | 14 | 2.3 | 1442 | 2.1 |
| D asp | aspartic acid | 34 | 5.5 | 3910 | 5.6 |
| E glu | glutamic acid | 31 | 5.0 | 4000 | 5.7 |
| F phe | phenylalanine | 34 | 5.5 | 5000 | 7.1 |
| G gly | glycine | 44 | 7.1 | 2508 | 3.6 |
| H his | histidine | 13 | 2.1 | 1781 | 2.5 |
| I ile | isoleucine | 37 | 6.0 | 4184 | 6.0 |
| K lys | lysine | 48 | 7.8 | 6148 | 8.8 |
| L leu | leucine | 75 | 12.1 | 8481 | 12.1 |
| M met | methionine | 11 | 1.8 | 1441 | 2.1 |
| N asn | asparagine | 21 | 3.4 | 2394 | 3.4 |
| P pro | proline | 21 | 3.4 | 2038 | 2.9 |
| Q gln | glutamine | 18 | 2.9 | 2305 | 3.3 |
| R arg | arginine | 27 | 4.4 | 4214 | 6.0 |
| S ser | serine | 40 | 6.5 | 3481 | 5.0 |
| T thr | threonine | 30 | 4.8 | 3031 | 4.3 |
| V val | valine | 51 | 8.2 | 5052 | 7.2 |
| W trp | tryptophan | 11 | 1.8 | 2046 | 2.9 |
| X ukw | unknown | -- | -- |   |   |
| Y tyr | tyrosine | 26 | 4.2 | 4239 | 6.1 |
| Z --- STOP |   |   |   |   |   |

FIG. 35B

```
1   MRAP--GAGAASVVSLALLW    hsFATP1pep
1   L-------------FSKL--    hsFATP4pep
1   MLLSWLTVLGAGMVLHFLQ     hsFATP6pep 19  LLGLPWTWSAAAALGVYVGS    hsFATP1pep
6   VLKLPWTQVGFSLFLYLGS     hsFATP4pep
21  KLLFPYFWDDF--------     hsFATP6pep 39  GGWRFLRIVCKTARRDLFGL    hsFATP1pep
26  GGWRFIRVFIKTIRRDIFGG    hsFATP4pep
32  --WFVLKV-----------     hsFATP6pep 59  SVLIRVRLELRRHQRAGHTI    hsFATP1pep
46  LVLLKVKAKVRQCLQERRTV    hsFATP4pep
38  -VLIIRLKKYEKRGELVTV     hsFATP6pep 79  PRIFQAVVQRQPERLALVDA    hsFATP1pep
66  PILFASTVRRHPDKTALIFE    hsFATP4pep
57  LDKFLSHAKRQPRKPFIIYE    hsFATP6pep
```

FIG. 36A

```
 99  GTGECWTFAQLDAYSNAVAN  hsFATP1pep
 86  GTDTHWTFRQLDEYSSSVAN  hsFATP4pep
 77  G--DIYTYQDVDKRSSRVAH  hsFATP6pep 119  -LFRQLGEAPGDVVAIFLEG  hsFATP1pep
106  -FLQARGLASGDVAAIEMEN  hsFATP4pep
 95  VFLNHSSLKKGDTVALLMSN  hsFATP6pep 138  RPEFVGLWLGLAKAGMEAAL  hsFATP1pep
125  RNEFVGLWLGMAKLGVEAAL  hsFATP4pep
115  EPDFVHVWFGLAKLGCVVAF  hsFATP6pep 158  LNVNLRREPLAFCLGTSGAK  hsFATP1pep
145  INTNLRRDALLHCLTTSRAR  hsFATP4pep
135  LNTNIRSNSLLNCIRACGPR  hsFATP6pep 178  ALIFGGEMVAAVAEVSGHLG  hsFATP1pep
165  ALVFGSEMASAICEVHASLD  hsFATP4pep
155  ALVVGADLLGTVEEILPSLS  hsFATP6pep
```

FIG. 36B

```
198  K S L I K F C S G D L G P E G I L P D T     hsFATP1pep
185  P S L F C S G S W E P G A V P P S T         hsFATP4pep
175  E N I S V W G M K D S V P Q G V I S - -     hsFATP6pep 218  H L D P L L K E A S T A P L A Q I P S       hsFATP1pep
205  E H L D P L L K D A P K - H L P S C P D     hsFATP4pep
193  - - L K E K L S T S P D E P V P R S H H     hsFATP6pep 238  K G - - M D D R L F Y I Y T S G T T G L     hsFATP1pep
224  K G - - F T D K L F Y I Y T S G T T G L     hsFATP4pep
211  V V S L L K S T C L Y I F T S G T T G L     hsFATP6pep 256  P K A A I V V H S R Y Y R M A A F G H H     hsFATP1pep
242  P K A A I V V H S R Y Y R M A A L V Y Y     hsFATP4pep
231  P K A A V I S Q L Q V L R G S A - V L W     hsFATP6pep 276  A Y R M Q A A D V L Y D C L P L Y H S A     hsFATP1pep
262  G F R M R P N D I V Y D C L P L Y H S A     hsFATP4pep
250  A F G C T A H D I V Y I T L P L Y H S S     hsFATP6pep
```

FIG. 36C

| | | |
|---|---|---|
| 296 GNIIGVGQCLIYGLTVVLRK | hsFATP1pep |
| 282 GNIVGIGQCLLHGMTVVIRK | hsFATP4pep |
| 270 AAILGISGCVELGATCVLKK | hsFATP6pep |
| | |
| 316 KFSASRFWDDCIKYNCTVVQ | hsFATP1pep |
| 302 KFSASRFWDDCIKYNCTIVQ | hsFATP4pep |
| 290 KFSASQFWSDCKKYDVTVFQ | hsFATP6pep |
| | |
| 336 YIGELCRYLLKQPVREAERR | hsFATP1pep |
| 322 YIGELCRYLLNQPPREAENQ | hsFATP4pep |
| 310 YIGELCRYLCKQSKREGEKD | hsFATP6pep |
| | |
| 356 HRVLAVGNGLRPAIWEEFT | hsFATP1pep |
| 342 HQVRMALGNGLRQSIWTNFS | hsFATP4pep |
| 330 HKVRLAIGNGIRSDVWREFL | hsFATP6pep |
| | |
| 376 ERFGVRQIGEFYGATECNCS | hsFATP1pep |
| 362 SRFHIPQVAEFYGATECNCS | hsFATP4pep |
| 350 DRFGNIKVCELYAATESSIS | hsFATP6pep |

FIG. 36D

```
396  I A N M D G K V G S C G F N S R I L P H   hsFATP1pep
382  L G N F D S Q V G A C G F N S R I L S F   hsFATP4pep
370  F M N Y T G R I G A I G R T N L F Y K L   hsFATP6pep 416  V Y P I R L V K V N E D T M E L L R D A   hsFATP1pep
402  V Y P I R L V R V N E D T M E L I R G P   hsFATP4pep
390  L S T F D L I K Y D F Q K D E P M R N E   hsFATP6pep 436  Q G L C I P C Q A G E P G L L V G Q I N   hsFATP1pep
422  D G V C I P C Q P G E P G Q L V G R I I   hsFATP4pep
410  Q G W C I H V K K G E P G L L I S R V N   hsFATP6pep 456  Q Q D P L R R F D G Y V S E S A T S K -   hsFATP1pep
442  Q K D P L R R F D G Y L N Q G A N N K -   hsFATP4pep
430  A K N P - - - F F G Y A G P Y K H T K D   hsFATP6pep 475  K I A H S V F S K G D S A Y L - S G D V   hsFATP1pep
461  K I A K D V F K K G D Q A Y L - T G D V   hsFATP4pep
447  K L L C D V F K K G D - V Y L N T G D L   hsFATP6pep
```

FIG. 36E

| | | | |
|---|---|---|---|
| 494 | L V M D E L G Y M Y F R D R S G D T F R | hsFATP1pep |
| 480 | L V M D E L G Y L Y F R D R T G D T F R | hsFATP4pep |
| 466 | I V Q D N F L Y F W D R T G D T F R | hsFATP6pep |
| | | |
| 514 | W R G E N V S T T E V E G V L S R L L G | hsFATP1pep |
| 500 | W K G E N V S T T E V E G T L S R L L D | hsFATP4pep |
| 486 | W K G E N V A T T E V A D V I G M L D F | hsFATP6pep |
| | | |
| 534 | Q T D V A V Y G V A V P G V E G K A G M | hsFATP1pep |
| 520 | M A D V A V Y G V E V P G T E G R A G M | hsFATP4pep |
| 506 | I Q E A N V Y G V A I S G Y E G R A G M | hsFATP6pep |
| | | |
| 554 | A A V A - D P H S L L D P N A I Y Q E L | hsFATP1pep |
| 540 | A A V A - S P T G N C D L E R F A Q V L | hsFATP4pep |
| 526 | A S I I L K P N T S L D L E K V Y E Q V | hsFATP6pep |
| | | |
| 573 | Q K V L A P Y A R P I F L R L L P Q V D | hsFATP1pep |
| 559 | E K E L P L Y A R P I F L R L L P E L H | hsFATP4pep |
| 546 | V T F L P A Y A C P R F L R I Q E K M E | hsFATP6pep |

FIG. 36F

```
593  T T G T F K I Q K T R L Q R E G F D P R   hsFATP1pep
579  K T G T Y K F Q K T E L R K E G F D P A   hsFATP4pep
566  A T G T F K L L K H Q L V E D G F N P L   hsFATP6pep 613  Q T S D R L F F L D L K Q G H Y L P L N   hsFATP1pep
599  I V K D P L F Y L D A Q K G R Y V P L D   hsFATP4pep
586  K I S E P L Y F M D N L K K S Y V L L T   hsFATP6pep 633  E A V Y T R I C S G A F A L             hsFATP1pep
619  Q E A Y S R I Q A G E E K L             hsFATP4pep
606  R E L Y D Q I M L G E I K L             hsFATP6pep
```

FIG. 36G

```
hsFATP4_ 427  ELIRGPDGVCIPCQPGEPGQLVGRIIQKDPLRR  459
mmFATP4_ 427  ELIRGPDGVCIPCQPGQPGQLVGRIIQQDPLRR  459
hsFATP1_ 430  ELIRDAQGLCIPCQAGEPGLLVGQINQQDPLRR  462 hsFATP4_ 460  FDGYLNQGANNKKIAKDVFKKGDQAYLTGDVLV   492
mmFATP4_ 460  FDGYLNQGANNKKIANDVFKKGDQAYLTGDVLV   492
hsFATP1_ 463  FDGYVSESATSKKIAHSVFSKGDSAYLSGDVLV   495 hsFATP4_ 493  MDELGYLYFRDRTGDTFRWKGENVSTTEVEGTL   525
mmFATP4_ 493  MDELGYLYFRDRTGDTFRWKGENVSTTEVEGTL   525
hsFATP1_ 496  MDELGYMYFRDRSGDTFRWRGENVSTTEVEGVL   528 hsFATP4_ 526  SRLLDMADVAVYGVEVPGTEGRAGMAAVASPTG   558
mmFATP4_ 526  SRLLHMADVAVYGVEVPGTEGRAGMAAVASPIS   558
hsFATP1_ 529  SRLLGQTDVAVYGVAVPGVEGKAGMAAVADPHS   561 hsFATP4_ 559  NCDLERFAQVLEKELPLYARPIFLRLLPELHKT   591
mmFATP4_ 559  NCDLESFAQTLKKELPLYARPIFLRFLPELHKT   591
hsFATP1_ 562  LLDPNAIYQELQKVLAPYARPIFLRLLPQVDTI   594 hsFATP4_ 592  GTYKFQKTELRKEGFDPAIVKDPLFYLDAQKGR   624
mmFATP4_ 592  GTFKFQKTELRKEGFDPSVVKDPLFYLDARKGC   624
hsFATP1_ 595  GTFKIIQKIRLQREGFDPRQTSDRLFFLDLKQGH   627 hsFATP4_ 625  YVPLDQEAYSRIQAGEEKL   643
mmFATP4_ 625  YVALDQEAYTRIQAGEEKL   643
hsFATP1_ 628  YLPLNEAVYTRICSGAFAL   646
```

FIG. 39C

```
hsFATP4_   1                       MLL-GASLVGVLLFSKL-VLKLPWTQVGFSLLF    31
mmFATP4_   1                       MLL-GASLVGVLLFSKL-VLKLPWTQVGFSLLX    31
hsFATP1_   1                       MRAPGAGAASVVSLALLWLLGLPWTWSAAAALG    33 hsFATP4_  32   LYLGSGGWRFIRVFIKTIRRDIFGGLVLLKVKA    64
mmFATP4_  32   LYLGSGGWRFIRVFIKTVRRDIFGGMVLLKVKT    64
hsFATP1_  34   VYVGSGGWRFLRIVCKTARRDLFGLSVLIRVRL    66 hsFATP4_  65   KVRQCLQERRTVPILFASTVRHPDKTALIFEG    97
mmFATP4_  65   KVRRYLQERKTVPLLFASMVQRHPDKTALIFEG   97
hsFATP1_  67   ELRRHQRAGHTIPRIEQAVVQRQPERLALVDAG   99 hsFATP4_  98   TDTHWTFRQLDEYSSSVANFLQARGLASGDVAA   130
mmFATP4_  98   TDTHWTFRQLDEYSSSVANFLQARGLASGNVVA   130
hsFATP1_ 100   IGECWTFAQLDAYSNAVANLFRQLGFAPGDVVA   132 hsFATP4_ 131   IFMENRNEFVGLWLGMAKLGVEAALINTNLRRD   163
mmFATP4_ 131   IFMENRNEFVGLWLXGMAKLGVEAALINTNLRRD  163
hsFATP1_ 133   IFLEGRPEFVGLWLGLLAKAGMEAALVNLRRE    165 hsFATP4_ 164   ALLHCLTTSRARALVFGSEMASAICEVHASLDP   196
mmFATP4_ 164   ALRHCLDTSKARALFGSEMASAICEIHASLEP    196
hsFATP1_ 166   PLAFCLGTSGAKALFGGEMVAAVAEVSGHLGK    198 hsFATP4_ 197   SLSLFCSGSWEPGAVPPSTEHLDPLLKDAP-KH   228
mmFATP4_ 197   TLSLFCSGSWEPSTVPVSTEHLDPLLEDAP-KH   228
hsFATP1_ 199   SLIKFCSGDLGPEGILPDTHLLDPLLKEASTAP   231
```

FIG. 39A

| | | |
|---|---|---|
| hsFATP4_229 | LPSCPDKGFTDKLFYIYTSGTTGLPKAAIVVHS | 261 |
| mmFATP4_229 | LPSHPDKGFTDKLFYIYTSGTTGLPKAAIVVHS | 261 |
| hsFATP1_232 | LAQIPSKGMDDRLFYIYTSGTTGLPKAAIVVHS | 264 |
| hsFATP4_262 | RYYRMAALVYYGFRMRPNDIVYDCLPLYHSAGN | 294 |
| mmFATP4_262 | RYYRMASLVYYGFRMRPDDIVYDCLPLYHSSRK | 294 |
| hsFATP1_265 | RYYRMAAFGHHAYRMQAADVLYDCLPLYHSAGN | 297 |
| hsFATP4_295 | IVGIGQCLLHGMTVVIRKKFSASRFWDDCIKYN | 327 |
| mmFATP4_295 | HRGDWQCLLHGMTVVIRKKFSASRFWDDCIKYN | 327 |
| hsFATP1_298 | IIGVGQCLIYGLTVVLRKKFSASRFWDDCIKYN | 330 |
| hsFATP4_328 | CTLVQYIGELCRYLLNQPPREAENQHQVRMALG | 360 |
| mmFATP4_328 | CTVVQYIGELCRYLLNQPPREAESRHKVRMALG | 360 |
| hsFATP1_331 | CTVVQYIGEICRYLLKQPVREAERRHRVALAVG | 363 |
| hsFATP4_361 | NGLRQSIWTNFSSRFHIPQVAEFYGATECNCSL | 393 |
| mmFATP4_361 | NGLRQSIWTDFSSRFHIPQVAEFYGATECNCSL | 393 |
| hsFATP1_364 | NGLRPAIWEEFTERFGVRQIGEFYGATECNCSI | 396 |
| hsFATP4_394 | GNFDSQVGACGFNSRILSFVYPIRLVRVNEDTM | 426 |
| mmFATP4_394 | GNFDSRVGACGFNSRILSFVYPIRLVRVNEDTM | 426 |
| hsFATP1_397 | ANMDGKVGSCGFNSRILPHVYPIRLVKVNEDTM | 429 |

FIG. 39B

| | | | |
|---|---|---|---|
|hsFATP4_ 427|ELIRGPDGVCIPCQPGEPGQLVGRIIQKDPLRR|459|
|mmFATP4_ 427|ELIRGPDGVCIPCQPGQPGQLVGRIIQQDPLRR|459|
|hsFATP1_ 430|ELILRDAQGLCIPCQAGEPGLLVGQINQQDPLRR|462|
| | | |
|hsFATP4_ 460|FDGYLNQGANNKKIAKDVFKKGDQAYLTGDVLV|492|
|mmFATP4_ 460|FDGYLNQGANNKKIANDVFKKGDQAYLTGDVLV|492|
|hsFATP1_ 463|FDGYVSESATSKKKIAHSVFSKGDSAYLSGDVLV|495|
| | | |
|hsFATP4_ 493|MDELGYLYFRDRTGDTFRWKGENVSTTEVEGTL|525|
|mmFATP4_ 493|MDELGYLYFRDRTGDTFRWKGENVSTTEVEGTL|525|
|hsFATP1_ 496|MDELGYMYFRDSGDTFRWRGENVSTTEVEGVL|528|
| | | |
|hsFATP4_ 526|SRLLDMADVAVYGVEVPGTEGRAGMAAVASPTG|558|
|mmFATP4_ 526|SRLLHMADVAVYGVEVPGTEGRAGMAAVASPIS|558|
|hsFATP1_ 529|SRLLGQTDVAVYGVAVPGVEGKAGMAAVADPHS|561|
| | | |
|hsFATP4_ 559|NCDLERFAQVLEKELPLYARPIFLRLLPELHKT|591|
|mmFATP4_ 559|NCDLESFAQTLKKELPLYARPIFLRFLPELHKT|591|
|hsFATP1_ 562|LLDPNAIYQELQKVLAPYARPIFLRLLPQVDTI|594|
| | | |
|hsFATP4_ 592|GTYKFQKTELRKEGFDPAIVKDPLFYLDAQKGR|624|
|mmFATP4_ 592|GTFKFQKTELRKEGFDPSVVKDPLFYLDARKGC|624|
|hsFATP1_ 595|GTFKTIQKTRLQREGFDPRQTSDRLFLDLKQGH|627|
| | | |
|hsFATP4_ 625|YVPLDQEAYSRIQAGEEKL|643|
|mmFATP4_ 625|YVALDQEAYTRIQAGEEKL|643|
|hsFATP1_ 628|YLPLNEAVYTRICSGAFAL|646|

FIG. 39C

```
ATGCTGCTTGGAGCCTCTCTGGTGGGGGCGCTACTGTTCTCCAAGC
TAGTGCTGAAGCTGCCCTGGACCCAGGTGGGATTCTCCCTGTTGCT
CCTGTACTTGGGGTCTGGTGGCTGGCGTTTCATCCGGGTCTTCATC
AAGACGGTCAGGAGAGATATCTTTGGTGGCATGGTGCTCCTGAAGG
TGAAGACCAAGGTGCGACGGTACCTTCAGGAGCGGAAGACGGTGCC
CCTGCTGTTTGCTTCAATGGTACAGCGCCACCCGACAAGACAGCC
CTGATTTTCGAGGGCACAGACTCACTGGACCTTCGCCAGCTGG
ATGAGTACTCCAGTAGTGTGGCCAACTTCCTGCAGGCCCGGGCCT
GGCCTCAGGCAATGTAGTTGCCCTCTTTATGGAAAACCGCAATGAG
TTTGTGGGTCTGTGGCTAGGCATGGCCAAGCTGGGCGTGGAGGCGG
CTCTCATCAACACCAACCTTAGGCGGGATGCCCTGCGCCACTGTCT
TGACACCTCAAAGGCACGAGCTCTCATCTTTGGCAGTGAGATGGCC
TCAGCTATCTGTGAGATCCATGCTAGCCTGGAGCCCACACTCAGCC
TCTTCTGCTCTGGATCCTGGGAGCCCAGCACAGTGCCCGTCAGCAC
AGAGCATCTGGACCCTCTTCTGGAAGATGCCCCGAAGCACCTGCCC
AGTCACCCAGACAAGGGTTTTACAGATAAGCTCTTCTACATCTACA
CATCGGGCACCACGGGCTACCCAAAGCTGCCATTGTGGTGCACAG
CAGGTATTATCGTATGCTTCCCTGGTGTACTATGGATTCCGCATG
CGGCCTGATGACATTGTCTATGACTGCCTCCCCCTCTACCACTCAA
GCAGGAAACATCGTGGGATTGGCAGTGCTTACTCCACGGCATGAC
TGTGGTGATCCGGAAGAAGTTCTCAGCCTCCCGGTTCTGGGATGAT
TGTATCAAGTACAACTGCACAGTGGTACAGTACATTGGCGAGCTCT
GCCGCTACCTCCTGAACCAGCCACCCGTGAGGCTGAGTCTCGGCA
CAAGGTGCGCATGGCACTGGGCAACGGTCTCCGGCAGTCCATCTGG
ACCGACTTCTCCAGCCGTTTCCACATCCCCCAGGTGGCTGAGTTCT
ATGGGCCACTGAATGCAACTGTAGCCTGGGCAACTTTGACAGCCG
GGTGGGGCCTGTGGCTTCAATAGCCGCATCCTGTCCTTTGTGTAC
CCTATCCGTTTGGTACGTGTCAATGAGGATACCATGAACTGATCC
GGGACCCGATGGAGTCTGCATTCCCTGTCAACCAGGTCAGCCAGG
CCAGCTGGTGGGTCGCATCATCCAGCAGGACCCTCTGCCGTTTC
```

FIG. 43A

```
GACGGGTACCTCAACCAGGGTGCCAACAACAAGAAGATTGCTAATG
ATGTCTTCAAGAAGGGGGACCAAGCCTACCTCACTGGTGACGTCCT
GGTGATGGATGAGCTGGGTTACCTGTACTTCCGAGATCGCACTGGG
GACACGTTCCGCTGGAAAGGGGAGAATGTATCTACCACTGAGGTGG
AGGGCACACTCAGCCGCCTGCTTCATATGGCAGATGTGGCAGTTTA
TGGTGTTGAGGTGCCAGGAACTGAAGGCCGAGCAGGAATGGCTGCC
GTTGCAAGTCCATCAGCAACTGTGACCTGGAGAGCTTTGCACAGA
CCTTGAAAAGGAGCTGCCTCTGTATGCCCGCCCATCTTCCTGCG
CTTCTTGCCTGAGCTGCACAAGACAGGGACCTTCAAGTTCAGAAG
ACAGAGTTGCGGAAGGAGGGCTTTGACCCATCTGTTGTGAAAGACC
CGCTGTTCTATCTGGATGCTCGGAAGGGCTGCTACGTTGCACTGGA
CCAGGAGGCCTATACCCGCATCCAGGCAGGCGAGGAGAAGCTGTGA
TTTCCCCCTACATCCTCTGAGGGCCAGAAGATGCTGGATTCAGAG
CCCTAGCGTCCACCCCAGAGGGTCCTGGGCAATGCCAGACCAAAGC
TAGCAGGGCCCGCACCTCCGCCCCTAGGTGCTGATCTCCCCTCTCC
CAAACTGCCAAGTGACTCACTGCCGCTTCCCCGACCCTCCAGAGGC
TTTCTGTGAAAGTCTCATCCAAGCTGTGTCTTCTGGTCCAGGCGTG
GCCCCTGGCCCCAGGGTTTCTGATAGGCTCCTTTAGGATGGTATCT
TGGGTCCAGCGGGCCAGGGTGTGGAGAGGAGTCACTAAGATCCCT
CCAATCAGAAGGGAGCTTACAAAGGAACCAAGGCAAAGCCTGTAGA
CTCAGGAAGCTAAGTGGCCAGAGACTATAGTGGCCAGTCATCCCAT
GTCCACAGAGGATCTTGGTCCAGAGCTGCCAAAGTGTCACCTCTCC
CTGCCTGCACCTCTGGGGAAAAGAGGACAGCATGTGGCCACTGGGC
ACCTGTCTCAAGAAGTCAGGATCACACACTCAGTCCTTGTTTCTCC
AGGTTCCCTTGTTCTTGTCTCGGGGAGGGAGGGACGAGTGTCCTGT
CTGTCCTTCCTGCCTGTCTGTGAGTCTGTGTTGCTTCTCCATCTGT
CCTAGCCTGAGTGTGGGTGGAACAGGCATGAGGAGAGTGTGGCTCA
GGGGCCAATAAACTCTGCCTTGACTCCTCTTAAAAAAAAAAAAAA
AAAAAAAAAAAAAAAAAAAAAAAAAAAAAAAAA
```

FIG. 43B mmFATP4 protein sequence

```
MLLGASLVGALLFSKLVLKLPWTQVGFSLLLLYLGSGGWRFIRVFI
KTVRRDIFGGMVLLKVKTKVRRYLQERKTVPLLFASMVQRHPDKTA
LIFEGTDTHWTFRQLDEYSSSVANFLQARGLASGNVVALFMENRNE
FVGLWLGMAKLGVEAALINTNLRRDALRHCLDTSKARALIFGSEMA
SAICEIHASLEPTLSLFCSGSWEPSTVPVSTEHLDPLLEDAPKHLP
SHPDKGFTDKLFYIYTSGTTGLPKAAIVVHSRYYRMASLVYYGFRM
RPDDIVYDCLPLYHSSRKHRGDWQCLLHGMTVVIRKKFSASRFWDD
CIKYNCTVVQYIGELCRYLLNQPPREAESRHKVRMALGNGLRQSIW
TDFSSRFHIPQVAEFYGATECNCSLGNFDSRVGACGFNSRILSFVY
PIRLVRVNEDTMELIRGPDGVCIPCQPGQPGQLVGRIIQQDPLRRF
DGYLNQGANNKKIANDVFKKGDQAYLTGDVLVMDELGYLYFRDRTG
DTFRWKGENVSTTEVEGTLSRLLHMADVAVYGVEVPGTEGRAGMAA
VASPISNCDLESFAQTLKKELPLYARPIFLRFLPELHKTGTFKFQK
TELRKEGFDPSVVKDPLFYLDARKGCYVALDQEAYTRIQAGEEKL
```

FIG. 43C hsFATP1 full length DNA

```
        10        20        30        40
TCGACCCACGGCGTCCGGGACCCCAAAGCAGAAGCCCGCA   40
CAGTAGGCACAGCGCACCCAAGAAGGGTCCAGGAGTCTGC   80
AGAAACAGAAAGGTCCCCGGCCTCAGCCTCCTAGTCCCTG  120
CCTGCCTCCTGCCTGAGCTTCTGGGAGACTGAAGGCACGG  160
CTTGCAGCTTCAGGATGCGGGCTCCGGGTGCGGGCGCGGC  200
       210       220       230       240
CTCGGTGGTCTCGCTGGCGCTGTTGTGGCTGCTGGGGCTG  240
CCGTGGACCTGGAGCGCGGCAGCGGCGCTCGGCGTGTACG  280
TGGGCAGCGGCGGCTGGCGCTTCCTGCGCATCGTCTGCAA  320
GACCGCGAGGCGAGACCTCTTCGGTCTCTCTGTGCTGATC  360
CGCGTGCGCCTGGAGCTGCGGCGGCACCAGCGTGCCGGCC  400
       410       420       430       440
ACACCATCCCGCGCATCTTTCAGGCGGTAGTGCAGCGACA  440
GCCCGAGCGCCTGGCGCTGGTGGATGCCGGGACCGGCGAG  480
TGCTGGACCTTTGCGCAGCTGGACGCCTACTCCAATGCGG  520
TAGCCAACCTCTTCCGCCAGCTGGGCTTCGCGCCGGGCGA  560
CGTGGTGGCCATCTTCCTGGAGGGCCGGCCGGAGTTCGTG  600
       610       620       630       640
GGGCTGTGGCTGGGCCTGGCCAAGGCGGGCATGGAGGCCG  640
CGCTGCTCAACGTGAACCTGCGGCGCGAGCCCCTGGCCTT  680
CTGCCTGGGCACCTCGGGCGCTAAGGCCCTGATCTTTGGA  720
GGAGAAATGGTGGCGGCGGTGGCCGAAGTGAGCGGGCATC  760
TGGGGAAAAGTTTGATCAAGTTCTGCTCTGGAGACTTGGG  800
       810       820       830       840
GCCCGAGGGCATCTTGCCGGACACCCACCTCCTGGACCCG  840
CTGCTGAAGGAGGCCTCTACTGCCCCCTTGGCACAGATCC  880
CCAGCAAGGGCATGGACGATCGTCTTTTCTACATCTACAC  920
GTCGGGGACCACCGGGCTGCCCAAGGCTGCCATTGTCGTG  960
CACAGCAGGTACTACCGCATGGCAGCCTTCGGCCACCACG 1000
      1010      1020      1030      1040
CCTACCGCATGCAGGCGGCTGACGTGCTCTATGACTGCCT 1040
GCCCTGTACCACTCGGCAGGAAACATCATCGGCGTGGGG  1080
CAGTGTCTCATCTATGGGCTGACAGTCGTCCTCCGCAAGA 1120
AATTCTCGGCCAGCCGCTTCTGGGACGACTGCATCAAGTA 1160
CAACTGCACGGTGGTTCAGTACATCGGGGAGATCTGCCGC 1200
```

FIG. 44A

```
            1210       1220       1230       1240
    |....|....|....|....|....|....|....|....|....|
    TACCTGCTGAAGCAGCCGGTGCGCGAGGCGGAGAGGCGAC  1240
    ACCGCGTGCGCCTGGCGGTGGGGAACGGGCTGCGTCCTGC  1280
    CATCTGGGAGGAGTTCACGGAGCGCTTCGGCGTACGCCAA  1320
    ATCGGGGAGTTCTACGGCGCCACCGAGTGCAACTGCAGCA  1360
    TTGCCAACATGGACGGCAAGGTCGGCTCCTGTGGTTTCAA  1400
            1410       1420       1430       1440
    |....|....|....|....|....|....|....|....|....|
    CAGCCGCATCCTGCCCCACGTGTACCCCATCCGGCTGGTG  1440
    AAGGTCAATGAGGACACAATGGAGCTGCTGCGGGATGCCC  1480
    AGGGCCTCTGCATCCCTGCCAGGCCGGGGAGCCTGGCCT   1520
    CCTTGTGGGTCAGATCAACCAACAGGACCCGCTGCGCCGC  1560
    TTCGATGGCTATGTCAGCGAGAGCGCCACCAGCAAGAAGA  1600
            1610       1620       1630       1640
    |....|....|....|....|....|....|....|....|....|
    TCGCCCACAGCGTCTTCAGCAAGGGCGACAGCGCCTACCT  1640
    CTCAGGTGACGTGCTAGTGATGGATGAGCTGGGCTACATG  1680
    TACTTCCGGGACCGTAGCGGGGACACCTTCCGCTGGCGAG  1720
    GGGAGAACGTCTCCACCACCGAGGTGGAGGGCGTGCTGAG  1760
    CCGCCTGCTGGGCCAGACAGACGTGGCCGTCTATGGGGTG  1800
            1810       1820       1830       1840
    |....|....|....|....|....|....|....|....|....|
    GCTGTTCCAGGAGTGGAGGGTAAGGCAGGGATGGCGGCCG  1840
    TCGCAGACCCCCACAGCCTGCTGGACCCCAACGCGATATA  1880
    CCAGGAGCTGCAGAAGGTGCTGGCACCCTATGCCCGGCCC  1920
    ATCTTCCTGCGCCTCCTGCCCCAGGTGGACACCACAGGCA  1960
    CCTTCAAGATCCAGAAGACGAGGCTGCAGCGAGAGGGCTT  2000
            2010       2020       2030       2040
    |....|....|....|....|....|....|....|....|....|
    TGACCCACGCCAGACCTCAGACCGGCTCTTCTTCCTGGAC  2040
    CTGAAGCAGGGCCACTACCTGCCCTTAAATGAGGCAGTCT  2080
    ACACTCGCATCTGCTCGGGCGCCTTCGCCCTCTGAAGCTG  2120
    TTCCTCTACTGGCCACAAACTCTGGGCCTGGTGGGAGAGG  2160
    CCAGCTTGAGCCAGACAGCGCTGCCCAGGGGTGGCCGCCT  2200
```

FIG. 44B

```
              2610      2620      2630      2640
     |....|....|....|....|....|....|....|....|
     GGTCAGGCTGGTCTTGAACTCCTGACCTCAGGTGATCCGC  2640
     TGGCCTCGGCCTCCCAGAGTGCTGGGATTATAGGCGTGAG  2680
     CCTCTGGCCCGGCCTTTCCTTTTCCTCTCCTCTCCTGCC   2720
     GAGAGTGGAACACACGTGTCCTGGGAGCTGCATCTTGTGT  2760
     AGGGTCCAGCTGCTTTTGGGGACTGCAGGAATCATCTCCC  2800
              2810      2820      2830      2840
     |....|....|....|....|....|....|....|....|
     CTGGGCCCTGGACTCGGACTGGGGCCTCCCCACCTCCCTC  2840
     TCGGCTGTGCCTTACGGAGCCCCAATCCAGGCCTCCTGTG  2880
     GCTGTTGGGTTCCAGATGCTGCAGCTCCATGTGACTTCCA  2920
     AGCAGGCCCTCCGCCCTCCTGCTGAATGGAGGAGCCGGG   2960
     GGTCCCCAGGCCAACTGGAAAATCTCCCAGGCTAGGCCA   3000
              3010      3020      3030      3040
     |....|....|....|....|....|....|....|....|
     ATTGCCTTTTGCACTTCCCCGTTCCTGTCACATTTCCCCA  3040
     GCCCCACCTTCCCCTCCTGATGCCCTGAAAGCTTCCGGAA  3080
     TTGACTGTGACCACTTGGATGTCACCACTGTCAGCCCCTG  3120
     CCTTGATGTCCCCATTTAGCCATCTCCATGGAGCTCCTGC  3160
     TGGAGGGCCCTGAACCCTGCACTGCGTGGCTGCCCAGCCA  3200
              3210      3220      3230      3240
     |....|....|....|....|....|....|....|....|
     GCTGCCTCCTGTCCTGGGAGGAGGCCTCCTGGGTGTCCTC  3240
     ATCTGGTGTGTCTACTGGAGGGTCCCACAGGAGAGGCAGC  3280
     AGAGGGGTCAGGGGAGGTCTCCTGCCGGGGGTTGGCCTCT  3320
     CAAGCCTCAGGGGTTCTAGCCTGTTGAATATACCCCACCT  3360
     GGTGGGTGGCCCCTCCGATGTCCCCACTGATGGCTCTGAC  3400
              3410      3420      3430      3440
     |....|....|....|....|....|....|....|....|
     ACCGTGTTGGTGGCGATGTCCCAGACAATCCCACCAGGAC  3440
     GGCCCAGACATCCCTACTGGCTTCGCTGGTGGCTCATCTC  3480
     GAACATCCACGCCAGCCTTTCTGGGGCCGGCCACCAGGC   3520
     CGCCTGTCCGTCTGTCCTCCCTCCAGCAGCACCCCCTGGC  3560
     CCCTGGAGTGGTGGGGCCATGGCAAGAGACACCGTGGCGT  3600
              3610      3620      3630      3640
     |....|....|....|....|....|....|....|....|
     CTCATGTGAACTTTCCTGGGCACTGTGGTTTTATTTCCTA  3640
     ATTGATTTAAGAAATAAACCTGAAGACCGTCTGGTGAAAA  3680
     AAAAAAAAAAAAAA                            3694
```

FIG. 44C

```
              2610        2620        2630        2640
     ....|....|....|....|....|....|....|....|....|
    GGTCAGGCTGGTCTTGAACTCCTGACCTCAGGTGATCCGC 2640
    TGGCCTCGGCCTCCCAGAGTGCTGGGATTATAGGCGTGAG 2680
    CCTCTGGCCCGGCCTTTCCTTTTCCTCTCCTCTCCTGCC  2720
    GAGAGTGGAACACACGTGTCCTGGGAGCTGCATCTTGTGT 2760
    AGGGTCCAGCTGCTTTTGGGGACTGCAGGAATCATCTCCC 2800
              2810        2820        2830        2840
     ....|....|....|....|....|....|....|....|....|
    CTGGGCCCTGGACTCGGACTGGGGCCTCCCCACCTCCCTC 2840
    TCGGCTGTGCCTTACGGAGCCCCAATCCAGGCCTCCTGTG 2880
    GCTGTTGGGTTCCAGATGCTGCAGCTCCATGTGACTTCCA 2920
    AGCAGGCCCTCCGCCCTCCCTGCTGAATGGAGGAGCCGGG 2960
    GGTCCCCAGGCCAACTGGAAAATCTCCCAGGCTAGGCCA  3000
              3010        3020        3030        3040
     ....|....|....|....|....|....|....|....|....|
    ATTGCCTTTTGCACTTCCCCGTTCCTGTCACATTTCCCCA 3040
    GCCCCACCTTCCCCTCCTGATGCCCTGAAAGCTTCCGGAA 3080
    TTGACTGTGACCACTTGGATGTCACCACTGTCAGCCCCTG 3120
    CCTTGATGTCCCCATTTAGCCATCTCCATGGAGCTCCTGC 3160
    TGGAGGGCCCTGAACCCTGCACTGCGTGGCTGCCCAGCCA 3200
              3210        3220        3230        3240
     ....|....|....|....|....|....|....|....|....|
    GCTGCCTCCTGTCCTGGGAGGAGGCCTCCTGGGTGTCCTC 3240
    ATCTGGTGTGTCTACTGGAGGGTCCCACAGGAGAGGCAGC 3280
    AGAGGGGTCAGGGGAGGTCTCCTGCCGGGGGTTGGCCTCT 3320
    CAAGCCTCAGGGGTTCTAGCCTGTTGAATATACCCCACCT  3360
    GGTGGGTGGCCCCTCCGATGTCCCCACTGATGGCTCTGAC 3400
              3410        3420        3430        3440
     ....|....|....|....|....|....|....|....|....|
    ACCGTGTTGGTGGCGATGTCCCAGACAATCCCACCAGGAC 3440
    GGCCCAGACATCCCTACTGGCTTCGCTGGTGGCTCATCTC 3480
    GAACATCCACGCCAGCCTTTCTGGGGCCGGCCACCCAGGC 3520
    CGCCTGTCCGTCTGTCCTCCCTCCAGCAGCACCCCCTGGC 3560
    CCCTGGAGTGGTGGGGCCATGGCAAGAGACCGTGGCCGT  3600
              3610        3620        3630        3640
     ....|....|....|....|....|....|....|....|....|
    CTCATGTGAACTTTCCTGGGCACTGTGGTTTTATTTCCTA 3640
    ATTGATTTAAGAAATAAACCTGAAGACCGTCTGGTGAAAA 3680
    AAAAAAAAAAAAAA                           3694
```

FIG. 44D hsFATP1 full length protein

```
          10         20         30         40
MRAPGAGAASVVSLALLWLLGLPWTWSAAAALGVYVGSGG   40
WRFLRIVCKTARRDLFGLSVLIRVRLELRRHQRAGHTIPR   80
IFQAVVQRQPERLALVDAGTGECWTFAQLDAYSNAVANLF  120
RQLGFAPGDVVAIFLEGRPEFVGLWLGLAKAGMEAALLNV  160
NLRREPLAFCLGTSGAKALIFGGEMVAAVAEVSGHLGKSL  200
          210        220        230        240
IKFCSGDLGPEGILPQTHLLDPLLKEASTAPLAQIPSKGM  240
DDRLFYIYTSGTTGLPKAAIVVHSRYYRMAAFGHHAYRMQ  280
AADVLYDCLPLYHSAGNIIGVGQCLIYGLTVVLRKKFSAS  320
RFWDDCIKYNCTVVQYIGEICRYLLKQPVREAERRHRVRL  360
AVGNGLRPAIWEEFTERFGVRQIGEFYGATECNCSIANMD  400
          410        420        430        440
GKVGSCGFNSRILPHVYPIRLVKVNEDTMELLRDAQGLCI  440
PCQAGEPGLLVGQINQQDPLRRFDGYVSESATSKKIAHSV  480
FSKGDSAYLSGDVLVMDELGYMYFRDRSGDTFRWRGENVS  520
TTEVEGVLSRLLGQTDVAVYGVAVPGVEGKAGMAAVADPH  560
SLLDPNAIYQELQKVLAPYARPIFLRLLPQVDTTGTFKIQ  600
          610        620        630        640
KTRLQREGFDPRQTSDRLFFLDLKQGHYLPLNEAVYTRIC  640
SGAFAL  646
```

FIG. 45

Hs VLACS full length DNA

```
         10        20        30        40
GGAATTCCAAAAAAAAAAAATACGACTACACCTGCTCCGG  40
AGCCCGCGGCGGTACCTGCAGCGGAGGAGCTCTGTCTTCC  80
CCTTCATCTCACGCGAGCCCGGCGTCCCGCCGCGTGCGCC  120
CCGGCGCAGCCCGCCAGTCCGCCCGGAGCCCGCCCAGTCG  160
CCGCGCTGCACGCCCGGGGTGAACCCTCTGCCCTCGCTGG  200
         210       220       230       240
GACAGAGGGCCCCGCAGCCGTCATGCTTTCCGCCATCTAC  240
ACAGTCCTGGCGGGACTGCTGTTCCTGCCGCTCCTGGTGA  280
ACCTCTGCTGCCCATACTTCTTCCAGGACATAGGCTACTT  320
CTTGAAGGTGGCCGCCGTGGGCCGGAGGGTGCGCAGCTAC  360
GGGCAGCGGCGGCCGGCGCGCACCATCCTGCGGGCGTTCC  400
         410       420       430       440
TGGAGAAAGCGCGCCAGACGCCACACAAGCCTTTTCTGCT  440
CTTCCGCGACGAGACTCTCACCTACGCGCAGGTGGACCGG  480
CGCAGCAATCAAGTGGCCCGGGCGCTGCACGACCACCTCG  520
GCCTGCGCCAGGGAGACTGCGTGGCGCTCCTTATGGGTAA  560
CGAGCCGGCCTACGTGTGGCTGTGGCTGGGGCTGGTGAAG  600
         610       620       630       640
CTGGGCTGTGCCATGGCGTGCCTCAATTACAACATCCGCG  640
CGAAGTCCCTGCTGCACTGCTTCCAGTGCTGCGGGGCGAA  680
GGTGCTGCTGGTGTCGCCAGAACTACAAGCAGCTGTCGAA  720
GAGATACTGCCAAGCCTTAAAAAAGATGATGTGTCCATCT  760
ATTATGTGAGCAGAACTTCTAACACAGATGGGATTGACTC  800
         810       820       830       840
TTTCCTGGACAAAGTGGATGAAGTATCAACTGAACCTATC  840
CCAGAGTCATGGAGGTCTGAAGTCACTTTTTCCACTCCTG  880
CCTTATACATTTATACTTCTGGAACCACAGGTCTTCCAAA  920
AGCAGCCATGATCACTCATCAGCGCATATGGTATGGAACT  960
GGCCTCACTTTTGTAAGCGGATTGAAGGCAGATGATGTCA  1000
         1010      1020      1030      1040
TCTATATCACTCTGCCCTTTTACCACAGTGCTGCACTACT  1040
GATTGGCATTCACGGATGTATTGTGGCTGGTGCTACTCTT  1080
GCCTTGCGGACTAAATTTTCAGCCAGCCAGTTTTGGGATG  1120
ACTGCAGAAAATACAACGTCACTGTCATTCAGTATATCGG  1160
TGAACTGCTTCGGTATTTATGCAACTCACCACAGAAACCA  1200
```

FIG. 46A

```
            1210      1220      1230      1240
     ┬┴┴┴┴┬┴┴┴┴┬┴┴┴┴┬┴┴┴┴┬┴┴┴┴┬┴┴┴┴┬┴┴┴┴┬┴┴┴┴┬
AATGACCGTGATCATAAAGTGAGACTGGCACTGGGAAATG  1240
GCTTACGAGGAGATGTGTGGAGACAATTTGTCAAGAGATT  1280
TGGGGACATATGCATCTATGAGTTCTATGCTGCCACTGAA  1320
GGCAATATTGGATTTATGAATTATGCGAGAAAGTTGGTG   1360
CTGTTGGAAGAGTAAACTACCTACAGAAAAAATCATAAC   1400
            1410      1420      1430      1440
     ┬┴┴┴┴┬┴┴┴┴┬┴┴┴┴┬┴┴┴┴┬┴┴┴┴┬┴┴┴┴┬┴┴┴┴┬┴┴┴┴┬
TTATGACCTGATTAAATATGATGTGGAGAAAGATGAACCT  1440
GTCCGAGATGAAAATGGATATTGCGTCAGAGTTCCCAAAG  1480
GTGAAGTTGGACTTCTGGTTTGCAAAATCACACAACTTAC  1520
ACCATTTAATGGCTATGCTGGAGCAAAGGCTCAGACAGAG  1560
AAGAAAAAACTGAGAGATGTCTTTAAGAAAGGAGACCTCT  1600
            1610      1620      1630      1640
     ┬┴┴┴┴┬┴┴┴┴┬┴┴┴┴┬┴┴┴┴┬┴┴┴┴┬┴┴┴┴┬┴┴┴┴┬┴┴┴┴┬
ATTTCAACAGTGGAGATCTCTTAATGGTTGACCATGAAAA  1640
TTTCATCTATTTCCACGACAGAGTTGGAGATACATTCCGG  1680
TGGAAAGGGGAAAATGTGGCCACCACTGAAGTTGCTGATA  1720
CAGTTGGACTGGTTGATTTTGTCCAAGAAGTAAATGTTTA  1760
TGGAGTGCATGTGCCAGATCATGAGGGTCGCATTGGCATG  1800
            1810      1820      1830      1840
     ┬┴┴┴┴┬┴┴┴┴┬┴┴┴┴┬┴┴┴┴┬┴┴┴┴┬┴┴┴┴┬┴┴┴┴┬┴┴┴┴┬
GCCTCCATCAAAATGAAAGAAAACCATGAATTTGATGGAA  1840
AGAAACTCTTTCAGCACATTGCTGATTACCTACCTAGTTA  1880
TGCAAGGCCCCGGTTTCTAAGAATACAGGACACCATTGAG  1920
ATCACTGGAACTTTTAAACACCGCAAAATGACCCTGGTGG  1960
AGGAGGGCTTTAACCCTGCTGTCATCAAAGATGCCTTGTA  2000
            2010      2020      2030      2040
     ┬┴┴┴┴┬┴┴┴┴┬┴┴┴┴┬┴┴┴┴┬┴┴┴┴┬┴┴┴┴┬┴┴┴┴┬┴┴┴┴┬
TTTCTTGGATGACACAGCAAAAATGTATGTGCCTATGACT  2040
GAGGACATCTATAATGCCATAAGTGCTAAAACCCTGAAAC  2080
TCTGAATATTCCCAGGAGGATAACTCAACATTTCCAGAAA  2120
GAAACTGAATGGACAGCCACTTGATATAATCCAACTTTAA  2160
TTTGATTGAAGATTGTGAGGAAATTTTGTAGGAAATTTGC  2200
            2210      2220      2230      2240
     ┬┴┴┴┴┬┴┴┴┴┬┴┴┴┴┬┴┴┴┴┬┴┴┴┴┬┴┴┴┴┬┴┴┴┴┬┴┴┴┴┬
ATACCCGTAAAGGGAGACTTTTTTAAATAACAGTTGAGTC  2240
TTTGCAAGTAAAAAGATTTAGAGATTATTATTTTTCAGTG  2280
TGCACCTACTGTTTGTATTTGCAAACTGAGCTTGTTGGAG  2320
GGAAGGCATTATTTTTTAAAATACTTAGTAAATTAAATGA  2360
AC                                        2362
```

FIG. 46B hs VLACS full length protein

```
         10         20         30         40
         |          |          |          |
MLSAIYTVLAGLLFLPLLVNLCCPYFFQDIGYFLKVAAVG    40
RRVRSYGQRRPARTILRAFLEKARQTPHKPFLLFRDETLT    80
YAQVDRRSNQVARALHDHLGLRQGDCVALLMGNEPAYVWL   120
WLGLVKLGCAMACLNYNIRAKSLLHCFQCCGAKVLLVSPE   160
LQAAVEEILPSLKKDDVSIYYVSRTSNTDGIDSFLDKVDE   200
        210        220        230        240
         |          |          |          |
VSTEPIPESWRSEVTFSTPALYIYTSGTTGLPKAAMITHQ   240
RIWYGTGLTFVSGLKADDVIYITLPFYHSAALLIGIHGCI   280
VAGATLALRTKFSASQFWDDCRKYNVTVIQYIGELLRYLC   320
NSPQKPNDRDHKVRLALGNGLRGQVWRQFVKRFGDICIYE   360
FYAATEGNIGFMNYARKVGAVGRVNYLQKKIITYDLIKYD   400
        410        420        430        440
         |          |          |          |
VEKDEPVRDENGYCVRVPKGEVGLLVCKITQLTPFNGYAG   440
AKAQTEKKKLRDVFKKGDLYFNSGDLLMVDHENFIYFHDR   480
VGDTFRWKGENVATTEVADTVGLVDFVQEVNVYGVHVPDH   520
EGRIGMASIKMKENHEFDGKKLFQHIADYLPSYARPRFLR   560
IQDTIEITGTFKHRKMTLVEEGFNPAVIKDALYFLDDTAK   600
        610        620        630        640
         |          |          |          |
MYVPMTEDIYNAISAKTLKL    620
```

FIG. 47 hsFATP3 partial DNA

```
          10        20        30        40
AAGTTCTCGGCTGGTCAGTTCTGGGAAGATTGCCAGCAGC  40
ACAGGGTGACGGTGTTCCAGTACATTGGGGAGCTGTGCCG  80
ATACCTTGTCAACCAGCCCCGAGCAAGGCAGAACGTGGC  120
CATAAGGTCCGGCTGGCAGTGGGCAGCGGGCTGCGCCCAG 160
ATACCTGGGAGCGTTTTGTGCGGCGCTTCGGGCCCCTGCA 200
         210       220       230       240
GGTGCTGGAGACATATGGACTGACAGAGGGCAACGTGGCC 240
ACCATCAACTACACAGGACAGCGGGGCGCTGTGGGCGTG  280
CTTCCTGGCTTTACAAGCATATCTTCCCCTTCTCCTTGAT 320
TCGCTATGATGTCACCACAGGAGAGCCAATTCGGGACCCC 360
CAGGGGCACTGTATGGCCACATCTCCAGGTGAGCCAGGGC 400
         410       420       430       440
TGCTGGTGGCCCCGGTAAGCCAGCAGTCCCCATTCCTGGG 440
CTATGCTGGCGGGCCAGAGCTGGCCCAGGGGAAGTTGCTA 480
AAGGATGTCTTCCGGCCTGGGGATGTTTTCTTCAACACTG 520
GGGACCTGCTGGTCTGCGATGACCAAGGTTTTCTCCGCTT 560
CCATGATCGTACTGGAGACACCTTCAGGTGGAAGGGGGAG 600
         610       620       630       640
AATGTGGCCACAACCGAGGTGGCAGAGGTCTTCGAGGCCC 640
TAGATTTTCTTCAGGAGGTGAACGTCTATGGAGTCACTGT 680
GCCAGGGCATGAAGGCAGGGCTGGAATGGCAGCCCTAGTT 720
CTGCGTCCCCCCCACGCTTTGGACCTTATGCAGCTCTACA 760
CCCACGTGTCTGAGAACTTGCCACCTTATGCCCGGCCCCG 800
         810       820       830       840
ATTCCTCAGGCTCCAGGAGTCTTTGGCCACCACAGAGACC 840
TTCAAACAGCAGAAAGTTCGGATGGCAAATGAGGGCTTCG 880
ACCCCAGCACCCTGTCTGACCCACTGTACGTTCTGGACCA 920
GGCTGTAGGTGCCTACCTGCCCCTCACAACTGCCCGGTAC 960
AGCGCCCTCCTGGCAGGAAACCTTCGAATCTGAGAACTTC 1000
        1010      1020      1030      1040
CACACCTGAGGCACCTGAGAGAGGAACTCTGTGGGGTGGG 1040
GGCCGTTGCAGGTGTACTGGGCTGTCAGGGATCTTTTCTA 1080
TACCAGAACTGCGGTCACTATTTTGTAATAAATGTGGCTG 1120
GAGCTGATCCAGCTGTCTCTGACAAAAAAAAAAAAAAAA  1160
AAAGGGCGGCCGC 1173
```

FIG. 48 hsFATP3 partial protein

```
         10        20        30        40
KFSAGQFWEDCQQHRVTVFQYIGELCRYLVNQPPSKAERG  40
HKVRLAVGSGLRPDTWERFVRRFGPLQVLETYGLTEGNVA  80
TINYTGQRGAVGRASWLYKHIFPFSLIRYDVTTGEPIRDP 120
QGHCMATSPGEPGLLVAPVSQQSPFLGYAGGPELAQGKLL 160
KDVFRPGDVFFNTGDLLVCDDQGFLRFHDRTGDTFRWKGE 200
        210       220       230       240
NVATTEVAEVFEALDFLQEVNVYGVTVPGHEGRAGMAALV 240
LRPPHALDLMQLYTHVSENLPPYARPRFLRLQESLATTET 280
FKQQKVRMANEGFDPSTLSDPLYVLDQAVGAYLPLTTARY 320
SALLAGNLRI    330
```

FIG. 49 hsFATP4 full length

```
         10        20        30        40
CGACCCACGCGTCCGGGCGGGCGGGGCCGGGCGGCGGGCG   40
GGGCTGGCGGGGCGGCCGGGCCATGCAGGGCGCAGAGCCG   80
GCTAAACCCTGCTGAGACCCGGCTCCGTGCGTCCAGGGGC  120
GGCTAATGCCCCTCACGCTGTCTACGCTGCTGCAACCGGG  160
CCGCATCTGGACGGGGCGCCGCGCGGCGGAGCCGACGCCG  200
        210       220       230       240
GGCCACAATGCTGCTTGGAGCCTCTCTGGTGGGGGTGCTG  240
CTGTTCTCCAAGCTGGTGCTGAAACTGCCCTGGACCCAGG  280
TGGGATTCTCCCTGTTGTTCCTCTACTTGGGATCTGGCGG  320
CTGGCGCTTCATCCGGGTCTTCATCAAGACCATCAGGCGC  360
GATATCTTTGGCGGCCTGGTCCTCCTGAAGGTGAAGGCAA  400
        410       420       430       440
AGGTGCGACAGTGCCTGCAGGAGCGGCGGACAGTGCCCAT  440
TTTGTTTGCCTCTACCGTTCGGCGCCACCCCGACAAGACG  480
GCCCTGATCTTCGAGGGCACAGATACCCACTGGACCTTCC  520
GCCAGCTGGATGAGTACTCAAGCAGTGTAGCCAACTTCCT  560
GCAGGCCCGGGGCCTGGCCTCGGGCGATGTGGCTGCCATC  600
        610       620       630       640
TTCATGGAGAACCGCAATGAGTTCGTGGGCCTATGGCTGG  640
GCATGGCCAAGCTCGGTGTGGAGGCAGCCCTCATCAACAC  680
CAACCTGCGGCGGGATGCTCTGCTCCACTGCCTCACCACC  720
TCGCGCGCACGGGCCCTTGTCTTTGGCAGCGAAATGGCCT  760
CAGCCATCTGTGAGGTCCATGCCAGCCTGGACCCCTCGCT  800
        810       820       830       840
CAGCCTCTTCTGCTCTGGCTCCTGGGAGCCCGGTGCGGTG  840
CCTCCAAGCACAGAACACCTGGACCCTCTGCTGAAAGATG  880
CTCCCAAGCACCTTCCCAGTTGCCCTGACAAGGGCTTCAC  920
AGATAAACTGTTCTACATCTACACATCCGGCACCACAGGG  960
CTGCCCAAGGCCGCCATCGTGGTGCACAGCAGGTATTACC 1000
       1010      1020      1030      1040
GCATGGCTGCCCTGGTGTACTATGGATTCCGCATGCGGCC 1040
CAACGACATCGTCTATGACTGCCTGCCCCTCTACCACTCA 1080
GCAGGAAACATCGTGGGAATCGGCCAGTGCCTGCTGCATG 1120
GCATGACGGTGGTGATTCGGAAGAAGTTCTCAGCCTCCCG 1160
GTTCTGGGACGATTGTATCAAGTACAACTGCACGATTGTG 1200
```

FIG. 50A

```
              1210      1220      1230      1240
         ┴┴┴┴┴┴┴┴┴┴┴┴┴┴┴┴┴┴┴┴┴┴┴┴┴┴┴┴┴┴┴┴┴┴┴┴┴
         CAGTACATTGGTGAACTGTGCCGCTACCTCCTGAACCAGC 1240
         CACCGCGGGAGGCAGAAAACCAGCACCAGGTTCGCATGGC 1280
         ACTAGGCAATGGCCTCCGGCAGTCCATCTGGACCAACTTT 1320
         TCCAGCCGCTTCCACATACCCCAGGTGGCTGAGTTCTACG 1360
         GGGCCACAGAGTGCAACTGTAGCCTGGGCAACTTCGACAG 1400
              1410      1420      1430      1440
         ┴┴┴┴┴┴┴┴┴┴┴┴┴┴┴┴┴┴┴┴┴┴┴┴┴┴┴┴┴┴┴┴┴┴┴┴┴
         CCAGGTGGGGGCCTGTGGTTTCAATAGCCGCATCCTGTCC 1440
         TTCGTGTACCCCATCCGGTTGGTACGTGTCAACGAGGACA 1480
         CCATGGAGCTGATCCGGGGGCCCGACGGCGTCTGCATTCC 1520
         CTGCCAGCCAGGTGAGCCGGGCCAGCTGGTGGGCCGCATC 1560
         ATCCAGAAAGACCCCCTGCGCCGCTTCGATGGCTACCTCA 1600
              1610      1620      1630      1640
         ┴┴┴┴┴┴┴┴┴┴┴┴┴┴┴┴┴┴┴┴┴┴┴┴┴┴┴┴┴┴┴┴┴┴┴┴┴
         ACCAGGGCGCCAACAACAAGAAGATTGCCAAGGATGTCTT 1640
         CAAGAAGGGGGACCAGGCCTACCTTACTGGTGATGTGCTG 1680
         GTGATGGACGAGCTGGGCTACCTGTACTTCGAGACCGCA 1720
         CTGGGGACACGTTCCGCTGGAAAGGTGAGAACGTGTCCAC 1760
         CACCGAGGTGGAAGGCACACTCAGCCGCCTGCTGGACATG 1800
              1810      1820      1830      1840
         ┴┴┴┴┴┴┴┴┴┴┴┴┴┴┴┴┴┴┴┴┴┴┴┴┴┴┴┴┴┴┴┴┴┴┴┴┴
         GCTGACGTGGCCGTGTATGGTGTCGAGGTGCCAGGAACCG 1840
         AGGGCCGGGCCGGAATGGCTGCTGTGGCCAGCCCCACTGG 1880
         CAACTGTGACCTGGAGCGCTTTGCTCAGGTCTTGGAGAAG 1920
         GAACTGCCCCTGTATGCGCGCCCCATCTTCCTGCGCCTCC 1960
         TGCCTGAGCTGCACAAAACAGGAACCTACAAGTTCCAGAA 2000
              2010      2020      2030      2040
         ┴┴┴┴┴┴┴┴┴┴┴┴┴┴┴┴┴┴┴┴┴┴┴┴┴┴┴┴┴┴┴┴┴┴┴┴┴
         GACAGAGCTACGGAAGGAGGGCTTTGACCCGGCTATTGTG 2040
         AAAGACCCGCTGTTCTATCTAGATGCCCAGAAGGGCCGCT 2080
         ACGTCCGCTGGACCAAGAGGCCTACAGCCGCATCCAGGC 2120
         AGGCGAGGAGAAGTGTGATTCCCCCATCCCTCTGAGGG 2160
         CCGGCGGATGCTGATCCGGAGCCCCAGGTTCCGCCCCAG 2200
```

FIG. 50B

```
              2210      2220      2230      2240
         |....|....|....|....|....|....|....|....|
         AGCGGTCCTGGACAAGGCCAGACCAAAGCAAGCAGGGCCT 2240
         GGCACCTCCATCCTGAGGTGCTGCCCCTCCATCCAAAACT 2280
         GCCAAGTGACTCATTGCCTTCCCAACCCTTCCAGAGGCTT 2320
         TCTGTGAAAGTCTCATGTCCAAGTTCCGTCTTCTGGGCTG 2360
         GGCAGGCCCTCTGGTTCCCAGGCTGAGACTGACGGGTTTT 2400
              2410      2420      2430      2440
         |....|....|....|....|....|....|....|....|
         CTCAGGATGATGTCTTGGGTGAGGGTAGGGAGAGGACAAG 2440
         GGGTCACCGAGCCCTTCCCAGAGAGCAGGGAGCTTATAAA 2480
         TGGAACCAGAGCAGAAGTCCCCAGACTCAGGAAGTCAACA 2520
         GAGTGGGCAGGGACAGTGGTAGCATCCATCTGGTGGCCAA 2560
         AGAGAATCGTAGCCCCAGAGCTGCCCAAGTTCACTGGGCT 2600
              2610      2620      2630      2640
         |....|....|....|....|....|....|....|....|
         CCACCCCCACCTCCAGGAGGGGAGGAGAGGACCTGACATC 2640
         TGTAGGTGGCCCCTGATGCCCCATCTACAGCAGGAGGTCA 2680
         GGACCACGCCCTGGCCTCTCCCCACTCCCCCATCCTCCT 2720
         CCCTGGGTGGCTGCCTGATTATCCCTCAGGCAGGGCCTCT 2760
         CAGTCCTTGTGGGTCTGTGTCACCTCCATCTCAGTCTTGG 2800
              2810      2820      2830      2840
         |....|....|....|....|....|....|....|....|
         CCTGGCTATGAGGGGAGGAGGAATGGGAGAGGGGGCTCAG 2840
         GGGCCAATAAACTCTGCCTTGAGTCCTCCTAAAAAAAAA 2880
         AAAAAAAAAAAAAAAAAAAAAAAAAA 2907
```

FIG. 50C hsFATP4 full length protein

```
          10        20        30        40
  ┴┴┴┴┴┴┴┴┴┴┴┴┴┴┴┴┴┴┴┴┴┴┴┴┴┴┴┴┴┴┴┴┴┴┴┴┴┴┴┴
MLLGASLVGVLLFSKLVLKLPWTQVGFSLLFLYLGSGGWR   40
FIRVFIKTIRRDIFGGLVLLKVKAKVRQCLQERRTVPILF   80
ASTVRRHPDKTALIFEGTDTHWTFRQLDEYSSSVANFLQA  120
RGLASGDVAAIFMENRNEFVGLWLGMAKLGVEAALINTNL  160
RRDALLHCLTTSRARALVFGSEMASAICEVHASLDPSLSL  200
         210       220       230       240
FCSGSWEPGAVPPSTEHLDPLLKDAPKHLPSCPDKGFTDK  240
LFYIYTSGTTGLPKAAIVVHSRYYRMAALVYYGFRMRPND  280
IVYDCLPLYHSAGNIVGIGQCLLHGMTVVIRKKFSASRFW  320
DDCIKYNCTIVQYIGELCRYLLNQPPREAENQHQVRMALG  360
NGLRQSIWTNFSSRFHIPQVAEFYGATECNCSLGNFDSQV  400
         410       420       430       440
GACGFNSRILSFVYPIRLVRVNEDTMELIRGPDGVCIPCQ  440
PGEPGQLVGRIIQKDPLRRFDGYLNQGANNKKIAKDVFKK  480
GDQAYLTGDVLVMDELGYLYFRDRTGDTFRWKGENVSTTE  520
VEGTLSRLLDMADVAVYGVEVPGTEGRAGMAAVASPTGNC  560
DLERFAQVLEKELPLYARPIFLRLLPELHKTGTYKFQKTE  600
         610       620       630       640
LRKEGFDPAIVKDPLFYLDAGKGRYVPLDQEAYSRIQAGE  640
EKL 643
```

FIG. 51 hsFATP5(partial)

```
GTCGTTGGGATCCTCGGCTGCTTAGATCTCGGAGCCACCTGTGTTCT
GGCCCCCAAGTTCTCTACTTCCTGCTTCTGGGATGACTGTCGGCAGC
ATGGCGTGACAGTGATCCTGTATGTGGGCGAGCTCCTGCGATACTTG
TGTAACATTCCCCAGCAACCAGAGGACCGGACACATACAGTCCGCC
TGGCAATGGGCAATGGACTACGGGCTGATGTGTGGGGAGACCTTCC
AGCAGCGTTTCGGTCCTATTTCGGATCTNGGGAAGTCTTACGGGCTT
CCACAGAAGGGCAACATGGGGCTTTAGTTCAAATATTGTTGGGGGC
GCTGCGGGGCCCTGGGGGCAAAGATGGAGCTTGCCTCCTCGAATG
CTGTCCCCCTTTGAGCTGGTGCAGTTCGACATGGAGGCGGCGGAGC
CTGTGAGGGACAATCAGGGCTTCTGCATCCCTGTAGGGCTAGGGGA
GCCGGGGCTGCTGTTGACCAAGGTGGTAAGCCAGCAACCCTTCGTG
GGCTACCGCGGCCCCCGAGAGCTGTCGGAACGGAAGCTGGTGCGCA
ACGTGCGGCAATCGGGCGACGTTTACTACAACACCGGGGACGTACT
GGCCATGGACCGCGAAGGCTTCCTCTACTTCCGCGACCGACTCGGG
GACACCTTCCGATGGAAGGGCGAGAACGTGTCCACGCACGAGGTGG
AGGGCGTGTTGTCGCAGGTGGACTTCTTGCAACAGGTTAACGTGTAT
GGCGTGTGCGTGCCAGGTTGTGAGGGTAAGGTGGGCATGGCTGCTG
TGGCATTAGCCCCCGGCCAGACTTCGACGGGGAGAAGTTGTACCA
GCACGTTCGCGCTTGGCTCCCTGCCTACGCTACCCCCATTTCATCC
GCATCCAGGACGCCATGGAGGTCACCAGCACGTTCAAACTGATGAA
GACCCGGTTGGTGCGTGAGGGCTTCAATGTGGGGATCGTGGTTGAC
CCTCTGTTTGTACTGGACAACCGGGCCCAGTCCTTCCGGCCCCTGAC
GGCAGAAATGTACCAGGCTGTGTGTGAGGGAACCTGGAGGCTCTGA
TCACCTGGCCAACCCACTGGGGTAGGGATCAAAGCCAGCCACCCCC
ACCCCAACACACTCGGTGTCCCTTTCATCCTGGGCCTGTGTGAATCC
CAGCCTGGCCATACCCTCAACCTCAGTGGGCTGGAAATGACAGTGG
GCCCTGTAGCAGTGGCAGAATAAACTCAGMTGYGTTCACAGAAA
```

FIG. 52 hsFATP5 partial protein

```
         10        20        30        40
VVGILGCLDLGATCVLAPKFSTSCFWDDCRQHGVTVILYV  40
GELLRYLCNIPQQPEDRTHTVRLAMGNGLRADVWGDLPAA  80
FRSYFGSXEVLRASTEGQHGALVQILLGALRGPGGKDGAC  120
LLRMLSPFELVQFDMEAAEPVRDNQGFCIPVGLGEPGLLL  160
TKVVSQQPFVGYRGPRELSERKLVRNVRQSGDVYYNTGDV  200
        210       220       230       240
LAMDREGFLYFRDRLGDTFRWKGENVSTHEVEGVLSQVDF  240
LQQVNVYGVCVPGCEGKVGMAAVALAPGQTFDGEKLYQHV  280
RAWLPAYATPHFIRIQDAMEVTSTFKLMKTRLVREGFNVG  320
IVVDPLFVLDNRAQSFRPLTAEMYQAVCEGTWRL  354
```

FIG. 53 hsFATP6 full length DNA

```
         10        20        30        40
AACGGCAAGTAAGCGCAACGCAATTAATGTGAGTAGCTCA  40
CTCATTAGGCACCCCAGGCTTTACACTTTATGCTTCCGGG  80
CTCGTATGTTGTGTGGAATTGTGAGCGGATACCAATTTCA  120
CACAGGAACCAGCTATGACATGATTACGAATTTAATACGA  160
CTCACTATAGGGAATTTGGCCCTCGAGGCCAAGAATTCGG  200
        210       220       230       240
CACGAGGGGTGCTGAGCCCCTGCGCGGTTTCTGGTGCGTA  240
GAGACTGTAAATCGCTGCGCTTCTCAGTCATCATCATCCC  280
AGCTTTTCCCGGCTCGAATTCAGCCTCCAACTCAAGCTCG  320
CGGGAAAGACTACCTGAGAGGAGAAAAGCTTCTGTCCCTG  360
GACCTTCTTCTGAGGGTGGAGTCGGAGGCTCCCTGCTTTC  400
        410       420       430       440
CAGCCGCCCAGTGACCCAAGCTTAATCTTCAGCACCACTT  440
GGGGCGACCTTTTCGGTGCAAACCTACGATTCTGTTTCTC  480
AGGATTCCTCCCCATCCCGCTTCGCCCCGGAAAAGCTGAC  520
AAGAACTTCAGGTGTAAGCCCTGAGTAGTGAGGATCTGCG  560
GTCTCCGTGGAGAGCTGTGCCTGGAAGAGAAGGACGCTGG  600
        610       620       630       640
TGGGGCTGAGATCAGAGCTGTCTTCTGGCCCAGTTGCCC   640
CCATGCTTCTGTCATGGCTAACAGTTCTAGGGGCTGGAAT  680
GGTCGTCCTGCACTTCTTGCAG-AACTCCTGTTCCCTTAC  720
TTTTGGGATGACTTCTGGTTCGTGTTGAAGGTGGTGCTCA  760
TTATAATTCGGCTGAAGAAGTATGAAAAGAGAGGGAGCT   800
        810       820       830       840
GGTGACTGTGCTGGATAAATTCTTGAGTCATGCCAAAAGA  840
CAACCTCGGAAACCTTTCATCATCTATGAGGGAGACATCT  880
ACACCTATCAGGATGTAGACAAAAGGAGCAGCAGAGTGGC  920
CCATGTCTTCCTGAACCATTCCTCTCTGAAAAAGGGGGAC  960
ACGGTGGCTCTGCTGATGAGCAATGAGCCGGACTTCGTTC 1000
        1010      1020      1030      1040
ACGTGTGGTTCGGCCTCGCCAAGCTGGGCTGCGTGGTGGC 1040
CTTTCTCAACACCAACATTCGCTCCAACTCCCTCCTGAAT 1080
TGCATCCGCGCCTGTGGCCCAGAGCCCTAGTGGTGGGCG  1120
CAGATTTGCTTGGAACGGTAGAAGAAATCCTTCCAAGCCT 1160
CTCAGAAAATATCAGTGTTTGGGGATGAAAGATTCTGTT  1200
```

FIG. 54A hsFATP6 full lenght.DNA

```
          1210      1220      1230      1240
     |....|....|....|....|....|....|....|....|
CCACAAGGTGTAATTTCACTCAAAGAAAAACTGAGCACCT 1240
CACCTGATGAGCCCGTGCCACGCAGCCACCATGTTGTCTC 1280
ACTCCTCAAGTCTACTTGTCTTTACATTTTTACCTCTGGA 1320
ACAACAGGTCTACCAAAAGCAGCTGTGATTAGTCAGCTGC 1360
AGGTTTTAAGGGGTTCTGCTGTCCTGTGGGCTTTTGGTTG 1400
          1410      1420      1430      1440
     |....|....|....|....|....|....|....|....|
TACTGCTCATGACATTGTTTATATAACCCTTCCTCTGTAT 1440
CATAGTTCAGCAGCTATCCTGGGAATTTCTGGATGTGTTG 1480
AGTTGGGTGCCACTTGTGTGTTAAAGAAGAAATTTTCAGC 1520
AAGCCAGTTTTGGAGTGACTGCAAGAAGTATGATGTGACT 1560
GTGTTTCAGTATATTGGAGAACTTTGTCGCTACCTTTGCA 1600
          1610      1620      1630      1640
     |....|....|....|....|....|....|....|....|
AACAATCTAAGAGAGAAGGAGAAAAGGATCATAAGGTGCG 1640
TTTGGCAATTGGAAATGGCATACGGAGTGATGTATGGAGA 1680
GAATTTTTAGACAGATTTGGAAATATAAAGGTGTGTGAAC 1720
TTTATGCAGCTACCGAATCAAGCATATCTTTCATGAACTA 1760
CACTGGGAGAATTGGAGCAATTGGGAGAACAAATTTGTTT 1800
          1810      1820      1830      1840
     |....|....|....|....|....|....|....|....|
TACAAACTTCTTTCCACTTTTGACTTAATAAAGTATGACT 1840
TTCAGAAAGATGAACCCATGAGAAATGAGCAGGGTTGGTG 1880
TATTCATGTGAAAAAAGGAGAACCTGGACTTCTCATTTCT 1920
CGAGTGAATGCAAAAAATCCCTTCTTTGGCTATGCTGGGC 1960
CTTATAAGCACACAAAAGACAAATTGCTTTGTGATGTTTT 2000
          2010      2020      2030      2040
     |....|....|....|....|....|....|....|....|
TAAGAAGGGAGATGTTTACCTTAATACTGGAGACTTAATA 2040
GTCCAGGATCAGGACAATTTCCTTTATTTTTGGGACCGTA 2080
CTGGAGACACTTTCAGATGGAAAGGAGAAAATGTCGCAAC 2120
CACTGAGGTTGCTGATGTTATTGGAATGTTGGATTTCATA 2160
CAGGAAGCAAACGTCTATGGTGTGGCTATATCAGGTTATG 2200
          2210      2220      2230      2240
     |....|....|....|....|....|....|....|....|
AAGGAAGAGCAGGAATGGCTTCTATTATTTTAAAACCAAA 2240
TACATCTTTAGATTTGGAAAAAGTTTATGAACAAGTTGTA 2280
ACATTTCTACCAGCTTATGCTTGTCCACGATTTTTAAGAA 2320
TTCAGGAAAAAATGGAAGCAACAGGAACATTCAAACTATT 2360
GAAGCATCAGTTGGTGGAAGATGGATTTAATCCACTGAAA 2400
          2410      2420      2430      2440
     |....|....|....|....|....|....|....|....|
ATTTCTGAACCACTTTACTTCATGGATAACTTGAAAAAGT 2440
CTTATGTTCTACTGACCAGGGAACTTTATGATCAAATAAT 2480
GTTAGGGGAAATAAAACTTTAAGATTTTTATATCTAGAAC 2520
TTTCATATGCTTTCTTAGGAAGAGTGAGAGGGGGGTATAT 2560
GATTCTTTATGAAATGGGGAAAGGGAGCTAACATTAATTA 2600
```

FIG. 54B hsFATP6 full lenght.DNA

```
         2610      2620      2630      2640
    ┬┴┴┴┴┴┴┴┴┴┴┴┴┴┴┴┴┴┴┴┴┴┴┴┴┴┴┴┴┴┴┴┴┴┴┴┴
TGCATGTACTATATTTCCTTAATATGAGAGATAATTTTTT  2640
AATTGCATAAGAATTTTAATTTCTTTTAATTGATATAAAC  2680
ATTAGTTGATTATTCTTTTTATCTATTTGGAGATTCAGTG  2720
CATAACTAAGTATTTTCCTTAATACTAAAGATTTTAAATA  2760
ATAAATAGTGGCTAGCGGTTTGGACAATCACTAAAAATGT  2800
         2810      2820      2830      2840
    ┬┴┴┴┴┴┴┴┴┴┴┴┴┴┴┴┴┴┴┴┴┴┴┴┴┴┴┴┴┴┴┴┴┴┴┴┴
ACTTTCTAATAAGTAAAATTTCTAATTTTGAATAAAAGAT  2840
TAAATTTTACTGAAAAAAAAAAAAAAAAAAAAAATTGGCG  2880
GCCGC  2885
```

FIG. 54C hsFATP6 full length protein

```
         10        20        30        40
MLLSWLTVLGAGMVVLHFLQKLLFPYFWDDFWFVLKVVLI  40
IIRLKKYEKRGELVTVLDKFLSHAKRQPRKPFIIYEGDIY  80
TYQDVDKRSSRVAHVFLNHSSLKKGDTVALLMSNEPDFVH  120
VWFGLAKLGCVVAFLNTNIRSNSLLNCIRACGPRALVVGA  160
DLLGTVEEILPSLSENISVWGMKDSVPQGVISLKEKLSTS  200
         210       220       230       240
PDEPVPRSHHVVSLLKSTCLYIFTSGTTGLPKAAVISQLQ  240
VLRGSAVLWAFGCTAHDIVYITLPLYHSSAAILGISGCVE  280
LGATCVLKKKFSASQFWSDCKKYDVTVFQYIGELCRYLCK  320
QSKREGEKDHKVRLAIGNGIRSDVWREFLDRFGNIKVCEL  360
YAATESSISFMNYTGRIGAIGRTNLFYKLLSTFDLIKYDF  400
         410       420       430       440
QKDEPMRNEQGWCIHVKKGEPGLLISRVNAKNPFFGYAGP  440
YKHTKQKLLCDVFKKGDVYLNTGDLIVQDQDNFLYFWDRT  480
GDTFRWKGENVATTEVADVIGMLDFIQEANVYGVAISGYE  520
GRAGMASIILKPNTSLDLEKVYEQVVTFLPAYACPRFLRI  560
QEKMEATGTFKLLKHQLVEDGFNPLKISEPLYFMDNLKKS  600
         610       620       630       640
YVLLTRELYDQIMLGEIKL  619
```

FIG. 55 mFATP1 full length DNA

```
          10        20        30        40
AAGTTCCCACTCCAGACTTCTGCGAGAACCCGTGAGGAAG  40
CAGCGAGAACCGGGGGTTTGCAAGCCAGAGAAGGATGCGG  80
ACTCCGGGAGCAGGAACAGCCTCTGTGGCCTCATTGGGGC  120
TGCTTTGGCTTCTGGGACTTCCGTGGACCTGGAGCGCGGC  160
GGCGGCGTTCGGTGTGTACGTGGGTAGCGGTGGCTGGCGA  200
          210       220       230       240
TTTCTGCGTATCGTCTGCAAGACGGCGAGGCGAGACCTCT  240
TTGGCCTCTCTGTTCTGATCCGCGTGCGGCTAGAGCTACG  280
ACGACACCGGCGAGCAGGAGACACGATCCCACGCATCTTC  320
CAGGCCGTGGCCCAGCGACAGCCGGAGCGCCTGGCGCTGG  360
TAGATGCGAGTAGCGGTATCTGCTGGACCTTCGCACAGCT  400
          410       420       430       440
AGACACCTACTCCAATGCTGTGGCCAATCTGTTCCTCCAG  440
CTGGGCTTTGCGCCAGGCGATGTGGTGGCTGTGTTCCTGG  480
AAGGCCGGCCCGAGTTCGTGGGACTGTGGCTGGGCCTGGC  520
CAAGGCCGGTGTAGTGGCTGCGCTTCTCAATGTCAACCTG  560
AGGCGGGAGCCCCTTGCCTTCTGCTTGGGCACATCAGCTG  600
          610       620       630       640
CCAAGGCCCTCATTTATGGCGGGGAGATGGCAGCGGCGGT  640
GGCGGAGGTGAGTGAGCAGCTGGGGAAGAGCCTGCTCAAG  680
TTCTGCTCTGGAGATCTGGGGCCTGAGAGCGTCCTGCCTG  720
ACACGCAGCTTCTGGACCCCATGCTTGCTGAGGCGCCCAC  760
CACACCCCTGGCACAGGCCCCAGGCAAGGGCATGGATGAT  800
          810       820       830       840
CGGCTATTTTACATCTATACTTCTGGGACCACCGGACTTC  840
CTAAGGCGGCCATTGTGGTGCACAGCAGGTACTACCGCAT  880
CGCAGCCTTCGGCCACCATTCCTACAGCATGCGGGCCAAC  920
GATGTGCTCTATGACTGCCTACCTCTCTACCACTCAGCAG  960
GGAACATCATGGGCGTGGGACAGTGTATCATCTACGGGTT  1000
          1010      1020      1030      1040
AACGGTGGTACTGCGCAAGAAGTTCTCCGCCAGCCGCTTC  1040
TGGGACGACTGTGTCAAATATAATTGCACGGTAGTGCAGT  1080
ACATCGGTGAAATATGCCGCTACCTGCTAAGGCAGCCGGT  1120
TCGCGATGTAGAGCGGCGGCACCGCGTGCGCCTGGCCGTG  1160
GGTAACGGACTGCGGCCAGCCATCTGGGAGGAGTTCACGC  1200
```

FIG. 56A

```
                1210      1220      1230      1240
         ┴┴┴┴┴┴┴┴┴┴┴┴┴┴┴┴┴┴┴┴┴┴┴┴┴┴┴┴┴┴┴┴┴┴┴┴┴┴┴┴
         AGGGTTTCGGTGTGCGACAGATTGGCGAGTTCTACGGCGC  1240
         CACCGAATGCAACTGCAGCATTGCCAACATGGACGGCAAG  1280
         GTCGGCTCCTGCGGCTTCAACAGCCGTATCCTCACGCATG  1320
         TGTACCCCATCCGTCTGGTCAAGGTCAACGAGGACACGAT  1360
         GGAGCCACTGAGGGACTCCCAAGGCCTCTGCATCCCGTGC  1400
                1410      1420      1430      1440
         ┴┴┴┴┴┴┴┴┴┴┴┴┴┴┴┴┴┴┴┴┴┴┴┴┴┴┴┴┴┴┴┴┴┴┴┴┴┴┴┴
         CAGCCCGGGGAACCTGGGCTTCTCGTGGGCCAGATCAACC  1440
         AGCAAGACCCTCTGCGGCGCTTCGATGGCTATGTTAGTGA  1480
         CAGCGCCACCAACAAGAAGATTGCCCACAGCGTGTTCCGA  1520
         AAGGGGGACAGCGCCTACCTTTCAGGTGACGTGCTAGTGA  1560
         TGGACGAGCTGGGGTACATGTACTTCCGTGACCGCAGCGG  1600
                1610      1620      1630      1640
         ┴┴┴┴┴┴┴┴┴┴┴┴┴┴┴┴┴┴┴┴┴┴┴┴┴┴┴┴┴┴┴┴┴┴┴┴┴┴┴┴
         GGATACCTTCCGATGGCGCGGCGAGAACGTATCCACCACG  1640
         GAGGTGGAAGCCGTGCTGAGCCGCCTGTTGGGCCAGACGG  1680
         ACGTGGCTGTGTATGGAGTGGCTGTGCCAGGAGTGGAGGG  1720
         GAAAAGCGGCATGGCGGCCATTGCAGACCCCACAACCAG   1760
         CTGGACCCTAACTCAATGTACCAGGAATTGCAGAAGGTTC  1800
                1810      1820      1830      1840
         ┴┴┴┴┴┴┴┴┴┴┴┴┴┴┴┴┴┴┴┴┴┴┴┴┴┴┴┴┴┴┴┴┴┴┴┴┴┴┴┴
         TTGCATCCTATGCCCAGCCCATCTTCCTGCGTCTTCTGCC  1840
         CCAAGTGGATACAACAGGCACCTTCAAGATCCAGAAGACC  1880
         CGACTACAGCGTGAAGGCTTTGACCCCGCCAGACCTCAG   1920
         ACCGGCTCTTCTTTCTAGACCTGAAACAGGGACGCTACCT  1960
         ACCCCTGGATGAGAGAGTCCATGCCCGCATCTGCGCAGGC  2000
                2010      2020      2030      2040
         ┴┴┴┴┴┴┴┴┴┴┴┴┴┴┴┴┴┴┴┴┴┴┴┴┴┴┴┴┴┴┴┴┴┴┴┴┴┴┴┴
         GACTTCTCACTCTGAGCCTGGTGAGTGGGATGGCCCTGGA  2040
         CTTGTGAGACCAGGGAGCCGGACACCCTGTTCAGGTGTT   2080
         TCTCCTGCCTGGCCACGTGGCCAGCAGCACCTGTGGGTGC  2120
         AGGAAACTGGAACCTGAGTGGCCGGGTGTCCCTTTCCTAC  2160
         AACCCACCATGCACACATCTAGCCTCTGCCTTGGTCTTTT  2200
```

FIG. 56B

```
                2210      2220      2230      2240
        |....|....|....|....|....|....|....|....|
        TCTCCATCTCTTTCCTCCGTGCCCAGCAGGAGCCCCACAG 2240
        ACACATTGGCTGCTGTGTCCTGCAGTGGGACCGGTGTCTA 2280
        GGGGTCCATGCTGCAGGCTGTGACCCGCACTGGTGCCCAC 2320
        CTCCCTTCCCCATTGTGCCTTAGGTTCCTCCACTGTGCGC 2360
        CGGTGAAGCAAGTGGGGACCCACATAGCTGTTGTCCCTGC 2400
                2410      2420      2430      2440
        |....|....|....|....|....|....|....|....|
        TGAGGGTTGGTAGCAAATGCACCCTCATGTCAGCTGGGAG 2440
        ACACATGCAGTCTCCCACTGACCCCAATCAACTGAAGAT   2480
        ACTGTTTTGTATTATTGTTTTGAGATAGGGTCTCACTGTG 2520
        GAGGCCAAGCTGGCCTCAGGCTCACCACTCTACTGCCTCC 2560
        GGGCACCAGCCTGCAGTTTGATGACATGTATGCACTATTG 2600
                2610      2620      2630      2640
        |....|....|....|....|....|....|....|....|
        TTCTAAGGGTCTTCTGAGTCCCTGCTTTCCCCTCATGTCC 2640
        TAAAACCTTCCAGAACTGACTCTGATCACTTGGATGTAGC 2680
        TAGTGTTGGCCCTGCCCACGTGTGTCAATTCAGGGGTCCC 2720
        CAGGCATCATCTCTGGAGGCCCTAACCTTGGCAAAGCTTG 2760
        GATGTCCTCACATCACAGCAGGAGACCCAGGAAGGTTGCT 2800
                2810      2820      2830      2840
        |....|....|....|....|....|....|....|....|
        GTGGTGTCTCTTGGGCACCCCTGGCGGCAGCCGTGGACAT 2840
        GCTTCCCTGCTGTGATAGCCCAAACTGTTGCCTATGACAT 2880
        TTGAGGTCTACCCTTCTGGCTGCCATGGTCCCCATTGAGA 2920
        TCTTTGGTGACTCACCTCAGCCACCAAGCCAGGCCTCTGC 2960
        CTTCCTTCAGCTCTAAGGGCATGAAGGGTGTGGACAGAGC 3000
                3010      3020      3030      3040
        |....|....|....|....|....|....|....|....|
        AGCCACAGGCTGCCCACAGTCACCCACATGCAAGTGTTAT 3040
        TTCCTTGTTTGTTTTAAAAAAATAAACATGCTGAGCCTTG 3080
        AAAAAAAAAAAAAAAAAA 3098
```

FIG. 56C mFATP1 full length protein

```
          10        20        30        40
          |         |         |         |
MRTPGAGTASVASLGLLWLLGLPWTWSAAAAFGVYVGSGG  40
WRFLRIVCKTARRDLFGLSVLIRVRLELRRHRRAGDTIPR  80
IFQAVAQRQPERLALVDASSGICWTFAQLDTYSNAVANLF 120
LQLGFAPGDVVAVFLEGRPEFVGLWLGLAKAGVVAALLNV 160
NLRREPLAFCLGTSAAKALIYGGEMAAAVAEVSEQLGKSL 200
         210       220       230       240
          |         |         |         |
LKFCSGDLGPESVLPDTQLLDPMLAEAPTTPLAQAPGKGM 240
DDRLFYIYTSGTTGLPKAAIVVHSRYYRIAAFGHHSYSMR 280
ANDVLYDCLPLYHSAGNIMGVGQCIIYGLTVVLRKKFSAS 320
RFWDDCVKYNCTVVQYIGEICRYLLRQPVRDVERRHRVRL 360
AVGNGLRPAIWEEFTQGFGVRQIGEFYGATECNCSIANMD 400
         410       420       430       440
          |         |         |         |
GKVGSCGFNSRILTHVYPIRLVKVNEDTMEPLRDSQGLCI 440
PCQPGEPGLLVGQINQQDPLRRFDGYVSDSATNKKIAHSV 480
FRKGDSAYLSGDVLVMDELGYMYFRDRSGDTFRWRGENVS 520
TTEVEAVLSRLLGQTQVAVYGVAVPGVEGKSGMAAIADPH 560
NQLDPNSMYQELQKVLASYAQPIFLRLLPQVDTTGTFKIQ 600
         610       620       630       640
          |         |         |         |
KTRLQREGFDPRQTSDRLFFLDLKQGRYLPLDERVHARIC 640
AGDFSL   646
```

FIG. 57 mVLACS (FATP2) full length DNA

```
          10        20        30        40
     ┴┴┴┴┴┴┴┴┴┴┴┴┴┴┴┴┴┴┴┴┴┴┴┴┴┴┴┴┴┴┴┴┴┴┴┴┴┴┴┴
     GACACAGTACTGCCGATGTTGGACAGAGGATCGCTTAACA  40
     GAACGAAATCTCAAAACAAATTAACAGGACCCGGTTGCTT  80
     GATTTCCCAAATCAGAAAAGGCTCGAAATGTCTAGAGGGG 120
     CTGACTGATGCAGCGGTGACCCGGACTGGAGACAGTTGGA 160
     CGCGATCATCTCTGGTGCTTTTGTTCAACCTTGAAACCTT 200
          210       220       230       240
     ┴┴┴┴┴┴┴┴┴┴┴┴┴┴┴┴┴┴┴┴┴┴┴┴┴┴┴┴┴┴┴┴┴┴┴┴┴┴┴┴
     CGCCACAGGAGACTTGCCTGAGCAGAGAAGCAAACGTGGA 240
     GAAACAAAGAGAGATCTAGCGAAAAGCCTCTGGGACCAAG 280
     GAGGGGAGGTGGGACTCTGGGTTGGCGGTGGCACCTGCTG 320
     CCGGCTATTAATAATAGGGTCGCGATGCGTTTATAAGGTG 360
     TTTGATTAAACAAAGACTCTATGAGAGAAGAATAACTAGC 400
          410       420       430       440
     ┴┴┴┴┴┴┴┴┴┴┴┴┴┴┴┴┴┴┴┴┴┴┴┴┴┴┴┴┴┴┴┴┴┴┴┴┴┴┴┴
     AACAGCCCCACGTCTGAGTCGTCGCCTCCGACCTTTTTCA 440
     ACGTGGGTTCTTTGGGCCGAGCGTCGTTTGCCGAGAACTA 480
     GATCTCACCTGACCCCAGACGCTGAAAACAAGCGCTGTGG 520
     CATCCTGGGCCACCCAAGCTGACAAGGGCGCGCCCCCTGA 560
     GCACACGAGGTGCCCCACGAGGGGGAGGGACCCACAGCCG 600
          610       620       630       640
     ┴┴┴┴┴┴┴┴┴┴┴┴┴┴┴┴┴┴┴┴┴┴┴┴┴┴┴┴┴┴┴┴┴┴┴┴┴┴┴┴
     TCCCGCCCGCACCGCGGTGTCCGCTGCGGGCACCTGCAGC 640
     CGAGCCGCCACCCGCAGTCGCAGCGCGTCCGGCGGCCGAA 680
     CCCGGTCGTCAGCTCGTCAGCACCTGCTCTGCTTCTCTCC 720
     CGCCCGCCGCCGCGCTGCACGCCTCGAGCGCTCCCTCGGC 760
     CCCGGCGGGGACCGGGGACCCCGCAGCCACCGCCATGCTG 800
          810       820       830       840
     ┴┴┴┴┴┴┴┴┴┴┴┴┴┴┴┴┴┴┴┴┴┴┴┴┴┴┴┴┴┴┴┴┴┴┴┴┴┴┴┴
     CCTGTGCTCTACACCGGCCTGGCGGGGCTGCTGCTGCTGC 840
     CTCTGCTGCTCACCTGCTGCTGCCCCTACCTCCTCCAGGA 880
     CGTGCGGTTCTTCCTGCAACTGGCCAACATGGCCCGGCAG 920
     GTGCGCAGCTACCGGCAGCGGCGACCCGTGCGCACCATCC 960
     TGCATGTCTTCTTGGAGCAAGCGCGCAAGACCCCGCACAA 1000
          1010      1020      1030      1040
     ┴┴┴┴┴┴┴┴┴┴┴┴┴┴┴┴┴┴┴┴┴┴┴┴┴┴┴┴┴┴┴┴┴┴┴┴┴┴┴┴
     GCCCTTCCTGCTGTTTCGCGACGAGACGCTTACCTACGCC 1040
     CAGGTAGACCGGCGCAGCAACCAAGTAGCGCGAGCGCTGC 1080
     ATGATCACCTGGGCCTGCGGCAGGGGGATTGCGTGGCCCT 1120
     CTTCATGGGCAATGAGCCGGCCTACGTGTGGCTCTGGCTG 1160
     GGACTGCTCAAACTGGGCTGTCCCATGGCGTGCCTCAACT 1200
```

FIG. 58A

```
            1210      1220      1230      1240
    |....|....|....|....|....|....|....|....|
    ACAACATCCGTGCCAAGTCTCTGCTACACTGCTTTCAGTG 1240
    CTGCGGGGCGAAGGTGCTGCTGGCCTCCCCAGAGCTACAC 1280
    GAAGCTGTCGAGGAGGTTCTTCCAACCCTGAAAAAGGAGG 1320
    GCGTGTCCGTCTTCTACGTAAGCAGAACTTCTAACACTAA 1360
    TGGCGTGGACACAGTACTGGACAAAGTAGACGGGGTGTCG 1400
            1410      1420      1430      1440
    |....|....|....|....|....|....|....|....|
    GCGGACCCCATCCCGGAGTCGTGGAGGTCTGAAGTCACGT 1440
    TCACCACACCCGCAGTCTACATATATACTTCGGGCACCAC 1480
    AGGTCTTCCAAAGGCTGCAACCATTAATCACCATCGCCTC 1520
    TGGTATGGGACCAGCCTTGCCCTGAGGTCCGGAATTAAGG 1560
    CTCATGACGTCATCTACACCACCATGCCCCTGTACCACAG 1600
            1610      1620      1630      1640
    |....|....|....|....|....|....|....|....|
    CGCGGCGCTCATGATTGGCCTCCACGGATGCATTGTGGTT 1640
    GGGGCTACATTTGCTTTGCGGAGCAAATTTTCAGCCAGCC 1680
    AGTTTTGGGACGACTGCAGGAAATACAACGCCACTGTCAT 1720
    TCAGTACATCGGTGAACTGCTTCGGTACCTCTGCAACACG 1760
    CCCCAGAAACCAAATGACCGGGACCACAAAGTGAAAATAG 1800
            1810      1820      1830      1840
    |....|....|....|....|....|....|....|....|
    CACTAGGAAATGGCTTACGAGGAGATGTGTGGAGAGAGTT 1840
    CATCAAGAGATTTGGGGACATTCACATTTATGAGTTCTAC 1880
    GCTTCCACTGAAGGCAACATTGGATTTATGAACTATCCAA 1920
    GAAAAATCGGAGCTGTTGGAAGAGAAAATTACCTACAAAA 1960
    AAAAGTTGTAAGGCACGAGCTGATCAAGTATGACGTGGAG 2000
            2010      2020      2030      2040
    |....|....|....|....|....|....|....|....|
    AAGGATGAGCCTGTCCGTGATGCAAATGGATATTGCATCA 2040
    AAGTCCCCAAAGGAGAGGTTGGACTCTTGATTTGCAAAAT 2080
    CACAGAGCTCACACCATTTTTGGCTATGCTGGAGGAAAG 2120
    ACCCAGACAGAGAAGAAAAAGCTCAGAGATGTTTTAAGA 2160
    AAGGAGACGTCTACTTCAACAGTGGCGATCTCCTGATGAT 2200
```

FIG. 58B

```
                 2210          2220          2230          2240
        |....|....|....|....|....|....|....|....|....|....|
        CGACCGTGAAAATTTCATCTATTTTCACGACAGAGTTGGA 2240
        GACACCTTCCGGTGGAAAGGAGAGAATGTAGCTACCACGG 2280
        AAGTCGCTGACATTGTGGGACTGGTAGATTTTGTTGAAGA 2320
        AGTGAATGTTTACGGTGTGCCCGTGCCAGGTCATGAAGGT 2360
        CGCATCGGGATGGCCTCGATCAAGATGAAAGAAAACTACG 2400
                 2410          2420          2430          2440
        |....|....|....|....|....|....|....|....|....|....|
        AGTTCAATGGAAAGAAACTCTTTCAGCACATCTCGGAGTA 2440
        CCTGCCCAGTTACTCGAGGCCTCGGTTCCTGAGAATACAA 2480
        GATACCATTGAGATCACCGGGACTTTTAAACACCGCAAAG 2520
        TGACCCTGATGGAAGAGGGCTTTAACCCCTCAGTCATCAA 2560
        AGATACCTTGTATTTCATGGATGACACAGAAAAAACATAC 2600

2610          2620          2630          2640
        |....|....|....|....|....|....|....|....|....|....|
        GTGCCCATGACTGAGGACATTTATAATGCCATAATTGATA 2640
        AGACTCTGAAGCTCTGAATGTTGCCTGGCTCCTAACACTT 2680
        CCAGAAAGAAACACAATAGGCCTAGCATAGCCCCTTCACA 2720
        TGTGTAATCCAACTTTAACTTGATTAAAGGTTATAGGTGT 2760
        GATTTTCCTAGGAAATTATTCATTTAAAGGACAATTGTT 2800
                 2810          2820          2830          2840
        |....|....|....|....|....|....|....|....|....|....|
        TGTTTGTTTGTTTGTTTTTATTAATTACACCAGAACGTT 2840
        TGCAAGTAAAAAGATTTAAAGTCACTTATTTTTCAATGTG 2880
        CACCTGCCATTTGTCCTTGCAAACTTAGCTTCTTGGAGAG 2920
        AGGGCCTTATTTTTTAAAGACATAATAAACTATGTAAAC 2960
        ACT 2963
```

FIG. 58C mVLACS (FATP2) full length protein

```
          10        20        30        40
          |         |         |         |
MLPVLYTGLAGLLLLPLLLTCCCPYLLQDVRFFLQLANMA   40
RQVRSYRQRRPVRTILHVFLEQARKTPHKPFLLFRDETLT   80
YAQVDRRSNQVARALHDHLGLRQGDCVALFMGNEPAYVWL  120
WLGLLKLGCPMACLNYNIRAKSLLHCFQCCGAKVLLASPE  160
LHEAVEEVLPTLKKEGVSVFYVSRTSNTNGVDTVLDKVDG  200
         210       220       230       240
          |         |         |         |
VSADPIPESWRSEVTFTTPAVYIYTSGTTGLPKAATINHH  240
RLWYGTSLALRSGIKAHDVIYTTMPLYHSAALMIGLHGCI  280
VVGATFALRSKFSASQFWDDCRKYNATVIQYIGELLRYLC  320
NTPQKPNDRQHKVKIALGNGLRGDVWREFIKRFGDIHIYE  360
FYASTEGNIGFMNYPRKIGAVGRENYLQKKVVRHELIKYD  400
         410       420       430       440
          |         |         |         |
VEKDEPVRDANGYCIKVPKGEVGLLICKITELTPFFGYAG  440
GKTQTEKKKLRDVFKKGDVYFNSGDLLMIDRENFIYFHDR  480
VGDTFRWKGENVATTEVADIVGLVDFVEEVNVYGVPVPGH  520
EGRIGMASIKMKENYEFNGKKLFQHISEYLPSYSRPRFLR  560
IQDTIEITGTFKHRKVTLMEEGFNPSVIKDTLYFMDDTEK  600
         610       620       630       640
          |         |         |         |
TYVPMTEDIYNAIIDKTLKL    620
```

FIG. 59 mFATP4 partial DNA

```
         10        20        30        40
GATCAGCTCTTCTATATCTACACGTCGGGCACCACGGGGC   40
TACCCAAAGCTGCCATTGTGGTGCACAGCAGGTATTACCG   80
AATGGCTGCCCTGGTGTACTATGGATTCCGCATGCGGCCT  120
GATGACATTGTCTATGACTGCCTCCCCCTCTACCACTCAG  160
CAGGAAACATTGTGGGGATTGGCCAGTGCGTACTCCACGG  200
         210       220       230       240
CATGACTGTGGTGATCCGGAAGAAGTTTTCAGCCTCCCGG  240
TTCTGGGATGACTGTATCAAGTACAACTGCACAATTGTAC  280
AGTACATTGGTGAGCTTTGCCGCTACCTCCTGAACCAGCC  320
ACCCCGTGAGGCTGAGTCTCGGCACAAGGTGCGCATGGCA  360
CTGGGCAACGGTCTCCGGCAGTCCATCTGGACCGACTTCT  400
         410       420       430       440
CCAGCCGTTTCCACATTCCCAAGGTGGCCGAGTTCTACGG  440
GGCCACCGAGTGCAACTGTAGCTTGGGCAACTTTGACAGC  480
CAGGTGGGGGCCTGTGGCTTCAATAGCCGCATCCTGTCCT  520
TTGTGTACCCCATCCGCTTGGTACGAGTCAATGAGGATAC  560
CATGGAACTGATCCGGGGACCCGATGGCGTCTGCATTCCC  600
         610       620       630       640
TGTCAACCAGGCCAGCCAGGCCAGCTGGTGGGTCGCATCA  640
TCCAGCAGGACCCCCTACGCCGTTTTGATGGCTACCTCAA  680
CCAGGGTGCCAACAACAAGAAGATTGCTAGTGATGTCTTC  720
AAGAAAGGGGACCAAGCCTACCTCACTGGTGACGTGCTGG  760
TGATGGATGAGCTGGGCTACCTGTACTTCCGAGACCGCAC  800
         810       820       830       840
AGGGGACACGTTCCGCTGGAAAGGGGAGAATGTGTCTACC  840
ACTGAAGTGGAGGGCACACTCAGCCGCCTGCTTCAGATGG  880
CAGATGTGGCTGTTTATGGTGTTGAGGTGCCAGGAGCTGA  920
GGGCCGAGCAGGAATGGCTGCTGTGGCAAGCCCCACTAGC  960
AACTGTGACCTGGAGAGCTTTGCACAGACCTTGAAAAAGG 1000
         1010      1020      1030      1040
AGCTGCCCCTGTACGCCCGCCCCATCTTCCTCCGCTTCTT 1040
GCCTGAGCTGCACAAAACAGGAACCTTCAAGTTCCAGAAG 1080
ACAGAGTTGCGGAAGGAGGGCTTTGACCCGTCTGTTGTGA 1120
AAGACCCACTCTTCTATTTGGATGCCCGGACAGGCTGCTA 1160
TGTTGCACTGGACCAAGAGGCCTATACCCGCATCCAGGCA 1200
```

FIG. 60A

```
              1210      1220      1230      1240
GGCGAGGAGAAGCTGTGATTTCCCCCACATCCCTCTGAGG 1240
GCCAGAGGATGCTGGATTCAGAGCCCCAGCTTCCACTCCA 1280
GAAGGGGTCTGGGCAAGGCCAGACCAAAGCTAGCAGGGCC 1320
CGCACCTTCACCCTAGGTGCTGATCCCCCT 1350
```

FIG. 60B mFATP4 partial DNA

```
              10        20        30        40
DQLFYIYTSGTTGLPKAAIVVHSRYYRMAALVYYGFRMRP  40
DDIVYDCLPLYHSAGNIVGIGQCVLHGMTVVIRKKFSASR  80
FWDDCIKYNCTIVQYIGELCRYLLNQPPREAESRHKVRMA 120
LGNGLRQSIWTDFSSRFHIPKVAEFYGATECNCSLGNFDS 160
QVGACGFNSRILSFVYPIRLVRVNEDTMELIRGPDGVCIP 200
              210       220       230       240
CQPGQPGQLVGRIIQQDPLRRFDGYLNQGANNKKIASDVF 240
KKGDQAYLTGDVLVMDELGYLYFRDRTGDTFRWKGENVST 280
TEVEGTLSRLLQMADVAVYGVEVPGAEGRAGMAAVASPTS 320
NCDLESFAQTLKKELPLYARPIFLRFLPELHKTGTFKFQK 360
TELRKEGFDPSVVKDPLFYLDARTGCYVALDQEAYTRIQA 400
              410       420       430       440
GEEKL 405
```

FIG. 61 mmFATP1 full length DNA

```
         10        20        30        40
ATGCGGGCTCCTGGAGCAGGAACAGCCTCTGTGGCCTCAC 40
TGGCGCTGCTTTGGTTTCTGGGACTTCCGTGGACCTGGAG 80
CGCGGCGGCGGCGTTCTGTGTGTACGTGGGTGGCGGCGGC 120
TGGCGCTTTCTGCGTATCGTCTGCAAGACGGCGAGGCGAG 160
ACCTCTTTGGCCTCTCTGTTCTGATTCGTGTTCGGCTAGA 200
        210       220       230       240
GCTGCGACGACACCGGCGAGCAGGAGACACGATCCCGTGC 240
ATCTTCCAGGCTGTGGCCCGGCGACAACCAGAGCGCCTGG 280
CACTGGTGGACGCCAGTAGTGGTATATGCTGGACCTTCGC 320
ACAGCTGGACACCTACTCCAATGCTGTAGCCAACCTGTTC 360
CGCCAGCTGGGCTTTGCACCAGGCGATGTGGTGGCTGTGT 400
        410       420       430       440
TCCTGGAGGGCCGGCCGGAGTTCGTGGGACTGTGGCTGGG 440
CCTGGCCAAGGCCGGTGTGGTGGCTGCTCTTCTCAATGTC 480
AACCTGAGGCGGGAGCCCCTGGCCTTCTGCCTGGGCACAT 520
CAGCTGCCAAGGCCCTCATTTATGGCGGGGAGATGGCAGC 560
GGCGGTGGCGGAGGTGAGCGAGCAGCTGGGGAAGAGCCTC 600
        610       620       630       640
CTCAAGTTCTGCTCTGGAGATCTGGGGCCTGAGAGCATCC 640
TGCCTGACACGCAGCTCCTGGACCCCATGCTTGCTGAGGC 680
GCCCACCACACCCCTGGCACAAGCCCCAGGCAAGGGCATG 720
GATGATCGGCTGTTTTACATCTATACTTCTGGGACCACCG 760
GGCTTCCTAAGGCTGCCATTGTGGTGCACAGCAGGTACTA 800
        810       820       830       840
CCGCATTGCTGCCTTTGGCCACCATTCCTACAGCATGCGT 840
GCCGCCGATGTGCTCTATGACTGCCTGCCACTCTACCACT 880
CTGCAGGGAACATCATGGGTGTGGGGCAGTGCGTCATCTA 920
CGGGTTGACGGTGGTACTGCGCAAGAAGTTCTCCGCCAGC 960
CGCTTCTGGGATGACTGTGTCAAGTACAATTGCACGGTAG 1000
       1010      1020      1030      1040
TGGATGACATAGGTGAAATCTGCCGCTACCTGCTGAGGCA 1040
GCCGGTTCGCGACGTGGAGCAGCGACACCGCGTGCGCCTG 1080
GCCGTGGGTAATGGGCTGCGGCCAGCCATCTGGGAGGAGT 1120
TCACGCAGCGCTTCGGTGTGCCACAGATCGGCGAGTTCTA 1160
CGGCGCTACCGAGTGCAACTGCAGCATTGCCAACATGGAC 1200
```

FIG. 62A

```
              1210      1220      1230      1240
         |,,,,|,,,,|,,,,|,,,,|,,,,|,,,,|,,,,|
         GGCAAGGTCGGCTCCTGCGGCTTCAACAGCCGTATCCTCA 1240
         CGCATGTGTACCCCATCCGTCTGGTCAAGGTCAATGAGGA 1280
         CACGATGGAGCCACTGCGGGACTCCGAGGGCCTCTGCATC 1320
         CCGTGCCAGCCCGGGGAACCCGGCCTTCTCGTGGGCCAGA 1360
         TCAACCAGCAGGACCCTCTGCGGCGTTTCGATGGTTATGT 1400
              1410      1420      1430      1440
         |,,,,|,,,,|,,,,|,,,,|,,,,|,,,,|,,,,|
         TAGTGACAGTGCCACCAACAAGAAGATTGCCCACAGCGTT 1440
         TTCCGAAAGGGCGATAGCGCCTACCTCTCAGGTGACGTGC 1480
         TAGTGATGGACGAGCTGGGCTACATGTATTCCGTGACCG  1520
         CAGCGGGGACACCTTCCGCTGGCGCGGGGAGAACGTGTCC 1560
         ACCACGGAGGTGGAAGCCGTGCTGAGCCGCCTACTGGGCC 1600
              1610      1620      1630      1640
         |,,,,|,,,,|,,,,|,,,,|,,,,|,,,,|,,,,|
         AGACGGACGTGGCTGTGTATGGGGTGGCTGTGCCAGGAGT 1640
         GGAGGGGAAAGCTGGCATGGCAGCCATCGCAGATCCCCAC 1680
         AGCCAGTTGGACCCTAACTCAATGTACCAGGAATTACAGA 1720
         AGGTTCTTGCATCCTATGCTCGGCCCATCTTCCTGCGTCT 1760
         TCTGCCCCAGGTGGATACCACAGGCACCTTCAAGATCCAG 1800
              1810      1820      1830      1840
         |,,,,|,,,,|,,,,|,,,,|,,,,|,,,,|,,,,|
         AAGACCCGGCTGCAGCGTGAAGGCTTTGACCCCCGTCAGA 1840
         CCTCAGACAGGCTCTTCTTTCTAGACCTGAAGTCCGGCAC 1880
         GAGGTATCTACCCCTGGATGAGAGTCCATGCCCGCATT   1920
         TGCGCAGGCGACTTCTCACTCTGAGCCTGGAGAGTGGGCT 1960
         GGGCCTGGACTCCTGAGACCTGGGAGCCTGACACCCCTCT 2000
              2010      2020      2030      2040
         |,,,,|,,,,|,,,,|,,,,|,,,,|,,,,|,,,,|
         TCGGGTGCTTCTCCTGCCTGGCCACATGGACAGCAGCACC 2040
         TGTGAGAGTAGGAAAATGGAACCTGAGTGGCTGGGACCCC 2080
         TCTCCTACTTCCCACTATGCATCCATTTGCCTCTGCCTT  2120
         GATCTTTTCTCCATCTCTTTCTCCCTACCCAGCAGGAG   2160
         CCCCACAAACACATGTTGGCTGCTGTGTCCTGCAGTTGGA 2200
```

FIG. 62B

```
           2210      2220      2230      2240
     |....|....|....|....|....|....|....|....|
     CCAGTGTCCAGGGGTACAGGCTTCAGGCTGTGACCCACAC 2240
     TGGTACCCACCTCCCTTTCCTATTTTGCCTTAGGTTCATC 2280
     CACGGTTCCCCTGTGGAGCAAGTGGGGCCCACATAGCTG  2320
     CTGTCCCTGCTGAGGGTTGGTAGCAATCACACCCTCATGT 2360
     CAGCTGGGAGACACGCGCAGTCTCCCACTGACCCCCAATC 2400
           2410      2420      2430      2440
     |....|....|....|....|....|....|....|....|
     AACTGAAAATATTGTTTTGACTACTTTTGTTTTTTTGTT  2440
     TTTTTGTTTTTTTTTTTTCGAGACAGAGTTTCTCTGTA   2480
     TAGCCCTGGCTGTCCTGGAACTCACTTTGTAGACCAGGCT 2520
     GGCCTCGAACTCAAAAATCCTCCTGACTCTGCCTCTGCTT 2560
     CCCAAGTGCTGGGATTAAAGACGTGCGCCACCACCGCCTG 2600
           2610      2620      2630      2640
     |....|....|....|....|....|....|....|....|
     GCTGTTTTGTATTTTTGTTTTGTTTTGACGATAGGGTCTC 2640
     ACTGTGGAGGCCAAGCTGGCCTCAGACTCCCCACCCCATT 2680
     GCCTCTGGGCACCATTCTATATTCTCAGACTGATGACAAT 2720
     GCACTAGTGTCCCTAGGAGTCTTGAGTCTGCACTTTCCCC 2760
     TCATAGCCTCAAGCTTCCAGAACTGACTCTGATCACTTGG 2800
           2810      2820      2830      2840
     |....|....|....|....|....|....|....|....|
     ATGTGGCTAGTGTTGGCTCTACCCACATGTGTCAATTCAG 2840
     GGGTCCCCAGGCATAGTCTCTGGAAGCCCTCACCCGGAAA 2880
     AAGCTTGGAGAGACCCAGGAAGGTTGTTGTGTTCTCTTGG 2920
     GCACCCCTGGTGGCAGTCCTGGGCATGCTTCCGCACTGT  2960
     ACTGGTGCATATAGCCCAGACCTATGACATTTGAGGTCTA 3000
           3010      3020      3030      3040
     |....|....|....|....|....|....|....|....|
     CCCTTCTGGCTCCTGTGGTCCCCATTGAGATCCTTGGTGA 3040
     CTCACCTCAGTCACCAAGCAGAGCCTCTGCCTGCCTTCAT 3080
     CTTCAAGGTCATGAAGGATGTGGACAGAGCAGCTACAGGC 3120
     TGCCAGCAGTCAACCACATGAGAGTGTTACTTCCTTGTTG 3160
     GTTTTTAAAAAATAAATGTGCTGAGCCTCGAAAAAAAAA  3200
           3210      3220      3230      3240
     |....|....|....|....|....|....|....|....|
     AAAAAAAAAAAAAAAAA 3217
```

FIG. 62C mmFATP1 full length protein

```
           10        20        30        40
  ┌────┬────┬────┬────┬────┬────┬────┬────┐
MRAPGAGTASVASLALLWFLGLPWTWSAAAAFCVYVGGGG  40
WRFLRIVCKTARRDLFGLSVLIRVRLELRRHRRAGDTIPC  80
IFQAVARRQPERLALVDASSGICWTFAQLDTYSNAVANLF 120
RQLGFAPGDVVAVFLEGRPEFVGLWLGLAKAGVVAALLNV 160
NLRREPLAFCLGTSAAKALIYGGEMAAAVAEVSEQLGKSL 200
          210       220       230       240
  ┌────┬────┬────┬────┬────┬────┬────┬────┐
LKFCSGDLGPESILPDTQLLDPMLAEAPTTPLAQAPGKGM 240
DDRLFYIYTSGTTGLPKAAIVVHSRYYRIAAFGHHSYSMR 280
AADVLYDCLPLYHSAGNIMGVGQCVIYGLTVVLRKKFSAS 320
RFWDDCVKYNCTVVDDIGEICRYLLRQPVRDVEQRHRVRL 360
AVGNGLRPAIWEEFTQRFGVPQIGEFYGATECNCSIANMD 400
          410       420       430       440
  ┌────┬────┬────┬────┬────┬────┬────┬────┐
GKVGSCGFNSRILTHVYPIRLVKVNEDTMEPLRDSEGLCI 440
PCQPGEPGLLVGQINQQDPLRRFDGYVSDSATNKKIAHSV 480
FRKGDSAYLSGDVLVMDELGYMYFRDRSGDTFRWRGENVS 520
TTEVEAVLSRLLGQTDVAVYGVAVPGVEGKAGMAAIADPH 560
SQLDPNSMYQELQKVLASYARPIFLRLLPQVDTTGTFKIQ 600
          610       620       630       640
  ┌────┬────┬────┬────┬────┬────┬────┬────┐
KTRLQREGFDPRQTSDRLFFLDLKSGTRYLPLDERVHARI 640
CAGDFSL 647
```

FIG. 63 mmFATP2 full length DNA

```
           10        20        30        40
     |.....|.....|.....|.....|.....|.....|.....|
     GGGCGGAGGCCGAGCCCAGTCGCCAGCTCCTGCTCTGCTC   40
     CTCTCCCGCCTGCCGCCGCGCTGCACGCCTCGAGCACTCC   80
     CTCGGCCCCGGCGGGGACCGGGGACCCCGCAGCTACCGCC  120
     ATGCTGCCAGTGCTCTACACCGGCCTGGCGGGGCTGCTGC  160
     TGCTGCCTCTGCTGCTCACCTGCTGCTGCCCCTACCTCCT  200
           210       220       230       240
     |.....|.....|.....|.....|.....|.....|.....|
     CCAAGATGTGCGGTACTTCCTGCGGCTGGCCAACATGGCC  240
     CGGCGGGTGCGCAGCTACCGGCAGCGGCGACCCGTGCGTA  280
     CCATCCTGCGGGCCTTCCTGGAACAAGCGCGCAAGACCCC  320
     ACACAAGCCCTTCCTGCTGTTCCGAGACGAGACGCTCACC  360
     TACGCCCAGGTGGACCGGCGCAGCAACCAAGTGGCGCGGG  400
           410       420       430       440
     |.....|.....|.....|.....|.....|.....|.....|
     CGCTGCACGATCAACTGGGCCTACGACAGGGGGATTGCGT  440
     AGCCCTCTTCATGGGCAATGAGCCGGCCTACGTGTGGATC  480
     TGGCTGGGACTGCTCAAACTGGGCTGTCCCATGGCGTGCC  520
     TCAACTACAACATTCGTGCCAAGTCTCTGCTGCACTGCTT  560
     TCAATGCTGCGGGGCGAAGGTGCTGCTGGCCTCCCCAGAT  600
           610       620       630       640
     |.....|.....|.....|.....|.....|.....|.....|
     CTACAAGAAGCTGTGGAGGAGGTTCTTCCAACCCTGAAAA  640
     AGGATGCCGTGTCCGTCTTTTACGTAAGCAGAACTTCTAA  680
     CACAAATGGTGTGGACACAATACTGGACAAAGTAGACGGA  720
     GTGTCGGCGGAACCCACCCCGGAGTCGTGGAGGTCTGAAG  760
     TCACTTTTACCACGCCAGCAGTATACATTTATACTTCGGG  800
           810       820       830       840
     |.....|.....|.....|.....|.....|.....|.....|
     AACCACAGGTCTTCCAAAAAGCGGAACCATCAATCATCAT  840
     CGCCTAAGGTATGGGACAAGCCTTGCTATGTCGAGTGGGA  880
     ATCACGGCCAAGGATGTCATCTATACCAACAATGCCCCTG  920
     TTCCAACAGTGCAACGCTCAAGATCGGCCTTCACGGATGC  960
     ATCCTGGGTTGGGGCTACTTTAACCTTGGCGGGGCAAATT 1000
           1010      1020      1030      1040
     |.....|.....|.....|.....|.....|.....|.....|
     CTCAAGCAAGCCAATTTTGGGAACGACTGGCAGGAAATAC 1040
     AACGTCAACGGTCATTCAGTACATTGGTGAACTGCTTCGG 1080
     TACCTGTGCAACACACCGCAGAAACCAAATGACCGGGACC 1120
     ACAAAGTGAAAAAAGCCCTGGGAAATGGCTTACGAGGAGA 1160
     TGTGTGGAGAGAGTTCATCAAGAGATTTGGGGACATCCAC 1200
```

FIG. 64A

```
                    1210      1220      1230      1240
         ┴┴┴┴┴┴┴┴┴┴┴┴┴┴┴┴┴┴┴┴┴┴┴┴┴┴┴┴┴┴┴┴┴┴┴┴┴┴┴┴
         GTGTATGAGTTCTACGCATCCACTGAAGGCAACATTGGAT 1240
         TTGTGAACTATCCAAGGAAAATCGGTGCTGTCGGGAGAGC 1280
         AAACTACCTACAAAGAAAAGTTGCAAGGTATGAGCTGATC 1320
         AAGTATGACGTGGAGAAGGACGAGCCGGTCCGTGACGCAA 1360
         ATGGATATTGCATCAAGTCCCCAAAGGTGAGGTTGGACT  1400
                    1410      1420      1430      1440
         ┴┴┴┴┴┴┴┴┴┴┴┴┴┴┴┴┴┴┴┴┴┴┴┴┴┴┴┴┴┴┴┴┴┴┴┴┴┴┴┴
         CTTGGTTTGCAAAATCACACAGCTCACACCATTTATTGGC 1440
         TATGCTGGAGGAAAGACCCAGACAGAGAAGAAAAAACTCA 1480
         GAGATGTCTTTAAGAAAGGCGACATCTACTTCAACAGCGG 1520
         AGACCTCCTGATGATCGACCGTGAGAACTTCGTCTACTTT 1560
         CACGACAGGGTTGGAGATACTTCCGGTGGAAAGGAGAGA  1600
                    1610      1620      1630      1640
         ┴┴┴┴┴┴┴┴┴┴┴┴┴┴┴┴┴┴┴┴┴┴┴┴┴┴┴┴┴┴┴┴┴┴┴┴┴┴┴┴
         ACGTAGCTACCACAGAAGTCGCTGACATCGTGGGACTGGT 1640
         AGATTTGTTGAAGAAGTGAATGTGTATGGCGTGCCTGTG  1680
         CCAGGTCATGAGGGTCGAATTGGGATGGCCTCCCTCAAGA 1720
         TCAAAGAAAACTACGAGTTCAATGGAAAGAAACTCTTTCA 1760
         ACACATCGCGGAGTACCTGCCCAGTTACGCGAGGCCTCGG 1800
                    1810      1820      1830      1840
         ┴┴┴┴┴┴┴┴┴┴┴┴┴┴┴┴┴┴┴┴┴┴┴┴┴┴┴┴┴┴┴┴┴┴┴┴┴┴┴┴
         TTCCTGAGGATACAAGATACCATTGAGATCACTGGGACTT 1840
         TTAAACACCGCAAAGTGACCCTGATGGAAGAGGGCTTCAA 1880
         TCCCACAGTCATCAAAGATACCTTGTATTTCATGGATGAT 1920
         GCAGAGAAAACATTTGTGCCCATGACTGAGAACATTTATA 1960
         ATGCCATAATTGATAAACTCTGAAGCTCTGAATATTCCC  2000
                    2010      2020      2030      2040
         ┴┴┴┴┴┴┴┴┴┴┴┴┴┴┴┴┴┴┴┴┴┴┴┴┴┴┴┴┴┴┴┴┴┴┴┴┴┴┴┴
         TGGTGGTTTAGCTCATGACATTTCCAGAAAGAAACTCGAT 2040
         AGACCTCGCAGAGCCACTTCATACGTAGAATCCAACTTTA 2080
         ACTTGATTGAAGACTATAAGGTGCGATTTTATTTTTAGGA 2120
         AATTATTCATTAAAAGGATAGTTTTTTTTTTTTTTTTTAA 2160
         TTACACCTGAACCTTTGCAAGTAAAAGATTTAGAGACAA  2200
                    2210      2220      2230      2240
         ┴┴┴┴┴┴┴┴┴┴┴┴┴┴┴┴┴┴┴┴┴┴┴┴┴┴┴┴┴┴┴┴┴┴┴┴┴┴┴┴
         TTATTTTTCAATGTGCACCTGCCATTTGTCCTTGCAAACT 2240
         AAGCTTCTTGGAGAGAGGGCCTTATTTTTTAAAGACATA  2280
         ATAAACTATATTAACACTAAAAAAAAAAAAAAAAAAAAA  2320
         AAAAAAAAAAAAAAAAA 2338
```

FIG. 64B mmFATP2 full length protein

```
         10         20         30         40
MLPVLYTGLAGLLLLPLLLTCCCPYLLQDVRYFLRLANMA    40
RRVRSYRQRRPVRTILRAFLEQARKTPHKPFLLFRDETLT    80
YAQVDRRSNQVARALHDQLGLRQGDCVALFMGNEPAYVWI   120
WLGLLKLGCPMACLNYNIRAKSLLHCFQCCGAKVLLASPD   160
LQEAVEEVLPTLKKDAVSVFYVSRTSNTNGVDTILDKVDG   200
        210        220        230        240
VSAEPTPESWRSEVTFTTPAVYIYTSGTTGLPKSGTINHH   240
RLRYGTSLAMSSGNHGQGCHLYQQCPCSNSATLKIGLHGC   280
ILGWGYFNLGGANSQASQFWERLAGNTTSTVIQYIGELLR   320
YLCNTPQKPNDRDHKVKKALGNGLRGDVWREFIKRFGDIH   360
VYEFYASTEGNIGFVNYPRKIGAVGRANYLQRKVARYELI   400
        410        420        430        440
KYDVEKDEPVRDANGYCIKVPKGEVGLLVCKITQLTPFIG   440
YAGGKTQTEKKKLRDVFKKGDIYFNSGDLLMIDRENFVYF   480
HDRVGDTFRWKGENVATTEVADIVGLVDFVEEVNVYGVPV   520
PGHEGRIGMASLKIKENYEFNGKKLFQHIAEYLPSYARPR   560
FLRIQDTIEITGTFKHRKVTLMEEGFNPTVIKDTLYFMDD   600
        610        620        630        640
AEKTFVPMTENIYNAIIDKTLKL   623
```

FIG. 65 mmFATP3 partial DNA

```
         10        20        30        40
GAAAGCTCTGAGAGCGGGTGCAGTCTGGCCTGGCGTCTCG  40
CGTACCTGGCCCGGGAGCAGCCGACACACCTTCCTCAT    80
CCACGGCGCGCAGCGCTTTAGCTACGCGGAGGCTGAGCGC 120
GAGAGCAACCGGATTGCTCGCGCCTTTCTGCGCGCACGGG 160
GCTGGACCGGGGGCCGCCGAGGCTCGGGCAGGGGCAGCAC 200
         210       220       230       240
TGAGGAAGGCGCACGCGTGGCGCCTCCGGCTGGAGATGCG 240
GCTGCTAGAGGGACGACCGCGCCCCTCTGGCACCCGGGG  280
CGACCGTGGCGCTGCTCCTCCCAGCGGGCCCGGATTTCCT 320
TTGGATTTGGTTCGGACTGGCCAAAGCTGGCCTGCGCACG 360
GCCTTTGTGCCCACCGCTTTACGCCGAGGACCCCTGCTGC 400
         410       420       430       440
ACTGCCTCCGCAGCTGCGGTGCGAGTGCGCTCGTGCTGGC 440
CACAGAGTTCCTGGAGTCCCTGGAGCCGGACCTGCCGGCC 480
TTGAGAGCCATGGGGCTCCACCTATGGGCGACGGGCCCTG 520
AAACTAATGTAGCTGGAATCAGCAATTTGCTATCGGAAGC 560
AGCAGACCAAGTGGATGAGCCAGTGCCGGGGTACCTCTCT 600
         610       620       630       640
GCCCCCAGAACATAATGGACACCTGCCTGTACATCTTCA  640
CCTCTGGCACTACTGGCCTGCCCAAGGCTGCTCGAATCAG 680
TCATCTGAAGGTTCTACAGTGCCAGGGATTCTACCATCTG 720
TGTGGAGTCCACCAGGAGGACGTGATCTACCTCGCACTCC 760
CACTGTACCACATGTCTGGCTCCCTTCTGGGCATTGTGGG 800
         810       820       830       840
CTGCTTGGGCATTGGGGCCACCGTGGTGCTGAAACCCAAG 840
TTCTCAGCTAGCCAGTTCTGGGACGATTGCCAGAAACACA 880
GGGTGACAGTGTTCCAGTACATTGGGGAGTTGTGCCGATA 920
CCTCGTCAACCAGCCCCCGAGCAAGGCAGAGTTTGACCAT 960
AAGGTGCGCTTGGCAGTGGGCAGTGGGTTGCGCCCAGACA 1000
         1010      1020      1030      1040
CCTGGGAGCGTTTCCTGCGGCGATTTGGACCTCTGCAGAT 1040
ACTGGAGACGTATGGCATGACAGAGGGCAACGTAGCTACG 1080
TTCAATTACACAGGACGGCAGGGTGCAGTGGGGCGAGCTT 1120
CCTGGCTTTACAAGCACATCTTCCCCTTCTCCTTGATTCG 1160
ATACGATGTCATGACAGGGGAGCCTATTCGGAATGCCCAG 1200
```

FIG. 66A

```
          1210      1220      1230      1240
     ┬┴┴┴┴┴┴┴┴┴┴┴┴┴┴┴┴┴┴┴┴┴┴┴┴┴┴┴┴┴┴┴┴┴┴┴
GGGCACTGCATGACCACATCTCCAGGTGAGCCAGGCCTAC 1240
TGGTGGCCCCAGTGAGCCAGCAGTCCCCCTTCCTGGGCTA 1280
TGCTGGGGCTCCGGAGCTGGCCAAGGACAAGCTGCTGAAG 1320
GATGTCTTCTGGTCTGGGGACGTTTTCTTCAATACTGGGG 1360
ACCTCTTGGTCTGTGATGAGCAAGGCTTTCTTCACTTCCA 1400
          1410      1420      1430      1440
     ┬┴┴┴┴┴┴┴┴┴┴┴┴┴┴┴┴┴┴┴┴┴┴┴┴┴┴┴┴┴┴┴┴┴┴┴
CGATCGTACTGGAGACACCATCAGGTGGAAGGGAGAGAAT 1440
GTGGCCACAACTGAAGTGGCTGAGGTCTTGGAGACCCTGG 1480
ACTTCCTTCAGGAGGTGAACATCTATGGAGTCACGGTGCC 1520
AGGGCACGAAGGCAGGGCAGGCATGGCGGCCTTGGCTCTG 1560
CGGCCCCGCAGGCTCTGAACCTGGTGCAGCTCTACAGCC 1600
          1610      1620      1630      1640
     ┬┴┴┴┴┴┴┴┴┴┴┴┴┴┴┴┴┴┴┴┴┴┴┴┴┴┴┴┴┴┴┴┴┴┴┴
ATGTTTCTGAGAACTTGCCACCGTATGCCCGACCTCGGTT 1640
TCTCAGGCTCCAGGAATCTTTGGCCACTACTGAGACCTTC 1680
AAACAGCAGAAGGTTAGGATGGCCAATGAGGGCTTTGACC 1720
CCAGTGTACTGTCTGACCCACTCTATGTTCTGGACCAAGA 1760
TATAGGGGCCTACCTGCCCCTCACACCTGCCCGGTACAGT 1800
          1810      1820      1830      1840
     ┬┴┴┴┴┴┴┴┴┴┴┴┴┴┴┴┴┴┴┴┴┴┴┴┴┴┴┴┴┴┴┴┴┴┴┴
GCCCTCCTGTCTGGAGACCTTCGAATCTGAAACCTTCCAC 1840
TTGAGGGAGGGGCTCGGAGGGTACAGGCCACCATGGCTGC 1880
ACCAGGGAGGGTTTTCGGGTATCTTTTGTATATGGAGTCA 1920
TTATTTTGTAATAAACAGCTGGAGCTTAAAAAAAAAAAAA 1960
AAAAAAAAAAAAAAAAAAAAAAAAAAAAAAAAAAAAAA  1998
```

FIG. 66B mmFATP3 partial protein

```
                10        20        30        40
ESSESGCSLAWRLAYLAREQPTHTFLIHGAQRFSYAEAER    40
ESNRIARAFLRARGWTGGRRGSGRGSTEEGARVAPPAGDA    80
AARGTTAPPLAPGATVALLLPAGPDFLWIWFGLAKAGLRT   120
AFVPTALRRGPLLHCLRSCGASALVLATEFLESLEPDLPA   160
LRAMGLHLWATGPETNVAGISNLLSEAADQVDEPVPGYLS   200
               210       220       230       240
APQNIMDTCLYIFTSGTTGLPKAARISHLKVLQCQGFYHL   240
CGVHQEDVIYLALPLYHMSGSLLGIVGCLGIGATVVLKPK   280
FSASQFWDDCQKHRVTVFQYIGELCRYLVNQPPSKAEFDH   320
KVRLAVGSGLRPDTWERFLRRFGPLQILETYGMTEGNVAT   360
FNYTGRQGAVGRASWLYKHIFPFSLIRYDVMTGEPIRNAQ   400
               410       420       430       440
GHCMTTSPGEPGLLVAPVSQQSPFLGYAGAPELAKDKLLK   440
DVFWSGDVFFNTGDLLVCDEQGFLHFHDRTGDTIRWKGEN   480
VATTEVAEVLETLDFLQEVNIYGVTVPGHEGRAGMAALAL   520
RPPQALNLVQLYSHVSENLPPYARPRFLRLQESLATTETF   560
KQQKVRMANEGFDPSVLSDPLYVLQQDIGAYLPLTPARYS   600
               610       620       630       640
ALLSGDLRI                                  609
```

FIG. 67 mmFATP4 full length DNA

```
        10        20        30        40
ATGCTGCTTGGAGCCTCTCTGGTGGGGGCGCTACTGTTCT 40
CCAAGCTAGTGCTGAAGCTGCCCTGGACCCAGGTGGGATT 80
CTCCCTGTTGCTCCTGTACTTGGGGTCTGGTGGCTGGCGT 120
TTCATCCGGGTCTTCATCAAGACGGTCAGGAGAGATATCT 160
TTGGTGGCATGGTGCTCCTGAAGGTGAAGACCAAGGTGCG 200
        210       220       230       240
ACGGTACCTTCAGGAGCGGAAGACGGTGCCCCTGCTGTTT 240
GCTTCAATGGTACAGCGCCACCCGGACAAGACAGCCCTGA 280
TTTTCGAGGGCACAGACACTCACTGGACCTTCCGCCAGCT 320
GGATGAGTACTCCAGTAGTGTGGCCAACTTCCTGCAGGCC 360
CGGGGCCTGGCCTCAGGCAATGTAGTTGCCCTCTTTATGG 400
        410       420       430       440
AAAACCGCAATGAGTTTGTGGGTCTGTGGCTAGGCATGGC 440
CAAGCTGGGCGTGGAGGCGGCTCTCATCAACACCAACCTT 480
AGGCGGGATGCCCTGCGCCACTGTCTTGACACCTCAAAGG 520
CACGAGCTCTCATCTTTGGCAGTGAGATGGCCTCAGCTAT 560
CTGTGAGATCCATGCTAGCCTGGAGCCCACACTCAGCCTC 600
        610       620       630       640
TTCTGCTCTGGATCCTGGGAGCCCAGCACAGTGCCCGTCA 640
GCACAGAGCATCTGGACCCTCTTCTGGAAGATGCCCCGAA 680
GCACCTGCCCAGTCACCCAGACAAGGGTTTTACAGATAAG 720
CTCTTCTACATCTACACATCGGGCACCACGGGGCTACCCA 760
AAGCTGCCATTGTGGTGCACAGCAGGTATTATCGTATGGC 800
        810       820       830       840
TTCCCTGGTGTACTATGGATTCCGCATGCGGCCTGATGAC 840
ATTGTCTATGACTGCCTCCCCCTCTACCACTCAAGCAGGA 880
AACATCGTGGGGATTGGCAGTGCTTACTCCACGGCATGAC 920
TGTGGTGATCCGGAAGAAGTTCTCAGCCTCCCGGTTCTGG 960
GATGATTGTATCAAGTACAACTGCACAGTGGTACAGTACA 1000
        1010      1020      1030      1040
TTGGCGAGCTCTGCCGCTACCTCCTGAACCAGCCACCCCG 1040
TGAGGCTGAGTCTCGGCACAAGGTGCGCATGGCACTGGGC 1080
AACGGTCTCCGGCAGTCCATCTGGACCGACTTCTCCAGCC 1120
GTTTCCACATCCCCCAGGTGGCTGAGTTCTATGGGGCCAC 1160
TGAATGCAACTGTAGCCTGGGCAACTTTGACAGCCGGGTG 1200
```

FIG. 68A

```
            1210      1220      1230      1240
GGGGCCTGTGGCTTCAATAGCCGCATCCTGTCCTTTGTGT  1240
ACCCTATCCGTTTGGTACGTGTCAATGAGGATACCATGGA  1280
ACTGATCCGGGGACCCGATGGAGTCTGCATTCCCTGTCAA  1320
CCAGGTCAGCCAGGCCAGCTGGTGGGTCGCATCATCCAGC  1360
AGGACCCTCTGCCGTTTCGACGGGTACCTCAACCAGGG    1400
            1410      1420      1430      1440
TGCCAACAACAAGAAGATTGCTAATGATGTCTTCAAGAAG  1440
GGGGACCAAGCCTACCTCACTGGTGACGTCCTGGTGATGG  1480
ATGAGCTGGGTTACCTGTACTTCGAGATCGCACTGGGGA   1520
CACGTTCCGCTGGAAAGGGGAGAATGTATCTACCACTGAG  1560
GTGGAGGGCACACTCAGCCGCCTGCTTCATATGGCAGATG  1600
            1610      1620      1630      1640
TGGCAGTTTATGGTGTTGAGGTGCCAGGAACTGAAGGCCG  1640
AGCAGGAATGGCTGCCGTTGCAAGTCCCATCAGCAACTGT  1680
GACCTGGAGAGCTTTGCACAGACCTTGAAAAGGAGCTGC   1720
CTCTGTATGCCCGCCCCATCTTCCTGCGCTTCTTGCCTGA  1760
GCTGCACAAGACAGGGACCTTCAAGTTCCAGAAGACAGAG  1800
            1810      1820      1830      1840
TTGCGGAAGGAGGGCTTTGACCCATCTGTTGTGAAAGACC  1840
CGCTGTTCTATCTGGATGCTCGGAAGGGCTGCTACGTTGC  1880
ACTGGACCAGGAGGCCTATACCCGCATCCAGGCAGGCGAG  1920
GAGAAGCTGTGATTTCCCCTACATCCCTCTGAGGGCCAG   1960
AAGATGCTGGATTCAGAGCCCTAGCGTCCACCCCAGAGGG  2000
```

FIG. 68B

```
                  2010        2020        2030        2040
          ╵╵╵╵╵╵╵╵╵╵╵╵╵╵╵╵╵╵╵╵╵╵╵╵╵╵╵╵╵╵╵╵╵╵╵╵╵╵╵╵╵╵
          TCCTGGGCAATGCCAGACCAAAGCTAGCAGGGCCCGCACC  2040
          TCCGCCCCTAGGTGCTGATCTCCCTCTCCCAAACTGCCA  2080
          AGTGACTCACTGCCGCTTCCCCGACCCTCCAGAGGCTTTC  2120
          TGTGAAAGTCTCATCCAAGCTGTGTCTTCTGGTCCAGGCG  2160
          TGGCCCCTGGCCCCAGGGTTTCTGATAGGCTCCTTTAGGA  2200
                  2210        2220        2230        2240
          ╵╵╵╵╵╵╵╵╵╵╵╵╵╵╵╵╵╵╵╵╵╵╵╵╵╵╵╵╵╵╵╵╵╵╵╵╵╵╵╵
          TGGTATCTTGGGTCCAGCGGGCCAGGGTGTGGGAGAGGAG  2240
          TCACTAAGATCCCTCCAATCAGAAGGGAGCTTACAAAGGA  2280
          ACCAAGGCAAAGCCTGTAGACTCAGGAAGCTAAGTGGCCA  2320
          GAGACTATAGTGGCCAGTCATCCATGTCCACAGAGGATC  2360
          TTGGTCCAGAGCTGCCAAAGTGTCACCTCTCCCTGCCTGC  2400
                  2410        2420        2430        2440
          ╵╵╵╵╵╵╵╵╵╵╵╵╵╵╵╵╵╵╵╵╵╵╵╵╵╵╵╵╵╵╵╵╵╵╵╵╵╵╵╵
          ACCTCTGGGGAAAAGAGGACAGCATGTGGCCACTGGGCAC  2440
          CTGTCTCAAGAAGTCAGGATCACACACTCAGTCCTTGTTT  2480
          CTCCAGGTTCCCTTGTTCTTGTCTCGGGGAGGGAGGGACG  2520
          AGTGTCCTGTCTGTCCTTCCTGCCTGTCTGTGAGTCTGTG  2560
          TTGCTTCTCCATCTGTCCTAGCCTGAGTGTGGGTGGAACA  2600
                  2610        2620        2630        2640
          ╵╵╵╵╵╵╵╵╵╵╵╵╵╵╵╵╵╵╵╵╵╵╵╵╵╵╵╵╵╵╵╵╵╵╵╵╵╵╵╵
          GGCATGAGGAGAGTGTGGCTCAGGGGCCAATAAACTCTGC  2640
          CTTGACTCCTCTTAAAAAAAAAAAAAAAAAAAAAAAAAA  2680
          AAAAAAAAAAAAAAAAAAAAAAAAAAAAAA  2710
```

FIG. 68C mmFATP4 full length protein

```
          10        20        30        40
 ┌─────────┴─────────┴─────────┴─────────┴─
 MLLGASLVGALLFSKLVLKLPWTQVGFSLLLLYLGSGGWR   40
 FIRVFIKTVRRDIFGGMVLLKVKTKVRRYLQERKTVPLLF   80
 ASMVQRHPDKTALIFEGTDTHWTFRQLDEYSSSVANFLQA  120
 RGLASGNVVALFMENRNEFVGLWLGMAKLGVEAALINTNL  160
 RRDALRHCLDTSKARALIFGSEMASAICEIHASLEPTLSL  200
         210       220       230       240
 ┌─────────┴─────────┴─────────┴─────────┴─
 FCSGSWEPSTVPVSTEHLDPLLEDAPKHLPSHPCKGFTDK  240
 LFYIYTSGTTGLPKAAIVVHSRYYRMASLVYYGFRMRPDD  280
 IVYDCLPLYHSSRKHRGDWQCLLHGMTVVIRKKFSASRFW  320
 DDCIKYNCTVVQYIGELCRYLLNQPPREAESRHKVRMALG  360
 NGLRQSIWTDFSSRFHIPQVAEFYGATECNCSLGNFDSRV  400
         410       420       430       440
 ┌─────────┴─────────┴─────────┴─────────┴─
 GACGFNSRILSFVYPIRLVRVNEDTMELIRGPDGVCIPCQ  440
 PGQPGQLVGRIIQQDPLRRFDGYLNQGANNKKIANDVFKK  480
 GDQAYLTGDVLVMDELGYLYFRDRTGDTFRWKGENVSTTE  520
 VEGTLSRLLHMADVAVYGVEVPGTEGRAGMAAVASPISNC  560
 DLESFAQTLKKELPLYARPIFLRFLPELHKTGTFKFQKTE  600
         610       620       630       640
 ┌─────────┴─────────┴─────────┴─────────┴─
 LRKEGFDPSVVKDPLFYLDARKGCYVALDQEAYTRIQAGE  640
 EKL  643
```

FIG. 69 mmFATP5 full length DNA

```
              10        20        30        40
CACTCATCAGAGCTAAGAGAGACTACACGCTCTCATCTAC  40
TTCAGAAAGAGCCAATGCCATGGGTATTTGGAAGAAACTA  80
ACCTTACTGCTGTTGCTGCTTCTGCTGGTTGGCCTGGGGC  120
AGCCCCCATGGCCAGCAGCTATGGCTCTGGCCCTGCGTTG  160
GTTCCTGGGAGACCCCACATGCCTTGTGCTGCTTGGCTTG  200
              210       220       230       240
GCATTGCTGGGCAGACCCTGGATCAGCTCCTGGATGCCCC  240
ACTGGCTGAGCCTGGTAGGAGCAGCTCTTACCTTATTCCT  280
ATTGCCTCTACAGCCACCCCCAGGGCTACGCTGGCTGCAT  320
AAAGATGTGGCTTTCACCTTCAAGATGCTTTTCTATGGCC  360
TAAAGTTCAGGCGACGCCTTAACAAACATCCTCCAGAGAC  400
              410       420       430       440
CTTTGTGGATGCTTTAGAGCGGCAAGCACTGGCATGGCCT  440
GACCGGGTGGCCTTGGTGTGTACTGGGTCTGAGGGCTCCT  480
CAATCACAAATAGCCAGCTGGATGCCAGGTCCTGTCAGGC  520
AGCATGGGTCCTGAAAGCAAAGCTGAAGGATGCCGTAATC  560
CAGAACACAAGAGATGCTGCTGCTATCTTAGTTCTCCCGT  600
              610       620       630       640
CCAAGACCATTTCTGCTTTGAGTGTGTTTCTGGGGTTGGC  640
CAAGTTGGGCTGCCCTGTGGCCTGGATCAATCCACACAGC  680
CGAGGGATGCCCTTGCTACACTCTGTACGGAGCTCTGGGG  720
CCAGTGTGCTGATTGTGGATCCAGACCTCCAGGAGAACCT  760
GGAAGAAGTCCTTCCCAAGCTGCTAGCTGAGAACATTCAC  800
              810       820       830       840
TGCTTCTACCTTGGCCACAGCTCACCCACCCCGGGAGTAG  840
AGGCTCTGGGAGCTTCCCTGGATGCTGCACCTTCTGACCC  880
AGTACCTGCCAGCCTTCGAGCTACGATTAAGTGGAAATCT  920
CCTGCCATATTCATCTTTACTTCAGGGACCACTGGACTCC  960
CAAAGCCAGCCATCTTATCACATGAGCGGGTCATACAAGT  1000
              1010      1020      1030      1040
GAGCAACGTGCTGTCCTTCTGTGGATGCAGAGCTGATGAT  1040
GTGGTCTATGACGTCCTACCTCTGTACCATACGATAGGGC  1080
TTGTCCTTGGATTCCTTGGCTGCTTACAAGTTGGAGCCAC  1120
CTGTGTCCTGGCCCCCAAGTTCTCTGCCTCCCGATTCTGG  1160
GCTGAGTGCCGGCAGCATGGCGTAACAGTGATCTTGTATG  1200
```

FIG. 70A

```
         1210      1220      1230      1240
     |....|....|....|....|....|....|....|
     TGGGTGAAATCCTGCGGTACTTGTGTAACGTCCCTGAGCA  1240
     ACCAGAAGACAAGATACATACAGTGCGCTTGGCCATGGGA  1280
     ACTGGACTTCGGGCAAATGTGTGGAAAAACTTCCAGCAAC  1320
     GCTTTGGTCCCATTCGGATCTGGGAATTCTACGGATCCAC  1360
     AGAGGGCAATGTGGGCTTAATGAACTATGTGGGCCACTGC  1400
         1410      1420      1430      1440
     |....|....|....|....|....|....|....|
     GGGGCTGTGGGAAGGACCAGCTGCATCCTTCGAATGCTGA  1440
     CTCCCTTTGAGCTTGTACAGTTCGACATAGAGACAGCAGA  1480
     GCCTCTGAGGGACAAACAGGGTTTTTGCATTCCTGTGGAG  1520
     CCAGGAAAGCCAGGACTTCTTTTGACCAAGGTTCGAAAGA  1560
     ACCAACCCTTCCTGGGCTACCGTGGTTCCCAGGCCGAGTC  1600
         1610      1620      1630      1640
     |....|....|....|....|....|....|....|
     CAATCGGAAACTTGTTGCGAATGTACGACGCGTAGGAGAC  1640
     CTGTACTTCAACACTGGGGACGTGCTGACCTTGGACCAGG  1680
     AAGGCTTCTTCTACTTTCAAGACCGCCTTGGTGACACCTT  1720
     CCGGTGGAAGGGCGAAAACGTATCTACTGGAGAGGTGGAG  1760
     TGTGTTTGTCTAGCCTAGACTTCCTAGAGGAAGTCAATG  1800
         1810      1820      1830      1840
     |....|....|....|....|....|....|....|
     TCTATGGTGTGCCTGTGCCAGGGTGTGAGGGTAAGGTTGG  1840
     CATGGCTGCTGTGAAACTGGCTCCTGGGAAGACTTTTGAT  1880
     GGGCAGAAGCTATACCAGCATGTCCGCTCCTGGCTCCCTG  1920
     CCTATGCCACACCTCATTTCATCCGTATCCAGGATTCCCT  1960
     GGAGATCACAAACACCTACAAGCTGGTAAAGTCACGGCTG  2000
         2010      2020      2030      2040
     |....|....|....|....|....|....|....|
     GTGCGTGAGGGTTTTGATGTGGGGATCATTGCTGACCCCC  2040
     TCTACATACTGGACAACAAGGCCCAGACCTTCCGGAGTCT  2080
     GATGCCAGATGTGTACCAGGCTGTGTGTGAAGGAACCTGG  2120
     AATCTCTGACCACCTAGCCAACTGGAAGGCAATCCAAAAG  2160
     TGTAGAGATTGACACTAGTCAGCTTCACAAAGTTGTCCGG  2200
         2210      2220      2230      2240
     |....|....|....|....|....|....|....|
     GTTCCAGATGCCCATGGCCCAGTAGTACTTAGAGAATAAA  2240
     CTTGAATGTGTATACAAAAAAAAAAAAAAAAAAAAAAA    2277
```

FIG. 70B mmFATP5 full length protein

```
          10         20         30         40
 ├┴┴┴┴┴┴┴┴┴┼┴┴┴┴┴┴┴┴┴┼┴┴┴┴┴┴┴┴┴┼┴┴┴┴┴┴┴┴┴┤
MGIWKKLTLLLLLLLLVGLGQPPWPAAMALALRWFLGDPT  40
CLVLLGLALLGRPWISSWMPHWLSLVGAALTLFLLPLQPP  80
PGLRWLHKDVAFTFKMLFYGLKFRRRLNKHPPETFVDALE  120
RQALAWPDRVALVCTGSEGSSITNSQLDARSCQAAWVLKA  160
KLKDAVIQNTRDAAAILVLPSKTISALSVFLGLAKLGCPV  200
         210        220        230        240
 ├┴┴┴┴┴┴┴┴┴┼┴┴┴┴┴┴┴┴┴┼┴┴┴┴┴┴┴┴┴┼┴┴┴┴┴┴┴┴┴┤
AWINPHSRGMPLLHSVRSSGASVLIVDPDLQENLEEVLPK  240
LLAENIHCFYLGHSSPTPGVEALGASLDAAPSDPVPASLR  280
ATIKWKSPAIFIFTSGTTGLPKPAILSHERVIQVSNVLSF  320
CGCRADDVVYDVLPLYHTIGLVLGFLGCLQVGATCVLAPK  360
FSASRFWAECRQHGVTVILYVGEILRYLCNVPEQPEDKIH  400
         410        420        430        440
 ├┴┴┴┴┴┴┴┴┴┼┴┴┴┴┴┴┴┴┴┼┴┴┴┴┴┴┴┴┴┼┴┴┴┴┴┴┴┴┴┤
TVRLAMGTGLRANVWKNFQQRFGPIRIWEFYGSTEGNVGL  440
MNYVGHCGAVGRTSCILRMLTPFELVQFDIETAEPLRDKQ  480
GFCIPVEPGKPGLLLTKVRKNQPFLGYRGSQAESNRKLVA  520
NVRRVGDLYFNTGDVLTLDQEGFFYFQDRLGDTFRWKGEN  560
VSTGEVECVLSSLDFLEEVNVYGVPVPGCEGKVGMAAVKL  600
         610        620        630        640
 ├┴┴┴┴┴┴┴┴┴┼┴┴┴┴┴┴┴┴┴┼┴┴┴┴┴┴┴┴┴┼┴┴┴┴┴┴┴┴┴┤
APGKTFDGQKLYQHVRSWLPAYATPHFIRIQDSLEITNTY  640
KLVKSRLVREGFDVGIIADPLYILDNKAQTFRSLMPDVYQ  680
AVCEGTWNL  689
```

FIG. 71 dmFATP partial DNA

```
          10        20        30        40
GCTCTCTGGGCCTATATCAAGCTGCTGAGGTACACGAAGC  40
GCCATGAGCGGCTCAACTACACGGTGGCGGACGTCTTCGA  80
ACGAAATGTTCAGGCCCATCCGGACAAGGTGGCTGTGGTC 120
AGTGAGACGCAACGCTGGACCTTCCGTCAGGTGAACGAGC 160
ATGCGAACAAGGTGGCCAATGTGCTGCAGGCTCAGGGCTA 200
         210       220       230       240
CAAAAAGGGCGATGTGGTGGCCCTGTTGCTGGAGAACCGC 240
GCCGAGTACGTGGCCACCTGGCTGGGTCTCTCCAAGATCG 280
GTGTGATCACACCGCTGATCAACACGAATCTGCGCGGTCC 320
CTCCCTGCTGCACAGCATCACGGTGGCCCATTGCTCGGCT 360
CTCATTTACGGCGAGGACTTCCTGGAAGCTGTCACCGACG 400
         410       420       430       440
TGGCCAAGGATCTGCCAGCGAACCTCACACTCTTCCAGTT 440
CAACAACGAGAACAACAACAGCGAGACGGAAAAGAACATA 480
CCGCAGGCCAAGAATCTGAACGCGCTGCTGACCACGGCCA 520
GCTATGAGAAGCCTAACAAGACGCAGGTTAACCACCACGA 560
CAAGCTGGTCTACATCTACACCTCCGGCACCACAGGATTG 600
         610       620       630       640
CCAAAGGCTGCGGTTATCTCTCACTCCCGTTATCTGTTTA 640
TCGCTGCTGGCATCCACTACACCATGGGTTTCCAGGAGGA 680
GGACATCTTCTACACGCCCTTGCCTTTGTACCACACCGCT 720
GGTGGCATTATGTGCATGGGTCAGTCGGTGCTCTTTGGCT 760
CCACGGTCTCCATTCGCAAGAAGTTCTCGGCATCCAACTA 800
         810       820       830       840
TTTCGCCGACTGCGCCAAGTATAATGCAACTATTGGTCAG 840
TATATCGGTGAGATGGCTCGCTACATTCTAGCTACGAAAC 880
CCTCGGAATACGACCAGAAACACCGAGTGCGTCTGGTCTT 920
TGGAAACGGACTGCGACCGCAGATTTGGCCACAGTTTGTG 960
CAGCGCTTCAACATTGCCAAGGTTGGCGAGTTCTACGGCG 1000
        1010      1020      1030      1040
CCACCGAGGGTAATGCGAACATCATGAATCATGACAACAC 1040
GGTGGGCGCCATCGGCTTTGTGTCGCGCATCCTGCCCAAG 1080
ATCTACCCAATCTCGATCATTCGCGCCGATCCGGACACCG 1120
GAGAGCCCATTAGAGATAGGAATGGCCTATGCCAACTGTG 1160
CGCTCCCAACGAGCCAGGCGTATTCATCGGCAAGATCGTC 1200
```

FIG. 72A

```
           1210       1220       1230       1240
         |    |    |    |    |    |    |    |    |    |
AAAGGAAATCCTTCTCGCGAATTCCTCGGATACGTCGATG 1240
AAAAGGCCTCCGCGAAGAAGATTGTTAAGGATGTGTTCAA 1280
GCATGGCGATATGGCTTTCATCTCCGGAGATCTGCTGGTT 1320
GCCGACGAGAAGGGTTATCTGTACTTCAAGGATCGCACCG 1360
GTGACACCTTCCGCTGGAAGGGCGAGAATGTTTCCACCAG 1400
           1410       1420       1430       1440
         |    |    |    |    |    |    |    |    |    |
CGAGGTGGAGGCGCAAGTCAGCAATGTGGCCGGTTACAAG 1440
GATACCGTCGTTTACGGCGTAACCATTCCGCACCGAGG   1480
GAAGGGCCGGCATGGCCGCCATCTATGATCCGGAGCGAGA 1520
ATTGGACCTCGACGTCTTCGCCGCTAGCTTGGCCAAGGTG 1560
CTGCCCGCGTACGCTCGTCCCAGATCATTCGATTGCTCA  1600
           1610       1620       1630       1640
         |    |    |    |    |    |    |    |    |    |
CCAAGGTGGACCTGACTGGAACCTTTAAGCTGCGCAAGGT 1640
AGACCTGCAGAAGGAGGGCTACGATCCGAACGCGATCAAG 1680
GACGCGCTGTACTACCAGACTTCCAAGGGTCGGTACGAGC 1720
TGCTCACGCCCCAGGTTTACGACCAGGTGCAGCGCAACGA 1760
AATCCGCTTCTAAGAGCTGCAATAGAGTTGTGTCTGAACC 1800
           1810       1820       1830       1840
         |    |    |    |    |    |    |    |    |    |
TTGCCTTTTGCCCAATATGCTGTTAATTAGTTTGTAAGGC 1840
TAAGTGTAGTAGAGGAAAATCGGGGGAAATCGGCAGCAAA 1880
GATCATTCAGCCTAGGAGAGATGCATCCGAAGCACATTTC 1920
CATGTCAACAATGCACTTTTGTATATCGTAAGCATATATA 1960
TATCGTATATCGTAAACGTAGTTGTATCTGCATTTGTGTA 2000
           2010       2020       2030       2040
         |    |    |    |    |    |    |    |    |    |
GATGATAGCCTCCTATACGCATTTCAATTGTTTTAGCGT  2040
GCTAAAGAACCTTGTTAAATGCAATTTCAGCTATTGTTTA 2080
GTCAGTTTTAGTGGCATTTACACTTCCATTCTCGTTGCGT 2120
TTCGTTTTTGCCTGTACATATGAAGCTCTGATGTTTTT   2160
GTATCAAATAAAGTTTTTCCTTCACCACGGACCACGTGA  2200
           2210       2220       2230       2240
         |    |    |    |    |    |    |    |    |    |
AAAAAAAAAAAAAAAAAAAAA 2221
```

FIG. 72B dm FATP partial protein

```
         10        20        30        40
ALWAYIKLLRYTKRHERLNYTVADVFERNVQAHPDKVAVV  40
SETQRWTFRQVNEHANKVANVLQAQGYKKGDVVALLLENR  80
AEYVATWLGLSKIGVITPLINTNLRGPSLLHSITVAHCSA  120
LIYGEDFLEAVTDVAKDLPANLTLFQFNNENNNSETEKNI  160
PQAKNLNALLTTASYEKPNKTQVNHHDKLVYIYTSGTTGL  200
         210       220       230       240
PKAAVISHSRYLFIAAGIHYTMGFQEEDIFYTPLPLYHTA  240
GGIMCMGQSVLFGSTVSIRKKFSASNYFADCAKYNATIGQ  280
YIGEMARYILATKPSEYDQKHRVRLVFGNGLRPQIWPQFV  320
QRFNIAKVGEFYGATEGNANIMNHDNTVGAIGFVSRILPK  360
IYPISIIRADPDTGEPIRDRNGLCQLCAPNEPGVFIGKIV  400
         410       420       430       440
KGNPSREFLGYVDEKASAKKIVKDVFKHGDMAFISGDLLV  440
ADEKGYLYFKDRTGDTFRWKGENVSTSEVEAQVSNVAGYK  480
DTVVYGVTIPHTEGRAGMAAIYDPERELDLDVFAASLAKV  520
LPAYARPQIIRLLTKVDLTGTFKLRKVDLQKEGYDPNAIK  560
DALYYQTSKGRYELLTPQVYDQVQRNEIRF            590
```

FIG. 73 drFATP partial DNA

```
         10        20        30        40
    |....|....|....|....|....|....|....|....|
    AGTGTAGATACCACAGGAACGTTTAAAATCCAGAAGACCA  40
    GACTGCAAAGGGAAGGATACGATCCACGGCTCACAACTGA  80
    CCAGATCTACTTCCTAAACTCCAGAGCAGGGCGTTACGAG  120
    CTTGTCAACGAGGAGCTGTACAATGCATTTGAACAAGGGC  160
    AGGATTTCCCTTT  173
```

FIG. 74 drFATP partial protein

```
         10        20        30        40
    |....|....|....|....|....|....|....|....|
    SVDTTGTFKIQKTRLQREGYDPRLTTDQIYFLNSRAGRYE  40
    LVNEELYNAFEQGQDFP  57
```

FIG. 75 ceFATPa coding only DNA

```
          10        20        30        40
 |....|....|....|....|....|....|....|....|
ATGAAGCTGGAGGAGCTTGTGACAGTTATGCTTCTCACAG  40
TGGCTGTCATTGCTCAGAATCTTCCGATTGGAGTAATATT  80
GGCTGGAGTTCTTATTTTATACATCACAGTGGTTCATGGA 120
GATTTCATTTATAGAAGTTATCTTACGTTGAATAGGGATT 160
TAACAGGATTGGCTCTAATTATTGAAGTCAAAATCGACCT 200
         210       220       230       240
 |....|....|....|....|....|....|....|....|
ATGGTGGAGGTTGCATCAGAATAAAGGAATCCATGAACTG 240
TTTTTGGATATTGTGAAAAGAATCCAAATAAGCCGGCGA  280
TGATTGACATCGAGACGAATACAACAGAAACATACGCAGA 320
GTTCAATGCACATTGTAATAGATATGCCAATTATTTCCAG 360
GGTCTTGGCTATCGATCCGGAGACGTTGTCGCCTTGTACA 400
         410       420       430       440
 |....|....|....|....|....|....|....|....|
TGGAGAACTCGGTCGAGTTTGTGGCCGCGTGGATGGGACT 440
CGCAAAAATCGGAGTTGTAACGGCTTGGATCAACTCGAAT 480
TTGAAAAGAGAGCAACTTGTTCATTGTATCACTGCGAGCA 520
AGACAAAGGCGATTATCACAAGTGTAACACTTCAGAATAT 560
TATGCTTGATGCTATCGATCAGAAGCTGTTTGATGTTGAG 600
         610       620       630       640
 |....|....|....|....|....|....|....|....|
GGAATTGAGGTTTACTCTGTCGGAGAGCCCAAGAAGAATT 640
CTGGATTCAAGAATCTCAAGAAGAAGTTGGATGCTCAAAT 680
TACTACGGAACCAAAGACCCTTGACATAGTAGATTTTAAA 720
AGTATTCTTTGCTTCATCTATACAAGTGGTACTACTGGAA 760
TGCCAAAAGCCGCTGTCATGAAGCACTTCAGATATTACTC 800
         810       820       830       840
 |....|....|....|....|....|....|....|....|
GATTGCCGTTGGAGCCGCAAAATCATTCGGAATCCGCCCT 840
TCTGATCGTATGTACGTCTCGATGCCAATTTATCACACTG 880
CAGCTGGAATTCTTGGAGTTGGGCAAGCTCTGTTGGGTGG 920
ATCATCGTGTGTCATTAGAAAAAAATTCTCGGCTAGCAAC 960
TTTTGGAGGGATTGTGTAAAGTATGATTGTACAGTTTCAC 1000
        1010      1020      1030      1040
 |....|....|....|....|....|....|....|....|
AATACATTGGAGAGATTTGTCGGTACTTGTTGGCTCAGCC 1040
AGTTGTGGAAGAGGAATCCAGGCATAGAATGAGATTGTTG 1080
GTTGGAAACGGACTCCGTGCTGAAATCTGGCAACCATTTG 1120
TAGATCGATTCCGTGTCAGAATTGGAGAACTTTATGGTTC 1160
AACTGAAGGAACTTCATCTCTCGTGAACATTGACGGACAT 1200
```

FIG. 76A

```
              1210      1220      1230      1240
     |....|....|....|....|....|....|....|....|
 GTCGGAGCTTGCGGATTCTTGCCAATATCCCCATTAACAA 1240
 AGAAAATGCATCCGGTTCGATTAATTAAGGTTGATGATGT 1280
 CACTGGAGAAGCAATCCGAACTTCCGATGGACTTTGCATT 1320
 GCATGTAATCCAGGAGAGTCTGGAGCAATGGTGTCGACGA 1360
 TCAGAAAAAATAATCCATTATTGCAATTCGAGGGATATCT 1400
              1410      1420      1430      1440
     |....|....|....|....|....|....|....|....|
 GAATAAGAAGGAAACGAATAAAAAGATTATCAGAGATGTC 1440
 TTCGCAAAGGGAGATAGTTGCTTTTGACTGGAGATCTTC  1480
 TTCATTGGGATCGTCTTGGTTATGTATATTTCAAGGATCG 1520
 TACTGGAGATACTTTCCGTTGGAAGGGAGAGAATGTGTCG 1560
 ACTACTGAAGTCGAGGCAATTCTTCATCCAATTACTGGAT 1600
              1610      1620      1630      1640
     |....|....|....|....|....|....|....|....|
 TGTCTGATGCAACTGTTTATGGTGTAGAGGTTCCTCAAAG 1640
 AGAGGGAAGAGTTGGAATGGCGTCAGTTGTTCGAGTTGTA 1680
 TCGCATGAGGAAGATGAAACTCAATTTGTTCATAGAGTTG 1720
 GAGCAAGACTTGCCTCTTCGCTTACCAGCTACGCGATTCC 1760
 TCAGTTTATGCGAATTTGTCAGGATGTTGAGAAACAGGT  1800
              1810      1820      1830      1840
     |....|....|....|....|....|....|....|....|
 ACATTCAAACTTGTGAAGACGAATCTACAACGATTAGGTA 1840
 TCATGGATGCTCCTTCAGATTCAATTTACATCTACAATTC 1880
 TGAAAATCGCAATTTTGTGCCGTTCGACAATGATTTGAGG 1920
 TGCAAGGTCTCACTGGGAAGTTATCCATTTTAA        1953
```

FIG. 76B ceFATPa coding only protein

```
          10        20        30        40
MKLEELVTVMLLTVAVIAQNLPIGVILAGVLILYITVVHG   40
DFIYRSYLTLNRDLTGLALIIEVKIDLWWRLHQNKGIHEL   80
FLDIVKKNPNKPAMIDIETNTTETYAEFNAHCNRYANYFQ  120
GLGYRSGDVVALYMENSVEFVAAWMGLAKIGVVTAWINSN  160
LKREQLVHCITASKTKAIITSVTLQNIMLDAIDQKLFDVE  200
          210       220       230       240
GIEVYSVGEPKKNSGFKNLKKKLDAQITTEPKTLDIVDFK  240
SILCFIYTSGTTGMPKAAVMKHFRYYSIAVGAAKSFGIRP  280
SDRMYVSMPIYHTAAGILGVGQALLGGSSCVIRKKFSASN  320
FWRDCVKYDCTVSQYIGEICRYLLAQPVVEEESRHRMRLL  360
VGNGLRAEIWQPFVDRFRVRIGELYGSTEGTSSLVNIDGH  400
          410       420       430       440
VGACGFLPISPLTKKMHPVRLIKVDDVTGEAIRTSDGLCI  440
ACNPGESGAMVSTIRKNNPLLQFEGYLNKKETNKKIIRDV  480
FAKGDSCFLTGDLLHWDRLGYVYFKDRTGDTFRWKGENVS  520
TTEVEAILHPITGLSDATVYGVEVPQREGRVGMASVVRVV  560
SHEEDETQFVHRVGARLASSLTSYAIPQFMRICQDVEKTG  600
          610       620       630       640
TFKLVKTNLQRLGIMDAPSDSIYIYNSENRNFVPFDNDLR  640
CKVSLGSYPF    650
```

FIG. 77 ceFATPb coding only DNA

```
          10        20        30        40
ATGAGGGAAATGCCGGACAGTCCCAAGTTTGCGTTAGTCA  40
CGTTTGTTGTGTATGCAGTGGTTTTGTACAATGTCAACAG  80
CGTTTTCTGGAAATTTGTATTCATCGGATATGTTGTATTT 120
AGGCTGCTTCGCACTGATTTTGGAAGAAGAGCACTTGCCA 160
CGTTACCTAGAGATTTTGCGGGACTGAAGCTCTTAATATC 200
         210       220       230       240
GGTTAAGTCGACAATTCGTGGCTTGTTCAAGAAAGATCGC 240
CCAATTCATGAAATCTTTTTGAATCAGGTGAAACAGCATC 280
CAAACAAAGTGGCGATTATTGAAATTGAAAGTGGTAGGCA 320
GTTGACGTATCAAGAATTGAATGCGTTAGCTAATCAGTAT 360
GCTAACCTTTACGTGAGTGAAGGTTACAAAATGGGCGACG 400
         410       420       430       440
TTGTCGCTTTGTTTATGGAAAATAGCATCGACTTCTTTGC 440
AATTTGGCTGGGACTTTCCAAGATTGGAGTCGTGTCGGCG 480
TTCATCAACTCAAACTTGAAGTTGGAGCCATTGGCACATT 520
CGATTAATGTTTCGAAGTGCAAATCATGCATTACCAATAT 560
CAATCTGTTGCCGATGTTCAAAGCCGCTCGTGAAAAGAAT 600
         610       620       630       640
CTGATCAGTGACGAGATCCACGTGTTTCTGGCTGGAACTC 640
AGGTTGATGGACGTCATAGAAGTCTTCAGCAAGATCTCCA 680
TCTTTTCTCTGAGGATGAACCTCCAGTTATAGACGGACTC 720
AATTTTAGAAGCGTTCTGTGTTATATTTACACTTCCGGTA 760
CTACCGGAAATCCAAAGCCAGCCGTCATTAAACACTTCCG 800
         810       820       830       840
TTACTTCTGGATTGCGATGGGAGCAGGAAAAGCATTTGGA 840
ATTAATAAGTCAGACGTTGTGTACATTACGATGCCAATGT 880
ATCACTCTGCCGCCGGTATCATGGGTATTGGATCATTAAT 920
TGCATTCGGGTCGACCGCTGTTATTAGGAAAAAGTTTTCG 960
GCAAGCAACTTCTGGAAAGATTGCGTCAAGTACAACGTCA 1000
         1010      1020      1030      1040
CAGCGACACAGTACATTGGAGAAATCTGCAGGTATCTTCT 1040
GGCAGCGAATCCATGTCCTGAAGAGAAACAACACAACGTG 1080
CGATTGATGTGGGGAAATGGTTTGAGAGGACAAATTTGGA 1120
AAGAGTTTGTAGGAAGATTTGGAATTAAGAAAATTGGAGA 1160
GTTGTACGGCTCAACAGAAGGAAACTCCAATATTGTTAAC 1200
```

FIG. 78A

```
         1210      1220      1230      1240
    |....|....|....|....|....|....|....|....|
    GTGGATAACCATGTTGGAGCTTGTGGATTCATGCCAATTT  1240
    ATCCCCATATTGGATCCCTCTACCCAGTTCGACTTATTAA  1280
    GGTTGATAGAGCCACTGGAGAGCTTGAACGTGATAAGAAC  1320
    GGACTCTGTGTGCCGTGTGTGCCTGGTGAAACTGGGGAAA  1360
    TGGTTGGCGTTATCAAGGAGAAAGATATTCTTCTAAAGTT  1400
         1410      1420      1430      1440
    |....|....|....|....|....|....|....|....|
    CGAAGGATATGTCAGCGAAGGGGATACTGCAAAGAAAATC  1440
    TACAGAGATGTGTTCAAGCATGGAGATAAGGTGTTTGCAA  1480
    GTGGAGATATTCTTCATTGGGATGATCTTGGATACTTGTA  1520
    CTTTGTGGACCGTTGTGGAGACACTTTCCGTTGGAAAGGG  1560
    GAGAACGTGTCAACTACTGAAGTTGAGGGAATTCTTCAGC  1600
         1610      1620      1630      1640
    |....|....|....|....|....|....|....|....|
    CTGTGATGGATGTGGAAGATGCAACTGTTTATGGAGTCAC  1640
    TGTCGGTAAAATGGAGGGGCGTGCCGGAATGGCTGGTATT  1680
    GTCGTCAAGGATGGAACGGATGTTGAGAAATTCATCGCCG  1720
    ATATTACTTCTCGACTGACCGAAAATCTGGCGTCTTACGC  1760
    AATCCCTGTTTTCATTCGGCTGTGCAAGGAAGTTGATCGA  1800
         1810      1820      1830      1840
    |....|....|....|....|....|....|....|....|
    ACCGGAACCTTCAAACTCAAGAAGACTGATCTTCAAAAAC  1840
    AAGGTTACGACCTGGTTGCTTGTAAAGGAGACCCAATTTA  1880
    CTACTGGTCAGCTGCAGAAAAATCCTACAAACCACTGACT  1920
    GACAAAATGCAACAGGATATTGACACTGGTGTTTATGATC  1960
    GCATTTAA  1968
```

FIG. 78B ceFATPb coding only protein

```
          10        20        30        40
MREMPDSPKFALVTFVVYAVVLYNVNSVFWKFVFIGYVVF  40
RLLRTDFGRRALATLPRDFAGLKLLISVKSTIRGLFKKDR  80
PIHEIFLNQVKQHPNKVAIIEIESGRQLTYQELNALANQY 120
ANLYVSEGYKMGDVVALFMENSIDFFAIWLGLSKIGVVSA 160
FINSNLKLEPLAHSINVSKCKSCITNINLLPMFKAAREKN 200
         210       220       230       240
LISDEIHVFLAGTQVDGRHRSLQQDLHLFSEDEPPVIDGL 240
NFRSVLCYIYTSGTTGNPKPAVIKHFRYFWIAMGAGKAFG 280
INKSDVVYITMPMYHSAAGIMGIGSLIAFGSTAVIRKKFS 320
ASNFWKDCVKYNVTATQYIGEICRYLLAANPCPEEKQHNV 360
RLMWGNLRGQIWKEFVGRFGIKKIGELYGSTEGNSNIVN  400
         410       420       430       440
VDNHVGACGFMPIYPHIGSLYPVRLIKVDRATGELERDKN 440
GLCVPCVPGETGEMVGVIKEKDILLKFEGYVSEGDTAKKI 480
YRDVFKHGDKVFASGDILHWDDLGYLYFVDRCGDTFRWKG 520
ENVSTTEVEGILQPVMDVEDATVYGVTVGKMEGRAGMAGI 560
VVKDGTDVEKFIADITSRLTENLASYAIPVFIRLCKEVDR 600
         610       620       630       640
TGTFKLKKTDLQKQGYDLVACKGDPIYYWSAAEKSYKPLT 640
DKMQQDIDTGVYDRI 655
```

FIG. 79 chFATP coding only DNA

```
          10        20        30        40
   ┬┬┬┬┬┴┬┬┬┬┴┬┬┬┬┴┬┬┬┬┴┬┬┬┬┴┬┬┬┬┴┬┬┬┬┴┬┬┬┬┴
   ATGGCGTGTATGCATCAGGCTCAGCTATACAATGATCTAG  40
   AGGAATTGCTAACTGGTCCATCAGTACCCATCGTTGCTGG  80
   AGCTGCTGGAGCTGCAGCTCTCACTGCCTACATTAACGCC  120
   AAATACCACATAGCCCATGATCTCAAGACCCTCGGTGGTG  160
   GATTGACACAATCGTCCGAAGCGATTGATTTCATAAACCG  200
         210       220       230       240
   ┬┬┬┬┬┴┬┬┬┬┴┬┬┬┬┴┬┬┬┬┴┬┬┬┬┴┬┬┬┬┴┬┬┬┬┴┬┬┬┬┴
   CCGCGTCGCACAAAAGCGCGTCCTCACGCACCACATCTTC  240
   CAGGAGCAGGTCCAAAAACAATCAAATCATCCCTTTCTTA  280
   TCTTTGAGGGCAAGACATGGTCTTACAAGGAGTTCTCTGA  320
   GGCATACACGAGGGTCGCGAACTGGCTGATTGATGAGCTG  360
   GACGTACAAGTAGGGGAGATGGTCGCAATTGATGGCGGAA  400
         410       420       430       440
   ┬┬┬┬┬┴┬┬┬┬┴┬┬┬┬┴┬┬┬┬┴┬┬┬┬┴┬┬┬┬┴┬┬┬┬┴┬┬┬┬┴
   ATAGTGCAGAGCACCTGATGCTTTGGCTTGCACTTGATGC  440
   AATCGGTGCGGCTACGAGTTTTTTGAACTGGAACCTGACA  480
   GGGGCAGGGTTAATTCATTGCATAAAGCTATGCGAATGTC  520
   GATTCGTTATCGCAGACATCGATATTAAAGCGAACATTGA  560
   ACCGTGCCGTGGCGAACTGGAGGAGACGGGCATCAACATT  600
         610       620       630       640
   ┬┬┬┬┬┴┬┬┬┬┴┬┬┬┬┴┬┬┬┬┴┬┬┬┬┴┬┬┬┬┴┬┬┬┬┴┬┬┬┬┴
   CACTACTATGACCCATCCTTCATCTCATCGCTACCGAATA  640
   ACACGCCAATTCCCGACAGCCGCACTGAGAACATTGAATT  680
   AGATTCAGTACGAGGACTGATATACACATCTGGAACCACT  720
   GGTCTACCTAAAGGCGTGTTTATAAGCACTGGCCGCGAGC  760
   TTAGGACTGACTGGTCGATTTCAAAGTATCTAAATCTCAA  800
         810       820       830       840
   ┬┬┬┬┬┴┬┬┬┬┴┬┬┬┬┴┬┬┬┬┴┬┬┬┬┴┬┬┬┬┴┬┬┬┬┴┬┬┬┬┴
   GCCCACGGATCGAATGTATACATGTATGCCGCTCTACCAT  840
   GCCGCTGCACACAGCCTCTGTACAGCATCAGTTATTCATG  880
   GTGGAGGTACCGTGGTATTGAGCAGGAAT.TCTCACACAA  920
   GAAGTTCTGGCCTGAAGTTGTGGCTTCGGAAGCAAATATC  960
   ATTCAGTACGTTGGTGAATTAGGTCGATATCTCCTGAATG  1000
         1010      1020      1030      1040
   ┬┬┬┬┬┴┬┬┬┬┴┬┬┬┬┴┬┬┬┬┴┬┬┬┬┴┬┬┬┬┴┬┬┬┬┴┬┬┬┬┴
   GTCCAAAGAGTCCTTACGACAGGGCCCATAAAGTCCAGAT  1040
   GGCGTGGGGCAATGGCATGCGTCCAGACGTGTGGGAAGCG  1080
   TTTCGTGAACGCTTCAACATACCAATTATTCATGAGCTCT  1120
   ATGCCGCAACCGATGGGCTCGGGTCAATGACCAATCGTAA  1160
   CGCGGGCCCTTTTACAGCAAACTGTATTGCGCTGCGAGGG  1200
```

FIG. 80A

```
         1210      1220      1230      1240
   ├┼┼┼┼┼┼┼┼┼┼┼┼┼┼┼┼┼┼┼┼┼┼┼┼┼┼┼┼┼┼┤
CTGATCTGGCACTGGAAATTTCGAAATCAGGAAGTGCTGG 1240
TCAAGATGGATCTCGATACTGATGAGATCATGAGAGATCG 1280
CAATGGGTTTGCGATACGATGCGCTGTCAATGAACCTGGA 1320
CAGATGCTTTTTCGGCTGACACCCGAAACTCTGGCTGGTG 1360
CACCAAGCTACTACAACAACGAAACGGCCACACAGAGCAG 1400
         1410      1420      1430      1440
   ├┼┼┼┼┼┼┼┼┼┼┼┼┼┼┼┼┼┼┼┼┼┼┼┼┼┼┼┼┼┼┤
GCGGATTACAGATGTGTTTCAAAAGGGTGACCTGTGGTTC 1440
AAGTCCGGTGACATGCTACGGCAAGACGCCGAAGGCCGCG 1480
TCTACTTTGTCGATCGACTAGGCGATACGTTCCGCTGGAA 1520
ATCCGAAAACGTTTCTACCAATGAAGTCGCGGACGTGATG 1560
GGCACATTTCCTCAGATTGCTGAAACGAATGTATACGGTG 1600
         1610      1620      1630      1640
   ├┼┼┼┼┼┼┼┼┼┼┼┼┼┼┼┼┼┼┼┼┼┼┼┼┼┼┼┼┼┼┤
TCCTTGTGCCGGGTAACGATGGTCGAGTGCGCAGCCTCAA 1640
TTGTCATGGCAGACGGCGTGACAGAGTCGACATTCGCTTC 1680
GCTGCCCTTGCAAAGCACGCCCGAGATCGGTTACCGGGTT 1720
ATGCTGTACCACTGTTTCTGAGGGTAACTCCAGCACTTGA 1760
ATATACGGGCACATTAAAGATTCAGAAAGGACGCCTCAAG 1800
         1810      1820      1830      1840
   ├┼┼┼┼┼┼┼┼┼┼┼┼┼┼┼┼┼┼┼┼┼┼┼┼┼┼┼┼┼┼┤
CAGGAAGGTATAGACCCAGATAAGATTTCCGGCGAAGATA 1840
AGTTATACTGGCTGCCGCCTGGTAGCGATATATATTTACC 1880
ATTTGGAAAGATGGAGTGGCAGGGAATTGTAGATAAGCGT 1920
ATACGGCTGTGA 1932
```

FIG. 80B chFATP coding only protein

```
                10        20        30        40
         |....|....|....|....|....|....|....|....|
         MACMHQAQLYNDLEELLTGPSVPIVAGAAGAAALTAYINA    40
         KYHIAHDLKTLGGGLTQSSEAIDFINRRVAQKRVLTHHIF    80
         QEQVQKQSNHPFLIFEGKTWSYKEFSEAYTRVANWLIDEL   120
         DVQVGEMVAIDGGNSAEHLMLWLALDAIGAATSFLNWNLT   160
         GAGLIHCIKLCECRFVIADIDIKANIEPCRGELEETGINI   200

210       220       230       240
         |....|....|....|....|....|....|....|....|
         HYYDPSFISSLPNNTPIPDSRTENIELDSVRGLIYTSGTT   240
         GLPKGVFISTGRELRTDWSISKYLNLKPTDRMYTCMPLYH   280
         AAAHSLCTASVIHGGGTVVLSRKFSHKKFWPEVVASEANI   320
         IQYVGELGRYLLNGPKSPYDRAHKVQMAWGNGMRPDVWEA   360
         FRERFNIPIIHELYAATDGLGSMTNRNAGPFTANCIALRG   400

410       420       430       440
         |....|....|....|....|....|....|....|....|
         LIWHWKFRNQEVLVKMDLDTDEIMRDRNGFAIRCAVNEPG   440
         QMLFRLTPETLAGAPSYYNNETATQSRRITDVFQKGDLWF   480
         KSGDMLRQDAEGRVYFVDRLGDTFRWKSENVSTNEVADVM   520
         GTFPQIAETNVYGVLVPGNDGRVRSLNCHGRRRDRVDIRF   560
         AALAKHARDRLPGYAVPLFLRVTPALEYTGTLKIQKGRLK   600

610       620       630       640
         |....|....|....|....|....|....|....|....|
         QEGIDPDKISGEDKLYWLPPGSDIYLPFGKMEWQGIVDKR   640
         IRL                                        643
```

FIG. 81 aspergillus partial.DNA

```
         10        20        30        40
   |||||||||||||||||||||||||||||||||||||||
CTTTACCATTCATCAGCTTCATTCTGCATTTTTAGCTTGA  40
CGGCAGCCGGGTCTACGCTGATCATCGGCCGCAAGTTCTC  80
CGCGAGAAACTTCATAAAGGAAGCGCGCGAGAACGACGCC 120
ACGGTCATCCAGTACGTGGGTGAGACCTTGCGATATCTGC 160
TCGCCACCCCCGGTGAAACCGATCCAGTTACTGGCGAAGA 200
        210       220       230       240
   |||||||||||||||||||||||||||||||||||||||
CCTGGACAAAAAGCACAATATTCGAGCAGTATACGGCAAC 240
GGGCTACGGCCGGATATCTGGAACCGCTTCAAGGAGCGCT 280
TCAACGTGCCGACGGTTGCCGAATTTTATGCTGCAACCGA 320
GAGCCCAGGCGGAACATGGAACTATTCAACAAATGACTTC 360
ACTGCCGGAGCCATTGGGCACACTGGCGTGCTTAGTGGAT 400
        410       420       430       440
   |||||||||||||||||||||||||||||||||||||||
GGCTTCTTGGACGCGGCCTTACTATTGTCGAGGTGGACCA 440
GGAATCACAGGAACCATGGCGCGATCCCCAAACCGGGTTC 480
TGCAAGCCGGTCCCGCGAGGCGAAGCAGGCGAGCTCCTGT 520
ATGCCATTGATCCGGCCGACCCGGGCGAGACCTTCCAGGG 560
CTACTACCGCAACTCCTTTAGAGCACACTGGCGGCCG    597
```

FIG. 82 aspergillus partial.protein

```
         10        20        30        40
    ....|....|....|....|....|....|....|....|.
    LYHSSASFCIFSLTAAGSTLIIGRKFSARNFIKEARENDA  40
    TVIQYVGETLRYLLATPGETDPVTGEDLDKKHNIRAVYGN  80
    GLRPDIWNRFKERFNVPTVAEFYAATESPGGTWNYSTNDF 120
    TAGAIGHTGVLSGWLLGRGLTIVEVDQESQEPWRDPQTGF 160
    CKPVPRGEAGELLYAIDPADPGETFQGYYRNSFRAHWRP  199
```

FIG. 83 mgFATP partial DNA

```
              10        20        30        40
         |....|....|....|....|....|....|....|....|
         GCAAAGGCCGACGCGTGGCTGCGGACGGGTAACGTGATCA   40
         GGGCGGACAACGAAGGGCGACTCTTCTTCCACGACCGGAT   80
         CGGAGACACGTTCCGATGGAAGGGAGAGACNGTCAGCACA  120
         CAAGAGGTCAGTTTGGTGCTCGGACGACACGACTCAATCA  160
         AGGAGGCCAACGTGTACGGCGTGACGGTGCCGAACCACGA  200
             210       220       230       240
         |....|....|....|....|....|....|....|....|
         CGGGCGGGCCGGCTGCGCTGCGCTCACGCTATCAGACGCT  240
         CTGGCGACTGAAAAGAAGCTGGGCGATGAGCTGCTAAAGG  280
         GATTGGCTACTCACTCGTCGACTTCGCTTCCCAAGTTTGC  320
         GGTGCCGCAGTTCCTACGGGTGGTGCGCGGCGAGATGCAG  360
         TCAACGGGCACCAACAAGCAACAGAAGCACGACCTGAGGG  400
             410       420       430       440
         |....|....|....|....|....|....|....|....|
         TGCAGGGTGTAGAGCCGGGCAAGGTGGGCGTAGACGAGGT  440
         GTACTGGTTGCGGGGAGGGACATATGTACCATTCGGAACA  480
         GAGGATTGGGATGGGTTGAAGAAGGGTCTTGTGAAGTTGT  520
         GA                                        522
```

FIG. 84 mgFATP partial protein

```
              10        20        30        40
         |....|....|....|....|....|....|....|....|
         AKADAWLRTGNVIRADNEGRLFFHDRIGDTFRWKGETVST   40
         QEVSLVLGRHDSIKEANVYGVTVPNHDGRAGCAALTLSDA   80
         LATEKKLGDELLKGLATHSSTSLPKFAVPQFLRVVRGEMQ  120
         STGTNKQQKHDLRVQGVEPGKVGVDEVYWLRGGTYVPFGT  160
         EDWDGLKKGLVKL                             173
```

FIG. 85 scFATP coding only DNA

```
         10        20        30        40
    |....|....|....|....|....|....|....|....|
ATGTCTCCCATACAGGTTGTTGTCTTTGCCTTGTCAAGGA  40
TTTTCCTGCTATTATTCAGACTTATCAAGCTAATTATAAC  80
CCCTATCCAGAAATCACTGGGTTATCTATTTGGTAATTAT 120
TTTGATGAATTAGACCGTAAATATAGATACAAGGAGGATT 160
GGTATATTATTCCTTACTTTTTGAAAAGCGTGTTTTGTTA 200
        210       220       230       240
    |....|....|....|....|....|....|....|....|
TATCATTGATGTGAGAAGACATAGGTTTCAAAACTGGTAC 240
TTATTTATTAAACAGGTCCAACAAATGGTGACCATTTAG  280
CGATTAGTTACACCCGTCCATGGCCGAAAAGGGAGAATT  320
TCAACTCGAAACCTTTACGTATATTGAAACTTATAACATA 360
GTGTTGAGATTGTCTCATATTTTGCATTTTGATTATAACG 400
        410       420       430       440
    |....|....|....|....|....|....|....|....|
TTCAGGCCGGTGACTACGTGGCAATCGATTGTACTAATAA 440
ACCTCTTTTCGTATTTTTATGGCTTTCTTTGTGGAACATT 480
GGGGCTATTCCAGCTTTTTTAAACTATAATACTAAAGGCA 520
CTCCGCTGGTTCACTCCCTAAAGATTTCCAATATTACGCA 560
GGTATTTATTGACCCTGATGCCAGTAATCCGATCAGAGAA 600
        610       620       630       640
    |....|....|....|....|....|....|....|....|
TCGGAAGAAGAAATCAAAAACGCACTTCCTGATGTTAAAT 640
TAAACTATCTTGAAGAACAAGACTTAATGCATGAACTTTT 680
AAATTCGCAATCACCGGAATTCTTACAACAAGACAACGTT 720
AGGACACCACTAGGCTTGACCGATTTTAAACCCTCTATGT 760
TAATTTATACATCTGGAACCACTGGTTTGCCTAAATCCGC 800
        810       820       830       840
    |....|....|....|....|....|....|....|....|
TATTATGTCTTGGAGAAAATCCTCCGTAGGTTGTCAAGTT 840
TTTGGTCATGTTTTACATATGACTAATGAAAGCACTGTGT 880
TCACAGCCATGCCATTGTTCCATTCAACTGCTGCCTTATT 920
AGGTGCGTGCGCCATTCTATCTCACGGTGGTTGCCTTGCG 960
TTATCGCATAAATTTTCTGCCAGTACATTTTGGAAGCAAG 1000
       1010      1020      1030      1040
    |....|....|....|....|....|....|....|....|
TTTATTTAACAGGAGCCACGCACATCCAATATGTCGGAGA 1040
AGTCTGTAGATACCTGTTACATACGCCAATTTCTAAGTAT 1080
GAAAAGATGCATAAGGTGAAGGTTGCTTATGGTAACGGGC 1120
TGAGACCTGACATCTGGCAGGACTTCAGGAAGAGGTTCAA 1160
CATAGAAGTTATTGGTGAATTCTATGCCGCAACTGAAGCT 1200
```

FIG. 86A

```
          1210      1220      1230      1240
CCTTTTGCTACAACTACCTTCCAGAAAGGTGACTTTGGAA 1240
TTGGCGCATGTAGGAACTATGGTACTATAATTCAATGGTT 1280
TTTGTCATTCCAACAAACATTGGTAAGGATGGACCCAAAT 1320
GACGATTCCGTTATATATAGAAATTCCAAGGGTTTCTGCG 1360
AAGTGGCCCCTGTTGGCGAACCAGGAGAAATGTTAATGAG 1400
          1410      1420      1430      1440
AATCTTTTCCCTAAAAAACCAGAAACATCTTTTCAAGGT   1440
TATCTTGGTAATGCCAAGGAAACAAAGTCCAAAGTTGTGA  1480
GGGATGTCTTCAGACGTGGCGATGCTTGGTATAGATGTGG  1520
AGATTTATTAAAAGCGGACGAATATGGATTATGGTATTTC  1560
CTTGATAGAATGGGTGATACTTTCAGATGGAAATCTGAAA  1600
          1610      1620      1630      1640
ATGTTTCCACTACTGAAGTAGAAGATCAGTTGACGGCCAG  1640
TAACAAAGAACAATATGCACAAGTTCTAGTTGTTGGTATT  1680
AAAGTACCTAAATATGAAGGTAGAGCTGGTTTTGCAGTTA  1720
TTAAACTAACTGACAACTCTCTTGACATCACTGCAAAGAC  1760
CAAATTATTAAATGATTCCTTGAGCCGGTTAAATCTACCG  1800
          1810      1820      1830      1840
TCTTATGCTATGCCCCTATTTGTTAAATTTGTTGATGAAA  1840
TTAAAATGACAGATAACCTCATAAAATTTTGA          1872
```

FIG. 86B scFATP coding only protein

```
          10        20        30        40
  ┬┬┬┬┬┬┬┬┬┬┬┬┬┬┬┬┬┬┬┬┬┬┬┬┬┬┬┬┬┬┬┬┬┬┬┬┬┬┬┬
MSPIQVVVFALSRIFLLLFRLIKLIITPIQKSLGYLFGNY  40
FDELDRKYRYKEDWYIIPYFLKSVFCYIIDVRRHRFQNWY  80
LFIKQVQQNGDHLAISYTRPMAEKGEFQLETFTYIETYNI  120
VLRLSHILHFDYNVQAGDYVAIDCTNKPLFVFLWLSLWNI  160
GAIPAFLNYNTKGTPLVHSLKISNITQVFIDPDASNPIRE  200
         210       220       230       240
  ┬┬┬┬┬┬┬┬┬┬┬┬┬┬┬┬┬┬┬┬┬┬┬┬┬┬┬┬┬┬┬┬┬┬┬┬┬┬┬┬
SEEEIKNALPDVKLNYLEEQDLMHELLNSQSPEFLQQDNV  240
RTPLGLTDFKPSMLIYTSGTTGLPKSAIMSWRKSSVGCQV  280
FGHVLHMTNESTVFTAMPLFHSTAALLGACAILSHGGCLA  320
LSHKFSASTFWKQVYLTGATHIQYVGEVCRYLLHTPISKY  360
EKMHKVKVAYGNGLRPDIWQDFRKRFNIEVIGEFYAATEA  400
         410       420       430       440
  ┬┬┬┬┬┬┬┬┬┬┬┬┬┬┬┬┬┬┬┬┬┬┬┬┬┬┬┬┬┬┬┬┬┬┬┬┬┬┬┬
PFATTTFQKGQFGIGACRNYGTIIQWFLSFQQTLVRMDPN  440
DDSVIYRNSKGFCEVAPVGEPGEMLMRIFFPKKPETSFQG  480
YLGNAKETKSKVVRDVFRRGDAWYRCGDLLKADEYGLWYF  520
LDRMGDTFRWKSENVSTTEVEDQLTASNKEQYAQVLVVGI  560
KVPKYEGRAGFAVIKLTDNSLDITAKTKLLNDSLSRLNLP  600
         610       620       630       640
  ┬┬┬┬┬┬┬┬┬┬┬┬┬┬┬┬┬┬┬┬┬┬┬┬┬┬┬┬┬┬┬┬┬┬┬┬┬┬┬┬
SYAMPLFVKFVDEIKMTDNLIKF   623
```

FIG. 87 mtFATP coding only DNA

```
          10        20        30        40
          |         |         |         |
GTGTCCGATTACTACGGCGGCGCACACACAACGGTCAGGC  40
TGATCGACCTGGCAACTCGGATGCCGCGAGTGTTGGCGGA  80
CACGCCGGTGATTGTGCGTGGGGCAATGACCGGGCTGCTG 120
GCCCGGCCGAATTCCAAGGCGTCGATCGGCACGGTGTTCC 160
AGGACCGGGCCGCTCGCTACGGTGACCGAGTCTTCCTGAA 200
         210       220       230       240
          |         |         |         |
ATTCGGCGATCAGCAGCTGACCTACCGCGACGCTAACGCC 240
ACCGCCAACCGGTACGCCGCGGTGTTGGCCGCCCGCGGCG 280
TCGGCCCCGGCGACGTCGTTGGCATCATGTTGCGTAACTC 320
ACCCAGCACAGTCTTGGCGATGCTGGCCACGGTCAAGTGC 360
GGCGCTATCGCCGGCATGCTCAACTACCACCAGCGCGGCG 400
         410       420       430       440
          |         |         |         |
AGGTGTTGGCGCACAGCCTGGGTCTGCTGGACGCGAAGGT 440
ACTGATCGCAGAGTCCGACTTGGTCAGCGCCGTCGCCGAA 480
TGCGGCGCCTCGCGCGGCCGGGTAGCGGGCGACGTGCTGA 520
CCGTCGAGGACGTGGAGCGATTCGCCACAACGGCGCCCGC 560
CACCAACCCGGCGTCGGCGTCGGCGGTGCAAGCCAAAGAC 600
         610       620       630       640
          |         |         |         |
ACCGCGTTCTACATCTTCACCTCGGGCACCACCGGATTTG 640
CCAAGGCCAGTGTCATGACGCATCATCGGTGGCTGCGGGC 680
GCTGGCCGTCTTCGGAGGGATGGGGCTGCGGCTGAAGGGT 720
TCCGACACGCTCTACAGCTGCCTGCCGCTGTACCACAACA 760
ACGCGTTAACGGTCGCGGTGTCGTCGGTGATCAATTCTGG 800
         810       820       830       840
          |         |         |         |
GGCGACCCTGGCGCTGGGTAAGTCGTTTTCGGCGTCGCGG 840
TTCTGGGATGAGGTGATTGCCAACCGGGCGACGGCGTTCG 880
TCTACATCGGCGAAATCTGCCGTTATCTGCTCAACCAGCC 920
GGCCAAGCCGACCGACCGTGCCCACCAGGTGCGGGTGATC 960
TGCGGTAACGGGCTGCGGCCGGAGATCTGGGATGAGTTCA 1000
        1010      1020      1030      1040
          |         |         |         |
CCACCCGCTTCGGGGTCGCGCGGGTGTGCGAGTTCTACGC 1040
CGCCAGCGAAGGCAACTCGGCCTTTATCAACATCTTCAAC 1080
GTGCCCAGGACCGCCGGGGTATCGCCGATGCCGCTTGCCT 1120
TTGTGGAATACGACCTGGACACCGGCGATCCGCTGCGGGA 1160
TGCGAGCGGGCGAGTGCGTCGGGTACCCGACGGTGAACCC 1200
```

FIG. 88A

```
          1210      1220      1230      1240
    ┬┴┴┴┴┴┬┴┴┴┴┬┴┴┴┴┬┴┴┴┴┬┴┴┴┴┬┴┴┴┴┬┴┴┴┴┬┴┴┴┴┬┴
    GGCCTGTTGCTTAGCCGGGTCAACCGGCTGCAGCCGTTCG   1240
    ACGGCTACACCGACCCGGTTGCCAGCGAAAAGAAGTTGGT   1280
    GCGCAACGCTTTTCGAGATGGCGACTGTTGGTTCAACACC   1320
    GGTGACGTGATGAGCCCGCAGGGCATGGGCCATGCCGCCT   1360
    TCGTCGATCGGCTGGGCGACACCTTCCGCTGGAAGGGCGA   1400
          1410      1420      1430      1440
    ┬┴┴┴┴┬┴┴┴┴┬┴┴┴┴┬┴┴┴┴┬┴┴┴┴┬┴┴┴┴┬┴┴┴┴┬┴┴┴┴┬┴
    GAATGTCGCCACCACTCAGGTCGAAGCGGCACTGGCCTCC   1440
    GACCAGACCGTCGAGGAGTGCACGGTCTACGGCGTCCAGA   1480
    TTCCGCGCACCGGCGGGCGCGCCGGAATGGCCGCGATCAC   1520
    ACTGCGCGCTGGCGCCGAATTCGACGGCCAGGCGCTGGCC   1560
    CGAACGGTTTACGGTCACTTGCCCGGCTATGCACTTCCGC   1600
          1610      1620      1630      1640
    ┬┴┴┴┴┬┴┴┴┴┬┴┴┴┴┬┴┴┴┴┬┴┴┴┴┬┴┴┴┴┬┴┴┴┴┬┴┴┴┴┬┴
    TCTTTGTTCGGGTAGTGGGGTCGCTGGCGCACACCACGAC   1640
    GTTCAAGAGTCGCAAGGTGGAGTTGCGCAACCAGGCCTAT   1680
    GGCGCCGACATCGAGGATCCGCTGTACGTACTGGCCGGCC   1720
    CGGACGAAGGATATGTGCCGTACTACGCCGAATACCCTGA   1760
    GGAGGTTTCGCTCGGAAGGCGACCGCAGGGCTAG         1794
```

FIG. 88B mtFATP coding only protein

```
          10        20        30        40
    ┬┴┴┴┴┬┴┴┴┴┬┴┴┴┴┬┴┴┴┴┬┴┴┴┴┬┴┴┴┴┬┴┴┴┴┬┴┴┴┴┬┴
    MSDYYGGAHTTVRLIDLATRMPRVLADTPVIVRGAMTGLL    40
    ARPNSKASIGTVFQDRAARYGDRVFLKFGDQQLTYRDANA    80
    TANRYAAVLAARGVGPGDVVGIMLRNSPSTVLAMLATVKC   120
    GAIAGMLNYHQRGEVLAHSLGLLDAKVLIAESDLVSAVAE   160
    CGASRGRVAGDVLTVEDVERFATTAPATNPASASAVQAKD   200
          210       220       230       240
    ┬┴┴┴┴┬┴┴┴┴┬┴┴┴┴┬┴┴┴┴┬┴┴┴┴┬┴┴┴┴┬┴┴┴┴┬┴┴┴┴┬┴
    TAFYIFTSGTTGFPKASVMTHHRWLRALAVFGGMGLRLKG   240
    SDTLYSCLPLYHNNALTVAVSSVINSGATLALGKSFSASR   280
    FWDEVIANRATAFVYIGEICRYLLNQPAKPTDRAHQVRVI   320
    CGNGLRPEIWDEFTTRFGVARVCEFYAASEGNSAFINIFN   360
    VPRTAGVSPMPLAFVEYDLDTGDPLRDASGRVRRVPDGEP   400
          410       420       430       440
    ┬┴┴┴┴┬┴┴┴┴┬┴┴┴┴┬┴┴┴┴┬┴┴┴┴┬┴┴┴┴┬┴┴┴┴┬┴┴┴┴┬┴
    GLLLSRVNRLQPFDGYTDPVASEKKLVRNAFRDGDCWFNT   440
    GDVMSPQGMGHAAFVDRLGDTFRWKGENVATTQVEAALAS   480
    DQTVEECTVYGVQIPRTGGRAGMAAITLRAGAEFDGQALA   520
    RTVYGHLPGYALPLFVRVVGSLAHTTTFKSRKVELRNQAY   560
    GADIEDPLYVLAGPDEGYVPYYAEYPEEVSLGRRPQG     597
```

FIG. 89 hsFATP3

```
1     cga ccc acg cgt ccg ggg atg ttt gcg agc
1                                 M   F   A   S 31    ggc tgg aac cag acg gtg ccg ata gag gaa
5      G   W   N   Q   T   V   P   I   E   E 61    gcg ggc tcc atg gct gcc ctc ctg ctg ctg
15     A   G   S   M   A   A   L   L   L   L 91    ccc ctg ctg ctg ttg cta ccg ctg ctg ctg
25     P   L   L   L   L   L   P   L   L   L 121   ctg ctg aag cta cac ctc tgg ccg cag ttg
35     L   L   K   L   H   L   W   P   Q   L 151   cgc tgg ctt ccg gcg gac ttg gcc ttt gcg
45     R   W   L   P   A   D   L   A   F   A 181   gtg cga gct ctg tgc tgc aaa agg gct ctt
55     V   R   A   L   C   C   K   R   A   L 211   cga gct cgc gcc ctg gcc gcg gct gcc gcc
65     R   A   R   A   L   A   A   A   A   A 241   gac ccg gaa ggt ccc gag ggg ggc tgc agc
75     D   P   E   G   P   E   G   G   C   S
```

FIG. 94A

```
271   ctg gcc tgg cgc ctc gcg gaa ctg gcc cag
85     L   A   W   R   L   A   E   L   A   Q 301   cag cgc gcc gcg cac acc ttt ctc att cac
95     Q   R   A   A   H   T   F   L   I   H 331   ggc tcg cgg cgc ttt agc tac tca gag gcg
105    G   S   R   R   F   S   Y   S   E   A 361   gag cgc gag agt aac agg gct gca cgc gcc
115    E   R   E   S   N   R   A   A   R   A 391   ttc cta cgt gcg cta ggc tgg gac tgg gga
125    F   L   R   A   L   G   W   D   W   G
```

FIG. 94B

```
421   ccc gac ggc ggc gac agc ggc gag ggg agc
135    P   D   G   G   D   S   G   E   G   S 451   gct gga gaa ggc gag cgg gca gcg ccg gga
145    A   G   E   G   E   R   A   A   P   G 481   gcc gga gat gca gcg gcc gga agc ggc gcg
155    A   G   D   A   A   A   G   S   G   A 521   gag ttt gcc gga ggg gac ggt gcc gcc aga
165    E   F   A   G   G   D   G   A   A   R 541   ggt gga gga gag ccc gcc gcc cct ctg tca
175    G   G   G   E   P   A   A   P   L   S 571   cct gga gca act gtg gcg ctg ctc ctc ccc
185    P   G   A   T   V   A   L   L   L   P 601   gct ggc cca gag ttt ctg tgg ctc tgg ttc
195    A   G   P   E   F   L   W   L   W   F
```

FIG. 94C

```
631    ggg ctg gcc aag gcc ggc ctg cgc act gcc
205     G   L   A   K   A   G   L   R   T   A 661    ttt gtg ccc acc gcc ctg cgc cgg ggc ccc
215     F   V   P   T   A   L   R   R   G   P 691    ctg ctg cac tgc ctc cgc agc tgc ggc gcg
225     L   L   H   C   L   R   S   C   G   A 721    cgc gcg ctg gtg ctg gcg cca gag ttt ctg
235     R   A   L   V   L   A   P   E   F   L 751    gag tcc ctg gag ccg gac ctg ccc gcc ctg
245     E   S   L   E   P   D   L   P   A   L 781    aga gcc atg ggg ctc cac ctg tgg gct gca
255     R   A   M   G   L   H   L   W   A   A 811    ggc cca gga acc cac cct gct gga att agc
265     G   P   G   T   H   P   A   G   I   S 841    gat ttg ctg gct gaa gtg tcc gct gaa gtg
275     D   L   L   A   E   V   S   A   E   V
```

FIG. 94D

| | | | | | | | | | | |
|---|---|---|---|---|---|---|---|---|---|---|
| 871 | gat | ggg | cca | gtg | cca | gga | tac | ctc | tct | tcc |
| 285 | D | G | P | V | P | G | Y | L | S | S |
| 901 | ccc | cag | agc | ata | aca | gac | acg | tgc | ctg | tac |
| 295 | P | Q | S | I | T | D | T | C | L | Y |
| 931 | atc | ttc | acc | tct | ggc | acc | acg | ggc | ctc | ccc |
| 305 | I | F | T | S | G | T | T | G | L | P |
| 961 | aag | gct | gct | cgg | atc | agt | cat | ctg | aag | atc |
| 315 | K | A | A | R | I | S | H | L | K | I |
| 991 | ctg | caa | tgc | cag | ggc | ttc | tat | cag | ctg | tgt |
| 325 | L | Q | C | Q | G | F | Y | Q | L | C |
| 1021 | ggt | gtc | cac | cag | gaa | gat | gtg | atc | tac | ctc |
| 335 | G | V | H | Q | E | D | V | I | Y | L |

FIG. 94E

```
1051    gcc   ctc   cca   ctc   tac   cac   atg   tcc   ggt   tcc
345      A     L     P     L     Y     H     M     S     G     S 1081    ctg   ctg   ggc   atc   gtg   ggc   tgc   atg   ggc   att
355      L     L     G     I     V     G     C     M     G     I 1111    ggg   gcc   aca   gtg   gtg   ctg   aaa   tcc   aag   ttc
365      G     A     T     V     V     L     K     S     K     F 1141    tcg   gct   ggt   cag   ttc   tgg   gaa   gat   tgc   cag
375      S     A     G     Q     F     W     E     D     C     Q 1171    cag   cac   agg   gtg   acg   gtg   ttc   cag   tac   att
385      Q     H     R     V     T     V     F     Q     Y     I 1201    ggg   gag   ctg   tgc   cga   tac   ctt   gtc   aac   cag
395      G     E     L     C     R     Y     L     V     N     Q 1231    ccc   ccg   agc   aag   gca   gaa   cgt   ggc   cat   aag
405      P     P     S     K     A     E     R     G     H     K 1261    gtc   cgg   ctg   gca   gtg   ggc   agc   ggg   ctg   cgc
415      V     R     L     A     V     G     S     G     L     R
```

FIG. 94F

```
1291  cca gat acc tgg gag cgt ttt gtg cgg cgc
425    P   D   T   W   E   R   F   V   R   R 1321  ttc ggg ccc ctg cag gtg ctg gag aca tat
435    F   G   P   L   Q   V   L   E   T   Y 1351  gga ctg aca gag ggc aac gtg gcc acc atc
445    G   L   T   E   G   N   V   A   T   I 1381  aac tac aca gga cag cgg ggc gct gtg ggg
455    N   Y   T   G   Q   R   G   A   V   G 1411  cgt gct tcc tgg ctt tac aag cat atc ttc
465    R   A   S   W   L   Y   K   H   I   F 1441  ccc ttc tcc ttg att cgc tat gat gtc acc
475    P   F   S   L   I   R   Y   D   V   T 1471  aca gga gag cca att cgg gac ccc cag ggg
485    T   G   E   P   I   R   D   P   Q   G 1501  cac tgt atg gcc aca tct cca ggt gag cca
495    H   C   M   A   T   S   P   G   E   P 1531  ggg ctg ctg gtg gcc ccg gta agc cag cag
505    G   L   L   V   A   P   V   S   Q   Q
```

FIG. 94G

```
1561    tcc cca ttc ctg ggc tat gct ggc ggg cca
515      S   P   F   L   G   Y   A   G   G   P 1591    gag ctg gcc cag ggg aag ttg cta aag gat
525      E   L   A   Q   G   K   L   L   K   D 1621    gtc ttc cgg cct ggg gat gtt ttc ttc aac
535      V   F   R   P   G   D   V   F   F   N 1651    act ggg gac ctg ctg gtc tgc gat gac caa
545      T   G   D   L   L   V   C   D   D   Q 1681    ggt ttt ctc cgc ttc cat gat cgt act gga
555      G   F   L   R   F   H   D   R   T   G 1711    gac acc ttc agg tgg aag ggg gag aat gtg
565      D   T   F   R   W   K   G   E   N   V 1741    gcc aca acc gag gtg gca gag gtc ttc gag
575      A   T   T   E   V   A   E   V   F   E
```

FIG. 94H

```
1741    gcc aca acc gag gtg gca gag gtc ttc gag
575      A   T   T   E   V   A   E   V   F   E 1771    gcc cta gat ttt ctt cag gag gtg aac gtc
585      A   L   D   F   L   Q   E   V   N   V 1801    tat gga gtc act gtg cca ggg cat gaa ggc
595      Y   G   V   T   V   P   G   H   E   G 1831    agg gct gga atg gca gcc cta gtt ctg cgt
605      R   A   G   M   A   A   L   V   L   R 1861    ccc ccc cac gct ttg gac ctt atg cag ctc
615      P   P   H   A   L   D   L   M   Q   L 1891    tac acc cac gtg tct gag aac ttg cca cct
625      Y   T   H   V   S   E   N   L   P   P 1921    tat gcc cgg ccc cga ttc ctc agg ctc cag
635      Y   A   R   P   R   F   L   R   L   Q
```

FIG. 94I

```
1951    gag tct ttg gcc acc aca gag acc ttc aaa
645      E   S   L   A   T   T   E   T   F   K 1981    cag cag aaa gtt cgg atg gca aat gag ggc
655      Q   Q   K   V   R   M   A   N   E   G 2011    ttc gac ccc agc acc ctg tct gac cca ctg
665      F   D   P   S   T   L   S   D   P   L 2041    tac gtt ctg gac cag gct gta ggt gcc tac
675      Y   V   L   D   Q   A   V   G   A   Y 2071    ctg ccc ctc aca act gcc cgg tac agc gcc
685      L   P   L   T   T   A   R   Y   S   A 2101    ctc ctg gca gga aac ctt cga atc tga gaa
695      L   L   A   G   N   L   R   I   *

2131    ctt cca cac ctg agg cac ctg aga gag gaa
2161    ctc tgt
```

FIG. 94J

METHODS OF IDENTIFYING INHIBITORS OF FATTY ACID TRANSPORT PROTEINS (FATP)

RELATED APPLICATIONS

This application is a continuation-in-part of U.S. patent application Ser. No. 09/232,201 filed Jan. 14, 1999, now U.S. Pat. No. 6,348,321, which claims the benefit of U.S. Provisional Application No. 60/110,941 filed Dec. 4, 1998; U.S. Provisional Application No. 60/093,491 filed Jul. 20, 1998; and U.S. Provisional Application No. 60/071,374 filed Jan. 15, 1998. The teachings of each of these referenced applications are incorporated herein by reference in their entirety.

GOVERNMENT SUPPORT

The invention was supported, in whole or in part, by a grant from the National Heart, Lung, and Blood Institute (HL41484), by National Institutes of Health Grant DK 47618 and National Institutes of Health Grant 5 T32 CA 09541. The United States Government has certain rights in the invention.

BACKGROUND OF THE INVENTION

Long chain fatty acids (LCFAs) are an important source of energy for most organisms. They also function as blood hormones, regulating key metabolic functions such as hepatic glucose production. Although LCFAs can diffuse through the hydrophobic core of the plasma membrane into cells, this nonspecific transport cannot account for the high affinity and specific transport of LCFAs exhibited by cells such as cardiac muscle, hepatocytes, enterocytes, and adipocytes. The molecular mechanisms of LCFA transport remains largely unknown. Identifying these mechanisms can lead to pharmaceuticals that modulate fatty acid uptake by the intestine and by other organs, thereby alleviating certain medical conditions (e.g. obesity).

SUMMARY OF THE INVENTION

Described herein is a diverse family of fatty acid transport proteins (FATPs) which are evolutionarily conserved; these FATPs are plasma membrane proteins which mediate transport of LCFAs across the membranes and into cells. Members of the FATP family described herein are present in a wide variety of organisms, from mycobacteria to humans, and exhibit very different expression patterns in tissues among the organisms. FATP family members are expressed in prokaryotic and eukaryotic organisms and comprise characteristic amino acid domains or sequences which are highly conserved across family members. In addition, the function of the FATP gene family is conserved throughout evolution, as shown by the fact that the *Caenorhabditis* (*C.*) *elegans* and mycobacterial FATPs described herein facilitate LCFA uptake when they are overexpressed in COS cells or *Escherichia* (*E.*) *coli*, respectively. FATPs are expressed in a wide variety of tissues, including all tissues which are important to fatty acid metabolism (uptake and processing).

In specific embodiments, FATPs of the present invention are from such diverse organisms as humans (*Homo* (*H.*) *sapiens*), mice, (*Mus* (*M.*) *musculus*), *F. rubripes, C. elegans, Drosophila* (*D.*) *melanogaster, Saccharomyces* (*S.*) *cerevisiae, Aspergillus nidulans, Cochliobolu heterostrophus, Magnaporthe grisea* and *Mycobacterium* (*M.*), such as *M. tuberculosis*. As described herein, four novel mouse FATPs, referred to as mmFATP2, mmFATP3, mmFATP4 and mmFATP5, and six human FATPs, referred to as hsFATP1, hsFATP2, hsFATP3, hsFATP4, hsFATP5 and hsFATP6, have been identified. All four novel murine FATPs (mmFATP2–5) and a previously identified murine FATP (renamed herein FATP1) have orthologs in humans (hsFATP1–5); the sixth human FATP (hsFATP6) does not as yet have a mouse ortholog. The expression patterns of these FATPs vary, as described in detail below.

The present invention relates to FATP family members from prokaryotes and eukaryotes, nucleic acids (DNA, RNA) encoding FATPs, and nucleic acids which are useful as probes or primers (e.g., for use in hybridization methods, amplification methods) for example, in methods of detecting FATP-encoding genes, producing FATPs, and purifying or isolating FATP-encoding DNA or RNA. Also the subject of this invention are antibodies (polyclonal or monoclonal) which bind an FATP or FATPs; methods of identifying additional FATP family members (for example, orthologs of those FATPs described herein by amino acid sequence) and variant alleles of known FATP genes; methods of identifying compounds which bind to an FATP, or modulate or alter (enhance or inhibit) FATP function; compounds which modulate or alter FATP function; methods of modulating or altering (enhancing or inhibiting) FATP function and, thus, LCFA uptake into tissues of a mammal (e.g. human) by administering a compound or molecule (a drug or agent) which increases or reduces FATP activity; and methods of targeting compounds to tissues by administering a complex of the compound to be targeted to tissues and a component which is bound by an FATP present on cells of the tissues to which the compound is to be targeted. For example, a complex of a drug to be delivered to the liver and a component which is bound by an FATP present on liver cells (e.g., FATP5) can be administered.

In one embodiment, the present invention relates to modulating or altering (enhancing or inhibiting/reducing) LCFA uptake in the small intestine and, thus, increasing or reducing the number of calories in the form of fats available to an individual. In another embodiment, the present invention relates to inhibiting or reducing LCFA uptake in the small intestine in order to reduce circulating fatty acid levels; that is, LCFA uptake in the small intestine is reduced and, therefore, circulating (blood) levels are not as high as they otherwise would be. FATP4 has been shown to be expressed in epithelial cells of the small intestine and particularly in the brush border layer of the small intestine. FATP2 has also been shown to be expressed at low levels in epithelial cells of the small intestine, particularly in the duodenum. In contrast, FATP1, FATP3, FATP5 and FATP6 were not detected in any of the intestinal tissues. Thus, also described herein are FATPs which are present in the epithelial cell layer of the small intestine where they mediate LCFA uptake. These FATPs, particularly FATP4 and also FATP2, are targets for methods and drugs which block their function or activity and are useful in treating obesity, diabetes and heart disease. The ability of these FATPs to mediate fat uptake can be modulated or altered (enhanced or inhibited), thus modulating fat uptake in the small intestine. This can be done, for example, by administering to an individual, such as a human or other animal, a drug which blocks interaction of LCFAs with FATP4 and/or FATP2 in the small intestine, thus inhibiting LCFA passage into the cells of the small intestine. As a result, fat absorption is reduced and, although the individual has consumed a certain quantity of fat, the LCFAs are not absorbed to the same extent they would have been in the absence of the compound administered.

Thus, one embodiment of this invention is a method of reducing LCFA uptake (absorption) in the small intestine and, as a result, reducing caloric uptake in the form of fat. A further embodiment is a compound (drug) useful in inhibiting or reducing fat absorption in the small intestine. In another embodiment, the invention is a method of reducing circulating fatty acid levels by administering to an individual a compound which blocks interactions of LCFAs with FATP4 and/or FATP2 in the small intestine, thus inhibiting LCFA passage into cells of the small intestine. As a result, fatty acids pass into the circulatory system at a diminished level and/or rate, and circulating fatty acid levels are lower than they would be in the absence of the compound administered. This method is particularly useful for therapy in individuals who are at risk for or have hyperlipidemia. That is, it can be used to prevent the occurrence of elevated levels of lipids in the blood or to treat an individual in whom blood lipid levels are elevated. Also the subject of this invention is a method of identifying compounds which alter FATP function (and thus, in the case of FATP2 and/or FATP4, alter LCFA uptake in the small intestine).

In another embodiment, the present invention relates to a method of modulating or altering (enhancing or inhibiting) the function of FATP6, which is expressed at high levels in the heart. A method of inhibiting FATP6 function is useful, for example, in individuals with heart disease, such as ischemia, since reducing LCFA uptake into heart muscle in an individual who has ischemic heart disease, which may be manifested by, for example, angina or heart attack, can reduce symptoms or reduce the extent of damage caused by the ischemia In this embodiment, a drug which inhibits FATP6 function is administered to an individual who has had or is having a heart attack, to reduce LCFA uptake by the individual's heart and, as a result, reduce the damage caused by ischemia. In a further embodiment, this invention is a method of targeting a compound, such as a therapeutic drug or an imaging reagent, to heart tissue by administering to an individual (e.g., a human) a complex of the compound and a component (e.g., a LCFA or LCFA-like compound) which is bound by an FATP (e.g., FATP6) present in cells of heart tissue.

In a further embodiment, LCFA uptake by the liver is modulated or altered (enhanced or reduced), in an individual. For example, a drug which inhibits the function of an FATP present in liver (e.g., FATP5) is administered to an individual who is diabetic, in order to reduce LCFA uptake by liver cells and, thus reduce insulin resistance.

The present invention, thus, provides methods which are useful to alter, particularly reduce, LCFA uptake in individuals and, as a result, to alter (particularly reduce), availability of the LCFAs for further metabolism. In a specific embodiment, the present invention provides methods useful to reduce LCFA uptake and, thus, fatty acid metabolism in individuals, with the result that caloric availability from fats is reduced, and circulating fatty acid levels are lower than they otherwise would be. These methods are useful, for example, as a means of weight control in individuals, (e.g., humans) and as a means of preventing elevated serum lipid levels or reducing serum lipid levels in humans. FATPs expressed in the small intestine, such as FATP4, are useful targets to be blocked in treating obesity (e.g., chronic obesity) or to be enhanced in treating conditions in which enhanced LCFA uptake is desired (e.g., malabsorption syndrome or other wasting conditions).

The identification of this evolutionarily conserved fatty acid transporter family will allow a better understanding of the mechanisms whereby LCFAs traverse the lipid bilayer as well as yield insight into the control of energy homeostasis and its dysregulation in diseases such as diabetes and obesity.

BRIEF DESCRIPTION OF THE DRAWINGS

Figures 1A, 1B:
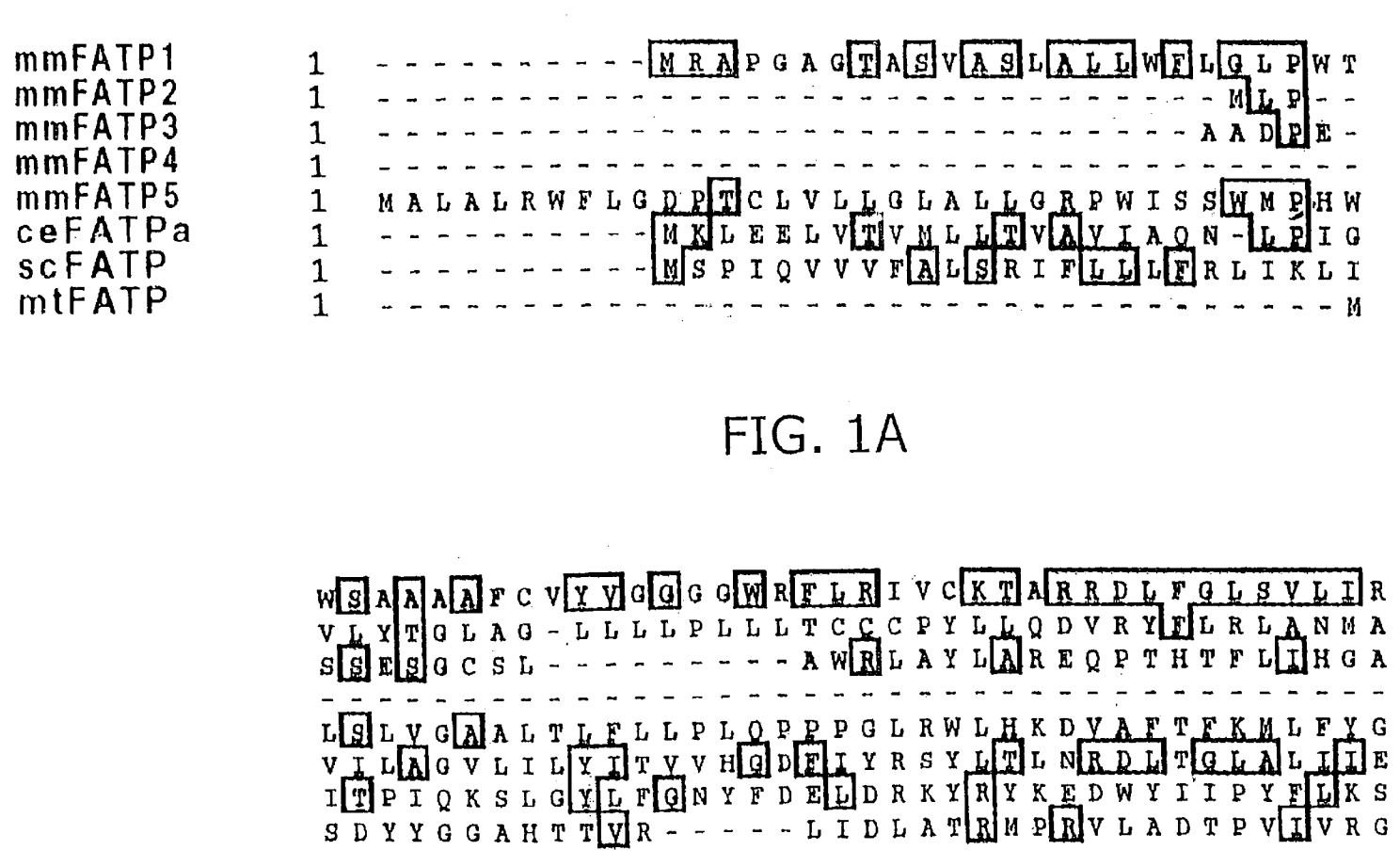
Figures 1E, 1F:
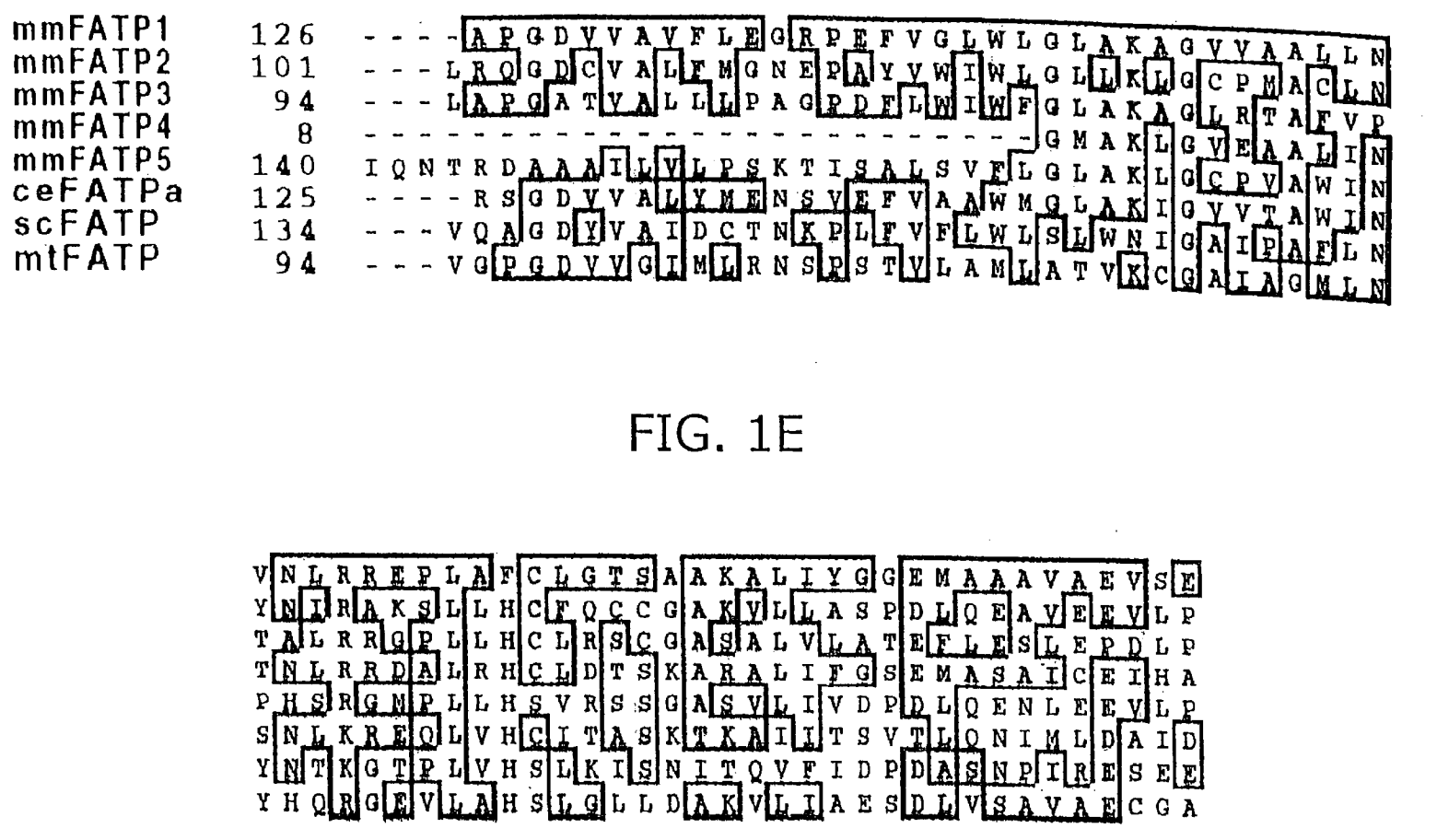
Figures 1G, 1H:
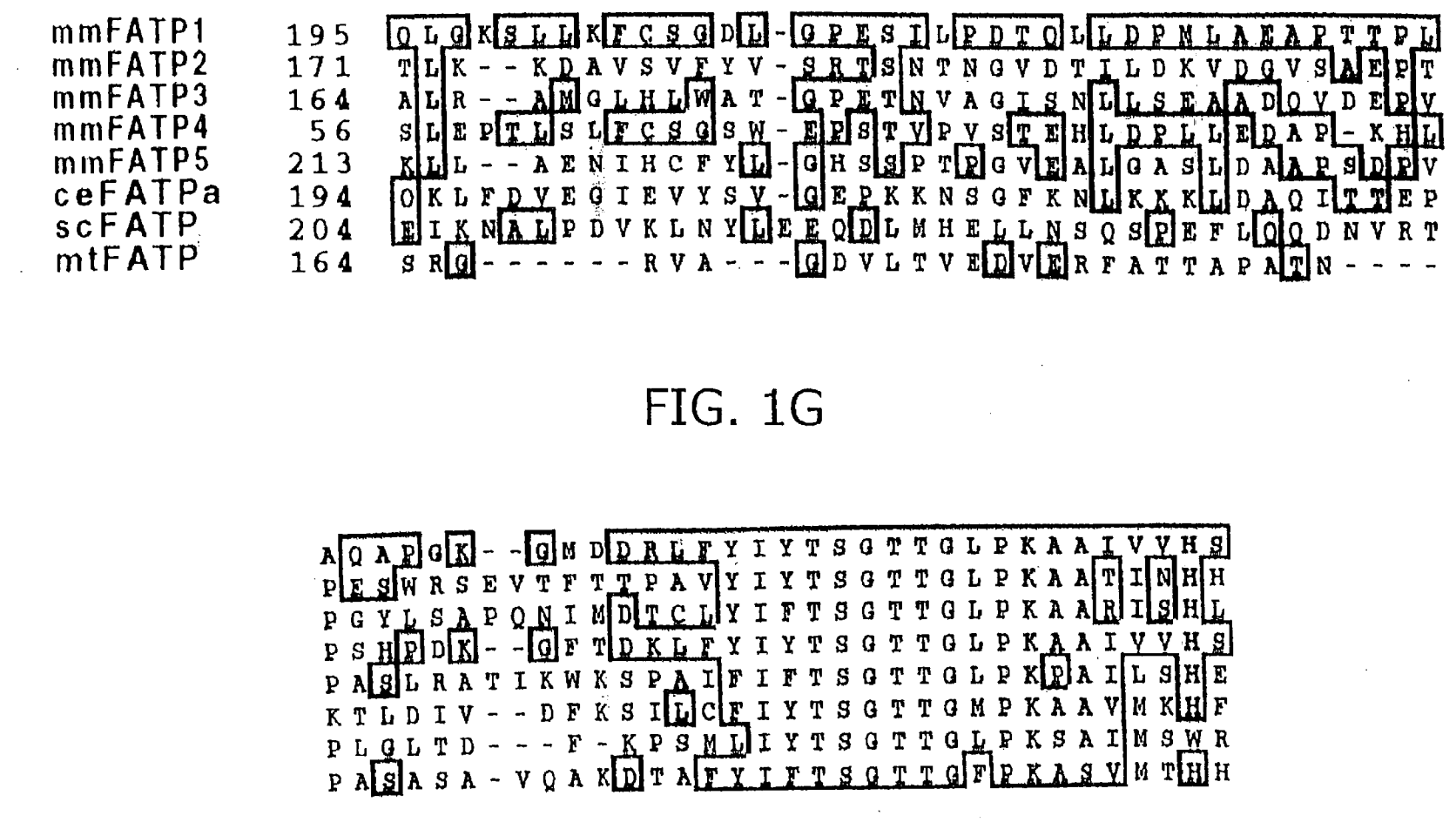
Figures 1K, 1L:
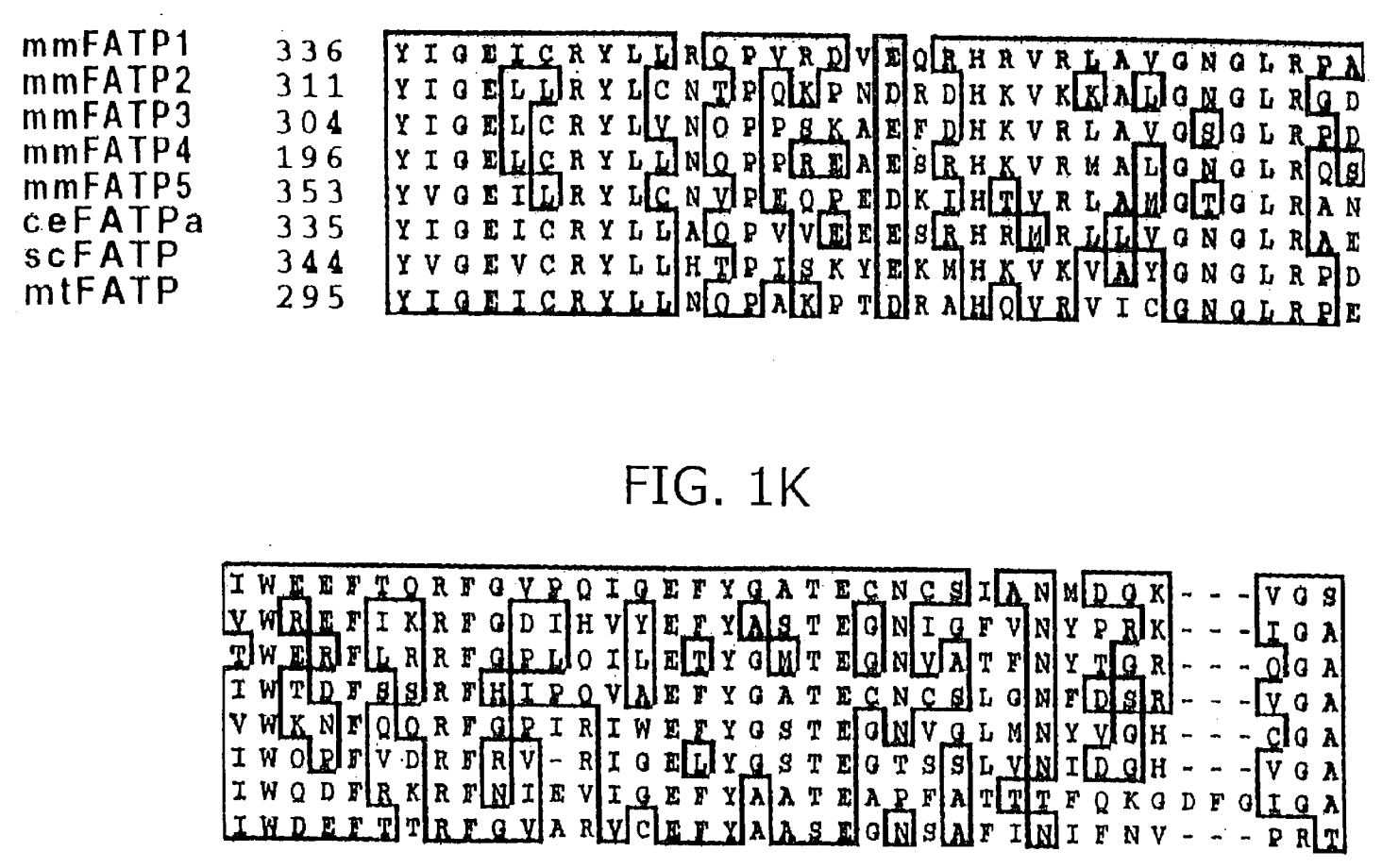
Figures 1M, 1N:
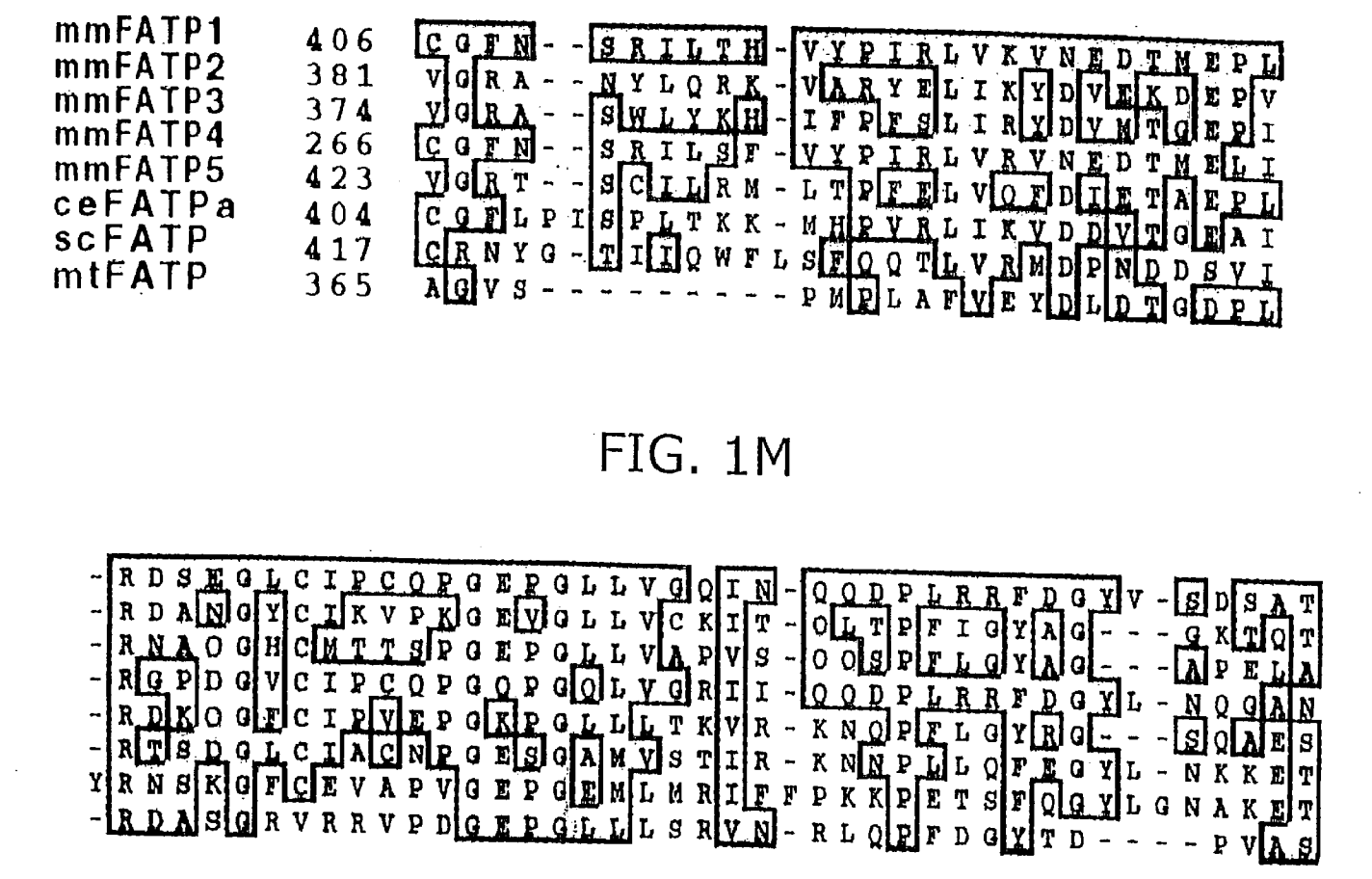
Figures 1O, 1P:
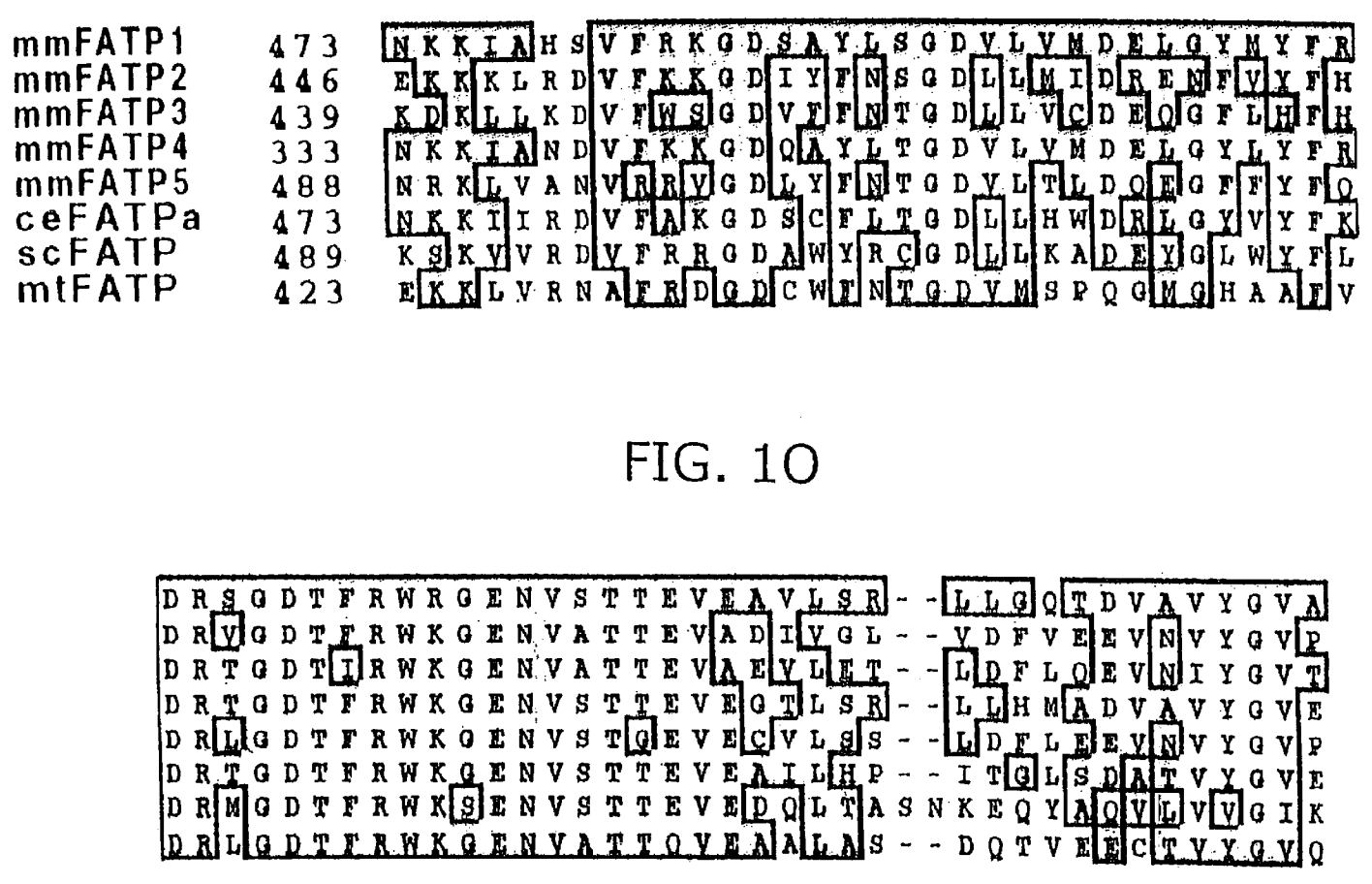
Figures 1Q, 1R:
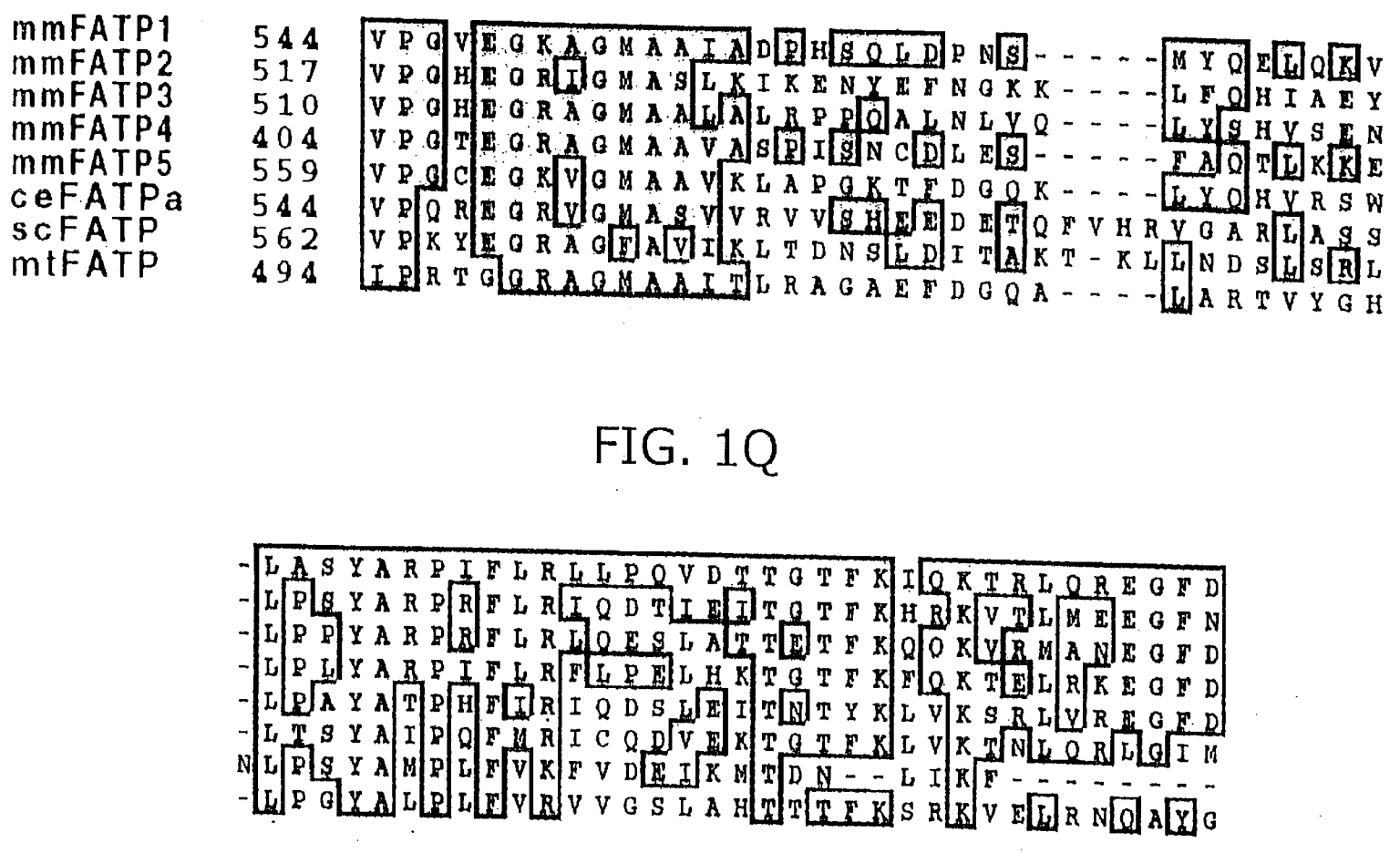
Figure 1S:
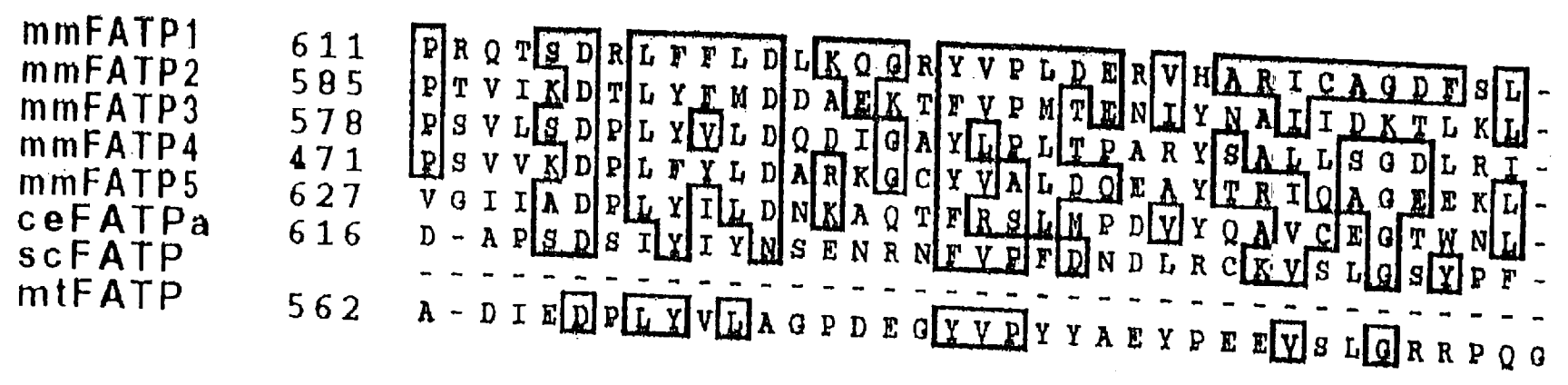

FIGS. 1A–1S show the amino acid sequence alignment of FATPs: mmFATP1 (SEQ ID NO:92), mmFATP2 (SEQ ID NO:93), mmFATP3 (SEQ ID NO:94), mmFATP4 (SEQ ID NO:95), mmFATP5 (SEQ ID NO:96), ceFATPa (SEQ ID NO:97), scFATP (SEQ ID NO:98) and mtFATP (SEQ ID NO:99). The underlining (amino acid residues 204–212 of mtFATP) indicates an AMP binding motif which is found in many classes of proteins; the underlining at amino acid residues 204–507 of the mtFATP sequence indicates the FATP 360 amino acid signature sequence.

FIGS. 2A–2D: COS cells were cotransfected using the DEAE-dextran method with the mammalian expression vectors pCDNA-CD2 either alone (control; FIG. 2A) or in combination with one of the FATP-containing expression vectors (pCDNA-mmFATP1, FIG. 2B; pCDNA-mmFATP2, FIG. 2C; or pCMV-SPORT2-mmFATP5, FIG. 2D) as described in Materials and Methods for Example 2. COS cells were gated on forward scatter (FSC) and side scatter (SS), and the results shown represent >10,000 cells. Cells exhibiting >300 CD2 fluorescence units (vertical line) representing 15% of all cells were deemed CD2 positive.

Figure 6:
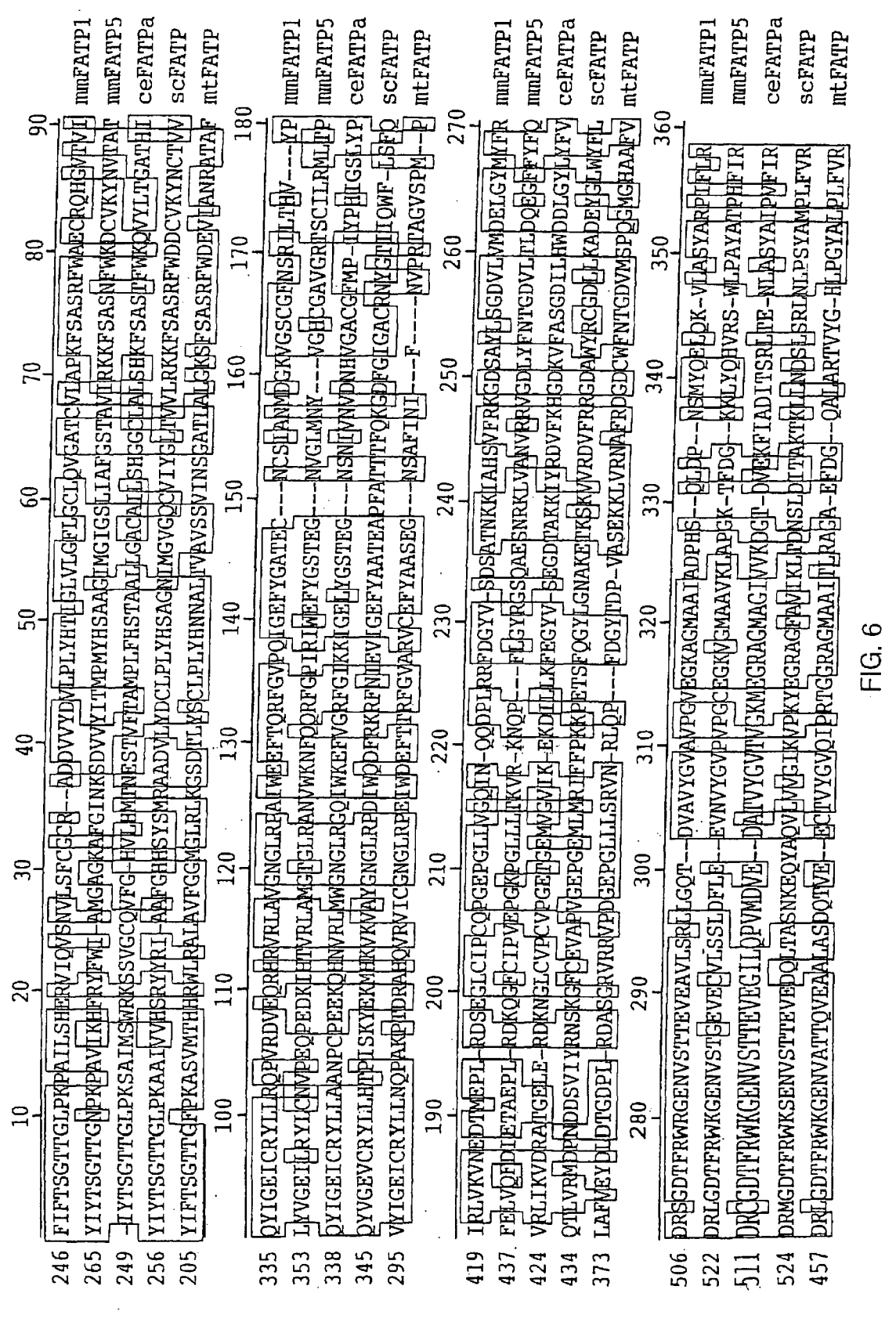

FIG. 6 shows a comparison of the FATP signature sequences of mmFATP1 (SEQ ID NO:1), mmFATP5, (SEQ ID NO:2), ceFATPa (SEQ ID NO:3), scFATP (SEQ ID NO:4) and mmFATP (SEQ ID NO:5).

Figure 8B:
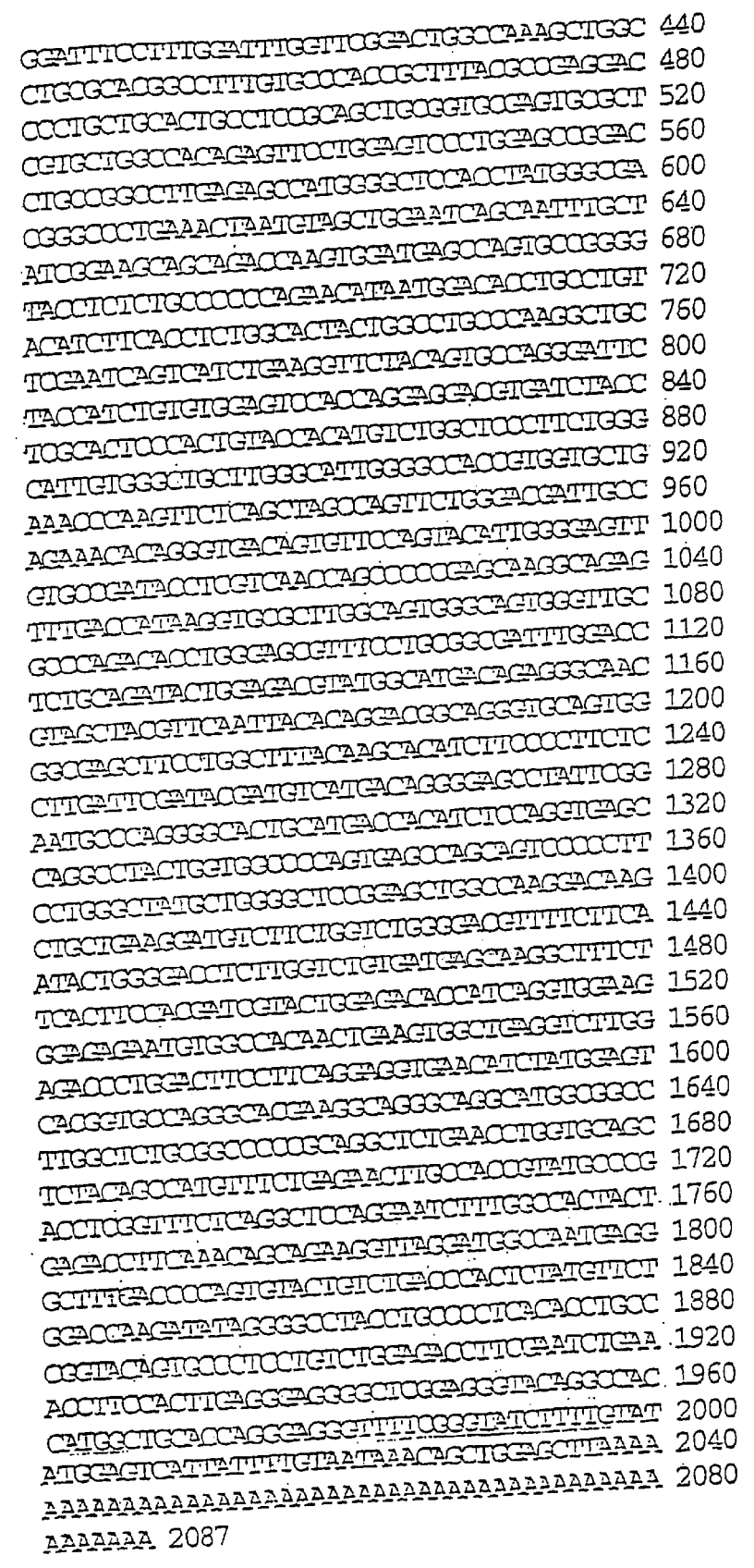

FIGS. 8A and 8B are the mmFATP3 DNA sequence (SEQ ID NO:6).

FIG. 9 is the mmFATP3 protein sequence (SEQ ID NO:7).

FIGS. 10A and 10B are the mmFATP4 DNA sequence (SEQ ID NO:8).

FIG. 11 is the mmFATP4 protein sequence (SEQ ID NO:9).

FIGS. 12A and 12B are the mmFATP5 DNA sequence (SEQ ID NO:10).

FIG. 13 is the mmFATP5 protein sequence (SEQ ID NO:11).

FIGS. 14A and 14B are the hsFATP2 DNA sequence (SEQ ID NO:12).

FIG. 15 is the hsFATP2 protein sequence (SEQ ID NO:13).

FIGS. 16A and 16B are the hsFATP3 DNA sequence (SEQ ID NO:14).

FIG. 17 is the hsFATP3 protein sequence (SEQ ID NO:15).

FIGS. 18A and 18B are the hsFATP4 DNA sequence (SEQ ID NO:16).

FIG. 19 is the hsFATP4 protein sequence (SEQ ID NO:17).

FIGS. 20A and 20B are the hsFATP5 DNA sequence (SEQ ID NO:18).

FIG. 21 is the hsFATP5 protein sequence (SEQ ID NO:19).

FIGS. 22A and 22B are the hsFATP6 DNA sequence (SEQ ID NO:20).

FIG. 23 is the hsFATP6 protein sequence (SEQ ID NO:21).

FIGS. 24A and 24B are the mtFATP DNA sequence (SEQ ID NO:22).

FIG. 25 is the mmFATP protein sequence (SEQ ID NO:23).

FIGS. 26A–26E show the DNA sequence (SEQ ID NO:24) and predicted amino acid sequence (SEQ ID NO:25) of human FATP1.

FIGS. 27A–27D show the DNA sequence (SEQ ID NO:26) and predicted amino acid sequence (SEQ ID NO:27) of human FATP4.

FIG. 28B is the amino acid composition of hsFATP1.

FIG. 29B is a listing of the amino acid composition of hsFATP4.

FIGS. 30A–30F show a comparison of the nucleotide sequence of human FATP1 (SEQ ID NO:28) and the nucleotide sequence of mouse FATP1 (SEQ ID NO:29).

Figure 31A:
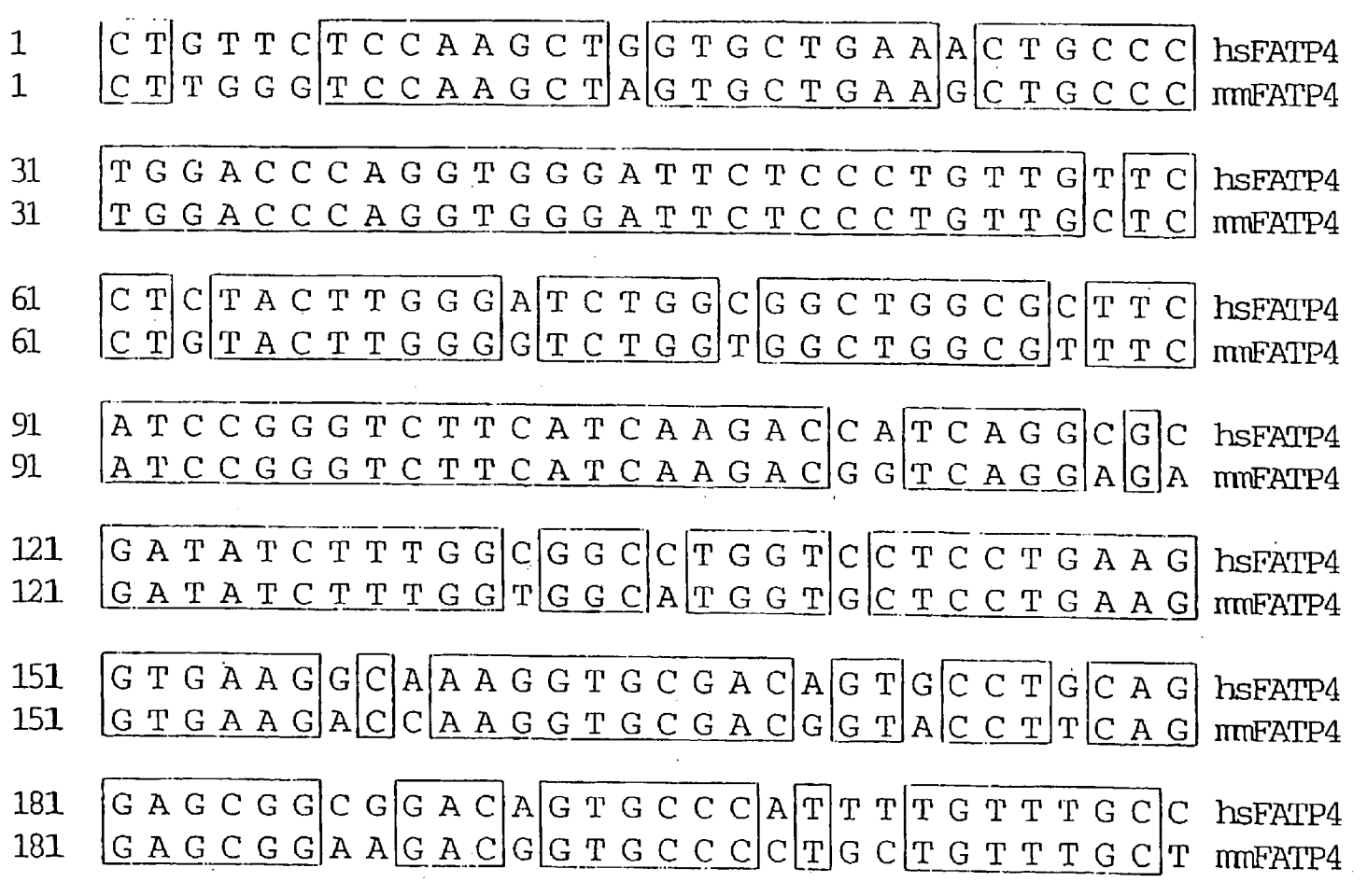

FIGS. 31A–31I show a comparison of the nucleotide sequence of human FATP4 (SEQ ID NO:30) and the nucleotide sequence of mouse FATP4 (SEQ ID NO:31).

FIGS. 32A–32C show a comparison of the amino acid sequence of human FATP1 (SEQ ID NO:32) and the amino acid sequence of mouse FATP1 (SEQ ID NO:33). Shaded amino acid residues match the consensus sequence exactly.

Figure 33A:
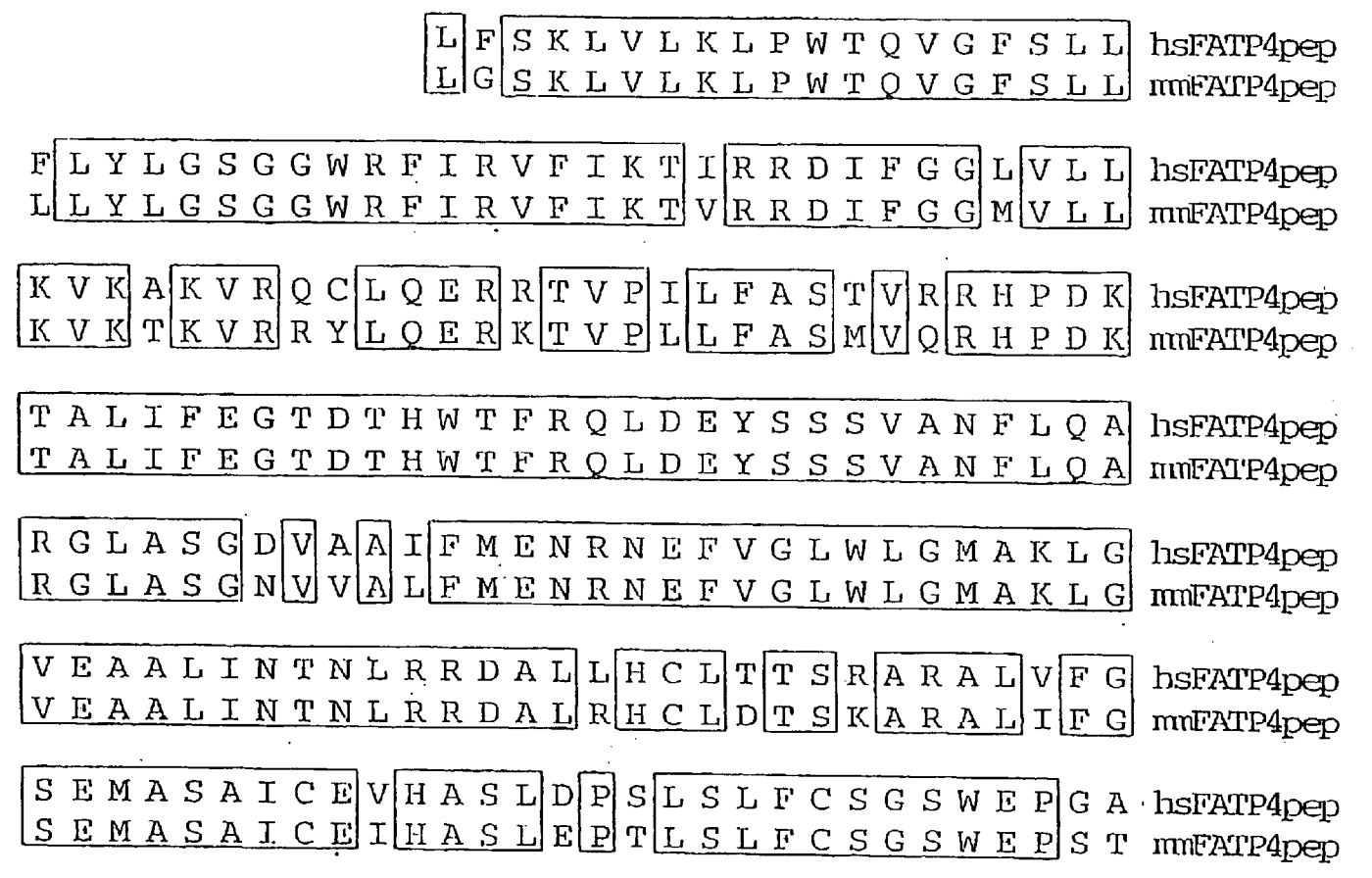

FIGS. 33A–33C show human FATP4 (SEQ ID NO:34) and mouse FATP4 (SEQ ID NO:35). Shaded amino acid residues match the consensus sequence exactly.

FIGS. 34A–34D show the nucleotide sequence (SEQ ID NO:36) and predicted amino acid sequence (SEQ ID NO:37) of hsFATP6.

FIG. 35B is a listing of the amino acid composition of hsFATP6.

FIGS. 36A–36G show an alignment of the amino acid sequences of hsFATP1 (SEQ ID NO:38), hsFATP4 (SEQ ID NO:39) and hsFATP6 (SEQ ID NO:40). Shaded amino acid residues match the consensus sequence exactly.

FIG. 37 shows results of assessment of fatty acid uptake by human FATP1 and human FATP4. The percent of CD2-positive cells exhibiting a BODIPY-fluorescence of more than 300 arbitrary units is plotted for the three different conditions tested.

FIGS. 39A–39C are an illustration of the amino acid sequences of human FATP4 (SEQ ID NO:41) and mouse FATP4 (SEQ ID NO:42) compared to human FATP1 (SEQ ID NO:43). Shown by underlining are the FATP consensus sequence (236–556 of hsFATP1) and the AMP-binding motif (246–254 of hsFATP1). The human FATPs were cloned by screening libraries with sequences from ESTs (expressed sequence tags). Mouse FATP4 was cloned by PCR using degenerate primers.

FIGS. 43A–43B show the nucleotide sequence of the gene encoding mouse FATP4 (SEQ ID NO:44).

FIG. 43C shows the amino acid sequence of mouse FATP4 protein (SEQ ID NO:45).

FIGS. 44A–44D show the hsFATP1 DNA sequence (SEQ ID NO:46). Coding region: 175–2115 (1941 nt).

FIG. 45 is the hsFATP1 protein sequence (SEQ ID NO:47).

FIGS. 46A and 46B are the hsFATP2 DNA sequence (SEQ ID NO:48). Coding region: 223–2085 (1863 nt).

FIG. 47 is the hsFATP2 protein sequence (SEQ ID NO:49).

FIG. 48 is the partial DNA sequence of hsFATP3 (SEQ ID NO:50). Coding region: 1–993.

FIG. 49 is the partial protein sequence of hsFATP3 (SEQ ID NO:51).

FIGS. 50A, 50B, and 50C are the hsFATP4 DNA sequence (SEQ ID NO:52). Coding region: 208–2139 (1932 nt).

FIG. 51 is the hsFATP4 protein sequence (SEQ ID NO:53).

FIG. 52 is the hsFATP5 partial DNA sequence (SEQ ID NO:54). Coding region: 1–1062.

FIG. 53 is the hsFATP5 partial protein sequence (SEQ ID NO:55).

FIGS. 54A, 54B, and 54C are the hsFATP6 DNA sequence (SEQ ID NO:56). Coding region: 643–2502 (1860 nt).

FIG. 55 is the hsFATP6 protein sequence (SEQ ID NO:57).

FIGS. 56A, 56B, and 56C are the rnFATP1 DNA sequence (rn=*Rattus norvegicus*; (SEQ ID NO:58). Coding region: 75–2015 (1941 nt).

FIG. 57 is the rnFATP1 protein sequence (SEQ ID NO:59).

FIG. 58A, 58B, and 58C are the rnFATP2 DNA sequence (SEQ ID NO:60). Coding region: 795–2657 (1863 nt).

FIG. 59 is the rnFATP2 protein sequence (SEQ ID NO:61).

FIG. 60A and 60B are the rnFATP4 partial DNA sequence (SEQ ID NO:62). Coding region: 1–1218.

FIG. 61 is the rnFATP4 partial DNA sequence (SEQ ID NO:63).

FIG. 62A, 62B, and 62C are the mmFATP1 DNA sequence (SEQ ID NO:64). Coding region: 1–1944.

FIG. 63 is the mmFATP1 protein sequence (SEQ ID NO:65).

FIGS. 64A and 64B are the mmFATP2 DNA sequence (SEQ ID NO:66). Coding region: 121–1992 (1872 nt).

FIG. 65 is the mmFATP2 protein sequence (SEQ ID NO:67).

FIGS. 66A and 66B are the mmFATP3 partial DNA sequence (SEQ ID NO:68). Coding region: 1–1830.

FIG. 67 is the mmFATP3 partial protein sequence (SEQ ID NO:69).

FIGS. 68A, 68B, and 68C are the mmFATP4 DNA sequence (SEQ ID NO:70). Coding region: 1–1932.

FIGS. 69 is the mmFATP4 protein sequence (SEQ ID NO:71).

FIGS. 70A and 70B are the mmFATP5 DNA sequence (SEQ ID NO:72). Coding region: 60–2129.

FIG. 71 is the mmFATP5 protein sequence (SEQ ID NO:73).

FIGS. 72A and 72B are the dmFATP partial DNA sequence (dm=*Drosophila melanogaster*; SEQ ID NO:74). Coding region: 1–1773.

FIGS. 73 is the dmFATP partial protein sequence (SEQ ID NO:75).

FIG. 74 is the drFATP partial DNA sequence (dr=*Danio rerio*, zebrafish; SEQ ID NO:76) Coding region: 1–173.

FIG. 75 is the drFATP partial protein sequence (SEQ ID NO:77).

FIG. 76A and 76B are the ceFATPa DNA sequence (SEQ ID NO:78). Coding region: 1–1953.

FIG. 77 is the ceFATPa protein sequence (SEQ ID NO:79).

FIGS. 78A and 78B are the ceFATPb DNA sequence (SEQ ID NO:80). Coding region: 1–1968.

FIG. 79 is the ceFATPb protein sequence (SEQ ID NO:81).

FIGS. 80A and 80B are the chFATP DNA sequence (SEQ ID NO:82; ch=*Cochliobolu heterostrophus*). Coding region: 1–1932.

FIG. 81 is the chFATP protein sequence (SEQ ID NO:83).

FIG. 82 is the anFATP partial protein sequence (an=*Aspergillus nidulans*; SEQ ID NO:84). Coding region: 1–597.

FIG. 83 is the anFATP partial protein sequence (SEQ ID NO:85).

FIG. 84 is the mgFATP partial DNA sequence (mg=*Magnaporthe grisea*, rice blast; SEQ ID NO:86). Coding region: 1–522.

FIG. 85 is the mgFATP partial protein sequence (SEQ ID NO:87).

FIGS. 86A and 86B are the scFATP DNA sequence (SEQ ID NO:88). Coding region: 1–1872.

FIG. 87 is the scFATP protein sequence (SEQ ID NO:89).

FIGS. 88A and 88B are the mtFATP DNA sequence (SEQ ID NO:90).

FIG. 89 is the mtFATP protein sequence (SEQ ID NO:91). Coding region: 1–1794.

FIGS. 94A–94J are a representation of the DNA sequence (SEQ ID NO:101) of the hsFATP5 gene, and the amino acid sequence (SEQ ID NO:102) of the hsFATP5 protein.

DETAILED DESCRIPTION OF THE INVENTION

Figure 90:
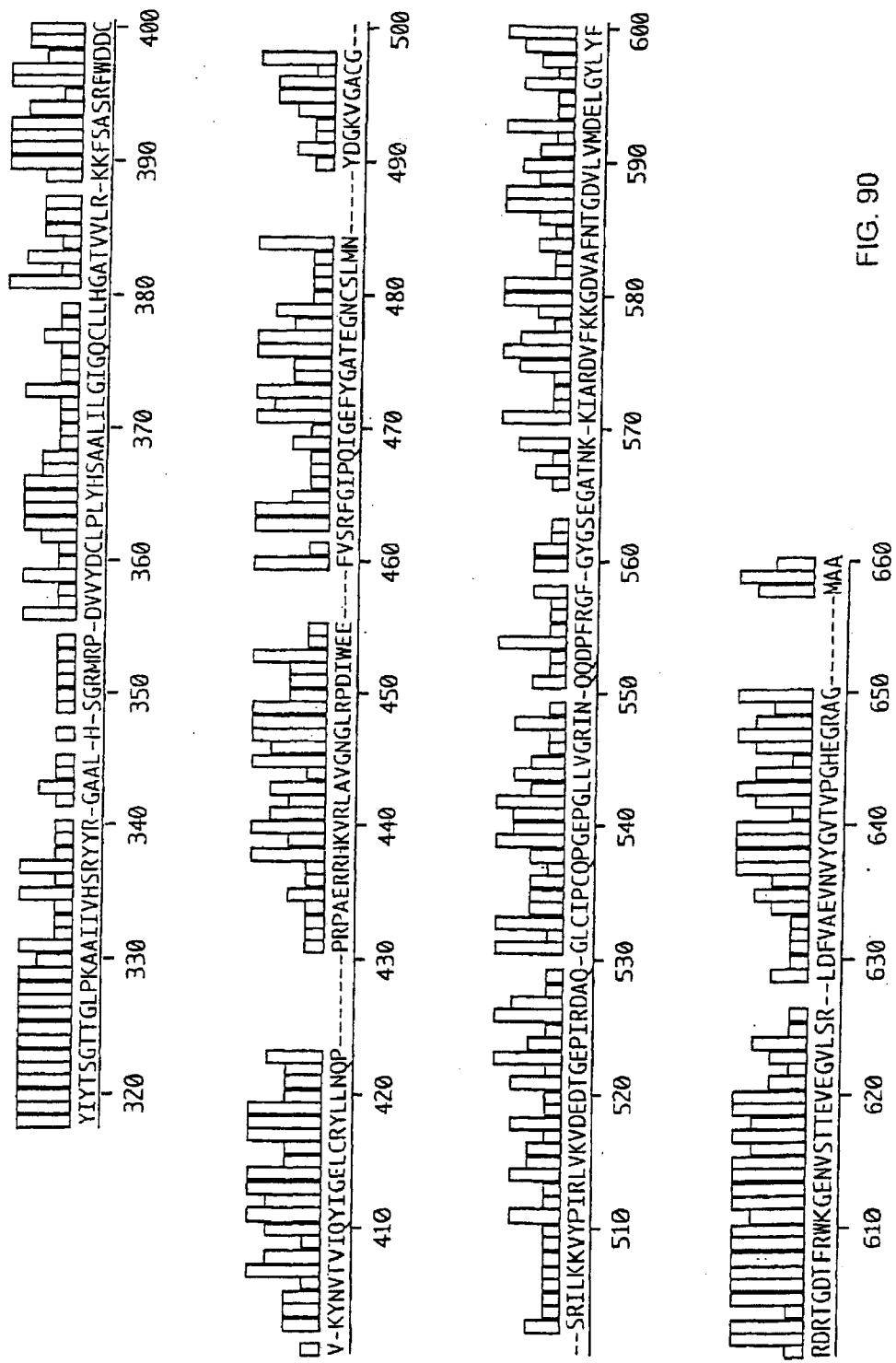
FIG. 90 is a concensus sequence of the FATP signature sequence (SEQ ID NO:100), based on 23 independent sequences aligned in ClustalX. The height of the bar at each amino acid residue position indicates the degree of conservation at that position. Gaps have been inserted to maintain the strength of the alignment.
Figure 91:
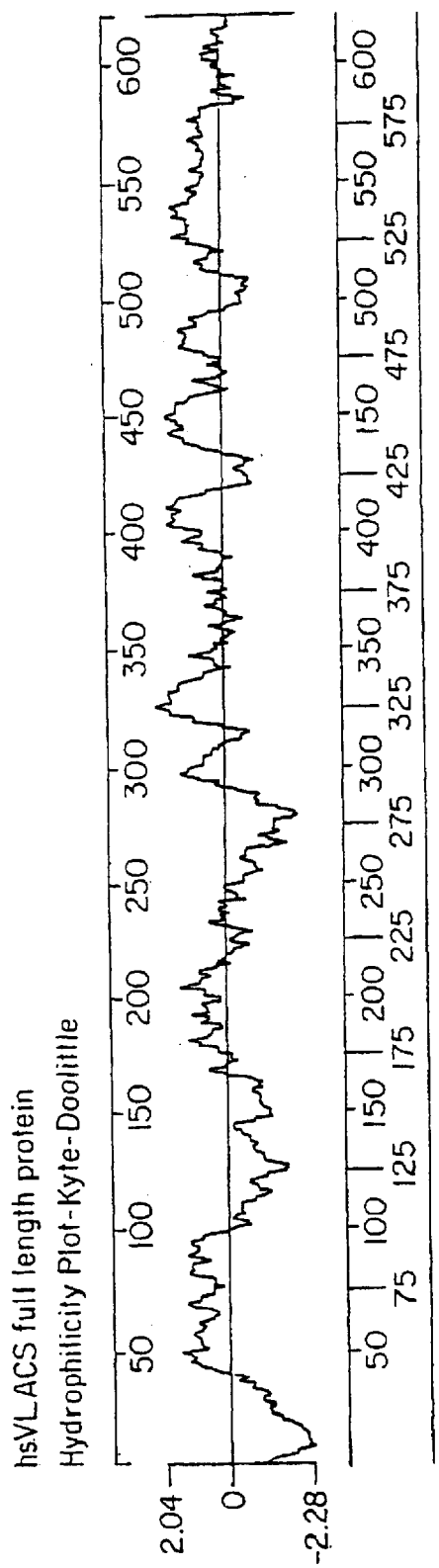
FIG. 91 is a hydrophilicity plot for hsFATP2, made using the Kyte-Doolittle method, averaging hydrophilicity values for 18 amino acid residues at a time.
Figure 92:
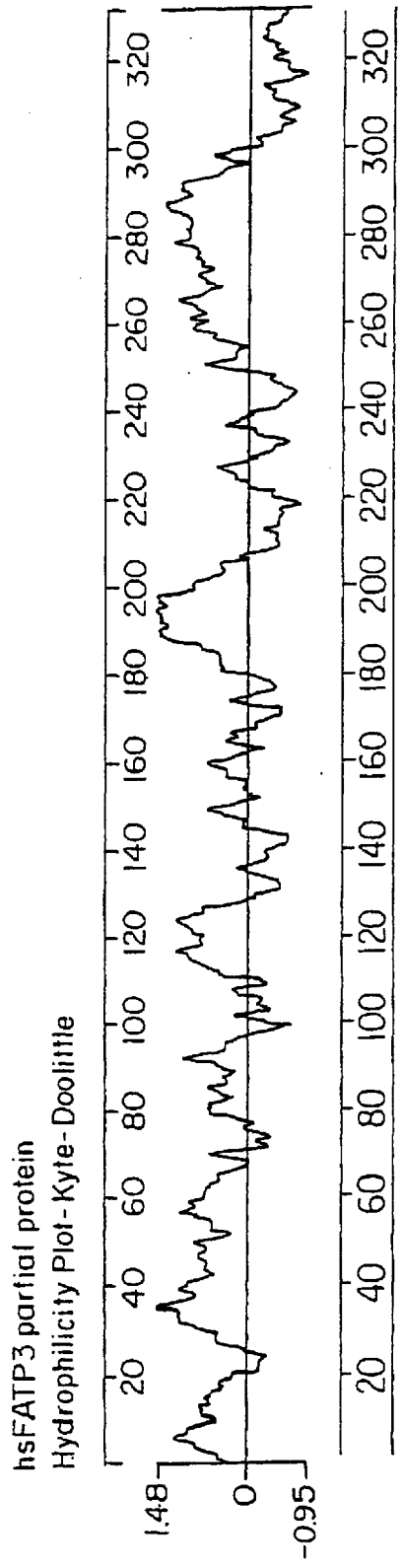
FIG. 92 is a hydrophilicity plot for the hsFATP3 partial protein, made using the Kyte-Doolittle method, averaging hydrophilicity values for 18 amino acid residues at a time.
Figure 93:
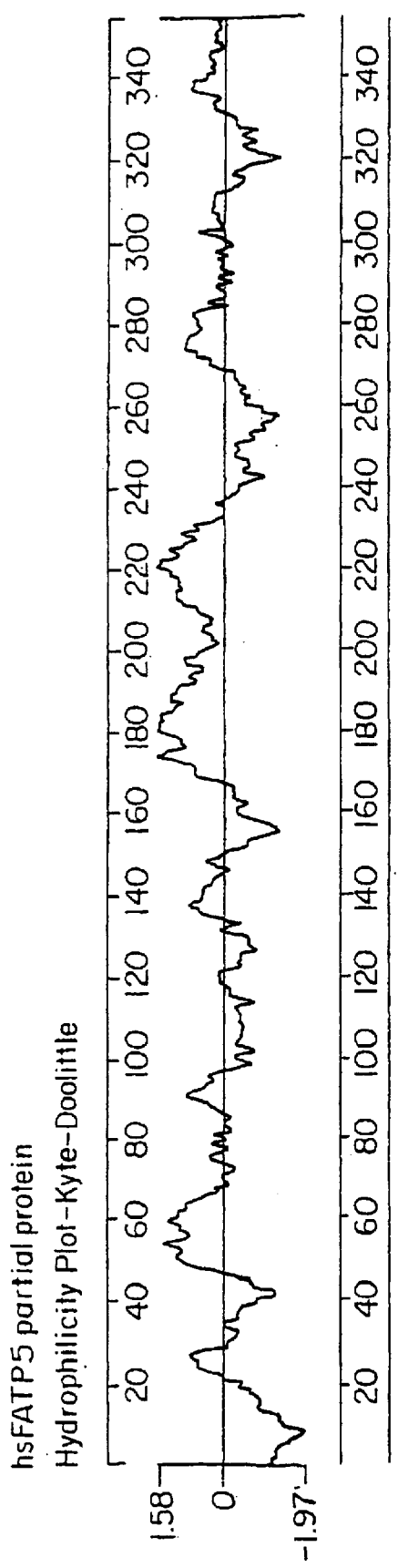
FIG. 93 is a hydrophilicity plot for the hsFATP5 partial protein, made using the Kyte-Doolittle method, averaging hydrophilicity values for 18 amino acid residues at a time.

As described herein, FATPs are a large evolutionarily conserved family of proteins that mediate the transport of LCFAs into cells. The family includes proteins which are conserved from mycobacteria to humans and exhibit very different expression patterns in tissues. Specific embodiments described include FATPs from mice, humans, nematodes, fungi and mycobacteria which have been shown to be functional LCFA transporters. The term "fatty acid transport proteins" ("FATPs") as used herein, refers to the proteins described herein as FATP1, FATP2, FATP3, FATP4, FATP5 and FATP6, which have been described in one or more species of mammals, as well as mtFATP, ceFATP, scFATP, anFATP, mgFATP, and chFATP, and other proteins sharing at least about 50% amino acid sequence similarity, preferably at least about 60% sequence similarity, more preferably at least about 70% sequence similarity, and still more preferably, at least about 80% sequence similarity, and most preferably, at least about 90% sequence similarity in the approximately 360 amino acid signature sequence. The approximaely 360 amino acid FATP signature sequence is shown in FIG. 1. The concensus sequence of the signature sequence is shown in FIG. 90. The nomenclature used herein to refer to FATPs includes a species-specific prefix (e.g., mm, *Mus musculus*; hs or h, *Homo sapiens* or human; mt *M. tuberculosis*; dm. *D. melanogaster*; ce, *C. elegans*; sc, *Saccharomyces cerevisiae*) and a number such that mammalian homologues in different species share the same number. For example, six human and five mouse FATP genes which are expressed in a variety of tissues are described herein and are referred to, respectively, as hsFATP1–hsFATP6 and mmFATP1–mmFATP5; for example, hsFATP4 and mmFATP4 are the human and mouse orthologs.

Expression patterns of human and mouse FATPs have been assessed and are described below. Briefly, results of these assessments show that FATP5 is a liver-specific gene. FATP2 is highly expressed in liver and kidney. Both of these proteins, as well as FATP4 and FATPs from nematodes and mycobacteria, have been shown to be functional LCFA transporters. Results have also shown that FATP4 mRNA is present at high levels in epithelial cells of two regions of the small intestine (the jejunum and ileum) and at lower, but significant, levels in a third region (the duodenum). They further showed that FATP2 mRNA is present in epithelial cells of the duodenum at a level similar to that of FATP4 mRNA levels, but is present at lower levels in the jejunum and ileum. FATP4 mRNA was absent from other cell types of the small intestine and no FATP4 mRNA could be detected in any cells of the colon. No signals above background could be detected for FATP1, FATP3 and FATP5 in any of the intestinal tissues. Thus, FATP4 is the major FATP in the mouse small intestine, which supports a major role for FATP4 (along with FATP2 to a lesser extent) in absorption of free fatty acids. hsFATP4 was clearly expressed in the jejunum and ileum; expression was absent in the stomach. This, too, is consistent with a major role for FATP4 in absorption of fatty acids in the human gut. Analysis of FATP expression in human tissues, also described in detail below, showed that hsFATP6, which has no mouse ortholog as yet, is expressed at high levels in the heart and at low levels in the placenta, but is undetectable in the other tissues assessed (Example 9). This is consistent with a major role for FATP6 in absorption of fatty acids in the heart.

Long chain fatty acids (LCFAs) are an important energy source for pro- and eukaryotes and are involved in diverse cellular processes, such as membrane synthesis, intracellular signaling, protein modification, and transcriptional regulation. In developed Western countries, human dietary lipids are mainly di- and triglycerides and account for approximately 40% of caloric intake (Weisburger, J. H. (1997) *J. Am. Diet. Assoc.* 97:S16–S23). These lipids are broken down into fatty acids and glycerol by pancreatic lipases in the small intestine (Chapus, C., Rovery, M., Sarda, L & Verger, R. (1988) *Biochimie* 70:1223–34); LCFAs are then transported into brush border cells, where the majority is re-esterified and secreted into the lymphatic system as chylomicrons (Green, P. H. & Riley, J. W. (1981) *Aust. N.Z.J. Med.* 11:84–90). Fatty acids are liberated from lipoproteins by the enzyme lipoprotein lipase, which is bound to the luminal side of endothelial cells (Scow, R. O. & Blachette-Mackie, E. J. (1992) *Mol. Cell. Biochem* 116:181–191). "Free" fatty acids in the circulation are bound to serum albumin (Spector, A. A. (1984) *Clin. Physiol. Biochem* 2:123–134) and are rapidly incorporated by adipocytes, hepatocytes, and cardiac muscle cells. The latter derive 60–90% of their energy through the oxidation of LCFAs (Neely, J. F. Rovetto, M. J. & Oram, J. F. (1972) *Prog. Cardiovasc. Dis*: 15:289–329). Although saturable and specific uptake of LCFAs has been demonstrated for intestinal cells, hepatocytes, cardiac myocytes, and adipocytes, the molecular mechanisms of LCFA transport across the plasma membrane have remained controversial (Hui, T. Y. & Bernlohr, D. A. (1997) *Front. Biosci*. 15:d222-31-d231; Schaffer, J. E. & Lodish, H. F, (1995) *Trends Cardiovasc. Med*. 5:218–224). Described herein is a large family of highly homologous mammalian LCFA transporters which show wide expression, including in all tissues relevant to fatty acid metabolism. Further described are novel members of this family in other species, including mycobacterial and nematode FATPs which, like their mammalian counterparts, are functional fatty acid transporters.

The discovery of a diverse but highly homologous family of FATPs is reminiscent of the glucose transporter family. In a manner similar to the FATPs, the glucose transporters have very divergent patterns of tissue expression (McGowan, K. M., Long, S. D. & Pekala, P. H. (1995) *Pharmacol. Ther*. 66:465–505). The FATPs, like glucose transporters, may also differ in their substrate specificities, uptake kinetics, and hormonal regulation (Thorens, B. (1996) *Am. J. Physiol*. 270:G541–G553). Indeed, the levels of fatty acids in the blood, like those of glucose, can be regulated by insulin and are dysregulated in diseases such as noninsulin-dependent diabetes and obesity (Boden, G. (1997) *Diabetes* 46:3–10). The underlying mechanisms for the regulation of free fatty acid concentrations in the blood are not understood, but could be explained by hormonal modulation of FATPs.

Insulin-resistance is thought to be the major defect in non insulin-dependent diabetes mellitus (NIDDM) and is one of the earliest manifestations of NIDDM (McGarry (1992) *Science* 258:766–770). Free fatty acids (FFAs) may provide an explanation for why obesity is a risk factor for NIDDM. Plasma levels of FFAs are elevated in diabetic patients (Reaven et al. (1988) *Diabetes* 37:1020). Elevated plasma free fatty acids (FFAs) have been demonstrated to induce insulin-resistance in whole animals and humans (Boden (1998) *Front. Biosci.* 3:D169–D175). This insulin-resistance is likely mediated by effects of FFAs on a variety of issues. FFAs added to adipocytes in vitro induce insulin resistance in this cell type as evidenced by inhibition of insulin-induced glucose transport (Van Epps-Fung et al. (1997) *Endocrinology* 138:4338–4345). Rats fed a high fat diet developed skeletal muscle insulin resistance as evidenced by a decrease in insulin-induced glucose uptake by skeletal muscle (Han et al., (1997) *Diabetes* 46:1761–1767). In addition, elevated plasma FFAs increase insulin-suppressed endogenous glucose production in the liver (Boden (1998) *Front. Biosci.* 3:D169–D175), thus increasing hepatic glucose output. It has been postulated that the adverse effects of plasma free fatty acids are due to the FFAs being taken up into the cell, leading to an increase in intracellular long chain fatty acyl CoA; intracellular long chain acyl CoAs are thought to mediate the effects of FFAs inside the cell. Thus, fatty acid induced insulin-resistance may be prevented by blocking uptake of FFAs into select tissues, in particular liver (by blocking FATP2 and/or FATP5), adipocyte (by blocking FATP1), and skeletal muscle (by blocking FATP1). Blocking intestinal fat absorption (by blocking FATP4) is also expected to reduce plasma FFA levels and thus improve insulin resistance.

During the pathogenesis of NIDDM insulin-resistance can initially be counteracted by increasing insulin output by the pancreatic beta cell. Ultimately, this compensation fails, beta cell function decreases and overt diabetes results (McGarry (1992) *Science* 258: 766–770). Manipulating beta cell function is a second point where fatty acid transporter blockers may be beneficial for diabetes. While no FATP homolog has been identified so far that is expressed in the beta cell of the pancreas, the data described below suggest the existence of such a transporter and the sequence information included herein provides the means to identify such a transporter by degenerate PCR, using primers to regions conserved in all FATP family members or by low stringency hybridization. It has been demonstrated that exposure of pancreatic beta-cells to FFAs increases the basal rate of insulin secretion; this in turn leads to a decrease in the intracellular stores of insulin, resulting in decreased capacity for insulin secretion after chronic exposure (Bollheimer et al., (1998) *J. Clin. Invest.* 101:1094–1101). The effects of FFAs are again likely to be mediated by intracellular long chain fatty acyl CoA molecules (Liu et al., (1998) *J. Clin. Invest.* 101: 1870–1875). FFAs have also been demonstrated to increase beta cell apoptosis (Shimabukuro et al., (1998) *Proc. Nat. Acad. Sci. USA* 95:2498–2502), possibly contributing to the decrease in beta cell numbers in late stage NIDDM.

Another finding with potentially broad implications is the identification of a FATP homologue in *M. tuberculosis*. Tuberculosis causes more deaths worldwide than any other infectious agent and drug-resistant *tuberculosis* is re-emerging as a problem in industrialized nations (Bloom, B. R. & Small, P. M. (1998) *N. Engl. J. Med.* 338:677–678). *Mycobacterium tuberculosis* has about 250 enzymes involved in fatty acid metabolism, compared with only about 50 in *E. coli*. It has been suggested that, living as a pathogen, the mycobacteria are largely lipolytic, rather than lipogenic, relying on the lipids within mammalian cells and the tubercle (Cole, S. T. et al., *Nature* 393:537–544 (1998)). The de novo synthesis of fatty acids in *Mycobacterium leprae* is insufficient to maintain growth (Wheeler, P. R., Bulmer, K & Ratledge, C. (1990) *J. Gene. Microbiol.* 136:211–217). Thus, it is reasonable to expect that inhibitors of mtFATP will serve as therapeutics for *tuberculosis*. FATPs expressed in mycobacteria can be targeted to reduce or prevent replication of mycobacteria (e.g., to reduce or prevent replication of *M. tuberculosis*) and, thus, reduce or prevent their adverse effects. For example, a FATP or FATPs expressed by *M. tuberculosis* can be targeted and inhibited, thus reducing or preventing growth of this pathogen (and *tuberculosis* in humans and other mammals). An inhibitor of an *M. tuberculosis* FATP can be identified, using methods described herein (e.g., expressing the FATP in an appropriate host cell, such as *E. coli* or COS cells; contacting the cells with an agent or drug to be assessed for its ability to inhibit the FATP and, as a result, mycobacterial growth, and assessing its effects on growth). A drug or agent identified in this manner can be further tested for its ability to inhibit a *M. tuberculosis* FATP and *M. tuberculosis* infection in an appropriate animal model or in humans. A method of inhibiting mycobacterial growth, particularly growth of *M. tuberculosis*, and compounds useful as drugs for doing so are also the subject of this invention.

An isolated polynucleotide encoding mtFATP, like other polynucleotides encoding FATPs of the FATP family, can be incorporated into vectors, nucleic acids of viruses, and other nucleic acid constructs that can be used in various types of host cells to produce mtFATP. This mtFATP can be used, as it appears on the surface of cells, or in various artificial membrane systems, to assess fatty acid transport function, to identify ligands and molecules that are modulators of fatty acid transport activity. Molecules found to be inhibitors of mtFATP function can be incorporated into pharmaceutical compositions to administer to a human for the treatment of *tuberculosis*.

Particular embodiments of the invention are polynucleotides encoding a FATP of *Cochliobolus* (*Helminthosporium*) *heterostrophus* or portions or variants thereof, the isolated or recombinantly produced FATP, methods for assessing whether an agent binds to the chFATP, and further methods for assessing the effect of an agent being tested for its ability to modulate fatty acid transport activity. *Cochliobolus heterostrophus* is an ascomycete that is the cause of southern corn leaf blight, an economically important threat to the corn crop in the United States. The related species *C. sativus* causes crown rot and common root rot in wheat and barley. One or more FATPs of *C. heterostrophus* can be targeted for the identification of an inhibitor of chFATP function, which can be then be used as an agent effective against infection of plants by *C. heterostrophus* and related organisms. Methods described herein that were applied in studying the expression of a FATP gene and the function of the FATP in its natural site of expression or in a host cell, can be used in the study of the chFATP gene and protein.

*Magnaporthe grisea* (rice blast) is an economically important fungal pathogen of rice. Further embodiments of the invention are nucleic acid molecules encoding a FATP of *Magnaporthe grisea*, portions thereof, or variants thereof, isolated mgFATP, nucleic acid constructs, and engineered cells expressing mgFATP. Other aspects of the invention are assays to identify an agent which binds to mgFATP and assays to identify an agent which modulates the function of mgFATP in cells in which mgFATP is expressed or in artificial membrane systems. Agents identified as inhibiting mgFATP activity can be developed into anti-fungal agents to be used to treat rice infected with rice blast.

*Caenorhabditis elegans* is a nematode related to plant pathogens and human parasites. An isolated polynucleotide which encodes ceFATP, like other polynucleotides encoding FATPs of the FATP family described herein, can be incorporated into nucleic acid vectors and other constructs that can be used in various types of cells to produce ceFATP. ceFATP as it occurs in cells or as it can be isolated or incorporated into various artificial or reconstructed membrane systems, can be used to assess fatty acid transport, and to identify ligands and agents that modulate fatty acid transport activity. Agents found by such assays to be inhibitors of ceFATP activity can be incorporated into compositions for the treatment of diseases caused by genetically related organisms with a FATP of similar sensitivity to the agents.

*Aspergillus nidulans* is one of a family of fungal species that can infect humans. Further embodiments of the invention of the family of polynucleotides encoding FATPs are polynucleotides encoding a FATP of *Aspergillus nidulans*, and vectors and host cells that can be constructed to comprise such polynucleotides. Further embodiments are a polypeptide encoded by such polynucleotides, portions thereof having one or more functions characteristic of a FATP, and various methods. The methods include those for identifying agents that bind to anFATP and those for assessing the effect of an agent being tested for its ability to modulate fatty acid transport activity. Those agents found to inhibit fatty acid transport function can be used in compositions as anti-fungal pharmaceuticals, or can be modified for greater effectiveness as a pharmaceutical.

One aspect of the invention relates to isolated nucleic acids that encode a FATP as described herein, such as those FATPs having an amino acid sequence in FIG. 45 (SEQ ID NO:47), FIG. 47 (SEQ ID NO:49), FIG. 49 (SEQ ID NO:51), FIG. 51 (SEQ ID NO:53), FIGS. 94A–94J (SEQ ID NO:102), and FIG. 55 (SEQ ID NO:57) and nucleic acids closely related thereto as described herein.

Using the information provided herein, such as a nucleic acid sequence set forth in FIGS. 44A–44D (SEQ ID NO:46), FIGS. 46A and 46B (SEQ ID NO:48), FIG. 48 (SEQ ID NO:50), FIGS. 50A–50C (SEQ ID NO:52), FIGS. 94A–94J (SEQ ID NO:101), and FIGS. 54A–54C (SEQ ID NO:56), a nucleic acid of the invention encoding a FATP polypeptide may be obtained using standard cloning and screening methods, such as those for cloning and sequencing cDNA library fragments, followed by obtaining a full length clone. For example, to obtain a nucleic acid of the invention, a library of clones of cDNA of human or other mammalian DNA can be probed with a labeled oligonucleotide, such as a radiolabeled oligonucleotide, preferably about 17 nucleotides or longer, derived from a partial sequence. Clones carrying DNA identical to that of the probe can then be distinguished using stringent (also, "high stringency") hybridization conditions. By sequencing the individual clones thus identified with sequencing primers designed from the original sequence it is then possible to extend the sequence in both directions to determine the full length sequence. Suitable techniques are described, for example, in *Current Protocols in Molecular Biology* (F. M. Ausubel et al., eds), containing supplements through Supplement 42, 1998, John Wiley and Sons, Inc., especially chapters 5, 6 and 7.

Embodiments of the invention include isolated nucleic acid molecules comprising any of the following nucleotide sequences: 1.) a nucleotide sequence which encodes a protein comprising the amino acid sequence of hsFATP1 (SEQ ID NO:47), the amino acid sequence of hsFATP2 (SEQ ID NO:49), the amino acid sequence of hsFATP3 (SEQ ID NO:102), the amino acid sequence of hsFATP4 (SEQ ID NO: 53), the amino acid sequence of hsFATP5 (SEQ ID NO:55) or the amino acid sequence of hsFATP6 (SEQ ID NO:57); 2.) nucleotide sequences of hsFATP1, hsFATP2, hsFATP3, hsFATP4, hsFATP5, or hsFATP6 (SEQ ID NO:46, 48, 101, 52, 54, or 56, respectively); 3.) a nucleotide sequence which is complementary to the nucleotide sequence of hsFATP1 (SEQ ID NO:46), hsFATP2 (SEQ ID NO:48), hsFATP3 (SEQ ID NO:101), hsFATP4 (SEQ ID NO:52), hsFATP5 (SEQ ID NO:54) or hsFATP6 (SEQ ID NO:56); 4.) a nucleotide sequence which consists of the coding region of hsFATP1 (SEQ ID NO:46), the coding region of hsFATP2 (SEQ ID NO:48), the coding region of hsFATP3 (SEQ ID NO:101), the coding region of hsFATP4 (SEQ ID NO:52), the coding region of hsFATP5 (SEQ ID NO:54), or the coding region of hsFATP6 (SEQ ID NO:56).

The invention further relates to nucleic acids (nucleic acid molecules or polynucleotides) having nucleotide sequences identical over their entire length to those shown in the figures, for instance FIGS. 44A–44D (SEQ ID NO:46), FIGS. 46A and 46B (SEQ ID NO:48), FIG. 48 (SEQ ID NO:50), FIGS. 50A–50C (SEQ ID NO:52), FIGS. 94A–94J (SEQ ID NO:101), and FIGS. 54A–54C (SEQ ID NO:56). It further relates to DNA, which due to the degeneracy of the genetic code, encodes a FATP encoded by one of the FATP-encoding DNAs, whose amino acid sequence is provided herein. Also provided by the invention are nucleic acids having the coding sequences for the mature polypeptides or fragments in reading frame with other coding sequences, such as those encoding a leader or secretory sequence, a pre-, or pro- or prepro-protein sequence. The nucleic acids of the invention encompass nucleic acids that include a single continuous region or discontinuous regions encoding the polypeptide, together with additional regions, that may also contain coding or non-coding sequences. The nucleic acids may also contain non-coding sequences, including, for example, but not limited to, non-coding 5' and 3' sequences, such as the transcribed, non-translated sequences, termination signals, ribosome binding sites, sequences that stabilize mRNA, introns, polyadenylation signals, and additional coding sequences which encode additional amino acids. For example, a marker sequence that facilitates purification of the fused polypeptide can be encoded. In certain embodiments of the invention, the marker sequence can be a hexa-histidine peptide, as provided in the pQE vector (Qiagen, Inc.) and described in Gentz et al., *Proc. Natl. Acad. Sci. USA* 86: 821–824 (1989), or an HA tag (Wilson et al., *Cell* 37: 767 (1984)), or a sequence encoding glutathione S-transferase of *Shistosoma japonicum* (vectors available from Pharmacia; see Smith, D. B. and Johnson K. S., *Gene* 67:31 (1988) and Kaelin, W. G. et al., *Cell* 70:351 (1992)). Nucleic acids of the invention also include, but are not limited to, nucleic acids comprising a structural gene and its naturally associated sequences that control gene expression.

The invention further relates to variants, including naturally-occurring allelic variants, of those nucleic acids described specifically herein by DNA sequence, that encode variants of such polypeptides as those having the amino acid sequences shown in FIG. 45 (SEQ ID NO:47), FIG. 47 (SEQ ID NO:49), FIG. 49 (SEQ ID NO:51), FIG. 51 (SEQ ID NO:53). FIGS. 94A–94J (SEQ ID NO:102), or FIG. 55 (SEQ ID NO:57). Such variants include nucleic acids encoding variants of the above-listed amino acid sequences, wherein those variants have several, such as 5 to 10, 1 to 5, or 3, 2 or 1 amino acids substituted, deleted, or added, in any combination. Variants include polynucleotides encoding polypeptides with at least 95% but less than 100% amino acid sequence identity to the polypeptides described herein by amino acid sequence. Variant polynucleotides hybridize, under low to high stringency conditions, to the alleles described herein by DNA sequence. In one embodiment, variants have silent substitutions, additions and deletions that do not alter the properties and activities of the FATP. Allelic variants of the polynucleotides encoding hsFATP1 (FIG. 45; SEQ ID NO:47), hsFATP2 (FIG. 47; SEQ ID NO:49), hsFATP3 (FIG. 49; SEQ ID NO:51), hsFATP4 (FIG. 51; SEQ ID NO:53), hsFATP5 (FIGS. 94A–94J; SEQ ID NO:102) and hsFATP6 (FIG. 55; SEQ ID NO:57) will be identified as mapping to chromosomal locations listed for the corresponding wild type genes in Table 2 in Example 1.

Orthologous genes are gene loci in different species that are sufficiently similar to each other in their nucleotide sequences to suggest that they originated from a common ancestral gene. Orthologous genes arise when a lineage splits into two species, rather than when a gene is duplicated within a genome. Proteins that are orthologs are encoded by genes of two different species, wherein the genes are said to be orthologous.

The invention further relates to polynucleotides encoding polypeptides which are orthologous to those polypeptides having a specific amino acid sequence described herein, such as the amino acid sequences shown in FIG. 45 (SEQ ID NO:47), FIG. 47 (SEQ ID NO:49), FIG. 49 (SEQ ID NO:51), FIG. 55 (SEQ ID NO:53), FIGS. 94A–94J (SEQ ID NO:102), or FIG. 55 (SEQ ID NO:57). These polynucleotides, which can be called ortholog polynucleotides, encode orthologous polypeptides that can range in amino acid sequence identity to a reference amino acid sequence described herein, from about 65% to less than 100%, but preferably 70% to 80%, more preferably 80% to 90%, and still more preferably 90% to less than 100%. Orthologous polypeptides can also be those polypeptides that range in amino acid sequence similarity to a reference amino acid sequence described herein from about 75% to 100%, within the signature sequence. The amino acid sequence similarity between the signature sequences of orthologous polypeptides is preferably 80%, more preferably 90%, and still more preferably, 95%. The ortholog polynucleotides encode polypeptides that have similar functional characteristics (e.g., fatty acid transport activity) and similar tissue distribution, as appropriate to the organism from which the ortholog polynucleotides can be isolated.

Ortholog polynucleotides can be isolated from (e.g., by cloning or nucleic acid amplification methods) a great number of species, as shown by the sample of FATPs from evolutionarily divergent species described herein (see, e.g., FIGS. 44A–D through FIG. 89). Ortholog polynucleotides corresponding to those in FIG. 45 (SEQ ID NO:47), FIG. 47 (SEQ ID NO:49), FIG. 49 (SEQ ID NO:51), FIG. 51 (SEQ ID NO:53), FIGS. 94A–94J (SEQ ID NO:102) and FIG. 55 (SEQ ID NO:57) are those which can be isolated from mammals such as rat, dog, chimpanzee, monkey, baboon, pig, rabbit and guinea pig, for example.

Further variants that are fragments of the nucleic acids of the invention may be used to synthesize full-length nucleic acids of the invention, such as by use as primers in a polymerase chain reaction. As used herein, the term primer refers to a single-stranded oligonucleotide which acts as a point of initiation of template-directed DNA synthesis under appropriate conditions (e.g., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term primer site refers to the area of the target DNA to which a primer hybridizes. The term primer pair refers to a set of primers including a 5' (upstream) primer that hybridizes with the 5' end of the DNA sequence to be amplified and a 3' (downstream) primer that hybridizes with the complement of the 3' end of the sequence to be amplified.

Further embodiments of the invention are nucleic acids that are at least 80% identical over their entire length to a nucleic acid described herein, for example a nucleic acid having the nucleotide sequence in FIGS. 44A–44D (SEQ ID NO:46), FIGS. 46A–46B (SEQ ID NO:48), FIG. 48 (SEQ ID NO:50), FIGS. 50A–50C (SEQ ID NO:52), FIGS. 94A–94J (SEQ ID NO:101), and FIGS. 54A–54C (SEQ ID NO:56). Additional embodiments are nucleic acids, and the complements of such nucleic acids, having at least 90% nucleotide sequence identity to the above-described sequences, and nucleic acids having at least 95% nucleotide sequence identity. In preferred embodiments, DNA of the present invention has 97% nucleotide sequence identity, 98% nucleotide sequence identity, or at least 99% nucleotide sequence identity with the DNA whose sequences are presented herein.

Other embodiments of the invention are nucleic acids that are at least 80% identical in nucleotide sequence to a nucleic acid encoding a polypeptide having an amino acid sequence as set forth in FIG. 45 (SEQ ID NO:47), FIG. 47 (SEQ ID NO:49), FIG. 49 (SEQ ID NO:51), FIG. 51 (SEQ ID NO:53), FIGS. 94A–94J (SEQ ID NO:102) or FIG. 55 (SEQ ID NO:57), or as such amino acid sequences are set forth elsewhere herein, and nucleic acids that are complementary to such nucleic acids. Specific embodiments are nucleic acids having at least 90% nucleotide sequence identity to a nucleic acid encoding a polypeptide having an amino acid sequence as described in the list above, nucleic acids having at least 95% sequence identity, and nucleic acids having at least 97% sequence identity.

The terms "complementary" or "complementarity" as used herein, refer to the natural binding of polynucleotides under permissive salt and temperature conditions by base-pairing. Complementarity between two single-stranded molecules may be "partial" in which only some of the nucleic acids bind, or it may be complete when total complementarity exists between the single-stranded molecules (that is, when A–T and G–C base pairing is 100% complete). The degree of complementarity between nucleic acid strands has significant effects on the efficiency and strength of hybridization between nucleic acid strands. This is of particular importance in amplification reactions, which depend on binding between nucleic acid strands.

The invention further includes nucleic acids that hybridize to the above-described nucleic acids, especially those nucleic acids that hybridize under stringent hybridization conditions. "Stringent hybridization conditions" or "high stringency conditions" generally occur within a range from about $T_m$ minus 5° C. (5° C. below the strand dissociation temperature or melting temperature ($T_m$) of the probe nucleic acid molecule) to about 20° C. to 25° C. below $T_m$. As will be understood by those of skill in the art, the stringency of hybridization may be altered in order to identify or detect molecules having identical or related polynucleotide sequences. An example of high stringency hybridization follows. Hybridization solution is (6×SSC/10 mM EDTA/0.5% SDS/5× Denhardt's solution/100 µg/ml sheared and denatured salmon sperm DNA). Hybridization is at 64–65° C. for 16 hours. The hybridized blot is washed two times with 2×SSC/0.5% SDS solution at room temperature for 15 minutes each, and two times with 0.2×SSC/0.5% SDS at 65° C., for one hour each. Further examples of high stringency conditions can be found on pages 2.10.1–2.10.16 (see particularly 2.10.8–11) and pages 6.3.1–6 in *Current Protocols in Molecular Biology* (Ausubel, F. M. et al., eds., containing supplements up through Supplement 42, 1998). Examples of high, medium, and low stringency conditions can be found on pages 36 and 37 of WO 98/40404, which are incorporated herein by reference.

The invention further relates to nucleic acids obtainable by screening an appropriate library with a probe having a nucleotide sequence such as that set forth in FIGS. 44A–44D (SEQ ID NO:46), FIGS. 46A–46B (SEQ ID NO:48), FIG. 48 (SEQ ID NO:50), FIGS. 50A–50C (SEQ ID NO:52), FIGS. 94A–94J (SEQ ID NO:101) or FIGS. 54A–54C (SEQ ID NO:56), or a probe which is a sufficiently long fragment of any of the above; and isolating the nucleic acid. Such probes generally can comprise at least 15 nucleotides. Nucleic acids obtainable by such screenings may include RNAs, cDNAs and genomic DNA, for example, encoding FATPs of the FATP family described herein.

Further uses for the nucleic acid molecules of the invention, whether encoding a full-length FATP or whether comprising a contiguous portion of a nucleic acid molecule such as one given in SEQ ID NO:46, 48, 101, 52, 54, or 56, include use as markers for tissues in which the corresponding protein is preferentially expressed (to identify constitutively expressed proteins or proteins produced at a particular stage of tissue differentiation or stage of development of a disease state); as molecular weight markers on southern gels; as chromosome markers or tags (when labeled, for example with biotin, a radioactive label or a fluorescent label) to identify chromosomes or to map related gene positions; to compare with endogenous DNA sequences in a mammal to identify potential genetic disorders; as probes to hybridize and thus identify, related DNA sequences; as a source of information to derive PCR primers for genetic fingerprinting; as a probe to "subtract-out" known sequences in the process of discovering other novel nucleic acid molecules; for selecting and making oligomers for attachment to a "gene chip" or other support, to be used, for example, for examination of expression patterns; to raise anti-protein antibodies using DNA immunization techniques; and as an antigen to raise anti-DNA antibodies or to elicit another immune response.

Further methods to obtain nucleic acids encoding FATPs of the FATP family include PCR and variations thereof (e.g., "RACE" PCR and semi-specific PCR methods). Portions of the nucleic acids having a nucleotide sequence set forth in FIGS. 44A–44D (SEQ ID NO:46), FIGS. 46A–46B (SEQ ID NO:48), FIG. 48 (SEQ ID NO:50), FIGS. 50A–50C (SEQ ID NO:52), FIGS. 94A–94J (SEQ ID NO:101) or FIGS. 54A–54C (SEQ ID NO:56), (especially "flanking sequences" on either side of a coding region) can be used as primers in methods using the polymerase chain reaction, to produce DNA from an appropriate template nucleic acid.

Once a fragment of the FATP gene is generated by PCR, it can be sequenced, and the sequence of the product can be compared to other DNA sequences, for example, by using the BLAST Network Service at the National Center for Biotechnology Information. The boundaries of the open reading frame can then be identified using semi-specific PCR or other suitable methods such as library screening. Once the 5' initiator methionine codon and the 3' stop codon have been identified, a PCR product encoding the full-length gene can be generated using genomic DNA as a template, with primers complementary to the extreme 5' and 3' ends of the gene or to their flanking sequences. The full-length genes can then be cloned into expression vectors for the production of functional proteins.

The invention also relates to isolated proteins or polypeptides such as those encoded by nucleic acids of the present invention. Isolated proteins can be purified from a natural source or can be made recombinantly. Proteins or polypeptides referred to herein as "isolated" are proteins or polypeptides that exist in a state different from the state in which they exist in cells in which they are normally expressed in an organism, and include proteins or polypeptides obtained by methods described herein, similar state in which they exist in cells in which they are normally expressed in an organism, and include proteins or polypeptides obtained by methods described herein, similar methods or other suitable methods, and also include essentially pure proteins or polypeptides, proteins or polypeptides produced by chemical synthesis or by combinations of biological and chemical methods, and recombinant proteins or polypeptides which are isolated. Thus, the term "isolated" as used herein, indicates that the polypeptide in question exists in a physical milieu distinct from that in which it occurs in nature. Thus, "isolated" includes existing in membrane fragments and vesicles membrane fractions, liposomes, lipid bilayers and other artificial membrane systems. An isolated FATP may be substantially isolated with respect to the complex cellular milieu in which it naturally occurs, and may even be purified essentially to homogeneity, for example as determined by PAGE or column chromatography (for example, HPLC), but may also have further cofactors or molecular stabilizers, such as detergents, added to the purified protein to enhance activity. In one embodiment, proteins or polypeptides are isolated to a state at least about 75% pure; more preferably at least about 85% pure, and still more preferably at least about 95% pure, as determined by Coomassie blue staining of proteins on SDS-polyacrylamide gels. Proteins or polypeptides referred to herein as "recombinant" are proteins or polypeptides produced by the expression of recombinant nucleic acids.

In a preferred embodiment, an isolated polypeptide comprising a FATP, a functional portion thereof, or a functional equivalent of the FATP, has at least one function characteristic of a FATP, for example, transport activity, binding function (e.g., a domain which binds to AMP), or antigenic function (e.g., binding of antibodies that also bind to a naturally-occurring FATP, as that function is found in an antigenic determinant). Functional equivalents can have activities that are quantitatively similar to, greater than, or less than, the reference protein. These proteins include, for example, naturally occurring FATPs that can be purified from tissues in which they are produced (including polymorphic or allelic variants), variants (e.g., mutants) of those proteins and/or portions thereof. Such variants include mutants differing by the addition, deletion or substitution of one or more amino acid residues, or modified polypeptides in which one or more residues are modified, and mutants comprising one or more modified residues. Portions or fragments of a FATP can range in size from four amino acid residues to the entire amino acid sequence minus one amino acid.

The isolated proteins of the invention preferably include mammalian fatty acid transport proteins of the FATP family of homologous proteins. In one embodiment, the extent of amino acid sequence similarity between a polypeptide having one of the amino acid sequences shown in FIG. 45 (SEQ ID NO:47), FIG. 47 (SEQ ID NO:49), FIG. 49 (SEQ ID NO:51), FIG. 51 (SEQ ID NO:53), FIGS. 94A–94J (SEQ ID NO:102), or FIG. 55 (SEQ ID NO:57), and the respective functional equivalents of these polypeptides is at least about 88%. In other embodiments, the degree of amino acid sequence similarity between a FATP and its respective functional equivalent is at least about 91%, at least about 94%, or at least about 97%.

The polypeptides of the invention also include those FATPs encoded by polynucleotides which are orthologous to those polynucleotides, the sequences of which are described herein in whole or in part. FATPs which are orthologs to those described herein by amino acid sequence, in whole or in part, are, for example fatty acid transport proteins 1–6 of dog, rat chimpanzee, monkey, rabbit, guinea pig, baboon and pig, and are also embodiments of the invention.

To determine the percent identity or similarity of two amino acid sequences or of two nucleic acid sequences, the sequences are aligned for optimal comparison purposes (e.g., gaps can be introduced in one or both of a first and a second amino acid or nucleic acid sequence for optimal alignment, and non-homologous (dissimilar) sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "similarity"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the polypeptides described herein by amino acid sequence. Similarity for a polypeptide is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent is found in Bowie et al., *Science* 247:1306–1310 (1990).

TABLE 1

| Conservative Amino Acid Substitutions | |
| --- | --- |
| Aromatic | Phenylalanine |
|  | Tryptophan |
|  | Tyrosine |
| Hydrophobic | Leucine |
|  | Isoleucine |
|  | Valine |
| Polar | Glutamine |
|  | Asparagine |
| Basic | Arginine |
|  | Lysine |
|  | Histidine |
| Acidic | Aspartic Acid |
|  | Glutamic Acid |
| Small | Alanine |
|  | Serine |
|  | Threonine |
|  | Methionine |
|  | Glycine |

The comparison of sequences and determination of percent identity and similarity between two sequences can be accomplished using a mathematical algorithm. (*Computational Molecular Biology*, Lesk, A. M.,ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereaux, J., eds., M. Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available on the worldwide web at gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS*, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, word length=12 to obtain nucleotide sequences homologous to (with calculatably significant similarity to) the nucleic acid molecules of the invention. BLAST protein searches can be performed with the XBLAST program, score=50, word length=3 to obtain amino acid sequences homologous to the proteins of the invention. To obtain gapped alignments for comparison purposes, Gapped BLAST can be utilized as described in Altschul et al., (*Nucleic Acids Res*. 25(17):3389–3402 (1997)). When utilizing BLAST and gapped BLAST programs, the default parameters of the respective programs (e.g., XBLAST and NBLAST) can be used. (see the worldwide web at ncbi.nlm.nih.gov).

Similarity for nucleotide and amino acid sequences can be defined in terms of the parameters set by the Advanced Blast search available from NCBI (the National Center for Biotechnology Information. (see, for Advanced BLAST the worldwide web at ncbi.nlm.nih.gov/cgi-bin/BLAST/nph-newblast?Jform=1) These default parameters, recommended for a query molecule of length greater than 85 amino acid residues or nucleotides have been set as follows: gap existence cost, 11, per residue gap cost, 1; lambda ratio, 0.85. Further explanation of version 2.0 of BLAST can be found on related website pages and in Altschul, S. F. et al., *Nucleic Acids Res*. 25:3389–3402 (1997).

The invention further relates to fusion proteins, comprising a FATP or functional portion thereof (as described above) as a first moiety, linked to second moiety not occurring in the FATP as found in nature. Thus, the second moiety can be an amino acid, peptide or polypeptide. The first moiety can be in an N-terminal location, C-terminal location or internal to the fusion protein. In one embodiment, the fusion protein comprises a FATP as the first moiety, and a second moiety comprising a linker sequence and an affinity ligand. Fusion proteins can be produced by a variety of methods. For example, a fusion protein can be produced by the insertion of a FATP gene or portion thereof into a suitable expression vector, such as Bluescript SK+/– (Stratagene), pGEX-4T-2 (Pharmacia), pET-24(+) (Novagen), or vectors of similar construction. The resulting construct can be introduced into a suitable host cell for expression. Upon expression, fusion protein can be purified from cells by means of a suitable affinity matrix (See e.g., *Current Protocols in Molecular Biology*, Ausubel, F. M. et al., eds., Vol. 2, pp. 16.4.1–16.7.8, containing supplements up through Supplement 42, 1998).

The invention also relates to enzymatically produced, synthetically produced, or recombinantly produced portions of a fatty acid transport protein. Portions of a FATP can be made which have full or partial function on their own, or which when mixed together (though fully, partially, or nonfunctional alone), spontaneously assemble with one or more other polypeptides to reconstitute a functional protein having at least one function characteristic of a FATP.

Fragments of a FATP can be produced by direct peptide synthesis, for example those using solid-phase techniques (Roberge, J. Y. et al., *Science* 269:202–204 (1995); Merrifield, J., *J. Am. Chem. Soc.* 85:2149–2154 (1963)). Protein synthesis can be performed using manual techniques or by automation. Automated synthesis can be carried out using, for instance, an Applied Biosystems 431A Peptide Synthesizer (Perkin Elmer). Various fragments of a FATP can be synthesized separately and combined using chemical methods.

One aspect of the invention is a peptide or polypeptide having the amino acid sequence of a portion of a fatty acid transport protein which is hydrophilic rather than hydrophobic, and ordinarily can be detected as facing the outside of the cell membrane. Such a peptide or polypeptide can be thought of as being an extracellular domain of the FATP, or a mimetic of said extracellular domain. It is known, for example, that a portion of human FATP4 that includes a highly conserved motif is involved in AMP-CoA binding function (Stuhlsatz-Krouper, S. M. et al., *J. Biol. Chem.* 44:28642–28650 (1998)).

The term "mimetic" as used herein, refers to a molecule, the structure of which is developed from knowledge of the structure of the FATP of interest, or one or more portions thereof, and, as such, is able to effect some or all of the functions of a FATP.

Portions of an FATP can be prepared by enzymatic cleavage of the isolated protein, or can be made by chemical synthesis methods. Portions of a FATP can also be made by recombinant DNA methods in which restriction fragments, or fragments that may have undergone further enzymatic processing, or synthetically made DNAs are joined together to construct an altered FATP gene. The gene can be made such that it encodes one or more desired portions of a FATP. These portions of FATP can be entirely homologous to a known FATP, or can be altered in amino acid sequence relative to naturally occurring FATPs to enhance or introduce desired properties such as solubility, stability, or affinity to a ligand. A further feature of the gene can be a sequence encoding an N-terminal signal peptide directed to the plasma membrane.

Figure 28A:
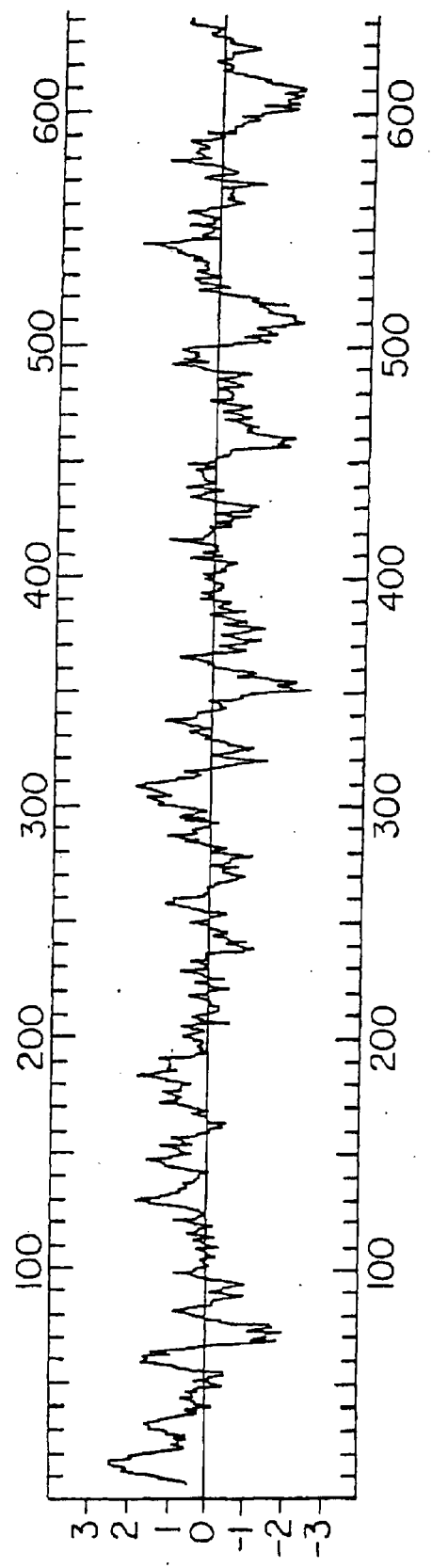
FIG. 28A is a hydrophobicity plot for hsFATP1, showing that it has multiple membrane-spanning domains.
Figure 28C:
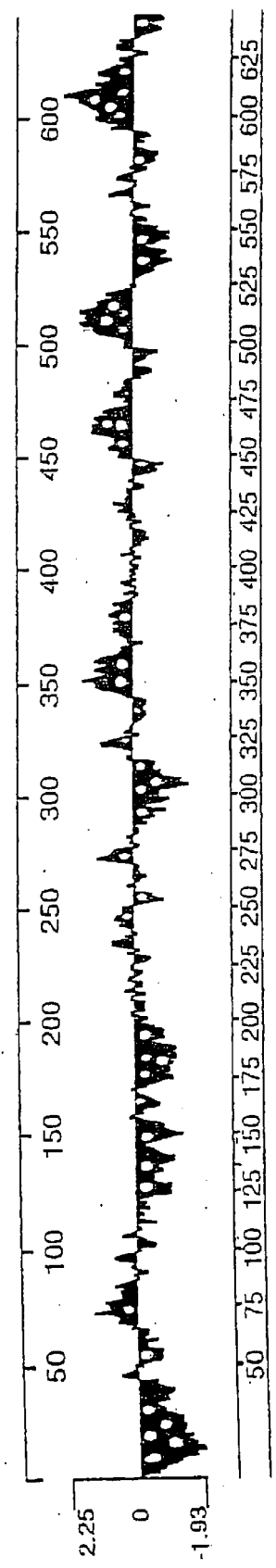
FIG. 28C is a hydrophilicity plot for hsFATP1, made using the Kyte-Doolittle method, averaging hydrophilicity values for 18 amino acid residues at a time.
Figure 29A:
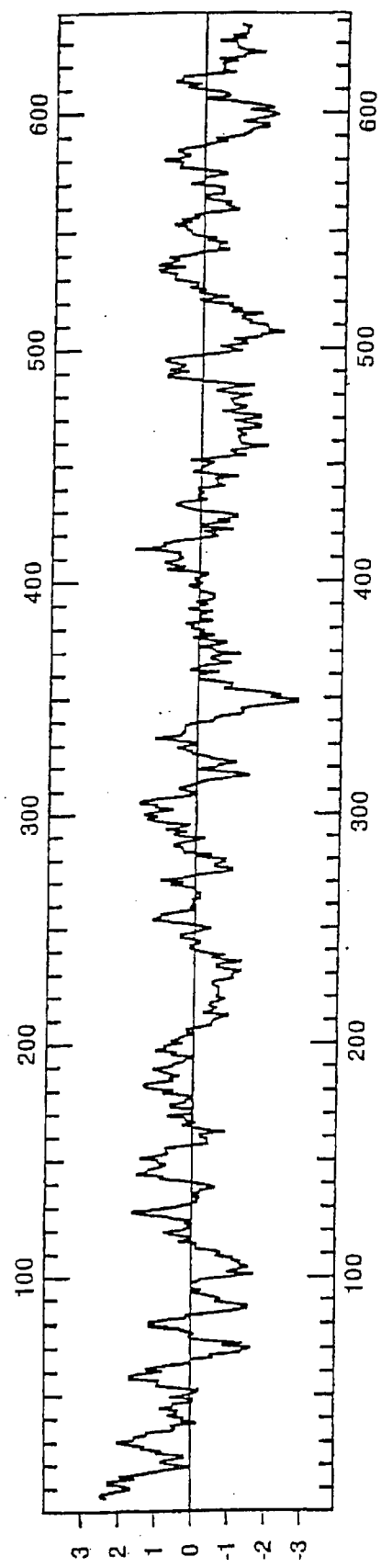
FIG. 29A is a hydrophobicity plot for hsFATP4, showing that it has multiple membrane-spanning domains.
Figure 29C:
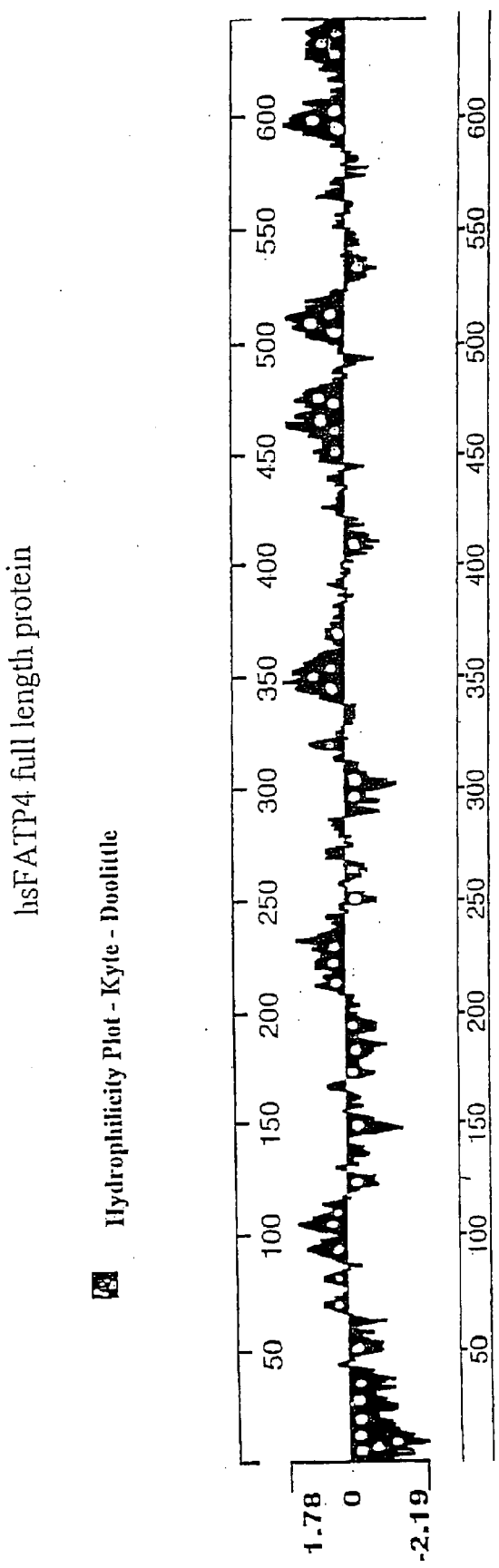
FIG. 29C is a hydrophilicity plot for hsFATP4, made using the Kyte-Doolittle method, averaging hydrophilicity values for 18 amino acid residues at a time.
Figure 35A:
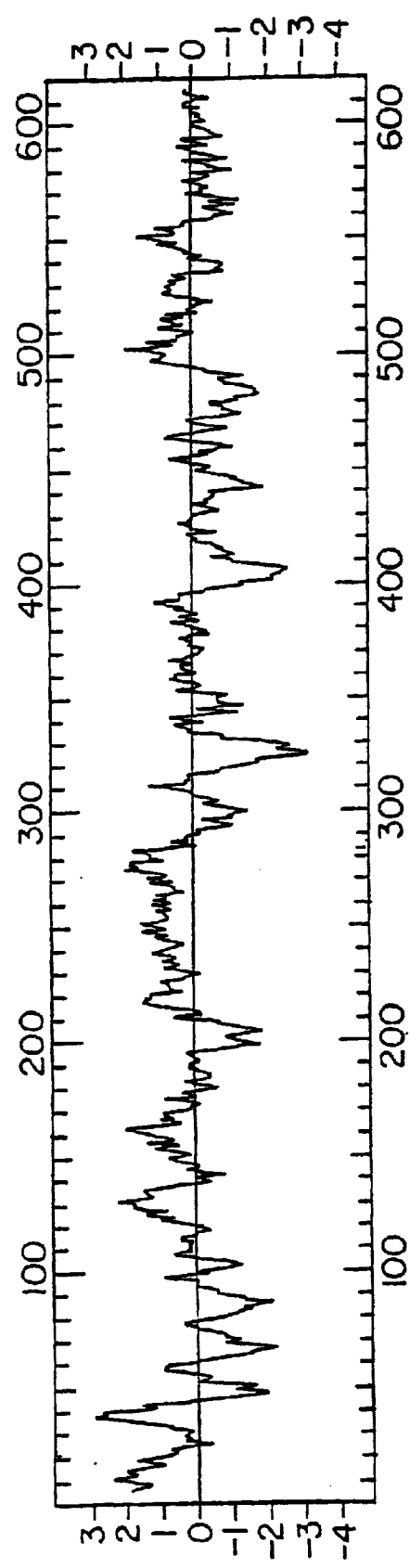
FIG. 35A is a hydrophobicity plot for hsFATP6, showing that it has multiple membrane-spanning domains.
Figure 35C:
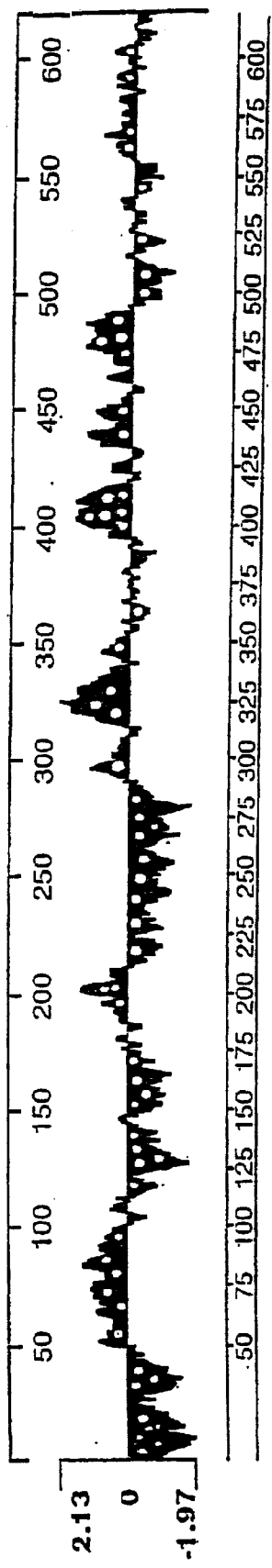
FIG. 35C is a hydrophilicity plot for hsFATP6, made using the Kyte-Doolittle method, averaging hydrophilicity values for 18 amino acid residues at a time.

An extracellular domain can be determined by a hydrophobicity plot, such as those shown in FIGS. 28A, 29A, and 35A, or by a hydrophilicity plot such as those shown in FIGS. 28C, 29C, 35C, 91, 92 and 93. A polypeptide or peptide comprising all or a portion of a FATP extracellular domain can be used in a pharmaceutical composition. When administered to a mammal by an appropriate route, the polypeptide or peptide can bind to fatty acids and compete with the native FATPs in the membrane of cells, thereby making fewer fatty acid molecules available as substrates for transport into cells, and reducing the amount of fatty acids taken up by, for example, the heart, in the case of FATP6.

Another aspect of the invention relates to a method of producing a fatty acid transport protein, variants or portions thereof, and to expression systems and host cells containing a vector appropriate for expression of a fatty acid transport protein.

Cells that express a FATP, a variant or a portion thereof, or an ortholog of a FATP described herein by amino acid sequence, can be made and maintained in culture, under conditions suitable for expression, to produce protein in the cells for cell-based assays, or to produce protein for isolation. These cells can be procaryotic or eucaryotic. Examples of procaryotic cells that can be used for expression include *Escherichia coli, Bacillus subtilis* and other bacteria. Examples of eucaryotic cells that can be used for expression include yeasts such as *Saccharomyces cerevisiae, Schizosaccharomyces pombe, Pichia pastoris* and other lower eucaryotic cells, and cells of higher eucaryotes such as those from insects and mammals, such as primary cells and cell lines such as CHO, HeLa, 3T3 and BHK cells, preferably COS cells and human kidney 293 cells, and more preferably Jurkat cells. (See, e.g., Ausubel, F. M. et al., eds. *Current Protocols in Molecular Biology*, Greene Publishing Associates and John Wiley & Sons, Inc., containing Supplements up through Supplement 42, 1998)).

In one embodiment, host cells that produce a recombinant FATP, or a portion thereof, a variant, or an ortholog of a FATP described herein by amino acid sequence, can be made as follows. A gene encoding a FATP, variant or a portion thereof can be inserted into a nucleic acid vector, e.g., a DNA vector, such as a plasmid, phage, cosmid, phagemid, virus, virus-derived vector (e.g., SV40, vaccinia, adenovirus, fowl pox virus, pseudorabies viruses, retroviruses) or other suitable replicon, which can be present in a single copy or multiple copies, or the gene can be integrated in a host cell chromosome. A suitable replicon or integrated gene can contain all or part of the coding sequence for a FATP or variant, operably linked to one or more expression control regions whereby the coding sequence is under the control of transcription signals and linked to appropriate translation signals to permit translation. The vector can be introduced into cells by a method appropriate to the type of host cells (e.g., transfection, electroporation, infection). For expression from the FATP gene, the host cells can be maintained under appropriate conditions (e.g., in the presence of inducer, normal growth conditions, etc.). Proteins or polypeptides thus produced can be recovered (e.g., from the cells, as in a membrane fraction, from the periplasmic space of bacteria, from culture medium) using suitable techniques. Appropriate membrane targeting signals may be incorporated into the expressed polypeptide. These signals may be endogenous to the polypeptide or they may be heterologous signals.

Polypeptides of the invention can be recovered and purified from cell cultures (or from their primary cell source) by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and high performance liquid chromatography. Known methods for refolding protein can be used to regenerate active conformation if the polypeptide is denatured during isolation or purification.

In a further aspect of the invention are methods for assessing the transport function of any of the fatty acid transport proteins or polypeptides described herein, including orthologs, and in variations of these, methods for identifying an inhibitor (or an enhancer) of such function and methods for assessing the transport function in the presence of a candidate inhibitor or a known inhibitor.

A variety of systems comprising living cells can be used for these methods. Cells to be used in fatty acid transport assays, and further in methods for identifying an inhibitor or enhancer of this function, express one or more FATPs. See Examples 3, 6, 9, 12 and 14 for data on tissue distribution of expression of FATPs, and Examples 10 and 11 describing recombinant cells expressing FATP. Cells for use in cell-based assays described herein can be drawn from a variety of sources, such as isolated primary cells of various organs and tissues wherein one or more FATPs are naturally expressed. In some cases, the cells can be from adult organs, and in some cases, from embryonic or fetal organs, such as heart, lung, liver, intestine, skeletal muscle, kidney and the like. Cells for this purpose can also include cells cultured as fragments of organs or in conditions simulating the cell type and/or tissue organization of organs, in which artificial materials may be used as substrates for cell growth. Other types of cells suitable for this purpose include cells of a cell strain or cell line (ordinarily comprising cells considered to be "transformed") transfected to express one or more FATPs.

A further embodiment of the invention is a method for detecting, in a sample of cells, a fatty acid transport protein, a portion or fragment thereof, a fusion protein comprising a FATP or a portion thereof, or an ortholog as described herein, wherein the cells can be, for instance, cells of a tissue, primary culture cells, or cells of a cell line, including cells into which nucleic acid has been introduced. The method comprises adding to the sample an agent that specifically binds to the protein, and detecting the agent specifically bound to the protein. Appropriate washing steps can be added to reduce nonspecific binding to the agent. The agent can be, for example, an antibody, a ligand or a substrate mimic. The agent can have incorporated into it, or have bound to it, covalently or by high affinity non-covalent interactions, for instance, a label that facilitates detection of the agent to which it is bound, wherein the label can be, but is not limited to, a phosphorescent label, a fluorescent label, a biotin or avidin label, or a radioactive label. The means of detection of a fatty acid transport protein can vary, as appropriate to the agent and label used. For example, for an antibody that binds to the fatty acid transport protein, the means of detection may call for binding a second antibody, which has been conjugated to an enzyme, to the antibody which binds the fatty acid transport protein, and detecting the presence of the second antibody by means of the enzymatic activity of the conjugated enzyme.

Similar principles can also be applied to a cell lysate or a more purified preparation of proteins from cells that may comprise a fatty acid transport protein of interest, for example in the methods of immunoprecipitation, immunoblotting, immunoaffinity methods, that in addition to detection of the particular FATP, can also be used in purification steps, and qualitative and quantitative immunoassays. See, for instance, chapters 11 through 14 in *Antibodies: A Laboratory Manual*, E. Harlow and D. Lane, eds., Cold Spring Harbor Laboratory, 1988.

Isolated fatty acid transport protein or, an antigenically similar portion thereof, especially a portion that is soluble, can be used in a method to select and identify molecules which bind specifically to the FATP. Fusion proteins comprising all of, or a portion of, the fatty acid transport protein linked to a second moiety not occurring in the FATP as found in nature, can be prepared for use in another embodiment of the method. Suitable fusion proteins for this purpose include those in which the second moiety comprises an affinity ligand (e.g., an enzyme, antigen, epitope). FATP fusion proteins can be produced by the insertion of a gene encoding the FATP or a variant thereof, or a suitable portion of such gene into a suitable expression vector, which encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix.

In one embodiment, the fusion protein can be immobilized on a suitable affinity matrix under conditions sufficient to bind the affinity ligand portion of the fusion protein to the matrix, and is contacted with one or more candidate binding agents (e.g., a mixture of peptides) to be tested, under conditions suitable for binding of the binding agents to the FATP portion of the bound fusion protein. Next, the affinity matrix with bound fusion protein can be washed with a suitable wash buffer to remove unbound candidate binding agents and non-specifically bound candidate binding agents. Those agents which remain bound can be released by contacting the affinity matrix with fusion protein bound thereto with a suitable elution buffer. Wash buffer can be formulated to permit binding of the fusion protein to the affinity matrix, without significantly disrupting binding of specifically bound binding agents. In this aspect, elution buffer can be formulated to permit retention of the fusion protein by the affinity matrix, but can be formulated to interfere with binding of the candidate binding agents to the target portion of the fusion protein. For example, a change in the ionic strength or pH of the elution buffer can lead to release of specifically bound agent, or the elution buffer can comprise a release component or components designed to disrupt binding of specifically bound agent to the target portion of the fusion protein.

Immobilization can be performed prior to, simultaneous with, or after, contacting the fusion protein with candidate binding agent, as appropriate. Various permutations of the method are possible, depending upon factors such as the candidate molecules tested, the affinity matrix-ligand pair selected, and elution buffer formulation. For example, after the wash step, fusion protein with binding agent molecules bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with the candidate agent bound thereto. Bound agent molecules can then be released from the fusion protein or its cleavage product by an appropriate method, such as extraction.

One or more candidate binding agents can be tested simultaneously. Where a mixture of candidate binding agents is tested, those found to bind by the foregoing processes can be separated (as appropriate) and identified by suitable methods (e.g., PCR, sequencing, chromatography). Large libraries of candidate binding agents (e.g., peptides, RNA oligonucleotides) produced by combinatorial chemical synthesis or by other methods can be tested (see e.g., Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; see also Rutter, W. J. et al. U.S. Pat. No. 5,010,175; Huebner, V. D. et al., U.S. Pat. No. 5,182,366; and Geysen, H. M., U.S. Pat. No. 4,833,092). Random sequence RNA libraries (see Ellington, A. D. et al., *Nature* 346:818–822 (1990); Bock, L. C. et al., *Nature* 355:584–566 (1992); and Szostak, J. W., *Trends in Biochem. Sci.* 17:89–93 (March, 1992)) can also be screened according to the present method to select RNA molecules which bind to a target FATP or FATP fusion protein. Where binding agents selected from a combinatorial library by the present method carry unique tags, identification of individual biomolecules by chromatographic methods is possible. Where binding agents do not carry tags, chromatographic separation, followed by mass spectrometry to ascertain structure, can be used to identify binding agents selected by the method, for example.

The invention also comprises a method for identifying an agent which inhibits interaction between a fatty acid transport protein (e.g., one comprising the amino acid sequence in SEQ ID NO:47, SEQ ID NO:49, SEQ ID NO:102; SEQ ID NO:53, SEQ ID NO:102, or SEQ ID NO:57), and a ligand of said protein. The FATP can be one described by amino acid sequence herein, a portion or fragment thereof, a variant thereof, or an ortholog thereof, or a FATP fusion protein. Here, a ligand can be, for instance, a substrate, or a substrate mimic, an antibody, or a compound, such as a peptide, that binds with specificity to a site on the protein. The method comprises combining, not limited to a particular order, the fatty acid protein, the ligand of the protein, and a candidate agent to be assessed for its ability to inhibit interaction between the protein and the ligand, under conditions appropriate for interaction between the protein and the ligand (e.g., pH, salt, temperature conditions conducive to appropriate conformation and molecular interactions); determining the extent to which the protein and ligand interact; and comparing (1) the extent of protein-ligand interaction in the presence of candidate agent with (2) the extent of protein-ligand interaction in the absence of candidate agent, wherein if (1) is less than (2), then the candidate agent is one which inhibits interaction between the protein and the ligand.

The method can be facilitated, for example, by using an experimental system which employs a solid support (column chromatography matrix, wall of a plate, microtiter wells, column pore glass, pins to be submerged in a solution, beads, etc.) to which the protein can be attached. Accordingly, in one embodiment, the protein can be fixed to a solid phase directly or indirectly, by a linker. The candidate agent to be tested is added under conditions conducive for interaction and binding to the protein. The ligand is added to the solid phase system under conditions appropriate for binding. Excess ligand is removed, as by a series of washes done under conditions that do not disrupt protein-ligand interactions. Detection of bound ligand can be facilitated by using a ligand that carries a label (e.g., fluorescent, chemiluminescent, radioactive). In a control experiment, protein and ligand are allowed to interact in the absence of any candidate agent, under conditions otherwise identical to those used for the "test" conditions where candidate inhibiting agent is present, and any washes used in the test conditions are also used in the control. The extent to which ligand binds to the protein in the presence of candidate agent is compared to the extent to which ligand binds to the protein in the absence of the candidate agent. If the extent to which interaction of the protein and the ligand occurs is less in the presence of the candidate agent than in the absence of the candidate agent, the candidate agent is an agent which inhibits interaction between the protein and the ligand of the protein.

In a further embodiment, an inhibitor (or an enhancer) of a fatty acid transport protein can be identified. The method comprises steps which are, or are variations of the following: contacting the cells with fatty acid, wherein the fatty acid can be labeled for convenience of detection; contacting a first aliquot of the cells with an agent being tested as an inhibitor (or enhancer) of fatty acid uptake while maintaining a second aliquot of cells under the same conditions but without contact with the agent; and measuring (e.g., quantitating) fatty acid in the first and second aliquots of cells; wherein a lesser quantity of fatty acid in the first aliquot compared to that in the second aliquot is indicative that the agent is an inhibitor of fatty acid uptake by a fatty acid transport protein. A greater quantity of fatty acid in the first aliquot compared to that in the second aliquot is indicative that the agent is an enhancer of fatty acid uptake by a fatty acid transport protein.

A particular embodiment of identifying an inhibitor or enhancer of fatty acid transport function employs the above steps, but also employs additional steps preceding those given above: introducing into cells of a cell strain or cell line ("host cells" for the intended introduction of, or after the introduction of, a vector) a vector comprising a fatty acid transport protein gene, wherein expression of the gene can be regulatable or constitutive, and providing conditions to the host cells under which expression of the gene can occur.

The terms "contacting" and "combining" as used herein in the context of bringing molecules into close proximity to each other, can be accomplished by conventional means. For example, when referring to molecules that are soluble, contacting is achieved by adding the molecules together in a solution. "Contacting" can also be adding an agent to a test system, such as a vessel containing cells in tissue culture.

The term "inhibitor" or "antagonist", as used herein, refers to an agent which blocks, diminishes, inhibits, hinders, limits, decreases, reduces, restricts or interferes with fatty acid transport into the cytoplasm of a cell, or alternatively and additionally, prevents or impedes the cellular effects associated with fatty acid transport. The term "enhancer" or "agonist", as used herein, refers to an agent which augments, enhances, or increases fatty acid transport into the cytoplasm of a cell. An antagonist will decrease fatty acid concentration, fatty acid metabolism and byproduct levels in the cell, leading to phenotypic and molecular changes.

In order to produce a "host cell" type suitable for fatty acid uptake assays and for assays derived therefrom for identifying inhibitors or enhancers thereof, a nucleic acid vector can be constructed to comprise a gene encoding a fatty acid transport protein, for example, human FATP1, FATP2, FATP3, FATP4, FATP5, FATP6, a mutant or variant thereof, an ortholog of the human proteins, such as mouse orthologs or orthologs found in other mammals, or a FATP family protein of origin in an organism other than a mammal. The gene of the vector can be regulatable, such as by the placement of the gene under the control of an inducible or repressible promoter in the vector (e.g., inducible or repressible by a change in growth conditions of the host cell harboring the vector, such as addition of inducer, binding or functional removal of repressor from the cell millieu, or change in temperature) such that expression of the FATP gene can be turned on or initiated by causing a change in growth conditions, thereby causing the protein encoded by the gene to be produced, in host cells comprising the vector, as a plasma membrane protein. Alternatively, the FATP gene can be constitutively expressed.

A vector comprising an FATP gene, such as a vector described herein, can be introduced into host cells by a means appropriate to the vector and to the host cell type. For example, commonly used methods such as electroporation, transfection, for instance, transfection using $CaCl_2$, and transduction (as for a virus or bacteriophage) can be used. Host cells can be, for example, mammalian cells such as primary culture cells or cells of cell lines such as COS cells, 293 cells or Jurkat cells. Host cells can also be, in some cases, cells derived from insects, cells of insect cell lines, bacterial cells, such as E. coli, or yeast cells, such as S. cerevisiae. It is preferred that the fatty acid transport protein whose function is to be assessed, with or without a candidate inhibitor or enhancer, be produced in host cells whose ancestor cells originated in a species related to the species of origin of the FATP gene encoding the fatty acid transport protein. For example, it is preferable that tests of function or of inhibition or enhancement of a mammalian FATP be carried out in host mammalian cells producing the FATP, rather than bacterial cells or yeast cells.

Host cells comprising a vector comprising a regulatable FATP gene can be treated so as to allow expression of the FATP gene and production of the encoded protein (e.g., by contacting the cells with an inducer compound that effects transcription from an inducible promoter operably linked to the FATP gene).

The test agent (e.g., an agonist or antagonist) is added to the cells to be used in a fatty acid transport assay, in the presence or absence of test agent, under conditions suitable for production and/or maintenance of the expressed FATP in a conformation appropriate for association of the FATP with test agent and substrate. For example, conditions under which an agent is assessed, such as media and temperature requirements, can, initially, be similar to those necessary for transport of typical fatty acid substrates across the plasma membrane. One of ordinary skill in the art will know how to vary experimental conditions depending upon the biochemical nature of the test agent. The test agent can be added to the cells in the presence of fatty acid, or in the absence of fatty acid substrate, with the fatty acid substrate being added following the addition of the test agent. The concentration at which the test agent can be evaluated can be varied, as appropriate, to test for an increased effect with increasing concentrations.

Test agents to be assessed for their effects on fatty acid transport can be any chemical (element, molecule, compound), made synthetically, made by recombinant techniques or isolated from a natural source. For example, test agents can be peptides, polypeptides, peptoids, sugars, hormones, or nucleic acid molecules, such as antisense nucleic acid molecules. In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates of cells, bacterial, animal or plant, or can be the cell lysates themselves. Presentation of test compounds to the test system can be in either an isolated form or as mixtures of compounds, especially in initial screening steps.

Thus, the invention relates to a method for identifying agents which alter fatty acid transport, the method comprising providing the test agent to the cell (wherein "cell" includes the plural, and can include cells of a cell strain, cell line or culture of primary cells or organ culture, for example), under conditions suitable for binding to its target, whether to the FATP itself or to another target on or in the cell, wherein the transformed cell comprises a FATP.

In greater detail, to test one or more agents or compounds (e.g., a mixture of compounds can conveniently be screened initially) for inhibition of the transport function of a fatty acid transport protein, the agent(s) can be contacted with the cells.

The cells can be contacted with a labeled fatty acid. The fatty acid can be, for example, a known substrate of the fatty acid transport protein such as oleate or palmitate. The fatty acid can itself be labeled with a radioactive isotope, (e.g., $^3H$ or $^{14}C$) or can have a radioactively labeled adduct attached. In other variations, the fatty acid can have chemically attached to it a fluorescent label, or a substrate for an enzyme occurring within the cells, wherein the substrate yields a detectable product, such as a highly colored or fluorescent product. Addition of candidate inhibitors and labeled substrate to the cells comprising fatty acid transport protein can be in either order or can be simultaneous.

A second aliquot of cells, which can be called "control" cells (a "first" aliquot of cells can be called "test" cells), is treated, if necessary (as in the case of transformed "host" cells), so as to allow expression of the FATP gene, and is contacted with the labeled substrate of the fatty acid transport protein. The second aliquot of cells is not contacted with one or more agents to be tested for inhibition of the transport function of the protein produced in the cells, but is otherwise kept under the same culture conditions as the first aliquot of cells.

In a further step of a method to identify inhibitors of a fatty acid transport protein, the labeled fatty acid is measured in the first and second aliquots of cells. A preliminary step of this measurement process can be to separate the external medium from the cells so as to be able to distinguish the labeled fatty acid external to the cells from that which has been transported inside the cells. This can be accomplished, for instance, by removing the cells from their growth container, centrifuging the cell suspension, removing the supernatant and performing one or more wash steps to extensively dilute the remaining medium which may contain labeled fatty acid. Detection of the labeled fatty acid can be by a means appropriate to the label used. For example, for a radioactive label, detection can be by scintillation counting of appropriately prepared samples of cells (e.g., lysates or protein extracts); for a fluorescent label, by measuring fluorescence in the cells by appropriate instrumentation.

If a compound tested as a candidate inhibitor of transport function causes the test cells to have less labeled fatty acid detected in the cells than that detected in the control cells, then the compound is an inhibitor of the fatty acid transport protein. Procedures analogous to those above can be devised for identifying enhancers (agonists of FATPs) of fatty acid transport function wherein if the test cells contain more labeled fatty acid than that detected in the control cells, or if the fatty acid is taken up at a higher rate, then the compound being tested can be concluded to be an enhancer of the fatty acid transport protein.

Example 13 describes use of an assay of this type to identify an inhibitor of a FATP. In Example 13, an antisense oligonucleotide which specifically inhibits biosynthesis of mmFATP4 was demonstrated to inhibit fatty acid uptake into mouse enterocytes. Similarly, antisense oligonucleotides directed towards specifically inhibiting the biosynthesis of FATP6 in heart cells, FATP5 in liver cells, FATP3 in lung cells, and FATP2 in colon cells, can be demonstrated as examples of "test agents" that inhibit fatty acid transport.

Another assay to determine whether an agent is an inhibitor (or enhancer) of fatty acid transport employs animals, one or more of which are administered the agent, and one or more of which are maintained under similar conditions, but are not administered the agent. Both groups of animals are given fatty acids (e.g., orally, intravenously, by tube inserted into stomach or intestine), and the fatty acids taken up into a bodily fluid (e.g., serum) or into an organ or tissue of interest are measured from comparable samples taken from each group of animals. The fatty acids may carry a label (e.g., radioactive) to facilitate detection and quantitation of fatty acids taken up into the fluid or tissue being sampled. This type of assay can be used alone or can be used in addition to in vitro assays of a candidate inhibitor or enhancer.

An agent determined to be an inhibitor (or enhancer) of FATP function, such as fatty acid binding and/or fatty acid uptake, can be administered to cells in culture, or in vivo, to a mammal (e.g. human) to inhibit (or enhance) FATP function. Such an agent may be one that acts directly on the FATP (for example, by binding) or can act on an intermediate in a biosynthetic pathway to produce FATP, such as transcription of the FATP gene, processing of the mRNA, or translation of the mRNA. An example of such an agent is antisense oligonucleotide.

Antisense methods similar to those illustrated in Example 13 can be used to determine the target FATP of a compound or agent that has an inhibitory or enhancing effect on fatty acid uptake. For example, antisense oligonucleotide directed to the inhibition of FATP4 biosynthesis can be added to lung cells or cell lines derived from lung cells. In addition, antisense oligonucleotides directed to the inhibition of other FATPs, except for FATP3, can also be added to the lung cells. The administration of antisense oligonucleotides in this manner ensures that the predominant FATP activity remaining in the cells comes from FATP3. After a period of incubation of the cells with the antisense oligonucleotides sufficient to deplete the plasma membrane of the FATPs whose biosynthesis has been inhibited, a test agent, preferably one that has been shown by some preliminary test to have an inhibitory or enhancing activity on fatty acid transport, can be added to the lung cells. If the test agent is now demonstrated, after treatment of the cells with antisense oligonucleotides, to have an inhibitory or enhancing activity on fatty acid transport in the lung cells, it can be concluded that the target of the test agent is FATP3, or a molecule involved in the biosynthesis or activity of FATP3.

In another type of cell-based assay for uptake of fatty acids, a change of intracellular pH resulting from the uptake of fatty acids can be followed by an indicator fluorophore. The fluorophore can be taken up by the cells in a preincubation step. Fatty acids can be added to the cell medium, and are some period of incubation to allow FATP-mediated uptake of fatty acids, the change in $\lambda_{max}$ of fluorescence can be measured, as an indicator of a change in intracellular pH, as the $\lambda_{max}$ of fluorescence of the fluorophore changes with the pH of its environment, thereby indicating uptake of fatty acids. One such fluorophore is BCECF (2',7'-bis(2-carboxyethyl)-5(6)-carboxyfluorescein; Rink, T. J. et al., *J. Cell. Biol.* 95: 189 (1982)).

In assays similar to those described above, a candidate inhibitor or enhancer of fatty acid transport function can be added (or mock-added, for control cultures) to cultures of cells engineered to express a desired FATP to which fatty acid substrate is also added. Inhibition of fatty acid uptake is indicated by a lack of the drop in pH, indicating fatty acid uptake, that is seen in control cells. Enhancement of fatty acid uptake is indicated by a decrease in intracellular pH, as compared to control cells not receiving the candidate enhancer of fatty acid transport function.

Yeast cells can be used in a similar cell-based assay for the uptake of fatty acids mediated by a FATP, and such an assay can be adapted to a screening assay for the identification of agents that inhibit or enhance fatty acid uptake by an FATP. Yeast cells lacking an endogenous FATP activity (mutated, disrupted or deleted for FAT1; Faergeman, N. J. et al., *J. Biol. Chem.* 272(13):8531–8538 (1997); Watkins, P. A. et al., *J. Biol. Chem.* 273(29):18210–18219 (1998)) can be engineered to harbor a related gene of the family of FATP-encoding genes, such as a mammalian FATP (e.g., human FATP4).

Examples of expression vectors include pEG (Mitchell, D. A., et al., *Yeast* 9:715–723 (1993)) and pDAD1 and pDAD2, which contain a GAL1 promoter (Davis, L. I. and Fink, G. R., *Cell* 61:965–978 (1990)). A variety of promoters are suitable for expression. Available yeast vectors offer a choice of promoters. In one embodiment, the inducible GAL1 promoter is used. In another embodiment, the constitutive ADH1 promoter (alcohol dehyrodrogenase; Bennetzen, J. L. and Hall, B. D., *J. Biol. Chem.* 257:3026–3031 (1982)) can be used to express an inserted gene on glucose-containing media. An example of a vector suitable for expression of a heterologous FATP gene in yeast is pQB169.

With the introduced FATP gene providing the only fatty acid transport protein function for the yeast cells, it is possible to study effect of the heterologous FATP on fatty acid transport into the yeast cells in isolation. Assays for the uptake of fatty acids into the yeast cells can be devised that are similar to those described above and/or those assays that have been illustrated in the Examples. Tests for candidate inhibitors or enhancers of the heterologous FATP can be done in cultures of yeast cells, wherein the yeast cells are incubated with fatty acid substrate and an agent to be tested as an inhibitor or enhancer of FATP function. FATP uptake after a period of time can be measured by analyzing the contents of the yeast cells for fatty acid substrate, as compared with control yeast cells incubated with the fatty acid, but not with the test agent. Yeast cells have the additional advantage, over mammalian cells in culture, for example, that yeast cells can be forced to rely upon fatty acids as their only source of carbon, if the growth medium supplied to the yeast cells is formulated to contain no other source of carbon. Thus, the effect of the heterologous FATP on fatty acid uptake and metabolism in the engineered yeast cells can be amplified. An agent that efficiently blocks transport function of the heterologous FATP could result in death of the yeast cells. Thus, in this case, inhibition of function of the heterologous FATP can result in loss of viability. A simple measure of viability is turbidity of the yeast suspension culture, which can be adapted to a high throughput screening assay for effects of various agents to be tested, using microtiter plates or similar devices for small-volume cultures of the engineered yeast cells.

Cell-free assays can also be used to measure the transport of fatty acids across a membrane, and therefor also to assess a test treatment or test agent for its effect on the rate or extent of fatty acid transport. An isolated FATP, for example in the presence of a detergent that preserves the native 3-dimensional structure of the FATP, or partially purified FATP, can be used in an artificial membrane system typically used to preserve the native conformation and activity of membrane proteins. Such systems include liposomes, artificial bilayers of phospholipids, isolated plasma membrane such as cell membrane fragments, cell membrane fractions, or cell membrane vesicles, and other systems in which the FATP can be properly oriented within the membrane to have transport activity. Assays for transport activity can be performed using methods analogous to those that can be used in cells engineered to predominantly express one FATP whose function is to be measured. A labeled (e.g., radioactively labeled) fatty acid substrate can be incubated with one side of a bilayer or in a suspension of liposomes constructed to integrate a properly oriented FATP. The accumulation of fatty acids with time can be measured, using appropriate means to detect the label (e.g., scintillation counting of medium on each side of the bilayer, or of the contents of liposomes isolated from the surrounding medium). Assays such as these can be adapted to use for the testing of agents which might interact with the FATP to produce an inhibitory or an enhancing effect on the rate or extent of fatty acid transport. That is, the above-described assay can be done in the presence or absence of the agent to be tested, and the results compared.

For examples of isolation of membrane proteins (ADP/ATP carrier and uncoupling protein), reconstitution into phospholipid vesicles, and assays of transport, see Klingenberg, M. et al., *Methods Enzymol.* 260:369–389 (1995). For an example of a membrane protein (phosphate carrier of *Saccharomyces cerevisiae*) that was purified and solubilized from *E. coli* inclusion bodies, see Schroer, A. et al., *J. Biol. Chem.* 273: 14269–14276 (1998). The Glut1 glucose transporter of rat has been expressed in yeast. A crude membrane fraction of the yeast was prepared and reconstituted with soybean phospholipids into liposomes. Glucose transport activity could be measured in the liposomes (Kasahara, T. and Kasahara, M., *J. Biol. Chem.* 273: 29113–29117 (1998)). Similar methods can be applied to the proteins and polypeptides of the invention.

Another embodiment of the invention is a method for inhibiting fatty acid uptake in a mammal (e.g., a human), comprising administering to the mammal a therapeutically effective amount of an inhibitor of the transport function of one or more of the fatty acid transport proteins, thereby decreasing fatty acid uptake by cells comprising the fatty acid protein(s). Where it is desirable to reduce the uptake of fatty acids, for example, in the treatment of chronic obesity or as a part of a program of weight control or hyperlipidemia control in a human, one or more inhibitors of one or more of the fatty acid transport proteins can be administered in an effective dose, and by an effective route, for example, orally, or by an indwelling device that can deliver doses to the small intestine. The inhibitor can be one identified by methods described herein, or can be one that is, for instance, structurally related to an inhibitor identified by methods described herein (e.g., having chemical adducts to better stabilize or solubilize the inhibitor). The invention further relates to compositions comprising inhibitors of fatty acid uptake in a mammal, which may further comprise pharmaceutical carriers suitable for administration to a subject mammal, such as sterile solubilizing or emulsifying agents.

A further embodiment of the present invention is a method of enhancing or increasing fatty acid uptake, such as enhancing or increasing LCFA uptake in the small intestine (e.g., to treat or prevent a malabsorption syndrome or other wasting condition) or in the liver (e.g., by an enhancer of FATP5 transport activity to treat acute liver failure) or in the kidney (e.g., by an enhancer of FATP2 transport activity to treat kidney failure). In this embodiment, a therapeutically effective amount of an enhancer of the transport function of one or more of the fatty acid transport proteins can be administered to a mammalian subject, with the result that fatty acid uptake in the small intestine is enhanced. In this embodiment, one or more enhancers of one or more of fatty acid transport proteins is administered in an effective dose and by a route (e.g., orally or by a device, such as an indwelling catheter or other device) which can deliver doses to the gut. The enhancer of FATP function (e.g., an enhancer of FATP4 function) can be identified by methods described herein or can be one that is structurally similar to an enhancer identified by methods described herein.

Aerobic reperfusion of ischemic myocardium is a common clinical event which can occur during such treatments as cardiac surgery, angioplasty, and thrombolytic therapy after a myocardial infarction. During reperfusion, a rapid recovery of myocardial energy production is essential for the complete recovery of contractile function. Not only the extent of recovery of myocardial energy metabolism but also the type of energy substrate used by the heart during reperfusion are important determinants of functional recovery. Circulating fatty acid levels increase following acute myocardial infarction or during cardiac surgery, such that during and following ischemia the heart muscle can be exposed to very high concentrations of fatty acids (Lopaschuk, G. D. and W. C. Stanley, *Science and Medicine* (November/December 1997)). High plasma fatty acid concentrations increase the severity of ischemic damage in a number of experimental models of cardiac ischemia and have been linked to depression of mechanical function during aerobic reperfusion of previously ischemic hearts. Further data show that modifying fatty acid utilization can be beneficial for heart function in ischemia and can be a useful approach for the treatment of angina. See, e.g., Desideri and Celegon, *Am. J. Cardiol.* 82(5A):50K–53K; Lopaschuk, *Am. J. Cardiol.* 82(5A):14K–17K. Plasma fatty acid concentrations can be reduced by administering to a human subject or other mammal an effective amount of an inhibitor of a FATP such as FATP2 or FATP4, thereby providing a way of reducing fatty acid utilization by the heart.

In a further embodiment of the invention, a therapeutically effective amount of an inhibitor of hsFATP6 can be administered to a human patient by a suitable route, to reduce the uptake of fatty acids by cardiac muscle. This treatment is desirable in patients who are diagnosed as having, or who are at risk of, abnormal accumulations of fatty acids in the heart or a detrimentally high rate of uptake of fatty acids into the heart, because of ischemic heart disease, or following ischemia or trauma to the heart.

The invention further relates to antibodies that bind to an isolated or recombinant fatty acid transport protein of the FATP family, including portions of antibodies, which can specifically recognize and bind to one or more FATPs. The antibodies and portions thereof of the invention include those which bind to one or more FATPs of mouse or other mammalian species. In a preferred embodiment, the antibodies specifically bind to a naturally occurring FATP of humans. The antibodies can be used in methods to detect or to purify a protein of the present invention or a portion thereof by various methods of immunoaffinity chromatography, to inhibit the function of a protein in a method of therapy, or to selectively inactivate an active site, or to study other aspects of the structure of these proteins, for example.

The antibodies of the present invention can be polyclonal or monoclonal. The term antibody is intended to encompass both polyclonal and monoclonal antibodies. Antibodies of the present invention can be raised against an appropriate immunogen, including proteins or polypeptides of the present invention, such as an isolated or recombinant FATP1, FATP2, FATP3, FATP4, FATP5, FATP6, mtFATP, ceFATPa, ceFATPb, scFATP or portions thereof, or synthetic molecules, such as synthetic peptides (e.g., conjugated to a suitable carrier). Preferred embodiments are antibodies that bind to any of the following: hsFATP1, hsFATP2, hsFATP3, hsFATP4, hsFATP5 or hsFATP6. The immunogen can be a polypeptide comprising a portion of a FATP and having at least one function of a fatty acid transport protein, as described herein.

The term antibody is also intended to encompass single chain antibodies, chimeric, humanized or primatized (CDR-grafted) antibodies and the like, as well as chimeric or CDR-grafted single chain antibodies, comprising portions from more than one species. For example, the chimeric antibodies can comprise portions of proteins derived from two different species, joined together chemically by conventional techniques or prepared as a single contiguous protein using genetic engineering techniques (e.g., DNA encoding the protein portions of the chimeric antibody can be expressed to produce a contiguous protein chain. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., U.S. Pat. No. 5,585,089; and Queen et al., European Patent No. EP 0 451 216 B1. See also, Newman, R. et al., *BioTechnology*, 10:1455–1460 (1992), regarding primatized antibody, and Ladner et al., U.S. Pat. No. 4,946,778 and Bird, R. E. et al., *Science*, 242:423–426 (1988) regarding single chain antibodies.)

Whole antibodies and biologically functional fragments thereof are also encompassed by the term antibody. Biologically functional antibody fragments which can be used include those fragments sufficient for binding of the antibody fragment to a FATP to occur, such as Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Preparation of immunizing antigen (whole cells comprising FATP on the cell surface or purified FATP), and polyclonal and monoclonal antibody production can be performed using any suitable technique. A variety of methods have been described (See e.g., Kohleretal., *Nature*, 256: 495–497(1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); Chapter 11 In *Current Protocols In Molecular Biology*, Vol. 2 (containing supplements up through Supplement 42, 1998), Ausubel, F. M. et al., eds., (John Wiley & Sons: New York, N.Y.)). Generally, a hybridoma can be produced by fusing a suitable immortal cell line (e.g., a myeloma cell line such as SP2/0) with antibody producing cells. The antibody producing cells, preferably those obtained from the spleen or lymph nodes, can be obtained from animals immunized with the antigen of interest. Immunization of animals can be by introduction of whole cells comprising fatty acid transport protein on the cell surface. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies (including human antibodies) of the requisite specificity can used, including, for example, methods which select recombinant antibody from a library (e.g., Hoogenboom et al., WO 93/06213; Hoogenboom et al., U.S. Pat. No. 5,565,332; WO 94/13804, published Jun. 23, 1994; and Dower, W. J. et al., U.S. Pat. No. 5,427,908), or which rely upon immunization of transgenic animals (e.g., mice) capable of producing a full repertoire of human antibodies (see e.g., Jakobovits et al., *Proc. Natl. Acad. Sci. USA*, 90: 2551–2555 (1993); Jakobovits et al., *Nature*, 362:255–258 (1993); Lonberg et al., U.S. Pat. No. 5,569,825; Lonberg et al., U.S. Pat. No. 5,545,806; Surani et al., U.S. Pat. No. 5,545,807; and Kucherlapati, R. et al., European Pat. No. EP 0 463 151 B1).

Another aspect of the invention is a method for directing an agent to cardiac muscle. The differential expression of FATP6 in cardiac muscle but not in other tissue types allows for the specific targeting of drugs, diagnostic agents, tagging labels, histological stains or other substances specifically to cardiac muscle. A targeting vehicle can be used for the delivery of such a substance. Targeting vehicles which bind specifically to FATP6 can be linked to a substance to be delivered to the cells of cardiac muscle. The linkage can be, for instance, via one or more covalent bonds, or by high affinity non-covalent bonds. A targeting vehicle can be an antibody, for instance, or other compound (e.g., a fatty acid or fatty acid analog) which binds to FATP6 with high specificity.

Targeting vehicles specific to the heart-specific protein FATP6 have in vivo (e.g., therapeutic and diagnostic) applications. For example, an antibody which specifically binds to FATP6 can be conjugated to a drug to be targeted to the heart (e.g., a cardiac glycoside to treat congestive heart failure, or β-adrenergic agents, sodium channel blockers or calcium channel blockers to treat arrhythmias). A substance (e.g., a radioactive substance) which can be detected (e.g., a label) in vivo can also be linked to a targeting vehicle which specifically binds to a heart-specific protein such as FATP6, and the conjugate can be used as a labeling agent to identify cardiac muscle cells.

Targeting vehicles specific to FATP6 find further applications in vitro. For example, an FATP6-specific targeting vehicle, such as an antibody (a polyclonal preparation or monoclonal) which specifically binds to FATP6, can be linked to a substance which can be used as a stain for a tissue sample (e.g., horseradish peroxidase) to provide a method for the identification of cardiac muscle in a sample, as can be used in embryology studies, for example.

In a similar manner, an agent can be directed to the liver of a mammal, as FATP5 is expressed in liver but not in other tissue types. A targeting vehicle which specifically binds to FATP5 can be conjugated to a drug for delivery of the drug to the liver, such as a drug to treat hepatitis, Wilson's disease, lipid storage diseases and liver cancer. As with targeting vehicles specific to FATP6, targeting vehicles specific to FATP5 can be used in studying tissue samples in vitro.

The invention also relates to compositions comprising a modulator of FATP function. The term "modulate" as used herein refers to the ability of a molecule to alter the function of another molecule. Thus, modulate could mean, for example, inhibit, antagonize, agonize, upregulate, downregulate, induce, or suppress. A modulator has the capability of altering function of its target. Such alteration can be accomplished at any stage of the transcription, translation, expression or function of the protein, so that, for example, modulation of a target gene can be accomplished by modulation of the DNA or RNA encoding the protein, and the protein itself.

Antagonists or agonists (inhibitors or enhancers) of the FATPs of the invention, antibodies that bind a FATP, or mimetics of a FATP can be employed in combination with a non-sterile or sterile carrier or carriers for use with cells, tissues or organisms, such as a pharmaceutical carrier suitable for administration to a mammalian subject. Such compositions comprise, for instance, a media additive or a therapeutically effective amount of an inhibitor or enhancer compound to be identified by an assay of the invention and a pharmaceutically acceptable carrier or excipient. Such carriers may include, but are not limited to, saline, buffered saline, dextrose, water, ethanol, surfactants, such as glycerol, excipients such as lactose and combinations thereof. The formulation can be chosen by one of ordinary skill in the art to suit the mode of administration. The chosen route of administration will be influenced by the predominant tissue or organ location of the FATP whose function is to be inhibited or enhanced. For example, for affecting the function of FATP4, a preferred administration can be oral or through a tube inserted into the stomach (e.g., direct stomach tube or nasopharyngeal tube), or through other means to accomplish delivery to the small intestine. The invention further relates to diagnostic and pharmaceutical packs and kits comprising one or more containers filled with one or more of the ingredients of the aforementioned compositions of the invention.

Compounds of the invention which are FATPs, FATP fusion proteins, FATP mimetics, FATP gene-specific antisense poly- or oligonucleotides, inhibitors or enhancers of a FATP may be employed alone or in conjunction with other compounds, such as therapeutic compounds. The pharmaceutical compositions may be administered in any effective, convenient manner, including administration by topical, oral, anal, vaginal, intravenous, intraperitoneal, intramuscular, subcutaneous, intranasal, transdermal or intradermal routes, among others. In therapy or as a prophylactic, the active agent may be administered to an individual as an injectable composition, for example as a sterile aqueous dispersion, preferably isotonic.

Alternatively, the composition may be formulated for topical application, for example, in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions.

In addition, the amount of the compound will vary depending on the size, age, body weight, general health, sex, and diet of the host, and the time of administration, the biological half-life of the compound, and the particular characteristics and symptoms of the disorder to be treated. Adjustment and manipulation of established dose ranges are well within the ability of those of skill in the art.

A further aspect of the invention is a method to identify a polymorphism, or the presence of an alternative or variant allele of a gene in the genome of an organism (of interest here, genes encoding FATPs). As used herein, polymorphism refers to the occurrence of two or more genetically determined alternative sequences or alleles in a population. A polymorphic locus may be as small as a base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified alleleic form, or the most frequently occurring form can be arbitrarily designated as the reference (usually, "wildtype") form, and other allelic forms are designated as alternative (sometimes, "mutant" or "variant"). Dipoid organisms may be homozygous or heterozygous for allelic forms.

An "allele" or "allelic sequence" is an alternative form of a gene which may result from at least one mutation in the nucleotide sequence. Alleles may result in altered mRNAs or polypeptides whose structure or function may or may not be altered. Any given gene may have none, one, or many alielic forms (polymorphism). Common mutational changes which give rise to alleles are generally ascribed to natural deletions, additions, or substitutions of nucleotides. Each of these types of changes may occur alone, or in combination with the others, one or more times in a given sequence.

Several different types of polymorphisms have been reported. A restriction fragment length polymorphism (RFLP) is a variation in DNA sequence that alters the length of a restriction fragment (Botstein et al., *Am. J. Hum. Genet.* 32:314–331(1980)). The restriction fragment length polymorphism may create or delete a restriction site, thus changing the length of the restriction fragment. RFLPs have been widely used in human and animal genetic analyses (see WO 90/13668; WO 90/11369; Donis-Keller, *Cell* 51:319–337 (1987); Lander et al., *Genetics* 121:85–99 (1989)). When a heritable trait can be linked to a particular RFLP, the presence of the RFLP in an individual can be used to predict the likelihood that the individual will also exhibit the trait.

Other polymorphisms take the form of short tandem repeats (STRs) that include tandem di-, tri- and tetra-nucleotide repeated motifs. These tandem repeats are also referred to as variable number tandem repeat (VNTR) polymorphisms. VNTRs have been used in identity and paternity analysis (U.S. Pat. No. 5,075,217; Armour et al., *FEBS Lett.* 307:113–115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPs, STRs (short tandem repeats) and VNTRs (variable number tandem repeats). Some single nucleotide polymorphisms occur in protein-coding sequences, in which case, one of the polymorphic forms may give rise to the expression of a defective or other variant protein and, potentially, a genetic disease. Other single nucleotide polymorphisms occur in noncoding regions. Some of these polymorphisms may also result in defective protein expression (e.g., as a result of defective splicing). Other single nucleotide polymorphisms have no phenotypic effects.

Many of the methods described below require amplification of DNA from target samples and purification of the amplified products. This can be accomplished by PCR, for instance. See generally, *PCR Technology, Principles and Applications for DNA Amplification* (ed. H. A. Erlich), Freeman Press, New York, N.Y., 1992; *PCR Protocols: A Guide to Methods and Applications* (eds. Innis, et al.), Academic Press, San Diego, Calif., 1990; Mattila et al., *Nucleic Acids Res.* 19:4967 (1991); Eckert et al., *PCR Methods and Applications* 1:17 (1991); PCR (eds. McPherson et al., IRS Press, Oxford); and U.S. Pat. No. 4,683,202.

Other suitable amplification methods include the ligase chain reaction (LCR) (see Wu and Wallace, *Genomics* 4:560 (1989); Landegren et al., *Science* 241:1077 (1988)), transcription amplification (Kwoh et al., *Proc. Natl. Acad. Sci. USA* 86:1173 (1989), self-sustained sequence replication (Guatelli et al., *Proc. Natl. Acad. Sci. USA* 87:1874 (1990), and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Another aspect of the invention is a method for detecting a variant allele of a human FATP gene, comprising preparing amplified, purified FATP DNA from a reference human and amplified, purified, FATP DNA from a "test" human to be compared to the reference as having a variant allele, using the same or comparable amplification procedures, and determining whether the reference DNA and test DNA differ in DNA sequence in the FATP gene, whether in a coding or a noncoding region, wherein, if the test DNA differs in sequence from the reference DNA, the test DNA comprises a variant allele of a human FATP gene. The following is a discussion of some of the methods by which it can be determined whether the reference FATP DNA and test FATP DNA differ in sequence.

Direct Sequencing. The direct analysis of the sequence of variant alleles of the present invention can be accomplished using either the dideoxy chain termination method or the Maxam and Gilbert method (see Sambrook et al., *Molecular Cloning: A Laboratory Manual*, 2nd ed., Cold Spring Harbor Press, New York 1989; Zyskind et al., *Recombinant DNA Laboratory Manual*, Acad. Press, 1988)).

Denaturing Gradient Gel Electrophoresis. Amplification products generated using the polymerase chain reaction can be analyzed by the use of denaturing gradient gel eletrophoresis. Different alleles can be identified based on the different sequence-dependent strand dissociation properties and electrophoretic migration of DNA in solution (chapter 7 in Erlich, ed. *PCR Technology, Principles and Applications for DNA Amplification*, W. H. Freeman and Co., New York, 1992).

Single-strand Conformation Polymorphism Analysis. Alleles of target sequences can be differentiated using single-strand conformation polymorphism analysis, which identifies base differences by alteration in electrophoretic migration of single stranded PCR products, as described in Orita et al., *Proc. Natl. Acad. Sci. USA* 86:2766–2770 (1989). Amplified PCR products can be generated as described above, and heated or otherwise denatured, to form single-stranded amplification products. Single-stranded nucleic acids may refold or form secondary structures which are partially dependent on the base sequence. The different electrophoretic mobilities of single-stranded amplification products can be related to base-sequence differences between alleles of target sequences.

Detection of Binding by Protein That Binds to Mismatches. Amplified DNA comprising the FATP gene or portion of the gene of interest from genomic DNA, for example, of a normal individual is prepared, using primers designed on the basis of the DNA sequences provided herein. Amplified DNA is also prepared, in a similar manner, from genomic DNA of an individual to be tested for bearing a distinguishable allele. The primers used in PCR carry different labels, for example, primer 1 with biotin, and primer 2 with $^{32}$P, Unused primers are separated form the PCR products, and the products are quantitated. The heteroduplexes are used in a mismatch detection assay using immobilized mismatch binding protein (MutS) bound to nitrocellulose. The presence of biotin-labeled DNA wherein mismatched regions are bound to the nitrocellulose via MutS protein, is detected by visualizing the binding of streptavidin to biotin. See WO 95/12689. MutS protein has also been used in the detection of point mutations in a gel-mobility-shift assay (Lishanski, A. et al., *Proc. Natl. Acad. Sci. USA* 91:2674–2678 (1994)).

Other methods, such as those described below, can be used to distinguish a FATP allele from a reference allele, once a particular allele has been characterized as to DNA sequence.

Allele-specific probes. The design and use of allele-specific probes for analyzing polymorphims is described by e.g., Saiki et al., *Nature* 324:163–166 (1986); Dattagupta, EP 235,726, Saiki, WO 89/11548. Allele-specific probes can be designed so that they hybridize to a segment of a target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

Allele-specific Primers. An allele-specific primer hybridizes to a site on target DNA overlapping a polymorphism, and only primes amplification of an allelic form to which the primer exhibits perfect complementarity. See Gibbs, *Nucleic Acid Res.* 17:2427–2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

Gene Chips. Allelic variants can also be identified by hybridization to nucleic acids immobilized on solid supports (gene chips), as described, for example, in WO 95/11995 and U.S. Pat. No. 5,143,854, both of which are incorporated herein by reference. WO 95/11995 describes subarrays that are optimized for detection of a characterized variant allele. Such a subarray contains probes designed to be complementary to a second reference sequence, which is an allelic variant of the first reference sequence.

The present method is illustrated by the following examples, which are not intended to be limiting in any way.

EXAMPLES

Materials and Methods

The following Materials and Methods were used in the work described in Examples 1–5.

Sequence Alignment of FATP Clones. The DNA sequence for mouse FATP1 was obtained from the National Center for Biotechnology Information nonredundant database. cDNAs for mmFATP2, 3, 4, and 5 were obtained by screening mouse expression libraries (purchased from GIBCO/BRL) with probes derived from the cloned expressed sequence tags (ESTS) (Research Genetics, Huntsville, Ala.). Full-length clones were obtained for mmFATP2 and 5 and partial sequences for mmFATP3 and 4. The sequences described herein have been deposited in the GenBank database (Accession Nos. FATP2, AF072760; FATP3, AF072759; FATP4, AF072758; FATP5, AF072757).

Neither FATP2 nor FATP5 contains an in-frame stop codon upstream of the putative initiator methionine; initiator methionines were assigned by homology with that in mmFATP1 and by the presence of a signal sequence immediately after it. The *Mycobacterium tuberculosis*, *Caenorhabditis elegans*, and *Saccharomyces cerevisiae* sequences were present in the dbEST database as part of the sequencing projects for these organisms. Sequences were aligned utilizing a ClustalX algorithm and the resulting alignment exported to ScqVu. Homologous amino acid substitutions are boxed in FIG. 1 and were determined using the Dayhoff 250 method with a 50% homology cutoff.

Cell Transfection and LCFA Uptake. COS cells were cotransfected using the DEAE-dextran method with the mammalian expression vector pCDNA 3.1 (Invitrogen) expressing the gene for CD2 (pCDNA-CD2) in combination with either a pCDNA 3.1 or pCMVSPORT2 (GIBCO/BRL) expression vector containing one of the murine or nematode FATP genes (pCDNA-mmFATP1, pCDNA-FATP2, pCMVSPORT-FATP5, pCDNA-ceFATPb). Two days after transfection, cells were assayed for CD2 expression with a phycoerythrin-coupled anti-CD2(PE-CD2) monoclonal antibody (PharMingen), and fatty acid uptake was assayed with a BODIPY-labeled fatty acid analogue (Molecular Probes). Briefly, cells were washed twice with PBS (phosphate buffered saline) and stained with PE-CD2 at 4° C. for 30 min in PBS containing 10% fetal calf serum. They were then washed three times with PBS/fetal calf serum for 5 min followed by an incubation for 2 min at 37° C. in fatty acid uptake solution, which contained 0.1 µM BODIPY-FA and 0.1% fatty acid-free BSA (bovine serum albumin) in PBS (Schaffer, J. E. & Lodish, H. F. (1994) *Cell* 79:427–436). After 2 min, the cells were washed four times with ice-cold PBS/0.1% BSA. The cells were then removed from the plates with PBS containing 5 mM EDTA and resuspended in PBS containing 10% fetal calf serum and 10 mM EDTA. PE-CD2 and BODIPY-FA fluorescence were measured using a FACScan (Becton Dickinson). COS cells were gated on forward scatter (FSC) and side scatter (SS). Cells exhibiting more than 300 CD2 fluorescence units (dsim) representing 15% of all cells were deemed CD2 positive and their BODIPY-FA fluorescence was quantitated.

*E. coli*-Based LCFA Uptake Assay. The full-length coding region of mtFATP and a control protein, the mammalian transcription factor TFE3, were subcloned into the inducible, prokaryotic expression vector pET (Novagen). Expression was induced with 1 mM isopropyl β-D-thiogalactoside (IPTG) for 1 hour, or cells were left uninduced. Cells were washed in PBS/0.1% BSA and resuspended in 1 ml PBS/0.1% BSA containing 0.1 µM [$^3$H] palmitate (NEN) at 37° C. Uptake was stopped after the indicated incubation time by transferring the cells onto filter paper using a cell harvester (Brandel, Bethesda, Md.). Filters were washed extensively with ice-cold PBS/0.1% BSA, and [$^3$H]palmitate was quantitated by scintillation counting.

Northern Blots. Northern blot analysis of murine FATP expression was done using poly(A) mRNA blots (Clontech). Probes of each of the FATPs were derived from the 3' untranslated regions of each gene and were <60% identical in sequence. Probes were labeled by random priming (Boehringer Mannheim) and hybridized at 65° C. Blots were extensively washed in 0.2% SSC/0.1% SDS at 65° C.

Figure 5:
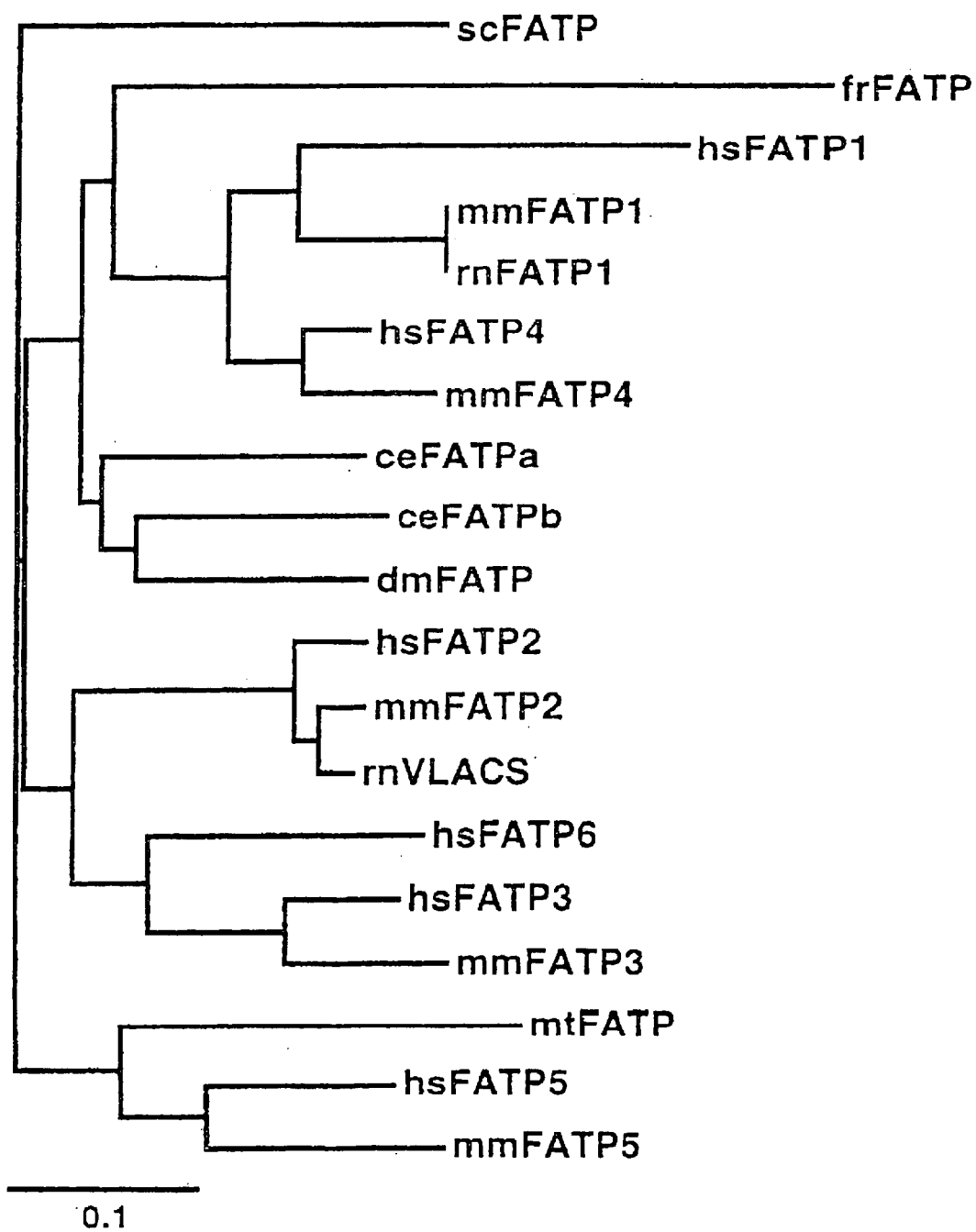
FIG. 5 is a phylogenetic tree produced by aligning complete and partial sequences for FATP genes from human, rat, mouse, puffer fish, $D.\ melanogaster$, $C.\ elegans$, $S.\ cerevisiae$, and $M.\ tuberculosis$ using ClustalX and using these data to produce a phylogenetic tree using TreeView-PPC. The bar indicates the number of substitutions per residue, i.e., 0.1 corresponds to a distance of 10 substitutions per 100 residues.
Figure 7:
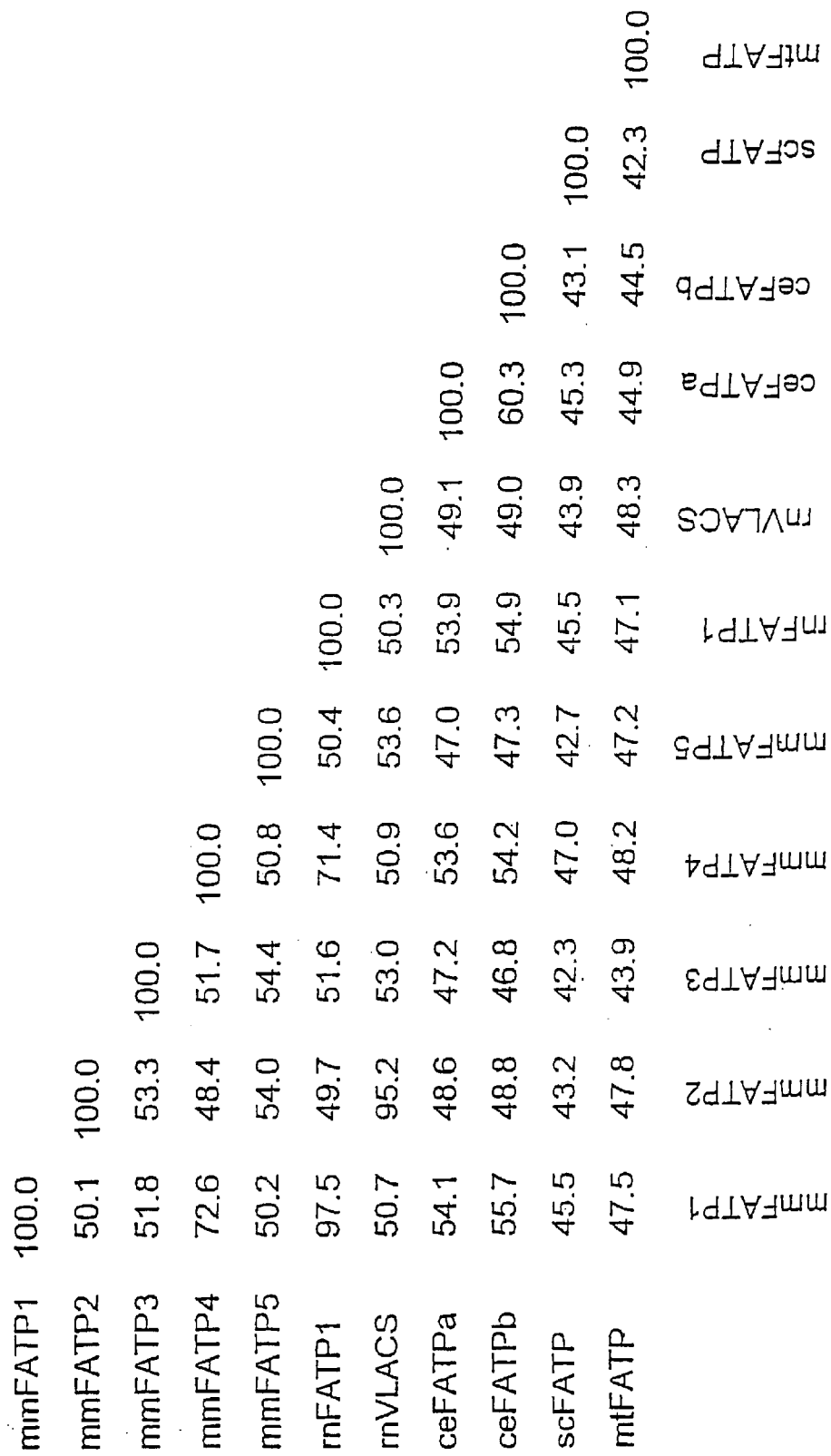
FIG. 7 shows the sequence identity among the FATP family members and VLACs, based on the 360 amino acid signature sequence of FATP from FIG. 1.

Generation of Phylogenetic Trees. Complete and partial sequences for FATP genes from human, rat, mouse, puffer fish, *Drosophila melanogaster, C. elegans, S. cerevisiae*, and *M. tuberculosis* were aligned using ClustalX. A homologous region of amino acids (residues 472–519 in mmFATP1) from all of the genes was used to determine phylogenetic relationship within ClustalX. Based on these data a phylogenetic tree was generated using Tree View PPC (FIG. 5).

Nomenclature. It is proposed that the FATP genes be given a species specific prefix (mm, *Mus musculus*; hs, *Homo sapiens*; mt, *M. tuberculosis*; dm, *D. melanogaster*; ce, *C. elegans*, sc, *S. cerevisiae*) and numbered such that mammalian homologues in different species share the same number but differ in their prefix. Since the two *C. elegans* genes cannot be paired with a specific human or mouse FATP, they have been designated ceFATPa and ceFATPb.

EXAMPLE 1

Identification of Novel Mammalian FATPs

The National Center for Biotechnology Information EST database was screened, using the mouse PATP protein sequence (mmFATP1), to identify novel FATPs. This strategy led to the identification of more than 50 murine EST sequences which could be assembled into five distinct contiguous DNA sequences (contigs). One contig was identical to the previously cloned FATP, which has been renamed FATP1. Another, which has been renamed FATP2, is the murine homologue of a rat gene previously identified by others as a very long chain acyl-CoA synthase (Uchiyama, A., Aoyama, T., Kamijo, K., Uchida, Y., Kondo, N., Orii, T. & Hashimoto, T. (1996) *J. Biol. Chem.* 271:30360–30365). The other three contigs represented novel genes (FATP3, 4, and 5). Full-length clones for FATP2 and FATP5 and nearly complete sequences for FATP3 and 4 (FIG. 1) were obtained by screening cDNA libraries made from mouse day 10.5 embryos and adult liver. Also identified were human homologues for each of the murine genes in the EST database. A sixth human gene was also identified; whether this gene is also present in the mouse will require additional studies. Map positions are given in Tables 2 and 3.

The genetic loci for all of the human genes, with the exception of FATP5 which was already mapped as an unknown EST, were determined using the radiation hybrid panels. The map positions given below show the distance (in centiRays) from the closest framework marker. As a guideline, there are approximately 300 kb/cR.

TABLE 2

Mapping Data for Human Genes

| | |
|---|---|
| hsFATP1 | Chromosome Chr19 |
| | places 13.35 cR from WI-6344 (lod >3.0) |
| hsFATP2 | Chromosome Chr15 |
| | places 4.92 cR from D15S126 (lod >3.0) |
| hsFATP3 | Chromosome Chr1 |
| | places 13.24 cR from WI-2862 (lod >3.0) |
| hsFATP4 | Chromosome Chr9 |
| | places 7.80 cR from WI-9685 (lod >3.0) |
| hsFATP5 | unknown EST previously mapped to near D19S418 |
| hsFATP6 | Chromosome Chr5 |
| | places 1.41 cR from WI-4907 (lod >3.0) |

The mouse map is an internal backcross panel consisting of 188 mouse backcross DNA's plus 4 controls (B6, Spretus, F1, Water). The backcross was constructed by crossing B6 by Spretus animals and then crossing those F1's back to B6. Mapping is accomplished by taking advantage of recombinational events during meiosis, and the use of PCR primers to detect the differences (by size or re-annealing events) at any given locus between the B6 and Spretus allele.

For the purposes of mapping, a novel set of primers (gene of interest) is used to amplify from all 188 DNA's and then typed as being a B6 ("B") or a Spretus ("S"). This string of B's and S's is entered into the Map Manager program, which does a best fit calculation by comparing the string of 188 typings from the gene of interest to all loci already extant in the panel, for all 20 chromosomes. The gene of interest is then assigned to a particular area on a particular chromosome according to a number of parameters, including the minimalization of double cross-overs, and the highest LOD scores. Indicated in Table 3 are distances to the closest markers on either side of the FATP locus.

TABLE 3

Mapping Data for Mouse Genes

| | |
|---|---|
| mmFATP1 | Chromosome 8 |
| | places 2.82 cM from D8Mit132 (lod 43.4) and 1.81 cM from D8Mit74 (lod 43.5) |

TABLE 3-continued

Mapping Data for Mouse Genes

| | |
|---|---|
| mmFATP2 | Chromosome 2 |
| | places 1.29 cM from D2Mit258 (lod 47.9) and 1.75 cM from D2NDS3 (lod 44.9) |
| mmFATP3 | Chromosome 3 |
| | places 2.54 cM from D3Mit22 (lod 29.5) and 19.62 cM from D3Mit42 (lod 13.6) |
| mmFATP4 | Chromosome 2 |
| | places 13.78 cM from D2Mit1 (lod 22.9) and 3.85 cM from D2Mit65 (lod 41.9) |
| mmFATP5 | Chromosome 7 |
| | places 7.28 cM proximal of D7Mit21 (lod 28.3) |

EXAMPLE 2

Assessment of Function

Figure 2B:
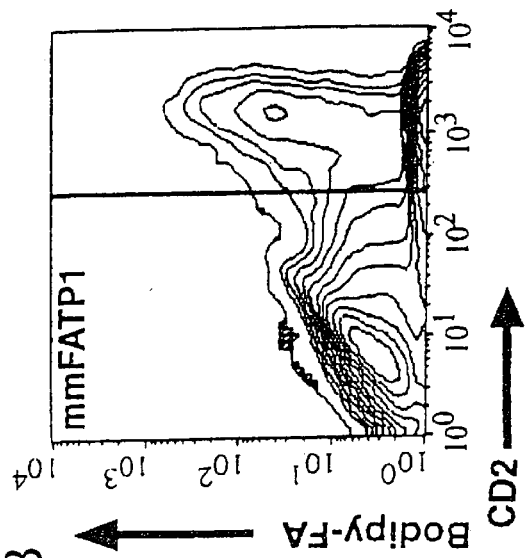
FIGS. 2A–2D show results of LCFA uptake assays.
Figure 2D:
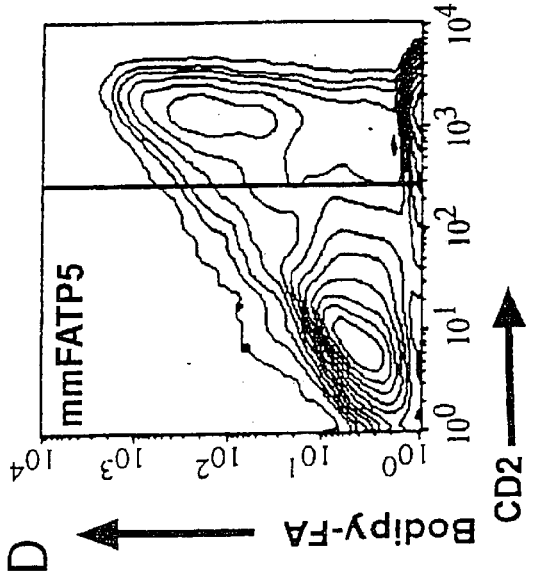
Figure 2A:
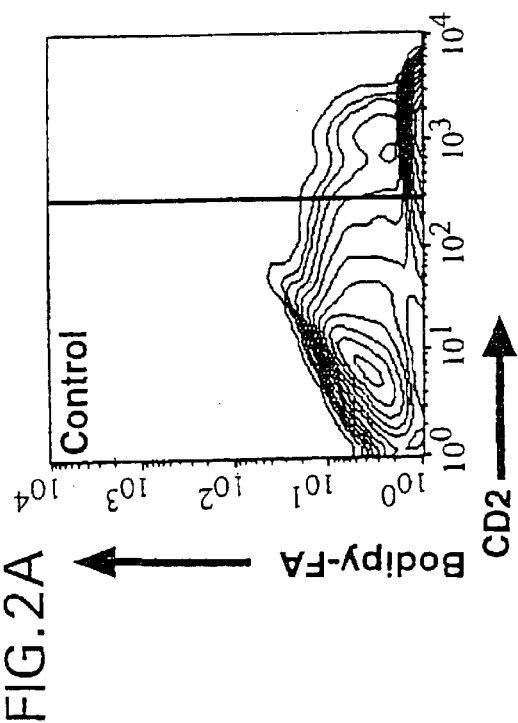
Figure 2C:
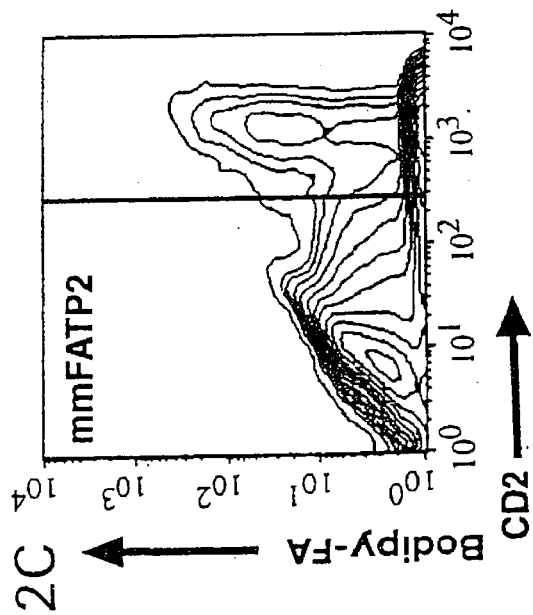

The ability of the newly identified mouse genes to function as fatty acid transporters was assessed using a fluorescence-activated cell sorting-based assay. COS cells were transiently cotransfected with expression vectors encoding the cell surface protein CD2 and either mmFATP1, mmFATP2, or mmFATP5, respectively. Two days after transfection, COS cells were stained with an antibody to CD2 and then incubated with a BODIPY-labeled fatty acid [BODIPY-FA, (Schaffer, J. E. & Lodish, H. F. (1994) *Cell* 79:427–436)]. The cells were then washed extensively, lifted off the dish, and analyzed by fluorescence-activated cell sorting. As judged by the number of CD2-positive cells, the transfection efficiency was approximately 20–30%. Fatty acid uptake was quantitated in the transiently transfected COS cells by measuring the BODIPY-FA fluorescence of the CD2-positive cells. Expression of CD2 had no effect on fatty acid uptake as shown by the finding that COS cells expressing only the transfected CD2 cDNA (CD2-positive) had the same low level of BODIPY-FA uptake as did untransfected (CD2-negative) control cells (FIG. 2A, control). In COS cells cotransfected with CD2 and mmFATP1, mmFATP2, or mmFATP5, uptake of BODIPY-FA by the transfected (CD2-positive) cells was increased between 15- to 90-fold over control (CD2 cDNA only) cells (FIGS. 2A–2D).

EXAMPLE 3

Expression Patterns of Murine FATPs

Expression patterns of members of the murine FATP gene family were characterized by Northern blot analysis; to avoid cross-hybridization, the probes used were from the 3' untranslated region of these genes, which are less than 60% identical in sequence. The expression pattern of FATP1 agrees with that previously found (Schaffer, J. E. & Lodish, H. F. (1994) *Cell* 79:427–436). Here, expression was seen primarily in heart and kidney. FATP2 is expressed almost exclusively in liver and kidney, which corresponds to the reported tissue distribution of the rat homologue [very long chain acyl-CoA (VLACS)] as assessed by Western blotting (Uchiyama, A., Aoyama, T., Kamijo, K., Uchida, Y., Kondo, N., Orii, T. & Hashimoto, T. (1996) *J. Biol. Chem.* 271:30360–30365). FATP3 is present in lung, liver, and testis. FATP5 is expressed only in liver and cannot be detected in other tissues even when the blot is overexposed. The human homologue of FATP5 is also liver specific and is not expressed in a wide array of other tissues tested, including fetal liver.

EXAMPLE 4

FATPs are Evolutionarily Conserved

Figure 3:
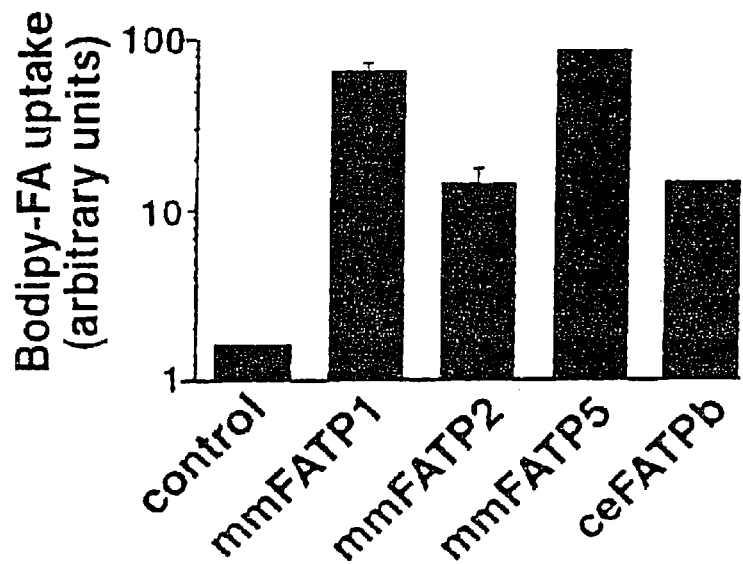
FIG. 3 is a graph of fluorescence of cells expressing a FATP gene. As in FIGS. 2A–2D, COS cells were cotransfected with pCDNA-CD2 either alone (control) or in combination with one of the FATP-containing expression vectors (pCDNA-mmFATP1, pCDNA-mmFATP2, pCMV-SPORT2-mmFATP5, or pCDNA-ceFATPb). The mean BODIPY-FA fluorescence of the CD2-positive cells is plotted; results shown represent the average of three experiments, each consisting of greater than 50,000 COS cells. Note that a logarithmic scale is used on the ordinate.
Figure 4:
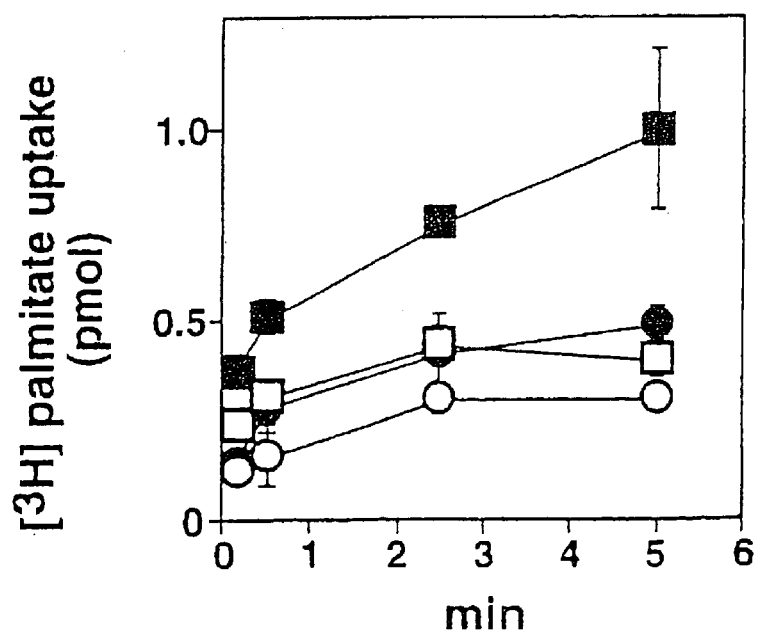
FIG. 4 is a graph of the uptake of palmitate with time. The full-length coding region of mtFATP (squares) or a control protein (TFE3; circles) was subcloned into the inducible, prokaryotic expression vector pET (Novagen). Expression from the resulting plasmid was induced (solid symbols) in transformed $E.\ coli$ cells with 1 mM isopropyl-β-D-thiogalactoside (IPTG) for 1 hour, or cells were left uninduced (open symbols). Data points were done in triplicate and counts were normalized to the number of bacteria as determined by $OD_{600}$.

The EST database was searched, using sequences conserved among the five murine FATP genes, for FATP genes in other organisms. Two homologues were found in *C. elegans* and one in *M. tuberculosis*. One of the *C. elegans* genes was cloned from a cDNA library and expressed in COS cells, as described for the murine FATPs. Overexpression of the nematode FATP resulted in a 15-fold increase of BODIPY-FA uptake compared with control cells (FIG. 3). The mycobacterial FATP gene was isolated from a phage library and assessed for its ability to facilitate fatty acid uptake. *E. coli* transformed with a prokaryotic, isopropyl β-D-thiogalactoside-inducible expression vector containing the mycobacterial FATP gene demonstrated a significant increase in the rate of [$^3$H]palmitate uptake after induction, compared with uninduced bacteria or *E. coli* transformed with a control protein (FIG. 4). Novel FATP genes were also identified in *F. rubripes* (puffer fish) and *D. melanogaster*.

EXAMPLE 5

Phylogenetic Tree of FATPs

Faergeman et al. (Faergeman, N. J., DiRusso. C. C., Elberger, A., Knudsen, J. & Black, P. N. (1997) *J. Biol. Chem.* 272:8531–8538) identified three regions of very strong conservation between the scFATP and mmFATP1 genes. The sequences of the FATP5 were compared over a 311-amino acid FATP "signature sequence" which includes these conserved regions corresponding to amino acids 246–557 in mmFATP1 (underlined in FIG. 1). When compared with the National Center for Biotechnology Information nonredundant database, only one region of the "FATP signature sequence" shows significant homology to other proteins. This small stretch of amino acids (underlined in FIG. 1) is an AMP-binding motif found in a multitude of other proteins, such as acyl-CoA synthase, several CoA lipases, and gramicidin S synthetase component II (Schaffer, J. E. & Lodish, H. F. (1994) *Cell* 79:427–436). The relevance of this motif to fatty acid transport is unclear. Other highly conserved regions among the FATPs, including long stretches of amino acids >90% identical from mycobacteria to humans, are not found in any other class of proteins. A 48-amino acid segment of the FATP signature sequence was used to construct a phylogenetic tree (FIG. 5). Each of the human and mouse genes form their own branch; hsFATP6, which as yet has no murine homologue, is most closely related to hsFATP3 and mmFATP3. As expected, rnVLACS is closer in sequence to mmFATP2 than to hsFATP2. The FATP genes of invertebrates i.e., *C. elegans* and *D. melanogaster*, are most closely related to each other. Surprisingly, the mycobacteral gene is more closely related to the human and mouse FATP5 genes than to the FATPs of any of the lower organisms. Whether this reflects coevolution of the mycobacterial and human genes awaits further study.

Materials and Methods

The following materials and methods were used in the work described in Examples 6–10.

Isolation of Full-length Human FATP1 and 4

Full-length clones encoding human FATP1 and human FATP4 were identified by searching databases for sequences similar to murine FATP1–5 coding regions using the BlastX algorithm (Altschul et al., *J. Mol. Biol.* 215: 403–410, 1990).

A concatamer of nucleotide sequences comprising the coding sequences of mmFATP1 (Genbank Accession U15976), mmFATP2, mmFATP3 (SEQ ID NO:6), mmFATP4 (SEQ ID NO:8) and mmFATP5 (SEQ ID NO:10) was used to search the Millennium database using the BLASTX algorithm. Sequences with a score >150 were evaluated for whether they represented known FATP coding sequences.

Human clones with similarity to the 5' end of murine FATP sequences were sequenced completely. Clones encoding full-length human FATP1 were obtained from a heart cDNA library constructed in the mammalian expression vector pMET7 (Tartaglia et al., *Cell*, 83: 1263–1271, 1995). Clones encoding full-length human FATP4 were obtained from a spleen cDNA library constructed in the mammalian expression vector pMET7.

Isolation of Full-length Human FATP6

Several clones encoding human FATP6 were identified by searching public databases as described above. Five clones were analyzed further by restriction digestion and DNA sequencing. One of these clones (Genbank Accession #AA412064) appeared to be full-length and its entire insert was sequenced.

DNA Sequence Analysis

Sequences were aligned with the DNAStar program using the Clustal method. Hydrophobicity plots were generated with DNA Strider using the Kyte Doolittle method.

In Situ Hybridization

Tissues were collected from 8 week old C57/B16 mice. Tissues were fresh frozen, cut on a cryostat at 10 μm thickness and mounted on Superfrost Plus slides (VWR). Sections were air dried for 20 minutes and then incubated with ice cold 4% paraformaldehyde (PFA)/phosphate buffered saline (PBS) for 10 minutes. Slides were washed 2 times 5 minutes with PBS, incubated with 0.25% acetic anhydride/1 M triethanolamine for 10 minutes, washed with PBS for 5 minutes and dehydrated with 70%, 80%, 95% and 100% ethanol for 1 minute each. Sections were incubated with chloroform for 5 minutes. Hybridizations were performed with $^{35}$S-radiolabeled (5×10$^7$ cpm/ml) cRNA probes generated from the 3' untranslated regions of mouse FATPs by PCR followed by in vitro transcription in the presence of 50% formamide, 10% dextran sulfate, 1×Denhardt's solution, 600 mM NaCl, 10 mM DTT, 0.25% SDS and 10 μg/ml tRNA for 18 hours at 55° C. After hybridization, slides were washed with 10 mM Tris-HCl pH 7.6, 500 mM NaCl, 1 mM EDTA (TNE) for 10 minutes, incubated in 40 μg/ml RNase A in TNE at 37° C. for 30 minutes, washed in TNE for 10 minutes, incubated once in 2×SSC at 60° C. for 1 hour, once in 0.2×SSC at 60° C. for 1 hour, once in 0.2×SSC at 65° C. for 1 hour and dehydrated with 50%, 70%, 80%, 90% and 100% ethanol. Localization of mRNA transcripts was detected by dipping slides in Kodak NBT-2 photoemulsion and exposing for 7 days at 4° C., followed by development with Kodak Dektol developer. Slides were counter stained with haematoxylon and eosin and photographed. Controls for the in situ hybridization experiments include the use of a sense probe which showed no signal above background in all cases.

Northern Blotting

Human mRNA blots were obtained from Invitrogen or Clontech. PCR fragments from the 3' untranslated regions of human FATPs were used as probes. Blots were probed with $^{32}$P-labeled DNA probes using the Rapid-Hyb buffer (Amersham) according to the manufacturer's instructions.

Cell transfection and LCFA uptake. COS cells were cotransfected, using lipofectamine (GIBCO BRL) according to the manufacturer's instructions, with the mammalian expression vector pCDNA3.1 (Invitrogen) expressing the gene for CD2 in combination with a pMET7 expression vector (Tartaglia et al., Cell, 83:1263–1271, 1995) containing hsFATP1 (pMET7-hsFATP1) or hsFATP4 (pMET7-hsFATP4) or pMET7 alone. Two days after transfection, cells were assayed for CD2 expression with a phycoerythrin-coupled anti-CD2 (PE-CD2) monoclonal antibody (PharMingen), and fatty acid uptake was assayed with a BODIPY-labeled fatty acid analog (Molecular Probes) as described above.

EXAMPLE 6

Determination of Expression of mmFATPs mmFATP4, and to lesser extent mmFATP2, are expressed at high levels in the brush border layer of the small intestine.

Cell transfection and LCFA uptake. COS cells were cotransfected, using lipofectamine (GIBCO BRL) according to the manufacturer's instructions, with the mammalian expression vector pCDNA3.1 (Invitrogen) expressing the gene for CD2 in combination with a pMET7 expression vector (Tartaglia et al., Cell, 83:1263–1271, 1995) containing hsFATP1 (pMET7-hsFATP1) or hsFATP4 (pMET7-hsFATP4) or pMET7 alone. Two days after transfection, cells were assayed for CD2 expression with a phycoerythrin-coupled anti-CD2 (PE-CD2) monoclonal antibody (PharMingen), and fatty acid uptake was assayed with a BODIPY-labeled fatty acid analog (Molecular Probes) as described above.

Absorption of dietary fat requires transport of free fatty acids across the apical membrane of epithelial cells in the small intestine. Previous studies suggested that this transport is protein-mediated; however, the transport protein had not yet been identified. In situ hybridization was performed on each of the three regions of the small intestine—duodenum, jejunum and ileum—as well as the colon, using probes from the 3' untranslated regions of mmFATP1, mmFATP2, mmFATP3, mmFATP4 and mmFATP5, to determine whether any of the mouse FATPs are expressed in the small intestine. It was expected that a protein involved in fatty acid absorption would be expressed in the epithelial cells of the small intestine, but absent from the colon.

Expression of mmFATPs in the jejunum was identical to that in the ileum in all cases. High levels of mmFATP4 mRNA were present in the epithelial cells of the jejunum and ileum, and lower, but significant, amounts were detected in the epithelial cells of the duodenum. Significantly, FATP4 mRNA was absent from other cell types of the small intestine and no FATP4 mRNA could be detected in any of the cells of the colon. FATP2 mRNA was present in the epithelial cells of the duodenum at a level similar to that of FATP4, but was present at lower levels in the jejunum and ileum. No signals above background were detected for mmFATP1, mmFATP3 and mmFATP5 in any of the intestinal tissues. mmFATP3 and FATP5 were clearly detectable by in situ hybridization in adult liver and mmFATP1 could be detected in a variety of tissues on a whole embryo in situ, indicating that the FATP1, 3, and 5 probes were working.

mmFATP4 expression is predominant in the small intestine compared to the other organs of the mouse embryo. In the small intestine, FATP4 expression is limited to differentiated enterocytes, while no signal is detected in the connective tissue or the undifferentiated epithelial cells in the crypts. Differentiated enterocytes are known to be the cells that mediate the uptake of fatty acids. FATP4 is specifically and strongly expressed in the epithelial cells of adult murine duodenum and ileum but not colon. Other FATPs, such as FATP5, are not expressed in the small intestine. Thus, FATP4 is the major FATP in the mouse small intestine. Given its high level of expression, it is likely that FATP4, and to a lesser extent FATP2, play an important role in the absorption of fatty acids.

mmFATP2, and mmFATP5 are Expressed in Hepatocytes

Northern analysis of mmFATP2, mmFATP3, mmFATP4 and mmFATP5 showed expression in the liver. To determine whether these proteins are present in hepatocytes or other cells types present in liver homogenates, in situ hybridizations were performed. mmFATP2, and mmFATP5 mRNA was clearly present in hepatocytes, and was not concentrated in other cell types such as endothelial cells or macrophages. No signal above background was detected for mmFATP1 in any of the cell types in the liver, consistent with the results of the Northern blotting.

EXAMPLE 7

Isolation and Sequence Analysis of Full-length Human FATP1 and Full-length Human FATP4

To identify human cDNA clones encoding FATP family members, Millennium databases were searched for sequences similar to murine FATP1–5 coding regions. Two clones were analyzed in detail; inspection of the entire DNA sequence of these two clones showed that they encode the human orthologs of mmFATP1 and mm FATP4, respectively. These two clones were designated hsFATP1 and hsFATP4, and their DNA and predicted protein sequences are shown in FIGS. 44A–44D and 45, and 50A–50C and 51. hsFATP1 is predicted to encode a 646 amino acid, 71 kD protein with multiple membrane-spanning domains (FIG. 28A). HsFATP4 is predicted to encode a 643 amino acid, 72 kD protein with multiple membrane spanning domains (See FIG. 29A). A comparison of the DNA sequences of mouse and human FATP1 and mouse and human FATP4 (FIGS. 30A–30F and 31A–31I) shows that the mouse and human orthologs are 85% (FATP1) and 87% (FATP4) identical to each other within the coding sequences given in these figures. At the amino acid level, hsFATP1 and hsFATP4 are ~90% identical to their respective mouse orthologs within the coding region shown in these figures (FIGS. 32A–32C and 33A–33C. The sequence identities between mouse and human FATP1 and FATP4 are considerably higher than the ones observed between different FATP family members within one species (~40%–60%) and are present in the N-terminal part of the protein, a region that is poorly conserved between different FATP family members. This high degree of sequence conservation clearly demonstrates that the newly identified human FATPs are orthologs of mouse FATP1 and FATP4 rather than novel FATP family members.

Table 4 is an identity/similarity matrix comparing the amino acid sequences of FATP1 and 4 from human and mouse. This shows that the gene whose sequence is shown in FIG. 43A is indeed human FATP4, since it is 91% identical with the murine FATP4 but only 62% identical with the closest related human FATP, which is FATP1.

TABLE 4

Identity/Similarity Matrix

|  | hsFATP4 | mmFATP4 | hsFATP1 | mmFATP1 |
|---|---|---|---|---|
| hsFATP4 | — | 93.2 | 72.3 | 72.0 |
| mmFATP4 | 91.0 | — | 71.2 | 71.1 |
| hsFATP1 | 61.9 | 61.0 | — | 92.4 |
| mmFATP1 | 60.7 | 59.6 | 89.5 | — |

EXAMPLE 8

Isolation and Sequence Analysis of Full-length Human FATP6

A search of EST databases identified a set of overlapping human sequences that were similar to FATPs, but did not have a clear mouse ortholog. One of these EST clones was found to encode a full-length cDNA. The entire insert of this clone was sequenced and designated hsFATP6, The DNA and predicted protein sequences of hsFATP6 are shown in FIGS. 54A–54C and 55. HsFATP6 is predicted to encode a 619 amino acid, 70 kD protein with multiple membrane-spanning domains (FIG. 35A). A comparison of the amino acid sequences of hsFATP6 with other human FATPs shows about 37% identity to either hsFATP1 or hsFATP4 (FIGS. 36A–36G). This degree of sequence identity is similar to what is observed between different mouse FATPs. The phylogenetic analysis described above clearly demonstrates that hsFATP6 is a member of the FATP family, but not an ortholog of any of the mouse FATPs. Comparisons were done with "ALIGN" (E. Myers and W. Miller, "Optimal Alignments in Linear Space," *CABIOS* 4:11–17 (1988) using standard settings.

EXAMPLE 9

Tissue Distribution of Human FATPs

The tissue distribution of human FATPs was assessed by Northern blotting. Human FATP3 was expressed in a large variety of tissues. In contrast, human FATP5 was present at high levels in the liver, but was undetectable in all other tissues examined. Thus, both hsFATP3 and hsFATP5 recapitulate the expression pattern of their mouse orthologs (see above). HsFATP6 is a novel FATP with no mouse ortholog as yet. Northern blotting shows that hsFATP6 is expressed at high levels in the heart, but is undetectable in other tissues, including skeletal and smooth muscle. This tissue distribution suggests that human FATP6 performs an important role in energy metabolism in the heart; blocking FATP6-mediated fatty acid transport may therefore be beneficial for a number of heart diseases, e.g., ischemic heart disease.

To identify the major FATP expressed in the human small intestine, Northern blotting was performed on a blot containing mRNA from human stomach, jejunum, ileum, colon, rectum and lung. hsFATP5 and hsFATP6 were undetectable in any of these tissues. FATP5 is only expressed in liver and FATP6 only in heart. hsFATP2 was weakly expressed in the colon, and an even weaker signal was detectable in jejunum, ileum and lung lanes. hsFATP3 was expressed well in the lung, but was only weakly expressed in the other tissues tested. Importantly, no difference was seen in the expression of hsFATP3 between small intestine and stomach or colon, suggesting that the expression observed is not related to fatty acid absorption in the small intestine. hsFATP4 was clearly expressed in both jejunum and ileum; expression was significantly lower in the colon and was absent in the stomach. This expression pattern is consistent with a major role for FATP4 in absorption of fatty acids in the human gut.

EXAMPLE 10

Expression of hsFATP1 and hsFATP4 Promotes Transport of Fatty Acids

COS cells were cotransfected using lipofectamine with the mammalian expression vector pCDNA-CD2 in combination with one of the FATP-containing expression vectors (pMET7-hsFATP1 or pMET7-hsFATP4) or an insertless expression vector (pMET7, control) as described in Materials and Methods for Examples 6–10. COS cells were gated on forward scatter and side scatter. Cells exhibiting more than 400 CD2 fluorescence units representing ~30% of all cells were deemed CD2-positive. The percent of CD2-positive cells exhibiting a BODIPY-fluorescence of >300 is plotted for the three different vectors tested (FIG. 37).

EXAMPLE 11

Stable Expression of Human FATP4 in 293 Cells

Stable cell lines were generated as follows. A DNA fragment containing the entire hsFATP4 coding sequence as well as 100 nucleotides of 5' and 50 nucleotides of 3' untranslated region was inserted into the vector pIRES-neo (Clontech) using standard cloning techniques. The resulting construct or a vector control (pIRES-neo) was transfected into 293 cells using the lipofectamine method (Gibco BRL) according to the manufacturer's directions. Cells that had taken up the DNA were selected with 1 mg/ml G418 (Gibco BRL). Single colonies were picked 1 to 2 weeks after transfection and grown in medium containing 0.8 mg/ml G418. Colonies were screened for the ability to take up fatty acids by measuring uptake of a fluorescently labeled fatty acid (BODIPY-FA). About 40 colonies transfeted with the pIRES-neo containing FATP4 and ~20 colonies transfected with pIRES-neo control were analyzed. All 20 of the vector control clones showed amounts of BODIFY-FA uptake similar to each other and to untransfected 293 cells. In contrast, among the 40 FATP4 transfected clones, 3 had a 5- to 10-fold increased BODIPY-FA uptake compared to any of the vector controls, and a large number (~20) showed an approximately two-fold increase in BODIPY-FA levels.

This distribution is consistent with FATP4 conferring increased fatty acid uptake in these cells. One of the cell lines with the highest amount of BODIPY-FA uptake was selected to be used for measuring uptake of tritiated fatty acid.

Figure 38:
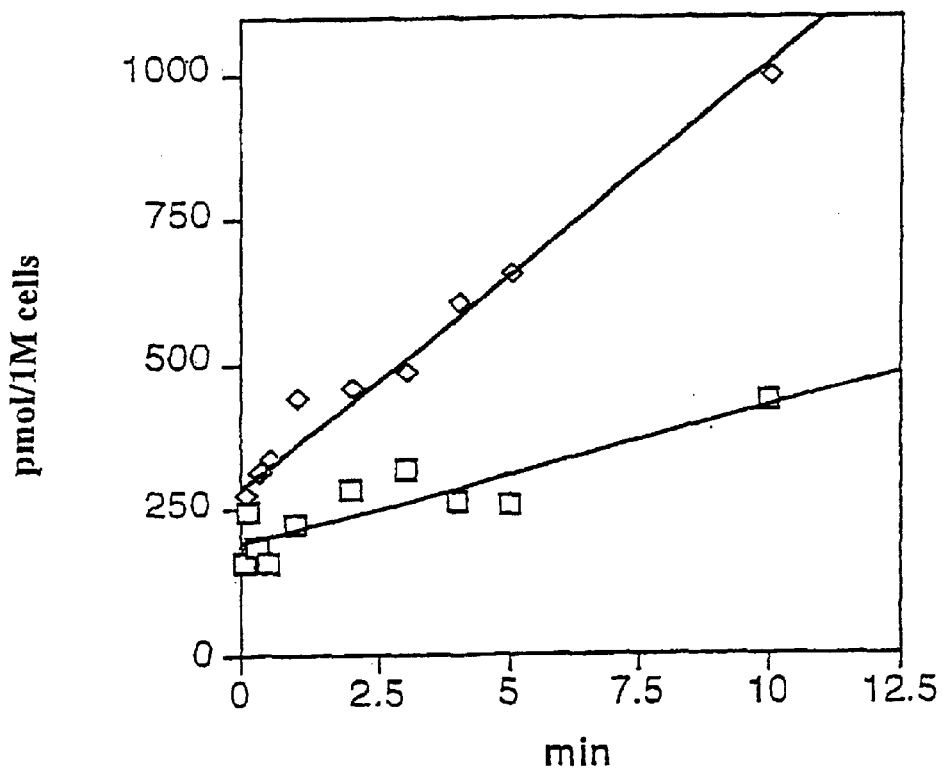
FIG. 38 is a graph showing uptake of tritiated oleate, with time, by 293 cells transfected with either (diamonds) a plasmid for expression of human FATP4 or (squares) a control plasmid.

The uptake of tritiated oleate over time by either FATP4 expressing or control cells was assayed over time. Expression of FATP4 increases the rate of fatty acid uptake by over 3-fold, demonstrating that FATP4 is, like the other FATPs, a functional fatty acid transporter (FIG. 38).

EXAMPLE 12

Immuno-staining with FATP4-specific Antiserum

A polyclonal antiserum against the C-terminus of mmFATP4 was raised using a GST-fusion protein having mmFATP4-specific amino acid sequence 552–643 (AVASP . . . GEEKL). In western blot experiments, the purified antibody reacted strongly with a synthetic peptide matching the C-terminus of mmFATP4, but not with a corresponding region of mmFATP2, mmFATP3, or mmFATP5. The mmFATP4 specific polyclonal antiserum detects, in western blot experiments with enterocyte lysates from 3 different mice, a ~70 kDa protein, which is in accordance with mmFATP4's predicted molecular weight of 72 kDa. The binding is specific for mmFATP4, since it can be completely abolished by preincubation of the antiserum with the GST-fusion peptide used to raise the antibody.

Immunofluorescence experiments were performed using the anti-mmFATP4 antiserum on fresh frozen sections of murine small intestine. The antibody binding demonstrates strong expression of mmFATP4 in enterocytes, confirming the results of the in situ hybridization experiments. At higher magnifications it is apparent that mmFATP4 is expressed at the apical side of the enterocyte, indicating that the transporter is present in the brush border membrane, which is known to mediate the uptake of fatty acids from the intestinal lumen.

Immuno-electron microscopy studies were performed on fresh frozen murine intestinal cells. The gold particles used, appearing as black specks on the electron micrographs, indicate the subcellular localization of mmFATP4 to be on the microvilli of the enterocyte. It can be seen from electron micrographs that mmFATP4 is localized exclusively in membranes, preferentially the apical plasma membrane, confirming that it is indeed a membrane protein.

Methods for Lunofluorescence and Immunogold Electron Microscopy

Unfixed mouse small intestine was washed with Hank's buffered salt solution containing 1 mM EDTA, infused with 2.3 M sucrose solution, and embedded in O.C.T., 4583 compound. The material was thick sectioned (15 μM–40 μM). The sections were washed in PBS containing 1% BSA and 0.075% glycine to block non-specific binding. Primary and secondary antibodies were diluted in PBS with 10% FCS and incubated for 1 h. The sections were mounted in 90% glycerol/PBS containing 1 mg/ml paraphenylinediamine, and examined with a Bio-Rad MRC 600 confocal, mounted on a Zeiss Axioscop.

For the immunogold labeling, the tissue was fixed with 2% paraformaldehyde in PBS for 10 minutes, after which it was cryoprotected by infiltration with 2.3 M sucrose in 0.1 M phosphate buffer (pH 7.4) containing 20% polyvinylpyrrolidone, and then mounted on aluminum cryo nails and frozen in liquid nitrogen (Tokuyasu, K. T., J. Microsc. 143:139–149, 1986). Ultrathin sections were collected on carbon/formvar-coated nickel grids. The primary antibody (anti-FATP4) was diluted in 10% FCS in PBS and incubated overnight at 4 C, followed by donkey anti-rabbit IgG-gold (12 nm) (Jackson Labs) for 1 h. The sections were stained in 2% neutral uranyl acetate (20 minutes) and absorption stained with 2% uranyl acetate in 0.2% methylcellulose containing 3.2% polyvinyl alcohol. The sections were examined with a Philips EM 410 electron microscope.

EXAMPLE 13

Inhibition of Fatty Acid Uptake Specific to FATP4 Demonstrated in Isolated Mouse Enterocytes Phosphorothioate derivatives of the following oligonucleotides were synthesized:

FATP4-AS2 CCCCCACCAGAGAGGCTCC (SEQ ID NO:103)

FATP4-AS2MM CCACCCCCGGAAAGCCTGC (SEQ ID NO:104)

FATP4-S2 GGAGCCTCTCTGGTGGGGG (SEQ ID NO:105)

FATP4 AS2 is the antisense oligo; it is designed to be complementary to the sequence extending from nucleotide 10 to nucleotide 28 of the mouse FATP4 coding sequence. FATP4-AS2MM is a control oligo; in the oligo every third nucleotide was changed creating mismatches; the overall nucleotide composition is identical to FATP4-AS2 (same number of G, A, T, C). FATP4-S2 is the sense control.

Figure 40:
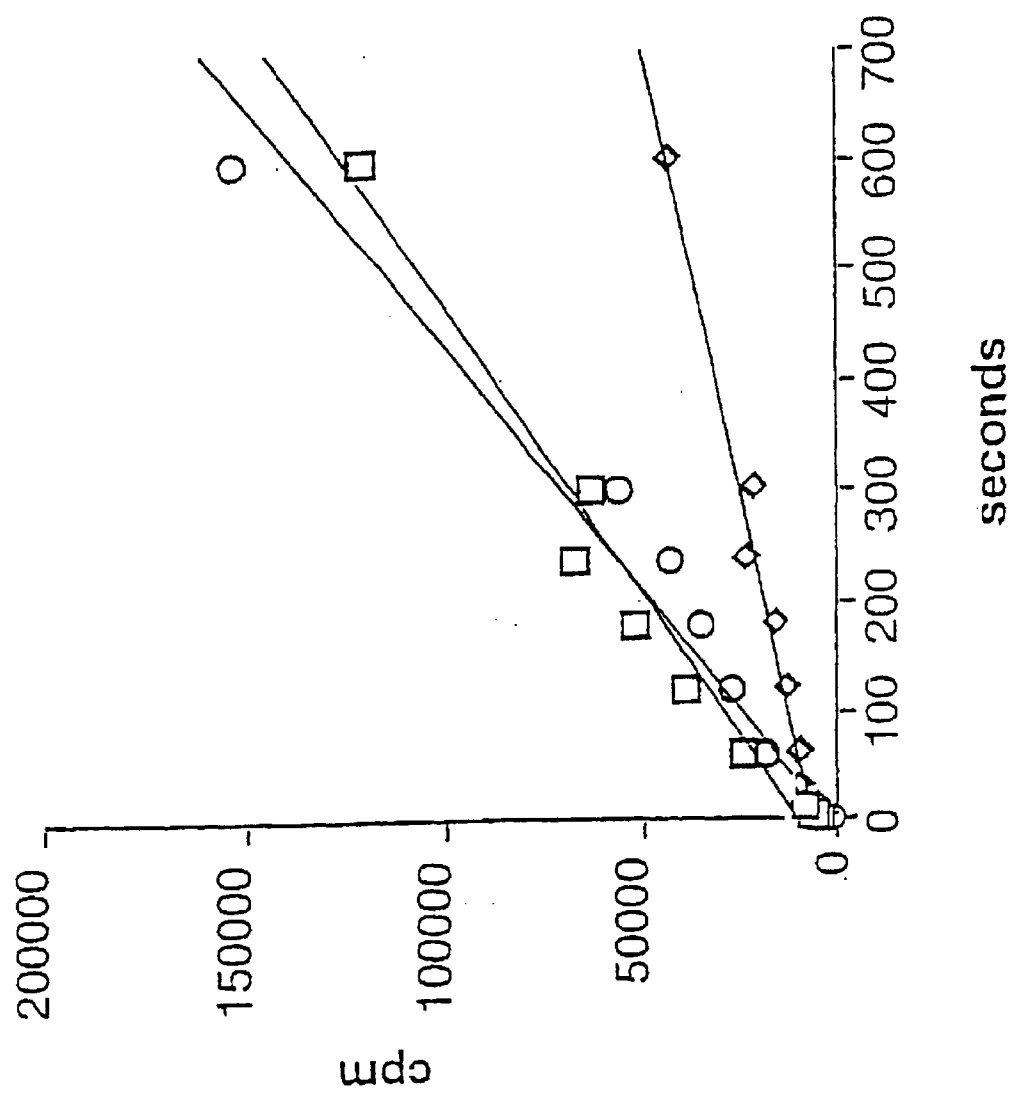
FIG. 40 is a graph showing the uptake, with time, of tritiated oleate by mouse enterocytes in the presence of no oligonucleotide (squares), sense oligonucleotide (circles) or antisense oligonucleotide (diamonds).

Enterocytes were isolated from the small intestine of mice and incubated for 48 h in tissue culture (FIG. 40) either without oligonucleotides (squares) or with 100 μM FATP4 specific sense (circles) or antisense (diamonds) oligonucleotides. The uptake over time of 25 μM oleate was then measured. While the FATP4 sense oligonucleotide did not significantly influence the uptake, the antisense oligonucleotide inhibited fatty acid uptake by ~50%.

Figure 41:
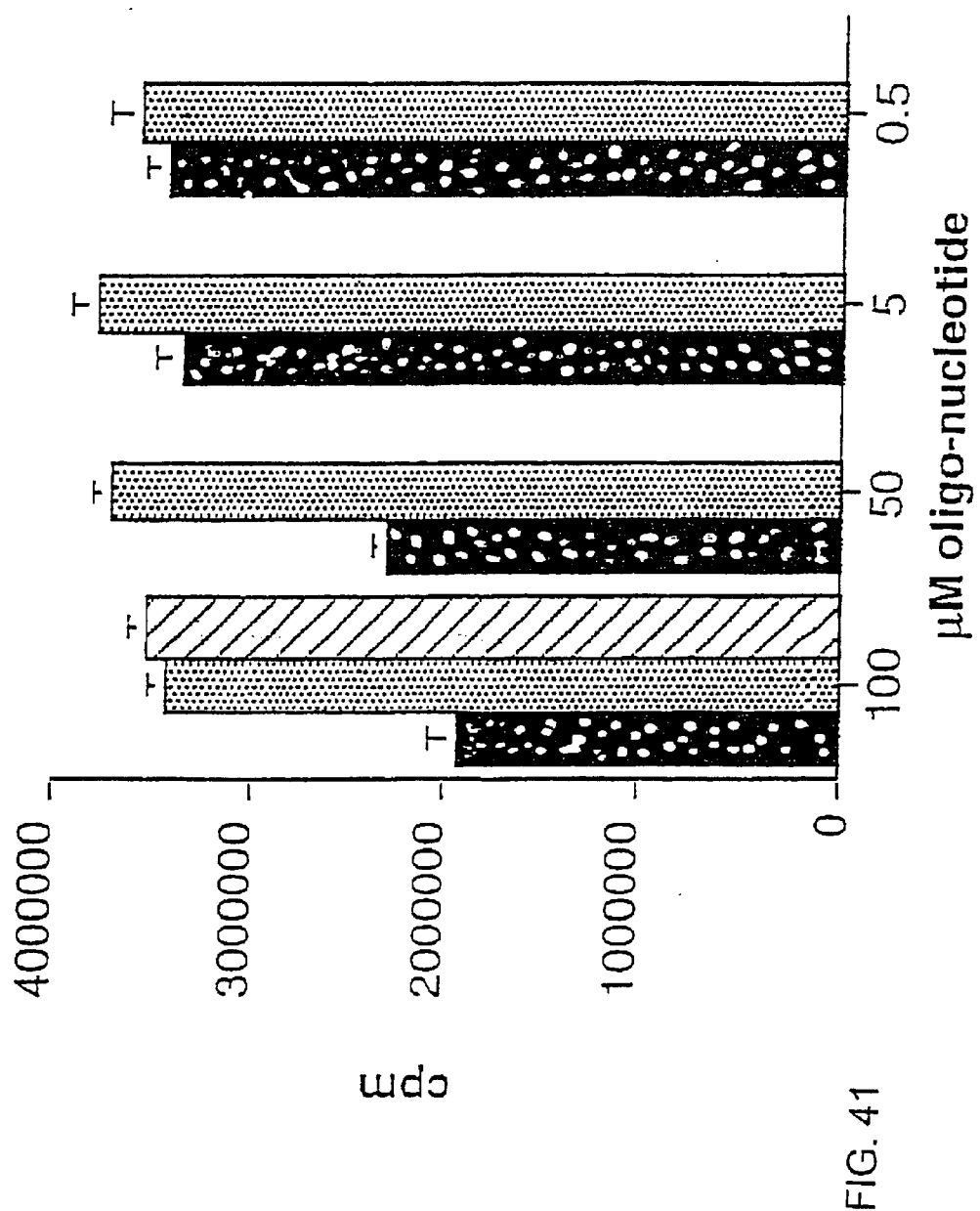
FIG. 41 is a bar graph showing uptake of tritiated oleate, by mouse enterocytes in the presence of various concentrations of antisense (solid bars), mismatch (stippled bars) or sense (lined bars) oligonucleotides.

The effect of either FATP4 sense, antisense or mismatch sequence oligonucleotides on the uptake of fatty acids was measured in enterocytes. Isolated enterocytes were incubated with increasing concentrations of FATP4 antisense oligonucleotides (solid bars in FIG. 41), or a mismatch control oligonucleotide with identical nucleotide composition (stippled bars), or with 100 μM of the FATP4 sense-oligonucleotide (lined bar). The medium for this incubation was Dulbecco's modified Eagle's medium with 4.5 g/L glucose, 1 mM sodium pyruvate, 0.01 mg/ml human transferrin and 10% fetal bovine serum. After 48 hours of incubation the uptake of oleate by enterocytes was measured over a 5 minute time interval. Measurements were done in quadruplicate. The uptake assay was done in Hank's buffered salt solution with 10 mM taurocholate. Only the enterocytes given FATP4 antisense oligonucleotide showed a concentration dependent decrease of fatty acid uptake, inhibiting it at a 100 μM concentration by ~50%. This effect was FATP4 specific, since only the antisense oligonucleotide which can bind to the FATP4 mRNA and block its translation inhibited uptake, but not a control oligonucleotide differing only in the sequence but not the nucleotide content, ruling out a toxic or otherwise nonspecific inhibitory effect of this oligonucleotide due to its chemical composition.

Figure 42:
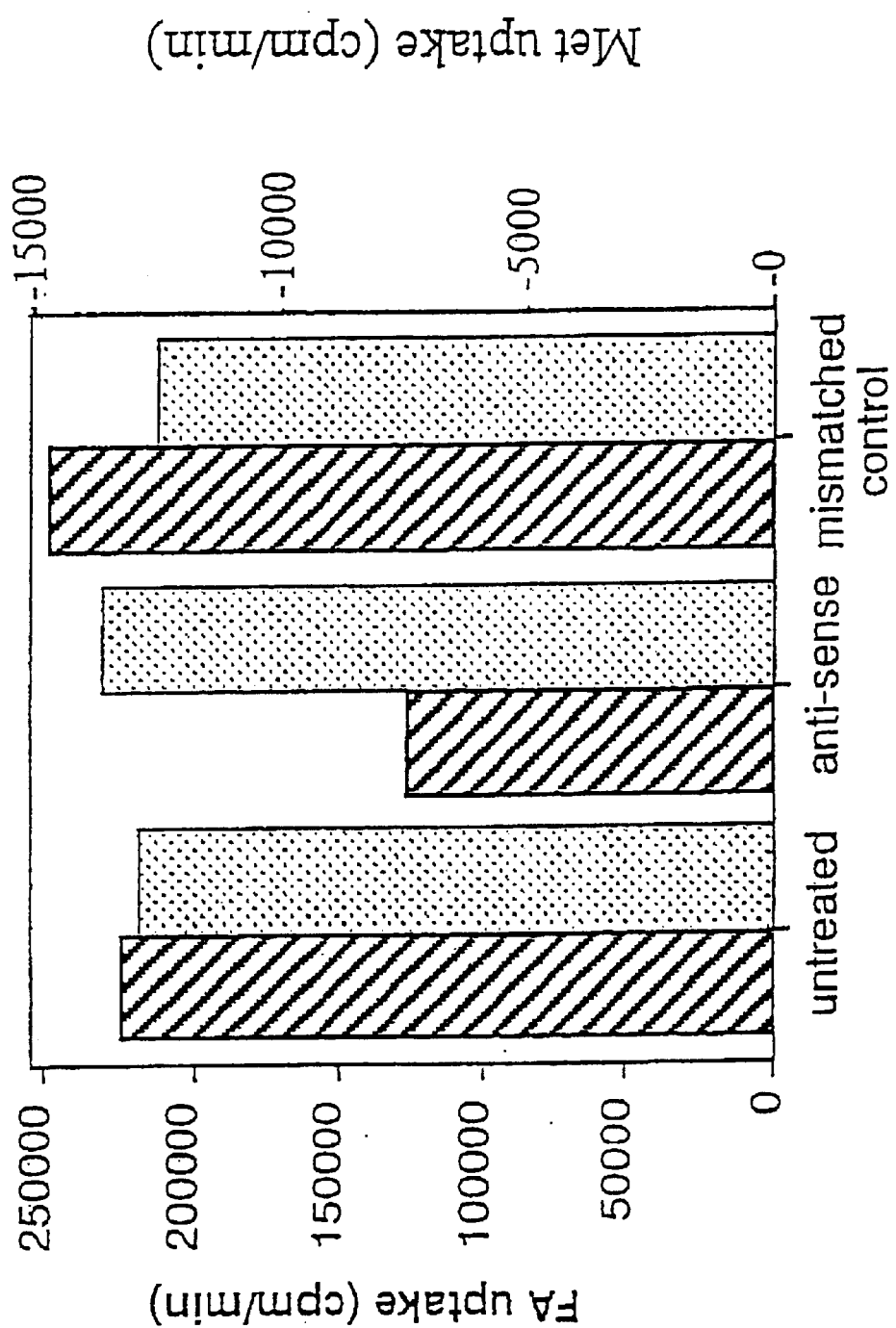
FIG. 42 is a bar graph showing uptake of tritiated oleate and uptake of $^{35}$S-labeled methionine by mouse enterocytes to which were added no oligonucleotide, the antisense oligonucleotide, or the mismatch oligonucleotide.

As a further control experiment, the uptake of oleate was measured along with the uptake of methionine in the same cultured enterocytes. Antisense oligonucleotide, mismatch sequence oligonucleotide, or no oligonucleotide was added to a concentration of 100 μM to cultures of enterocytes. After incubation for 48 hours, the uptake of both $^3$H-labeled oleate and $^{35}$S-labeled methionine was assayed. Results are shown in FIG. 42. Fatty acid uptake is at the left side of the paired bars; methionine uptake is on the right side of the paired bars. The fact that amino acid uptake was not influenced by the antisense oligonucleotide treatment further supports the conclusion that the antisense oligonucleotide causes a specific reduction in translation of FATP4-specific mRNA.

EXAMPLE 14 mmFATP2 is Expressed in Proximal Renal Tubule Epithelium

Northern analysis showed that mmFATP1, mmFATP2, and mmFATP4 are present in the kidney. In situ hybridization (methods as for Example 6) was performed to determine which cell type(s) of the kidney these mRNAs are expressed in. mmFATP1 mRNA was present in virtually all cells throughout the kidney with no obvious preference for a particular cell type. In contrast, mmFATP2 was expressed only in the renal cortex. Within the cortex, expression of mmFATP2 was restricted to the epithelial cells of the proximal renal tubules. The primary function of proximal renal tubule cells is the reabsorption of filtered salts and nutrients (e.g., glucose), a process that requires mitochondrial oxidation and that can utilize fatty acids as energy substrates. Based on the localization of mmFATP2, it is possible that mmFATP2 is important for reabsorption in the kidney by allowing uptake of an energy source (fatty acids) from the blood into renal epithelial cells. Alternatively, if fatty acids need to be reabsorbed in the kidney, similarly to glucose, FATP2 could be involved in the reabsorption of fatty acids. Determination of the subcellular localization of FATP2 will distinguish between these two possibilities.

nated hsFATP3. The DNA and predicted protein sequences of hsFATP3 are shown in FIGS. 94A–94J. hsFATP5 is predicted to encode a 703 amino acid 75.6 kD protein with multiple membrane-spanning domains. A comparison of the DNA sequences of mouse and human FATP3 shows that the mouse and human orthologs are 81% identical to each other within the coding region. At the amino acid level, hsFATP3 is ~86% identical to mm FATP3 within the coding region. The sequence identities between mouse and human FATP3 are considerably higher than those observed between different FATP family members within one species (~40%) and

TABLE 5

Mouse FATP mRNA Expression

| Mouse Probes | mFATP1 | mFATP2 | mFATP3 | mFATP4 | mFATP5 |
|---|---|---|---|---|---|
| E18.5 embryo expression | everywhere, brain = thymus > heart > brown fat, others | liver (hepatocytes) | — | Brain, small intestine, superior cervical ganglion (SCG), dorsal root ganglion (DRG), other regions have lower expression | Mouse Probes |
| Duodenum | — | villi (surface epithelium) | — | villi (surface epithelium) | — |
| Jejunum | — | villi (surface epithelium) | — | villi (surface epithelium) | — |
| Ileum | — | villi (surface epithelium) | — | villi (surface epithelium) | — |
| Colon | low expression in the crypt | very low level in the crypt | — | — | — |
| Kidney | cortex and medulla | proximal tubules | — | — | — |
| Liver | — | hepatocytes | hepatocytes | — | hepatocytes |
| Pancreas | exocrine secretory units or acinar cells; endocrine pancreas (islet) are negative | exocrine secretory units or acinar cells; endocrine pancreas (islet) are negative | — | — | — |
| Brain | Neuronal expression throughout the brain including hypothalamus | — | — | Neuronal expression throughout the brain including hypothalamus | — |
| Heart | myocytes | — | — | | |
| Testis | seminiferous tubules | — | seminiferous tubules | | |
| Lung | bronchiole | — | — | | |
| Adipose | adipocyte | adipocyte | — | | |

EXAMPLE 15

Isolation of full-length human FATP3

Full-length clones encoding human FATP3 were identified by searching databases for sequences similar to the murine FATP1–5 coding regions using the BlastX algorithm (Altschul et al., *J. Mol. Biol.* 215: 403–410, 1990). Human clones with similarity to the 5' end of murine FATP sequences were sequenced completely. A clone encoding full-length human FATP3 was obtained from a human bone library constructed in the mammalian expression vector pMET7 (Tartaglia, L. A. et al., *Cell* 83: 1263–1271, 1995). To identify human cDNA clones encoding FATP family members, databases were searched for sequences similar to murine FATP1–5 coding regions. One clone was found to encode the human ortholog of mmFATP3 and was desigare present in the N-terminal part of the protein, a region that is poorly conserved between different FATP family members.

EXAMPLE 16

Substrate Specificity of Fatty Acid Transport in hsFATP-transfected Clones

Figure 95:
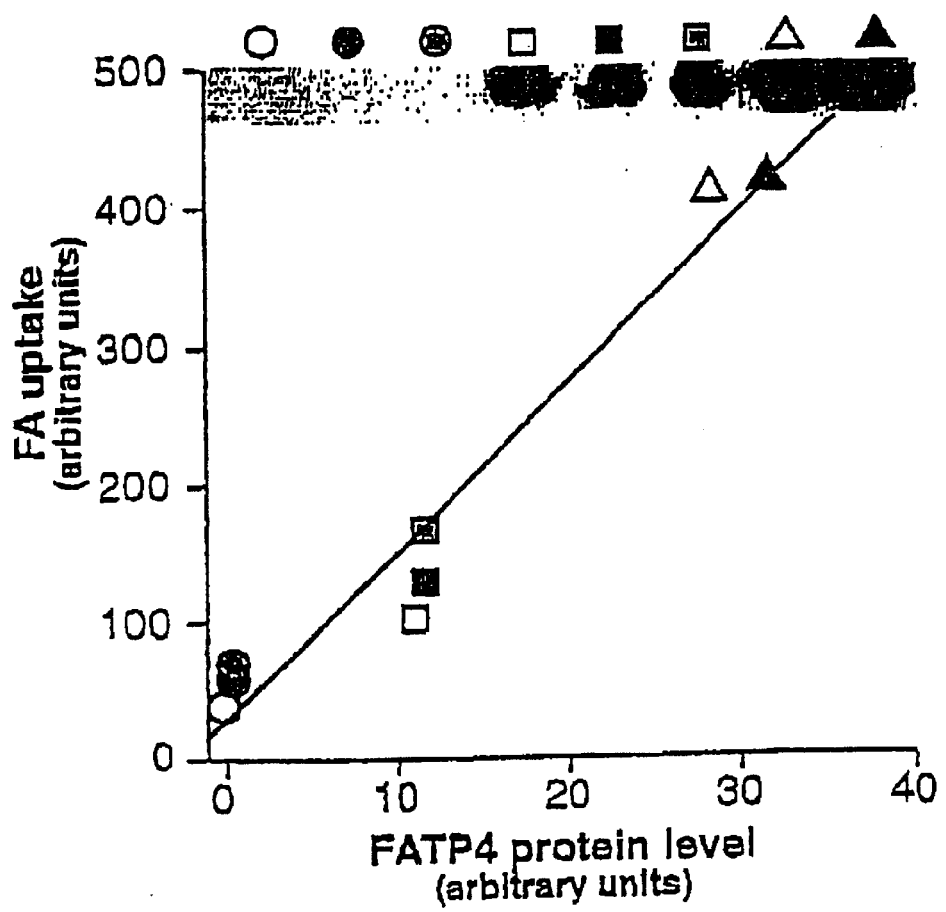
FIG. 95. Mammalian expression constructs containing either hsFATP4 (squares and triangles) or empty control vector (circles) were stably transfected into 293 cells. Short-term uptake of Bodipy-FA in the presence of BSA was determined by FACS. The mean fluorescence of the viable cell population is expressed in arbitrary fluorescence units. FATP4 protein expression was determined by densitometry of anti-FATP4 Western blots, and is expressed in arbitrary units.

Using a mammalian expression vector, we generated 40 stable 239 cell lines expressing hsFATP4 and 20 cell lines transfected with a control plasmid. The ability of the different cell lines to take up FA, as assessed by uptake assays using the fluorescently labeled Bodipy-palmitate, correlated well with their FATP4 expression levels determined by Western blotting (FIG. 95). All 20 vector control clones showed amounts of Bodipy-FA uptake similar to each other and to untransfected 239 cells. In contrast, among the 40 FATP4 transfected clones, a large number (~20) showed an approximately 2-fold increase in Bodipy-FA uptake compared to any of the vector controls, and three had a 5- to 10-fold increase in Bodipy-FA uptake.

Figure 97:
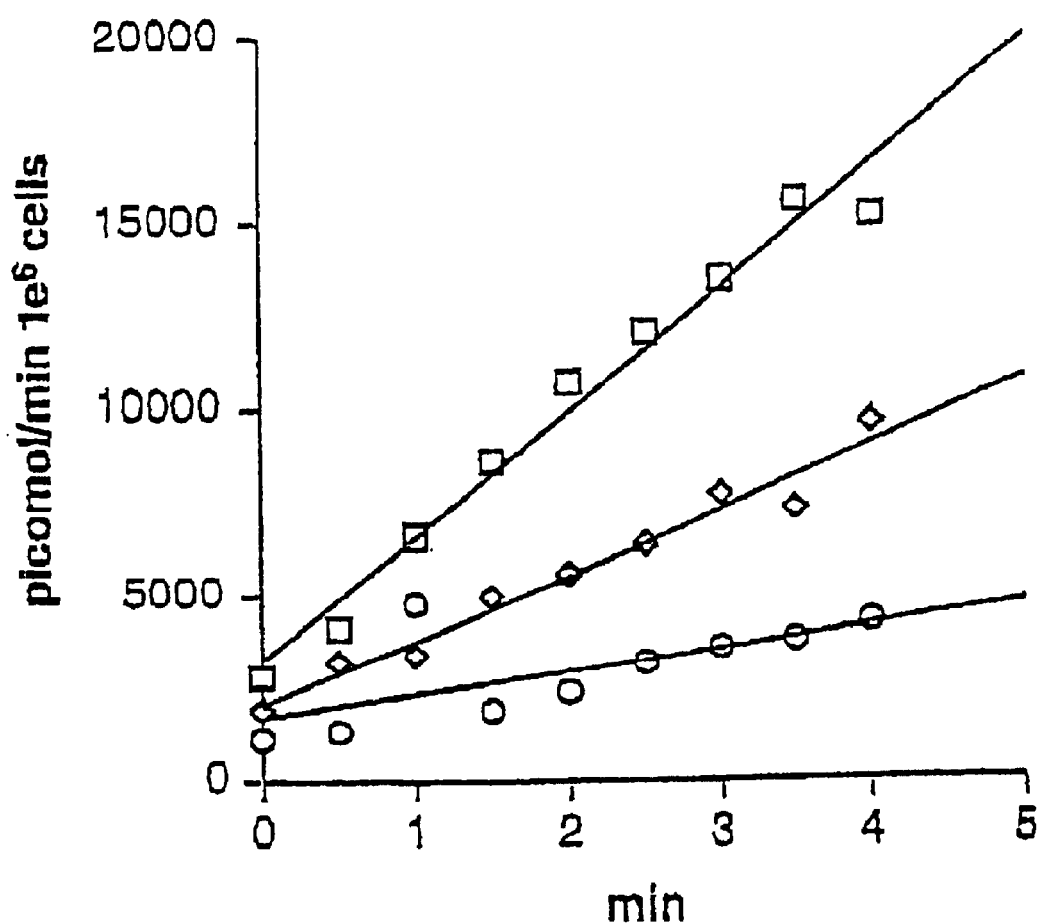
FIG. 97. The rate of [$^2$H]palmitate uptake by 293 cells, which were stably transfected with a construct for either human FATP4 (diamonds) or an empty vector (circles), was compared to that of isolated enterocytes (squares).
Figure 98:
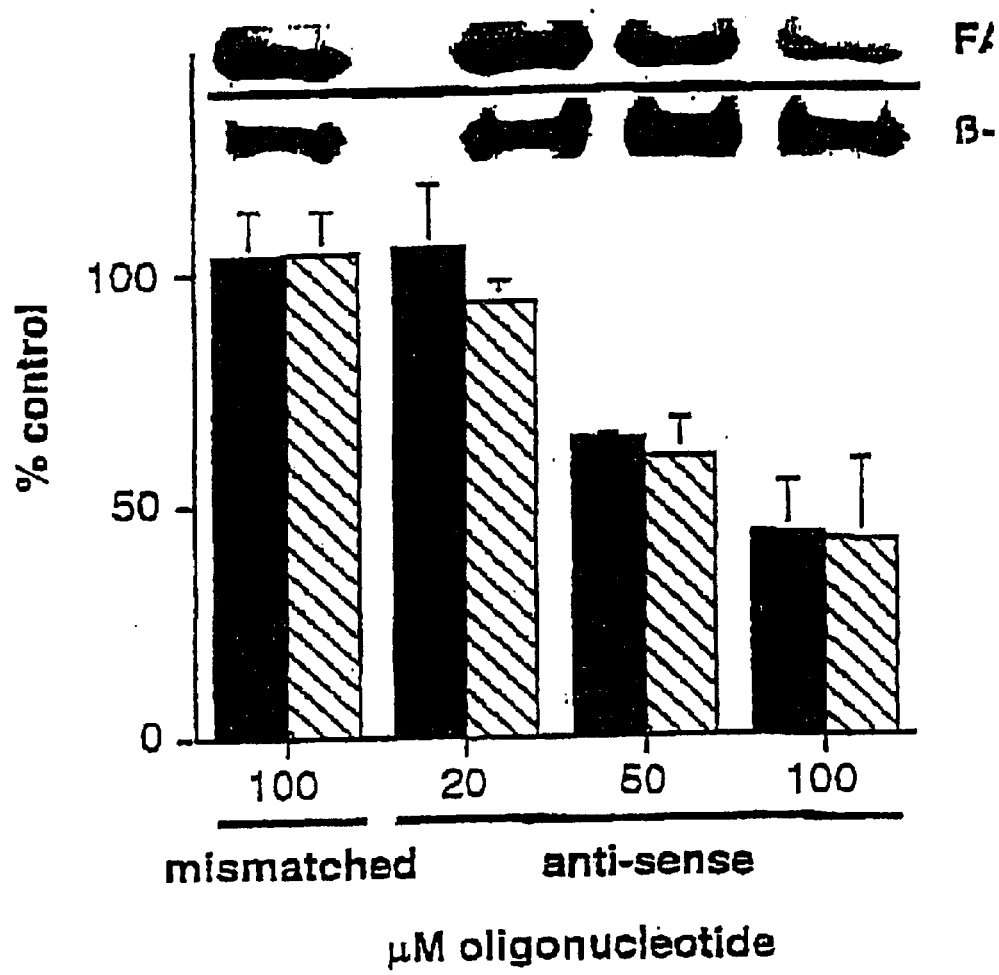
FIG. 98. Isolated enterocytes were incubated for 48 h with increasing concentrations of the FATP4 antisense oligonucleotide or with 100 µM of a randomized control oligonucleotide with identical nucleotide composition to the FATP4 antisense oligonucleotide. The uptake of oleate by the enterocytes was then measured over a 5 min time interval (solid bars). In parallel, the levels of FATP4 protein and, as a loading control, β-catenin, were determined by Western blotting and quantitated using densitometry (hatched bars). FA uptake and FATP4 protein levels were normalized to that of untreated cells. The averages and standard deviations of 4 independent experiments are shown.
Figure 99:
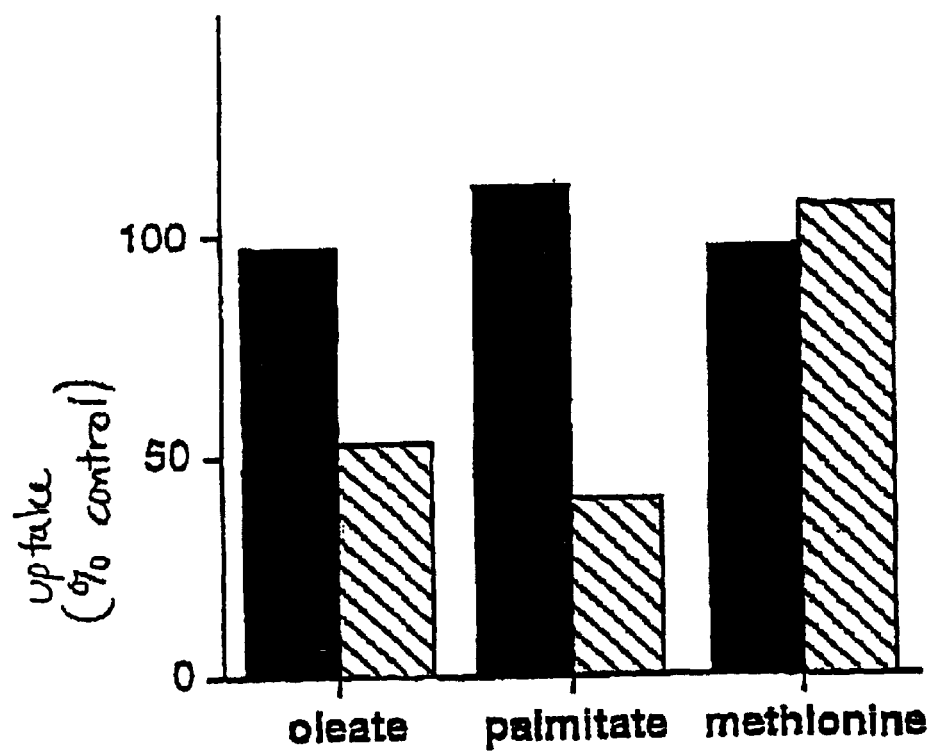
FIG. 99. Uptake rates of [$^3$H]oleate, [$^3$H]palmitate and [$^{35}$S]methionine by primary enterocytes were measured after 48 h incubation with either 100 µM FATP4 antisense (solid bars) or 100 µM randomized control oligonucleotide (hatched bars) and expressed as % of untreated cells.

Several of the cell lines with the highest amount of Bodipy-FA uptake as well as isolated primary enterocytes were used to measure the uptake of radiolabeled FAs. Short-term uptake by 293 cells and enterocytes of all FAs tested was linear (FIG. 97). hsFATP4 expression enhanced the rate of palmitate uptake approximately 3 fold over 293 cells transfected with vector alone (FIG. 97) and also accelerated the uptake of oleate but not of linolate, arachidonate, octanoate, butyrate or cholesterol (Table 6). Isolated primary enterocytes showed a similar preference for palmitate and oleate, and absence of transport of arachidonate, octanoate, and butyrate, but displayed a more robust transport of linolate and cholesterol than the transfected 293 cells.

Figure 96:
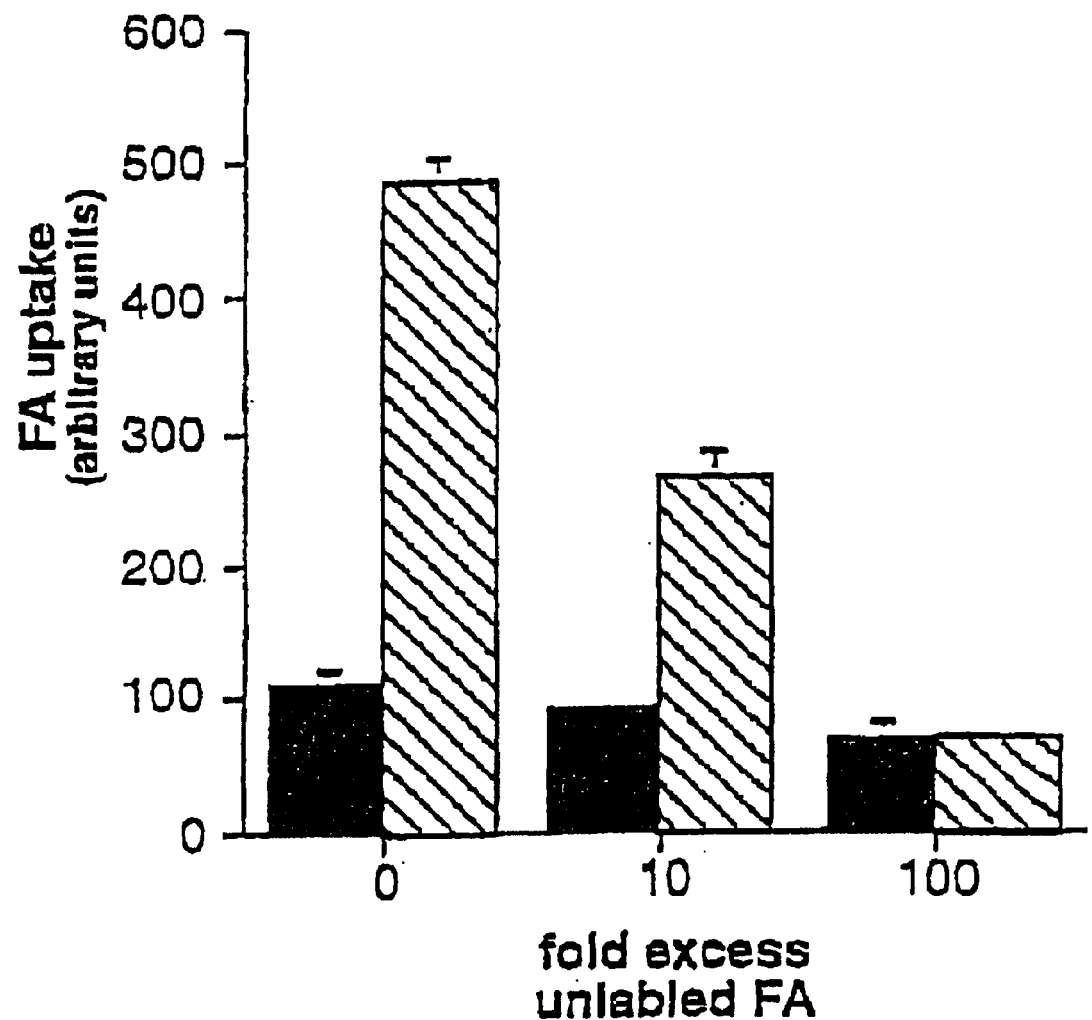
FIG. 96. Short-term uptake of Bodipy-palmitate (1 µM), either by control cells (black bars) or FATP4-expressing cells (hatched bars), was measured in the presence of 0, 10, 100 µM unlabeled palmitate. FA uptake was quantified by FACS and expressed in arbitrary fluorescence units.

To further characterize the substrate specificity of FATP4, we measured the uptake by stably transfected 293 cells of 5 µM Bodipy-FA in the presence of a 20 fold molar excess (i.e., 100 µM) of FAs, FA-derivatives and lipid soluble vitamins and hormones. Both saturated and non-saturated fatty acids containing 10 to 26 C atoms strongly competed for uptake of Bodipy-palmitate (FIG. 96 and Table 7) and thus are presumed to be substrates of FATP4. In contrast, fatty acids with eight of fewer C atoms did not compete and thus are presumed not to be FATP4 substrates. Similarly, esters of long chain FAs and other hydrophobic molecules tested had no effect on uptake of Bodipy-palmitate.

LCFA Uptake Assays (Methods)

Bodipy-FA uptake assays using FACS were performed, adapted to a 96-well format. LCFA uptake assays with enterocytes or with stably transfected 293 cells were done as follows. Mixed micelles of radiolabeled FA (NEN) and taurocholate (Sigma) in HBS were generated by brief sonication at 37° C. Equal volumes of cells and micelle solution were mixed, resulting in a final FA concentration of 25 µM for antisense assays and 10 µM for substrate specificity assays. Final taurocholate concentration was 5 mM. Cells were incubated for the indicated amount of time at 37° C. The assay was stopped by transferring the cells onto filter paper followed by extensive washes with ice-cold HBS containing 0.1% BSA using a cell harvester (Brandell). Incorporated oleate was then determined by β-scintillation counting (Beckman).

TABLE 6

Uptake of Different Substrates by FATP4 Expressing Cell Lines and Enterocytes

| Fatty Acid | 293 Cells Control* | 293 Cells Stably Expressing FATP4 | FATP4 specific | Enterocytes* |
|---|---|---|---|---|
| Palmitate | 564 | 1695 | 1131 | 3036 |
| Oleate | 662 | 1122 | 459 | 117 |
| Linolate | 640 | 673 | 33 | 116 |
| Arachidonate | 3 | 5 | 2 | 0 |
| Octanoate | 0 | 0 | 0 | 5 |
| Butyrate | 0 | 50 | 50 | 73 |
| Cholesterol | 319 | 345 | 26 | 531 |

Uptake of different substrates by enterocytes and by control and stable FATP4-expressing 293 cells. The rates of uptake for the indicated fatty acids was measured over 4 min taking measurements every 30 s. All fatty acids were at a concentration of 10 µM in HBS containing 5 mM taurocholate.
*Uptake measured as pmol/min $10^6$ cells

TABLE 7

Competition of Bodipy-FA Uptake by FATP4 Expressing Cells

| Fatty Acids | Formula | Competition |
|---|---|---|
| Butyric Acid | $C_4H_8O_2$ | − |
| Caproic Acid | $C_6H_{12}O_2$ | − |
| Caprylic Acid | $C_8H_{16}O_2$ | − |
| Capric Acid | $C_{10}H_{20}O_2$ | ++ |
| Lauric Acid | $C_{12}H_{24}O_2$ | ++ |
| Myristic Acid | $C_{14}H_{28}O_2$ | ++ |
| Palmitic Acid | $C_{16}H_{32}O_2$ | ++ |
| Stearic Acid | $C_{18}H_{36}O_2$ | + |
| Oleic Acid | $C_{18}H_{34}O_2$ | ++ |
| Linoleic Acid | $C_{18}H_{32}O_2$ | ++ |
| Arachidic Acid | $C_{20}H_{40}O_2$ | ++ |
| Lignoceric Acid | $C_{24}H_{48}O_2$ | ++ |
| Cerotic Acid | $C_{26}H_{52}O_2$ | ++ |
| Fatty Acid Derivatives | | |
| Palmitic Acid Methyl Ester | $C_{17}H_{34}O_2$ | − |
| Stearic Acid Methyl Ester | $C_{19}H_{38}O_2$ | − |
| Oleic Acid Ethyl Ester | $C_{20}H_{38}O_2$ | − |
| Oleic Acid Oley Ester | $C_{36}H_{68}O_2$ | − |
| Oleoyl CoA | $C_{39}H_{68}N_7O_{17}P_3S$ | − |
| Cholesteryl Oleate | $C_{45}H_{78}O_2$ | − |
| Lipid-Soluble Vitamins & Homones | | |
| Retinoic Acid (Pro-Vitamin A) | $C_{20}H_{28}O_2$ | ± |
| Ergocalciferol (Vitamin D2) | $C_{28}H_{44}O_2$ | − |
| Tocopherol (Vitamin E) | $C_{29}H_{50}O_2$ | − |
| 3-Phytylamenadione (Vitamin K1) | $C_{31}H_{46}O_2$ | − |
| Prostaglandin E2 | $C_{20}H_{32}O_5$ | − |

Competition for Bodipy-FA uptake by FATP4 expressing cells by different hydrophobic compounds. The uptake of 5 µM Bodipy-FA, C1-Bodipy-C12 was measured in the presence of a 20-fold molar excess (i.e., 100 µM) of the indicated fatty acids or fatty acid derivatives. The maximal 100% inhibition was defined as the amount of Bodipy-FA incorporated in the presence of 200 µM lauric acid which was on average 18% ± 5% that of untreated cells.
−: 0%–30% inhibition by the indicated substance
±: 30%–50% inhibition
+: 50%–70% inhibition
++: 70%–100% inhibition All references cited herein are incorporated by reference in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for identifying an agent which is an inhibitor of FATP1, comprising the steps of:
   (a) introducing into cells one or more vectors comprising a gene encoding a cell surface protein and a nucleic acid encoding FATP1 comprising the amino acid sequence of SEQ ID NO:25;
   (b) contacting the host cells with an antibodies to said cell surface protein and labeled fatty acid substrate of FATP1;
   (c) contacting a first aliquot of the host cells with an agent being tested as an inhibitor of FATP1, while leaving a second aliquot of the host cells uncontacted with the agent;
   (d) identifying, in said first and second aliquots, host cells expressing said cell surface protein by detecting said antibody to said cell surface protein bound to the host cells; and
   (e) measuring, in the first and second aliquots, uptake of the fatty acid substrate of the host cells identified as expressing the cell surface protein;
wherein less uptake of the fatty acid substrate in the first aliquot compared to the second aliquot is indicative that the agent is an inhibitor of FATP1.

2. The method of claim 1 wherein the cell surface protein is CD2.

3. The method of claim 1 wherein the fatty acid substrate is BODIPY-labeled.

4. A method for identifying an agent which is an inhibitor of fatty acid uptake by a FATP, said FATP comprising the amino acid sequence of SEQ ID NO: 25, comprising the steps of:
   a) maintaining test cells expressing said FATP in the presence of a fatty acid and an agent to be tested as an inhibitor of fatty acid uptake;
   b) measuring uptake of the fatty acid in the test cells; and
   c) comparing uptake of the fatty acid in the test cells with uptake of the fatty acid in suitable control cells;
wherein lower uptake of the fatty acid in the test cells compared to uptake of the fatty acid in the control cells is indicative that the agent is an inhibitor of fatty acid uptake by said FATP.

5. A method for identifying an agent which is an inhibitor of fatty acid uptake by a protein, said protein having FATP1 activity and encoded by a polynucleotide which hybridizes to a complement of the polynucleotide of SEQ ID NO: 24 under stringent conditions comprising incubation in 6×SSC at 65° C., followed by two or more washes in 0.2×SSC/0.5% SDS at 65° C., comprising the steps of:
   a) maintaining test cells expressing said polynucleotide in the presence of a fatty acid and an agent to be tested as an inhibitor of fatty acid uptake;
   b) measuring uptake of the fatty acid in the test cells; and
   c) comparing uptake of the fatty acid in the test cells with uptake of the fatty acid in suitable control cells;
wherein lower uptake of the fatty acid in the test cells compared to uptake of the fatty acid in the control cells is indicative that the agent is an inhibitor of fatty acid uptake by said protein.

6. A method of identifying an agent which is an inhibitor of fatty acid uptake by a protein, said protein having FATP1 activity and encoded by a polynucleotide which hybridizes to a complement of the polynucleotide of SEQ ID NO: 46 under stringent conditions comprising incubation in 6×SSC at 65° C., followed by two or more washes in 0.2×SSC/0.5% SDS at 65° C., comprising the steps of:
   a) maintaining test cells expressing said polynucleotide in the presence of a fatty acid and an agent to be tested as an inhibitor of fatty acid uptake;
   b) measuring uptake of the fatty acid in the test cells; and
   c) comparing uptake of the fatty acid in the test cells with uptake of the fatty acid in suitable control cells;
wherein lower uptake of the fatty acid in the test cells compared to uptake of the fatty acid in the control cells is indicative that the agent is an inhibitor of fatty acid uptake by said protein.

7. A method for identifying an agent which is an inhibitor of a protein comprising the amino acid sequence of SEQ ID NO: 25, comprising the steps of:
   (a) introducing into host cells one or more vectors comprising a polynucleotide expressing said protein;
   (b) culturing a first aliquot of the host cells with fatty acid substrate of said protein and with an agent being tested as an inhibitor of said protein;
   (c) culturing a second aliquot of the host cells with fatty acid substrate of said protein;
   (d) measuring, in the first and second aliquots, uptake of the fatty acid substrate of the host cells;
wherein less uptake of the fatty acid substrate in the first aliquot compared to the second aliquot is indicative that the agent is an inhibitor of said protein.

8. A method for identifying an agent which is an inhibitor of a protein, said protein having FATP1 activity and being encoded by a polynucleotide comprising a nucleotide sequence which hybridizes to a complement of the polynucleotide of SEQ ID NO: 24 under stringent conditions comprising incubation in 6×SSC at 65° C., followed by two or more washes in 0.2×SSC/0.5% SDS at 65° C., comprising the steps of:
   (a) introducing into host cells one or more vectors comprising a polynucleotide expressing said protein;
   (b) culturing a first aliquot of the host cells with fatty acid substrate of said protein and with an agent being tested as an inhibitor of said protein;
   (c) culturing a second aliquot of the host cells with fatty acid substrate of said protein;
   (d) measuring, in the first and second aliquots, uptake of the fatty acid substrate of the host cells;
wherein less uptake of the fatty acid substrate in the first aliquot compared to the second aliquot is indicative that the agent is an inhibitor of said protein.

9. A method for identifying an agent which is an inhibitor of a protein, said protein having FATP1 activity and being encoded by a polynucleotide comprising a nucleotide sequence which hybridizes to a complement of the polynucleotide of SEQ ID NO: 46 under stringent conditions comprising incubation in 6×SSC at 65° C., followed by two or more washes in 0.2×SSC/0.5% SDS at 65° C., comprising the steps of:

(a) introducing into host cells one or more vectors comprising a polynucleotide expressing said protein;

(b) culturing a first aliquot of the host cells with fatty acid substrate of said protein and with an agent being tested as an inhibitor of said protein;

(c) culturing a second aliquot of the host cells with fatty acid substrate of said protein;

(d) measuring, in the first and second aliquots, uptake of the fatty acid substrate of the host cells;

wherein less uptake of the fatty acid substrate in the first aliquot compared to the second aliquot is indicative that the agent is an inhibitor of said protein.

10. A method for identifying an agent which is an inhibitor of fatty acid uptake by a FATP comprising the amino acid sequence of SEQ ID NO:25, comprising the steps of:

a) maintaining test cells expressing said FATP in the presence of a complex of a fatty acid and an agent to be tested as an inhibitor of fatty acid uptake;

b) measuring uptake of the complex in the test cells; and c) comparing uptake of the complex in the test cells with uptake of the complex in suitable control cells;

wherein lower uptake of the complex in the test cells compared to uptake of the complex in the control cells is indicative that the agent is an inhibitor of fatty acid uptake by said protein.

11. The method of claim 5, wherein the protein has an amino acid sequence at least about 95% identical to the amino acid sequence of SEQ ID NO:25.

12. The method of claim 6, wherein the protein has an amino acid sequence at least about 95% identical to the amino acid sequence of SEQ ID NO:25.

13. The method of claim 8, wherein the protein has an amino acid sequence at least about 95% identical to the amino acid sequence of SEQ ID NO:25.

14. The method of claim 9, wherein the protein has an amino acid sequence at least about 95% identical to the amino acid sequence of SEQ ID NO:25.

15. A method for identifying an agent which is an inhibitor of fatty acid uptake by a protein, said protein having FATP1 activity and encoded by a polynucleotide which hybridizes to a complement of the polynucleotide of SEQ ID NO: 24 under stringent conditions comprising incubation in 6×SSC at 65° C. followed by two or more washes in 0.2×SSC/0.5% SDS at 65° C., comprising the steps of:

a) maintaining test cells expressing said FATP in the presence of a complex of a fatty acid and an agent to be tested as an inhibitor of fatty acid uptake;

b) measuring uptake of the complex in the test cells; and c) comparing uptake of the complex in the test cells with uptake of the complex in suitable control cells;

wherein lower uptake of the complex in the test cells compared to uptake of the complex in the control cells is indicative that the agent is an inhibitor of fatty acid uptake by said protein.

16. The method of claim 15, wherein the protein has an amino acid sequence at least abut 95% identical to the amino acid sequence of SEQ ID NO:25.

17. A method for identifying an agent which is an inhibitor of fatty acid uptake by a protein, said protein having FATP1 activity and encoded by a polynucleotide which hybridizes to a complement of the polynucleotide of SEQ ID NO: 24 under stringent conditions comprising incubation in 6×SSC at 65° C., followed by two or more washes in 0.2×SSC/0.5% SDS at 65° C., comprising the steps of:

(a) introducing into cells one or more vectors comprising a gene encoding a cell surface protein not endogenously expressed in said cells and a nucleic acid encoding FATP1 comprising the amino acid sequence of SEQ ID NO:25 to produce transformed host cells;

(b) contacting said host cells with an antibody to the cell surface protein and labeled fatty acid substrate of FATP1;

(c) contacting a first aliquot of said host cells with an agent being tested as an inhibitor of FATP1, while leaving a second aliquot of said host cells uncontacted with the agent;

(d) identifying, in the first and second aliquots, said host cells expressing the cell surface protein by detecting the antibody to the cell surface protein bound to said host cells; and (e) measuring, in the first and second aliquots, uptake of the fatty acid substrate of said host cells identified as expressing the cell surface protein;

wherein less uptake of the fatty acid substrate in the first aliquot compared to the second aliquot is indicative that the agent is an inhibitor of FATP1.

18. The method of claim 17, wherein the cell surface protein is CD2.

19. The method of claim 17, wherein the fatty acid substrate is BODIPY-labeled.

20. A method for identifying an agent which is an inhibitor of fatty acid uptake by a protein, said protein having FATP1 activity and encoded by a polynucleotide which hybridizes to a complement of the polynucleotide of SEQ ID NO: 46 under stringent conditions comprising incubation in 6×SSC at 65° C., followed by two or more washes in 0.2×SSC/0.5% SDS at 65° C., comprising the steps of:

a) maintaining test cells expressing said FATP in the presence of a complex of a fatty acid and an agent to be tested as an inhibitor of fatty acid uptake;

b) measuring uptake of the complex in the test cells; and c) comparing uptake of the complex in the test cells with uptake of the complex in suitable control cells;

wherein lower uptake of the complex in the test cells compared to uptake of the complex in the control cells is indicative that the agent is an inhibitor of fatty acid uptake by said protein.

21. A method for identifying an agent which is an inhibitor of fatty acid uptake by a protein, said protein having FATP1 activity and encoded by a polynucleotide which hybridizes to a complement of the polynucleotide of SEQ ID NO: 46 under stringent conditions comprising incubation in 6×SSC at 65° C., followed by two or more washes in 0.2×SSC/0.5% SDS at 65° C., comprising the steps of:

(a) introducing into cells one or more vectors comprising a gene encoding a cell surface protein not endogenously expressed in said cells and a nucleic acid encoding FATP1 comprising the amino acid sequence of SEQ ID NO:25 to produce transformed host cells;

(b) contacting said host cells with an antibody to the cell surface protein and labeled fatty acid substrate of FATP1;

(c) contacting a first aliquot of said host cells with an agent being tested as an inhibitor of FATP1, while leaving a second aliquot of said host cells uncontacted with the agent;

(d) identifying, in the first and second aliquots, said host cells expressing the cell surface protein by detecting the antibody to the cell surface protein bound to said host cells; and (e) measuring, in the first and second aliquots, uptake of the fatty acid substrate of said host cells identified as expressing the cell surface protein;

wherein less uptake of the fatty acid substrate in the first aliquot compared to the second aliquot is indicative that the agent is an inhibitor of FATP1.

22. The method of claim 21, wherein the cell surface protein is CD2.

23. The method of claim 21, wherein the fatty acid substrate is BODIPY-labeled.

* * * * *

SEQUENCE LISTING

<160> NUMBER OF SEQ ID NOS: 105

<210> SEQ ID NO 1
<211> LENGTH: 340
<212> TYPE: PRT
<213> ORGANISM: Mus musculus

<400> SEQUENCE: 1

```
Phe Ile Phe Thr Ser Gly Thr Thr Gly Leu Pro Lys Pro Ala Ile Leu
 1               5                  10                  15

Ser His Glu Arg Val Ile Gln Val Ser Asn Val Leu Ser Phe Cys Gly
            20                  25                  30

Cys Arg Ala Asp Asp Val Val Tyr Asp Val Leu Pro Leu Tyr His Thr
        35                  40                  45

Ile Gly Leu Val Leu Gly Phe Leu Gly Cys Leu Gln Val Gly Ala Thr
    50                  55                  60

Cys Val Leu Ala Pro Lys Phe Ser Ala Ser Arg Phe Trp Ala Glu Cys
65                  70                  75                  80

Arg Gln His Gly Val Thr Val Ile Gln Tyr Ile Gly Glu Ile Cys Arg
                85                  90                  95

Tyr Leu Leu Arg Gln Pro Val Arg Asp Val Glu Gln Arg His Arg Val
            100                 105                 110

Arg Leu Ala Val Gly Asn Gly Leu Arg Pro Ala Ile Trp Glu Glu Phe
        115                 120                 125

Thr Gln Arg Phe Gly Val Pro Gln Ile Gly Glu Phe Tyr Gly Ala Thr
    130                 135                 140

Glu Cys Asn Cys Ser Ile Ala Asn Met Asp Gly Lys Val Gly Ser Cys
145                 150                 155                 160

Gly Phe Asn Ser Arg Ile Leu Thr His Val Tyr Pro Ile Arg Leu Val
                165                 170                 175

Lys Val Asn Glu Asp Thr Met Glu Pro Leu Arg Asp Ser Glu Gly Leu
            180                 185                 190

Cys Ile Pro Cys Gln Pro Gly Glu Pro Gly Leu Leu Val Gly Gln Ile
        195                 200                 205

Asn Gln Gln Asp Pro Leu Arg Arg Phe Asp Gly Tyr Val Ser Asp Ser
    210                 215                 220

Ala Thr Asn Lys Lys Ile Ala His Ser Val Phe Arg Lys Gly Asp Ser
225                 230                 235                 240

Ala Tyr Leu Ser Gly Asp Val Leu Val Met Asp Glu Leu Gly Tyr Met
                245                 250                 255

Tyr Phe Arg Asp Arg Ser Gly Asp Thr Phe Arg Trp Arg Gly Glu Asn
            260                 265                 270

Val Ser Thr Thr Glu Val Glu Ala Val Leu Ser Arg Leu Leu Gly Gln
        275                 280                 285

Thr Asp Val Ala Val Tyr Gly Val Ala Val Pro Gly Val Glu Gly Lys
    290                 295                 300

Ala Gly Met Ala Ala Ile Ala Asp Pro His Ser Gln Leu Asp Pro Asn
305                 310                 315                 320

Ser Met Tyr Gln Glu Leu Gln Lys Val Leu Ala Ser Tyr Ala Arg Pro
                325                 330                 335

Ile Phe Leu Arg
            340
```

-continued

```
<210> SEQ ID NO 2
<211> LENGTH: 339
<212> TYPE: PRT
<213> ORGANISM: Mus musculus

<400> SEQUENCE: 2

Tyr Ile Tyr Thr Ser Gly Thr Thr Gly Asn Pro Lys Pro Ala Val Ile
1               5                   10                  15

Lys His Phe Arg Tyr Phe Trp Ile Ala Met Gly Ala Gly Lys Ala Phe
            20                  25                  30

Gly Ile Asn Lys Ser Asp Val Val Tyr Ile Thr Met Pro Met Tyr His
        35                  40                  45

Ser Ala Gly Ile Met Gly Ile Gly Ser Leu Ile Ala Phe Gly Ser
50                  55                  60

Thr Ala Val Ile Arg Lys Lys Phe Ser Ala Ser Asn Phe Trp Lys Asp
65                  70                  75                  80

Cys Val Lys Tyr Asn Val Thr Ala Thr Leu Tyr Val Gly Glu Ile Leu
                85                  90                  95

Arg Tyr Leu Cys Asn Val Pro Glu Gln Pro Glu Asp Lys Ile His Thr
            100                 105                 110

Val Arg Leu Ala Met Gly Thr Gly Leu Arg Ala Asn Val Trp Lys Asn
        115                 120                 125

Phe Gln Gln Arg Phe Gly Pro Ile Arg Ile Trp Glu Phe Tyr Gly Ser
130                 135                 140

Thr Glu Gly Asn Val Gly Leu Met Asn Tyr Val Gly His Cys Gly Ala
145                 150                 155                 160

Val Gly Arg Thr Ser Cys Ile Leu Arg Met Leu Thr Pro Phe Glu Leu
                165                 170                 175

Val Gln Phe Asp Ile Glu Thr Ala Glu Pro Leu Arg Asp Lys Gln Gly
            180                 185                 190

Phe Cys Ile Pro Val Glu Pro Gly Lys Pro Gly Leu Leu Leu Thr Lys
        195                 200                 205

Val Arg Lys Asn Gln Pro Phe Leu Gly Tyr Arg Gly Ser Gln Ala Glu
210                 215                 220

Ser Asn Arg Lys Leu Val Ala Asn Val Arg Arg Val Gly Asp Leu Tyr
225                 230                 235                 240

Phe Asn Thr Gly Asp Val Leu Thr Leu Asp Gln Glu Gly Phe Phe Tyr
                245                 250                 255

Phe Gln Asp Arg Leu Gly Asp Thr Phe Arg Trp Lys Gly Glu Asn Val
            260                 265                 270

Ser Thr Gly Glu Val Glu Cys Val Leu Ser Ser Leu Asp Phe Leu Glu
        275                 280                 285

Glu Val Asn Val Tyr Gly Val Pro Val Pro Gly Cys Glu Gly Lys Val
290                 295                 300

Gly Met Ala Ala Val Lys Leu Ala Pro Gly Lys Thr Phe Asp Gly Lys
305                 310                 315                 320

Lys Tyr Gln His Val Arg Ser Trp Leu Pro Ala Tyr Ala Thr Pro His
                325                 330                 335

Phe Ile Arg

<210> SEQ ID NO 3
<211> LENGTH: 345
<212> TYPE: PRT
<213> ORGANISM: Caenorhabditis elegans

<400> SEQUENCE: 3
```

Ile Tyr Thr Ser Gly Thr Thr Gly Leu Pro Lys Ser Ala Ile Met Ser
1               5                   10                  15

Trp Arg Lys Ser Ser Val Gly Cys Gln Val Phe Gly His Val Leu His
            20                  25                  30

Met Thr Asn Glu Ser Thr Val Phe Thr Ala Met Pro Leu Phe His Ser
        35                  40                  45

Thr Ala Leu Leu Gly Ala Cys Ala Ile Leu Ser His Gly Gly Cys
    50                  55                  60

Leu Ala Leu Ser His Lys Phe Ser Ala Ser Thr Phe Trp Lys Gln Val
65                  70                  75                  80

Tyr Leu Thr Gly Ala Thr His Ile Gln Tyr Ile Gly Glu Ile Cys Arg
                85                  90                  95

Tyr Leu Ala Ala Asn Pro Cys Pro Glu Leu Lys Gln His Asn Val
                100                 105                 110

Arg Leu Met Trp Gly Asn Gly Leu Arg Gly Gln Ile Trp Lys Glu Phe
            115                 120                 125

Val Gly Arg Phe Gly Ile Lys Lys Ile Gly Glu Leu Tyr Gly Ser Thr
130                 135                 140

Glu Gly Asn Ser Asn Ile Val Asn Val Asp Asn His Val Gly Ala Cys
145                 150                 155                 160

Gly Phe Met Pro Ile Tyr Pro His Ile Gly Ser Leu Tyr Pro Val Arg
                165                 170                 175

Leu Ile Lys Val Asp Arg Ala Thr Gly Glu Leu Glu Arg Asp Lys Asn
                180                 185                 190

Gly Leu Cys Val Pro Cys Val Pro Gly Glu Thr Gly Glu Met Val Gly
            195                 200                 205

Val Ile Lys Glu Lys Asp Ile Leu Leu Lys Phe Glu Gly Tyr Val Ser
210                 215                 220

Glu Gly Asp Thr Ala Lys Lys Ile Tyr Arg Asp Val Phe Lys His Gly
225                 230                 235                 240

Asp Lys Val Phe Ala Ser Gly Asp Ile Leu His Trp Asp Asp Leu Gly
                245                 250                 255

Tyr Leu Tyr Phe Val Asp Arg Cys Gly Asp Thr Phe Arg Trp Lys Gly
                260                 265                 270

Glu Asn Val Ser Thr Thr Glu Val Glu Gly Ile Leu Gln Pro Val Met
                275                 280                 285

Asp Val Glu Asp Ala Thr Val Tyr Gly Val Thr Val Gly Lys Met Glu
290                 295                 300

Gly Arg Ala Gly Met Ala Gly Ile Val Val Lys Asp Gly Thr Asp Val
305                 310                 315                 320

Glu Lys Phe Ile Ala Asp Ile Thr Ser Arg Leu Thr Glu Asn Leu Ala
                325                 330                 335

Ser Tyr Ala Ile Pro Val Phe Ile Arg
            340                 345

<210> SEQ ID NO 4
<211> LENGTH: 356
<212> TYPE: PRT
<213> ORGANISM: Saccharomyces cerevisiae

<400> SEQUENCE: 4

Tyr Ile Tyr Thr Ser Gly Thr Thr Gly Leu Pro Lys Ala Ala Ile Val
1               5                   10                  15

Val His Ser Arg Tyr Tyr Arg Ile Ala Ala Phe Gly His His Ser Tyr

```
                    20                  25                  30
Ser Met Arg Ala Ala Asp Val Leu Tyr Asp Cys Leu Pro Leu Tyr His
            35                  40                  45

Ser Ala Gly Asn Ile Met Gly Val Gly Gln Cys Val Ile Tyr Gly Leu
        50                  55                  60

Thr Val Val Leu Arg Lys Lys Phe Ser Ala Ser Arg Phe Trp Asp Asp
65                  70                  75                  80

Cys Val Lys Tyr Asn Cys Thr Val Val Gln Tyr Val Gly Glu Val Cys
                85                  90                  95

Arg Tyr Leu Leu His Thr Pro Ile Ser Lys Tyr Glu Lys Met His Lys
            100                 105                 110

Val Lys Val Ala Tyr Gly Asn Gly Leu Arg Pro Asp Ile Trp Gln Asp
        115                 120                 125

Phe Arg Lys Arg Phe Asn Ile Glu Val Ile Gly Glu Phe Tyr Ala Ala
130                 135                 140

Thr Glu Ala Pro Phe Ala Thr Thr Thr Phe Gln Lys Gly Asp Phe Gly
145                 150                 155                 160

Ile Gly Ala Cys Arg Asn Tyr Gly Thr Ile Ile Gln Trp Phe Leu Ser
                165                 170                 175

Phe Gln Gln Thr Leu Val Arg Met Asp Pro Asn Asp Asp Ser Val Ile
            180                 185                 190

Tyr Arg Asn Ser Lys Gly Phe Cys Glu Val Ala Pro Val Gly Glu Pro
        195                 200                 205

Gly Glu Met Leu Met Arg Ile Phe Phe Pro Lys Lys Pro Glu Thr Ser
210                 215                 220

Phe Gln Gly Tyr Leu Gly Asn Ala Lys Glu Thr Lys Ser Lys Val Val
225                 230                 235                 240

Arg Asp Val Phe Arg Arg Gly Asp Ala Trp Tyr Arg Cys Gly Asp Leu
                245                 250                 255

Leu Lys Ala Asp Glu Tyr Gly Leu Trp Tyr Phe Leu Asp Arg Met Gly
            260                 265                 270

Asp Thr Phe Arg Trp Lys Ser Glu Asn Val Ser Thr Thr Glu Val Glu
        275                 280                 285

Asp Gln Leu Thr Ala Ser Asn Lys Glu Gln Tyr Ala Gln Val Leu Val
290                 295                 300

Val Gly Ile Lys Val Pro Lys Tyr Glu Gly Arg Ala Gly Phe Ala Val
305                 310                 315                 320

Ile Lys Leu Thr Asp Asn Ser Leu Asp Ile Thr Ala Lys Thr Lys Leu
                325                 330                 335

Leu Asn Asp Ser Leu Ser Arg Leu Asn Leu Pro Ser Tyr Ala Met Pro
            340                 345                 350

Leu Phe Val Lys
        355

<210> SEQ ID NO 5
<211> LENGTH: 334
<212> TYPE: PRT
<213> ORGANISM: Mycobacterium tuberculosis

<400> SEQUENCE: 5

Tyr Ile Phe Thr Ser Gly Thr Thr Gly Phe Pro Lys Ala Ser Val Met
 1               5                  10                  15

Thr His His Arg Trp Leu Arg Ala Leu Ala Val Phe Gly Gly Met Gly
            20                  25                  30
```

| | | | | | | | | | | |
|---|---|---|---|---|---|---|---|---|---|---|
|Leu|Arg|Leu|Lys|Gly|Ser|Asp|Thr|Leu|Tyr|Ser|Cys|Leu|Pro|Leu|Tyr|
| |35| | | |40| | | |45| | | | | | |
|His|Asn|Asn|Ala|Leu|Thr|Val|Ala|Val|Ser|Ser|Val|Ile|Asn|Ser|Gly|
| |50| | | |55| | | |60| | | | | | |

```
Leu Arg Leu Lys Gly Ser Asp Thr Leu Tyr Ser Cys Leu Pro Leu Tyr
        35                  40                  45

His Asn Asn Ala Leu Thr Val Ala Val Ser Ser Val Ile Asn Ser Gly
 50                  55                  60

Ala Thr Leu Ala Leu Gly Lys Ser Phe Ser Ala Ser Arg Phe Trp Asp
 65                  70                  75                  80

Glu Val Ile Ala Asn Arg Ala Thr Ala Phe Val Tyr Ile Gly Glu Ile
                     85                  90                  95

Cys Arg Tyr Leu Leu Asn Gln Pro Ala Lys Pro Thr Asp Arg Ala His
                100                 105                 110

Gln Val Arg Val Ile Cys Gly Asn Gly Leu Arg Pro Glu Ile Trp Asp
                115                 120                 125

Glu Phe Thr Thr Arg Phe Gly Val Ala Arg Val Cys Glu Phe Tyr Ala
130                 135                 140

Ala Ser Glu Gly Asn Ser Ala Phe Ile Asn Ile Phe Asn Val Pro Arg
145                 150                 155                 160

Thr Ala Gly Val Ser Pro Met Pro Leu Ala Phe Val Glu Tyr Asp Leu
                165                 170                 175

Asp Thr Gly Asp Pro Leu Arg Asp Ala Ser Gly Arg Val Arg Arg Val
                180                 185                 190

Pro Asp Gly Glu Pro Gly Leu Leu Leu Ser Arg Val Asn Arg Leu Gln
                195                 200                 205

Pro Phe Asp Gly Tyr Thr Asp Pro Val Ala Ser Glu Lys Lys Leu Val
                210                 215                 220

Arg Asn Ala Phe Arg Asp Gly Asp Cys Trp Phe Asn Thr Gly Asp Val
225                 230                 235                 240

Met Ser Pro Gln Gly Met Gly His Ala Ala Phe Val Asp Arg Leu Gly
                245                 250                 255

Asp Thr Phe Arg Trp Lys Gly Glu Asn Val Ala Thr Thr Gln Val Glu
                260                 265                 270

Ala Ala Leu Ala Ser Asp Gln Thr Val Glu Glu Cys Thr Val Tyr Gly
                275                 280                 285

Val Gln Ile Pro Arg Thr Gly Gly Arg Ala Gly Met Ala Ala Ile Thr
                290                 295                 300

Leu Arg Ala Gly Ala Glu Phe Asp Gly Gln Ala Leu Ala Arg Thr Val
305                 310                 315                 320

Tyr Gly His Leu Pro Gly Tyr Ala Leu Pro Leu Phe Val Arg
                325                 330
```

<210> SEQ ID NO 6
<211> LENGTH: 2087
<212> TYPE: DNA
<213> ORGANISM: Mus musculus

<400> SEQUENCE: 6

```
acgactcact ataggqagag agctatgacg tcgcatgcac gcgtaagctt gggcccctcg    60
agggatcctc tagagcggcc gccgaccccg aaagctctga gagcgggtgc agtctggcct   120
ggcgtctcgc gtacctggcc cgggagcagc cgacacacac cttcctcatc cacggcgcgc   180
agcgctttag ctacgcggag gctgagcgca gagcaaccg gattgctcgc gcctttctgc    240
gcgcacgggg ctggaccggg ggccgccgag gctcgggcag ggcagcact gaggaaggcg    300 cacgcgtggc gcctccggct ggagatgcgc ctgctagagg gacgaccgcg ccccctctgg   360
cacccggggc gaccgtggcg ctgctcctcc cagcgggccc ggatttcctt tggatttggt   420
```

-continued

```
tcggactggc caaagctggc ctgcgcacgg cctttgtgcc caccgcttta cgccgaggac    480
ccctgctgca ctgcctccgc agctgcggtg cgagtgcgct cgtgctggcc acagagttcc    540
tggagtccct ggagccggac ctgccggcct tgagagccat ggggctccac ctatgggcga    600
cgggccctga actaatgta gctggaatca gcaatttgct atcggaagca gcagaccaag     660
tggatgagcc agtgccgggg tacctctctg ccccccagaa cataatggac acctgcctgt    720
acatcttcac ctctggcact actggcctgc ccaaggctgc tcgaatcagt catctgaagg    780
ttctacagtg ccagggattc taccatctgt gtggagtcca ccaggaggac gtgatctacc    840
tcgcactccc actgtaccac atgtctggct cccttctggg cattgtgggc tgcttgggca    900
ttggggccac cgtggtgctg aaacccaagt ctcagctag ccagttctgg gacgattgcc     960
agaaacacag ggtgacagtg ttccagtaca ttggggagtt gtgccgatac ctcgtcaacc    1020
agcccccgag caaggcagag tttgaccata aggtgcgctt ggcagtgggc agtgggttgc    1080
gcccagacac ctgggagcgt ttcctgcggc gatttggacc tctgcagata ctggagacgt    1140
atggcatgac agagggcaac gtagctacgt tcaattacac aggacggcag ggtgcagtgg    1200
ggcgagcttc ctggctttac aagcacatct tccccttctc cttgattcga tacgatgtca    1260
tgacagggga gcctattcgg aatgcccagg ggcactgcat gaccacatct ccaggtgagc    1320
caggcctact ggtggccca gtgagccagc agtccccctt cctgggctat gctgggctc     1380
cggagctggc caaggacaag ctgctgaagg atgtcttctg gtctggggac gttttcttca    1440
atactgggga cctcttggtc tgtgatgagc aaggctttct tcacttccac gatcgtactg    1500
agacaccat caggtggaag ggagagaatg tggccacaac tgaagtggct gaggtcttgg     1560
agaccctgga cttccttcag gaggtgaaca tctatggagt cacggtgcca gggcacgaag    1620
gcagggcagg catggcggcc ttggctctgc ggcccccgca ggctctgaac ctggtgcagc    1680
tctacagcca tgtttctgag aacttgccac cgtatgcccg acctcggttt ctcaggctcc    1740
aggaatcttt ggccactact gagaccttca acagcagaa ggttaggatg ccaatgagg     1800
gctttgaccc cagtgtactg tctgacccac tctatgttct ggaccaagat ataggggcct    1860
acctgcccct cacacctgcc cggtacagtg ccctcctgtc tggagacctt cgaatctgaa    1920
accttccact tgagggaggg gctcggaggg tacaggccac catggctgca ccagggaggg    1980
ttttcgggta tcttttgtat atggagtcat tattttgtaa taaacagctg gagcttaaaa    2040
aaaaaaaaaa aaaaaaaaaa aaaaaaaaaa aaaaaaaaaa aaaaaaa                  2087
```

<210> SEQ ID NO 7
<211> LENGTH: 613
<212> TYPE: PRT
<213> ORGANISM: Mus musculus

<400> SEQUENCE: 7

```
Ala Ala Asp Pro Glu Ser Ser Glu Ser Gly Cys Ser Leu Ala Trp Arg
  1               5                  10                  15

Leu Ala Tyr Leu Ala Arg Glu Gln Pro Thr His Thr Phe Leu Ile His
                 20                  25                  30

Gly Ala Gln Arg Phe Ser Tyr Ala Glu Ala Glu Arg Glu Ser Asn Arg
             35                  40                  45

Ile Ala Arg Ala Phe Leu Arg Ala Arg Gly Trp Thr Gly Gly Arg Arg
         50                  55                  60

Gly Ser Gly Arg Gly Ser Thr Glu Glu Gly Ala Arg Val Ala Pro Pro
 65                  70                  75                  80
```

-continued

```
Ala Gly Asp Ala Ala Ala Arg Gly Thr Thr Ala Pro Pro Leu Ala Pro
                85                  90                  95

Gly Ala Thr Val Ala Leu Leu Leu Pro Ala Gly Pro Asp Phe Leu Trp
            100                 105                 110

Ile Trp Phe Gly Leu Ala Lys Ala Gly Leu Arg Thr Ala Phe Val Pro
        115                 120                 125

Thr Ala Leu Arg Arg Gly Pro Leu Leu His Cys Leu Arg Ser Cys Gly
    130                 135                 140

Ala Ser Ala Leu Val Leu Ala Thr Glu Phe Leu Glu Ser Leu Glu Pro
145                 150                 155                 160

Asp Leu Pro Ala Leu Arg Ala Met Gly Leu His Leu Trp Ala Thr Gly
                165                 170                 175

Pro Glu Thr Asn Val Ala Gly Ile Ser Asn Leu Leu Ser Glu Ala Ala
            180                 185                 190

Asp Gln Val Asp Glu Pro Val Pro Gly Tyr Leu Ser Ala Pro Gln Asn
        195                 200                 205

Ile Met Asp Thr Cys Leu Tyr Ile Phe Thr Ser Gly Thr Gly Leu
    210                 215                 220

Pro Lys Ala Ala Arg Ile Ser His Leu Lys Val Leu Gln Cys Gln Gly
225                 230                 235                 240

Phe Tyr His Leu Cys Gly Val His Gln Glu Asp Val Ile Tyr Leu Ala
                245                 250                 255

Leu Pro Leu Tyr His Met Ser Gly Ser Leu Gly Ile Val Gly Cys
            260                 265                 270

Leu Gly Ile Gly Ala Thr Val Leu Lys Pro Lys Phe Ser Ala Ser
        275                 280                 285

Gln Phe Trp Asp Asp Cys Gln Lys His Arg Val Thr Val Phe Gln Tyr
    290                 295                 300

Ile Gly Glu Leu Cys Arg Tyr Leu Val Asn Gln Pro Pro Ser Lys Ala
305                 310                 315                 320

Glu Phe Asp His Lys Val Arg Leu Ala Val Gly Ser Gly Leu Arg Pro
                325                 330                 335

Asp Thr Trp Glu Arg Phe Leu Arg Arg Phe Gly Pro Leu Gln Ile Leu
            340                 345                 350

Glu Thr Tyr Gly Met Thr Glu Gly Asn Val Ala Thr Phe Asn Tyr Thr
        355                 360                 365

Gly Arg Gln Gly Ala Val Gly Arg Ala Ser Trp Leu Tyr Lys His Ile
    370                 375                 380

Phe Pro Phe Ser Leu Ile Arg Tyr Asp Val Met Thr Gly Glu Pro Ile
385                 390                 395                 400

Arg Asn Ala Gln Gly His Cys Met Thr Thr Ser Pro Gly Glu Pro Gly
                405                 410                 415

Leu Leu Val Ala Pro Val Ser Gln Gln Ser Pro Phe Leu Gly Tyr Ala
            420                 425                 430

Gly Ala Pro Glu Leu Ala Lys Asp Lys Leu Leu Lys Asp Val Phe Trp
        435                 440                 445

Ser Gly Asp Val Phe Phe Asn Thr Gly Asp Leu Leu Val Cys Asp Glu
450                 455                 460

Gln Gly Phe Leu His Phe His Asp Arg Thr Gly Asp Thr Ile Arg Trp
                465                 470                 475                 480

Lys Gly Glu Asn Val Ala Thr Thr Glu Val Ala Glu Val Leu Glu Thr
            485                 490                 495

Leu Asp Phe Leu Gln Glu Val Asn Ile Tyr Gly Val Thr Val Pro Gly
```

```
                500              505             510
      His Glu Gly Arg Ala Gly Met Ala Ala Leu Ala Leu Arg Pro Pro Gln
                    515                 520                 525

Ala Leu Asn Leu Val Gln Leu Tyr Ser His Val Ser Glu Asn Leu Pro
              530                 535                 540

Pro Tyr Ala Arg Pro Arg Phe Leu Arg Leu Gln Glu Ser Leu Ala Thr
      545                 550                 555                 560

Thr Glu Thr Phe Lys Gln Gln Lys Val Arg Met Ala Asn Glu Gly Phe
                      565                 570                 575

Asp Pro Ser Val Leu Ser Asp Pro Leu Tyr Val Leu Asp Gln Asp Ile
                  580                 585                 590

Gly Ala Tyr Leu Pro Leu Thr Pro Ala Arg Tyr Ser Ala Leu Leu Ser
              595                 600                 605

Gly Asp Leu Arg Ile
              610

<210> SEQ ID NO 8
<211> LENGTH: 2301
<212> TYPE: DNA
<213> ORGANISM: Mus musculus

<400> SEQUENCE: 8
cccacgcgtc cgcccacgcg tccggcatgg ccaagctggg cgtggaggcg gctctcatca    60
acaccaacct taggcgggat gccctgcgcc actgtcttga cacctcaaag gcacgagctc   120
tcatctttgg cagtgagatg gcctcagcta tctgtgagat ccatgctagc ctggagccca   180
cactcagcct cttctgctct ggatcctggg agcccagcac agtgcccgtc agcacagagc   240
atctggaccc tcttctggaa gatgccccga agcacctgcc cagtcaccca gacaagggtt   300
ttacagataa gctcttctac atctacacat cgggcaccac ggggctaccc aaagctgcca   360
ttgtggtgca cagcaggtat tatcgtatgg cttccctggt gtactatgga ttccgcatgc   420
ggcctgatga cattgtctat gactgcctcc ccctctacca ctcaagcagg aaacatcgtg   480
gggattggca gtgcttactc cacggcatga ctgtggtgat ccggaagaag ttctcagcct   540
cccggttctg ggatgattgt atcaagtaca actgcacagt ggtacagtac attggcgagc   600
tctgccgcta cctcctgaac cagccacccc gtgaggctga gtctcggcac aaggtgcgca   660
tggcactggg caacggtctc cggcagtcca tctggaccga cttctccagc cgtttccaca   720 tccccccaggt ggctgagttc tatggggcca ctgaatgcaa ctgtagcctg gcaactttg   780 acagccgggt gggggcctgt ggcttcaata gccgcatcct gtcctttgtg taccctatcc   840
gtttggtacg tgtcaatgag gataccatgg aactgatccg gggacccgat ggagtctgca   900
ttccctgtca accaggtcag ccaggccagc tggtgggtcg catcatccag caggaccctc   960
tgcgccgttt cgacgggtac ctcaaccagg tgccaacaa caagaagatt gctaatgatg  1020
tcttcaagaa gggggaccaa gcctacctca ctggtgacgt cctggtgatg gatgagctgg  1080
gttacctgta cttccgagat cgcactgggg acacgttccg ctggaaaggg gagaatgtat  1140
ctaccactga ggtggagggc acactcagcc gcctgcttca tatggcagat gtggcagttt  1200
atggtgttga ggtgccagga actgaaggcc gagcaggaat ggctgccgtt gcaagtccca  1260
tcagcaactg tgacctggag agctttgcac agaccttgaa aaaggagctg cctctgtatg  1320
cccgccccat cttcctgcgc ttcttgcctg agctgcacaa gacagggacc ttcaagttcc  1380
agaagacaga gttgcggaag gagggctttg acccatctgt tgtgaaagac ccgctgttct  1440
```

-continued

```
atctggatgc tcggaagggc tgctacgttg cactggacca ggaggcctat acccgcatcc    1500
aggcaggcga ggagaagctg tgatttcccc ctacatccct ctgagggcca agatgctg      1560 gattcagagc cctagcgtcc accccagagg gtcctgggca atgccagacc aaagctagca    1620
gggcccgcac ctccgcccct aggtgctgat ctcccctctc ccaaactgcc aagtgactca    1680
ctgccgcttc cccgaccctc cagaggcttt ctgtgaaagt ctcatccaag ctgtgtcttc    1740
tggtccaggc gtggccctg gccccagggt ttctgatagg ctcctttagg atggtatctt     1800
gggtccagcg ggccagggtg tgggagagga gtcactaaga tccctccaat cagaagggag    1860
cttacaaagg aaccaaggca aagcctgtag actcaggaag ctaagtggcc agagactata    1920
gtggccagtc atcccatgtc cacagaggat cttggtccag agctgccaaa gtgtcacctc    1980
tccctgcctg cacctctggg gaaaagagga cagcatgtgg ccactgggca cctgtctcaa    2040
gaagtcagga tcacacactc agtccttgtt tctccaggtt cccttgttct tgtctcgggg    2100
agggagggac gagtgtcctg tctgtccttc ctgcctgtct gtgagtctgt gttgcttctc    2160
catctgtcct agcctgagtg tgggtggaac aggcatgagg agagtgtggc tcagggcca    2220 ataaactctg ccttgactcc tcttaaaaaa aaaaaaaaa aaaaaaaaaa aaaaaaaaa     2280 aaaaaaaaaa aaaaaaaaaa a                                             2301
```

<210> SEQ ID NO 9
<211> LENGTH: 506
<212> TYPE: PRT
<213> ORGANISM: Mus musculus

<400> SEQUENCE: 9

```
His Ala Ser Ala His Ala Ser Gly Met Ala Lys Leu Gly Val Glu Ala
  1               5                  10                  15

Ala Leu Ile Asn Thr Asn Leu Arg Arg Asp Ala Leu Arg His Cys Leu
             20                  25                  30

Asp Thr Ser Lys Ala Arg Ala Leu Ile Phe Gly Ser Glu Met Ala Ser
         35                  40                  45

Ala Ile Cys Glu Ile His Ala Ser Leu Glu Pro Thr Leu Ser Leu Phe
     50                  55                  60

Cys Ser Gly Ser Trp Glu Pro Ser Thr Val Pro Val Ser Thr Glu His
 65                  70                  75                  80

Leu Asp Pro Leu Leu Glu Asp Ala Pro Lys His Leu Pro Ser His Pro
                 85                  90                  95

Asp Lys Gly Phe Thr Asp Lys Leu Phe Tyr Ile Tyr Thr Ser Gly Thr
            100                 105                 110

Thr Gly Leu Pro Lys Ala Ala Ile Val Val His Ser Arg Tyr Tyr Arg
        115                 120                 125

Met Ala Ser Leu Val Tyr Tyr Gly Phe Arg Met Arg Pro Asp Asp Ile
    130                 135                 140

Val Tyr Asp Cys Leu Pro Leu Tyr His Ser Ser Arg Lys His Arg Gly
145                 150                 155                 160

Asp Trp Gln Cys Leu Leu His Gly Met Thr Val Val Ile Arg Lys Lys
                165                 170                 175

Phe Ser Ala Ser Arg Phe Trp Asp Asp Cys Ile Lys Tyr Asn Cys Thr
            180                 185                 190

Val Val Gln Tyr Ile Gly Glu Leu Cys Arg Tyr Leu Leu Asn Gln Pro
        195                 200                 205

Pro Arg Glu Ala Glu Ser Arg His Lys Val Arg Met Ala Leu Gly Asn
    210                 215                 220
```

-continued

```
Gly Leu Arg Gln Ser Ile Trp Thr Asp Phe Ser Ser Arg Phe His Ile
225                 230                 235                 240

Pro Gln Val Ala Glu Phe Tyr Gly Ala Thr Glu Cys Asn Cys Ser Leu
            245                 250                 255

Gly Asn Phe Asp Ser Arg Val Gly Ala Cys Gly Phe Asn Ser Arg Ile
        260                 265                 270

Leu Ser Phe Val Tyr Pro Ile Arg Leu Val Arg Val Asn Glu Asp Thr
    275                 280                 285

Met Glu Leu Ile Arg Gly Pro Asp Gly Val Cys Ile Pro Cys Gln Pro
290                 295                 300

Gly Gln Pro Gly Gln Leu Val Gly Arg Ile Ile Gln Gln Asp Pro Leu
305                 310                 315                 320

Arg Arg Phe Asp Gly Tyr Leu Asn Gln Gly Ala Asn Asn Lys Lys Ile
                325                 330                 335

Ala Asn Asp Val Phe Lys Lys Gly Asp Gln Ala Tyr Leu Thr Gly Asp
            340                 345                 350

Val Leu Val Met Asp Glu Leu Gly Tyr Leu Tyr Phe Arg Asp Arg Thr
        355                 360                 365

Gly Asp Thr Phe Arg Trp Lys Gly Glu Asn Val Ser Thr Thr Glu Val
    370                 375                 380

Glu Gly Thr Leu Ser Arg Leu Leu His Met Ala Asp Val Ala Val Tyr
385                 390                 395                 400

Gly Val Glu Val Pro Gly Thr Glu Gly Arg Ala Gly Met Ala Ala Val
                405                 410                 415

Ala Ser Pro Ile Ser Asn Cys Asp Leu Glu Ser Phe Ala Gln Thr Leu
            420                 425                 430

Lys Lys Glu Leu Pro Leu Tyr Ala Arg Pro Ile Phe Leu Arg Phe Leu
        435                 440                 445

Pro Glu Leu His Lys Thr Gly Thr Phe Lys Phe Gln Lys Thr Glu Leu
    450                 455                 460

Arg Lys Glu Gly Phe Asp Pro Ser Val Val Lys Asp Pro Leu Phe Tyr
465                 470                 475                 480

Leu Asp Ala Arg Lys Gly Cys Tyr Val Ala Leu Asp Gln Glu Ala Tyr
                485                 490                 495

Thr Arg Ile Gln Ala Gly Glu Glu Lys Leu
            500                 505
```

<210> SEQ ID NO 10
<211> LENGTH: 2277
<212> TYPE: DNA
<213> ORGANISM: Mus musculus

<400> SEQUENCE: 10

```
cactcatcag agctaagaga gactacacgc tctcatctac ttcagaaaga gccaatgcca    60
tgggtatttg aagaaactaa accttactgc tgttgctgct tctgctggtt ggcctggggc   120
agcccccatg ccagcagct atggctctgg ccctgcgttg gttcctggga ccccacat     180
gccttgtgct gcttggcttg gcattgctgg gcagaccctg atcagctcc tggatgcccc    240
actggctgag cctggtagga gcagctctta cctattcct attgcctcta cagccacccc    300
cagggctacg ctggctgcat aaagatgtgg cttttcacctt caagatgctt ttctatggcc   360
taaagttcag gcgacgcctt aacaaacatc ctccagagac ctttgtggat gctttagagc   420
ggcaagcact ggcatggcct gaccgggtgg ccttggtgtg tactgggtct gagggctcct   480
```

```
caatcacaaa tagccagctg atgccaggt cctgtcaggc agcatgggtc ctgaaagcaa      540
agctgaagga tgccgtaatc cagaacacaa gagatgctgc tgctatctta gttctcccgt      600
ccaagaccat ttctgctttg agtgtgtttc tggggttggc caagttgggc tgccctgtgg      660
cctggatcaa tccacacagc cgagggatgc ccttgctaca ctctgtacgg agctctgggg      720
ccagtgtgct gattgtggat ccagacctcc aggagaacct ggaagaagtc cttcccaagc      780
tgctagctga gaacattcac tgcttctacc ttggccacag ctcacccacc ccgggagtag      840
aggctctggg agcttccctg gatgctgcac cttctgaccc agtacctgcc agccttcgag      900
ctacgattaa gtggaaatct cctgccatat tcatctttac ttcagggacc actggactcc      960
caaagccagc catcttatca catgagcggg tcatacaagt gagcaacgtg ctgtccttct     1020
gtggatgcag agctgatgat gtggtctatg acgtcctacc tctgtaccat acgatagggc     1080
ttgtccttgg attccttggc tgcttacaag ttggagccac ctgtgtcctg cccccaagt     1140 tctctgcctc ccgattctgg gctgagtgcc ggcagcatgg cgtaacagtg atcttgtatg     1200
tgggtgaaat cctgcggtac ttgtgtaacg tccctgagca accagaagac aagatacata     1260
cagtgcgctt ggccatggga actggacttc gggcaaatgt gtggaaaaac ttccagcaac     1320
gctttggtcc cattcggatc tgggaattct acggatccac agagggcaat gtgggcttaa     1380
tgaactatgt gggccactgc ggggctgtgg aaggaccag ctgcatcctt cgaatgctga     1440
ctccctttga gcttgtacag ttcgacatag agacagcaga gcctctgagg gacaaacagg     1500 gttttttgcat tcctgtggag ccaggaaagc caggacttct tttgaccaag gttcgaaaga     1560
accaaccctt cctgggctac cgtggttccc aggccgagtc caatcggaaa cttgttgcga     1620
atgtacgacg cgtaggagac ctgtacttca acactgggga cgtgctgacc ttggaccagg     1680
aaggcttctt ctactttcaa gaccgccttg gtgacacctt ccggtggaag ggcgaaaacg     1740
tatctactgg agaggtggag tgtgttttgt ctagcctaga cttcctagag gaagtcaatg     1800
tctatggtgt gcctgtgcca gggtgtgagg gtaaggttgg catggctgct gtgaaactgg     1860
ctcctgggaa gactttttgat gggcagaagc tataccagca tgtccgctcc tggctccctg     1920
cctatgccac acctcatttc atccgtatcc aggattccct ggagatcaca aacacctaca     1980
agctggtaaa gtcacggctg gtgcgtgagg gttttgatgt ggggatcatt gctgacccc     2040 tctacatact ggacaacaag gcccagacct tccggagtct gatgccagat gtgtaccagg     2100
ctgtgtgtga aggaacctgg aatctctgac cacctagcca actggaaggc aatccaaaag     2160
tgtagagatt gacactagtc agcttcacaa agttgtccgg gttccagatg cccatggccc     2220
agtagtactt agagaataaa cttgaatgtg tatacaaaaa aaaaaaaaaa aaaaaaa       2277
```

<210> SEQ ID NO 11
<211> LENGTH: 662
<212> TYPE: PRT
<213> ORGANISM: Mus musculus

<400> SEQUENCE: 11

Met Ala Leu Ala Leu Arg Trp Phe Leu Gly Asp Pro Thr Cys Leu Val
 1               5                  10                  15

Leu Leu Gly Leu Ala Leu Leu Gly Arg Pro Trp Ile Ser Ser Trp Met
            20                  25                  30

Pro His Trp Leu Ser Leu Val Gly Ala Ala Leu Thr Leu Phe Leu Leu
        35                  40                  45

Pro Leu Gln Pro Pro Gly Leu Arg Trp Leu His Lys Asp Val Ala
    50                  55                  60

```
Phe Thr Phe Lys Met Leu Phe Tyr Gly Leu Lys Phe Arg Arg Leu
 65                  70                  75                  80

Asn Lys His Pro Pro Glu Thr Phe Val Asp Ala Leu Glu Arg Gln Ala
                 85                  90                  95

Leu Ala Trp Pro Asp Arg Val Ala Leu Val Cys Thr Gly Ser Glu Gly
            100                 105                 110

Ser Ser Ile Thr Asn Ser Gln Leu Asp Ala Arg Ser Cys Gln Ala Ala
                115                 120                 125

Trp Val Leu Lys Ala Lys Leu Lys Asp Ala Val Ile Gln Asn Thr Arg
130                 135                 140

Asp Ala Ala Ile Leu Val Leu Pro Ser Lys Thr Ile Ser Ala Leu
145                 150                 155                 160

Ser Val Phe Leu Gly Leu Ala Lys Leu Gly Cys Pro Val Ala Trp Ile
                165                 170                 175

Asn Pro His Ser Arg Gly Met Pro Leu Leu His Ser Val Arg Ser Ser
            180                 185                 190

Gly Ala Ser Val Leu Ile Val Asp Pro Asp Leu Gln Glu Asn Leu Glu
            195                 200                 205

Glu Val Leu Pro Lys Leu Leu Ala Glu Asn Ile His Cys Phe Tyr Leu
            210                 215                 220

Gly His Ser Ser Pro Thr Pro Gly Val Glu Ala Leu Gly Ala Ser Leu
225                 230                 235                 240

Asp Ala Ala Pro Ser Asp Pro Val Pro Ala Ser Leu Arg Ala Thr Ile
                245                 250                 255

Lys Trp Lys Ser Pro Ala Ile Phe Ile Phe Thr Ser Gly Thr Thr Gly
            260                 265                 270

Leu Pro Lys Pro Ala Ile Leu Ser His Glu Arg Val Ile Gln Val Ser
            275                 280                 285

Asn Val Leu Ser Phe Cys Gly Cys Arg Ala Asp Asp Val Val Tyr Asp
            290                 295                 300

Val Leu Pro Leu Tyr His Thr Ile Gly Leu Val Leu Gly Phe Leu Gly
305                 310                 315                 320

Cys Leu Gln Val Gly Ala Thr Cys Val Leu Ala Pro Lys Phe Ser Ala
                325                 330                 335

Ser Arg Phe Trp Ala Glu Cys Arg Gln His Gly Val Thr Val Ile Leu
            340                 345                 350

Tyr Val Gly Glu Ile Leu Arg Tyr Leu Cys Asn Val Pro Glu Gln Pro
            355                 360                 365

Glu Asp Lys Ile His Thr Val Arg Leu Ala Met Gly Thr Gly Leu Arg
370                 375                 380

Ala Asn Val Trp Lys Asn Phe Gln Gln Arg Phe Gly Pro Ile Arg Ile
385                 390                 395                 400

Trp Glu Phe Tyr Gly Ser Thr Glu Gly Asn Val Gly Leu Met Asn Tyr
                405                 410                 415

Val Gly His Cys Gly Ala Val Gly Arg Thr Ser Cys Ile Leu Arg Met
            420                 425                 430

Leu Thr Pro Phe Glu Leu Val Gln Phe Asp Ile Glu Thr Ala Glu Pro
            435                 440                 445

Leu Arg Asp Lys Gln Gly Phe Cys Ile Pro Val Glu Pro Gly Lys Pro
            450                 455                 460

Gly Leu Leu Leu Thr Lys Val Arg Lys Asn Gln Pro Phe Leu Gly Tyr
465                 470                 475                 480
```

```
Arg Gly Ser Gln Ala Glu Ser Asn Arg Lys Leu Val Ala Asn Val Arg
                485                 490                 495

Arg Val Gly Asp Leu Tyr Phe Asn Thr Gly Asp Val Leu Thr Leu Asp
            500                 505                 510

Gln Glu Gly Phe Phe Tyr Phe Gln Asp Arg Leu Gly Asp Thr Phe Arg
        515                 520                 525

Trp Lys Gly Glu Asn Val Ser Thr Gly Glu Val Glu Cys Val Leu Ser
    530                 535                 540

Ser Leu Asp Phe Leu Glu Val Asn Val Tyr Gly Val Pro Val Pro
545                 550                 555                 560

Gly Cys Glu Gly Lys Val Gly Met Ala Ala Val Lys Leu Ala Pro Gly
                565                 570                 575

Lys Thr Phe Asp Gly Gln Lys Leu Tyr Gln His Val Arg Ser Trp Leu
            580                 585                 590

Pro Ala Tyr Ala Thr Pro His Phe Ile Arg Ile Gln Asp Ser Leu Glu
        595                 600                 605

Ile Thr Asn Thr Tyr Lys Leu Val Lys Ser Arg Leu Val Arg Glu Gly
    610                 615                 620

Phe Asp Val Gly Ile Ile Ala Asp Pro Leu Tyr Ile Leu Asp Asn Lys
625                 630                 635                 640

Ala Gln Thr Phe Arg Ser Leu Met Pro Asp Val Tyr Gln Ala Val Cys
                645                 650                 655

Glu Gly Thr Trp Asn Leu
                660

<210> SEQ ID NO 12
<211> LENGTH: 1622
<212> TYPE: DNA
<213> ORGANISM: Homo sapiens
<220> FEATURE:
<221> NAME/KEY: misc_feature
<222> LOCATION: (1)...(1622)
<223> OTHER INFORMATION: n = A,T,C or G

<400> SEQUENCE: 12
atgggattga ctctttcctg acaaagtgg atgaagtatc aactgaacct atcccagagt      60
catggaggtc tgaagtcact ttttccactc ctgccttata catttatact tctggaacca    120
caggtcttcc aaaagcagcc atgatcactc atcagcgcat atggtatgga actggcctca    180
cttttgtaag cggattgaag gcagatgatg tcatctatat cactctgccc ttttaccaca    240
gtgctgcact actgattggc attcacggat gtattgtggc tggtgctact cttgccttgc    300
ggactaaatt ttcagccagc cagttttggg atgactgcag aaaatacaac gtcactgtca    360
ttcagtatat cggtgaactg cttcggtatt tatgcaactc accacagaaa ccaaatgacc    420
gtgatcataa agtgagactg gcactgggaa atggcttacg aggagatgtg tggagacaat    480
ttgtcaagag atttggggac atatgcatct atgagttcta tgctgccact gaaggcaata    540
ttggatttat gaattatgcg agaaagttg gtgctgttgg aagagtaaac tacctacaga    600
aaaaaatcat aacttatgac ctgattaaat atgatgtgga aaagatgaa cctgtccgtg    660 atgaaaatgg atattgcgtc agagttccca aggtgaagt tggacttctg gtttgcaaaa    720
tcacacaact tacaccattt aatggctatg ctggagcaaa ggctcagaca gagaagaaaa    780
aactgagaga tgtctttaag aaaggagacc tctatttcaa cagtggagat ctcttaatgg    840
ttgaccatga aaatttcatc tatttccacg acagagttgg agatacattc cggtggaaag    900
gggaaaatgt ggccaccact gaagttgctg atatagttgg actggttgat ttttttccaa    960
```

-continued

```
ggaagtaaaa tgtttatggg agtgcatggg ccaagatnat ggaggttcga attggcatgg    1020
cnttccnttc aaaatggaaa gaaaaccatg gaatttgatg gaaagaaatt ttttcagnac    1080
attgctgata accnacctag ttatgcaagg ccccggtttt ntaagaanac aggacaccat    1140
tgagatcact ggaatttta aacaccgcaa atgacctttt ggtggaggag ggctttaacc     1200
cngctgtcat caaagatgcc ttgtatttc ttggatgaca cagcaaaaat gtatgtgcct     1260
atgactgagg acatntataa tgccataagt gntaaaaccc tgaaattntg aatattccca    1320
ggaggataat tcaacatttc cagaaagaaa ctgaatggac agccacttga tataatccaa    1380
ctttaatttg attgaagatt gtgaggaaat tttgtaggaa atttgcatac ccgtaaaggg    1440 agacttttt aaataacagt tgagtctttg caagtaaaaa gatttagaga ttattatttt     1500
tcagtgtgca cctactgttt gtatttgcaa actgagcttg ttggagggaa ggcattattt    1560
tttaaaatac ttagtaaatt aaagaacacc aacatgtgaa aaaaaaaaaa aaaaaaaaa     1620 aa                                                                   1622
```

<210> SEQ ID NO 13
<211> LENGTH: 286
<212> TYPE: PRT
<213> ORGANISM: Homo sapiens

<400> SEQUENCE: 13

```
Tyr Ile Tyr Thr Ser Gly Thr Thr Gly Leu Pro Lys Ala Ala Met Ile
 1               5                  10                  15

Thr His Gln Arg Ile Trp Tyr Gly Thr Gly Leu Thr Phe Val Ser Gly
            20                  25                  30

Leu Lys Ala Asp Asp Val Ile Tyr Ile Thr Leu Pro Phe Tyr His Ser
        35                  40                  45

Ala Ala Leu Leu Ile Gly Ile His Gly Cys Ile Val Ala Gly Ala Thr
    50                  55                  60

Leu Ala Leu Arg Thr Lys Phe Ser Ala Ser Gln Phe Trp Asp Asp Cys
65                  70                  75                  80

Arg Lys Tyr Asn Val Thr Val Ile Gln Tyr Ile Gly Glu Leu Leu Arg
                85                  90                  95

Tyr Leu Cys Asn Ser Pro Gln Lys Pro Asn Asp Arg Asp His Lys Val
            100                 105                 110

Arg Leu Ala Leu Gly Asn Gly Leu Arg Gly Asp Val Trp Arg Gln Phe
        115                 120                 125

Val Lys Arg Phe Gly Asp Ile Cys Ile Tyr Glu Phe Tyr Ala Ala Thr
    130                 135                 140

Glu Gly Asn Ile Gly Phe Met Asn Tyr Ala Arg Lys Val Gly Ala Val
145                 150                 155                 160

Gly Arg Val Asn Tyr Leu Gln Lys Lys Ile Ile Thr Tyr Asp Leu Ile
                165                 170                 175

Lys Tyr Asp Val Glu Lys Asp Glu Pro Val Arg Asp Glu Asn Gly Tyr
            180                 185                 190

Cys Val Arg Val Pro Lys Gly Glu Val Gly Leu Leu Val Cys Lys Ile
        195                 200                 205

Thr Gln Leu Thr Pro Phe Asn Gly Tyr Ala Gly Ala Lys Ala Gln Thr
    210                 215                 220

Glu Lys Lys Lys Leu Arg Asp Val Phe Lys Lys Gly Asp Leu Tyr Phe
225                 230                 235                 240

Asn Ser Gly Asp Leu Leu Met Val Asp His Glu Asn Phe Ile Tyr Phe
```

```
                245              250              255
His Asp Arg Val Gly Asp Thr Phe Arg Trp Lys Gly Glu Asn Val Ala
        260              265              270

Thr Thr Glu Val Ala Asp Ile Val Gly Leu Val Asp Phe Phe
        275              280              285

<210> SEQ ID NO 14
<211> LENGTH: 753
<212> TYPE: DNA
<213> ORGANISM: Homo sapiens

<400> SEQUENCE: 14
caattcggga ccccccagggg cactgtatgg ccacatctcc aggtgagcca ggggaagttg      60
ctaaaggatg tcttccggcc tggggatgtt tcttcaaca ctgggggacct gctggtctgc     120 gatgaccaag gttttctccg cttccatgat cgtactggag acaccttcag gtggaaggg     180 gagaatgtgg ccacaaccga ggtggcagag gtcttcgagg ccctagattt tcttcaggag     240
gtgaacgtct atggagtcac tgtgccaggg catgaaggca gggctggaat ggcagcccta     300
gttctgcgtc cccccacgc tttggacctt atgcagctct acaccacgt gtctgagaac      360 ttgccacctt atgcccggcc ccgattcctc aggctccagg agtctttggc caccacagag     420
accttcaaac agcagaaagt tcggatggca aatgagggct cgacccccag cacctgtct      480 gacccactgt acgttctgga ccaggctgta ggtgcctacc tgcccctcac aactgcccgg     540
tacagcgccc tcctggcagg aaaccttcga atctgagaac ttccacacct gaggcacctg     600
agagaggaac tctgtggggt ggggggccgtt gcaggtgtac tgggctgtca gggatctttt     660
ctataccaga actgcggtca ctattttgta ataaatgtgg ctggagctga tccagctgtc     720
tctgacctac aaaaaaaaaa aaaaaaaaaa aaa                                  753

<210> SEQ ID NO 15
<211> LENGTH: 191
<212> TYPE: PRT
<213> ORGANISM: Homo sapiens

<400> SEQUENCE: 15

Gln Phe Gly Thr Pro Arg Gly Thr Val Trp Pro His Leu Gln Val Ser
  1               5                  10                  15

Gln Gly Lys Leu Leu Lys Asp Val Phe Arg Pro Gly Asp Val Phe Phe
             20                  25                  30

Asn Thr Gly Asp Leu Leu Val Cys Asp Asp Gln Gly Phe Leu Arg Phe
         35                  40                  45

His Asp Arg Thr Gly Asp Thr Phe Arg Trp Lys Gly Glu Asn Val Ala
     50                  55                  60

Thr Thr Glu Val Ala Glu Val Phe Glu Ala Leu Asp Phe Leu Gln Glu
 65                  70                  75                  80

Val Asn Val Tyr Gly Val Thr Val Pro Gly His Glu Gly Arg Ala Gly
                 85                  90                  95

Met Ala Ala Leu Val Leu Arg Pro Pro His Ala Leu Asp Leu Met Gln
            100                 105                 110

Leu Tyr Thr His Val Ser Glu Asn Leu Pro Pro Tyr Ala Arg Pro Arg
        115                 120                 125

Phe Leu Arg Leu Gln Glu Ser Leu Ala Thr Thr Glu Thr Phe Lys Gln
    130                 135                 140

Gln Lys Val Arg Met Ala Asn Glu Gly Phe Asp Pro Ser Thr Leu Ser
145                 150                 155                 160
```

```
Asp Pro Leu Tyr Val Leu Asp Gln Ala Val Gly Ala Tyr Leu Pro Leu
            165                 170                 175

Thr Thr Ala Arg Tyr Ser Ala Leu Leu Ala Gly Asn Leu Arg Ile
        180                 185                 190

<210> SEQ ID NO 16
<211> LENGTH: 734
<212> TYPE: DNA
<213> ORGANISM: Homo sapiens
<220> FEATURE:
<221> NAME/KEY: misc_feature
<222> LOCATION: (1)...(734)
<223> OTHER INFORMATION: n = A,T,C or G

<400> SEQUENCE: 16
tcaagtacaa ctgcacgatt gtcatancat tggtgaactg tgccgntacc tcctgaacca      60
gccaccgcgg gaggcagaaa accagcacca ggttcgcatg cactaggca atggcctccg     120 gcagtccatc tggaccaact tttccagccg cttccacata ccccaggtgg ctgagttyta    180
cggggccaca gagtgcaact gtagcctggg caacttcgac agccaggtgg gggcctgtgg    240
tttcaatagc cgcatcctgt ccttcgtgta ccccatccgg ttggtacgtg tcaacgagga    300
caccatggag ctgatccggg ggcccgacgg cgtctgcatt ccctgccagc caggtgagcc    360
gggccagctg gtgggccgca tcatccagaa agaccccctg cgccgcttcg atggctacct    420 caaccgggc gccaacaaca gaagattgc caaggatgtc ttcaagaagg gggaccaggc      480
ctaccttact ggtgatgtgc tggtgatgga cgagctgggc tacctgtact ccgagaccg    540 cactggggac acgttccgct ggaaaggtga gaacgtgtcc accaccgagg tggaaggcac    600
actcagccgc ctgctggaca tggctgacgt ggccgtgtat ggtgtcgagg tgccaggaac    660
cgagggccgg gccggaatgg ctgctgtggc cagccccact ggcaactgtg acctgggagc    720
gctttgctca ggtc                                                      734

<210> SEQ ID NO 17
<211> LENGTH: 213
<212> TYPE: PRT
<213> ORGANISM: Homo sapiens

<400> SEQUENCE: 17

Ile Gly Glu Leu Cys Arg Tyr Leu Leu Asn Gln Pro Pro Arg Glu Ala
1               5                   10                  15

Glu Asn Gln His Gln Val Arg Met Ala Leu Gly Asn Gly Leu Arg Gln
            20                  25                  30

Ser Ile Trp Thr Asn Phe Ser Ser Arg Phe His Ile Pro Gln Val Ala
        35                  40                  45

Glu Phe Tyr Gly Ala Thr Glu Cys Asn Cys Ser Leu Gly Asn Phe Asp
    50                  55                  60

Ser Gln Val Gly Ala Cys Gly Phe Asn Ser Arg Ile Leu Ser Phe Val
65                  70                  75                  80

Tyr Pro Ile Arg Leu Val Arg Val Asn Glu Asp Thr Met Glu Leu Ile
                85                  90                  95

Arg Gly Pro Asp Gly Val Cys Ile Pro Cys Gln Pro Gly Glu Pro Gly
            100                 105                 110

Gln Leu Val Gly Arg Ile Ile Gln Lys Asp Pro Leu Arg Arg Phe Asp
        115                 120                 125

Gly Tyr Leu Asn Gln Gly Ala Asn Asn Lys Lys Ile Ala Lys Asp Val
    130                 135                 140
```

Phe Lys Lys Gly Asp Gln Ala Tyr Leu Thr Gly Asp Val Leu Val Met
145                 150                 155                 160

Asp Glu Leu Gly Tyr Leu Tyr Phe Arg Asp Arg Thr Gly Asp Thr Phe
                165                 170                 175

Arg Trp Lys Gly Glu Asn Val Ser Thr Thr Glu Val Glu Gly Thr Leu
            180                 185                 190

Ser Arg Leu Leu Asp Met Ala Asp Val Ala Val Tyr Gly Val Glu Val
        195                 200                 205

Pro Gly Thr Glu Gly
    210

<210> SEQ ID NO 18
<211> LENGTH: 1278
<212> TYPE: DNA
<213> ORGANISM: Homo sapiens
<220> FEATURE:
<221> NAME/KEY: misc_feature
<222> LOCATION: (1)...(1278)
<223> OTHER INFORMATION: n = A,T,C or G

<400> SEQUENCE: 18

| | | | | |
|---|---|---|---|---|
| cntgcctctt | gtaccacgtg | atgggacttt | gtcgttggga | tcctcggctg | cttagatctc | 60 |
| ggagccacct | gtgttctggc | ccccaagttc | tctacttcct | gcttctggga | tgactgtcgg | 120 |
| cagcatggcg | tgacagtgat | cctgtatgtg | ggcgagctcc | tgcgntactt | gtgtaacatt | 180 |
| ccccagcaac | cagaggaccg | gacacataca | gtccgcctgg | caatgggcaa | tggactacgg | 240 |
| gctgatgtgt | ggggagacct | tccagcagcg | tttcggtcct | atttcggatc | tngggaagtc | 300 |
| ttacgggcty | ccacagaagg | gcaacatggg | gctttagttc | aactattgtt | ggggcgctg | 360 |
| cggggscctg | grggcaaaga | tggagcttgc | ctcctccgaa | tgctgtcccc | ctttgagctg | 420 |
| gtgcagttcg | acatggaggc | ggcggagcct | gtgagggaca | atcagggctt | ctgcatccct | 480 |
| gtagggctag | gggagccggg | gctgctgttg | accaaggtgg | taagccagca | acccttcgtg | 540 |
| ggctaccgcg | gccccccgaga | gctgtcggaa | cggaagctgg | tgcgcaacgt | gcggcaatcg | 600 |
| ggcgacgttt | actacaacac | cggggacgta | ctggccatgg | accgcgaagg | cttcctctac | 660 |
| ttccgcgacc | gactcgggga | caccttccga | tggaagggcg | agaacgtgtc | cacgcacgag | 720 |
| gtggagggcg | tgttgtcgca | ggtggacttc | ttgcaacagg | ttaacgtgta | tggcgtgtgc | 780 |
| gtgccaggtt | gtgagggtaa | ggtgggcatg | gctgctgtgg | cattagcccc | cggccagact | 840 |
| ttcgacgggg | agaagttgta | ccagcacgtt | cgcgcttggc | tccctgccta | cgctaccccc | 900 |
| catttcatcc | gcatccagga | cgccatggag | gtcaccagca | cgttcaaact | gatgaagacc | 960 |
| cggttggtgc | gtgagggctt | caatgtgggg | atcgtggttg | accctctgtt | tgtactggac | 1020 |
| aaccgggccc | agtccttccg | gcccctgacg | gcagaaatgt | accaggctgt | gtgtgaggga | 1080 |
| acctggaggc | tctgatcacc | tggccaaccc | actggggtag | ggatcaaagc | cagccacccc | 1140 |
| cacccccaaca | cactcggtgt | ccctttcatc | ctgggcctgt | gtgaatccca | gcctggccat | 1200 |
| accctcaacc | tcagtgggct | ggaaatgaca | gtgggccctg | tagcagtggc | agaataaact | 1260 |
| cagmtgygtt | cacagaaa | | | | | 1278 |

<210> SEQ ID NO 19
<211> LENGTH: 199
<212> TYPE: PRT
<213> ORGANISM: Homo sapiens

<400> SEQUENCE: 19

```
Glu Gly Gln His Gly Ala Leu Val Gln Leu Leu Leu Gly Ala Leu Arg
  1               5                  10                  15

Gly Pro Gly Gly Lys Asp Gly Ala Cys Leu Leu Arg Met Leu Ser Pro
             20                  25                  30

Phe Glu Leu Val Gln Phe Asp Met Glu Ala Ala Glu Pro Val Arg Asp
         35                  40                  45

Asn Gln Gly Phe Cys Ile Pro Val Gly Leu Gly Glu Pro Gly Leu Leu
     50                  55                  60

Leu Thr Lys Val Val Ser Gln Gln Pro Phe Val Gly Tyr Arg Gly Pro
 65                  70                  75                  80

Arg Glu Leu Ser Glu Arg Lys Leu Val Arg Asn Val Arg Gln Ser Gly
                 85                  90                  95

Asp Val Tyr Tyr Asn Thr Gly Asp Val Leu Ala Met Asp Arg Glu Gly
            100                 105                 110

Phe Leu Tyr Phe Arg Asp Arg Leu Gly Asp Thr Phe Arg Trp Lys Gly
            115                 120                 125

Glu Asn Val Ser Thr His Glu Val Glu Gly Val Leu Ser Gln Val Asp
130                 135                 140

Phe Leu Gln Gln Val Asn Val Tyr Gly Val Cys Val Pro Gly Cys Glu
145                 150                 155                 160

Gly Lys Val Gly Met Ala Ala Val Ala Leu Ala Pro Gly Gln Thr Phe
                165                 170                 175

Asp Gly Glu Lys Leu Tyr Gln His Val Arg Ala Trp Leu Pro Ala Tyr
            180                 185                 190

Ala Thr Pro His Phe Ile Arg
            195

<210> SEQ ID NO 20
<211> LENGTH: 1361
<212> TYPE: DNA
<213> ORGANISM: Homo sapiens

<400> SEQUENCE: 20
cgcttgtgtg ttaaagaaga aattttcagc aagccagttt tggagtgact gcaagaagta      60
tgatgtgact gtgtttcagt atattggaga actttgtcgc tacctttgca acaatctaa     120 gagagaagga gaaaggatc ataaggtgcg tttggcaatt ggaaatggca tacggagtga     180
tgtatggaga gaatttttag acagatttgg aaatataaag gtgtgtgaac tttatgcagc     240
taccgaatca agcatatctt tcatgaacta cactgggaga attggagcaa ttgggagaac     300
aaatttgttt tacaaacttc tttccacttt tgacttaata agtatgactt tcagaaaga     360 tgaacccatg agaaatgagc agggttgggt attcatgaga aaaggagac ctggacttct     420 catttctcga gtgaatgcaa aaatcccctt ctttggctat gctgggcctt ataagcacac     480
aaaagacaaa ttgctttgtg atgtttttaa gagggagag tttaccttaa atactggaga     540
cttaatagtc caggatcagg acaatttcct ttattttggg gaccgtactg gagacacttt     600
cagatggaaa ggagaaaatg tcgcaaccac tgaggttgct gatgttattg gaatgttgga     660
tttcatacag gaagcaaacg tctatggtgt ggctatatca ggttatgaag gaagagcagg     720
aatggcttct attattttaa accaaatac atctttagat ttggaaaaag tttatgaaca     780
agttgtaaca tttctaccag cttatgcttg tccacgattt ttaagaattc aggaaaaaat     840
ggaagcaaca ggaacattca actattgaa gcatcagttg gtggaagatg gattaatcc     900 actgaaaatt tctgaaccac tttacttcat ggataacttg aaaaagtctt atgttctact     960
```

-continued

```
gaccagggaa ctttatgatc aaataatgtt aggggaaata aaactttaag attttttatat    1020 ctagaacttt catatgcttt cttaggaaga gtgagagggg ggtatatgat tctttatgaa    1080
atggggaaag ggagctaaca ttaattatgc atgtactata tttccttaat atgagagata    1140 atttttaat tgcataagaa ttttaatttc ttttaattga tataaacaga gttgattatt     1200
ctttttatct atttggagat tcagtgcata actaagtatt ttccttaata ctaaagattt    1260
taaataataa atagtggcta gcggtttgga caatcactaa aaatgtactt tctaataagt    1320
aaaatttcta attttgaata aaagattaaa ttttactgaa a                         1361
```

<210> SEQ ID NO 21
<211> LENGTH: 335
<212> TYPE: PRT
<213> ORGANISM: Homo sapiens

<400> SEQUENCE: 21

```
Ala Cys Val Leu Lys Lys Phe Ser Ala Ser Gln Phe Trp Ser Asp
 1               5                  10                  15

Cys Lys Lys Tyr Asp Val Thr Val Phe Gln Tyr Ile Gly Glu Leu Cys
                20                  25                  30

Arg Tyr Leu Cys Lys Gln Ser Lys Arg Glu Gly Glu Lys Asp His Lys
            35                  40                  45

Val Arg Leu Ala Ile Gly Asn Gly Ile Arg Ser Asp Val Trp Arg Glu
        50                  55                  60

Phe Leu Asp Arg Phe Gly Asn Ile Lys Val Cys Glu Leu Tyr Ala Ala
65                  70                  75                  80

Thr Glu Ser Ser Ile Ser Phe Met Asn Tyr Thr Gly Arg Ile Gly Ala
                85                  90                  95

Ile Gly Arg Thr Asn Leu Phe Tyr Lys Leu Leu Ser Thr Phe Asp Leu
            100                 105                 110

Ile Lys Tyr Asp Phe Gln Lys Asp Glu Pro Met Arg Asn Glu Gln Gly
        115                 120                 125

Trp Val Phe Met Arg Lys Arg Arg Pro Gly Leu Leu Ile Ser Arg Val
    130                 135                 140

Asn Ala Lys Asn Pro Phe Phe Gly Tyr Ala Gly Pro Tyr Lys His Thr
145                 150                 155                 160

Lys Asp Lys Leu Leu Cys Asp Val Phe Lys Lys Gly Asp Val Tyr Leu
                165                 170                 175

Asn Thr Gly Asp Leu Ile Val Gln Asp Gln Asp Asn Phe Leu Tyr Phe
            180                 185                 190

Trp Asp Arg Thr Gly Asp Thr Phe Arg Trp Lys Gly Glu Asn Val Ala
        195                 200                 205

Thr Thr Glu Val Ala Asp Val Ile Gly Met Leu Asp Phe Ile Gln Glu
    210                 215                 220

Ala Asn Val Tyr Gly Val Ala Ile Ser Gly Tyr Glu Gly Arg Ala Gly
225                 230                 235                 240

Met Ala Ser Ile Ile Leu Lys Pro Asn Thr Ser Leu Asp Leu Glu Lys
                245                 250                 255

Val Tyr Glu Gln Val Val Thr Phe Leu Pro Ala Tyr Ala Cys Pro Arg
            260                 265                 270

Phe Leu Arg Ile Gln Glu Lys Met Glu Ala Thr Gly Thr Phe Lys Leu
        275                 280                 285

Leu Lys His Gln Leu Val Glu Asp Gly Phe Asn Pro Leu Lys Ile Ser
    290                 295                 300
```

| Glu | Pro | Leu | Tyr | Phe | Met | Asp | Asn | Leu | Lys | Lys | Ser | Tyr | Val | Leu | Leu |
|---|---|---|---|---|---|---|---|---|---|---|---|---|---|---|---|
| 305 | | | | 310 | | | | | 315 | | | | | 320 | |

| Thr | Arg | Glu | Leu | Tyr | Asp | Gln | Ile | Met | Leu | Gly | Glu | Ile | Lys | Leu |
|---|---|---|---|---|---|---|---|---|---|---|---|---|---|---|
| | | | | 325 | | | | | 330 | | | | 335 | |

<210> SEQ ID NO 22
<211> LENGTH: 2007
<212> TYPE: DNA
<213> ORGANISM: Mycobacterium tuberculosis

<400> SEQUENCE: 22

```
tagtcgataa cgtcaaggac gctctgcggg cctgcgcacc ttcctgaggt tggtcgacaa      60
ccaattcgac atttcgcaaa cgaatcgagg cttacgtgt ccgattacta cggcggcgca     120
cacacaacgg tcaggctgat cgacctggca actcggatgc cgcgagtgtt ggcggacacg     180
ccggtgattg tgcgtggggc aatgaccggg ctgctggccc ggccgaattc caaggcgtcg     240
atcggcacgg tgttccagga ccgggccgct cgctacggtg accgagtctt cctgaaattc     300
ggcgatcagc agctgaccta ccgcgacgct aacgccaccg ccaaccggta cgccgcggtg     360
ttggccgccc gcggcgtcgg ccccggcgac gtcgttggca tcatgttgcg taactcaccc     420
agcacagtct tggcgatgct ggccacggtc aagtgcggcg ctatcgccgg catgctcaac     480
taccaccagc gcggcgaggt gttggcgcac agcctgggtc tgctggacgc gaaggtactg     540
atcgcagagt ccgacttggt cagcgccgtc gccgaatgcg cgcctcgcg cggccgggta     600
gcgggcgacg tgctgaccgt cgaggacgtg gagcgattcg ccacaacggc gcccgccacc     660
aacccggcgt cggcgtcggc ggtgcaagcc aaagacaccg cgttctacat cttcacctcg     720
ggcaccaccg gatttcccaa ggccagtgtc atgacgcatc atcggtggct gcgggcgctg     780
gccgtcttcg gagggatggg gctgcggctg aagggttccg acacgctcta cagctgcctg     840
ccgctgtacc acaacaacgc gttaacggtc gcggtgtcgt cggtgatcaa ttctggggcg     900
accctggcgc tgggtaagtc gttttcggcg tcgcggttct gggatgaggt gattgccaac     960
cgggcgacgg cgttcgtcta catcggcgaa atctgccgtt atctgctcaa ccagccggcc    1020
aagccgaccg accgtgccca ccaggtgcgg gtgatctgcg gtaacgggct gcggccggag    1080
atctgggatg agttcaccac ccgcttcggg gtcgcgcggg tgtgcgagtt ctacgccgcc    1140
agcgaaggca actcggcctt tatcaacatc ttcaacgtgc caggaccgc cggggtatcg    1200
ccgatgccgc ttgcctttgt ggaatacgac ctggacaccg cgatccgct gcgggatgcg    1260
agcgggcgag tgcgtcgggt acccgacggt gaacccggcc tgttgcttag ccgggtcaac    1320
cggctgcagc cgttcgacgg ctacaccgac ccggttgcca gcgaaaagaa gttggtgcgc    1380
aacgcttttc gagatggcga ctgttggttc aacaccggtg acgtgatgag cccgcagggc    1440
atgggccatg ccgccttcgt cgatcggctg gcgacacct tccgctggaa gggcgagaat    1500
gtcgccacca ctcaggtcga agcggcactg gcctccgacc agaccgtcga ggagtgcacg    1560
gtctacggcg tccagattcc gcgcaccggc gggcgcgccg aatggccgc gatcacactg    1620
cgcgctggcg ccgaattcga cggccaggcg ctggcccgaa cggtttacgg tcacttgccc    1680
ggctatgcac ttccgctctt tgttcgggta gtggggtcgc tggcgcacac cacgacgttc    1740
aagagtcgca aggtggagtt gcgcaaccag gcctatggcg ccgacatcga ggatccgctg    1800
tacgtactgg ccggcccgga cgaaggatat gtgccgtact acgccgaata ccctgaggag    1860
gtttcgctcg gaaggcgacc gcagggctag cggattccgg gcgcagtctc gatacccgca    1920
```

```
ctggacgctc gacggtaacc aggcactatg gatgcgtgcg ttcaacaccg ccggcctcag   1980
ccggtcgttc aacaccgccg gcgttag                                      2007
```

<210> SEQ ID NO 23
<211> LENGTH: 597
<212> TYPE: PRT
<213> ORGANISM: Mycobacterium tuberculosis

<400> SEQUENCE: 23

```
Met Ser Asp Tyr Tyr Gly Gly Ala His Thr Thr Val Arg Leu Ile Asp
  1               5                  10                  15

Leu Ala Thr Arg Met Pro Arg Val Leu Ala Asp Thr Pro Val Ile Val
                 20                  25                  30

Arg Gly Ala Met Thr Gly Leu Leu Ala Arg Pro Asn Ser Lys Ala Ser
             35                  40                  45

Ile Gly Thr Val Phe Gln Asp Arg Ala Ala Arg Tyr Gly Asp Arg Val
         50                  55                  60

Phe Leu Lys Phe Gly Asp Gln Gln Leu Thr Tyr Arg Asp Ala Asn Ala
 65                  70                  75                  80

Thr Ala Asn Arg Tyr Ala Ala Val Leu Ala Ala Arg Gly Val Gly Pro
                 85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
        115                 120                 125

Tyr His Gln Arg Gly Glu Val Leu Ala His Ser Leu Gly Leu Leu Asp
    130                 135                 140

Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
                165                 170                 175

Asp Val Glu Arg Phe Ala Thr Thr Ala Pro Ala Thr Asn Pro Ala Ser
            180                 185                 190

Ala Ser Ala Val Gln Ala Lys Asp Thr Ala Phe Tyr Ile Phe Thr Ser
        195                 200                 205

Gly Thr Thr Gly Phe Pro Lys Ala Ser Val Met Thr His His Arg Trp
    210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
            340                 345                 350

Ser Ala Phe Ile Asn Ile Phe Asn Val Pro Arg Thr Ala Gly Val Ser
```

```
                355             360                 365
Pro Met Pro Leu Ala Phe Val Glu Tyr Asp Leu Asp Thr Gly Asp Pro
        370                 375                 380

Leu Arg Asp Ala Ser Gly Arg Val Arg Val Pro Asp Gly Glu Pro
385                 390                 395                 400

Gly Leu Leu Leu Ser Arg Val Asn Arg Leu Gln Pro Phe Asp Gly Tyr
                405                 410                 415

Thr Asp Pro Val Ala Ser Glu Lys Lys Leu Val Arg Asn Ala Phe Arg
            420                 425                 430

Asp Gly Asp Cys Trp Phe Asn Thr Gly Asp Val Met Ser Pro Gln Gly
        435                 440                 445

Met Gly His Ala Ala Phe Val Asp Arg Leu Gly Asp Thr Phe Arg Trp
    450                 455                 460

Lys Gly Glu Asn Val Ala Thr Thr Gln Val Glu Ala Leu Ala Ser
465                 470                 475                 480

Asp Gln Thr Val Glu Glu Cys Thr Val Tyr Gly Val Gln Ile Pro Arg
                485                 490                 495

Thr Gly Gly Arg Ala Gly Met Ala Ala Ile Thr Leu Arg Ala Gly Ala
            500                 505                 510

Glu Phe Asp Gly Gln Ala Leu Ala Arg Thr Val Tyr Gly His Leu Pro
        515                 520                 525

Gly Tyr Ala Leu Pro Leu Phe Val Arg Val Val Gly Ser Leu Ala His
    530                 535                 540

Thr Thr Thr Phe Lys Ser Arg Lys Val Glu Leu Arg Asn Gln Ala Tyr
545                 550                 555                 560

Gly Ala Asp Ile Glu Asp Pro Leu Tyr Val Leu Ala Gly Pro Asp Glu
                565                 570                 575

Gly Tyr Val Pro Tyr Tyr Ala Glu Tyr Pro Glu Glu Val Ser Leu Gly
            580                 585                 590

Arg Arg Pro Gln Gly
        595
```

```
<210> SEQ ID NO 24
<211> LENGTH: 3704
<212> TYPE: DNA
<213> ORGANISM: Homo sapiens
<220> FEATURE:
<221> NAME/KEY: CDS
<222> LOCATION: (175)...(2112)

<400> SEQUENCE: 24
tcgacccacg gcgtccggga ccccaaagca gaagcccgca cagtaggcac agcgcaccca      60
agaagggtcc aggagtctgc agaaacagaa aggtccccgg cctcagcctc ctagtccctg     120
cctgcctcct gcctgagctt ctgggagact gaaggcacgg cttgcagctt cagg atg      177
                                                                Met
                                                                  1 cgg gct ccg ggt gcg ggc gcg gcc tcg gtg gtc tcg ctg gcg ctg ttg      225
Arg Ala Pro Gly Ala Gly Ala Ala Ser Val Val Ser Leu Ala Leu Leu
            5                  10                  15 tgg ctg ctg ggg ctg ccg tgg acc tgg agc gcg gca gcg gcg ctc ggc      273
Trp Leu Leu Gly Leu Pro Trp Thr Trp Ser Ala Ala Ala Ala Leu Gly
        20                  25                  30 gtg tac gtg ggc agc ggc ggc tgg cgc ttc ctg cgc atc gtc tgc aag      321
Val Tyr Val Gly Ser Gly Gly Trp Arg Phe Leu Arg Ile Val Cys Lys
    35                  40                  45 acc gcg agg cga gac ctc ttc ggt ctc tct gtg ctg atc cgc gtg cgc      369
```

```
      Thr Ala Arg Arg Asp Leu Phe Gly Leu Ser Val Leu Ile Arg Val Arg
       50                  55                  60                  65 ctg gag ctg cgg cgg cac cag cgt gcc ggc cac acc atc ccg cgc atc      417
Leu Glu Leu Arg Arg His Gln Arg Ala Gly His Thr Ile Pro Arg Ile
                 70                  75                  80 ttt cag gcg gta gtg cag cga cag ccc gag cgc ctg gcg ctg gtg gat      465
Phe Gln Ala Val Val Gln Arg Gln Pro Glu Arg Leu Ala Leu Val Asp
             85                  90                  95 gcc ggg acc ggc gag tgc tgg acc ttt gcg cag ctg gac gcc tac tcc      513
Ala Gly Thr Gly Glu Cys Trp Thr Phe Ala Gln Leu Asp Ala Tyr Ser
         100                 105                 110 aat gcg gta gcc aac ctc ttc cgc cag ctg ggc ttc gcg ccg ggc gac      561
Asn Ala Val Ala Asn Leu Phe Arg Gln Leu Gly Phe Ala Pro Gly Asp
     115                 120                 125 gtg gtg gcc atc ttc ctg gag ggc cgg ccg gag ttc gtg ggg ctg tgg      609
Val Val Ala Ile Phe Leu Glu Gly Arg Pro Glu Phe Val Gly Leu Trp
 130                 135                 140                 145 ctg ggc ctg gcc aag gcg ggc atg gag gcc gcg ctc aac gtg aac          657
Leu Gly Leu Ala Lys Ala Gly Met Glu Ala Ala Leu Leu Asn Val Asn
                 150                 155                 160 ctg cgg cgc gag ccc ctg gcc ttc tgc ctg ggc acc tcg ggc gct aag      705
Leu Arg Arg Glu Pro Leu Ala Phe Cys Leu Gly Thr Ser Gly Ala Lys
             165                 170                 175 gcc ctg atc ttt gga gga gaa atg gtg gcg gcg gtg gcc gaa gtg agc      753
Ala Leu Ile Phe Gly Gly Glu Met Val Ala Ala Val Ala Glu Val Ser
         180                 185                 190 ggg cat ctg ggg aaa agt ttg atc aag ttc tgc tct gga gac ttg ggg      801
Gly His Leu Gly Lys Ser Leu Ile Lys Phe Cys Ser Gly Asp Leu Gly
     195                 200                 205 ccc gag ggc atc ttg ccg gac acc cac ctc ctg gac ccg ctg ctg aag      849
Pro Glu Gly Ile Leu Pro Asp Thr His Leu Leu Asp Pro Leu Leu Lys
 210                 215                 220                 225 gag gcc tct act gcc ccc ttg gca cag atc ccc agc aag ggc atg gac      897
Glu Ala Ser Thr Ala Pro Leu Ala Gln Ile Pro Ser Lys Gly Met Asp
                 230                 235                 240 gat cgt ctt ttc tac atc tac acg tcg ggg acc acc ggg ctg ccc aag      945
Asp Arg Leu Phe Tyr Ile Tyr Thr Ser Gly Thr Thr Gly Leu Pro Lys
             245                 250                 255 gct gcc att gtc gtg cac agc agg tac tac cgc atg gca gcc ttc ggc      993
Ala Ala Ile Val Val His Ser Arg Tyr Tyr Arg Met Ala Ala Phe Gly
         260                 265                 270 cac cac gcc tac cgc atg cag gcg gct gac gtg ctc tat gac tgc ctg     1041
His His Ala Tyr Arg Met Gln Ala Ala Asp Val Leu Tyr Asp Cys Leu
     275                 280                 285 ccc ctg tac cac tcg gca gga aac atc atc ggc gtg ggg cag tgt ctc     1089
Pro Leu Tyr His Ser Ala Gly Asn Ile Ile Gly Val Gly Gln Cys Leu
 290                 295                 300                 305 atc tat ggg ctg aca gtc gtc ctc cgc aag aaa ttc tcg gcc agc cgc     1137
Ile Tyr Gly Leu Thr Val Val Leu Arg Lys Lys Phe Ser Ala Ser Arg
                 310                 315                 320 ttc tgg gac gac tgc atc aag tac aac tgc acg gtg gtt cag tac atc     1185
Phe Trp Asp Asp Cys Ile Lys Tyr Asn Cys Thr Val Val Gln Tyr Ile
             325                 330                 335 ggg gag atc tgc cgc tac ctg ctg aag cag ccg gtg cgc gag gcg gag     1233
Gly Glu Ile Cys Arg Tyr Leu Leu Lys Gln Pro Val Arg Glu Ala Glu
         340                 345                 350 agg cga cac cgc gtg cgc ctg gcg gtg ggg aac ggg ctg cgt cct gcc     1281
Arg Arg His Arg Val Arg Leu Ala Val Gly Asn Gly Leu Arg Pro Ala
     355                 360                 365
```

```
atc tgg gag gag ttc acg gag cgc ttc ggc gta cgc caa atc ggg gag    1329
Ile Trp Glu Glu Phe Thr Glu Arg Phe Gly Val Arg Gln Ile Gly Glu
370             375                 380                 385 ttc tac ggc gcc acc gag tgc aac tgc agc att gcc aac atg gac ggc    1377
Phe Tyr Gly Ala Thr Glu Cys Asn Cys Ser Ile Ala Asn Met Asp Gly
                390                 395                 400 aag gtc ggc tcc tgt ggt ttc aac agc cgc atc ctg ccc cac gtg tac    1425
Lys Val Gly Ser Cys Gly Phe Asn Ser Arg Ile Leu Pro His Val Tyr
            405                 410                 415 ccc atc cgg ctg gtg aag gtc aat gag gac aca atg gag ctg ctg cgg    1473
Pro Ile Arg Leu Val Lys Val Asn Glu Asp Thr Met Glu Leu Leu Arg
        420                 425                 430 gat gcc cag ggc ctc tgc atc ccc tgc cag gcc ggg gag cct ggc ctc    1521
Asp Ala Gln Gly Leu Cys Ile Pro Cys Gln Ala Gly Glu Pro Gly Leu
    435                 440                 445 ctt gtg ggt cag atc aac caa cag gac ccg ctg cgc cgc ttc gat ggc    1569
Leu Val Gly Gln Ile Asn Gln Gln Asp Pro Leu Arg Arg Phe Asp Gly
450                 455                 460                 465 tat gtc agc gag agc gcc acc agc aag aag atc gcc cac agc gtc ttc    1617
Tyr Val Ser Glu Ser Ala Thr Ser Lys Lys Ile Ala His Ser Val Phe
                470                 475                 480 agc aag ggc gac agc gcc tac ctc tca ggt gac gtg cta gtg atg gat    1665
Ser Lys Gly Asp Ser Ala Tyr Leu Ser Gly Asp Val Leu Val Met Asp
            485                 490                 495 gag ctg ggc tac atg tac ttc cgg gac cgt agc ggg gac acc ttc cgc    1713
Glu Leu Gly Tyr Met Tyr Phe Arg Asp Arg Ser Gly Asp Thr Phe Arg
        500                 505                 510 tgg cga ggg gag aac gtc tcc acc acc gag gtg gag ggc gtg ctg agc    1761
Trp Arg Gly Glu Asn Val Ser Thr Thr Glu Val Glu Gly Val Leu Ser
    515                 520                 525 cgc ctg ctg ggc cag aca gac gtg gcc gtc tat ggg gtg gct gtt cca    1809
Arg Leu Leu Gly Gln Thr Asp Val Ala Val Tyr Gly Val Ala Val Pro
530                 535                 540                 545 gga gtg gag ggt aag gca ggg atg gcg gcc gtc gca gac ccc cac agc    1857
Gly Val Glu Gly Lys Ala Gly Met Ala Ala Val Ala Asp Pro His Ser
                550                 555                 560 ctg ctg gac ccc aac gcg ata tac cag gag ctg cag aag gtg ctg gca    1905
Leu Leu Asp Pro Asn Ala Ile Tyr Gln Glu Leu Gln Lys Val Leu Ala
            565                 570                 575 ccc tat gcc cgg ccc atc ttc ctg cgc ctc ctg ccc cag gtg gac acc    1953
Pro Tyr Ala Arg Pro Ile Phe Leu Arg Leu Leu Pro Gln Val Asp Thr
        580                 585                 590 aca ggc acc ttc aag atc cag aag acg agg ctg cag cga gag ggc ttt    2001
Thr Gly Thr Phe Lys Ile Gln Lys Thr Arg Leu Gln Arg Glu Gly Phe
    595                 600                 605 gac cca cgc cag acc tca gac cgg ctc ttc ctg gac ctg aag cag        2049
Asp Pro Arg Gln Thr Ser Asp Arg Leu Phe Phe Leu Asp Leu Lys Gln
610                 615                 620                 625 ggc cac tac ctg ccc tta aat gag gca gtc tac act cgc atc tgc tcg    2097
Gly His Tyr Leu Pro Leu Asn Glu Ala Val Tyr Thr Arg Ile Cys Ser
                630                 635                 640 ggc gcc ttc gcc ctc tgaagctgtt cctctactgg ccacaaactc tgggcctggt    2152
Gly Ala Phe Ala Leu
                645 gggagaggcc agcttgagcc agacagcgct gcccaggggt ggccgcctag tacacaccca   2212 cctggccgag ctgtacctgg cacggcccat cctggactga gaaactggaa cctcagagga   2272 acccgtgcct ctctgctgcc ttggtgcccc tgtgtctgcc tcctctccct gcttttcagc   2332 ctctgtctcc ttccatccct gtccctgtct ggccttaact cttccctctc tttcttttct   2392
```

```
ttctttcttt cttttttttt aagatagagt ctcactctgc tgcccgggct agagtgcagt    2452
ggtgggatct cggctcactg caacctctgc ctcctgggt  tcaagtgatc ctcccacctc    2512
agcctcctga gtagctggga ttacaggcac ccgccaccac gtccagctaa tttttatatt    2572
tttagtagag acggggtttc accatgttgg tcaggctggt cttgaactcc tgacctcagg    2632
tgatccgctg gcctcggcct cccagagtgc tgggattata gcgtgagcc  tctgccccgg    2692 cctttccttt ttcctctcct ctcctgccga gagtggaaca cacgtgtcct gggagctgca    2752
tcttgtgtag ggtccagctg cttttgggga ctgcaggaat catctcccct gggccctgga    2812
ctcggactgg ggcctcccca cctccctctc ggctgtgcct tacggagccc caatccaggc    2872
ctcctgtggc tgttgggttc cagatgctgc agctccatgt gacttccaag caggccctcc    2932
gccctccctg ctgaatggag gagccggggg tcccccaggc caactggaaa atctcccagg    2992
ctaggccaat tgccttttgc acttccccgt tcctgtcaca tttccccagc cccaccttcc    3052
cctcctgatg ccctgaaagc ttccggaatt gactgtgacc acttggatgt caccactgtc    3112 agccctgcc ttgatgtccc catttagcca tctccatgga gctcctgctg gagggccctg    3172
aaccctgcac tgcgtggctg cccagccagc tgcctcctgt cctgggagga ggcctcctgg    3232
gtgtcctcat ctggtgtgtc tactggaggg tcccacagga gaggcagcag aggggtcagg    3292
ggaggtctcc tgccgggggt tggcctctca agcctcaggg gttctagcct gttgaatata    3352
ccccacctgg tgggtggccc ctccgatgtc cccactgatg gctctgacac cgtgttggtg    3412
gcgatgtccc agacaatccc accaggacgg cccagacatc cctactggct tcgctggtgg    3472
ctcatctcga acatccacgc cagcctttct ggggccggcc acccaggccg cctgtccgtc    3532
tgtcctccct ccagcagcac cccctggccc ctggagtggg gggccatgg  caagagacac    3592 cgtggcgtct catgtgaact ttcctgggca ctgtggtttt atttcctaat tgatttaaga    3652
aataaacctg aagaccgtct ggtgaaaaaa aaaaaaaaaa aagggcggcc gc            3704
```

<210> SEQ ID NO 25
<211> LENGTH: 646
<212> TYPE: PRT
<213> ORGANISM: Homo sapiens

<400> SEQUENCE: 25

```
Met Arg Ala Pro Gly Ala Gly Ala Ala Ser Val Val Ser Leu Ala Leu
1               5                   10                  15

Leu Trp Leu Leu Gly Leu Pro Trp Thr Trp Ser Ala Ala Ala Ala Leu
            20                  25                  30

Gly Val Tyr Val Gly Ser Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Gln Arg Ala Gly His Thr Ile Pro Arg
65                  70                  75                  80

Ile Phe Gln Ala Val Gln Arg Gln Pro Glu Arg Leu Ala Leu Val
                85                  90                  95

Asp Ala Gly Thr Gly Glu Cys Trp Thr Phe Ala Gln Leu Asp Ala Tyr
            100                 105                 110

Ser Asn Ala Val Ala Asn Leu Phe Arg Gln Leu Gly Phe Ala Pro Gly
        115                 120                 125

Asp Val Val Ala Ile Phe Leu Glu Gly Arg Pro Glu Phe Val Gly Leu
    130                 135                 140
```

-continued

```
Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
            165                 170                 175

Lys Ala Leu Ile Phe Gly Gly Glu Met Val Ala Ala Val Ala Glu Val
            180                 185                 190

Ser Gly His Leu Gly Lys Ser Leu Ile Lys Phe Cys Ser Gly Asp Leu
            195                 200                 205

Gly Pro Glu Gly Ile Leu Pro Asp Thr His Leu Leu Asp Pro Leu Leu
            210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
                260                 265                 270

Gly His His Ala Tyr Arg Met Gln Ala Ala Asp Val Leu Tyr Asp Cys
                275                 280                 285

Leu Pro Leu Tyr His Ser Ala Gly Asn Ile Ile Gly Val Gly Gln Cys
            290                 295                 300

Leu Ile Tyr Gly Leu Thr Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
            340                 345                 350

Glu Arg Arg His Arg Val Arg Leu Ala Val Gly Asn Gly Leu Arg Pro
            355                 360                 365

Ala Ile Trp Glu Glu Phe Thr Glu Arg Phe Gly Val Arg Gln Ile Gly
            370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
                420                 425                 430

Arg Asp Ala Gln Gly Leu Cys Ile Pro Cys Gln Ala Gly Glu Pro Gly
            435                 440                 445

Leu Leu Val Gly Gln Ile Asn Gln Gln Asp Pro Leu Arg Arg Phe Asp
450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
            515                 520                 525

Ser Arg Leu Leu Gly Gln Thr Asp Val Ala Val Tyr Gly Val Ala Val
            530                 535                 540

Pro Gly Val Glu Gly Lys Ala Gly Met Ala Ala Val Ala Asp Pro His
545                 550                 555                 560
```

```
Ser Leu Leu Asp Pro Asn Ala Ile Tyr Gln Glu Leu Gln Lys Val Leu
            565                 570                 575

Ala Pro Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
            595                 600                 605

Phe Asp Pro Arg Gln Thr Ser Asp Arg Leu Phe Phe Leu Asp Leu Lys
    610                 615                 620

Gln Gly His Tyr Leu Pro Leu Asn Glu Ala Val Tyr Thr Arg Ile Cys
625                 630                 635                 640

Ser Gly Ala Phe Ala Leu
                645

<210> SEQ ID NO 26
<211> LENGTH: 2917
<212> TYPE: DNA
<213> ORGANISM: Homo sapiens
<220> FEATURE:
<221> NAME/KEY: CDS
<222> LOCATION: (208)...(2136)

<400> SEQUENCE: 26
```

| | |
|---|---:|
| cgacccacgc gtccgggcgg gcggggccgg gcggcgggcg gggctggcgg ggcggccggg | 60 |
| ccatgcaggg cgcagagccg gctaaaccct gctgagaccc ggctccgtgc gtccaggggc | 120 |
| ggctaatgcc cctcacgctg tctacgctgc tgcaaccggg ccgcatctgg acggggcgcc | 180 |

```
gcgcggcgga gccgacgccg ggccaca atg ctg ctt gga gcc tct ctg gtg ggg    234
                                Met Leu Leu Gly Ala Ser Leu Val Gly
                                  1               5 gtg ctg ctg ttc tcc aag ctg gtg ctg aaa ctg ccc tgg acc cag gtg       282
Val Leu Leu Phe Ser Lys Leu Val Leu Lys Leu Pro Trp Thr Gln Val
 10                  15                  20                  25 gga ttc tcc ctg ttg ttc ctc tac ttg gga tct ggc ggc tgg cgc ttc       330
Gly Phe Ser Leu Leu Phe Leu Tyr Leu Gly Ser Gly Gly Trp Arg Phe
                 30                  35                  40 atc cgg gtc ttc atc aag acc atc agg cgc gat atc ttt ggc ggc ctg       378
Ile Arg Val Phe Ile Lys Thr Ile Arg Arg Asp Ile Phe Gly Gly Leu
             45                  50                  55 gtc ctc ctg aag gtg aag gca aag gtg cga cag tgc ctg cag gag cgg       426
Val Leu Leu Lys Val Lys Ala Lys Val Arg Gln Cys Leu Gln Glu Arg
         60                  65                  70 cgg aca gtg ccc att ttg ttt gcc tct acc gtt cgg cgc cac ccc gac       474
Arg Thr Val Pro Ile Leu Phe Ala Ser Thr Val Arg Arg His Pro Asp
     75                  80                  85 aag acg gcc ctg atc ttc gag ggc aca gat acc cac tgg acc ttc cgc       522
Lys Thr Ala Leu Ile Phe Glu Gly Thr Asp Thr His Trp Thr Phe Arg
 90                  95                 100                 105 cag ctg gat gag tac tca agc agt gta gcc aac ttc ctg cag gcc cgg       570
Gln Leu Asp Glu Tyr Ser Ser Ser Val Ala Asn Phe Leu Gln Ala Arg
                110                 115                 120 ggc ctg gcc tcg ggc gat gtg gct gcc atc ttc atg gag aac cgc aat       618
Gly Leu Ala Ser Gly Asp Val Ala Ala Ile Phe Met Glu Asn Arg Asn
            125                 130                 135 gag ttc gtg ggc cta tgg ctg ggc atg gcc aag ctc ggt gtg gag gca       666
Glu Phe Val Gly Leu Trp Leu Gly Met Ala Lys Leu Gly Val Glu Ala
        140                 145                 150 gcc ctc atc aac acc aac ctg cgg cgg gat gct ctg ctc cac tgc ctc       714
Ala Leu Ile Asn Thr Asn Leu Arg Arg Asp Ala Leu Leu His Cys Leu
    155                 160                 165
```

-continued

```
acc acc tcg cgc gca cgg gcc ctt gtc ttt ggc agc gaa atg gcc tca      762
Thr Thr Ser Arg Ala Arg Ala Leu Val Phe Gly Ser Glu Met Ala Ser
170             175                 180                 185 gcc atc tgt gag gtc cat gcc agc ctg gac ccc tcg ctc agc ctc ttc      810
Ala Ile Cys Glu Val His Ala Ser Leu Asp Pro Ser Leu Ser Leu Phe
            190                 195                 200 tgc tct ggc tcc tgg gag ccc ggt gcg gtg cct cca agc aca gaa cac      858
Cys Ser Gly Ser Trp Glu Pro Gly Ala Val Pro Pro Ser Thr Glu His
        205                 210                 215 ctg gac cct ctg ctg aaa gat gct ccc aag cac ctt ccc agt tgc cct      906
Leu Asp Pro Leu Leu Lys Asp Ala Pro Lys His Leu Pro Ser Cys Pro
    220                 225                 230 gac aag ggc ttc aca gat aaa ctg ttc tac atc tac aca tcc ggc acc      954
Asp Lys Gly Phe Thr Asp Lys Leu Phe Tyr Ile Tyr Thr Ser Gly Thr
235                 240                 245 aca ggg ctg ccc aag gcc gcc atc gtg gtg cac agc agg tat tac cgc     1002
Thr Gly Leu Pro Lys Ala Ala Ile Val Val His Ser Arg Tyr Tyr Arg
250                 255                 260                 265 atg gct gcc ctg gtg tac tat gga ttc cgc atg cgg ccc aac gac atc     1050
Met Ala Ala Leu Val Tyr Tyr Gly Phe Arg Met Arg Pro Asn Asp Ile
                270                 275                 280 gtc tat gac tgc ctc ccc ctc tac cac tca gca gga aac atc gtg gga     1098
Val Tyr Asp Cys Leu Pro Leu Tyr His Ser Ala Gly Asn Ile Val Gly
            285                 290                 295 atc ggc cag tgc ctg ctg cat ggc atg acg gtg gtg att cgg aag aag     1146
Ile Gly Gln Cys Leu Leu His Gly Met Thr Val Val Ile Arg Lys Lys
        300                 305                 310 ttc tca gcc tcc cgg ttc tgg gac gat tgt atc aag tac aac tgc acg     1194
Phe Ser Ala Ser Arg Phe Trp Asp Asp Cys Ile Lys Tyr Asn Cys Thr
    315                 320                 325 att gtg cag tac att ggt gaa ctg tgc cgc tac ctc ctg aac cag cca     1242
Ile Val Gln Tyr Ile Gly Glu Leu Cys Arg Tyr Leu Leu Asn Gln Pro
330                 335                 340                 345 ccg cgg gag gca gaa aac cag cac cag gtt cgc atg gca cta ggc aat     1290
Pro Arg Glu Ala Glu Asn Gln His Gln Val Arg Met Ala Leu Gly Asn
                350                 355                 360 ggc ctc cgg cag tcc atc tgg acc aac ttt tcc agc cgc ttc cac ata     1338
Gly Leu Arg Gln Ser Ile Trp Thr Asn Phe Ser Ser Arg Phe His Ile
            365                 370                 375 ccc cag gtg gct gag ttc tac ggg gcc aca gag tgc aac tgt agc ctg     1386
Pro Gln Val Ala Glu Phe Tyr Gly Ala Thr Glu Cys Asn Cys Ser Leu
        380                 385                 390 ggc aac ttc gac agc cag gtg ggg gcc tgt ggt ttc aat agc cgc atc     1434
Gly Asn Phe Asp Ser Gln Val Gly Ala Cys Gly Phe Asn Ser Arg Ile
    395                 400                 405 ctg tcc ttc gtg tac ccc atc cgg ttg gta cgt gtc aac gag gac acc     1482
Leu Ser Phe Val Tyr Pro Ile Arg Leu Val Arg Val Asn Glu Asp Thr
410                 415                 420                 425 atg gag ctg atc cgg ggg ccc gac ggc gtc tgc att ccc tgc cag cca     1530
Met Glu Leu Ile Arg Gly Pro Asp Gly Val Cys Ile Pro Cys Gln Pro
                430                 435                 440 ggt gag ccg ggc cag ctg gtg ggc cgc atc atc cag aaa gac ccc ctg     1578
Gly Glu Pro Gly Gln Leu Val Gly Arg Ile Ile Gln Lys Asp Pro Leu
            445                 450                 455 cgc cgc ttc gat ggc tac ctc aac cag ggc gcc aac aac aag aag att     1626
Arg Arg Phe Asp Gly Tyr Leu Asn Gln Gly Ala Asn Asn Lys Lys Ile
        460                 465                 470 gcc aag gat gtc ttc aag aag ggg gac cag gcc tac ctt act ggt gat     1674
Ala Lys Asp Val Phe Lys Lys Gly Asp Gln Ala Tyr Leu Thr Gly Asp
    475                 480                 485
```

```
gtg ctg gtg atg gac gag ctg ggc tac ctg tac ttc cga gac cgc act      1722
Val Leu Val Met Asp Glu Leu Gly Tyr Leu Tyr Phe Arg Asp Arg Thr
490                 495                 500                 505 ggg gac acg ttc cgc tgg aaa ggt gag aac gtg tcc acc acc gag gtg      1770
Gly Asp Thr Phe Arg Trp Lys Gly Glu Asn Val Ser Thr Thr Glu Val
            510                 515                 520 gaa ggc aca ctc agc cgc ctg ctg gac atg gct gac gtg gcc gtg tat      1818
Glu Gly Thr Leu Ser Arg Leu Leu Asp Met Ala Asp Val Ala Val Tyr
        525                 530                 535 ggt gtc gag gtg cca gga acc gag ggc cgg gcc gga atg gct gct gtg      1866
Gly Val Glu Val Pro Gly Thr Glu Gly Arg Ala Gly Met Ala Ala Val
    540                 545                 550 gcc agc ccc act ggc aac tgt gac ctg gag cgc ttt gct cag gtc ttg      1914
Ala Ser Pro Thr Gly Asn Cys Asp Leu Glu Arg Phe Ala Gln Val Leu
555                 560                 565 gag aag gaa ctg ccc ctg tat gcg cgc ccc atc ttc ctg cgc ctc ctg      1962
Glu Lys Glu Leu Pro Leu Tyr Ala Arg Pro Ile Phe Leu Arg Leu Leu
570                 575                 580                 585 cct gag ctg cac aaa aca gga acc tac aag ttc cag aag aca gag cta      2010
Pro Glu Leu His Lys Thr Gly Thr Tyr Lys Phe Gln Lys Thr Glu Leu
            590                 595                 600 cgg aag gag ggc ttt gac ccg gct att gtg aaa gac ccg ctg ttc tat      2058
Arg Lys Glu Gly Phe Asp Pro Ala Ile Val Lys Asp Pro Leu Phe Tyr
        605                 610                 615 cta gat gcc cag aag ggc cgc tac gtc ccg ctg gac caa gag gcc tac      2106
Leu Asp Ala Gln Lys Gly Arg Tyr Val Pro Leu Asp Gln Glu Ala Tyr
    620                 625                 630 agc cgc atc cag gca ggc gag gag aag ctg tgattccccc catccctctg        2156
Ser Arg Ile Gln Ala Gly Glu Glu Lys Leu
635                 640 agggccggcg gatgctggat ccggagcccc aggttccgcc ccagagcggt cctggacaag    2216
gccagaccaa agcaagcagg gcctggcacc tccatcctga ggtgctgccc ctccatccaa    2276
aactgccaag tgactcattg ccttcccaac ccttccagag gctttctgtg aaagtctcat    2336
gtccaagttc cgtcttctgg gctgggcagg ccctctggtt cccaggctga gactgacggg    2396
ttttctcagg atgatgtctt gggtgagggt agggagagga caagggtca ccgagccctt     2456 cccagagagc agggagctta taatggaac cagagcagaa gtccccagac tcaggaagtc    2516
aacagagtgg gcagggacag tggtagcatc catctggtgg ccaaagagaa tcgtagcccc   2576
agagctgccc aagttcactg ggctccaccc ccacctccag gaggggagga gaggacctga   2636
catctgtagg tggcccctga tgccccatct acagcaggag gtcaggacca cgcccctggc   2696
ctctccccac tcccccatcc tcctccctgg gtggctgcct gattatccct caggcagggc   2756
ctctcagtcc ttgtgggtct gtgtcacctc catctcagtc ttggcctggc tatgagggga   2816
ggaggaatgg gagaggggc tcaggggcca ataaactctg ccttgagtcc tcctaaaaaa    2876
aaaaaaaaaa aaaaaaaaa aaaaaaaaa agggcggccg                           2917

<210> SEQ ID NO 27
<211> LENGTH: 643
<212> TYPE: PRT
<213> ORGANISM: Homo sapiens

<400> SEQUENCE: 27

Met Leu Leu Gly Ala Ser Leu Val Gly Val Leu Leu Phe Ser Lys Leu
1               5                   10                  15

Val Leu Lys Leu Pro Trp Thr Gln Val Gly Phe Ser Leu Leu Phe Leu
```

```
                    20                  25                  30
Tyr Leu Gly Ser Gly Gly Trp Arg Phe Ile Arg Val Phe Ile Lys Thr
                35                  40                  45
Ile Arg Arg Asp Ile Phe Gly Gly Leu Val Leu Leu Lys Val Lys Ala
 50                  55                  60
Lys Val Arg Gln Cys Leu Gln Glu Arg Arg Thr Val Pro Ile Leu Phe
 65                  70                  75                  80
Ala Ser Thr Val Arg Arg His Pro Asp Lys Thr Ala Leu Ile Phe Glu
                 85                  90                  95
Gly Thr Asp Thr His Trp Thr Phe Arg Gln Leu Asp Glu Tyr Ser Ser
                100                 105                 110
Ser Val Ala Asn Phe Leu Gln Ala Arg Gly Leu Ala Ser Gly Asp Val
                115                 120                 125
Ala Ala Ile Phe Met Glu Asn Arg Asn Glu Phe Val Gly Leu Trp Leu
130                 135                 140
Gly Met Ala Lys Leu Gly Val Glu Ala Ala Leu Ile Asn Thr Asn Leu
145                 150                 155                 160
Arg Arg Asp Ala Leu Leu His Cys Leu Thr Thr Ser Arg Ala Arg Ala
                165                 170                 175
Leu Val Phe Gly Ser Glu Met Ala Ser Ala Ile Cys Glu Val His Ala
                180                 185                 190
Ser Leu Asp Pro Ser Leu Ser Leu Phe Cys Ser Gly Ser Trp Glu Pro
                195                 200                 205
Gly Ala Val Pro Pro Ser Thr Glu His Leu Asp Pro Leu Leu Lys Asp
                210                 215                 220
Ala Pro Lys His Leu Pro Ser Cys Pro Asp Lys Gly Phe Thr Asp Lys
225                 230                 235                 240
Leu Phe Tyr Ile Tyr Thr Ser Gly Thr Thr Gly Leu Pro Lys Ala Ala
                245                 250                 255
Ile Val Val His Ser Arg Tyr Tyr Arg Met Ala Ala Leu Val Tyr Tyr
                260                 265                 270
Gly Phe Arg Met Arg Pro Asn Asp Ile Val Tyr Asp Cys Leu Pro Leu
                275                 280                 285
Tyr His Ser Ala Gly Asn Ile Val Gly Ile Gly Gln Cys Leu Leu His
                290                 295                 300
Gly Met Thr Val Val Ile Arg Lys Lys Phe Ser Ala Ser Arg Phe Trp
305                 310                 315                 320
Asp Asp Cys Ile Lys Tyr Asn Cys Thr Ile Val Gln Tyr Ile Gly Glu
                325                 330                 335
Leu Cys Arg Tyr Leu Leu Asn Gln Pro Pro Arg Glu Ala Glu Asn Gln
                340                 345                 350
His Gln Val Arg Met Ala Leu Gly Asn Gly Leu Arg Gln Ser Ile Trp
                355                 360                 365
Thr Asn Phe Ser Ser Arg Phe His Ile Pro Gln Val Ala Glu Phe Tyr
                370                 375                 380
Gly Ala Thr Glu Cys Asn Cys Ser Leu Gly Asn Phe Asp Ser Gln Val
385                 390                 395                 400
Gly Ala Cys Gly Phe Asn Ser Arg Ile Leu Ser Phe Val Tyr Pro Ile
                405                 410                 415
Arg Leu Val Arg Val Asn Glu Asp Thr Met Glu Leu Ile Arg Gly Pro
                420                 425                 430
Asp Gly Val Cys Ile Pro Cys Gln Pro Gly Glu Pro Gly Gln Leu Val
                435                 440                 445
```

```
Gly Arg Ile Ile Gln Lys Asp Pro Leu Arg Arg Phe Asp Gly Tyr Leu
        450                 455                 460
Asn Gln Gly Ala Asn Asn Lys Lys Ile Ala Lys Asp Val Phe Lys Lys
465                 470                 475                 480
Gly Asp Gln Ala Tyr Leu Thr Gly Asp Val Leu Met Asp Glu Leu
                485                 490                 495
Gly Tyr Leu Tyr Phe Arg Asp Arg Thr Gly Asp Thr Phe Arg Trp Lys
            500                 505                 510
Gly Glu Asn Val Ser Thr Thr Glu Val Glu Gly Thr Leu Ser Arg Leu
        515                 520                 525
Leu Asp Met Ala Asp Val Ala Val Tyr Gly Val Glu Val Pro Gly Thr
    530                 535                 540
Glu Gly Arg Ala Gly Met Ala Ala Val Ala Ser Pro Thr Gly Asn Cys
545                 550                 555                 560
Asp Leu Glu Arg Phe Ala Gln Val Leu Glu Lys Glu Leu Pro Leu Tyr
                565                 570                 575
Ala Arg Pro Ile Phe Leu Arg Leu Leu Pro Glu Leu His Lys Thr Gly
            580                 585                 590
Thr Tyr Lys Phe Gln Lys Thr Glu Leu Arg Lys Glu Gly Phe Asp Pro
        595                 600                 605
Ala Ile Val Lys Asp Pro Leu Phe Tyr Leu Asp Ala Gln Lys Gly Arg
    610                 615                 620
Tyr Val Pro Leu Asp Gln Glu Ala Tyr Ser Arg Ile Gln Ala Gly Glu
625                 630                 635                 640
Glu Lys Leu

<210> SEQ ID NO 28
<211> LENGTH: 1941
<212> TYPE: DNA
<213> ORGANISM: Homo sapiens

<400> SEQUENCE: 28
atgcgggctc cggtgcggg cgcggcctcg gtggtctcgc tggcgctgtt gtggctgctg      60
gggctgccgt ggacctggag cgcggcagcg gcgctcggcg tgtacgtggg cagcggcggc     120
tggcgcttcc tgcgcatcgt ctgcaagacc gcgaggcgag acctcttcgg tctctctgtg     180
ctgatccgcg tgcgcctgga gctgcggcgg caccagcgtg ccggccacac catcccgcgc     240
atctttcagg cggtagtgca gcgacagccc gagcgcctgg cgctggtgga tgccgggacc     300
ggcgagtgct ggacctttgc gcagctggac gcctactcca atgcggtagc caacctcttc     360
cgccagctgg gcttcgcgcc gggcgacgtg gtggccatct tcctggaggg ccggccggag     420
ttcgtgggc tgtggctggg cctggccaag gcgggcatgg aggccgcgct gctcaacgtg     480
aacctgcggc gcgagcccct ggccttctgc ctgggcacct cgggcgctaa ggccctgatc     540
tttggaggag aaatggtggc ggcggtggcc gaagtgagcg ggcatctggg gaaaagtttg     600
atcaagttct gctctggaga cttggggccc gagggcatct tgccggacac ccacctcctg     660
gacccgctgc tgaaggaggc ctctactgcc cccttggcac agatccccag caagggcatg     720
gacgatcgtc ttttctacat ctacgtcggg gaccaccg ggctgcccaa ggctgccatt     780
gtcgtgcaca gcaggtacta ccgcatggca gccttcggcc accacgccta ccgcatgcag     840
gcggctgacg tgctctatga ctgcctgccc ctgtaccact cggcaggaaa catcatcggc     900
gtggggcagt gtctcatcta tgggctgaca gtcgtcctcc gcaagaaatt ctcggccagc     960
```

| | | | |
|---|---|---|---|
| cgcttctggg | acgactgcat | caagtacaac tgcacggtgg ttcagtacat cggggagatc | 1020 |
| tgccgctacc | tgctgaagca | gccggtgcgc gaggcggaga ggcgacaccg cgtgcgcctg | 1080 |
| gcggtgggga | acgggctgcg | tcctgccatc tgggaggagt tcacggagcg cttcggcgta | 1140 |
| cgccaaatcg | gggagttcta | cggcgccacc gagtgcaact gcagcattgc caacatggac | 1200 |
| ggcaaggtcg | gctcctgtgg | tttcaacagc cgcatcctgc cccacgtgta ccccatccgg | 1260 |
| ctggtgaagg | tcaatgagga | cacaatggag ctgctgcggg atgcccaggg cctctgcatc | 1320 |
| ccctgccagg | ccggggagcc | tggcctcctt gtgggtcaga tcaaccaaca ggacccgctg | 1380 |
| cgccgcttcg | atggctatgt | cagcgagagc gccaccagca agaagatcgc ccacagcgtc | 1440 |
| ttcagcaagg | gcgacagcgc | ctacctctca ggtgacgtgc tagtgatgga tgagctgggc | 1500 |
| tacatgtact | ccggggaccg | tagcggggac accttccgct ggcgagggga gaacgtctcc | 1560 |
| accaccgagg | tggagggcgt | gctgagccgc ctgctgggcc agacagacgt ggccgtctat | 1620 |
| gggtggctg | ttccaggagt | ggagggtaag gcagggatgg cggccgtcgc agaccccac | 1680 |
| agcctgctgg | accccaacgc | gatataccag gagctgcaga aggtgctggc accctatgcc | 1740 |
| cggcccatct | tcctgcgcct | cctgcccag gtggacacca caggcacctt caagatccag | 1800 |
| aagacgaggc | tgcagcgaga | gggctttgac ccacgccaga cctcagaccg gctcttcttc | 1860 |
| ctggacctga | agcagggcca | ctacctgccc ttaaatgagg cagtctacac tcgcatctgc | 1920 |
| tcgggcgcct | tcgccctctg | a | 1941 |

<210> SEQ ID NO 29
<211> LENGTH: 1938
<212> TYPE: DNA
<213> ORGANISM: Mus musculus

<400> SEQUENCE: 29

| | | | |
|---|---|---|---|
| atgcgggctc | ctggagcagg | aacagcctct gtggcctcac tggcgctgct ttggtttctg | 60 |
| ggacttccgt | ggacctggag | cgcggcggcg gcgttctgtg tgtacgtggg tggcggcggc | 120 |
| tggcgctttc | tgcgtatcgt | ctgcaagacg gcgaggcgag acctctttgg cctctctgtt | 180 |
| ctgattcgtg | ttcggctaga | gctgcgacga caccggcgag caggagacac gatcccgtgc | 240 |
| atcttccagg | ctgtggcccg | cgacaaccca gagcgcctgg cactggtgga cgccagtagt | 300 |
| ggtatatgct | ggaccttcgc | acagctggac acctactcca atgctgtagc caacctgttc | 360 |
| cgccagctgg | gctttgcacc | aggcgatgtg gtgctgtgt tcctggaggg ccggccggag | 420 |
| ttcgtgggac | tgtggctggg | cctggccaag gccggtgtgt tggctgctct tctcaatgtc | 480 |
| aacctgaggc | gggagcccct | ggccttctgc ctgggcacat cagctgccaa ggccctcatt | 540 |
| tatggcgggg | agatggcagc | ggcggtggcg gaggtgagcg agcagctggg gaagagcctc | 600 |
| ctcaagttct | gctctggaga | tctgggggcct gagagcatcc tgcctgacac gcagctcctg | 660 |
| gaccccatgc | ttgctgaggc | gcccaccaca cccctggcac aagccccagg caagggcatg | 720 |
| gatgatcggc | tgttttacat | ctatacttct ggaccaccg ggcttcctaa ggctgccatt | 780 |
| gtggtgcaca | gcaggtacta | ccgcattgct gcctttggcc accattccta cagcatgcgt | 840 |
| gccgccgatg | tgctctatga | ctgcctgcca ctctaccact ctgcaggaa catcatgggt | 900 |
| gtggggcagt | gcgtcatcta | cggttgacg gtggtactgc gcaagaagtt ctccgccagc | 960 |
| cgcttctggg | atgactgtgt | caagtacaat tgcacggtag tgcagtacat aggtgaaatc | 1020 |
| tgccgctacc | tgctgaggca | gccggttcgc gacgtggagc agcgacaccg cgtgcgcctg | 1080 |
| gccgtgggta | atgggctgcg | gccagccatc tgggaggagt tcacgcagcg cttcggtgtg | 1140 |

-continued

```
ccacagatcg gcgagttcta cggcgctacc gagtgcaact gcagcattgc caacatggac      1200
ggcaaggtcg gctcctgcgg cttcaacagc cgtatcctca cgcatgtgta ccccatccgt      1260
ctggtcaagg tcaatgagga cacgatggag ccactgcggg actccgaggg cctctgcatc      1320
ccgtgccagc ccggggaacc cggccttctc gtgggccaga tcaaccagca ggaccctctg      1380
cggcgtttcg atggttatgt tagtgacagt gccaccaaca agaagattgc ccacagcgtt      1440
ttccgaaagg gcgatagcgc ctacctctca gtgacgtgc tagtgatgga cgagctgggc       1500
tacatgtatt tccgtgaccg cagcggggac accttccgct ggcgcgggga gaacgtgtcc      1560
accacggagg tggaagccgt gctgagccgc ctactgggcc agacggacgt ggctgtgtat      1620
ggggtggctg tgccaggagt ggagggaaaa gctggcatgg cagccatcgc agatccccac      1680
agccagttgg accctaactc aatgtaccag gaattacaga aggttcttgc atcctatgct      1740
cggcccatct tcctgcgtct tctgccccag gtggatacca caggcacctt caagatccag      1800
aagacccggc tgcagcgtga aggctttgac ccccgtcaga cctcagacag gctcttcttt      1860
ctagacctga gcagggacg ctatgtaccc ctggatgaga gagtccatgc ccgcatttgt       1920
gcaggcgact tctcactc                                                    1938

<210> SEQ ID NO 30
<211> LENGTH: 1896
<212> TYPE: DNA
<213> ORGANISM: Homo sapiens

<400> SEQUENCE: 30
ctgttctcca agctggtgct gaaactgccc tggacccagg tgggattctc cctgttgttc      60
ctctacttgg gatctggcgg ctggcgcttc atccgggtct tcatcaagac catcaggcgc     120
gatatctttg gcggcctggt cctcctgaag gtgaaggcaa aggtgcgaca gtgcctgcag     180
gagcggcgga cagtgcccat ttgtttgcc tctaccgttc ggcgccaccc cgacaagacg      240
gccctgatct tcgagggcac agatacccac tggaccttcc gccagctgga tgagtactca     300
agcagtgtag ccaacttcct gcaggcccgg ggcctggcct cgggcgatgt ggctgccatc     360
ttcatggaga accgcaatga gttcgtgggc ctatggctgg gcatggccaa gctcggtgtg     420
gaggcagccc tcatcaacac caacctgcgg cgggatgctc tgctccactg cctcaccacc     480
tcgcgcgcac gggcccttgt cttttggcagc gaaatggcct cagccatctg tgaggtccat    540
gccagcctgg accctcgct cagcctcttc tgctctggct cctgggagcc cggtgcggtg     600
cctccaagca cagaacacct ggaccctctg ctgaaagatg ctcccaagca ccttcccagt     660
tgccctgaca agggcttcac agataaactg ttctacatct acacatccgg caccacaggg     720
ctgcccaagg ccgccatcgt ggtgcacagc aggtattacc gcatggctgc cctggtgtac     780
tatggattcc gcatgcggcc caacgacatc gtctatgact gcctccccct ctaccactca     840
gcaggaaaca tcgtgggaat cggccagtgc ctgctgcatg gcatgacggt ggtgattcgg     900
aagaagttct cagcctcccg gttctgggac gattgtatca gtacaactg cacgattgtg      960 cagtacattg gtgaactgtg ccgctacctc ctgaaccagc caccgcggga ggcagaaaac     1020
cagcaccagg ttcgcatggc actaggcaat ggcctccggc agtccatctg gaccaacttt    1080
tccagccgct tccacatacc ccaggtggct gagttctacg ggccacagag tgcaactgt     1140 agcctgggca acttcgacag ccaggtgggg gcctgtggtt tcaatagccg catcctgtcc   1200
ttcgtgtacc ccatccggtt ggtacgtgtc aacgaggaca ccatggagct gatccggggg   1260
```

-continued

```
cccgacggcg tctgcattcc ctgccagcca ggtgagccgg gccagctggt gggccgcatc    1320
atccagaaag accccctgcg ccgcttcgat ggctacctca accagggcgc caacaacaag    1380
aagattgcca aggatgtctt caagaagggg gaccaggcct accttactgg tgatgtgctg    1440
gtgatggacg agctgggcta cctgtacttc cgagaccgca ctggggacac gttccgctgg    1500
aaaggtgaga acgtgtccac caccgaggtg aaggcacac tcagccgcct gctggacatg     1560
gctgacgtgg ccgtgtatgg tgtcgaggtg ccaggaaccg agggccgggc cggaatggct    1620
gctgtggcca gccccactgg caactgtgac ctggagcgct ttgctcaggt cttggagaag    1680
gaactgcccc tgtatgcgcg ccccatcttc ctgcgcctcc tgcctgagct gcacaaaaca    1740
ggaacctaca agttccagaa gacagagcta cggaaggagg ctttgacccc ggctattgtg    1800
aaagacccgc tgttctatct agatgcccag aagggccgct acgtcccgct ggaccaagag    1860
gcctacagcc gcatccaggc aggcgaggag aagctg                              1896
```

<210> SEQ ID NO 31
<211> LENGTH: 1896
<212> TYPE: DNA
<213> ORGANISM: Mus musculus

<400> SEQUENCE: 31

```
cttgggtcca agctagtgct gaagctgccc tggacccagg tgggattctc cctgttgctc      60
ctgtacttgg ggtctggtgg ctggcgtttc atccgggtct tcatcaagac ggtcaggaga     120
gatatctttg gtggcatggt gctcctgaag gtgaagacca aggtgcgacg gtaccttcag     180
gagcggaaga cggtgcccct gctgtttgct tcaatggtac agcgccaccc ggacaagaca     240
gccctgattt cgagggcac agacactcac tggaccttcc gccagctgga tgagtactcc      300
agtagtgtgg ccaacttcct gcaggcccgg ggcctggcct caggcaatgt agttgccctc     360
tttatggaaa accgcaatga gtttgtgggt ctgtggctag gcatggccaa gctgggcgtg     420
gaggcggctc tcatcaacac caaccttagg cgggatgccc tgcgccactg tcttgacacc     480
tcaaaggcac gagctctcat cttggcagt gagatggcct cagctatctg tgagatccat      540
gctagcctgg agcccacact cagcctcttc tgctctggat cctgggagcc cagcacagtg     600
cccgtcagca cagagcatct ggaccctctt ctggaagatg ccccgaagca cctgcccagt     660
cacccagaca agggttttac agataagctc ttctacatct acacatcggg caccacgggg    720
ctacccaaag ctgccattgt ggtgcacagc aggtattatc gtatggcttc cctggtgtac    780
tatggattcc gcatgcggcc tgatgacatt gtctatgact gcctcccccct ctaccactca    840
agcaggaaac atcgtgggga ttggcagtgc ttactccacg gcatgactgt ggtgatccgg    900
aagaagttct cagcctcccg gttctgggat gattgtatca agtacaactg cacagtggta    960
cagtacattg gcgagctctg ccgctacctc ctgaaccagc caccccgtga ggctgagtct    1020
cggcacaagg tgcgcatggc actgggcaac ggtctccggc agtccatctg gaccgacttc    1080
tccagccgtt tccacatccc ccaggtggct gagttctatg ggccactga atgcaactgt    1140
agcctgggca actttgacag ccgggtgggg gcctgtggct tcaatagccg catcctgtcc    1200
tttgtgtacc ctatccgttt ggtacgtgtc aatgaggata ccatggaact gatccgggga    1260
cccgatggag tctgcattcc ctgtcaacca ggtcagccag ccagctggt gggtcgcatc      1320
atccagcagg accctctgcg ccgtttcgac gggtacctca accagggtgc caacaacaag    1380
aagattgcta atgatgtctt caagaagggg gaccaagcct acctcactgg tgacgtcctg    1440
gtgatggatg agctgggtta cctgtacttc cgagatcgca ctggggacac gttccgctgg    1500
```

-continued

```
aaaggggaga atgtatctac cactgaggtg gagggcacac tcagccgcct gcttcatatg   1560
gcagatgtgg cagtttatgg tgttgaggtg ccaggaactg aaggccgagc aggaatggct   1620
gccgttgcaa gtcccatcag caactgtgac ctggagagct tgcacagac cttgaaaaag    1680 gagctgcctc tgtatgcccg ccccatcttc ctgcgcttct tgcctgagct gcacaagaca   1740
gggaccttca gttccagaa acagagttg cggaaggagg gctttgaccc atctgttgtg     1800
aaagacccgc tgttctatct ggatgctcgg aagggctgct acgttgcact ggaccaggag   1860
gcctataccc gcatccaggc aggcgaggag aagctg                              1896
```

<210> SEQ ID NO 32
<211> LENGTH: 646
<212> TYPE: PRT
<213> ORGANISM: Homo sapiens

<400> SEQUENCE: 32

```
Met Arg Ala Pro Gly Ala Gly Ala Ala Ser Val Val Ser Leu Ala Leu
 1               5                  10                  15

Leu Trp Leu Leu Gly Leu Pro Trp Thr Trp Ser Ala Ala Ala Ala Leu
                20                  25                  30

Gly Val Tyr Val Gly Ser Gly Gly Trp Arg Phe Leu Arg Ile Val Cys
            35                  40                  45

Lys Thr Ala Arg Arg Asp Leu Phe Gly Leu Ser Val Leu Ile Arg Val
        50                  55                  60

Arg Leu Glu Leu Arg Arg His Gln Arg Ala Gly His Thr Ile Pro Arg
65                  70                  75                  80

Ile Phe Gln Ala Val Val Gln Arg Gln Pro Glu Arg Leu Ala Leu Val
                85                  90                  95

Asp Ala Gly Thr Gly Glu Cys Trp Thr Phe Ala Gln Leu Asp Ala Tyr
            100                 105                 110

Ser Asn Ala Val Ala Asn Leu Phe Arg Gln Leu Gly Phe Ala Pro Gly
        115                 120                 125

Asp Val Val Ala Ile Phe Leu Glu Gly Arg Pro Glu Phe Val Gly Leu
    130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
                165                 170                 175

Lys Ala Leu Ile Phe Gly Gly Glu Met Val Ala Val Ala Glu Val
            180                 185                 190

Ser Gly His Leu Gly Lys Ser Leu Ile Lys Phe Cys Ser Gly Asp Leu
        195                 200                 205

Gly Pro Glu Gly Ile Leu Pro Asp Thr His Leu Leu Asp Pro Leu Leu
    210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
            260                 265                 270

Gly His His Ala Tyr Arg Met Gln Ala Ala Asp Val Leu Tyr Asp Cys
        275                 280                 285

Leu Pro Leu Tyr His Ser Ala Gly Asn Ile Ile Gly Val Gly Gln Cys
    290                 295                 300
```

```
Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
            340                 345                 350

Glu Arg Arg His Arg Val Arg Leu Ala Val Gly Asn Gly Leu Arg Pro
        355                 360                 365

Ala Ile Trp Glu Glu Phe Thr Glu Arg Phe Gly Val Arg Gln Ile Gly
370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
            420                 425                 430

Arg Asp Ala Gln Gly Leu Cys Ile Pro Cys Gln Ala Gly Glu Pro Gly
        435                 440                 445

Leu Leu Val Gly Gln Ile Asn Gln Gln Asp Pro Leu Arg Arg Phe Asp
450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
        515                 520                 525

Ser Arg Leu Leu Gly Gln Thr Asp Val Ala Val Tyr Gly Val Ala Val
530                 535                 540

Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
610                 615                 620

Gln Gly His Tyr Leu Pro Leu Asn Glu Ala Val Tyr Thr Arg Ile Cys
625                 630                 635                 640

Ser Gly Ala Phe Ala Leu
                645

<210> SEQ ID NO 33
<211> LENGTH: 646
<212> TYPE: PRT
<213> ORGANISM: Mus musculus

<400> SEQUENCE: 33

Met Arg Ala Pro Gly Ala Gly Thr Ala Ser Val Ala Ser Leu Ala Leu
1               5                   10                  15

Leu Trp Phe Leu Gly Leu Pro Trp Thr Trp Ser Ala Ala Ala Ala Phe
```

-continued

```
                 20              25              30
Cys Val Tyr Val Gly Gly Gly Trp Arg Phe Leu Arg Ile Val Cys
         35              40              45
Lys Thr Ala Arg Arg Asp Leu Phe Gly Leu Ser Val Leu Ile Arg Val
 50              55              60
Arg Leu Glu Leu Arg Arg His Arg Arg Ala Gly Asp Thr Ile Pro Cys
 65              70              75              80
Ile Phe Gln Ala Val Ala Arg Arg Gln Pro Glu Arg Leu Ala Leu Val
             85              90              95
Asp Ala Ser Ser Gly Ile Cys Trp Thr Phe Ala Gln Leu Asp Thr Tyr
             100             105             110
Ser Asn Ala Val Ala Asn Leu Phe Arg Gln Leu Gly Phe Ala Pro Gly
             115             120             125
Asp Val Val Ala Val Phe Leu Glu Gly Arg Pro Glu Phe Val Gly Leu
             130             135             140
Trp Leu Gly Leu Ala Lys Ala Gly Val Val Ala Ala Leu Leu Asn Val
 145             150             155             160
Asn Leu Arg Arg Glu Pro Leu Ala Phe Cys Leu Gly Thr Ser Ala Ala
             165             170             175
Lys Ala Leu Ile Tyr Gly Gly Glu Met Ala Ala Ala Val Ala Glu Val
             180             185             190
Ser Glu Gln Leu Gly Lys Ser Leu Leu Lys Phe Cys Ser Gly Asp Leu
             195             200             205
Gly Pro Glu Ser Ile Leu Pro Asp Thr Gln Leu Leu Asp Pro Met Leu
 210             215             220
Ala Glu Ala Pro Thr Thr Pro Leu Ala Gln Ala Pro Gly Lys Gly Met
 225             230             235             240
Asp Asp Arg Leu Phe Tyr Ile Tyr Thr Ser Gly Thr Thr Gly Leu Pro
             245             250             255
Lys Ala Ala Ile Val Val His Ser Arg Tyr Tyr Arg Ile Ala Ala Phe
             260             265             270
Gly His His Ser Tyr Ser Met Arg Ala Ala Asp Val Leu Tyr Asp Cys
             275             280             285
Leu Pro Leu Tyr His Ser Ala Gly Asn Ile Met Gly Val Gly Gln Cys
 290             295             300
Val Ile Tyr Gly Leu Thr Val Leu Arg Lys Lys Phe Ser Ala Ser
 305             310             315             320
Arg Phe Trp Asp Asp Cys Val Lys Tyr Asn Cys Thr Val Val Gln Tyr
             325             330             335
Ile Gly Glu Ile Cys Arg Tyr Leu Leu Arg Gln Pro Val Arg Asp Val
             340             345             350
Glu Gln Arg His Arg Val Arg Leu Ala Val Gly Asn Gly Leu Arg Pro
             355             360             365
Ala Ile Trp Glu Glu Phe Thr Gln Arg Phe Gly Val Pro Gln Ile Gly
             370             375             380
Glu Phe Tyr Gly Ala Thr Glu Cys Asn Cys Ser Ile Ala Asn Met Asp
 385             390             395             400
Gly Lys Val Gly Ser Gly Phe Asn Ser Arg Ile Leu Thr His Val
             405             410             415
Tyr Pro Ile Arg Leu Val Lys Val Asn Glu Asp Thr Met Glu Pro Leu
             420             425             430
Arg Asp Ser Glu Gly Leu Cys Ile Pro Cys Gln Pro Gly Glu Pro Gly
             435             440             445
```

-continued

```
Leu Leu Val Gly Gln Ile Asn Gln Gln Asp Pro Leu Arg Arg Phe Asp
    450                 455                 460
Gly Tyr Val Ser Asp Ser Ala Thr Asn Lys Lys Ile Ala His Ser Val
465                 470                 475                 480
Phe Arg Lys Gly Asp Ser Ala Tyr Leu Ser Gly Asp Val Leu Val Met
                485                 490                 495
Asp Glu Leu Gly Tyr Met Tyr Phe Arg Asp Arg Ser Gly Asp Thr Phe
            500                 505                 510
Arg Trp Arg Gly Glu Asn Val Ser Thr Thr Glu Val Glu Ala Val Leu
        515                 520                 525
Ser Arg Leu Leu Gly Gln Thr Asp Val Ala Val Tyr Gly Val Ala Val
    530                 535                 540
Pro Gly Val Glu Gly Lys Ala Gly Met Ala Ala Ile Ala Asp Pro His
545                 550                 555                 560
Ser Gln Leu Asp Pro Asn Ser Met Tyr Gln Glu Leu Gln Lys Val Leu
                565                 570                 575
Ala Ser Tyr Ala Arg Pro Ile Phe Leu Arg Leu Leu Pro Gln Val Asp
            580                 585                 590
Thr Thr Gly Thr Phe Lys Ile Gln Lys Thr Arg Leu Gln Arg Glu Gly
        595                 600                 605
Phe Asp Pro Arg Gln Thr Ser Asp Arg Leu Phe Leu Asp Leu Lys
    610                 615                 620
Gln Gly Arg Tyr Val Pro Leu Asp Glu Arg Val His Ala Arg Ile Cys
625                 630                 635                 640
Ala Gly Asp Phe Ser Leu
                645

<210> SEQ ID NO 34
<211> LENGTH: 632
<212> TYPE: PRT
<213> ORGANISM: Homo sapiens

<400> SEQUENCE: 34

Leu Phe Ser Lys Leu Val Leu Lys Leu Pro Trp Thr Gln Val Gly Phe
1               5                   10                  15
Ser Leu Leu Phe Leu Tyr Leu Gly Ser Gly Gly Trp Arg Phe Ile Arg
            20                  25                  30
Val Phe Ile Lys Thr Ile Arg Arg Asp Ile Phe Gly Gly Leu Val Leu
        35                  40                  45
Leu Lys Val Lys Ala Lys Val Arg Gln Cys Leu Gln Glu Arg Arg Thr
    50                  55                  60
Val Pro Ile Leu Phe Ala Ser Thr Val Arg Arg His Pro Asp Lys Thr
65                  70                  75                  80
Ala Leu Ile Phe Glu Gly Thr Asp Thr His Trp Thr Phe Arg Gln Leu
                85                  90                  95
Asp Glu Tyr Ser Ser Val Ala Asn Phe Leu Gln Ala Arg Gly Leu
            100                 105                 110
Ala Ser Gly Asp Val Ala Ala Ile Phe Met Glu Asn Arg Asn Glu Phe
        115                 120                 125
Val Gly Leu Trp Leu Gly Met Ala Lys Leu Gly Val Glu Ala Ala Leu
    130                 135                 140
Ile Asn Thr Asn Leu Arg Arg Asp Ala Leu Leu His Cys Leu Thr Thr
145                 150                 155                 160
Ser Arg Ala Arg Ala Leu Val Phe Gly Ser Glu Met Ala Ser Ala Ile
```

-continued

```
            165                 170                 175
Cys Glu Val His Ala Ser Leu Asp Pro Ser Leu Ser Leu Phe Cys Ser
            180                 185                 190

Gly Ser Trp Glu Pro Gly Ala Val Pro Pro Ser Thr Glu His Leu Asp
        195                 200                 205

Pro Leu Leu Lys Asp Ala Pro Lys His Leu Pro Ser Cys Pro Asp Lys
    210                 215                 220

Gly Phe Thr Asp Lys Leu Phe Tyr Ile Tyr Thr Ser Gly Thr Thr Gly
225                 230                 235                 240

Leu Pro Lys Ala Ala Ile Val Val His Ser Arg Tyr Tyr Arg Met Ala
                245                 250                 255

Ala Leu Val Tyr Tyr Gly Phe Arg Met Arg Pro Asn Asp Ile Val Tyr
                260                 265                 270

Asp Cys Leu Pro Leu Tyr His Ser Ala Gly Asn Ile Val Gly Ile Gly
            275                 280                 285

Gln Cys Leu Leu His Gly Met Thr Val Val Ile Arg Lys Lys Phe Ser
        290                 295                 300

Ala Ser Arg Phe Trp Asp Asp Cys Ile Lys Tyr Asn Cys Thr Ile Val
305                 310                 315                 320

Gln Tyr Ile Gly Glu Leu Cys Arg Tyr Leu Leu Asn Gln Pro Pro Arg
                325                 330                 335

Glu Ala Glu Asn Gln His Gln Val Arg Met Ala Leu Gly Asn Gly Leu
            340                 345                 350

Arg Gln Ser Ile Trp Thr Asn Phe Ser Ser Arg Phe His Ile Pro Gln
        355                 360                 365

Val Ala Glu Phe Tyr Gly Ala Thr Glu Cys Asn Cys Ser Leu Gly Asn
    370                 375                 380

Phe Asp Ser Gln Val Gly Ala Cys Gly Phe Asn Ser Arg Ile Leu Ser
385                 390                 395                 400

Phe Val Tyr Pro Ile Arg Leu Val Arg Val Asn Glu Asp Thr Met Glu
                405                 410                 415

Leu Ile Arg Gly Pro Asp Gly Val Cys Ile Pro Cys Gln Pro Gly Glu
            420                 425                 430

Pro Gly Gln Leu Val Gly Arg Ile Ile Gln Lys Asp Pro Leu Arg Arg
        435                 440                 445

Phe Asp Gly Tyr Leu Asn Gln Gly Ala Asn Asn Lys Lys Ile Ala Lys
    450                 455                 460

Asp Val Phe Lys Lys Gly Asp Gln Ala Tyr Leu Thr Gly Asp Val Leu
465                 470                 475                 480

Val Met Asp Glu Leu Gly Tyr Leu Tyr Phe Arg Asp Arg Thr Gly Asp
                485                 490                 495

Thr Phe Arg Trp Lys Gly Glu Asn Val Ser Thr Thr Glu Val Glu Gly
            500                 505                 510

Thr Leu Ser Arg Leu Leu Asp Met Ala Asp Val Ala Val Tyr Gly Val
        515                 520                 525

Glu Val Pro Gly Thr Glu Gly Arg Ala Gly Met Ala Ala Val Ala Ser
    530                 535                 540

Pro Thr Gly Asn Cys Asp Leu Glu Arg Phe Ala Gln Val Leu Glu Lys
545                 550                 555                 560

Glu Leu Pro Leu Tyr Ala Arg Pro Ile Phe Leu Arg Leu Leu Pro Glu
                565                 570                 575

Leu His Lys Thr Gly Thr Tyr Lys Phe Gln Lys Thr Glu Leu Arg Lys
            580                 585                 590
```

```
Glu Gly Phe Asp Pro Ala Ile Val Lys Asp Pro Leu Phe Tyr Leu Asp
        595                 600                 605

Ala Gln Lys Gly Arg Tyr Val Pro Leu Asp Gln Glu Ala Tyr Ser Arg
        610                 615                 620

Ile Gln Ala Gly Glu Glu Lys Leu
625                 630

<210> SEQ ID NO 35
<211> LENGTH: 632
<212> TYPE: PRT
<213> ORGANISM: Mus musculus

<400> SEQUENCE: 35

Leu Gly Ser Lys Leu Val Leu Lys Leu Pro Trp Thr Gln Val Gly Phe
1               5                   10                  15

Ser Leu Leu Leu Tyr Leu Gly Ser Gly Gly Trp Arg Phe Ile Arg
            20                  25                  30

Val Phe Ile Lys Thr Val Arg Arg Asp Ile Phe Gly Gly Met Val Leu
            35                  40                  45

Leu Lys Val Lys Thr Lys Val Arg Arg Tyr Leu Gln Glu Arg Lys Thr
50                  55                  60

Val Pro Leu Leu Phe Ala Ser Met Val Gln Arg His Pro Asp Lys Thr
65                  70                  75                  80

Ala Leu Ile Phe Glu Gly Thr Asp Thr His Trp Thr Phe Arg Gln Leu
            85                  90                  95

Asp Glu Tyr Ser Ser Val Ala Asn Phe Leu Gln Ala Arg Gly Leu
            100                 105                 110

Ala Ser Gly Asn Val Val Ala Leu Phe Met Glu Asn Arg Asn Glu Phe
            115                 120                 125

Val Gly Leu Trp Leu Gly Met Ala Lys Leu Gly Val Glu Ala Ala Leu
        130                 135                 140

Ile Asn Thr Asn Leu Arg Arg Asp Ala Leu Arg His Cys Leu Asp Thr
145                 150                 155                 160

Ser Lys Ala Arg Ala Leu Ile Phe Gly Ser Glu Met Ala Ser Ala Ile
            165                 170                 175

Cys Glu Ile His Ala Ser Leu Glu Pro Thr Leu Ser Leu Phe Cys Ser
            180                 185                 190

Gly Ser Trp Glu Pro Ser Thr Val Pro Val Ser Thr Glu His Leu Asp
        195                 200                 205

Pro Leu Leu Glu Asp Ala Pro Lys His Leu Pro Ser His Pro Asp Lys
        210                 215                 220

Gly Phe Thr Asp Lys Leu Phe Tyr Ile Tyr Thr Ser Gly Thr Thr Gly
225                 230                 235                 240

Leu Pro Lys Ala Ala Ile Val Val His Ser Arg Tyr Tyr Arg Met Ala
            245                 250                 255

Ser Leu Val Tyr Tyr Gly Phe Arg Met Arg Pro Asp Asp Ile Val Tyr
            260                 265                 270

Asp Cys Leu Pro Leu Tyr His Ser Ser Arg Lys His Arg Gly Asp Trp
            275                 280                 285

Gln Cys Leu Leu His Gly Met Thr Val Ile Arg Lys Lys Phe Ser
        290                 295                 300

Ala Ser Arg Phe Trp Asp Asp Cys Ile Lys Tyr Asn Cys Thr Val Val
305                 310                 315                 320

Gln Tyr Ile Gly Glu Leu Cys Arg Tyr Leu Leu Asn Gln Pro Pro Arg
```

```
                     325                 330                 335
Glu Ala Glu Ser Arg His Lys Val Arg Met Ala Leu Gly Asn Gly Leu
            340                 345                 350
Arg Gln Ser Ile Trp Thr Asp Phe Ser Ser Arg Phe His Ile Pro Gln
        355                 360                 365
Val Ala Glu Phe Tyr Gly Ala Thr Glu Cys Asn Cys Ser Leu Gly Asn
    370                 375                 380
Phe Asp Ser Arg Val Gly Ala Cys Gly Phe Asn Ser Arg Ile Leu Ser
385                 390                 395                 400
Phe Val Tyr Pro Ile Arg Leu Val Arg Val Asn Glu Asp Thr Met Glu
                405                 410                 415
Leu Ile Arg Gly Pro Asp Gly Val Cys Ile Pro Cys Gln Pro Gly Gln
            420                 425                 430
Pro Gly Gln Leu Val Gly Arg Ile Ile Gln Gln Asp Pro Leu Arg Arg
        435                 440                 445
Phe Asp Gly Tyr Leu Asn Gln Gly Ala Asn Asn Lys Lys Ile Ala Asn
    450                 455                 460
Asp Val Phe Lys Lys Gly Asp Gln Ala Tyr Leu Thr Gly Asp Val Leu
465                 470                 475                 480
Val Met Asp Glu Leu Gly Tyr Leu Tyr Phe Arg Asp Arg Thr Gly Asp
                485                 490                 495
Thr Phe Arg Trp Lys Gly Glu Asn Val Ser Thr Thr Glu Val Glu Gly
            500                 505                 510
Thr Leu Ser Arg Leu Leu His Met Ala Asp Val Ala Val Tyr Gly Val
        515                 520                 525
Glu Val Pro Gly Thr Glu Gly Arg Ala Gly Met Ala Ala Val Ala Ser
    530                 535                 540
Pro Ile Ser Asn Cys Asp Leu Glu Ser Phe Ala Gln Thr Leu Lys Lys
545                 550                 555                 560
Glu Leu Pro Leu Tyr Ala Arg Pro Ile Phe Leu Arg Phe Leu Pro Glu
                565                 570                 575
Leu His Lys Thr Gly Thr Phe Lys Phe Gln Lys Thr Glu Leu Arg Lys
            580                 585                 590
Glu Gly Phe Asp Pro Ser Val Val Lys Asp Pro Leu Phe Tyr Leu Asp
        595                 600                 605
Ala Arg Lys Gly Cys Tyr Val Ala Leu Asp Gln Glu Ala Tyr Thr Arg
    610                 615                 620
Ile Gln Ala Gly Glu Glu Lys Leu
625                 630

<210> SEQ ID NO 36
<211> LENGTH: 2885
<212> TYPE: DNA
<213> ORGANISM: Homo sapiens

<400> SEQUENCE: 36
aacggcaagt aagcgcaacg caattaatgt gagtagctca ctcattaggc accccaggct    60
ttacacttta tgcttccggg ctcgtatgtt gtgtggaatt gtgagcggat accaatttca   120
cacaggaacc agctatgaca tgattacgaa tttaatacga ctcactatag ggaatttggc   180
cctcgaggcc aagaattcgg cacgagggt gctgagcccc tgcgcggttt ctggtgcgta   240
gagactgtaa atcgctgcgc ttctcagtca tcatcatccc agcttttccc ggctcgaatt   300
cagcctccaa ctcaagctcg cgggaaagac tacctgagag gagaaaagct tctgtccctg   360
```

```
gaccttcttc tgagggtgga gtcggaggct ccctgctttc cagccgccca gtgacccaag    420
cttaatcttc agcaccactt ggggcgacct tttcggtgca aacctacgat tctgtttctc    480
aggattcctc cccatcccgc ttcgccccgg aaaagctgac aagaacttca ggtgtaagcc    540
ctgagtagtg aggatctgcg gtctccgtgg agagctgtgc ctggaagaga aggacgctgg    600
tgggggctga gatcagagct gtcttctggc ccagttgccc ccatgcttct gtcatggcta    660
acagttctag gggctggaat ggtcgtcctg cacttcttgc agaaactcct gttcccttac    720
ttttgggatg acttctggtt cgtgttgaag gtggtgctca ttataattcg gctgaagaag    780
tatgaaaaga gaggggagct ggtgactgtg ctggataaat tcttgagtca tgccaaaaga    840
caacctcgga aacctttcat catctatgag ggagacatct acacctatca ggatgtagac    900
aaaaggagca gcagagtggc ccatgtcttc ctgaaccatt cctctctgaa aaaggggac     960 acggtggctc tgctgatgag caatgagccg gacttcgttc acgtgtggtt cggcctcgcc   1020
aagctgggct gcgtggtggc ctttctcaac accaacattc gctccaactc cctcctgaat   1080
tgcatccgcg cctgtgggcc cagagcccta gtggtgggcg cagatttgct tggaacggta   1140
gaagaaatcc ttccaagcct ctcagaaaat atcagtgttt gggggatgaa agattctgtt   1200
ccacaaggtg taatttcact caaagaaaaa ctgagcacct cacctgatga gcccgtgcca   1260
cgcagccacc atgttgtctc actcctcaag tctacttgtc tttacatttt tacctctgga   1320
acaacaggtc taccaaaagc agctgtgatt agtcagctgc aggttttaag gggttctgct   1380
gtcctgtggg cttttggttg tactgctcat gacattgttt atataaccct tcctctgtat   1440
catagttcag cagctatcct gggaatttct ggatgtgttg agttgggtgc acttgtgtg    1500 ttaaagaaga aattttcagc aagccagttt tggagtgact gcaagaagta tgatgtgact   1560
gtgtttcagt atattggaga actttgtcgc tacctttgca aacaatctaa gagagaagga   1620
gaaaaggatc ataaggtgcg tttggcaatt ggaaatggca tacggagtga tgtatggaga   1680
gaatttttag acagatttgg aaatataaag gtgtgtgaac tttatgcagc taccgaatca   1740
agcatatctt tcatgaacta cactgggaga attggagcaa ttgggagaac aaatttgttt   1800
tacaaacttc tttccacttt tgacttaata agtatgact ttcagaaaga tgaacccatg    1860
agaaatgagc agggttggtg tattcatgtg aaaaaaggag aacctggact tctcatttct   1920
cgagtgaatg caaaaaatcc cttctttggc tatgctgggc cttataagca cacaaaagac   1980
aaattgcttt gtgatgtttt taagaaggga gatgtttacc ttaatactgg agacttaata   2040
gtccaggatc aggacaattt cctttatttt tgggaccgta ctggagacac tttcagatgg   2100
aaaggagaaa atgtcgcaac cactgaggtt gctgatgtta ttggaatgtt ggatttcata   2160
caggaagcaa acgtctatgg tgtggctata tcaggttatg aaggaagagc aggaatggct   2220
tctattattt taaaaccaaa tacatcttta gatttggaaa agtttatga acaagttgta    2280 acatttctac cagcttatgc ttgtccacga tttttaagaa ttcaggaaaa atgaagca    2340 acaggaacat tcaaactatt gaagcatcag ttggtggaag atggatttaa tccactgaaa   2400
atttctgaac cactttactt catggataac ttgaaaagt cttatgttct actgaccagg    2460
gaactttatg atcaaataat gttagggaa ataaaacttt aagattttta tatctagaac    2520
tttcatatgc tttcttagga agagtgagag ggggtatat gattctttat gaatgggga    2580 aagggagcta acattaatta tgcatgtact atatttcctt aatatgagag ataattttt    2640 aattgcataa gaatttaat ttcttttaat tgatataaac attagttgat tattcttttt    2700
atctatttgg agattcagtg cataactaag tattttcctt aatactaaag attttaaata   2760
```

```
ataaatagtg gctagcggtt tggacaatca ctaaaaatgt actttctaat aagtaaaatt    2820
tctaattttg aataaaagat taaattttac tgaaaaaaaa aaaaaaaaaa aaaattggcg    2880
gccgc                                                                2885
```

<210> SEQ ID NO 37
<211> LENGTH: 619
<212> TYPE: PRT
<213> ORGANISM: Homo sapiens

<400> SEQUENCE: 37

```
Met Leu Leu Ser Trp Leu Thr Val Leu Gly Ala Gly Met Val Val Leu
1               5                   10                  15

His Phe Leu Gln Lys Leu Leu Phe Pro Tyr Phe Trp Asp Asp Phe Trp
            20                  25                  30

Phe Val Leu Lys Val Val Leu Ile Ile Ile Arg Leu Lys Lys Tyr Glu
        35                  40                  45

Lys Arg Gly Glu Leu Val Thr Val Leu Asp Lys Phe Leu Ser His Ala
    50                  55                  60

Lys Arg Gln Pro Arg Lys Pro Phe Ile Ile Tyr Glu Gly Asp Ile Tyr
65                  70                  75                  80

Thr Tyr Gln Asp Val Asp Lys Arg Ser Ser Arg Val Ala His Val Phe
                85                  90                  95

Leu Asn His Ser Ser Leu Lys Lys Gly Asp Thr Val Ala Leu Leu Met
            100                 105                 110

Ser Asn Glu Pro Asp Phe Val His Val Trp Phe Gly Leu Ala Lys Leu
        115                 120                 125

Gly Cys Val Val Ala Phe Leu Asn Thr Asn Ile Arg Ser Asn Ser Leu
    130                 135                 140

Leu Asn Cys Ile Arg Ala Cys Gly Pro Arg Ala Leu Val Val Gly Ala
145                 150                 155                 160

Asp Leu Leu Gly Thr Val Glu Glu Ile Leu Pro Ser Leu Ser Glu Asn
                165                 170                 175

Ile Ser Val Trp Gly Met Lys Asp Ser Val Pro Gln Gly Val Ile Ser
            180                 185                 190

Leu Lys Glu Lys Leu Ser Thr Ser Pro Asp Glu Pro Val Pro Arg Ser
        195                 200                 205

His His Val Val Ser Leu Leu Lys Ser Thr Cys Leu Tyr Ile Phe Thr
    210                 215                 220

Ser Gly Thr Thr Gly Leu Pro Lys Ala Ala Val Ile Ser Gln Leu Gln
225                 230                 235                 240

Val Leu Arg Gly Ser Ala Val Leu Trp Ala Phe Gly Cys Thr Ala His
                245                 250                 255

Asp Ile Val Tyr Ile Thr Leu Pro Leu Tyr His Ser Ser Ala Ala Ile
            260                 265                 270

Leu Gly Ile Ser Gly Cys Val Glu Leu Gly Ala Thr Cys Val Leu Lys
        275                 280                 285

Lys Lys Phe Ser Ala Ser Gln Phe Trp Ser Asp Cys Lys Lys Tyr Asp
    290                 295                 300

Val Thr Val Phe Gln Tyr Ile Gly Glu Leu Cys Arg Tyr Leu Cys Lys
305                 310                 315                 320

Gln Ser Lys Arg Glu Gly Glu Lys Asp His Lys Val Arg Leu Ala Ile
                325                 330                 335

Gly Asn Gly Ile Arg Ser Asp Val Trp Arg Glu Phe Leu Asp Arg Phe
```

```
                  340                 345                 350
Gly Asn Ile Lys Val Cys Glu Leu Tyr Ala Ala Thr Glu Ser Ser Ile
            355                 360                 365
Ser Phe Met Asn Tyr Thr Gly Arg Ile Gly Ala Ile Gly Arg Thr Asn
370                 375                 380
Leu Phe Tyr Lys Leu Leu Ser Thr Phe Asp Leu Ile Lys Tyr Asp Phe
385                 390                 395                 400
Gln Lys Asp Glu Pro Met Arg Asn Glu Gln Gly Trp Cys Ile His Val
                405                 410                 415
Lys Lys Gly Glu Pro Gly Leu Leu Ile Ser Arg Val Asn Ala Lys Asn
            420                 425                 430
Pro Phe Phe Gly Tyr Ala Gly Pro Tyr Lys His Thr Lys Asp Lys Leu
            435                 440                 445
Leu Cys Asp Val Phe Lys Lys Gly Asp Val Tyr Leu Asn Thr Gly Asp
        450                 455                 460
Leu Ile Val Gln Asp Gln Asp Asn Phe Leu Tyr Phe Trp Asp Arg Thr
465                 470                 475                 480
Gly Asp Thr Phe Arg Trp Lys Gly Glu Asn Val Ala Thr Thr Glu Val
                485                 490                 495
Ala Asp Val Ile Gly Met Leu Asp Phe Ile Gln Glu Ala Asn Val Tyr
            500                 505                 510
Gly Val Ala Ile Ser Gly Tyr Glu Gly Arg Ala Gly Met Ala Ser Ile
        515                 520                 525
Ile Leu Lys Pro Asn Thr Ser Leu Asp Leu Glu Lys Val Tyr Glu Gln
    530                 535                 540
Val Val Thr Phe Leu Pro Ala Tyr Ala Cys Pro Arg Phe Leu Arg Ile
545                 550                 555                 560
Gln Glu Lys Met Glu Ala Thr Gly Thr Phe Lys Leu Leu Lys His Gln
                565                 570                 575
Leu Val Glu Asp Gly Phe Asn Pro Leu Lys Ile Ser Glu Pro Leu Tyr
            580                 585                 590
Phe Met Asp Asn Leu Lys Lys Ser Tyr Val Leu Leu Thr Arg Glu Leu
            595                 600                 605
Tyr Asp Gln Ile Met Leu Gly Glu Ile Lys Leu
        610                 615

<210> SEQ ID NO 38
<211> LENGTH: 646
<212> TYPE: PRT
<213> ORGANISM: Homo sapiens

<400> SEQUENCE: 38

Met Arg Ala Pro Gly Ala Gly Ala Ala Ser Val Val Ser Leu Ala Leu
1               5                   10                  15
Leu Trp Leu Leu Gly Leu Pro Trp Thr Trp Ser Ala Ala Ala Ala Leu
            20                  25                  30
Gly Val Tyr Val Gly Ser Gly Gly Trp Arg Phe Leu Arg Ile Val Cys
        35                  40                  45
Lys Thr Ala Arg Arg Asp Leu Phe Gly Leu Ser Val Leu Ile Arg Val
    50                  55                  60
Arg Leu Glu Leu Arg Arg His Gln Arg Ala Gly His Thr Ile Pro Arg
65                  70                  75                  80
Ile Phe Gln Ala Val Val Gln Arg Gln Pro Glu Arg Leu Ala Leu Val
                85                  90                  95
```

-continued

```
Asp Ala Gly Thr Gly Glu Cys Trp Thr Phe Ala Gln Leu Asp Ala Tyr
            100                 105                 110

Ser Asn Ala Val Ala Asn Leu Phe Arg Gln Leu Gly Phe Ala Pro Gly
            115                 120                 125

Asp Val Ala Ile Phe Leu Glu Gly Arg Pro Glu Phe Val Gly Leu
            130                 135             140

Trp Leu Gly Leu Ala Lys Ala Gly Met Glu Ala Leu Leu Asn Val
145                 150                 155                 160

Asn Leu Arg Arg Glu Pro Leu Ala Phe Cys Leu Gly Thr Ser Gly Ala
                165                 170                 175

Lys Ala Leu Ile Phe Gly Gly Glu Met Val Ala Val Ala Glu Val
            180                 185                 190

Ser Gly His Leu Gly Lys Ser Leu Ile Lys Phe Cys Ser Gly Asp Leu
            195                 200                 205

Gly Pro Glu Gly Ile Leu Pro Asp Thr His Leu Leu Asp Pro Leu Leu
            210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
            260                 265                 270

Gly His His Ala Tyr Arg Met Gln Ala Ala Asp Val Leu Tyr Asp Cys
            275                 280                 285

Leu Pro Leu Tyr His Ser Ala Gly Asn Ile Ile Gly Val Gly Gln Cys
            290                 295                 300

Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
            340                 345                 350

Glu Arg Arg His Arg Val Arg Leu Ala Val Gly Asn Gly Leu Arg Pro
            355                 360                 365

Ala Ile Trp Glu Glu Phe Thr Glu Arg Phe Gly Val Arg Gln Ile Gly
            370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
            420                 425                 430

Arg Asp Ala Gln Gly Leu Cys Ile Pro Cys Gln Ala Gly Glu Pro Gly
            435                 440                 445

Leu Leu Val Gly Gln Ile Asn Gln Gln Asp Pro Leu Arg Arg Phe Asp
            450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
```

-continued

```
                515                 520                 525
Ser Arg Leu Leu Gly Gln Thr Asp Val Ala Val Tyr Gly Val Ala Val
            530                 535                 540
Pro Gly Val Glu Gly Lys Ala Gly Met Ala Ala Val Ala Asp Pro His
545                 550                 555                 560
Ser Leu Leu Asp Pro Asn Ala Ile Tyr Gln Glu Leu Gln Lys Val Leu
                565                 570                 575
Ala Pro Tyr Ala Arg Pro Ile Phe Leu Arg Leu Leu Pro Gln Val Asp
            580                 585                 590
Thr Thr Gly Thr Phe Lys Ile Gln Lys Thr Arg Leu Gln Arg Glu Gly
            595                 600                 605
Phe Asp Pro Arg Gln Thr Ser Asp Arg Leu Phe Phe Leu Asp Leu Lys
610                 615                 620
Gln Gly His Tyr Leu Pro Leu Asn Glu Ala Val Tyr Thr Arg Ile Cys
625                 630                 635                 640
Ser Gly Ala Phe Ala Leu
            645

<210> SEQ ID NO 39
<211> LENGTH: 632
<212> TYPE: PRT
<213> ORGANISM: Homo sapiens

<400> SEQUENCE: 39

Leu Phe Ser Lys Leu Val Leu Lys Leu Pro Trp Thr Gln Val Gly Phe
1               5                   10                  15
Ser Leu Leu Phe Leu Tyr Leu Gly Ser Gly Gly Trp Arg Phe Ile Arg
            20                  25                  30
Val Phe Ile Lys Thr Ile Arg Arg Asp Ile Phe Gly Gly Leu Val Leu
            35                  40                  45
Leu Lys Val Lys Ala Lys Val Arg Gln Cys Leu Gln Glu Arg Arg Thr
        50                  55                  60
Val Pro Ile Leu Phe Ala Ser Thr Val Arg Arg His Pro Asp Lys Thr
65                  70                  75                  80
Ala Leu Ile Phe Glu Gly Thr Asp Thr His Trp Thr Phe Arg Gln Leu
                85                  90                  95
Asp Glu Tyr Ser Ser Val Ala Asn Phe Leu Gln Ala Arg Gly Leu
            100                 105                 110
Ala Ser Gly Asp Val Ala Ala Ile Phe Met Glu Asn Arg Asn Glu Phe
        115                 120                 125
Val Gly Leu Trp Leu Gly Met Ala Lys Leu Gly Val Glu Ala Ala Leu
    130                 135                 140
Ile Asn Thr Asn Leu Arg Arg Asp Ala Leu Leu His Cys Leu Thr Thr
145                 150                 155                 160
Ser Arg Ala Arg Ala Leu Val Phe Gly Ser Glu Met Ala Ser Ala Ile
                165                 170                 175
Cys Glu Val His Ala Ser Leu Asp Pro Ser Leu Ser Leu Phe Cys Ser
            180                 185                 190
Gly Ser Trp Glu Pro Gly Ala Val Pro Pro Ser Thr Glu His Leu Asp
        195                 200                 205
Pro Leu Leu Lys Asp Ala Pro Lys His Leu Pro Ser Cys Pro Asp Lys
    210                 215                 220
Gly Phe Thr Asp Lys Leu Phe Tyr Ile Tyr Thr Ser Gly Thr Thr Gly
225                 230                 235                 240
```

```
Leu Pro Lys Ala Ala Ile Val Val His Ser Arg Tyr Arg Met Ala
                245                 250                 255

Ala Leu Val Tyr Tyr Gly Phe Arg Met Arg Pro Asn Asp Ile Val Tyr
            260                 265                 270

Asp Cys Leu Pro Leu Tyr His Ser Ala Gly Asn Ile Val Gly Ile Gly
            275                 280                 285

Gln Cys Leu Leu His Gly Met Thr Val Val Ile Arg Lys Lys Phe Ser
    290                 295                 300

Ala Ser Arg Phe Trp Asp Asp Cys Ile Lys Tyr Asn Cys Thr Ile Val
305                 310                 315                 320

Gln Tyr Ile Gly Glu Leu Cys Arg Tyr Leu Leu Asn Gln Pro Pro Arg
                325                 330                 335

Glu Ala Glu Asn Gln His Gln Val Arg Met Ala Leu Gly Asn Gly Leu
            340                 345                 350

Arg Gln Ser Ile Trp Thr Asn Phe Ser Ser Arg Phe His Ile Pro Gln
        355                 360                 365

Val Ala Glu Phe Tyr Gly Ala Thr Glu Cys Asn Cys Ser Leu Gly Asn
    370                 375                 380

Phe Asp Ser Gln Val Gly Ala Cys Gly Phe Asn Ser Arg Ile Leu Ser
385                 390                 395                 400

Phe Val Tyr Pro Ile Arg Leu Val Arg Val Asn Glu Asp Thr Met Glu
                405                 410                 415

Leu Ile Arg Gly Pro Asp Gly Val Cys Ile Pro Cys Gln Pro Gly Glu
            420                 425                 430

Pro Gly Gln Leu Val Gly Arg Ile Ile Gln Lys Asp Pro Leu Arg Arg
        435                 440                 445

Phe Asp Gly Tyr Leu Asn Gln Gly Ala Asn Asn Lys Lys Ile Ala Lys
    450                 455                 460

Asp Val Phe Lys Lys Gly Asp Gln Ala Tyr Leu Thr Gly Asp Val Leu
465                 470                 475                 480

Val Met Asp Glu Leu Gly Tyr Leu Tyr Phe Arg Asp Arg Thr Gly Asp
                485                 490                 495

Thr Phe Arg Trp Lys Gly Glu Asn Val Ser Thr Thr Glu Val Glu Gly
            500                 505                 510

Thr Leu Ser Arg Leu Leu Asp Met Ala Asp Val Ala Val Tyr Gly Val
        515                 520                 525

Glu Val Pro Gly Thr Glu Gly Arg Ala Gly Met Ala Ala Val Ala Ser
    530                 535                 540

Pro Thr Gly Asn Cys Asp Leu Glu Arg Phe Ala Gln Val Leu Glu Lys
545                 550                 555                 560

Glu Leu Pro Leu Tyr Ala Arg Pro Ile Phe Leu Arg Leu Leu Pro Glu
                565                 570                 575

Leu His Lys Thr Gly Thr Tyr Lys Phe Gln Lys Thr Glu Leu Arg Lys
            580                 585                 590

Glu Gly Phe Asp Pro Ala Ile Val Lys Asp Pro Leu Phe Tyr Leu Asp
        595                 600                 605

Ala Gln Lys Gly Arg Tyr Val Pro Leu Asp Gln Glu Ala Tyr Ser Arg
    610                 615                 620

Ile Gln Ala Gly Glu Glu Lys Leu
625                 630

<210> SEQ ID NO 40
<211> LENGTH: 619
<212> TYPE: PRT
```

<213> ORGANISM: Homo sapiens

<400> SEQUENCE: 40

```
Met Leu Leu Ser Trp Leu Thr Val Leu Gly Ala Gly Met Val Val Leu
 1               5                  10                  15

His Phe Leu Gln Lys Leu Leu Phe Pro Tyr Phe Trp Asp Asp Phe Trp
             20                  25                  30

Phe Val Leu Lys Val Val Leu Ile Ile Ile Arg Leu Lys Lys Tyr Glu
         35                  40                  45

Lys Arg Gly Glu Leu Val Thr Val Leu Asp Lys Phe Leu Ser His Ala
     50                  55                  60

Lys Arg Gln Pro Arg Lys Pro Phe Ile Ile Tyr Gly Asp Ile Tyr
 65                  70                  75                  80

Thr Tyr Gln Asp Val Asp Lys Arg Ser Ser Arg Val Ala His Val Phe
                 85                  90                  95

Leu Asn His Ser Ser Leu Lys Lys Gly Asp Thr Val Ala Leu Leu Met
            100                 105                 110

Ser Asn Glu Pro Asp Phe Val His Val Trp Phe Gly Leu Ala Lys Leu
        115                 120                 125

Gly Cys Val Val Ala Phe Leu Asn Thr Asn Ile Arg Ser Asn Ser Leu
    130                 135                 140

Leu Asn Cys Ile Arg Ala Cys Gly Pro Arg Ala Leu Val Val Gly Ala
145                 150                 155                 160

Asp Leu Leu Gly Thr Val Glu Glu Ile Leu Pro Ser Leu Ser Glu Asn
                165                 170                 175

Ile Ser Val Trp Gly Met Lys Asp Ser Val Pro Gln Gly Val Ile Ser
            180                 185                 190

Leu Lys Glu Lys Leu Ser Thr Ser Pro Asp Glu Pro Val Pro Arg Ser
        195                 200                 205

His His Val Val Ser Leu Leu Lys Ser Thr Cys Leu Tyr Ile Phe Thr
    210                 215                 220

Ser Gly Thr Thr Gly Leu Pro Lys Ala Ala Val Ile Ser Gln Leu Gln
225                 230                 235                 240

Val Leu Arg Gly Ser Ala Val Leu Trp Ala Phe Gly Cys Thr Ala His
                245                 250                 255

Asp Ile Val Tyr Ile Thr Leu Pro Leu Tyr His Ser Ser Ala Ala Ile
            260                 265                 270

Leu Gly Ile Ser Gly Cys Val Glu Leu Gly Ala Thr Cys Val Leu Lys
        275                 280                 285

Lys Lys Phe Ser Ala Ser Gln Phe Trp Ser Asp Cys Lys Lys Tyr Asp
    290                 295                 300

Val Thr Val Phe Gln Tyr Ile Gly Glu Leu Cys Arg Tyr Leu Cys Lys
305                 310                 315                 320

Gln Ser Lys Arg Glu Gly Glu Lys Asp His Lys Val Arg Leu Ala Ile
                325                 330                 335

Gly Asn Gly Ile Arg Ser Asp Val Trp Arg Glu Phe Leu Asp Arg Phe
            340                 345                 350

Gly Asn Ile Lys Val Cys Glu Leu Tyr Ala Ala Thr Glu Ser Ser Ile
        355                 360                 365

Ser Phe Met Asn Tyr Thr Gly Arg Ile Gly Ala Ile Gly Arg Thr Asn
    370                 375                 380

Leu Phe Tyr Lys Leu Leu Ser Thr Phe Asp Leu Ile Lys Tyr Asp Phe
385                 390                 395                 400
```

-continued

```
Gln Lys Asp Glu Pro Met Arg Asn Glu Gln Gly Trp Cys Ile His Val
                405                 410                 415
Lys Lys Gly Glu Pro Gly Leu Leu Ile Ser Arg Val Asn Ala Lys Asn
            420                 425                 430
Pro Phe Phe Gly Tyr Ala Gly Pro Tyr Lys His Thr Lys Asp Lys Leu
        435                 440                 445
Leu Cys Asp Val Phe Lys Lys Gly Asp Val Tyr Leu Asn Thr Gly Asp
    450                 455                 460
Leu Ile Val Gln Asp Gln Asp Asn Phe Leu Tyr Phe Trp Asp Arg Thr
465                 470                 475                 480
Gly Asp Thr Phe Arg Trp Lys Gly Glu Asn Val Ala Thr Thr Glu Val
                485                 490                 495
Ala Asp Val Ile Gly Met Leu Asp Phe Ile Gln Glu Ala Asn Val Tyr
            500                 505                 510
Gly Val Ala Ile Ser Gly Tyr Glu Gly Arg Ala Gly Met Ala Ser Ile
        515                 520                 525
Ile Leu Lys Pro Asn Thr Ser Leu Asp Leu Glu Lys Val Tyr Glu Gln
    530                 535                 540
Val Val Thr Phe Leu Pro Ala Tyr Ala Cys Pro Arg Phe Leu Arg Ile
545                 550                 555                 560
Gln Glu Lys Met Glu Ala Thr Gly Thr Phe Lys Leu Leu Lys His Gln
                565                 570                 575
Leu Val Glu Asp Gly Phe Asn Pro Leu Lys Ile Ser Glu Pro Leu Tyr
            580                 585                 590
Phe Met Asp Asn Leu Lys Lys Ser Tyr Val Leu Leu Thr Arg Glu Leu
        595                 600                 605
Tyr Asp Gln Ile Met Leu Gly Glu Ile Lys Leu
    610                 615

<210> SEQ ID NO 41
<211> LENGTH: 643
<212> TYPE: PRT
<213> ORGANISM: Homo sapiens

<400> SEQUENCE: 41

Met Leu Leu Gly Ala Ser Leu Val Gly Val Leu Leu Phe Ser Lys Leu
1               5                   10                  15
Val Leu Lys Leu Pro Trp Thr Gln Val Gly Phe Ser Leu Leu Phe Leu
            20                  25                  30
Tyr Leu Gly Ser Gly Gly Trp Arg Phe Ile Arg Val Phe Ile Lys Thr
        35                  40                  45
Ile Arg Arg Asp Ile Phe Gly Gly Leu Val Leu Leu Lys Val Lys Ala
    50                  55                  60
Lys Val Arg Gln Cys Leu Gln Glu Arg Arg Thr Val Pro Ile Leu Phe
65                  70                  75                  80
Ala Ser Thr Val Arg Arg His Pro Asp Lys Thr Ala Leu Ile Phe Glu
                85                  90                  95
Gly Thr Asp Thr His Trp Thr Phe Arg Gln Leu Asp Glu Tyr Ser Ser
            100                 105                 110
Ser Val Ala Asn Phe Leu Gln Ala Arg Gly Leu Ala Ser Gly Asp Val
        115                 120                 125
Ala Ala Ile Phe Met Glu Asn Arg Asn Glu Phe Val Gly Leu Trp Leu
    130                 135                 140
Gly Met Ala Lys Leu Gly Val Glu Ala Ala Leu Ile Asn Thr Asn Leu
145                 150                 155                 160
```

-continued

```
Arg Arg Asp Ala Leu Leu His Cys Leu Thr Thr Ser Arg Ala Arg Ala
                165                 170                 175
Leu Val Phe Gly Ser Glu Met Ala Ser Ala Ile Cys Glu Val His Ala
            180                 185                 190
Ser Leu Asp Pro Ser Leu Ser Leu Phe Cys Ser Gly Ser Trp Glu Pro
        195                 200                 205
Gly Ala Val Pro Pro Ser Thr Glu His Leu Asp Pro Leu Leu Lys Asp
    210                 215                 220
Ala Pro Lys His Leu Pro Ser Cys Pro Asp Lys Gly Phe Thr Asp Lys
225                 230                 235                 240
Leu Phe Tyr Ile Tyr Thr Ser Gly Thr Thr Gly Leu Pro Lys Ala Ala
                245                 250                 255
Ile Val Val His Ser Arg Tyr Tyr Arg Met Ala Ala Leu Val Tyr Tyr
            260                 265                 270
Gly Phe Arg Met Arg Pro Asn Asp Ile Val Tyr Asp Cys Leu Pro Leu
        275                 280                 285
Tyr His Ser Ala Gly Asn Ile Val Gly Ile Gly Gln Cys Leu Leu His
    290                 295                 300
Gly Met Thr Val Val Ile Arg Lys Lys Phe Ser Ala Ser Arg Phe Trp
305                 310                 315                 320
Asp Asp Cys Ile Lys Tyr Asn Cys Thr Ile Val Gln Tyr Ile Gly Glu
                325                 330                 335
Leu Cys Arg Tyr Leu Leu Asn Gln Pro Pro Arg Glu Ala Glu Asn Gln
            340                 345                 350
His Gln Val Arg Met Ala Leu Gly Asn Gly Leu Arg Gln Ser Ile Trp
        355                 360                 365
Thr Asn Phe Ser Ser Arg Phe His Ile Pro Gln Val Ala Glu Phe Tyr
    370                 375                 380
Gly Ala Thr Glu Cys Asn Cys Ser Leu Gly Asn Phe Asp Ser Gln Val
385                 390                 395                 400
Gly Ala Cys Gly Phe Asn Ser Arg Ile Leu Ser Phe Val Tyr Pro Ile
                405                 410                 415
Arg Leu Val Arg Val Asn Glu Asp Thr Met Glu Leu Ile Arg Gly Pro
            420                 425                 430
Asp Gly Val Cys Ile Pro Cys Gln Pro Gly Glu Pro Gly Gln Leu Val
        435                 440                 445
Gly Arg Ile Ile Gln Lys Asp Pro Leu Arg Arg Phe Asp Gly Tyr Leu
    450                 455                 460
Asn Gln Gly Ala Asn Asn Lys Lys Ile Ala Lys Asp Val Phe Lys Lys
465                 470                 475                 480
Gly Asp Gln Ala Tyr Leu Thr Gly Asp Val Leu Val Met Asp Glu Leu
                485                 490                 495
Gly Tyr Leu Tyr Phe Arg Asp Arg Thr Gly Asp Thr Phe Arg Trp Lys
            500                 505                 510
Gly Glu Asn Val Ser Thr Thr Glu Val Glu Gly Thr Leu Ser Arg Leu
        515                 520                 525
Leu Asp Met Ala Asp Val Ala Val Tyr Gly Val Glu Val Pro Gly Thr
    530                 535                 540
Glu Gly Arg Ala Gly Met Ala Ala Val Ala Ser Pro Thr Gly Asn Cys
545                 550                 555                 560
Asp Leu Glu Arg Phe Ala Gln Val Leu Glu Lys Glu Leu Pro Leu Tyr
                565                 570                 575
```

```
Ala Arg Pro Ile Phe Leu Arg Leu Leu Pro Glu Leu His Lys Thr Gly
            580                 585                 590

Thr Tyr Lys Phe Gln Lys Thr Glu Leu Arg Lys Glu Gly Phe Asp Pro
        595                 600                 605

Ala Ile Val Lys Asp Pro Leu Phe Tyr Leu Asp Ala Gln Lys Gly Arg
    610                 615                 620

Tyr Val Pro Leu Asp Gln Glu Ala Tyr Ser Arg Ile Gln Ala Gly Glu
625                 630                 635                 640

Glu Lys Leu
```

<210> SEQ ID NO 42
<211> LENGTH: 643
<212> TYPE: PRT
<213> ORGANISM: Mus musculus
<220> FEATURE:
<221> NAME/KEY: VARIANT
<222> LOCATION: (1)...(643)
<223> OTHER INFORMATION: Xaa = Any Amino Acid

<400> SEQUENCE: 42

```
Met Leu Leu Gly Ala Ser Leu Val Gly Val Leu Leu Phe Ser Lys Leu
  1                 5                  10                  15

Val Leu Lys Leu Pro Trp Thr Gln Val Gly Phe Ser Leu Leu Xaa Leu
             20                  25                  30

Tyr Leu Gly Ser Gly Gly Trp Arg Phe Ile Arg Val Phe Ile Lys Thr
         35                  40                  45

Val Arg Arg Asp Ile Phe Gly Gly Met Val Leu Leu Lys Val Lys Thr
     50                  55                  60

Lys Val Arg Arg Tyr Leu Gln Glu Arg Lys Thr Val Pro Leu Leu Phe
 65                  70                  75                  80

Ala Ser Met Val Gln Arg His Pro Asp Lys Thr Ala Leu Ile Phe Glu
                 85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asn Val
        115                 120                 125

Val Ala Leu Phe Met Glu Asn Arg Asn Glu Phe Val Gly Leu Trp Xaa
    130                 135                 140

Gly Met Ala Lys Leu Gly Val Glu Ala Ala Leu Ile Asn Thr Asn Leu
145                 150                 155                 160

Arg Arg Asp Ala Leu Arg His Cys Leu Asp Thr Ser Lys Ala Arg Ala
                165                 170                 175

Leu Ile Phe Gly Ser Glu Met Ala Ser Ala Ile Cys Glu Ile His Ala
            180                 185                 190

Ser Leu Gly Pro Thr Leu Ser Leu Phe Cys Ser Gly Ser Trp Glu Pro
        195                 200                 205

Ser Thr Val Pro Val Ser Thr Glu His Leu Asp Pro Leu Leu Glu Asp
    210                 215                 220

Ala Pro Lys His Leu Pro Ser His Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255

Ile Val Val His Ser Arg Tyr Tyr Arg Met Ala Ser Leu Val Tyr Tyr
            260                 265                 270

Gly Phe Arg Met Arg Pro Asp Asp Ile Val Tyr Asp Cys Leu Pro Leu
        275                 280                 285
```

```
Tyr His Ser Ser Arg Lys His Arg Gly Asp Trp Gln Cys Leu Leu His
    290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Ile Val Gln Tyr Ile Gly Glu
                325                 330                 335

Leu Cys Arg Tyr Leu Leu Asn Gln Pro Pro Arg Glu Ala Glu Ser Arg
            340                 345                 350

His Lys Val Arg Met Ala Leu Gly Asn Gly Leu Arg Gln Ser Ile Trp
        355                 360                 365

Thr Asp Phe Ser Ser Arg Phe His Ile Pro Gln Val Ala Glu Phe Tyr
    370                 375                 380

Gly Ala Thr Glu Cys Asn Cys Ser Leu Gly Asn Phe Asp Ser Arg Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
            420                 425                 430

Asp Gly Val Cys Ile Pro Cys Gln Pro Gly Gln Pro Gly Gln Leu Val
        435                 440                 445

Gly Arg Ile Ile Gln Lys Asp Pro Leu Arg Arg Phe Asp Gly Tyr Leu
    450                 455                 460

Asn Gln Gly Ala Asn Asn Lys Lys Ile Ala Asn Asp Val Phe Lys Lys
465                 470                 475                 480

Gly Asp Gln Ala Tyr Leu Thr Gly Asp Val Leu Val Met Asp Glu Leu
                485                 490                 495

Gly Tyr Leu Tyr Phe Arg Asp Arg Thr Gly Asp Thr Phe Arg Trp Lys
            500                 505                 510

Gly Glu Asn Val Ser Thr Thr Glu Val Glu Gly Thr Leu Ser Arg Leu
        515                 520                 525

Leu His Met Ala Asp Val Ala Val Tyr Gly Val Glu Val Pro Gly Thr
    530                 535                 540

Glu Gly Arg Ala Gly Met Ala Ala Val Ala Ser Pro Ile Ser Asn Cys
545                 550                 555                 560

Asp Leu Glu Ser Phe Ala Gln Thr Leu Lys Lys Glu Leu Pro Leu Tyr
                565                 570                 575

Ala Arg Pro Ile Phe Leu Arg Phe Leu Pro Glu Leu His Lys Thr Gly
            580                 585                 590

Thr Phe Lys Phe Gln Lys Thr Glu Leu Arg Lys Glu Gly Phe Asp Pro
        595                 600                 605

Ser Val Val Lys Asp Pro Leu Phe Tyr Leu Asp Ala Arg Lys Gly Cys
    610                 615                 620

Tyr Val Ala Leu Asp Gln Glu Ala Tyr Thr Arg Ile Gln Ala Gly Glu
625                 630                 635                 640

Glu Lys Leu

<210> SEQ ID NO 43
<211> LENGTH: 646
<212> TYPE: PRT
<213> ORGANISM: Homo sapiens

<400> SEQUENCE: 43

Met Arg Ala Pro Gly Ala Gly Ala Ala Ser Val Val Ser Leu Ala Leu
1               5                   10                  15
```

```
Leu Trp Leu Leu Gly Leu Pro Trp Thr Trp Ser Ala Ala Ala Leu
             20                  25                  30

Gly Val Tyr Val Gly Ser Gly Gly Trp Arg Phe Leu Arg Ile Val Cys
             35                  40                  45

Lys Thr Ala Arg Arg Asp Leu Phe Gly Leu Ser Val Leu Ile Arg Val
 50                  55                  60

Arg Leu Glu Leu Arg Arg His Gln Arg Ala Gly His Thr Ile Pro Arg
 65                  70                  75                  80

Ile Phe Gln Ala Val Val Gln Arg Gln Pro Glu Arg Leu Ala Leu Val
                 85                  90                  95

Asp Ala Gly Thr Gly Glu Cys Trp Thr Phe Ala Gln Leu Asp Ala Tyr
            100                 105                 110

Ser Asn Ala Val Ala Asn Leu Phe Arg Gln Leu Gly Phe Ala Pro Gly
            115                 120                 125

Asp Val Val Ala Ile Phe Leu Glu Gly Arg Pro Glu Phe Val Gly Leu
            130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
                165                 170                 175

Lys Ala Leu Ile Phe Gly Gly Glu Met Val Ala Val Ala Glu Val
            180                 185                 190

Ser Gly His Leu Gly Lys Ser Leu Ile Lys Phe Cys Ser Gly Asp Leu
            195                 200                 205

Gly Pro Glu Gly Ile Leu Pro Asp Thr His Leu Leu Asp Pro Leu Leu
            210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
            260                 265                 270

Gly His His Ala Tyr Arg Met Gln Ala Ala Asp Val Leu Tyr Asp Cys
            275                 280                 285

Leu Pro Leu Tyr His Ser Ala Gly Asn Ile Ile Gly Val Gly Gln Cys
            290                 295                 300

Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
            340                 345                 350

Glu Arg Arg His Arg Val Arg Leu Ala Val Gly Asn Gly Leu Arg Pro
            355                 360                 365

Ala Ile Trp Glu Glu Phe Thr Glu Arg Phe Gly Val Arg Gln Ile Gly
            370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
            420                 425                 430
```

-continued

| | | | | | | | | | | | |
|---|---|---|---|---|---|---|---|---|---|---|---|
|Arg|Asp|Ala|Gln|Gly|Leu|Cys|Ile|Pro|Cys|Gln|Ala|Gly|Glu|Pro|Gly|
| |435| | | |440| | | |445| | |

Leu Leu Val Gly Gln Ile Asn Gln Gln Asp Pro Leu Arg Arg Phe Asp
    450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
        515                 520                 525

Ser Arg Leu Leu Gly Gln Thr Asp Val Ala Val Tyr Gly Val Ala Val
    530                 535                 540

Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
    610                 615                 620

Gln Gly His Tyr Leu Pro Leu Asn Glu Ala Val Tyr Thr Arg Ile Cys
625                 630                 635                 640

Ser Gly Ala Phe Ala Leu
                645

<210> SEQ ID NO 44
<211> LENGTH: 2710
<212> TYPE: DNA
<213> ORGANISM: Mus musculus

<400> SEQUENCE: 44

| | | |
|---|---|---|
|atgctgcttg gagcctctct ggtgggggcg ctacttgggt ccaagctagt gctgaagctg|60|
|ccctggaccc aggtgggatt ctccctgttg ctcctgtact ggggtctgg tggctggcgt|120|
|ttcatccggg tcttcatcaa gacggtcagg agagatatct tggtggcat ggtgctcctg|180|
|aaggtgaaga ccaaggtgcg acggtacctt caggagcgga gacggtgcc cctgctgttt|240|
|gcttcaatgg tacagcgcca cccggacaag acagccctga ttttcgaggg cacagacact|300|
|cactggacct tccgccagct ggatgagtac tccagtagtg tggccaactt cctgcaggcc|360|
|cggggcctgg cctcaggcaa tgtagttgcc ctctttatgg aaaaccgcaa tgagtttgtg|420|
|ggtctgtggc taggcatggc caagctgggc gtggaggcgg ctctcatcaa caccaacctt|480|
|aggcgggatg ccctgcgcca ctgtcttgac acctcaaagg cacgagctct catctttggc|540|
|agtgagatgg cctcagctat ctgtgagatc catgctagcc tggagcccac actcagcctc|600|
|ttctgctctg gatcctggga gcccagcaca gtgcccgtca gcacagagca tctggaccct|660|
|cttctggaag atgccccgaa gcacctgccc agtcacccag acaagggttt tacagataag|720|
|ctcttctaca tctacacatc gggcaccacg gggctaccca agctgccat tgtggtgcac|780|
|agcaggtatt atcgtatggc ttccctggtg tactatggat tccgcatgcg gcctgatgac|840|
|attgtctatg actgcctccc cctctaccac tcaagcagga acatcgtggg ggattggcag|900|

-continued

```
tgcttactcc acggcatgac tgtggtgatc cggaagaagt tctcagcctc ccggttctgg      960
gatgattgta tcaagtacaa ctgcacagtg gtacagtaca ttggcgagct ctgccgctac     1020
ctcctgaacc agccacccg  tgaggctgag tctcggcaca aggtgcgcat ggcactgggc     1080
aacggtctcc ggcagtccat ctggaccgac ttctccagcc gtttccacat ccccaggtg     1140 gctgagttct atgggccac  tgaatgcaac tgtagcctgg caactttga  cagccgggtg     1200 ggggcctgtg gcttcaatag ccgcatcctg tcctttgtgt accctatccg tttggtacgt     1260
gtcaatgagg ataccatgga actgatccgg ggacccgatg gagtctgcat tccctgtcaa     1320
ccaggtcagc caggccagct ggtgggtcgc atcatccagc aggaccctct cgcccgtttc     1380
gacgggtacc tcaaccaggg tgccaacaac aagaagattg ctaatgatgt cttcaagaag     1440
ggggaccaag cctacctcac tggtgacgtc ctggtgatgg atgagctggg ttacctgtac     1500
ttccgagatc gcactgggga cacgttccgc tggaaagggg agaatgtatc taccactgag     1560
gtggagggca cactcagccg cctgcttcat atggcagatg tggcagttta tggtgttgag     1620
gtgccaggaa ctgaaggccg agcaggaatg gctgccgttg caagtcccat cagcaactgt     1680
gacctggaga gctttgcaca gaccttgaaa aaggagctgc tctgtatgc  ccgccccatc     1740 ttcctgcgct tcttgcctga gctgcacaag acagggacct tcaagttcca gaagacagag     1800
ttgcggaagg agggctttga cccatctgtt gtgaaagacc cgctgttcta tctggatgct     1860
cggaagggct gctacgttgc actgaccag  gaggcctata cccgcatcca ggcaggcgag     1920
gagaagctgt gatttccccc tacatccctc tgagggccag aagatgctgg attcagagcc     1980
ctagcgtcca ccccagaggg tcctgggcaa tgccagacca aagctagcag ggcccgcacc     2040 tccgcccta  ggtgctgatc tcccctctcc caaactgcca agtgactcac tgccgcttcc     2100
ccgaccctcc agaggctttc tgtgaaagtc tcatccaagc tgtgtcttct ggtccaggcg     2160
tggcccctgg ccccagggtt tctgataggc tcctttagga tggtatcttg ggtccagcgg     2220
gccagggtgt gggagaggag tcactaagat ccctccaatc agaagggagc ttacaaagga     2280
accaaggcaa agcctgtaga ctcaggaagc taagtggcca gagactatag tggccagtca     2340
tcccatgtcc acagaggatc ttggtccaga gctgccaaag tgtcacctct ccctgcctgc     2400
acctctgggg aaaagaggac agcatgtggc cactgggcac ctgtctcaag aagtcaggat     2460
cacacactca gtccttgttt ctccaggttc ccttgttctt gtctcgggga gggagggacg     2520
agtgtcctgt ctgtccttcc tgcctgtctg tgagtctgtg ttgcttctcc atctgtccta     2580
gcctgagtgt gggtggaaca ggcatgagga gagtgtggct caggggccaa taaactctgc     2640
cttgactcct cttaaaaaaa aaaaaaaaaa aaaaaaaaaa aaaaaaaaaa aaaaaaaaa      2700 aaaaaaaaa                                                             2710
```

<210> SEQ ID NO 45
<211> LENGTH: 643
<212> TYPE: PRT
<213> ORGANISM: Mus musculus

<400> SEQUENCE: 45

```
Met Leu Leu Gly Ala Ser Leu Val Gly Ala Leu Leu Phe Ser Lys Leu
 1               5                  10                  15

Val Leu Lys Leu Pro Trp Thr Gln Val Gly Phe Ser Leu Leu Leu Leu
            20                  25                  30

Tyr Leu Gly Ser Gly Gly Trp Arg Phe Ile Arg Val Phe Ile Lys Thr
        35                  40                  45
```

-continued

```
Val Arg Arg Asp Ile Phe Gly Gly Met Val Leu Leu Lys Val Lys Thr
 50                  55                  60

Lys Val Arg Arg Tyr Leu Gln Glu Arg Lys Thr Val Pro Leu Leu Phe
 65                  70                  75                  80

Ala Ser Met Val Gln Arg His Pro Asp Lys Thr Ala Leu Ile Phe Glu
                 85                  90                  95

Gly Thr Asp Thr His Trp Thr Phe Arg Gln Leu Asp Glu Tyr Ser Ser
                100                 105                 110

Ser Val Ala Asn Phe Leu Gln Ala Arg Gly Leu Ala Ser Gly Asn Val
                115                 120                 125

Val Ala Leu Phe Met Glu Asn Arg Asn Glu Phe Val Gly Leu Trp Leu
130                 135                 140

Gly Met Ala Lys Leu Gly Val Glu Ala Ala Leu Ile Asn Thr Asn Leu
145                 150                 155                 160

Arg Arg Asp Ala Leu Arg His Cys Leu Asp Thr Ser Lys Ala Arg Ala
                165                 170                 175

Leu Ile Phe Gly Ser Glu Met Ala Ser Ala Ile Cys Glu Ile His Ala
                180                 185                 190

Ser Leu Glu Pro Thr Leu Ser Leu Phe Cys Ser Gly Ser Trp Glu Pro
                195                 200                 205

Ser Thr Val Pro Val Ser Thr Glu His Leu Asp Pro Leu Leu Glu Asp
                210                 215                 220

Ala Pro Lys His Leu Pro Ser His Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255

Ile Val Val His Ser Arg Tyr Tyr Arg Met Ala Ser Leu Val Tyr Tyr
                260                 265                 270

Gly Phe Arg Met Arg Pro Asp Asp Ile Val Tyr Asp Cys Leu Pro Leu
                275                 280                 285

Tyr His Ser Ser Arg Lys His Arg Gly Asp Trp Gln Cys Leu Leu His
                290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Val Val Gln Tyr Ile Gly Glu
                325                 330                 335

Leu Cys Arg Tyr Leu Leu Asn Gln Pro Pro Arg Glu Ala Glu Ser Arg
                340                 345                 350

His Lys Val Arg Met Ala Leu Gly Asn Gly Leu Arg Gln Ser Ile Trp
                355                 360                 365

Thr Asp Phe Ser Ser Arg Phe His Ile Pro Gln Val Ala Glu Phe Tyr
                370                 375                 380

Gly Ala Thr Glu Cys Asn Cys Ser Leu Gly Asn Phe Asp Ser Arg Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
                420                 425                 430

Asp Gly Val Cys Ile Pro Cys Gln Pro Gly Gln Pro Gly Gln Leu Val
                435                 440                 445

Gly Arg Ile Ile Gln Gln Asp Pro Leu Arg Arg Phe Asp Gly Tyr Leu
450                 455                 460
```

-continued

```
Asn Gln Gly Ala Asn Asn Lys Lys Ile Ala Asn Asp Val Phe Lys Lys
465                 470                 475                 480
Gly Asp Gln Ala Tyr Leu Thr Gly Asp Val Leu Val Met Asp Glu Leu
            485                 490                 495
Gly Tyr Leu Tyr Phe Arg Asp Arg Thr Gly Asp Thr Phe Arg Trp Lys
        500                 505                 510
Gly Glu Asn Val Ser Thr Thr Glu Val Glu Gly Thr Leu Ser Arg Leu
    515                 520                 525
Leu His Met Ala Asp Val Ala Val Tyr Gly Val Glu Val Pro Gly Thr
    530                 535                 540
Glu Gly Arg Ala Gly Met Ala Ala Val Ala Ser Pro Ile Ser Asn Cys
545                 550                 555                 560
Asp Leu Glu Ser Phe Ala Gln Thr Leu Lys Lys Glu Leu Pro Leu Tyr
                565                 570                 575
Ala Arg Pro Ile Phe Leu Arg Phe Leu Pro Glu Leu His Lys Thr Gly
            580                 585                 590
Thr Phe Lys Phe Gln Lys Thr Glu Leu Arg Lys Glu Gly Phe Asp Pro
        595                 600                 605
Ser Val Val Lys Asp Pro Leu Phe Tyr Leu Asp Ala Arg Lys Gly Cys
    610                 615                 620
Tyr Val Ala Leu Asp Gln Glu Ala Tyr Thr Arg Ile Gln Ala Gly Glu
625                 630                 635                 640
Glu Lys Leu
```

<210> SEQ ID NO 46
<211> LENGTH: 3694
<212> TYPE: DNA
<213> ORGANISM: Homo sapiens

<400> SEQUENCE: 46

```
tcgacccacg gcgtccggga ccccaaagca gaagcccgca cagtaggcac agcgcaccca      60
agaagggtcc aggagtctgc agaaacagaa aggtccccgg cctcagcctc ctagtccctg     120
cctgcctcct gcctgagctt ctgggagact gaaggcacgg cttgcagctt caggatgcgg     180
gctccgggtg cgggcgcggc ctcggtggtc tcgctggcgc tgttgtggct gctggggctg     240
ccgtggacct ggagcgcggc agcggcgctc ggcgtgtacg tgggcagcgg cggctggcgc     300
ttcctgcgca tcgtctgcaa gaccgcgagg cgagacctct tcggtctctc tgtgctgatc     360
cgcgtgcgcc tggagctgcg gcggcaccag cgtgccggcc acaccatccc gcgcatcttt     420
caggcggtag tgcagcgaca gcccgagcgc ctggcgctgg tggatgccgg gaccggcgag     480
tgctggacct ttgcgcagct ggacgcctac tccaatgcgg tagccaacct cttccgccag     540
ctgggcttcg cgccgggcga cgtggtggcc atcttcctgg agggccggcc ggagttcgtg     600
gggctgtggc tgggcctggc caaggcgggc atggaggccg cgctgctcaa cgtgaacctg     660
cggcgcgagc ccctggcctt ctgcctgggc acctcgggcg ctaaggccct gatctttgga     720
ggagaaatgg tggcggcggt ggccgaagtg agcgggcatc tggggaaaag tttgatcaag     780
ttctgctctg gagacttggg gcccgagggc atcttgccgg acacccacct cctggacccg     840
ctgctgaagg aggcctctac tgccccccttg gcacagatcc ccagcaaggg catggacgat     900
cgtctttttct acatctacac gtcggggacc accgggctgc ccaaggctgc cattgtcgtg     960
cacagcaggt actaccgcat ggcagccttc ggccaccacg cctaccgcat gcaggcggct    1020
gacgtgctct atgactgcct gcccctgtac cactcggcag gaaacatcat cggcgtgggg    1080
```

-continued

```
cagtgtctca tctatgggct gacagtcgtc ctccgcaaga aattctcggc cagccgcttc    1140
tgggacgact gcatcaagta caactgcacg gtggttcagt acatcgggga gatctgccgc    1200
tacctgctga agcagccggt gcgcgaggcg gagaggcgac accgcgtgcg cctggcggtg    1260
gggaacgggc tgcgtcctgc catctgggag gagttcacgg agcgcttcgg cgtacgccaa    1320
atcggggagt tctacggcgc caccgagtgc aactgcagca ttgccaacat ggacggcaag    1380
gtcggctcct gtggtttcaa cagccgcatc ctgccccacg tgtaccccat ccggctggtg    1440
aaggtcaatg aggacacaat ggagctgctg cgggatgccc agggcctctg catcccctgc    1500
caggccgggg agcctggcct ccttgtgggt cagatcaacc aacaggaccc gctgcgccgc    1560
ttcgatggct atgtcagcga gagcgccacc agcaagaaga tcgcccacag cgtcttcagc    1620
aagggcgaca gcgcctacct ctcaggtgac gtgctagtga tggatgagct gggctacatg    1680
tacttccggg accgtagcgg ggacaccttc cgctggcgag gggagaacgt ctccaccacc    1740
gaggtggagg gcgtgctgag ccgcctgctg gccagacag acgtggccgt ctatggggtg     1800
gctgttccag gagtggaggg taaggcaggg atggcggccg tcgcagaccc ccacagcctg    1860
ctggacccca acgcgatata ccaggagctg cagaaggtgc tggcacccta tgcccggccc    1920
atcttcctgc gcctcctgcc ccaggtggac accacaggca ccttcaagat ccagaagacg    1980
aggctgcagc gagagggctt tgacccacgc cagacctcag accggctctt cttcctggac    2040
ctgaagcagg gccactacct gcccttaaat gaggcagtct acactcgcat ctgctcgggc    2100
gccttcgccc tctgaagctg ttcctctact ggccacaaac tctgggcctg gtgggagagg    2160
ccagcttgag ccagacagcg ctgcccaggg gtggccgcct agtacacacc cacctggccg    2220
agctgtacct ggcacggccc atcctggact gagaaactgg aacctcagag gaacccgtgc    2280
ctctctgctg ccttggtgcc cctgtgtctg cctcctctcc ctgcttttca gcctctgtct    2340
ccttccatcc ctgtccctgt ctggccttaa ctcttccctc tctttctttt ctttctttct    2400
ttcttttttt ttaagataga gtctcactct gctgcccggg ctagagtgca gtggtgggat    2460
ctcggctcac tgcaacctct gcctcctggg gttcaagtga tcctcccacc tcagcctcct    2520
gagtagctgg gattacaggc acccgccacc acgtccagct aatttttata tttttagtag    2580
agacggggtt tcaccatgtt ggtcaggctg gtcttgaact cctgacctca ggtgatccgc    2640
tggcctcggc ctcccagagt gctgggatta taggcgtgag cctctggccc ggcctttcct    2700
ttttcctctc ctctcctgcc gagagtggaa cacacgtgtc ctgggagctg catcttgtgt    2760
agggtccagc tgcttttggg gactgcagga atcatctccc ctgggccctg gactcggact    2820
ggggcctccc cacctccctc tcggctgtgc cttacggagc cccaatccag gcctcctgtg    2880
gctgttgggt tccagatgct gcagctccat gtgacttcca agcaggccct ccgccctccc    2940
tgctgaatgg aggagccggg ggtcccccag gccaactgga aaatctccca ggctaggcca    3000
attgcctttt gcacttcccc gttcctgtca catttcccca gccccacctt ccctcctga    3060
tgccctgaaa gcttccggaa ttgactgtga ccacttggat gtcaccactg tcagcccctg    3120
ccttgatgtc cccatttagc catctccatg gagctcctgc tggagggccc tgaaccctgc    3180
actgcgtggc tgcccagcca gctgcctcct gtcctgggag gaggcctcct gggtgtcctc    3240
atctggtgtg tctactggag ggtccccacag gagaggcagc agaggggtca ggggaggtct    3300
cctgccgggg gttggcctct caagcctcag gggttctagc ctgttgaata taccccacct    3360
ggtgggtggc cctccgatg tccccactga tggctctgac accgtgttgg tggcgatgtc    3420
ccagacaatc ccaccaggac ggcccagaca tccctactgg cttcgctggt ggctcatctc    3480
```

-continued

```
gaacatccac gccagccttt ctggggccgg ccacccaggc cgcctgtccg tctgtcctcc    3540
ctccagcagc accccctggc ccctggagtg gtggggccat ggcaagagac accgtggcgt    3600
ctcatgtgaa ctttcctggg cactgtggtt ttatttccta attgatttaa gaaataaacc    3660
tgaagaccgt ctggtgaaaa aaaaaaaaaa aaaa                                 3694
```

<210> SEQ ID NO 47
<211> LENGTH: 646
<212> TYPE: PRT
<213> ORGANISM: Homo sapiens
<400> SEQUENCE: 47

```
Met Arg Ala Pro Gly Ala Gly Ala Ser Val Val Ser Leu Ala Leu
 1               5                  10                  15

Leu Trp Leu Leu Gly Leu Pro Trp Thr Trp Ser Ala Ala Ala Leu
                20                  25                  30

Gly Val Tyr Val Gly Ser Gly Gly Trp Arg Phe Leu Arg Ile Val Cys
                35                  40                      45

Lys Thr Ala Arg Arg Asp Leu Phe Gly Leu Ser Val Leu Ile Arg Val
 50                  55                      60

Arg Leu Glu Leu Arg Arg His Gln Arg Ala Gly His Thr Ile Pro Arg
 65                      70                  75                  80

Ile Phe Gln Ala Val Val Gln Arg Gln Pro Glu Arg Leu Ala Leu Val
                    85                  90                      95

Asp Ala Gly Thr Gly Glu Cys Trp Thr Phe Ala Gln Leu Asp Ala Tyr
                100                 105                 110

Ser Asn Ala Val Ala Asn Leu Phe Arg Gln Leu Gly Phe Ala Pro Gly
                115                 120                 125

Asp Val Val Ala Ile Phe Leu Glu Gly Arg Pro Glu Phe Val Gly Leu
130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
                    165                 170                 175

Lys Ala Leu Ile Phe Gly Gly Glu Met Val Ala Val Ala Glu Val
                180                 185                 190

Ser Gly His Leu Gly Lys Ser Leu Ile Lys Phe Cys Ser Gly Asp Leu
                195                 200                 205

Gly Pro Glu Gly Ile Leu Pro Asp Thr His Leu Leu Asp Pro Leu Leu
210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                    245                 250                 255

Lys Ala Ala Ile Val Val His Ser Arg Tyr Tyr Arg Met Ala Ala Phe
                260                 265                 270

Gly His His Ala Tyr Arg Met Gln Ala Ala Asp Val Leu Tyr Asp Cys
                275                 280                 285

Leu Pro Leu Tyr His Ser Ala Gly Asn Ile Ile Gly Val Gly Gln Cys
                290                 295                 300

Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                    325                 330                 335
```

```
Ile Gly Glu Ile Cys Arg Tyr Leu Leu Lys Gln Pro Val Arg Glu Ala
        340                 345                 350

Glu Arg Arg His Arg Val Arg Leu Ala Val Gly Asn Gly Leu Arg Pro
        355                 360                 365

Ala Ile Trp Glu Glu Phe Thr Glu Arg Phe Gly Val Arg Gln Ile Gly
        370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
            420                 425                 430

Arg Asp Ala Gln Gly Leu Cys Ile Pro Cys Gln Ala Gly Glu Pro Gly
        435                 440                 445

Leu Leu Val Gly Gln Ile Asn Gln Gln Asp Pro Leu Arg Arg Phe Asp
450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
                500                 505                 510

Arg Trp Arg Gly Glu Asn Val Ser Thr Thr Glu Val Glu Gly Val Leu
            515                 520                 525

Ser Arg Leu Leu Gly Gln Thr Asp Val Ala Val Tyr Gly Val Ala Val
530                 535                 540

Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Leu Asp Leu Lys
        610                 615                 620

Gln Gly His Tyr Leu Pro Leu Asn Glu Ala Val Tyr Thr Arg Ile Cys
625                 630                 635                 640

Ser Gly Ala Phe Ala Leu
                645

<210> SEQ ID NO 48
<211> LENGTH: 2362
<212> TYPE: DNA
<213> ORGANISM: Homo sapiens

<400> SEQUENCE: 48
ggaattccaa aaaaaaaaaa tacgactaca cctgctccgg agcccgcggc ggtacctgca    60
gcggaggagc tctgtcttcc ccttcatctc acgcgagccc ggcgtcccgc cgcgtgcgcc   120
ccggcgcagc ccgccagtcc gcccggagcc cgcccagtcg ccgcgctgca cgcccggggt   180
gaaccctctg ccctcgctgg acagagggc cccgcagccg tcatgctttc cgccatctac   240
acagtcctgg cgggactgct gttcctgccg ctcctggtga acctctgctg cccatacttc   300
```

-continued

| | |
|---|---|
| ttccaggaca taggctactt cttgaaggtg gccgccgtgg gccggagggt gcgcagctac | 360 |
| gggcagcggc ggccggcgcg caccatcctg cgggcgttcc tggagaaagc gcgccagacg | 420 |
| ccacacaagc ctttctgct cttccgcgac gagactctca cctacgcgca ggtggaccgg | 480 |
| cgcagcaatc aagtggcccg ggcgctgcac gaccacctcg gcctgcgcca gggagactgc | 540 |
| gtggcgctcc ttatgggtaa cgagccggcc tacgtgtggc tgtggctggg gctggtgaag | 600 |
| ctgggctgtg ccatggcgtg cctcaattac aacatccgcg cgaagtccct gctgcactgc | 660 |
| ttccagtgct gcggggcgaa ggtgctgctg gtgtcgccag aactacaagc agctgtcgaa | 720 |
| gagatactgc caagccttaa aaagatgat gtgtccatct attatgtgag cagaacttct | 780 |
| aacacagatg ggattgactc tttcctggac aaagtggatg aagtatcaac tgaacctatc | 840 |
| ccagagtcat ggaggtctga agtcactttt tccactcctg ccttatacat ttatacttct | 900 |
| ggaaccacag gtcttccaaa agcagccatg atcactcatc agcgcatatg gtatggaact | 960 |
| ggcctcactt tgtaagcgg attgaaggca gatgatgtca tctatatcac tctgcccttt | 1020 |
| taccacagtg ctgcactact gattggcatt cacggatgta ttgtggctgg tgctactctt | 1080 |
| gccttgcgga ctaaattttc agccagccag ttttgggatg actgcagaaa atacaacgtc | 1140 |
| actgtcattc agtatatcgg tgaactgctt cggtatttat gcaactcacc acagaaacca | 1200 |
| aatgaccgtg atcataaagt gagactggca ctgggaaatg gcttacgagg agatgtgtgg | 1260 |
| agacaatttg tcaagagatt tggggacata tgcatctatg agttctatgc tgccactgaa | 1320 |
| ggcaatattg gatttatgaa ttatgcgaga aaagttggtg ctgttggaag agtaaactac | 1380 |
| ctacagaaaa aaatcataac ttatgacctg attaaatatg atgtggagaa agatgaacct | 1440 |
| gtccgagatg aaaatggata ttgcgtcaga gttcccaaag gtgaagttgg acttctggtt | 1500 |
| tgcaaaatca cacaacttac accatttaat ggctatgctg gagcaaaggc tcagacagag | 1560 |
| aagaaaaaac tgagagatgt ctttaagaaa ggagacctct atttcaacag tggagatctc | 1620 |
| ttaatggttg accatgaaaa tttcatctat ttccacgaca gagttggaga tacattccgg | 1680 |
| tggaaagggg aaaatgtggc caccactgaa gttgctgata cagttggact ggttgatttt | 1740 |
| gtccaagaag taaatgttta tggagtgcat gtgccagatc atgagggtcg cattggcatg | 1800 |
| gcctccatca aaatgaaaga aaaccatgaa tttgatggaa agaaactctt tcagcacatt | 1860 |
| gctgattacc tacctagtta tgcaaggccc cggtttctaa gaatacagga caccattgag | 1920 |
| atcactggaa cttttaaaca ccgcaaaatg accctggtgg aggagggctt taaccctgct | 1980 |
| gtcatcaaag atgccttgta tttcttggat gacacagcaa aaatgtatgt gcctatgact | 2040 |
| gaggacatct ataatgccat aagtgctaaa accctgaaac tctgaatatt cccaggagga | 2100 |
| taactcaaca tttccagaaa gaaactgaat ggacagccac ttgatataat ccaactttaa | 2160 |
| tttgattgaa gattgtgagg aaattttgta ggaaatttgc atacccgtaa agggagactt | 2220 |
| ttttaaataa cagttgagtc tttgcaagta aaaagattta gagattatta ttttttcagtg | 2280 |
| tgcacctact gtttgtattt gcaaactgag cttgttggag ggaaggcatt atttttttaaa | 2340 |
| atacttagta aattaaatga ac | 2362 |

<210> SEQ ID NO 49
<211> LENGTH: 620
<212> TYPE: PRT
<213> ORGANISM: Homo sapiens

<400> SEQUENCE: 49

Met Leu Ser Ala Ile Tyr Thr Val Leu Ala Gly Leu Leu Phe Leu Pro

-continued

```
  1               5                   10                  15
Leu Leu Val Asn Leu Cys Cys Pro Tyr Phe Gln Asp Ile Gly Tyr
             20                  25                  30

Phe Leu Lys Val Ala Ala Val Gly Arg Arg Val Arg Ser Tyr Gly Gln
             35                  40                  45

Arg Arg Pro Ala Arg Thr Ile Leu Arg Ala Phe Leu Glu Lys Ala Arg
 50                  55                  60

Gln Thr Pro His Lys Pro Phe Leu Leu Phe Arg Asp Glu Thr Leu Thr
 65                  70                  75                  80

Tyr Ala Gln Val Asp Arg Arg Ser Asn Gln Val Ala Arg Ala Leu His
             85                  90                  95

Asp His Leu Gly Leu Arg Gln Gly Asp Cys Val Ala Leu Leu Met Gly
             100                 105                 110

Asn Glu Pro Ala Tyr Val Trp Leu Trp Leu Gly Leu Val Lys Leu Gly
             115                 120                 125

Cys Ala Met Ala Cys Leu Asn Tyr Asn Ile Arg Ala Lys Ser Leu Leu
             130                 135                 140

His Cys Phe Gln Cys Cys Gly Ala Lys Val Leu Leu Val Ser Pro Glu
145                  150                 155                 160

Leu Gln Ala Ala Val Glu Glu Ile Leu Pro Ser Leu Lys Lys Asp Asp
                 165                 170                 175

Val Ser Ile Tyr Tyr Val Ser Arg Thr Ser Asn Thr Asp Gly Ile Asp
             180                 185                 190

Ser Phe Leu Asp Lys Val Asp Glu Val Ser Thr Glu Pro Ile Pro Glu
             195                 200                 205

Ser Trp Arg Ser Glu Val Thr Phe Ser Thr Pro Ala Leu Tyr Ile Tyr
 210                 215                 220

Thr Ser Gly Thr Thr Gly Leu Pro Lys Ala Ala Met Ile Thr His Gln
225                  230                 235                 240

Arg Ile Trp Tyr Gly Thr Gly Leu Thr Phe Val Ser Gly Leu Lys Ala
             245                 250                 255

Asp Asp Val Ile Tyr Ile Thr Leu Pro Phe Tyr His Ser Ala Ala Leu
             260                 265                 270

Leu Ile Gly Ile His Gly Cys Ile Val Ala Gly Ala Thr Leu Ala Leu
             275                 280                 285

Arg Thr Lys Phe Ser Ala Ser Gln Phe Trp Asp Asp Cys Arg Lys Tyr
 290                 295                 300

Asn Val Thr Val Ile Gln Tyr Ile Gly Glu Leu Leu Arg Tyr Leu Cys
305                  310                 315                 320

Asn Ser Pro Gln Lys Pro Asn Asp Arg Asp His Lys Val Arg Leu Ala
             325                 330                 335

Leu Gly Asn Gly Leu Arg Gly Asp Val Trp Arg Gln Phe Val Lys Arg
             340                 345                 350

Phe Gly Asp Ile Cys Ile Tyr Glu Phe Tyr Ala Ala Thr Glu Gly Asn
             355                 360                 365

Ile Gly Phe Met Asn Tyr Ala Arg Lys Val Gly Ala Val Gly Arg Val
             370                 375                 380

Asn Tyr Leu Gln Lys Lys Ile Ile Thr Tyr Asp Leu Ile Lys Tyr Asp
385                  390                 395                 400

Val Glu Lys Asp Glu Pro Val Arg Asp Glu Asn Gly Tyr Cys Val Arg
                 405                 410                 415

Val Pro Lys Gly Glu Val Gly Leu Leu Val Cys Lys Ile Thr Gln Leu
             420                 425                 430
```

```
Thr Pro Phe Asn Gly Tyr Ala Gly Ala Lys Ala Gln Thr Glu Lys Lys
            435                 440                 445
Lys Leu Arg Asp Val Phe Lys Lys Gly Asp Leu Tyr Phe Asn Ser Gly
        450                 455                 460
Asp Leu Leu Met Val Asp His Glu Asn Phe Ile Tyr Phe His Asp Arg
465                 470                 475                 480
Val Gly Asp Thr Phe Arg Trp Lys Gly Glu Asn Val Ala Thr Thr Glu
                485                 490                 495
Val Ala Asp Thr Val Gly Leu Val Asp Phe Val Gln Glu Val Asn Val
            500                 505                 510
Tyr Gly Val His Val Pro Asp His Glu Gly Arg Ile Gly Met Ala Ser
        515                 520                 525
Ile Lys Met Lys Glu Asn His Glu Phe Asp Gly Lys Lys Leu Phe Gln
        530                 535                 540
His Ile Ala Asp Tyr Leu Pro Ser Tyr Ala Arg Pro Arg Phe Leu Arg
545                 550                 555                 560
Ile Gln Asp Thr Ile Glu Ile Thr Gly Thr Phe Lys His Arg Lys Met
                565                 570                 575
Thr Leu Val Glu Glu Gly Phe Asn Pro Ala Val Ile Lys Asp Ala Leu
            580                 585                 590
Tyr Phe Leu Asp Asp Thr Ala Lys Met Tyr Val Pro Met Thr Glu Asp
        595                 600                 605
Ile Tyr Asn Ala Ile Ser Ala Lys Thr Leu Lys Leu
        610                 615                 620

<210> SEQ ID NO 50
<211> LENGTH: 1173
<212> TYPE: DNA
<213> ORGANISM: Homo sapiens

<400> SEQUENCE: 50
aagttctcgg ctggtcagtt ctgggaagat tgccagcagc acagggtgac ggtgttccag      60
tacattgggg agctgtgccg ataccttgtc aaccagcccc cgagcaaggc agaacgtggc     120
cataaggtcc ggctggcagt gggcagcggg ctgcgcccag atacctggga gcgttttgtg     180
cggcgcttcg ggcccctgca ggtgctggag acatatggac tgacagaggg caacgtggcc     240
accatcaact acacaggaca gcggggcgct gtggggcgtg cttcctggct ttacaagcat     300
atcttcccct tctccttgat tcgctatgat gtcaccacag agagccaatc tcgggacccc     360
caggggcact gtatggccac atctccaggt gagccagggc tgctggtggc cccggtaagc     420
cagcagtccc cattcctggg ctatgctggc gggccagagc tggcccaggg gaagttgcta     480
aaggatgtct tccggcctgg ggatgttttc ttcaacactg gggacctgct ggtctgcgat     540
gaccaaggtt ttctccgctt ccatgatcgt actggagaca ccttcaggtg aagggggag      600 aatgtggcca caaccgaggt ggcagaggtc ttcgaggccc tagattttct tcaggaggtg     660
aacgtctatg gagtcactgt gccagggcat gaaggcaggg ctggaatggc agccctagtt     720
ctgcgtcccc cccacgcttt ggaccttatg cagctctaca cccacgtgtc tgagaacttg     780
ccaccttatg cccggccccg attcctcagg ctccaggagt cttttggcca cacagagacc     840
ttcaaacagc agaaagttcg gatggcaaat gagggcttcg accccagcac cctgtctgac     900
ccactgtacg ttctggacca ggctgtaggt gcctacctgc ccctcacaac tgcccggtac     960
agcgccctcc tggcaggaaa ccttcgaatc tgagaacttc cacacctgag gcacctgaga    1020
```

-continued

```
gaggaactct gtggggtggg ggccgttgca ggtgtactgg gctgtcaggg atcttttcta     1080
taccagaact gcggtcacta ttttgtaata aatgtggctg gagctgatcc agctgtctct     1140
gacaaaaaaa aaaaaaaaaa aaagggcggc cgc                                  1173
```

<210> SEQ ID NO 51
<211> LENGTH: 330
<212> TYPE: PRT
<213> ORGANISM: Homo sapiens

<400> SEQUENCE: 51

```
Lys Phe Ser Ala Gly Gln Phe Trp Glu Asp Cys Gln Gln His Arg Val
  1               5                  10                  15

Thr Val Phe Gln Tyr Ile Gly Glu Leu Cys Arg Tyr Leu Val Asn Gln
             20                  25                  30

Pro Pro Ser Lys Ala Glu Arg Gly His Lys Val Arg Leu Ala Val Gly
         35                  40                  45

Ser Gly Leu Arg Pro Asp Thr Trp Glu Arg Phe Val Arg Arg Phe Gly
     50                  55                  60

Pro Leu Gln Val Leu Glu Thr Tyr Gly Leu Thr Glu Gly Asn Val Ala
 65                  70                  75                  80

Thr Ile Asn Tyr Thr Gly Gln Arg Gly Ala Val Gly Arg Ala Ser Trp
                 85                  90                  95

Leu Tyr Lys His Ile Phe Pro Phe Ser Leu Ile Arg Tyr Asp Val Thr
            100                 105                 110

Thr Gly Glu Pro Ile Arg Asp Pro Gln Gly His Cys Met Ala Thr Ser
        115                 120                 125

Pro Gly Glu Pro Gly Leu Leu Val Ala Pro Val Ser Gln Gln Ser Pro
    130                 135                 140

Phe Leu Gly Tyr Ala Gly Gly Pro Glu Leu Ala Gln Gly Lys Leu Leu
145                 150                 155                 160

Lys Asp Val Phe Arg Pro Gly Asp Val Phe Phe Asn Thr Gly Asp Leu
                165                 170                 175

Leu Val Cys Asp Asp Gln Gly Phe Leu Arg Phe His Asp Arg Thr Gly
            180                 185                 190

Asp Thr Phe Arg Trp Lys Gly Glu Asn Val Ala Thr Thr Glu Val Ala
        195                 200                 205

Glu Val Phe Glu Ala Leu Asp Phe Leu Gln Glu Val Asn Val Tyr Gly
    210                 215                 220

Val Thr Val Pro Gly His Glu Gly Arg Ala Gly Met Ala Ala Leu Val
225                 230                 235                 240

Leu Arg Pro Pro His Ala Leu Asp Leu Met Gln Leu Tyr Thr His Val
                245                 250                 255

Ser Glu Asn Leu Pro Pro Tyr Ala Arg Pro Arg Phe Leu Arg Leu Gln
            260                 265                 270

Glu Ser Leu Ala Thr Thr Glu Thr Phe Lys Gln Gln Lys Val Arg Met
        275                 280                 285

Ala Asn Glu Gly Phe Asp Pro Ser Thr Leu Ser Asp Pro Leu Tyr Val
    290                 295                 300

Leu Asp Gln Ala Val Gly Ala Tyr Leu Pro Leu Thr Thr Ala Arg Tyr
305                 310                 315                 320

Ser Ala Leu Leu Ala Gly Asn Leu Arg Ile
                325                 330
```

<210> SEQ ID NO 52

```
<211> LENGTH: 2907
<212> TYPE: DNA
<213> ORGANISM: Homo sapiens

<400> SEQUENCE: 52
cgacccacgc gtccgggcgg gcggggccgg gcggcgggcg gggctggcgg ggcggccggg      60
ccatgcaggg cgcagagccg gctaaaccct gctgagaccc ggctccgtgc gtccaggggc     120
ggctaatgcc cctcacgctg tctacgctgc tgcaaccggg ccgcatctgg acggggcgcc     180
gcgcggcgga gccgacgccg ggccacaatg ctgcttggag cctctctggt gggggtgctg     240
ctgttctcca agctggtgct gaaactgccc tggacccagg tgggattctc cctgttgttc     300
ctctacttgg gatctggcgg ctggcgcttc atccgggtct tcatcaagac catcaggcgc     360
gatatctttg gcgcctggt cctcctgaag gtgaaggcaa aggtgcgaca gtgcctgcag     420
gagcggcgga cagtgcccat tttgtttgcc tctaccgttc ggcgccaccc cgacaagacg     480
gccctgatct tcgagggcac agatacccac tggaccttcc gccagctgga tgagtactca     540
agcagtgtag ccaacttcct gcaggcccgg ggcctggcct cgggcgatgt ggctgccatc     600
ttcatggaga accgcaatga gttcgtgggc ctatggctgg gcatggccaa gctcggtgtg     660
gaggcagccc tcatcaacac caacctgcgg cgggatgctc tgctccactg cctcaccacc     720
tcgcgcgcac gggcccttgt cttttggcagc gaaatggcct cagccatctg tgaggtccat     780
gccagcctgg accctcgct cagcctcttc tgctctggct cctgggagcc cggtgcggtg     840
cctccaagca cagaacacct ggaccctctg ctgaaagatg ctcccaagca ccttcccagt     900
tgccctgaca agggcttcac agataaactg ttctacatct acacatccgg caccacaggg     960
ctgcccaagg ccgccatcgt ggtgcacagc aggtattacc gcatggctgc cctggtgtac    1020
tatggattcc gcatgcggcc caacgacatc gtctatgact gcctccccct ctaccactca    1080
gcaggaaaca tcgtgggaat cggccagtgc ctgctgcatg gcatgacggt ggtgattcgg    1140
aagaagttct cagcctcccg gttctgggac gattgtatca agtacaactg cacgattgtg    1200
cagtacattg gtgaactgtg ccgctacctc ctgaaccagc caccgcggga ggcagaaaac    1260
cagcaccagg ttcgcatggc actaggcaat ggcctccggc agtccatctg gaccaacttt    1320
tccagccgct tccacatacc ccaggtggct gagttctacg gggccacaga gtgcaactgt    1380
agcctgggca acttcgacag ccaggtgggg gcctgtggtt tcaatagccg catcctgtcc    1440
ttcgtgtacc ccatccggtt ggtacgtgtc aacgaggaca ccatggagct gatccggggg    1500
cccgacggcg tctgcattcc ctgccagcca ggtgagccgg ccagctggt gggccgcatc    1560 atccagaaag accccctgcg ccgcttcgat ggctacctca accagggcgc caacaacaag    1620
aagattgcca aggatgtctt caaggagggg accaggcct accttactgg tgatgtgctg    1680
gtgatggacg agctgggcta cctgtacttc cgagaccgca ctgggacac gttccgctgg    1740 aaaggtgaga acgtgtccac caccgaggtg gaaggcacac tcagccgcct gctggacatg    1800
gctgacgtgg ccgtgtatgg tgtcgaggtg ccaggaaccg agggccgggc cggaatggct    1860
gctgtggcca gccccactgg caactgtgac ctggagcgct tgctcaggt cttggagaag    1920 gaactgcccc tgtatgcgcg ccccatcttc ctgcgcctcc tgcctgagct gcacaaaaca    1980
ggaacctaca gttccagaa acagagcta cggaaggagg ctttgacccc ggctattgtg    2040
aaagacccgc tgttctatct agatgcccag aagggccgct acgtccgct ggaccaagag    2100 gcctacagcc gcatccaggc aggcgaggag aagctgtgat tccccccatc cctctgaggg    2160
ccggcggatg ctggatccgg agccccaggt tccgccccag agcggtcctg gacaaggcca    2220
```

```
gaccaaagca agcagggcct ggcacctcca tcctgaggtg ctgcccctcc atccaaaact    2280
gccaagtgac tcattgcctt cccaacccct ccagaggctt tctgtgaaag tctcatgtcc    2340
aagttccgtc ttctgggctg ggcaggccct ctggttccca ggctgagact gacgggtttt    2400
ctcaggatga tgtcttgggt gagggtaggg agaggacaag gggtcaccga gcccttccca    2460
gagagcaggg agcttataaa tggaaccaga gcagaagtcc ccagactcag gaagtcaaca    2520
gagtgggcag ggacagtggt agcatccatc tggtggccaa agagaatcgt agccccagag    2580
ctgcccaagt tcactgggct ccaccccac ctccaggagg ggaggagagg acctgacatc     2640
tgtaggtggc ccctgatgcc ccatctacag caggaggtca ggaccacgcc cctggcctct    2700
ccccactccc ccatcctcct ccctgggtgg ctgcctgatt atccctcagg cagggcctct    2760
cagtccttgt gggtctgtgt cacctccatc tcagtcttgg cctggctatg aggggaggag    2820
gaatgggaga gggggctcag gggccaataa actctgcctt gagtcctcct aaaaaaaaaa    2880
aaaaaaaaaa aaaaaaaaaa aaaaaaa                                       2907
```

<210> SEQ ID NO 53
<211> LENGTH: 643
<212> TYPE: PRT
<213> ORGANISM: Homo sapiens

<400> SEQUENCE: 53

```
Met Leu Leu Gly Ala Ser Leu Val Gly Val Leu Leu Phe Ser Lys Leu
  1               5                  10                  15

Val Leu Lys Leu Pro Trp Thr Gln Val Gly Phe Ser Leu Leu Phe Leu
             20                  25                  30

Tyr Leu Gly Ser Gly Gly Trp Arg Phe Ile Arg Val Phe Ile Lys Thr
         35                  40                  45

Ile Arg Arg Asp Ile Phe Gly Gly Leu Val Leu Leu Lys Val Lys Ala
     50                  55                  60

Lys Val Arg Gln Cys Leu Gln Glu Arg Arg Thr Val Pro Ile Leu Phe
 65                  70                  75                  80

Ala Ser Thr Val Arg Arg His Pro Asp Lys Thr Ala Leu Ile Phe Glu
                 85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asp Val
        115                 120                 125

Ala Ala Ile Phe Met Glu Asn Arg Asn Glu Phe Val Gly Leu Trp Leu
    130                 135                 140

Gly Met Ala Lys Leu Gly Val Glu Ala Ala Leu Ile Asn Thr Asn Leu
145                 150                 155                 160

Arg Arg Asp Ala Leu Leu His Cys Leu Thr Thr Ser Arg Ala Arg Ala
                165                 170                 175

Leu Val Phe Gly Ser Glu Met Ala Ser Ala Ile Cys Glu Val His Ala
            180                 185                 190

Ser Leu Asp Pro Ser Leu Ser Leu Phe Cys Ser Gly Ser Trp Glu Pro
        195                 200                 205

Gly Ala Val Pro Pro Ser Thr Glu His Leu Asp Pro Leu Leu Lys Asp
    210                 215                 220

Ala Pro Lys His Leu Pro Ser Cys Pro Asp Lys Gly Phe Thr Asp Lys
225                 230                 235                 240

Leu Phe Tyr Ile Tyr Thr Ser Gly Thr Thr Gly Leu Pro Lys Ala Ala
```

```
                245                 250                 255
Ile Val Val His Ser Arg Tyr Tyr Arg Met Ala Ala Leu Val Tyr Tyr
            260                 265                 270
Gly Phe Arg Met Arg Pro Asn Asp Ile Val Tyr Asp Cys Leu Pro Leu
        275                 280                 285
Tyr His Ser Ala Gly Asn Ile Val Gly Ile Gly Gln Cys Leu Leu His
    290                 295                 300
Gly Met Thr Val Val Ile Arg Lys Lys Phe Ser Ala Ser Arg Phe Trp
305                 310                 315                 320
Asp Asp Cys Ile Lys Tyr Asn Cys Thr Ile Val Gln Tyr Ile Gly Glu
                325                 330                 335
Leu Cys Arg Tyr Leu Leu Asn Gln Pro Pro Arg Glu Ala Glu Asn Gln
            340                 345                 350
His Gln Val Arg Met Ala Leu Gly Asn Gly Leu Arg Gln Ser Ile Trp
        355                 360                 365
Thr Asn Phe Ser Ser Arg Phe His Ile Pro Gln Val Ala Glu Phe Tyr
    370                 375                 380
Gly Ala Thr Glu Cys Asn Cys Ser Leu Gly Asn Phe Asp Ser Gln Val
385                 390                 395                 400
Gly Ala Cys Gly Phe Asn Ser Arg Ile Leu Ser Phe Val Tyr Pro Ile
                405                 410                 415
Arg Leu Val Arg Val Asn Glu Asp Thr Met Glu Leu Ile Arg Gly Pro
            420                 425                 430
Asp Gly Val Cys Ile Pro Cys Gln Pro Gly Glu Pro Gly Gln Leu Val
        435                 440                 445
Gly Arg Ile Ile Gln Lys Asp Pro Leu Arg Arg Phe Asp Gly Tyr Leu
    450                 455                 460
Asn Gln Gly Ala Asn Asn Lys Lys Ile Ala Lys Asp Val Phe Lys Lys
465                 470                 475                 480
Gly Asp Gln Ala Tyr Leu Thr Gly Asp Val Leu Val Met Asp Glu Leu
                485                 490                 495
Gly Tyr Leu Tyr Phe Arg Asp Arg Thr Gly Asp Thr Phe Arg Trp Lys
            500                 505                 510
Gly Glu Asn Val Ser Thr Thr Glu Val Glu Gly Thr Leu Ser Arg Leu
        515                 520                 525
Leu Asp Met Ala Asp Val Ala Val Tyr Gly Val Glu Val Pro Gly Thr
    530                 535                 540
Glu Gly Arg Ala Gly Met Ala Ala Val Ala Ser Pro Thr Gly Asn Cys
545                 550                 555                 560
Asp Leu Glu Arg Phe Ala Gln Val Leu Glu Lys Glu Leu Pro Leu Tyr
                565                 570                 575
Ala Arg Pro Ile Phe Leu Arg Leu Leu Pro Glu Leu His Lys Thr Gly
            580                 585                 590
Thr Tyr Lys Phe Gln Lys Thr Glu Leu Arg Lys Glu Gly Phe Asp Pro
        595                 600                 605
Ala Ile Val Lys Asp Pro Leu Phe Tyr Leu Asp Ala Gln Lys Gly Arg
    610                 615                 620
Tyr Val Pro Leu Asp Gln Glu Ala Tyr Ser Arg Ile Gln Ala Gly Glu
625                 630                 635                 640
Glu Lys Leu

<210> SEQ ID NO 54
<211> LENGTH: 1248
```

```
<212> TYPE: DNA
<213> ORGANISM: Homo sapiens
<220> FEATURE:
<221> NAME/KEY: misc_feature
<222> LOCATION: (1)...(1248)
<223> OTHER INFORMATION: n = A,T,C or G

<400> SEQUENCE: 54
gtcgttggga tcctcggctg cttagatctc ggagccacct gtgttctggc ccccaagttc      60
tctacttcct gcttctggga tgactgtcgg cagcatggcg tgacagtgat cctgtatgtg     120
ggcgagctcc tgcgatactt gtgtaacatt ccccagcaac cagaggaccg gacacataca     180
gtccgcctgg caatgggcaa tggactacgg gctgatgtgt ggggagacct tccagcagcg     240
tttcggtcct atttcggatc tngggaagtc ttacgggctt ccacagaagg caacatggg      300
gctttagttc aaatattgtt gggggcgctg cggggccctg ggggcaaaga tggagcttgc     360
ctcctccgaa tgctgtcccc ctttgagctg gtgcagttcg acatggaggc ggcggagcct     420
gtgagggaca atcagggctt ctgcatccct gtagggctag gggagccggg gctgctgttg     480
accaaggtgg taagccagca acccttcgtg ggctaccgcg gccccgaga gctgtcggaa      540
cggaagctgg tgcgcaacgt gcggcaatcg ggcgacgttt actacaacac cggggacgta     600
ctggccatgg accgcgaagg cttcctctac ttccgcgacc gactcgggga caccttccga     660
tggaagggcg agaacgtgtc cacgcacgag gtggagggcg tgttgtcgca ggtggacttc     720
ttgcaacagg ttaacgtgta tggcgtgtgc gtgccaggtt gtgagggtaa ggtgggcatg     780
gctgctgtgg cattagcccc cggccagact ttcgacgggg agaagttgta ccagcacgtt     840
cgcgcttggc tccctgccta cgctaccccc catttcatcc gcatccagga cgccatggag     900
gtcaccagca cgttcaaact gatgaagacc cggttggtgc gtgagggctt caatgtgggg     960
atcgtggttg accctctgtt tgtactggac aaccgggccc agtccttccg gcccctgacg    1020
gcagaaatgt accaggctgt gtgtgaggga acctggaggc tctgatcacc tggccaaccc    1080
actggggtag ggatcaaagc cagccacccc caccccaaca cactcggtgt cccttcatc     1140
ctgggcctgt gtgaatccca gcctggccat accctcaacc tcagtgggct ggaaatgaca    1200
gtgggccctg tagcagtggc agaataaact cagmtgygtt cacagaaa                 1248

<210> SEQ ID NO 55
<211> LENGTH: 354
<212> TYPE: PRT
<213> ORGANISM: Homo sapiens
<220> FEATURE:
<221> NAME/KEY: VARIANT
<222> LOCATION: (1)...(354)
<223> OTHER INFORMATION: Xaa = Any Amino Acid

<400> SEQUENCE: 55

Val Val Gly Ile Leu Gly Cys Leu Asp Leu Gly Ala Thr Cys Val Leu
 1               5                  10                  15

Ala Pro Lys Phe Ser Thr Ser Cys Phe Trp Asp Asp Cys Arg Gln His
                20                  25                  30

Gly Val Thr Val Ile Leu Tyr Val Gly Glu Leu Leu Arg Tyr Leu Cys
            35                  40                  45

Asn Ile Pro Gln Gln Pro Glu Asp Arg Thr His Thr Val Arg Leu Ala
        50                  55                  60

Met Gly Asn Gly Leu Arg Ala Asp Val Trp Gly Asp Leu Pro Ala Ala
65                  70                  75                  80

Phe Arg Ser Tyr Phe Gly Ser Xaa Glu Val Leu Arg Ala Ser Thr Glu
```

85                  90                  95
Gly Gln His Gly Ala Leu Val Gln Ile Leu Leu Gly Ala Leu Arg Gly
                100                 105                 110
Pro Gly Gly Lys Asp Gly Ala Cys Leu Leu Arg Met Leu Ser Pro Phe
            115                 120                 125
Glu Leu Val Gln Phe Asp Met Glu Ala Ala Glu Pro Val Arg Asp Asn
        130                 135                 140
Gln Gly Phe Cys Ile Pro Val Gly Leu Gly Glu Pro Gly Leu Leu Leu
145                 150                 155                 160
Thr Lys Val Val Ser Gln Gln Pro Phe Val Gly Tyr Arg Gly Pro Arg
                165                 170                 175
Glu Leu Ser Glu Arg Lys Leu Val Arg Asn Val Arg Gln Ser Gly Asp
            180                 185                 190
Val Tyr Tyr Asn Thr Gly Asp Val Leu Ala Met Asp Arg Glu Gly Phe
        195                 200                 205
Leu Tyr Phe Arg Asp Arg Leu Gly Asp Thr Phe Arg Trp Lys Gly Glu
        210                 215                 220
Asn Val Ser Thr His Glu Val Glu Gly Val Leu Ser Gln Val Asp Phe
225                 230                 235                 240
Leu Gln Gln Val Asn Val Tyr Gly Val Cys Val Pro Gly Cys Glu Gly
                245                 250                 255
Lys Val Gly Met Ala Ala Val Ala Leu Ala Pro Gly Gln Thr Phe Asp
                260                 265                 270
Gly Glu Lys Leu Tyr Gln His Val Arg Ala Trp Leu Pro Ala Tyr Ala
            275                 280                 285
Thr Pro His Phe Ile Arg Ile Gln Asp Ala Met Glu Val Thr Ser Thr
        290                 295                 300
Phe Lys Leu Met Lys Thr Arg Leu Val Arg Glu Gly Phe Asn Val Gly
305                 310                 315                 320
Ile Val Val Asp Pro Leu Phe Val Leu Asp Asn Arg Ala Gln Ser Phe
                325                 330                 335
Arg Pro Leu Thr Ala Glu Met Tyr Gln Ala Val Cys Glu Gly Thr Trp
            340                 345                 350
Arg Leu

<210> SEQ ID NO 56
<211> LENGTH: 2885
<212> TYPE: DNA
<213> ORGANISM: Homo sapiens

<400> SEQUENCE: 56
aacggcaagt aagcgcaacg caattaatgt gagtagctca ctcattaggc acccaggct      60
ttacacttta tgcttccggg ctcgtatgtt gtgtggaatt gtgagcggat accaatttca    120
cacaggaacc agctatgaca tgattacgaa tttaatacga ctcactatag ggaatttggc    180
cctcgaggcc aagaattcgg cacgagggt gctgagcccc tgcgcggttt ctggtgcgta     240
gagactgtaa atcgctgcgc ttctcagtca tcatcatccc agcttttccc ggctcgaatt    300
cagcctccaa ctcaagctcg cgggaaagac tacctgagag agaaaagct tctgtccctg     360
gaccttcttc tgagggtgga gtcggaggct ccctgctttc cagccgccca gtgacccaag    420
cttaatcttc agcaccactt ggggcgacct tttcggtgca aacctacgat tctgtttctc    480
aggattcctc cccatcccgc ttcgccccgg aaaagctgac aagaacttca ggtgtaagcc    540
ctgagtagtg aggatctgcg gtctccgtgg agagctgtgc ctggaagaga aggacgctgg    600

-continued

| | |
|---|---|
| tgggggctga gatcagagct gtcttctggc ccagttgccc ccatgcttct gtcatggcta | 660 |
| acagttctag gggctggaat ggtcgtcctg cacttcttgc agaaactcct gttcccttac | 720 |
| ttttgggatg acttctggtt cgtgttgaag gtggtgctca ttataattcg gctgaagaag | 780 |
| tatgaaaaga gagggagct ggtgactgtg ctggataaat tcttgagtca tgccaaaaga | 840 |
| caacctcgga aacctttcat catctatgag ggagacatct acacctatca ggatgtagac | 900 |
| aaaaggagca gcagagtggc ccatgtcttc ctgaaccatt cctctctgaa aaaggggac | 960 |
| acggtggctc tgctgatgag caatgagccg gacttcgttc acgtgtggtt cggcctcgcc | 1020 |
| aagctgggct gcgtggtggc ctttctcaac accaacattc gctccaactc cctcctgaat | 1080 |
| tgcatccgcg cctgtgggcc cagagcccta gtggtgggcg cagatttgct tggaacggta | 1140 |
| gaagaaatcc ttccaagcct ctcagaaaat atcagtgttt ggggatgaa agattctgtt | 1200 |
| ccacaaggtg taatttcact caagaaaaa ctgagcacct cacctgatga gcccgtgcca | 1260 |
| cgcagccacc atgttgtctc actcctcaag tctacttgtc tttacatttt tacctctgga | 1320 |
| acaacaggtc taccaaaagc agctgtgatt agtcagctgc aggttttaag gggttctgct | 1380 |
| gtcctgtggg cttttggttg tactgctcat gacattgttt atataaccct tcctctgtat | 1440 |
| catagttcag cagctatcct gggaatttct ggatgtgttg agttgggtgc cacttgtgtg | 1500 |
| ttaaagaaga aattttcagc aagccagttt tggagtgact gcaagaagta tgatgtgact | 1560 |
| gtgtttcagt atattggaga actttgtcgc tacctttgca aacaatctaa gagagaagga | 1620 |
| gaaaggatc ataaggtgcg tttggcaatt ggaaatggca tacggagtga tgtatggaga | 1680 |
| gaatttttag acagatttgg aaatataaag gtgtgtgaac tttatgcagc taccgaatca | 1740 |
| agcatatctt tcatgaacta cactgggaga attggagcaa ttgggagaac aaatttgttt | 1800 |
| tacaaacttc tttccacttt tgacttaata agtatgact ttcagaaaga tgaacccatg | 1860 |
| agaaatgagc agggttggtg tattcatgtg aaaaaggag aacctggact tctcatttct | 1920 |
| cgagtgaatg caaaaaatcc cttctttggc tatgctgggc cttataagca cacaaaagac | 1980 |
| aaaattgcttt gtgatgtttt taagaaggga gatgtttacc ttaatactgg agacttaata | 2040 |
| gtccaggatc aggacaattt cctttatttt tgggaccgta ctggagacac tttcagatgg | 2100 |
| aaaggagaaa atgtcgcaac cactgaggtt gctgatgtta ttggaatgtt ggatttcata | 2160 |
| caggaagcaa acgtctatgg tgtggctata tcaggttatg aaggaagagc aggaatggct | 2220 |
| tctattattt taaaccaaa tacatcttta gatttggaaa aagtttatga acaagttgta | 2280 |
| acatttctac cagcttatgc ttgtccacga ttttttaagaa ttcaggaaaa aatggaagca | 2340 |
| acaggaacat tcaaactatt gaagcatcag ttggtggaag atggatttaa tccactgaaa | 2400 |
| atttctgaac cactttactt catggataac ttgaaaaagt cttatgttct actgaccagg | 2460 |
| gaactttatg atcaaataat gttaggggaa ataaaacttt aagattttta tatctagaac | 2520 |
| tttcatatgc tttcttagga agagtgagag ggggtatat gattctttat gaaatgggga | 2580 |
| aagggagcta acattaatta tgcatgtact atatttcctt aatatgagag ataatttttt | 2640 |
| aattgcataa gaatttttaat ttcttttaat tgatataaac attagttgat tattcttttt | 2700 |
| atctatttgg agattcagtg cataactaag tattttcctt aatactaaag attttaaata | 2760 |
| ataaatagtg gctagcggtt tggacaatca ctaaaaatgt actttctaat aagtaaaatt | 2820 |
| tctaattttg aataaaagat taaattttac tgaaaaaaaa aaaaaaaaaa aaaattggcg | 2880 |
| gccgc | 2885 |

```
<210> SEQ ID NO 57
<211> LENGTH: 619
<212> TYPE: PRT
<213> ORGANISM: Homo sapiens

<400> SEQUENCE: 57

Met Leu Leu Ser Trp Leu Thr Val Leu Gly Ala Gly Met Val Val Leu
 1               5                  10                  15

His Phe Leu Gln Lys Leu Leu Phe Pro Tyr Phe Trp Asp Asp Phe Trp
             20                  25                  30

Phe Val Leu Lys Val Val Leu Ile Ile Ile Arg Leu Lys Lys Tyr Glu
         35                  40                  45

Lys Arg Gly Glu Leu Val Thr Val Leu Asp Lys Phe Leu Ser His Ala
     50                  55                  60

Lys Arg Gln Pro Arg Lys Pro Phe Ile Ile Tyr Glu Gly Asp Ile Tyr
 65                  70                  75                  80

Thr Tyr Gln Asp Val Asp Lys Arg Ser Ser Arg Val Ala His Val Phe
                 85                  90                  95

Leu Asn His Ser Ser Leu Lys Lys Gly Asp Thr Val Ala Leu Leu Met
            100                 105                 110

Ser Asn Glu Pro Asp Phe Val His Val Trp Phe Gly Leu Ala Lys Leu
        115                 120                 125

Gly Cys Val Val Ala Phe Leu Asn Thr Asn Ile Arg Ser Asn Ser Leu
    130                 135                 140

Leu Asn Cys Ile Arg Ala Cys Gly Pro Arg Ala Leu Val Val Gly Ala
145                 150                 155                 160

Asp Leu Leu Gly Thr Val Glu Glu Ile Leu Pro Ser Leu Ser Glu Asn
                165                 170                 175

Ile Ser Val Trp Gly Met Lys Asp Ser Val Pro Gln Gly Val Ile Ser
            180                 185                 190

Leu Lys Glu Lys Leu Ser Thr Ser Pro Asp Glu Pro Val Pro Arg Ser
        195                 200                 205

His His Val Val Ser Leu Leu Lys Ser Thr Cys Leu Tyr Ile Phe Thr
    210                 215                 220

Ser Gly Thr Thr Gly Leu Pro Lys Ala Ala Val Ile Ser Gln Leu Gln
225                 230                 235                 240

Val Leu Arg Gly Ser Ala Val Leu Trp Ala Phe Gly Cys Thr Ala His
                245                 250                 255

Asp Ile Val Tyr Ile Thr Leu Pro Leu Tyr His Ser Ser Ala Ala Ile
            260                 265                 270

Leu Gly Ile Ser Gly Cys Val Glu Leu Gly Ala Thr Cys Val Leu Lys
        275                 280                 285

Lys Lys Phe Ser Ala Ser Gln Phe Trp Ser Asp Cys Lys Lys Tyr Asp
    290                 295                 300

Val Thr Val Phe Gln Tyr Ile Gly Glu Leu Cys Arg Tyr Leu Cys Lys
305                 310                 315                 320

Gln Ser Lys Arg Glu Gly Glu Lys Asp His Lys Val Arg Leu Ala Ile
                325                 330                 335

Gly Asn Gly Ile Arg Ser Asp Val Trp Arg Glu Phe Leu Asp Arg Phe
            340                 345                 350

Gly Asn Ile Lys Val Cys Glu Leu Tyr Ala Ala Thr Glu Ser Ser Ile
        355                 360                 365

Ser Phe Met Asn Tyr Thr Gly Arg Ile Gly Ala Ile Gly Arg Thr Asn
    370                 375                 380
```

Leu Phe Tyr Lys Leu Leu Ser Thr Phe Asp Leu Ile Lys Tyr Asp Phe
385                 390                 395                 400

Gln Lys Asp Glu Pro Met Arg Asn Glu Gln Gly Trp Cys Ile His Val
            405                 410                 415

Lys Lys Gly Glu Pro Gly Leu Leu Ile Ser Arg Val Asn Ala Lys Asn
        420                 425                 430

Pro Phe Gly Tyr Ala Gly Pro Tyr Lys His Thr Lys Asp Lys Leu
    435                 440                 445

Leu Cys Asp Val Phe Lys Lys Gly Asp Val Tyr Leu Asn Thr Gly Asp
    450                 455                 460

Leu Ile Val Gln Asp Gln Asp Asn Phe Leu Tyr Phe Trp Asp Arg Thr
465                 470                 475                 480

Gly Asp Thr Phe Arg Trp Lys Gly Glu Asn Val Ala Thr Thr Glu Val
            485                 490                 495

Ala Asp Val Ile Gly Met Leu Asp Phe Ile Gln Glu Ala Asn Val Tyr
            500                 505                 510

Gly Val Ala Ile Ser Gly Tyr Glu Gly Arg Ala Gly Met Ala Ser Ile
515                 520                 525

Ile Leu Lys Pro Asn Thr Ser Leu Asp Leu Glu Lys Val Tyr Glu Gln
530                 535                 540

Val Val Thr Phe Leu Pro Ala Tyr Ala Cys Pro Arg Phe Leu Arg Ile
545                 550                 555                 560

Gln Glu Lys Met Glu Ala Thr Gly Thr Phe Lys Leu Leu Lys His Gln
            565                 570                 575

Leu Val Glu Asp Gly Phe Asn Pro Leu Lys Ile Ser Glu Pro Leu Tyr
            580                 585                 590

Phe Met Asp Asn Leu Lys Lys Ser Tyr Val Leu Leu Thr Arg Glu Leu
            595                 600                 605

Tyr Asp Gln Ile Met Leu Gly Glu Ile Lys Leu
610                 615

<210> SEQ ID NO 58
<211> LENGTH: 3098
<212> TYPE: DNA
<213> ORGANISM: Rattus norvegicus

<400> SEQUENCE: 58
aagttcccac tccagacttc tgcgagaacc cgtgaggaag cagcgagaac cgggggtttg     60
caagccagag aaggatgcgg actccgggag caggaacagc ctctgtggcc tcattggggc    120
tgctttggct tctggacttt ccgtggacct ggagcgcggc ggcggcgttc ggtgtgtacg    180
tgggtagcgg tggctggcga tttctgcgta tcgtctgcaa gacggcgagg cgagacctct    240
ttggcctctc tgttctgatc cgcgtgcggc tagagctacg acgacaccgg cgagcaggag    300
acacgatccc acgcatcttc caggccgtgg cccagcgaca gccggagcgc ctggcgctgg    360
tagatgcgag tagcggtatc tgctggacct tcgcacagct agacacctac tccaatgctg    420
tggccaatct gttcctccag ctgggctttg cgccaggcga tgtggtggct gtgttcctgg    480
aaggccggcc cgagttcgtg ggactgtggc tgggcctggc caaggccggt gtagtggctg    540
cgcttctcaa tgtcaacctg aggcgggagc cccttgcctt ctgcttgggc acatcagctg    600
ccaaggccct catttatggc ggggagatgg cagcggcggt ggcggaggtg agtgagcagc    660
tggggaagag cctgctcaag ttctgctctg gagatctggg gcctgagagc gtcctgcctg    720
acacgcagct tctggacccc atgcttgctg aggcgcccac cacacccctg gcacaggccc    780

-continued

| | |
|---|---|
| caggcaaggg catggatgat cggctatttt acatctatac ttctgggacc accggacttc | 840 |
| ctaaggcggc cattgtggtg cacagcaggt actaccgcat cgcagccttc ggccaccatt | 900 |
| cctacagcat gcgggccaac gatgtgctct atgactgcct acctctctac cactcagcag | 960 |
| ggaacatcat gggcgtggga cagtgtatca tctacgggtt aacggtggta ctgcgcaaga | 1020 |
| agttctccgc cagccgcttc tgggacgact gtgtcaaata taattgcacg gtagtgcagt | 1080 |
| acatcggtga aatatgccgc tacctgctaa ggcagccggt tcgcgatgta gagcggcggc | 1140 |
| accgcgtgcg cctggccgtg ggtaacggac tgcggccagc catctgggag gagttcacgc | 1200 |
| agggtttcgg tgtgcgacag attggcgagt tctacgcgcg caccgaatgc aactgcagca | 1260 |
| ttgccaacat ggacggcaag gtcggctcct gcggcttcaa cagccgtatc ctcacgcatg | 1320 |
| tgtaccccat ccgtctggtc aaggtcaacg aggacacgat ggagccactg agggactccc | 1380 |
| aaggcctctg catcccgtgc cagcccgggg aacctgggct tctcgtgggc cagatcaacc | 1440 |
| agcaagaccc tctgcggcgc ttcgatggct atgttagtga cagcgccacc aacaagaaga | 1500 |
| ttgcccacag cgtgttccga aaggggggaca gcgcctacct ttcaggtgac gtgctagtga | 1560 |
| tggacgagct ggggtacatg tacttccgtg accgagcgg ggataccttc cgatggcgcg | 1620 |
| gcgagaacgt atccaccacg gaggtggaag ccgtgctgag ccgcctgttg ggccagacgg | 1680 |
| acgtggctgt gtatggagtg gctgtgccag gagtggaggg gaaaagcggc atggcggcca | 1740 |
| ttgcagaccc ccacaaccag ctggaccccta actcaatgta ccaggaattg cagaaggttc | 1800 |
| ttgcatccta tgcccagccc atcttcctgc gtcttctgcc ccaagtggat acaacaggca | 1860 |
| ccttcaagat ccagaagacc cgactacagc gtgaaggctt tgaccccgc cagacctcag | 1920 |
| accggctctt ctttctagac ctgaaacagg gacgctacct accctggat gagagagtcc | 1980 |
| atgcccgcat ctgcgcaggc gacttctcac tctgagcctg gtgagtggga tggccctgga | 2040 |
| cttgtgagac cagggagccg gacacccctg ttcaggtgtt tctcctgcct ggccacgtgg | 2100 |
| ccagcagcac ctgtgggtgc aggaaactgg aacctgagtg gccgggtgtc cctttcctac | 2160 |
| aacccaccat gcacacatct agcctctgcc ttggtctttt tctccatctc tttcctccgt | 2220 |
| gcccagcagg agccccacag acacattggc tgctgtgtcc tgcagtggga ccggtgtcta | 2280 |
| ggggtccatg ctgcaggctg tgacccgcac tggtgcccac ctcccttccc cattgtgcct | 2340 |
| taggttcctc cactgtgcgc cggtgaagca agtggggacc cacatagctg ttgtccctgc | 2400 |
| tgagggttgg tagcaaatgc accctcatgt cagctgggag acacatgcag tctcccactg | 2460 |
| acccccaatc aactgaagat actgttttgt attattgttt tgagataggg tctcactgtg | 2520 |
| gaggccaagc tggcctcagg ctcaccactc tactgcctcc gggcaccagc ctgcagtttg | 2580 |
| atgacatgta tgcactattg ttctaagggt cttctgagtc cctgctttcc cctcatgtcc | 2640 |
| taaaaccttc cagaactgac tctgatcact tggatgtagc tagtgttggc cctgcccacg | 2700 |
| tgtgtcaatt caggggtccc caggcatcat ctctggaggc cctaaccttg gcaaagcttg | 2760 |
| gatgtcctca catcacagca ggagacccag gaaggttgct gtggtgtctc ttgggcaccc | 2820 |
| ctggcggcag ccgtggacat gcttccctgc tgtgatagcc caaactgttg cctatgacat | 2880 |
| ttgaggtcta cccttctggc tgccatggtc cccattgaga tctttggtga ctcacctcag | 2940 |
| ccaccaagcc aggcctctgc cttccttcag ctctaagggc atgaagggtg tggacagagc | 3000 |
| agccacaggc tgcccacagt cacccacatg caagtgttat ttccttgttt gttttaaaaa | 3060 |
| aataaacatg ctgagccttg aaaaaaaaaa aaaaaaa | 3098 |

-continued

```
<210> SEQ ID NO 59
<211> LENGTH: 646
<212> TYPE: PRT
<213> ORGANISM: Rattus norvegicus

<400> SEQUENCE: 59
```

| | | | | | | | | | | | | | | | |
|---|---|---|---|---|---|---|---|---|---|---|---|---|---|---|---|
| Met | Arg | Thr | Pro | Gly | Ala | Gly | Thr | Ala | Ser | Val | Ala | Ser | Leu | Gly | Leu |
| 1 | | | | 5 | | | | | 10 | | | | | 15 | |
| Leu | Trp | Leu | Leu | Gly | Leu | Pro | Trp | Thr | Trp | Ser | Ala | Ala | Ala | Ala | Phe |
| | | | 20 | | | | | 25 | | | | | 30 | | |
| Gly | Val | Tyr | Val | Gly | Ser | Gly | Gly | Trp | Arg | Phe | Leu | Arg | Ile | Val | Cys |
| | | | | 35 | | | | | 40 | | | | | 45 | |
| Lys | Thr | Ala | Arg | Arg | Asp | Leu | Phe | Gly | Leu | Ser | Val | Leu | Ile | Arg | Val |
| | 50 | | | | | 55 | | | | | 60 | | | | |
| Arg | Leu | Glu | Leu | Arg | Arg | His | Arg | Arg | Ala | Gly | Asp | Thr | Ile | Pro | Arg |
| 65 | | | | | 70 | | | | | 75 | | | | | 80 |
| Ile | Phe | Gln | Ala | Val | Ala | Gln | Arg | Gln | Pro | Glu | Arg | Leu | Ala | Leu | Val |
| | | | | 85 | | | | | 90 | | | | | 95 | |
| Asp | Ala | Ser | Ser | Gly | Ile | Cys | Trp | Thr | Phe | Ala | Gln | Leu | Asp | Thr | Tyr |
| | | | 100 | | | | | 105 | | | | | 110 | | |
| Ser | Asn | Ala | Val | Ala | Asn | Leu | Phe | Leu | Gln | Leu | Gly | Phe | Ala | Pro | Gly |
| | | | | 115 | | | | | 120 | | | | | 125 | |
| Asp | Val | Val | Ala | Val | Phe | Leu | Glu | Gly | Arg | Pro | Glu | Phe | Val | Gly | Leu |
| | | | 130 | | | | | 135 | | | | | 140 | | |
| Trp | Leu | Gly | Leu | Ala | Lys | Ala | Gly | Val | Val | Ala | Ala | Leu | Leu | Asn | Val |
| 145 | | | | | 150 | | | | | 155 | | | | | 160 |
| Asn | Leu | Arg | Arg | Glu | Pro | Leu | Ala | Phe | Cys | Leu | Gly | Thr | Ser | Ala | Ala |
| | | | | 165 | | | | | 170 | | | | | 175 | |
| Lys | Ala | Leu | Ile | Tyr | Gly | Gly | Glu | Met | Ala | Ala | Val | Ala | Glu | Val |
| | | | 180 | | | | | 185 | | | | | 190 | | |
| Ser | Glu | Gln | Leu | Gly | Lys | Ser | Leu | Leu | Lys | Phe | Cys | Ser | Gly | Asp | Leu |
| | | | 195 | | | | | 200 | | | | | 205 | | |
| Gly | Pro | Glu | Ser | Val | Leu | Pro | Asp | Thr | Gln | Leu | Leu | Asp | Pro | Met | Leu |
| | 210 | | | | | 215 | | | | | 220 | | | | |
| Ala | Glu | Ala | Pro | Thr | Thr | Pro | Leu | Ala | Gln | Ala | Pro | Gly | Lys | Gly | Met |
| 225 | | | | | 230 | | | | | 235 | | | | | 240 |
| Asp | Asp | Arg | Leu | Phe | Tyr | Ile | Tyr | Thr | Ser | Gly | Thr | Thr | Gly | Leu | Pro |
| | | | | 245 | | | | | 250 | | | | | 255 | |
| Lys | Ala | Ala | Ile | Val | Val | His | Ser | Arg | Tyr | Tyr | Arg | Ile | Ala | Ala | Phe |
| | | | 260 | | | | | 265 | | | | | 270 | | |
| Gly | His | His | Ser | Tyr | Ser | Met | Arg | Ala | Asn | Asp | Val | Leu | Tyr | Asp | Cys |
| | | | | 275 | | | | | 280 | | | | | 285 | |
| Leu | Pro | Leu | Tyr | His | Ser | Ala | Gly | Asn | Ile | Met | Gly | Val | Gly | Gln | Cys |
| | | 290 | | | | | 295 | | | | | 300 | | | |
| Ile | Ile | Tyr | Gly | Leu | Thr | Val | Val | Leu | Arg | Lys | Lys | Phe | Ser | Ala | Ser |
| 305 | | | | | 310 | | | | | 315 | | | | | 320 |
| Arg | Phe | Trp | Asp | Asp | Cys | Val | Lys | Tyr | Asn | Cys | Thr | Val | Val | Gln | Tyr |
| | | | | 325 | | | | | 330 | | | | | 335 | |
| Ile | Gly | Glu | Ile | Cys | Arg | Tyr | Leu | Leu | Arg | Gln | Pro | Val | Arg | Asp | Val |
| | | | 340 | | | | | 345 | | | | | 350 | | |
| Glu | Arg | Arg | His | Arg | Val | Arg | Leu | Ala | Val | Gly | Asn | Gly | Leu | Arg | Pro |
| | | | | 355 | | | | | 360 | | | | | 365 | |
| Ala | Ile | Trp | Glu | Glu | Phe | Thr | Gln | Gly | Phe | Gly | Val | Arg | Gln | Ile | Gly |
| | | 370 | | | | | 375 | | | | | 380 | | | |

-continued

```
Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Thr His Val
            405                 410                 415

Tyr Pro Ile Arg Leu Val Lys Val Asn Glu Asp Thr Met Glu Pro Leu
        420                 425                 430

Arg Asp Ser Gln Gly Leu Cys Ile Pro Cys Gln Pro Gly Glu Pro Gly
    435                 440                 445

Leu Leu Val Gly Gln Ile Asn Gln Gln Asp Pro Leu Arg Arg Phe Asp
450                 455                 460

Gly Tyr Val Ser Asp Ser Ala Thr Asn Lys Lys Ile Ala His Ser Val
465                 470                 475                 480

Phe Arg Lys Gly Asp Ser Ala Tyr Leu Ser Gly Asp Val Leu Val Met
            485                 490                 495

Asp Glu Leu Gly Tyr Met Tyr Phe Arg Asp Arg Ser Gly Asp Thr Phe
        500                 505                 510

Arg Trp Arg Gly Glu Asn Val Ser Thr Thr Glu Val Glu Ala Val Leu
    515                 520                 525

Ser Arg Leu Leu Gly Gln Thr Asp Val Ala Val Tyr Gly Val Ala Val
530                 535                 540

Pro Gly Val Glu Gly Lys Ser Gly Met Ala Ala Ile Ala Asp Pro His
545                 550                 555                 560

Asn Gln Leu Asp Pro Asn Ser Met Tyr Gln Glu Leu Gln Lys Val Leu
            565                 570                 575

Ala Ser Tyr Ala Gln Pro Ile Phe Leu Arg Leu Leu Pro Gln Val Asp
        580                 585                 590

Thr Thr Gly Thr Phe Lys Ile Gln Lys Thr Arg Leu Gln Arg Glu Gly
    595                 600                 605

Phe Asp Pro Arg Gln Thr Ser Asp Arg Leu Phe Phe Leu Asp Leu Lys
610                 615                 620

Gln Gly Arg Tyr Leu Pro Leu Asp Glu Arg Val His Ala Arg Ile Cys
625                 630                 635                 640

Ala Gly Asp Phe Ser Leu
            645

<210> SEQ ID NO 60
<211> LENGTH: 2963
<212> TYPE: DNA
<213> ORGANISM: Rattus norvegicus

<400> SEQUENCE: 60
gacacagtac tgccgatgtt ggacagagga tcgcttaaca gaacgaaatc tcaaaacaaa    60
ttaacaggac ccggttgctt gatttcccaa atcagaaaag gctcgaaatg tctagagggg   120
ctgactgatg cagcggtgac ccggactgga gacagttgga cgcgatcatc tctggtgctt   180 tgttcaacc ttgaaacctt cgccacagga gacttgcctg agcagagaag caaacgtgga   240
gaaacaaaga gagatctagc gaaaagcctc tgggaccaag aggggaggt gggactctgg   300 gttggcggtg gcacctgctg ccggctatta ataatagggt cgcgatgcgt ttataaggtg   360
tttgattaaa caaagactct atgagagaag aataactagc aacagcccca cgtctgagtc   420
gtcgcctccg accttttca acgtgggttc tttgggccga gcgtcgtttg ccagaaacta   480
gatctcacct gaccccagac gctgaaaaca agcgctgtgg catcctgggc acccaagct   540 gacaagggcg cgcccctga gcacgcgagg tgccccacga gggggaggga cccacagccg   600
```

-continued

```
tcccgcccgc accgcggtgt ccgctgcggg cacctgcagc cgagccgcca cccgcagtcg    660
cagcgcgtcc ggcggccgaa cccggtcgtc agctcgtcag cacctgctct gcttctctcc    720
cgcccgccgc cgccgctgcac gcctcgagcg ctccctcggc cccggcgggg accggggacc   780
ccgcagccac cgccatgctg cctgtgctct acaccggcct ggcggggctg ctgctgctgc    840
ctctgctgct cacctgctgc tgcccctacc tcctccagga cgtgcggttc ttcctgcaac    900
tggccaacat ggcccggcag gtgcgcagct accggcagcg cgacccgtg cgcaccatcc     960
tgcatgtctt cttggagcaa gcgcgcaaga ccccgcacaa gcccttcctg ctgtttcgcg   1020
acgagacgct tacctacgcc caggtagacc ggcgcagcaa ccaagtagcg cgagcgctgc   1080
atgatcacct gggcctgcgg caggggatt gcgtggccct cttcatgggc aatgagccgg    1140
cctacgtgtg gctctggctg ggactgctca aactgggctg tcccatggcg tgcctcaact   1200
acaacatccg tgccaagtct ctgctacact gctttcagtg ctgcggggcg aaggtgctgc   1260
tggcctcccc agagctacac gaagctgtcg aggaggttct tccaaccctg aaaaaggagg   1320
gcgtgtccgt cttctacgta agcagaactt ctaacactaa tggcgtggac acagtactgg   1380
acaaagtaga cggggtgtcg gcggacccca tcccggagtc gtggaggtct gaagtcacgt   1440
tcaccacacc cgcagtctac atatatactt cgggcaccac aggtcttcca aaggctgcaa   1500
ccattaatca ccatcgcctc tggtatggga ccagccttgc cctgaggtcc ggaattaagg   1560
ctcatgacgt catctacacc accatgcccc tgtaccacag cgcggcgctc atgattggcc   1620
tccacggatg cattgtggtt ggggctacat ttgctttgcg gagcaaattt tcagccagcc   1680
agttttggga cgactgcagg aaatacaacg ccactgtcat tcagtacatc ggtgaactgc   1740
ttcggtacct ctgcaacacg ccccagaaac caaatgaccg ggaccacaaa gtgaaaatag   1800
cactaggaaa tggcttacga ggagatgtgt ggagagagtt catcaagaga tttggggaca   1860
ttcacattta tgagttctac gcttccactg aaggcaacat tggatttatg aactatccaa   1920
gaaaaatcgg agctgttgga agagaaaatt acctacaaaa aaaagttgta aggcacgagc   1980
tgatcaagta tgacgtggag aaggatgagc ctgtccgtga tgcaaatgga tattgcatca   2040
aagtccccaa aggagaggtt ggactcttga tttgcaaaat cacagagctc acaccatttt   2100
ttggctatgc tggaggaaag acccagacag agaagaaaaa gctcagagat gttttttaaga  2160
aaggagacgt ctacttcaac agtggcgatc tcctgatgat cgaccgtgaa aatttcatct   2220
atttttcacga cagagttgga gacaccttcc ggtggaaagg agagaatgta gctaccacgg   2280
aagtcgctga cattgtggga ctggtagatt ttgttgaaga agtgaatgtt tacggtgtgc   2340
ccgtgccagg tcatgaaggt cgcatcggga tggcctcgat caagatgaaa gaaaactacg   2400
agttcaatga aaagaaactc tttcagcaca tctcggagta cctgcccagt tactcgaggc   2460
ctcggttcct gagaatacaa gataccattg agatcaccgg gactttaaaa caccgcaaag   2520
tgaccctgat ggaagagggc tttaaccct cagtcatcaa agataccttg tatttcatgg    2580
atgacacaga aaaacatac gtgcccatga ctgaggacat ttataatgcc ataattgata    2640
agactctgaa gctctgaatg ttgcctggct cctaacactt ccagaaagaa acacaatagg   2700
cctagcatag ccccttcaca tgtgtaatcc aactttaact tgattaaagg ttataggtgt   2760
gattttttcct aggaaattat tcatttaaag gacaattgtt tgtttgtttg tttgtttttt  2820
attaattaca ccagaacgtt tgcaagtaaa aagatttaaa gtcacttatt tttcaatgtg   2880
cacctgccat ttgtccttgc aaacttagct tcttggagag agggccttat ttttttaaag   2940
acataataaa ctatgtaaac act                                           2963
```

-continued

<210> SEQ ID NO 61
<211> LENGTH: 620
<212> TYPE: PRT
<213> ORGANISM: Rattus norvegicus

<400> SEQUENCE: 61

```
Met Leu Pro Val Leu Tyr Thr Gly Leu Ala Gly Leu Leu Leu Pro
  1               5                  10                  15

Leu Leu Leu Thr Cys Cys Pro Tyr Leu Leu Gln Asp Val Arg Phe
             20                  25                  30

Phe Leu Gln Leu Ala Asn Met Ala Arg Gln Val Arg Ser Tyr Arg Gln
         35                  40                  45

Arg Arg Pro Val Arg Thr Ile Leu His Val Phe Leu Glu Gln Ala Arg
     50                  55                  60

Lys Thr Pro His Lys Pro Phe Leu Leu Phe Arg Asp Glu Thr Leu Thr
 65                  70                  75                  80

Tyr Ala Gln Val Asp Arg Arg Ser Asn Gln Val Ala Arg Ala Leu His
                 85                  90                  95

Asp His Leu Gly Leu Arg Gln Gly Asp Cys Val Ala Leu Phe Met Gly
                100                 105                 110

Asn Glu Pro Ala Tyr Val Trp Leu Trp Leu Gly Leu Leu Lys Leu Gly
            115                 120                 125

Cys Pro Met Ala Cys Leu Asn Tyr Asn Ile Arg Ala Lys Ser Leu Leu
        130                 135                 140

His Cys Phe Gln Cys Cys Gly Ala Lys Val Leu Leu Ala Ser Pro Glu
145                 150                 155                 160

Leu His Glu Ala Val Glu Glu Val Leu Pro Thr Leu Lys Lys Glu Gly
                165                 170                 175

Val Ser Val Phe Tyr Val Ser Arg Thr Ser Asn Thr Asn Gly Val Asp
            180                 185                 190

Thr Val Leu Asp Lys Val Asp Gly Val Ser Ala Asp Pro Ile Pro Glu
        195                 200                 205

Ser Trp Arg Ser Glu Val Thr Phe Thr Thr Pro Ala Val Tyr Ile Tyr
    210                 215                 220

Thr Ser Gly Thr Thr Gly Leu Pro Lys Ala Ala Thr Ile Asn His His
225                 230                 235                 240

Arg Leu Trp Tyr Gly Thr Ser Leu Ala Leu Arg Ser Gly Ile Lys Ala
                245                 250                 255

His Asp Val Ile Tyr Thr Thr Met Pro Leu Tyr His Ser Ala Ala Leu
            260                 265                 270

Met Ile Gly Leu His Gly Cys Ile Val Val Gly Ala Thr Phe Ala Leu
        275                 280                 285

Arg Ser Lys Phe Ser Ala Ser Gln Phe Trp Asp Asp Cys Arg Lys Tyr
    290                 295                 300

Asn Ala Thr Val Ile Gln Tyr Ile Gly Glu Leu Leu Arg Tyr Leu Cys
305                 310                 315                 320

Asn Thr Pro Gln Lys Pro Asn Asp Arg Asp His Lys Val Lys Ile Ala
                325                 330                 335

Leu Gly Asn Gly Leu Arg Gly Asp Val Trp Arg Glu Phe Ile Lys Arg
            340                 345                 350

Phe Gly Asp Ile His Ile Tyr Glu Phe Tyr Ala Ser Thr Glu Gly Asn
        355                 360                 365

Ile Gly Phe Met Asn Tyr Pro Arg Lys Ile Gly Ala Val Gly Arg Glu
    370                 375                 380
```

```
Asn Tyr Leu Gln Lys Lys Val Val Arg His Glu Leu Ile Lys Tyr Asp
385                 390                 395                 400
Val Glu Lys Asp Glu Pro Val Arg Asp Ala Asn Gly Tyr Cys Ile Lys
            405                 410                 415
Val Pro Lys Gly Glu Val Gly Leu Leu Ile Cys Lys Ile Thr Glu Leu
            420                 425                 430
Thr Pro Phe Phe Gly Tyr Ala Gly Gly Lys Thr Gln Thr Glu Lys Lys
            435                 440                 445
Lys Leu Arg Asp Val Phe Lys Lys Gly Asp Val Tyr Phe Asn Ser Gly
450                 455                 460
Asp Leu Leu Met Ile Asp Arg Glu Asn Phe Ile Tyr Phe His Asp Arg
465                 470                 475                 480
Val Gly Asp Thr Phe Arg Trp Lys Gly Glu Asn Val Ala Thr Thr Glu
            485                 490                 495
Val Ala Asp Ile Val Gly Leu Val Asp Phe Val Glu Glu Val Asn Val
            500                 505                 510
Tyr Gly Val Pro Val Pro Gly His Glu Gly Arg Ile Gly Met Ala Ser
            515                 520                 525
Ile Lys Met Lys Glu Asn Tyr Glu Phe Asn Gly Lys Lys Leu Phe Gln
530                 535                 540
His Ile Ser Glu Tyr Leu Pro Ser Tyr Ser Arg Pro Arg Phe Leu Arg
545                 550                 555                 560
Ile Gln Asp Thr Ile Glu Ile Thr Gly Thr Phe Lys His Arg Lys Val
            565                 570                 575
Thr Leu Met Glu Glu Gly Phe Asn Pro Ser Val Ile Lys Asp Thr Leu
            580                 585                 590
Tyr Phe Met Asp Asp Thr Glu Lys Thr Tyr Val Pro Met Thr Glu Asp
            595                 600                 605
Ile Tyr Asn Ala Ile Ile Asp Lys Thr Leu Lys Leu
610                 615                 620

<210> SEQ ID NO 62
<211> LENGTH: 1350
<212> TYPE: DNA
<213> ORGANISM: Rattus norvegicus

<400> SEQUENCE: 62
gatcagctct tctatatcta cacgtcgggc accacggggc tacccaaagc tgccattgtg      60
gtgcacagca ggtattaccg aatggctgcc ctggtgtact atggattccg catgcggcct     120
gatgacattg tctatgactg cctcccctc taccactcag caggaaacat tgtgggatt     180
ggccagtgcg tactccacgg catgactgtg gtgatccgga agagttttc agcctcccgg     240
ttctgggatg actgtatcaa gtacaactgc acaattgtac agtacattgg tgagctttgc     300
cgctacctcc tgaaccagcc accccgtgag gctgagtctc ggcacaaggt gcgcatggca     360
ctgggcaacg gtctccggca gtccatctgg accgacttct ccagccgttt ccacattccc     420
aaggtggccg agttctacgg ggccaccgag tgcaactgta gcttgggcaa ctttgacagc     480
caggtggggg cctgtggctt caatagccgc atcctgtcct tgtgtaccc catccgcttg     540
gtacgagtca atgaggatac catggaactg atccggggac ccgatggcgt ctgcattccc     600
tgtcaaccag gccagccagg ccagctggtg ggtcgcatca tccagcagga cccctacgc     660
cgttttgatg gctacctcaa ccagggtgcc aacaacaaga agattgctag tgatgtcttc     720
aagaaagggg accaagccta cctcactggt gacgtgctgg tgatggatga gctgggctac     780
```

-continued

```
ctgtacttcc gagaccgcac aggggacacg ttccgctgga aagggagaa tgtgtctacc    840 actgaagtgg agggcacact cagccgcctg cttcagatgg cagatgtggc tgtttatggt    900
gttgaggtgc caggagctga gggccgagca ggaatggctg ctgtggcaag ccccactagc    960
aactgtgacc tggagagctt tgcacagacc ttgaaaaagg agctgcccct gtacgcccgc   1020
cccatcttcc tccgcttctt gcctgagctg cacaaaacag gaaccttcaa gttccagaag   1080
acagagttgc ggaaggaggg ctttgacccg tctgttgtga agacccact cttctatttg   1140 gatgcccgga caggctgcta tgttgcactg gaccaagagg cctataccg catccaggca   1200 ggcgaggaga agctgtgatt tccccacat ccctctgagg gccagaggat gctggattca   1260
gagccccagc ttccactcca gaagggtct gggcaaggcc agaccaaagc tagcagggcc   1320
cgcaccttca ccctaggtgc tgatccccct                                    1350
```

<210> SEQ ID NO 63
<211> LENGTH: 405
<212> TYPE: PRT
<213> ORGANISM: Rattus norvegicus

<400> SEQUENCE: 63

```
Asp Gln Leu Phe Tyr Ile Tyr Thr Ser Gly Thr Thr Gly Leu Pro Lys
 1               5                  10                  15

Ala Ala Ile Val Val His Ser Arg Tyr Tyr Arg Met Ala Ala Leu Val
            20                  25                  30

Tyr Tyr Gly Phe Arg Met Arg Pro Asp Asp Ile Val Tyr Asp Cys Leu
        35                  40                  45

Pro Leu Tyr His Ser Ala Gly Asn Ile Val Gly Ile Gly Gln Cys Val
    50                  55                  60

Leu His Gly Met Thr Val Val Ile Arg Lys Lys Phe Ser Ala Ser Arg
65                  70                  75                  80

Phe Trp Asp Asp Cys Ile Lys Tyr Asn Cys Thr Ile Val Gln Tyr Ile
                85                  90                  95

Gly Glu Leu Cys Arg Tyr Leu Leu Asn Gln Pro Pro Arg Glu Ala Glu
            100                 105                 110

Ser Arg His Lys Val Arg Met Ala Leu Gly Asn Gly Leu Arg Gln Ser
        115                 120                 125

Ile Trp Thr Asp Phe Ser Ser Arg Phe His Ile Pro Lys Val Ala Glu
    130                 135                 140

Phe Tyr Gly Ala Thr Glu Cys Asn Cys Ser Leu Gly Asn Phe Asp Ser
145                 150                 155                 160

Gln Val Gly Ala Cys Gly Phe Asn Ser Arg Ile Leu Ser Phe Val Tyr
                165                 170                 175

Pro Ile Arg Leu Val Arg Val Asn Glu Asp Thr Met Glu Leu Ile Arg
            180                 185                 190

Gly Pro Asp Gly Val Cys Ile Pro Cys Gln Pro Gly Gln Pro Gly Gln
        195                 200                 205

Leu Val Gly Arg Ile Ile Gln Gln Asp Pro Leu Arg Arg Phe Asp Gly
    210                 215                 220

Tyr Leu Asn Gln Gly Ala Asn Asn Lys Lys Ile Ala Ser Asp Val Phe
225                 230                 235                 240

Lys Lys Gly Asp Gln Ala Tyr Leu Thr Gly Asp Val Leu Val Met Asp
                245                 250                 255

Glu Leu Gly Tyr Leu Tyr Phe Arg Asp Arg Thr Gly Asp Thr Phe Arg
            260                 265                 270
```

```
Trp Lys Gly Glu Asn Val Ser Thr Thr Glu Val Glu Gly Thr Leu Ser
            275                 280                 285

Arg Leu Leu Gln Met Ala Asp Val Ala Val Tyr Gly Val Glu Val Pro
        290                 295                 300

Gly Ala Glu Gly Arg Ala Gly Met Ala Ala Val Ala Ser Pro Thr Ser
305                 310                 315                 320

Asn Cys Asp Leu Glu Ser Phe Ala Gln Thr Leu Lys Lys Glu Leu Pro
                325                 330                 335

Leu Tyr Ala Arg Pro Ile Phe Leu Arg Phe Leu Pro Glu Leu His Lys
            340                 345                 350

Thr Gly Thr Phe Lys Phe Gln Lys Thr Glu Leu Arg Lys Glu Gly Phe
        355                 360                 365

Asp Pro Ser Val Val Lys Asp Pro Leu Phe Tyr Leu Asp Ala Arg Thr
370                 375                 380

Gly Cys Tyr Val Ala Leu Asp Gln Glu Ala Tyr Thr Arg Ile Gln Ala
385                 390                 395                 400

Gly Glu Glu Lys Leu
            405

<210> SEQ ID NO 64
<211> LENGTH: 3217
<212> TYPE: DNA
<213> ORGANISM: Mus musculus

<400> SEQUENCE: 64
atgcgggctc ctggagcagg aacagcctct gtggcctcac tggcgctgct ttggtttctg      60
ggacttccgt ggacctggag cgcggcggcg gcgttctgtg tgtacgtggg tggcggcggc     120
tggcgctttc tgcgtatcgt ctgcaagacg gcgaggcgag acctctttgg cctctctgtt     180
ctgattcgtg ttcggctaga gctgcgacga caccggcgag caggagacac gatcccgtgc     240
atcttccagg ctgtggcccg cgacaaccca gagcgcctgg cactggtgga cgccagtagt     300
ggtatatgct ggaccttcgc acagctggac acctactcca atgctgtagc caacctgttc     360
cgccagctgg gctttgcacc aggcgatgtg gtggctgtgt cctggaggg ccggccggag     420 ttcgtgggac tgtggctggg cctggccaag gccggtgtgg tggctgctct tctcaatgtc     480
aacctgaggc gggagcccct ggccttctgc ctgggcacat cagctgccaa ggccctcatt     540
tatggcgggg agatggcagc ggcggtggcg gaggtgagcg agcagctggg gaagagcctc     600
ctcaagttct gctctggaga tctggggcct gagagcatcc tgcctgacac gcagctcctg     660
gaccccatgc ttgctgaggc gcccaccaca cccctggcac aagccccagg caagggcatg     720
gatgatcggc tgttttacat ctatacttct gggaccaccg gcttcctaa ggctgccatt     780 gtggtgcaca gcaggtacta ccgcattgct gcctttggcc accattccta cagcatgcgt     840
gccgccgatg tgctctatga ctgcctgcca ctctaccact ctgcaggaa catcatgggt     900 gtggggcagt gcgtcatcta cgggttgacg gtggtactgc gcaagaagtt ctccgccagc     960
cgcttctggg atgactgtgt caagtacaat gcacggtag tggatgacat aggtgaaatc    1020
tgccgctacc tgctgaggca gccggttcgc gacgtggagc agcgacaccg cgtgcgcctg    1080
gccgtgggta atgggctgcg gccagccatc tgggaggagt tcacgcagcg cttcggtgtg    1140
ccacagatcg gcgagttcta cggcgctacc gagtgcaact gcagcattgc caacatggac    1200
ggcaaggtcg gctcctgcgg cttcaacagc cgtatcctca gcatgtgta ccccatccgt    1260 ctggtcaagg tcaatgagga cacgatggag ccactgcggg actccgaggg cctctgcatc    1320
```

-continued

```
ccgtgccagc ccggggaacc cggccttctc gtgggccaga tcaaccagca ggaccctctg   1380
cggcgtttcg atggttatgt tagtgacagt gccaccaaca agaagattgc ccacagcgtt   1440
ttccgaaagg gcgatagcgc ctacctctca ggtgacgtgc tagtgatgga cgagctgggc   1500
tacatgtatt tccgtgaccg cagcggggac accttccgct ggcgcgggga gaacgtgtcc   1560
accacggagg tggaagccgt gctgagccgc tactgggcc agacggacgt ggctgtgtat   1620
ggggtggctg tgccaggagt ggaggggaaa gctggcatgg cagccatcgc agatccccac   1680
agccagttgg accctaactc aatgtaccag gaattacaga aggttcttgc atcctatgct   1740
cggcccatct tcctgcgtct tctgccccag gtggatacca caggcaccttc aagatccag   1800 aagacccggc tgcagcgtga aggctttgac ccccgtcaga cctcagacag gctcttcttt   1860
ctagacctga agtccggcac gaggtatcta ccctggatg agagagtcca tgcccgcatt   1920
tgcgcaggcg acttctcact ctgagcctgg agagtgggct gggcctggac tcctgagacc   1980
tgggagcctg acacccctct tcgggtgctt ctcctgcctg gccacatgga cagcagcacc   2040
tgtgagagta ggaaaatgga acctgagtgg ctgggacccc tctcctactt cccactatgc   2100
atccattttg cctctgcctt gatctttttc tccatctctt ttctccctac ccagcaggag   2160
ccccacaaac acatgttggc tgctgtgtcc tgcagttgga ccagtgtcca ggggtacagg   2220
cttcaggctg tgacccacac tggtacccac ctcccttttcc tattttgcct taggttcatc   2280
cacggttccc ctgtggagca agtgggggcc cacatagctg ctgtccctgc tgagggttgg   2340
tagcaatcac accctcatgt cagctgggag acacgcgcag tctcccactg accccaatc    2400 aactgaaaat attgttttga ctacttttg tttttttgtt tttttgtttt tttttttttt    2460
cgagacagag tttctctgta tagccctggc tgtcctggaa ctcactttgt agaccaggct   2520
ggcctcgaac tcaaaaatcc tcctgactct gcctctgctt cccaagtgct gggattaaag   2580
acgtgcgcca ccaccgcctg gctgttttgt attttgttt tgttttgacg atagggtctc   2640
actgtggagg ccaagctggc ctcagactcc caccccatt gcctctgggc accattctat    2700
attctcagac tgatgacaat gcactagtgt ccctaggagt cttgagtctg cactttcccc   2760
tcatagcctc aagcttccag aactgactct gatcacttgg atgtggctag tgttggctct   2820
acccacatgt gtcaattcag gggtccccag gcatagtctc tggaagccct cacccggaaa   2880
aagcttggag agacccagga aggttgttgt gttctcttgg cacccctg gtggcagtcc    2940 tgggcatgct tccgcactgt actggtgcat atagcccaga cctatgacat tgaggtcta    3000 cccttctggc tcctgtggtc cccattgaga tccttggtga ctcacctcag tcaccaagca   3060
gagcctctgc ctgccttcat cttcaaggtc atgaaggatg tggacagagc agctacaggc   3120
tgccagcagt caaccacatg agagtgttac ttccttgttg gttttaaaa aataaatgtg    3180 ctgagcctcg aaaaaaaaaa aaaaaaaaaa aaaaaa                              3217
```

<210> SEQ ID NO 65
<211> LENGTH: 647
<212> TYPE: PRT
<213> ORGANISM: Mus musculus

<400> SEQUENCE: 65

Met Arg Ala Pro Gly Ala Gly Thr Ala Ser Val Ala Ser Leu Ala Leu
1               5                   10                  15

Leu Trp Phe Leu Gly Leu Pro Trp Thr Trp Ser Ala Ala Ala Ala Phe
            20                  25                  30

-continued

```
Cys Val Tyr Val Gly Gly Gly Trp Arg Phe Leu Arg Ile Val Cys
         35                  40                  45

Lys Thr Ala Arg Arg Asp Leu Phe Gly Leu Ser Val Leu Ile Arg Val
 50                  55                  60

Arg Leu Glu Leu Arg Arg His Arg Arg Ala Gly Asp Thr Ile Pro Cys
 65                  70                  75                  80

Ile Phe Gln Ala Val Ala Arg Arg Gln Pro Glu Arg Leu Ala Leu Val
                 85                  90                  95

Asp Ala Ser Ser Gly Ile Cys Trp Thr Phe Ala Gln Leu Asp Thr Tyr
             100                 105                 110

Ser Asn Ala Val Ala Asn Leu Phe Arg Gln Leu Gly Phe Ala Pro Gly
         115                 120                 125

Asp Val Val Ala Val Phe Leu Glu Gly Arg Pro Glu Phe Val Gly Leu
     130                 135                 140

Trp Leu Gly Leu Ala Lys Ala Gly Val Val Ala Ala Leu Leu Asn Val
145                 150                 155                 160

Asn Leu Arg Arg Glu Pro Leu Ala Phe Cys Leu Gly Thr Ser Ala Ala
                165                 170                 175

Lys Ala Leu Ile Tyr Gly Gly Glu Met Ala Ala Ala Val Ala Glu Val
            180                 185                 190

Ser Glu Gln Leu Gly Lys Ser Leu Leu Lys Phe Cys Ser Gly Asp Leu
        195                 200                 205

Gly Pro Glu Ser Ile Leu Pro Asp Thr Gln Leu Leu Asp Pro Met Leu
    210                 215                 220

Ala Glu Ala Pro Thr Thr Pro Leu Ala Gln Ala Pro Gly Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Ile Ala Ala Phe
            260                 265                 270

Gly His His Ser Tyr Ser Met Arg Ala Ala Asp Val Leu Tyr Asp Cys
        275                 280                 285

Leu Pro Leu Tyr His Ser Ala Gly Asn Ile Met Gly Val Gly Gln Cys
    290                 295                 300

Val Ile Tyr Gly Leu Thr Val Val Leu Arg Lys Lys Phe Ser Ala Ser
305                 310                 315                 320

Arg Phe Trp Asp Asp Cys Val Lys Tyr Asn Cys Thr Val Val Asp Asp
                325                 330                 335

Ile Gly Glu Ile Cys Arg Tyr Leu Leu Arg Gln Pro Val Arg Asp Val
            340                 345                 350

Glu Gln Arg His Arg Val Arg Leu Ala Val Gly Asn Gly Leu Arg Pro
        355                 360                 365

Ala Ile Trp Glu Glu Phe Thr Gln Arg Phe Gly Val Pro Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Thr His Val
                405                 410                 415

Tyr Pro Ile Arg Leu Val Lys Val Asn Glu Asp Thr Met Glu Pro Leu
            420                 425                 430

Arg Asp Ser Glu Gly Leu Cys Ile Pro Cys Gln Pro Gly Glu Pro Gly
        435                 440                 445

Leu Leu Val Gly Gln Ile Asn Gln Gln Asp Pro Leu Arg Arg Phe Asp
```

```
               450              455              460
Gly Tyr Val Ser Asp Ser Ala Thr Asn Lys Lys Ile Ala His Ser Val
465              470              475              480

Phe Arg Lys Gly Asp Ser Ala Tyr Leu Ser Gly Asp Val Leu Val Met
             485              490              495

Asp Glu Leu Gly Tyr Met Tyr Phe Arg Asp Arg Ser Gly Asp Thr Phe
             500              505              510

Arg Trp Arg Gly Glu Asn Val Ser Thr Thr Glu Val Glu Ala Val Leu
             515              520              525

Ser Arg Leu Leu Gly Gln Thr Asp Val Ala Val Tyr Gly Val Ala Val
530              535              540

Pro Gly Val Glu Gly Lys Ala Gly Met Ala Ala Ile Ala Asp Pro His
545              550              555              560

Ser Gln Leu Asp Pro Asn Ser Met Tyr Gln Glu Leu Gln Lys Val Leu
             565              570              575

Ala Ser Tyr Ala Arg Pro Ile Phe Leu Arg Leu Leu Pro Gln Val Asp
             580              585              590

Thr Thr Gly Thr Phe Lys Ile Gln Lys Thr Arg Leu Gln Arg Glu Gly
             595              600              605

Phe Asp Pro Arg Gln Thr Ser Asp Arg Leu Phe Phe Leu Asp Leu Lys
             610              615              620

Ser Gly Thr Arg Tyr Leu Pro Leu Asp Glu Arg Val His Ala Arg Ile
625              630              635              640

Cys Ala Gly Asp Phe Ser Leu
             645

<210> SEQ ID NO 66
<211> LENGTH: 2338
<212> TYPE: DNA
<213> ORGANISM: Mus musculus

<400> SEQUENCE: 66
gggcggaggc cgagcccagt cgccagctcc tgctctgctc ctctcccgcc tgccgccgcg      60
ctgcacgcct cgagcactcc ctcggccccg gcggggaccg ggacccccgc agctaccgcc     120
atgctgccag tgctctacac cggcctggcg gggctgctgc tgctgcctct gctgctcacc     180
tgctgctgcc cctacctcct ccaagatgtg cggtacttcc tgcggctggc caacatggcc     240
cggcgggtgc gcagctaccg gcagcggcga cccgtgcgta ccatcctgcg ggccttcctg     300
gaacaagcgc gcaagacccc acacaagccc ttcctgctgt tccagacgac gcgctcacc     360
tacgcccagg tggaccggcg cagcaaccaa gtggcgcggg cgctcacgac tcaactgggc     420
ctacgacagg gggattgcgt agccctcttc atgggcaatg agccggccta cgtgtggatc     480
tggctgggac tgctcaaact gggctgtccc atggcgtgcc tcaactacaa cattcgtgcc     540
aagtctctgc tgcactgctt tcaatgctgc ggggcgaagt gctgctggc ctccccagat     600
ctacaagaag ctgtggagga ggttcttcca accctgaaaa aggatgccgt gtccgtcttt     660
tacgtaagca gaacttctaa cacaaatggt gtggacacaa tactggacaa gtagacgga      720
gtgtcggcgg aacccacccc ggagtcgtgg aggtctgaag tcacttttac cacgccagca     780
gtatacattt atacttcggg aaccacaggt cttccaaaaa gcggaaccat caatcatcat     840
cgcctaaggt atgggacaag ccttgctatg tcgagtggga atcacggcca aggatgtcat     900
ctataccaac aatgccctg ttccaacagt gcaacgctca agatcggcct tcacggatgc     960
atcctgggtt ggggctactt taaccttggc gggcaaatt ctcaagcaag ccaattttgg    1020
```

-continued

```
gaacgactgg caggaaatac aacgtcaacg gtcattcagt acattggtga actgcttcgg   1080
tacctgtgca acacaccgca gaaaccaaat gaccgggacc acaaagtgaa aaaagccctg   1140
ggaaatggct tacgaggaga tgtgtggaga gagttcatca agagatttgg ggacatccac   1200
gtgtatgagt tctacgcatc cactgaaggc aacattggat ttgtgaacta tccaaggaaa   1260
atcggtgctg tcgggagagc aaactaccta caaagaaaag ttgcaaggta tgagctgatc   1320
aagtatgacg tggagaagga cgagccggtc cgtgacgcaa atggatattg catcaaagtc   1380
cccaaaggtg aggttggact cttggtttgc aaaatcacac agctcacacc atttattggc   1440
tatgctggag gaaagaccca gacagagaag aaaaaactca gagatgtctt taagaaaggc   1500
gacatctact tcaacagcgg agacctcctg atgatcgacc gtgagaactt cgtctacttt   1560
cacgacaggg ttggagatac tttccggtgg aaaggagaga acgtagctac cacagaagtc   1620
gctgacatcg tgggactggt agattttgtt gaagaagtga atgtgtatgg cgtgcctgtg   1680
ccaggtcatg agggtcgaat tgggatggcc tccctcaaga tcaaagaaaa ctacgagttc   1740
aatggaaaga aactctttca acacatcgcg gagtacctgc ccagttacgc gaggcctcgg   1800
ttcctgagga tacaagatac cattgagatc actgggactt ttaaacaccg caaagtgacc   1860
ctgatggaag agggcttcaa tcccacagtc atcaaagata ccttgtattt catggatgat   1920
gcagagaaaa catttgtgcc catgactgag aacatttata atgccataat tgataaaact   1980
ctgaagctct gaatattccc tggtggttta gctcatgaca tttccagaaa gaaactcgat   2040
agacctcgca gagccacttc atacgtagaa tccaacttta acttgattga agactataag   2100
gtgcgatttt attttaggaa aattattcat taaaaggata gttttttttt tttttttaa    2160 ttacacctga acctttgcaa gtaaaaagat ttagagacaa ttatttttca atgtgcacct   2220
gccatttgtc cttgcaaact aagcttcttg gagagagggc cttatttttt taaagacata   2280
ataaactata ttaacactaa aaaaaaaaaa aaaaaaaaaa aaaaaaaaaa aaaaaaa      2338
```

<210> SEQ ID NO 67
<211> LENGTH: 623
<212> TYPE: PRT
<213> ORGANISM: Mus musculus

<400> SEQUENCE: 67

```
Met Leu Pro Val Leu Tyr Thr Gly Leu Ala Gly Leu Leu Leu Leu Pro
 1               5                  10                  15

Leu Leu Leu Thr Cys Cys Pro Tyr Leu Leu Gln Asp Val Arg Tyr
            20                  25                  30

Phe Leu Arg Leu Ala Asn Met Ala Arg Arg Val Arg Ser Tyr Arg Gln
        35                  40                  45

Arg Arg Pro Val Arg Thr Ile Leu Arg Ala Phe Leu Glu Gln Ala Arg
    50                  55                  60

Lys Thr Pro His Lys Pro Phe Leu Leu Phe Arg Asp Glu Thr Leu Thr
65                  70                  75                  80

Tyr Ala Gln Val Asp Arg Arg Ser Asn Gln Val Ala Arg Ala Leu His
                85                  90                  95

Asp Gln Leu Gly Leu Arg Gln Gly Asp Cys Val Ala Leu Phe Met Gly
            100                 105                 110

Asn Glu Pro Ala Tyr Val Trp Ile Trp Leu Gly Leu Leu Lys Leu Gly
        115                 120                 125

Cys Pro Met Ala Cys Leu Asn Tyr Asn Ile Arg Ala Lys Ser Leu Leu
    130                 135                 140
```

```
His Cys Phe Gln Cys Cys Gly Ala Lys Val Leu Leu Ala Ser Pro Asp
145                 150                 155                 160

Leu Gln Glu Ala Val Glu Val Leu Pro Thr Leu Lys Lys Asp Ala
            165                 170                 175

Val Ser Val Phe Tyr Val Ser Arg Thr Ser Asn Thr Asn Gly Val Asp
            180                 185                 190

Thr Ile Leu Asp Lys Val Asp Gly Val Ser Ala Glu Pro Thr Pro Glu
            195                 200             205

Ser Trp Arg Ser Glu Val Thr Phe Thr Pro Ala Val Tyr Ile Tyr
    210                 215                 220

Thr Ser Gly Thr Thr Gly Leu Pro Lys Ser Gly Thr Ile Asn His His
225                 230                 235                 240

Arg Leu Arg Tyr Gly Thr Ser Leu Ala Met Ser Ser Gly Asn His Gly
                245                 250                 255

Gln Gly Cys His Leu Tyr Gln Gln Cys Pro Cys Ser Asn Ser Ala Thr
                260                 265                 270

Leu Lys Ile Gly Leu His Gly Cys Ile Leu Gly Trp Gly Tyr Phe Asn
            275                 280                 285

Leu Gly Gly Ala Asn Ser Gln Ala Ser Gln Phe Trp Glu Arg Leu Ala
290                 295                 300

Gly Asn Thr Thr Ser Thr Val Ile Gln Tyr Ile Gly Glu Leu Leu Arg
305                 310                 315                 320

Tyr Leu Cys Asn Thr Pro Gln Lys Pro Asn Asp Arg Asp His Lys Val
                325                 330                 335

Lys Lys Ala Leu Gly Asn Gly Leu Arg Gly Asp Val Trp Arg Glu Phe
            340                 345                 350

Ile Lys Arg Phe Gly Asp Ile His Val Tyr Glu Phe Tyr Ala Ser Thr
            355                 360                 365

Glu Gly Asn Ile Gly Phe Val Asn Tyr Pro Arg Lys Ile Gly Ala Val
            370                 375                 380

Gly Arg Ala Asn Tyr Leu Gln Arg Lys Val Ala Arg Tyr Glu Leu Ile
385                 390                 395                 400

Lys Tyr Asp Val Glu Lys Asp Glu Pro Val Arg Asp Ala Asn Gly Tyr
                405                 410                 415

Cys Ile Lys Val Pro Lys Gly Glu Val Gly Leu Leu Val Cys Lys Ile
            420                 425                 430

Thr Gln Leu Thr Pro Phe Ile Gly Tyr Ala Gly Gly Lys Thr Gln Thr
            435                 440                 445

Glu Lys Lys Lys Leu Arg Asp Val Phe Lys Lys Gly Asp Ile Tyr Phe
450                 455                 460

Asn Ser Gly Asp Leu Leu Met Ile Asp Arg Glu Asn Phe Val Tyr Phe
465                 470                 475                 480

His Asp Arg Val Gly Asp Thr Phe Arg Trp Lys Gly Glu Asn Val Ala
                485                 490                 495

Thr Thr Glu Val Ala Asp Ile Val Gly Leu Val Asp Phe Val Glu Glu
                500                 505                 510

Val Asn Val Tyr Gly Val Pro Val Pro Gly His Glu Gly Arg Ile Gly
            515                 520                 525

Met Ala Ser Leu Lys Ile Lys Glu Asn Tyr Glu Phe Asn Gly Lys Lys
            530                 535                 540

Leu Phe Gln His Ile Ala Glu Tyr Leu Pro Ser Tyr Ala Arg Pro Arg
545                 550                 555                 560
```

| | | | | | | | | | | | |
|---|---|---|---|---|---|---|---|---|---|---|---|
|Phe|Leu|Arg|Ile|Gln|Asp|Thr|Ile|Glu|Ile|Thr|Gly|Thr|Phe|Lys|His|
| | | |565| | | |570| | | |575|

Arg Lys Val Thr Leu Met Glu Glu Gly Phe Asn Pro Thr Val Ile Lys
            580            585            590

Asp Thr Leu Tyr Phe Met Asp Asp Ala Glu Lys Thr Phe Val Pro Met
            595            600            605

Thr Glu Asn Ile Tyr Asn Ala Ile Ile Asp Lys Thr Leu Lys Leu
            610            615            620

<210> SEQ ID NO 68
<211> LENGTH: 1998
<212> TYPE: DNA
<213> ORGANISM: Mus musculus

<400> SEQUENCE: 68

```
gaaagctctg agagcgggtg cagtctggcc tggcgtctcg cgtacctggc ccgggagcag      60
ccgacacaca ccttcctcat ccacggcgcg cagcgcttta gctacgcgga ggctgagcgc     120
gagagcaacc ggattgctcg cgcctttctg cgcgcacggg gctggaccgg ggccgccga     180
ggctcgggca ggggcagcac tgaggaaggc gcacgcgtgg cgcctccggc tggagatgcg     240
gctgctagag ggacgaccgc gccccctctg gcacccgggg cgaccgtggc gctgctcctc     300
ccagcgggcc cggatttcct ttggatttgg ttcggactgg ccaaagctgg cctgcgcacg     360
gcctttgtgc ccaccgcttt acgccgagga ccctgctgc actgcctccg cagctgcggt     420
gcgagtgcgc tcgtgctggc cacagagttc ctggagtccc tggagccgga cctgccggcc     480
ttgagagcca tggggctcca cctatgggcg acgggccctg aaactaatgt agctggaatc     540
agcaatttgc tatcggaagc agcagaccaa gtggatgagc cagtgccggg gtacctctct     600
gcccccaga acataatgga cacctgcctg tacatcttca cctctggcac tactggcctg     660
cccaaggctg ctcgaatcag tcatctgaag gttctacagt gccagggatt ctaccatctg     720
tgtggagtcc accaggagga cgtgatctac ctcgcactcc cactgtacca catgtctggc     780
tcccttctgg gcattgtggg ctgcttggc attggggcca ccgtggtgct gaaacccaag     840
ttctcagcta gccagttctg ggacgattgc cagaaacaca gggtgacagt gttccagtac     900
attggggagt tgtgccgata cctcgtcaac cagcccccga gcaaggcaga gttttgaccat     960
aaggtgcgct ggcagtgggg cagtgggttg cgcccagaca cctgggagcg tttcctgcgg    1020
cgatttggac ctctgcagat actggagacg tatggcatga cagagggcaa cgtagctacg    1080
ttcaattaca caggacggca gggtgcagtg gggcgagctt cctggctta caagcacatc    1140
ttccccttct ccttgattcg atacgatgtc atgacagggg agcctattcg gaatgcccag    1200
gggcactgca tgaccacatc tccaggtgag ccaggcctac tggtggcccc agtgagccag    1260
cagtccccct tcctgggcta tgctggggct ccggagctgg ccaaggacaa gctgctgaag    1320
gatgtcttct ggtctgggga cgtttttcttc aatactgggg acctcttggt ctgtgatgag    1380
caaggctttc ttcacttcca cgatcgtact ggagacacca tcaggtggaa gggagagaat    1440
gtggccacaa ctgaagtggc tgaggtcttg agaccctgg acttccttca ggaggtgaac    1500
atctatggag tcacggtgcc agggcacgaa ggcagggcag gcatggcggc cttggctctg    1560
cggcccccgc aggctctgaa cctggtgcag ctctacagcc atgtttctga acttgcca     1620
ccgtatgccc gacctcggtt tctcaggctc caggaatctt tggccactac tgagaccttc    1680
aaacagcaga aggttaggat ggccaatgag ggctttgacc ccagtgtact gtctgaccca    1740
ctctatgttc tggaccaaga tatagggggcc tacctgcccc tcacacctgc ccggtacagt    1800
```

-continued

```
gccctcctgt ctggagacct tcgaatctga aaccttccac ttgagggagg ggctcggagg    1860
gtacaggcca ccatggctgc accagggagg gttttcgggt atcttttgta tatggagtca    1920 ttatttgta ataaacagct ggagcttaaa aaaaaaaaaa aaaaaaaaaa aaaaaaaaaa    1980
aaaaaaaaaa aaaaaaaa                                                  1998
```

<210> SEQ ID NO 69
<211> LENGTH: 609
<212> TYPE: PRT
<213> ORGANISM: Mus musculus

<400> SEQUENCE: 69

```
Glu Ser Ser Glu Ser Gly Cys Ser Leu Ala Trp Arg Leu Ala Tyr Leu
 1               5                  10                  15

Ala Arg Glu Gln Pro Thr His Thr Phe Leu Ile His Gly Ala Gln Arg
            20                  25                  30

Phe Ser Tyr Ala Glu Ala Glu Arg Glu Ser Asn Arg Ile Ala Arg Ala
        35                  40                  45

Phe Leu Arg Ala Arg Gly Trp Thr Gly Gly Arg Arg Gly Ser Gly Arg
    50                  55                  60

Gly Ser Thr Glu Glu Gly Ala Arg Val Ala Pro Pro Ala Gly Asp Ala
65                  70                  75                  80

Ala Ala Arg Gly Thr Thr Ala Pro Pro Leu Ala Pro Gly Ala Thr Val
                85                  90                  95

Ala Leu Leu Leu Pro Ala Gly Pro Asp Phe Leu Trp Ile Trp Phe Gly
            100                 105                 110

Leu Ala Lys Ala Gly Leu Arg Thr Ala Phe Val Pro Thr Ala Leu Arg
        115                 120                 125

Arg Gly Pro Leu Leu His Cys Leu Arg Ser Cys Gly Ala Ser Ala Leu
    130                 135                 140

Val Leu Ala Thr Glu Phe Leu Glu Ser Leu Glu Pro Asp Leu Pro Ala
145                 150                 155                 160

Leu Arg Ala Met Gly Leu His Leu Trp Ala Thr Gly Pro Glu Thr Asn
                165                 170                 175

Val Ala Gly Ile Ser Asn Leu Leu Ser Glu Ala Ala Asp Gln Val Asp
            180                 185                 190

Glu Pro Val Pro Gly Tyr Leu Ser Ala Pro Gln Asn Ile Met Asp Thr
        195                 200                 205

Cys Leu Tyr Ile Phe Thr Ser Gly Thr Thr Gly Leu Pro Lys Ala Ala
    210                 215                 220

Arg Ile Ser His Leu Lys Val Leu Gln Cys Gln Gly Phe Tyr His Leu
225                 230                 235                 240

Cys Gly Val His Gln Glu Asp Val Ile Tyr Leu Ala Leu Pro Leu Tyr
                245                 250                 255

His Met Ser Gly Ser Leu Leu Gly Ile Val Gly Cys Leu Gly Ile Gly
            260                 265                 270

Ala Thr Val Val Leu Lys Pro Lys Phe Ser Ala Ser Gln Phe Trp Asp
        275                 280                 285

Asp Cys Gln Lys His Arg Val Thr Val Phe Gln Tyr Ile Gly Glu Leu
    290                 295                 300

Cys Arg Tyr Leu Val Asn Gln Pro Pro Ser Lys Ala Glu Phe Asp His
305                 310                 315                 320

Lys Val Arg Leu Ala Val Gly Ser Gly Leu Arg Pro Asp Thr Trp Glu
                325                 330                 335
```

```
Arg Phe Leu Arg Arg Phe Gly Pro Leu Gln Ile Leu Glu Thr Tyr Gly
            340                 345                 350
Met Thr Glu Gly Asn Val Ala Thr Phe Asn Tyr Thr Gly Arg Gln Gly
            355                 360                 365
Ala Val Gly Arg Ala Ser Trp Leu Tyr Lys His Ile Phe Pro Phe Ser
        370                 375                 380
Leu Ile Arg Tyr Asp Val Met Thr Gly Glu Pro Ile Arg Asn Ala Gln
385                 390                 395                 400
Gly His Cys Met Thr Thr Ser Pro Gly Glu Pro Gly Leu Leu Val Ala
                405                 410                 415
Pro Val Ser Gln Gln Ser Pro Phe Leu Gly Tyr Ala Gly Ala Pro Glu
                420                 425                 430
Leu Ala Lys Asp Lys Leu Leu Lys Asp Val Phe Trp Ser Gly Asp Val
            435                 440                 445
Phe Phe Asn Thr Gly Asp Leu Leu Val Cys Asp Glu Gln Gly Phe Leu
        450                 455                 460
His Phe His Asp Arg Thr Gly Asp Thr Ile Arg Trp Lys Gly Glu Asn
465                 470                 475                 480
Val Ala Thr Thr Glu Val Ala Glu Val Leu Glu Thr Leu Asp Phe Leu
                485                 490                 495
Gln Glu Val Asn Ile Tyr Gly Val Thr Val Pro Gly His Glu Gly Arg
                500                 505                 510
Ala Gly Met Ala Ala Leu Ala Leu Arg Pro Pro Gln Ala Leu Asn Leu
            515                 520                 525
Val Gln Leu Tyr Ser His Val Ser Glu Asn Leu Pro Pro Tyr Ala Arg
        530                 535                 540
Pro Arg Phe Leu Arg Leu Gln Glu Ser Leu Ala Thr Thr Glu Thr Phe
545                 550                 555                 560
Lys Gln Gln Lys Val Arg Met Ala Asn Glu Gly Phe Asp Pro Ser Val
                565                 570                 575
Leu Ser Asp Pro Leu Tyr Val Leu Asp Gln Asp Ile Gly Ala Tyr Leu
            580                 585                 590
Pro Leu Thr Pro Ala Arg Tyr Ser Ala Leu Leu Ser Gly Asp Leu Arg
        595                 600                 605
Ile
```

<210> SEQ ID NO 70
<211> LENGTH: 2710
<212> TYPE: DNA
<213> ORGANISM: Mus musculus

<400> SEQUENCE: 70

```
atgctgcttg gagcctctct ggtgggggcg ctactgttct ccaagctagt gctgaagctg    60
ccctggaccc agtgggatt  ctccctgttg ctcctgtact ggggtctgg  tggctggcgt   120
ttcatccggg tcttcatcaa gacggtcagg agagatatct tggtggcat  ggtgctcctg   180
aaggtgaaga ccaaggtgcg acggtacctt caggagcgga agacggtgcc cctgctgttt   240
gcttcaatgg tacagcgcca cccggacaag acagccctga ttttcgaggg cacagacact   300
cactggacct tccgccagct ggatgagtac tccagtagtg tggccaactt cctgcaggcc   360
cggggcctgg cctcaggcaa tgtagttgcc ctctttatgg aaaaccgcaa tgagtttgtg   420
ggtctgtggc taggcatggc caagctgggc gtggaggcgg ctctcatcaa caccaacctt   480
aggcgggatg ccctgcgcca ctgtcttgac acctcaaagg cacgagctct catctttggc   540
```

-continued

```
agtgagatgg cctcagctat ctgtgagatc catgctagcc tggagcccac actcagcctc    600
ttctgctctg gatcctggga gcccagcaca gtgcccgtca gcacagagca tctggaccct    660
cttctggaag atgccccgaa gcacctgccc agtcacccag acaagggttt tacagataag    720
ctcttctaca tctacacatc gggcaccacg gggctaccca agctgccat  tgtggtgcac    780
agcaggtatt atcgtatggc ttccctggtg tactatggat ccgcatgcg  gcctgatgac    840
attgtctatg actgcctccc cctctaccac tcaagcagga acatcgtgg  ggattggcag    900
tgcttactcc acggcatgac tgtggtgatc cggaagaagt tctcagcctc ccggttctgg    960
gatgattgta tcaagtacaa ctgcacagtg gtacagtaca ttggcgagct ctgccgctac   1020
ctcctgaacc agccacccg  tgaggctgag tctcggcaca aggtgcgcat ggcactgggc   1080
aacggtctcc ggcagtccat ctggaccgac ttctccagcc gtttccacat ccccaggtg   1140
gctgagttct atgggccac  tgaatgcaac tgtagcctgg caactttga  cagccgggtg   1200
ggggcctgtg gcttcaatag ccgcatcctg tcctttgtgt accctatccg tttggtacgt   1260
gtcaatgagg ataccatgga actgatccgg ggacccgatg gagtctgcat tccctgtcaa   1320
ccaggtcagc caggccagct ggtgggtcgc atcatccagc aggaccctct gcgccgtttc   1380
gacgggtacc tcaaccaggg tgccaacaac aagaagattg ctaatgatgt cttcaagaag   1440
ggggaccaag cctacctcac tggtgacgtc ctggtgatgg atgagctggg ttacctgtac   1500
ttccgagatc gcactgggga cacgttccgc tggaaagggg agaatgtatc taccactgag   1560
gtggagggca cactcagccg cctgcttcat atggcagatg tggcagttta tggtgttgag   1620
gtgccaggaa ctgaaggccg agcaggaatg gctgccgttg caagtcccat cagcaactgt   1680
gacctggaga gctttgcaca gaccttgaaa aaggagctgc ctctgtatgc ccgccccatc   1740
ttcctgcgct tcttgcctga gctgcacaag acagggacct tcaagttcca gaagacagag   1800
ttgcggaagg agggctttga cccatctgtt gtgaaagacc cgctgttcta tctgatgct   1860
cggaagggct gctacgttgc actggaccag gaggcctata cccgcatcca ggcaggcgag   1920
gagaagctgt gatttccccc tacatccctc tgagggccag aagatgctgg attcagagcc   1980
ctagcgtcca ccccagaggg tcctgggcaa tgccagacca agctagcag  ggcccgcacc   2040
tccgccccta ggtgctgatc tcccctctcc caaactgcca agtgactcac tgccgcttcc   2100
ccgaccctcc agaggctttc tgtgaaagtc tcatccaagc tgtgtcttct ggtccaggcg   2160
tggcccctgg cccagggtt  tctgataggc tcctttagga tggtatcttg ggtccagcgg   2220
gccagggtgt gggagaggag tcactaagat ccctccaatc agaagggagc ttacaaagga   2280
accaaggcaa agcctgtaga ctcaggaagc taagtggcca gagactatag tggccagtca   2340
tcccatgtcc acagaggatc ttggtccaga gctgccaaag tgtcacctct ccctgcctgc   2400
acctctgggg aaaagaggac agcatgtggc cactgggcac ctgtctcaag aagtcaggat   2460
cacacactca gtccttgttt ctccaggttc ccttgttctt gtctcgggga gggagggacg   2520
agtgtcctgt ctgtccttcc tgcctgtctg tgagtctgtg ttgcttctcc atctgtccta   2580
gcctgagtgt gggtggaaca ggcatgagga gagtgtggcc caggggccaa taaactctgc   2640
cttgactcct cttaaaaaaa aaaaaaaaaa aaaaaaaaa  aaaaaaaaaa aaaaaaaaa    2700
aaaaaaaaaa                                                         2710
```

<210> SEQ ID NO 71
<211> LENGTH: 643
<212> TYPE: PRT

<213> ORGANISM: Mus musculus

<400> SEQUENCE: 71

```
Met Leu Leu Gly Ala Ser Leu Val Gly Ala Leu Leu Gly Ser Lys Leu
 1               5                  10                  15

Val Leu Lys Leu Pro Trp Thr Gln Val Gly Phe Ser Leu Leu Leu Leu
             20                  25                  30

Tyr Leu Gly Ser Gly Gly Trp Arg Phe Ile Arg Val Phe Ile Lys Thr
         35                  40                  45

Val Arg Arg Asp Ile Phe Gly Gly Met Val Leu Leu Lys Val Lys Thr
 50                  55                  60

Lys Val Arg Arg Tyr Leu Gln Glu Arg Lys Thr Val Pro Leu Leu Phe
 65                  70                  75                  80

Ala Ser Met Val Gln Arg His Pro Asp Lys Thr Ala Leu Ile Phe Glu
                 85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asn Val
        115                 120                 125

Val Ala Leu Phe Met Glu Asn Arg Asn Glu Phe Val Gly Leu Trp Leu
130                 135                 140

Gly Met Ala Lys Leu Gly Val Glu Ala Ala Leu Ile Asn Thr Asn Leu
145                 150                 155                 160

Arg Arg Asp Ala Leu Arg His Cys Leu Asp Thr Ser Lys Ala Arg Ala
                165                 170                 175

Leu Ile Phe Gly Ser Glu Met Ala Ser Ala Ile Cys Glu Ile His Ala
            180                 185                 190

Ser Leu Glu Pro Thr Leu Ser Leu Phe Cys Ser Gly Ser Trp Glu Pro
        195                 200                 205

Ser Thr Val Pro Val Ser Thr Glu His Leu Asp Pro Leu Leu Glu Asp
210                 215                 220

Ala Pro Lys His Leu Pro Ser His Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255

Ile Val His Ser Arg Tyr Tyr Arg Met Ala Ser Leu Val Tyr Tyr
            260                 265                 270

Gly Phe Arg Met Arg Pro Asp Asp Ile Val Tyr Asp Cys Leu Pro Leu
        275                 280                 285

Tyr His Ser Ser Arg Lys His Arg Gly Asp Trp Gln Cys Leu Leu His
        290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Val Val Gln Tyr Ile Gly Glu
                325                 330                 335

Leu Cys Arg Tyr Leu Leu Asn Gln Pro Pro Arg Glu Ala Glu Ser Arg
            340                 345                 350

His Lys Val Arg Met Ala Leu Gly Asn Gly Leu Arg Gln Ser Ile Trp
        355                 360                 365

Thr Asp Phe Ser Ser Arg Phe His Ile Pro Gln Val Ala Glu Phe Tyr
        370                 375                 380

Gly Ala Thr Glu Cys Asn Cys Ser Leu Gly Asn Phe Asp Ser Arg Val
385                 390                 395                 400
```

-continued

```
Gly Ala Cys Gly Phe Asn Ser Arg Ile Leu Ser Phe Val Tyr Pro Ile
                405                 410                 415
Arg Leu Val Arg Val Asn Glu Asp Thr Met Glu Leu Ile Arg Gly Pro
            420                 425                 430
Asp Gly Val Cys Ile Pro Cys Gln Pro Gly Gln Pro Gly Gln Leu Val
        435                 440                 445
Gly Arg Ile Ile Gln Gln Asp Pro Leu Arg Arg Phe Asp Gly Tyr Leu
    450                 455                 460
Asn Gln Gly Ala Asn Asn Lys Lys Ile Ala Asn Asp Val Phe Lys Lys
465                 470                 475                 480
Gly Asp Gln Ala Tyr Leu Thr Gly Asp Val Leu Met Asp Glu Leu
                485                 490                 495
Gly Tyr Leu Tyr Phe Arg Asp Arg Thr Gly Asp Thr Phe Arg Trp Lys
            500                 505                 510
Gly Glu Asn Val Ser Thr Thr Glu Val Glu Gly Thr Leu Ser Arg Leu
        515                 520                 525
Leu His Met Ala Asp Val Ala Val Tyr Gly Val Glu Val Pro Gly Thr
    530                 535                 540
Glu Gly Arg Ala Gly Met Ala Ala Val Ala Ser Pro Ile Ser Asn Cys
545                 550                 555                 560
Asp Leu Glu Ser Phe Ala Gln Thr Leu Lys Lys Glu Leu Pro Leu Tyr
                565                 570                 575
Ala Arg Pro Ile Phe Leu Arg Phe Leu Pro Glu Leu His Lys Thr Gly
            580                 585                 590
Thr Phe Lys Phe Gln Lys Thr Glu Leu Arg Lys Glu Gly Phe Asp Pro
        595                 600                 605
Ser Val Val Lys Asp Pro Leu Phe Tyr Leu Asp Ala Arg Lys Gly Cys
    610                 615                 620
Tyr Val Ala Leu Asp Gln Glu Ala Tyr Thr Arg Ile Gln Ala Gly Glu
625                 630                 635                 640
Glu Lys Leu
```

<210> SEQ ID NO 72
<211> LENGTH: 2277
<212> TYPE: DNA
<213> ORGANISM: Mus musculus

<400> SEQUENCE: 72

| | |
|---|---|
| cactcatcag agctaagaga gactacacgc tctcatctac ttcagaaaga gccaatgcca | 60 |
| tgggtatttg aagaaactaa accttactgc tgttgctgct tctgctggtt ggcctggggc | 120 |
| agccccatg ccagcagct atggctctgg ccctgcgttg gttcctggga gaccccacat | 180 |
| gccttgtgct gcttggcttg gcattgctgg gcagacctg gatcagctcc tggatgcccc | 240 |
| actggctgag cctggtagga gcagctctta ccttattcct attgcctcta cagccacccc | 300 |
| cagggctacg ctggctgcat aaagatgtgg ctttcacctt caagatgctt ttctatggcc | 360 |
| taaagttcag gcgacgcctt aacaaacatc ctccagagac ctttgtggat gctttagagc | 420 |
| ggcaagcact ggcatggcct gaccgggtgg ccttggtgtg tactgggtct gagggctcct | 480 |
| caatcacaaa tagccagctg gatgccaggt cctgtcaggc agcatgggtc ctgaaagcaa | 540 |
| agctgaagga tgccgtaatc cagaacacaa gagatgctgc tgctatctta gttctcccgt | 600 |
| ccaagaccat ttctgctttg agtgtgtttc tggggttggc caagttgggc tgccctgtgg | 660 |
| cctggatcaa tccacacagc cgagggatgc ccttgctaca ctctgtacgg agctctgggg | 720 |
| ccagtgtgct gattgtggat ccagacctcc aggagaacct ggaagaagtc cttcccaagc | 780 |

-continued

```
tgctagctga gaacattcac tgcttctacc ttggccacag ctcacccacc ccgggagtag      840
aggctctggg agcttccctg gatgctgcac cttctgaccc agtacctgcc agccttcgag      900
ctacgattaa gtggaaatct cctgccatat tcatctttac ttcagggacc actggactcc      960
caaagccagc catcttatca catgagcggg tcatacaagt gagcaacgtg ctgtccttct     1020
gtggatgcag agctgatgat gtggtctatg acgtcctacc tctgtaccat acgatagggc     1080
ttgtccttgg attccttggc tgcttacaag ttggagccac ctgtgtcctg gcccccaagt     1140
tctctgcctc ccgattctgg gctgagtgcc ggcagcatgg cgtaacagtg atcttgtatg     1200
tgggtgaaat cctgcggtac ttgtgtaacg tccctgagca accagaagac aagatacata     1260
cagtgcgctt ggccatggga actggacttc gggcaaatgt gtggaaaaac ttccagcaac     1320
gctttggtcc cattcggatc tgggaattct acggatccac agagggcaat gtgggcttaa     1380
tgaactatgt gggccactgc ggggctgtgg aaggaccag ctgcatcctt cgaatgctga     1440 ctcccttga gcttgtacag ttcgacatag agacagcaga gcctctgagg gacaaacagg     1500 gttttttgcat tcctgtggag ccaggaaagc caggacttct tttgaccaag gttcgaaaga     1560
accaaccctt cctgggctac cgtggttccc aggccgagtc caatcggaaa cttgttgcga     1620
atgtacgacg cgtaggagac ctgtacttca cactgggga cgtgctgacc ttggaccagg     1680
aaggcttctt ctactttcaa gaccgccttg gtgacacctt ccggtggaag ggcgaaaacg     1740
tatctactgg agaggtggag tgtgttttgt ctagcctaga cttcctagag gaagtcaatg     1800
tctatggtgt gcctgtgcca gggtgtgagg gtaaggttgg catggctgct gtgaaactgg     1860
ctcctgggaa gacttttgat gggcagaagc tataccagca tgtccgctcc tggctccctg     1920
cctatgccac acctcatttc atccgtatcc aggattccct ggagatcaca aacacctaca     1980
agctggtaaa gtcacggctg gtgcgtgagg gttttgatgt ggggatcatt gctgaccccc     2040
tctacatact ggacaacaag gcccagacct tccggagtct gatgccagat gtgtaccagg     2100
ctgtgtgtga aggaacctgg aatctctgac cacctagcca actggaaggc aatccaaaag     2160
tgtagagatt gacactagtc agcttcacaa agttgtccgg gttccagatg cccatggccc     2220
agtagtactt agagaataaa cttgaatgtg tatacaaaaa aaaaaaaaaa aaaaaaa       2277
```

<210> SEQ ID NO 73
<211> LENGTH: 689
<212> TYPE: PRT
<213> ORGANISM: Mus musculus

<400> SEQUENCE: 73

Met Gly Ile Trp Lys Lys Leu Thr Leu Leu Leu Leu Leu Leu
1               5                   10                  15

Val Gly Leu Gly Gln Pro Pro Trp Pro Ala Ala Met Ala Leu Ala Leu
            20                  25                  30

Arg Trp Phe Leu Gly Asp Pro Thr Cys Leu Val Leu Leu Gly Leu Ala
        35                  40                  45

Leu Leu Gly Arg Pro Trp Ile Ser Ser Trp Met Pro His Trp Leu Ser
    50                  55                  60

Leu Val Gly Ala Ala Leu Thr Leu Phe Leu Leu Pro Leu Gln Pro Pro
65                  70                  75                  80

Pro Gly Leu Arg Trp Leu His Lys Asp Val Ala Phe Thr Phe Lys Met
                85                  90                  95

Leu Phe Tyr Gly Leu Lys Phe Arg Arg Leu Asn Lys His Pro Pro
            100                 105                 110

```
Glu Thr Phe Val Asp Ala Leu Glu Arg Gln Ala Leu Ala Trp Pro Asp
            115                 120                 125
Arg Val Ala Leu Val Cys Thr Gly Ser Glu Gly Ser Ser Ile Thr Asn
        130                 135                 140
Ser Gln Leu Asp Ala Arg Ser Cys Gln Ala Ala Trp Val Leu Lys Ala
145                 150                 155                 160
Lys Leu Lys Asp Ala Val Ile Gln Asn Thr Arg Asp Ala Ala Ala Ile
                165                 170                 175
Leu Val Leu Pro Ser Lys Thr Ile Ser Ala Leu Ser Val Phe Leu Gly
            180                 185                 190
Leu Ala Lys Leu Gly Cys Pro Val Ala Trp Ile Asn Pro His Ser Arg
        195                 200                 205
Gly Met Pro Leu Leu His Ser Val Arg Ser Ser Gly Ala Ser Val Leu
    210                 215                 220
Ile Val Asp Pro Asp Leu Gln Glu Asn Leu Glu Glu Val Leu Pro Lys
225                 230                 235                 240
Leu Leu Ala Glu Asn Ile His Cys Phe Tyr Leu Gly His Ser Ser Pro
                245                 250                 255
Thr Pro Gly Val Glu Ala Leu Gly Ala Ser Leu Asp Ala Ala Pro Ser
            260                 265                 270
Asp Pro Val Pro Ala Ser Leu Arg Ala Thr Ile Lys Trp Lys Ser Pro
        275                 280                 285
Ala Ile Phe Ile Phe Thr Ser Gly Thr Thr Gly Leu Pro Lys Pro Ala
    290                 295                 300
Ile Leu Ser His Glu Arg Val Ile Gln Val Ser Asn Val Leu Ser Phe
305                 310                 315                 320
Cys Gly Cys Arg Ala Asp Asp Val Val Tyr Asp Val Leu Pro Leu Tyr
                325                 330                 335
His Thr Ile Gly Leu Val Leu Gly Phe Leu Gly Cys Leu Gln Val Gly
            340                 345                 350
Ala Thr Cys Val Leu Ala Pro Lys Phe Ser Ala Ser Arg Phe Trp Ala
        355                 360                 365
Glu Cys Arg Gln His Gly Val Thr Val Ile Leu Tyr Val Gly Glu Ile
    370                 375                 380
Leu Arg Tyr Leu Cys Asn Val Pro Glu Gln Pro Glu Asp Lys Ile His
385                 390                 395                 400
Thr Val Arg Leu Ala Met Gly Thr Gly Leu Arg Ala Asn Val Trp Lys
                405                 410                 415
Asn Phe Gln Gln Arg Phe Gly Pro Ile Arg Ile Trp Glu Phe Tyr Gly
            420                 425                 430
Ser Thr Glu Gly Asn Val Gly Leu Met Asn Tyr Val Gly His Cys Gly
        435                 440                 445
Ala Val Gly Arg Thr Ser Cys Ile Leu Arg Met Leu Thr Pro Phe Glu
    450                 455                 460
Leu Val Gln Phe Asp Ile Glu Thr Ala Glu Pro Leu Arg Asp Lys Gln
465                 470                 475                 480
Gly Phe Cys Ile Pro Val Glu Pro Gly Lys Pro Gly Leu Leu Leu Thr
                485                 490                 495
Lys Val Arg Lys Asn Gln Pro Phe Leu Gly Tyr Arg Gly Ser Gln Ala
            500                 505                 510
Glu Ser Asn Arg Lys Leu Val Ala Asn Val Arg Arg Val Gly Asp Leu
        515                 520                 525
```

-continued

| | | | | | | | | | | | |
|---|---|---|---|---|---|---|---|---|---|---|---|
Tyr Phe Asn Thr Gly Asp Val Leu Thr Leu Asp Gln Glu Gly Phe Phe
        530                 535                 540

Tyr Phe Gln Asp Arg Leu Gly Asp Thr Phe Arg Trp Lys Gly Glu Asn
545                 550                 555                 560

Val Ser Thr Gly Glu Val Glu Cys Val Leu Ser Ser Leu Asp Phe Leu
                565                 570                 575

Glu Glu Val Asn Val Tyr Gly Val Pro Val Pro Gly Cys Glu Gly Lys
                580                 585                 590

Val Gly Met Ala Ala Val Lys Leu Ala Pro Gly Lys Thr Phe Asp Gly
            595                 600                 605

Gln Lys Leu Tyr Gln His Val Arg Ser Trp Leu Pro Ala Tyr Ala Thr
    610                 615                 620

Pro His Phe Ile Arg Ile Gln Asp Ser Leu Glu Ile Thr Asn Thr Tyr
625                 630                 635                 640

Lys Leu Val Lys Ser Arg Leu Val Arg Glu Gly Phe Asp Val Gly Ile
                645                 650                 655

Ile Ala Asp Pro Leu Tyr Ile Leu Asp Asn Lys Ala Gln Thr Phe Arg
                660                 665                 670

Ser Leu Met Pro Asp Val Tyr Gln Ala Val Cys Glu Gly Thr Trp Asn
        675                 680                 685

Leu

<210> SEQ ID NO 74
<211> LENGTH: 2221
<212> TYPE: DNA
<213> ORGANISM: Drosophila melanogaster

<400> SEQUENCE: 74

| | |
|---|---|
| gctctctggg cctatatcaa gctgctgagg tacacgaagc gccatgagcg gctcaactac | 60 |
| acggtggcgg acgtcttcga acgaaatgtt caggcccatc cggacaaggt ggctgtggtc | 120 |
| agtgagacgc aacgctggac cttccgtcag gtgaacgagc atgcgaacaa ggtggccaat | 180 |
| gtgctgcagg ctcagggcta caaaaagggc gatgtggtgg ccctgttgct ggagaaccgc | 240 |
| gccgagtacg tggccacctg gctgggtctc tccaagatcg gtgtgatcac accgctgatc | 300 |
| aacacgaatc tgcgcggtcc ctccctgctg cacagcatca cggtggccca ttgctcggct | 360 |
| ctcatttacg gcgaggactt cctggaagct gtcaccgacg tggccaagga tctgccagcg | 420 |
| aacctcacac tcttccagtt caacaacgag aacaacaaca gcgagacgga aaagaacata | 480 |
| ccgcaggcca agaatctgaa cgcgctgctg accacggcca gctatgagaa gcctaacaag | 540 |
| acgcaggtta accaccacga caagctggtc tacatctaca cctccggcac cacaggattg | 600 |
| ccaaaggctg cggttatctc tcactcccgt tatctgttta tcgctgctgg catccactac | 660 |
| accatgggtt tccaggagga ggacatcttc tacacgccct tgcctttgta ccacaccgct | 720 |
| ggtggcatta tgtgcatggg tcagtcggtg ctctttggct ccacggtctc cattcgcaag | 780 |
| aagttctcgg catccaacta tttcgccgac tgcgccaagt ataatgcaac tattggtcag | 240 |
| tatatcggtg agatggctcg ctacattcta gctacgaaac cctcggaata cgaccagaaa | 900 |
| caccgagtgc gtctggtctt tggaaacgga ctgcgaccgc agatttggcc acagtttgtg | 960 |
| cagcgcttca acattgccaa ggttggcgag ttctacggcg ccaccgaggg taatgcgaac | 1020 |
| atcatgaatc atgacaacac ggtgggcgcc atcggctttg tgtcgcgcat cctgcccaag | 1080 |
| atctacccaa tctcgatcat tcgcgccgat ccggacaccg gagagcccat tagagatagg | 1140 |
| aatggcctat gccaactgtg cgctcccaac gagccaggcg tattcatcgg caagatcgtc | 1200 |

-continued

```
aaaggaaatc cttctcgcga attcctcgga tacgtcgatg aaaaggcctc cgcgaagaag       1260
attgttaagg atgtgttcaa gcatggcgat atggctttca tctccggaga tctgctggtt       1320
gccgacgaga agggttatct gtacttcaag gatcgcaccg gtgacacctt ccgctggaag       1380
ggcgagaatg tttccaccag cgaggtggag gcgcaagtca gcaatgtggc cggttacaag       1440
gataccgtcg tttacggcgt aaccattccg cacaccgagg gaagggccgg catggccgcc       1500
atctatgatc cggagcgaga attggacctc gacgtcttcg ccgctagctt ggccaaggtg       1560
ctgcccgcgt acgctcgtcc ccagatcatt cgattgctca ccaaggtgga cctgactgga       1620
acctttaagc tgcgcaaggt agacctgcag aaggagggct acgatccgaa cgcgatcaag       1680
gacgcgctgt actaccagac ttccaagggt cggtacgagc tgctcacgcc ccaggtttac       1740
gaccaggtgc agcgcaacga aatccgcttc taagagctgc aatagagttg tgtctgaacc       1800
ttgccttttg cccaatatgc tgttaattag tttgtaaggc taagtgtagt agaggaaaat       1860
cgggggaaat cggcagcaaa gatcattcag cctaggagag atgcatccga agcacatttc       1920
catgtcaaca atgcactttt gtatatcgta agcatatata tatcgtatat cgtaaacgta       1980
gttgtatctg catttgtgta gatgatagcc tcctatacgc atttcaattg tttttagcgt       2040
gctaaagaac cttgttaaat gcaatttcag ctattgttta gtcagttttta gtggcattta       2100 cacttccatt ctcgttgcgt ttcgtttttg cctgtacata tgagaagctc tgatgttttt       2160
gtatcaaata aagttttttc cttcaccacg gaccacgtga aaaaaaaaa aaaaaaaaa        2220 a                                                                       2221
```

<210> SEQ ID NO 75
<211> LENGTH: 590
<212> TYPE: PRT
<213> ORGANISM: Drosophila melanogaster

<400> SEQUENCE: 75

```
Ala Leu Trp Ala Tyr Ile Lys Leu Leu Arg Tyr Thr Lys Arg His Glu
 1               5                  10                  15

Arg Leu Asn Tyr Thr Val Ala Asp Val Phe Glu Arg Asn Val Gln Ala
            20                  25                  30

His Pro Asp Lys Val Ala Val Ser Glu Thr Gln Arg Trp Thr Phe
        35                  40                  45

Arg Gln Val Asn Glu His Ala Asn Lys Val Ala Asn Val Leu Gln Ala
    50                  55                  60

Gln Gly Tyr Lys Lys Gly Asp Val Val Ala Leu Leu Glu Asn Arg
65                  70                  75                  80

Ala Glu Tyr Val Ala Thr Trp Leu Gly Leu Ser Lys Ile Gly Val Ile
                85                  90                  95

Thr Pro Leu Ile Asn Thr Asn Leu Arg Gly Pro Ser Leu Leu His Ser
            100                 105                 110

Ile Thr Val Ala His Cys Ser Ala Leu Ile Tyr Gly Glu Asp Phe Leu
        115                 120                 125

Glu Ala Val Thr Asp Val Ala Lys Asp Leu Pro Ala Asn Leu Thr Leu
    130                 135                 140

Phe Gln Phe Asn Asn Glu Asn Asn Ser Glu Thr Glu Lys Asn Ile
145                 150                 155                 160

Pro Gln Ala Lys Asn Leu Asn Ala Leu Leu Thr Thr Ala Ser Tyr Glu
                165                 170                 175

Lys Pro Asn Lys Thr Gln Val Asn His His Asp Lys Leu Val Tyr Ile
```

-continued

```
                180             185             190
Tyr Thr Ser Gly Thr Thr Gly Leu Pro Lys Ala Ala Val Ile Ser His
            195             200             205
Ser Arg Tyr Leu Phe Ile Ala Ala Gly Ile His Tyr Thr Met Gly Phe
210             215             220
Gln Glu Glu Asp Ile Phe Tyr Thr Pro Leu Pro Leu Tyr His Thr Ala
225             230             235             240
Gly Gly Ile Met Cys Met Gly Gln Ser Val Leu Phe Gly Ser Thr Val
                245             250             255
Ser Ile Arg Lys Lys Phe Ser Ala Ser Asn Tyr Phe Ala Asp Cys Ala
            260             265             270
Lys Tyr Asn Ala Thr Ile Gly Gln Tyr Ile Gly Glu Met Ala Arg Tyr
            275             280             285
Ile Leu Ala Thr Lys Pro Ser Glu Tyr Asp Gln Lys His Arg Val Arg
            290             295             300
Leu Val Phe Gly Asn Gly Leu Arg Pro Gln Ile Trp Pro Gln Phe Val
305             310             315             320
Gln Arg Phe Asn Ile Ala Lys Val Gly Glu Phe Tyr Gly Ala Thr Glu
                325             330             335
Gly Asn Ala Asn Ile Met Asn His Asp Asn Thr Val Gly Ala Ile Gly
            340             345             350
Phe Val Ser Arg Ile Leu Pro Lys Ile Tyr Pro Ile Ser Ile Ile Arg
            355             360             365
Ala Asp Pro Asp Thr Gly Glu Pro Ile Arg Asp Arg Asn Gly Leu Cys
            370             375             380
Gln Leu Cys Ala Pro Asn Glu Pro Gly Val Phe Ile Gly Lys Ile Val
385             390             395             400
Lys Gly Asn Pro Ser Arg Glu Phe Leu Gly Tyr Val Asp Glu Lys Ala
                405             410             415
Ser Ala Lys Lys Ile Val Lys Asp Val Phe Lys His Gly Asp Met Ala
            420             425             430
Phe Ile Ser Gly Asp Leu Leu Val Ala Asp Glu Lys Gly Tyr Leu Tyr
            435             440             445
Phe Lys Asp Arg Thr Gly Asp Thr Phe Arg Trp Lys Gly Glu Asn Val
            450             455             460
Ser Thr Ser Glu Val Glu Ala Gln Val Ser Asn Val Ala Gly Tyr Lys
465             470             475             480
Asp Thr Val Val Tyr Gly Val Thr Ile Pro His Thr Glu Gly Arg Ala
                485             490             495
Gly Met Ala Ala Ile Tyr Asp Pro Glu Arg Glu Leu Asp Leu Asp Val
            500             505             510
Phe Ala Ala Ser Leu Ala Lys Val Leu Pro Ala Tyr Ala Arg Pro Gln
            515             520             525
Ile Ile Arg Leu Leu Thr Lys Val Asp Leu Thr Gly Thr Phe Lys Leu
            530             535             540
Arg Lys Val Asp Leu Gln Lys Glu Gly Tyr Asp Pro Asn Ala Ile Lys
545             550             555             560
Asp Ala Leu Tyr Tyr Gln Thr Ser Lys Gly Arg Tyr Glu Leu Leu Thr
                565             570             575
Pro Gln Val Tyr Asp Gln Val Gln Arg Asn Glu Ile Arg Phe
            580             585             590
```

<210> SEQ ID NO 76

```
<211> LENGTH: 173
<212> TYPE: DNA
<213> ORGANISM: Danio rerio

<400> SEQUENCE: 76
agtgtagata ccacaggaac gtttaaaatc cagaagacca gactgcaaag ggaaggatac      60
gatccacggc tcacaactga ccagatctac ttcctaaact ccagagcagg gcgttacgag     120
cttgtcaacg aggagctgta caatgcattt gaacaagggc aggatttccc ttt            173

<210> SEQ ID NO 77
<211> LENGTH: 57
<212> TYPE: PRT
<213> ORGANISM: Danio rerio

<400> SEQUENCE: 77

Ser Val Asp Thr Thr Gly Thr Phe Lys Ile Gln Lys Thr Arg Leu Gln
  1               5                  10                  15

Arg Glu Gly Tyr Asp Pro Arg Leu Thr Thr Asp Gln Ile Tyr Phe Leu
             20                  25                  30

Asn Ser Arg Ala Gly Arg Tyr Glu Leu Val Asn Glu Glu Leu Tyr Asn
         35                  40                  45

Ala Phe Glu Gln Gly Gln Asp Phe Pro
     50                  55

<210> SEQ ID NO 78
<211> LENGTH: 1953
<212> TYPE: DNA
<213> ORGANISM: Caenorhabditis elegans

<400> SEQUENCE: 78
atgaagctgg aggagcttgt gacagttatg cttctcacag tggctgtcat tgctcagaat      60
cttccgattg gagtaatatt ggctggagtt cttattttat acatcacagt ggttcatgga     120
gatttcattt atagaagtta tcttacgttg aataggagatt taacaggatt ggctctaatt     180
attgaagtca aaatcgacct atggtggagg ttgcatcaga ataaaggaat ccatgaactg     240
tttttggata ttgtgaaaaa gaatccaaat aagccggcga tgattgacat cgagacgaat     300
acaacagaaa catacgcaga gttcaatgca cattgtaata gatatgccaa ttatttccag     360
ggtcttggct atcgatccgg agacgttgtc gccttgtaca tggagaactc ggtcgagttt     420
gtggccgcgt ggatgggact cgcaaaaatc ggagttgtaa cggcttggat caactcgaat     480
ttgaaaagag agcaacttgt tcattgtatc actgcgagca gacaaaaggc gattatcaca     540
agtgtaacac ttcagaatat tatgcttgat gctatcgatc agaagctgtt tgatgttgag     600
ggaattgagg tttactctgt cggagagccc aagaagaatt ctggattcaa gaatctcaag     660
aagaagttgg atgctcaaat tactacggaa ccaaagaccc ttgacatagt agatttaaa     720 agtattcttt gcttcatcta caagtggt actactggaa tgccaaaagc cgctgtcatg     780
aagcacttca gatattactc gattgccgtt ggagccgcaa atcattcgg aatccgccct     840 tctgatcgta tgtacgtctc gatgccaatt tatcacactg cagctggaat tcttggagtt     900
gggcaagctc tgttgggtgg atcatcgtgt gtcattagaa aaaaattctc ggctagcaac     960
ttttggaggg attgtgtaaa gtatgattgt acagttcac aatacattgg agagatttgt    1020
cggtacttgt tggctcagcc agttgtggaa gaggaatcca ggcatagaat gagattgttg    1080 gttgaaacg gactccgtgc tgaaatctgg caaccatttg tagatcgatt ccgtgtcaga    1140
attggagaac tttatggttc aactgaagga acttcatctc tcgtgaacat tgacggacat    1200
```

```
gtcggagctt gcggattctt gccaatatcc ccattaacaa agaaaatgca tccggttcga    1260
ttaattaagg ttgatgatgt cactggagaa gcaatccgaa cttccgatgg actttgcatt    1320
gcatgtaatc caggagagtc tggagcaatg gtgtcgacga tcagaaaaaa taatccatta    1380
ttgcaattcg aggatatctc gaataagaag gaaacgaata aaaagattat cagagatgtc    1440
ttcgcaaagg gagatagttg cttttttgact ggagatcttc ttcattggga tcgtcttggt    1500
```
*(line 1440 shown as written)*

```
tatgtatatt tcaaggatcg tactggagat actttccgtt ggaagggaga gaatgtgtcg    1560
actactgaag tcgaggcaat tcttcatcca attactggat tgtctgatgc aactgtttat    1620
ggtgtagagg ttcctcaaag agagggaaga gttggaatgg cgtcagttgt tcgagttgta    1680
tcgcatgagg aagatgaaac tcaatttgtt catagagttg gagcaagact tgcctcttcg    1740
cttaccagct acgcgattcc tcagtttatg cgaatttgtc aggatgttga gaaaacaggt    1800
acattcaaac ttgtgaagac gaatctacaa cgattaggta tcatggatgc tccttcagat    1860
tcaatttaca tctacaattc tgaaaatcgc aattttgtgc cgttcgacaa tgatttgagg    1920
tgcaaggtct cactgggaag ttatccattt taa    1953
```

<210> SEQ ID NO 79
<211> LENGTH: 650
<212> TYPE: PRT
<213> ORGANISM: Caenorhabditis elegans

<400> SEQUENCE: 79

Met Lys Leu Glu Glu Leu Val Thr Val Met Leu Leu Thr Val Ala Val
1               5                   10                  15

Ile Ala Gln Asn Leu Pro Ile Gly Val Ile Leu Ala Gly Val Leu Ile
            20                  25                  30

Leu Tyr Ile Thr Val Val His Gly Asp Phe Ile Tyr Arg Ser Tyr Leu
        35                  40                  45

Thr Leu Asn Arg Asp Leu Thr Gly Leu Ala Leu Ile Ile Glu Val Lys
    50                  55                  60

Ile Asp Leu Trp Trp Arg Leu His Gln Asn Lys Gly Ile His Glu Leu
65                  70                  75                  80

Phe Leu Asp Ile Val Lys Lys Asn Pro Asn Lys Pro Ala Met Ile Asp
                85                  90                  95

Ile Glu Thr Asn Thr Thr Glu Thr Tyr Ala Glu Phe Asn Ala His Cys
            100                 105                 110

Asn Arg Tyr Ala Asn Tyr Phe Gln Gly Leu Gly Tyr Arg Ser Gly Asp
        115                 120                 125

Val Val Ala Leu Tyr Met Glu Asn Ser Val Glu Phe Val Ala Ala Trp
    130                 135                 140

Met Gly Leu Ala Lys Ile Gly Val Val Thr Ala Trp Ile Asn Ser Asn
145                 150                 155                 160

Leu Lys Arg Glu Gln Leu Val His Cys Ile Thr Ala Ser Lys Thr Lys
                165                 170                 175

Ala Ile Ile Thr Ser Val Thr Leu Gln Asn Ile Met Leu Asp Ala Ile
            180                 185                 190

Asp Gln Lys Leu Phe Asp Val Glu Gly Ile Glu Val Tyr Ser Val Gly
        195                 200                 205

Glu Pro Lys Lys Asn Ser Gly Phe Lys Asn Leu Lys Lys Leu Asp
    210                 215                 220

Ala Gln Ile Thr Thr Glu Pro Lys Thr Leu Asp Ile Val Asp Phe Lys
225                 230                 235                 240

```
Ser Ile Leu Cys Phe Ile Tyr Thr Ser Gly Thr Thr Gly Met Pro Lys
                245                 250                 255

Ala Ala Val Met Lys His Phe Arg Tyr Tyr Ser Ile Ala Val Gly Ala
                260                 265                 270

Ala Lys Ser Phe Gly Ile Arg Pro Ser Asp Arg Met Tyr Val Ser Met
                275                 280                 285

Pro Ile Tyr His Thr Ala Ala Gly Ile Leu Gly Val Gly Gln Ala Leu
                290                 295                 300

Leu Gly Gly Ser Ser Cys Val Ile Arg Lys Lys Phe Ser Ala Ser Asn
305                 310                 315                 320

Phe Trp Arg Asp Cys Val Lys Tyr Asp Cys Thr Val Ser Gln Tyr Ile
                325                 330                 335

Gly Glu Ile Cys Arg Tyr Leu Leu Ala Gln Pro Val Val Glu Glu
                340                 345                 350

Ser Arg His Arg Met Arg Leu Leu Val Gly Asn Gly Leu Arg Ala Glu
                355                 360                 365

Ile Trp Gln Pro Phe Val Asp Arg Phe Arg Val Arg Ile Gly Glu Leu
                370                 375                 380

Tyr Gly Ser Thr Glu Gly Thr Ser Ser Leu Val Asn Ile Asp Gly His
385                 390                 395                 400

Val Gly Ala Cys Gly Phe Leu Pro Ile Ser Pro Leu Thr Lys Lys Met
                405                 410                 415

His Pro Val Arg Leu Ile Lys Val Asp Asp Val Thr Gly Glu Ala Ile
                420                 425                 430

Arg Thr Ser Asp Gly Leu Cys Ile Ala Cys Asn Pro Gly Glu Ser Gly
                435                 440                 445

Ala Met Val Ser Thr Ile Arg Lys Asn Asn Pro Leu Leu Gln Phe Glu
                450                 455                 460

Gly Tyr Leu Asn Lys Lys Glu Thr Asn Lys Lys Ile Ile Arg Asp Val
465                 470                 475                 480

Phe Ala Lys Gly Asp Ser Cys Phe Leu Thr Gly Asp Leu Leu His Trp
                485                 490                 495

Asp Arg Leu Gly Tyr Val Tyr Phe Lys Asp Arg Thr Gly Asp Thr Phe
                500                 505                 510

Arg Trp Lys Gly Glu Asn Val Ser Thr Thr Glu Val Glu Ala Ile Leu
                515                 520                 525

His Pro Ile Thr Gly Leu Ser Asp Ala Thr Val Tyr Gly Val Glu Val
                530                 535                 540

Pro Gln Arg Glu Gly Arg Val Gly Met Ala Ser Val Val Arg Val Val
545                 550                 555                 560

Ser His Glu Glu Asp Glu Thr Gln Phe Val His Arg Val Gly Ala Arg
                565                 570                 575

Leu Ala Ser Ser Leu Thr Ser Tyr Ala Ile Pro Gln Phe Met Arg Ile
                580                 585                 590

Cys Gln Asp Val Glu Lys Thr Gly Thr Phe Lys Leu Val Lys Thr Asn
                595                 600                 605

Leu Gln Arg Leu Gly Ile Met Asp Ala Pro Ser Asp Ser Ile Tyr Ile
                610                 615                 620

Tyr Asn Ser Glu Asn Arg Asn Phe Val Pro Phe Asp Asn Asp Leu Arg
625                 630                 635                 640

Cys Lys Val Ser Leu Gly Ser Tyr Pro Phe
                645                 650
```

<210> SEQ ID NO 80
<211> LENGTH: 1968
<212> TYPE: DNA
<213> ORGANISM: Caenorhabditis elegans

<400> SEQUENCE: 80

| | | | | | |
|---|---|---|---|---|---|
| atgagggaaa | tgccggacag | tcccaagttt | gcgttagtca | cgtttgttgt | gtatgcagtg | 60 |
| gttttgtaca | atgtcaacag | cgttttctgg | aaatttgtat | tcatcggata | tgttgtattt | 120 |
| aggctgcttc | gcactgattt | tggaagaaga | gcacttgcca | cgttacctag | agattttgcg | 180 |
| ggactgaagc | tcttaatatc | ggttaagtcg | acaattcgtg | gcttgttcaa | gaaagatcgc | 240 |
| ccaattcatg | aaatctttt | gaatcaggtg | aaacagcatc | aaacaaagt | ggcgattatt | 300 |
| gaaattgaaa | gtggtaggca | gttgacgtat | caagaattga | atgcgttagc | taatcagtat | 360 |
| gctaaccttt | acgtgagtga | aggttacaaa | atgggcgacg | ttgtcgcttt | gtttatggaa | 420 |
| aatagcatcg | acttctttgc | aatttggctg | gactttcca | agattggagt | cgtgtcggcg | 480 |
| ttcatcaact | caaacttgaa | gttggagcca | ttggcacatt | cgattaatgt | ttcgaagtgc | 540 |
| aaatcatgca | ttaccaatat | caatctgttg | ccgatgttca | aagccgctcg | tgaaaagaat | 600 |
| ctgatcagtg | acgagatcca | cgtgtttctg | gctggaactc | aggttgatgg | acgtcataga | 660 |
| agtcttcagc | aagatctcca | tcttttctct | gaggatgaac | ctccagttat | agacggactc | 720 |
| aattttagaa | gcgttctgtg | ttatatttac | acttccggta | ctaccggaaa | tccaaagcca | 780 |
| gccgtcatta | aacacttccg | ttacttctgg | attgcgatgg | gagcaggaaa | agcatttgga | 840 |
| attaataagt | cagacgttgt | gtacattacg | atgccaatgt | atcactctgc | cgccggtatc | 900 |
| atgggtattg | gatcattaat | tgcattcggg | tcgaccgctg | ttattaggaa | aaagttttcg | 960 |
| gcaagcaact | tctggaaaga | ttgcgtcaag | tacaacgtca | cagcgacaca | gtacattgga | 1020 |
| gaaatctgca | ggtatcttct | ggcagcgaat | ccatgtcctg | aagagaaaca | cacaacgtg | 1080 |
| cgattgatgt | ggggaaatgg | tttgagagga | caaatttgga | aagagtttgt | aggaagattt | 1140 |
| ggaattaaga | aaattggaga | gttgtacggc | tcaacagaag | gaaactccaa | tattgttaac | 1200 |
| gtggataacc | atgttggagc | ttgtggattc | atgccaattt | atccccatat | ggatccctc | 1260 |
| tacccagttc | gacttattaa | ggttgataga | gccactggag | agcttgaacg | tgataagaac | 1320 |
| ggactctgtg | tgccgtgtgt | gcctggtgaa | actggggaaa | tggttggcgt | tatcaaggag | 1380 |
| aaagatattc | ttctaaagtt | cgaaggatat | gtcagcgaag | gggatactgc | aaagaaaatc | 1440 |
| tacagagatg | tgttcaagca | tggagataag | gtgtttgcaa | gtggagatat | tcttcattgg | 1500 |
| gatgatcttg | gatacttgta | ctttgtggac | cgttgtggag | acactttccg | ttggaaaggg | 1560 |
| gagaacgtgt | caactactga | agttgaggga | attcttcagc | ctgtgatgga | tgtggaagat | 1620 |
| gcaactgttt | atggagtcac | tgtcggtaaa | atggaggggc | gtgccggaat | ggctggtatt | 1680 |
| gtcgtcaagg | atgaacgga | tgttgagaaa | ttcatcgccg | atattacttc | tcgactgacc | 1740 |
| gaaaatctgg | cgtcttacgc | aatccctgtt | ttcattcggc | tgtgcaagga | agttgatcga | 1800 |
| accggaacct | tcaaactcaa | gaagactgat | cttcaaaaac | aaggttacga | cctggttgct | 1860 |
| tgtaaaggag | acccaattta | ctactggtca | gctgcagaaa | atcctacaa | accactgact | 1920 |
| gacaaaatgc | aacaggatat | tgacactggt | gtttatgatc | gcatttaa | | 1968 |

<210> SEQ ID NO 81
<211> LENGTH: 655
<212> TYPE: PRT
<213> ORGANISM: Caenorhabditis elegans

<400> SEQUENCE: 81

```
Met Arg Glu Met Pro Asp Ser Pro Lys Phe Ala Leu Val Thr Phe Val
1               5                   10                  15
Val Tyr Ala Val Val Leu Tyr Asn Val Asn Ser Val Phe Trp Lys Phe
            20                  25                  30
Val Phe Ile Gly Tyr Val Val Phe Arg Leu Leu Arg Thr Asp Phe Gly
        35                  40                  45
Arg Arg Ala Leu Ala Thr Leu Pro Arg Asp Phe Ala Gly Leu Lys Leu
    50                  55                  60
Leu Ile Ser Val Lys Ser Thr Ile Arg Gly Leu Phe Lys Lys Asp Arg
65                  70                  75                  80
Pro Ile His Glu Ile Phe Leu Asn Gln Val Lys Gln His Pro Asn Lys
                85                  90                  95
Val Ala Ile Ile Glu Ile Glu Ser Gly Arg Gln Leu Thr Tyr Gln Glu
            100                 105                 110
Leu Asn Ala Leu Ala Asn Gln Tyr Ala Asn Leu Tyr Val Ser Glu Gly
        115                 120                 125
Tyr Lys Met Gly Asp Val Val Ala Leu Phe Met Glu Asn Ser Ile Asp
    130                 135                 140
Phe Phe Ala Ile Trp Leu Gly Leu Ser Lys Ile Gly Val Val Ser Ala
145                 150                 155                 160
Phe Ile Asn Ser Asn Leu Lys Leu Glu Pro Leu Ala His Ser Ile Asn
                165                 170                 175
Val Ser Lys Cys Lys Ser Cys Ile Thr Asn Ile Asn Leu Leu Pro Met
            180                 185                 190
Phe Lys Ala Ala Arg Glu Lys Asn Leu Ile Ser Asp Glu Ile His Val
        195                 200                 205
Phe Leu Ala Gly Thr Gln Val Asp Gly Arg His Arg Ser Leu Gln Gln
    210                 215                 220
Asp Leu His Leu Phe Ser Glu Asp Glu Pro Pro Val Ile Asp Gly Leu
225                 230                 235                 240
Asn Phe Arg Ser Val Leu Cys Tyr Ile Tyr Thr Ser Gly Thr Thr Gly
                245                 250                 255
Asn Pro Lys Pro Ala Val Ile Lys His Phe Arg Tyr Phe Trp Ile Ala
            260                 265                 270
Met Gly Ala Gly Lys Ala Phe Gly Ile Asn Lys Ser Asp Val Val Tyr
        275                 280                 285
Ile Thr Met Pro Met Tyr His Ser Ala Ala Gly Ile Met Gly Ile Gly
    290                 295                 300
Ser Leu Ile Ala Phe Gly Ser Thr Ala Val Ile Arg Lys Lys Phe Ser
305                 310                 315                 320
Ala Ser Asn Phe Trp Lys Asp Cys Val Lys Tyr Asn Val Thr Ala Thr
                325                 330                 335
Gln Tyr Ile Gly Glu Ile Cys Arg Tyr Leu Leu Ala Ala Asn Pro Cys
            340                 345                 350
Pro Glu Glu Lys Gln His Asn Val Arg Leu Met Trp Gly Asn Gly Leu
        355                 360                 365
Arg Gly Gln Ile Trp Lys Glu Phe Val Arg Phe Gly Ile Lys Lys
    370                 375                 380
Ile Gly Glu Leu Tyr Gly Ser Thr Glu Gly Asn Ser Asn Ile Val Asn
385                 390                 395                 400
Val Asp Asn His Val Gly Ala Cys Gly Phe Met Pro Ile Tyr Pro His
```

```
                    405                 410                 415
Ile Gly Ser Leu Tyr Pro Val Arg Leu Ile Lys Val Asp Arg Ala Thr
            420                 425                 430
Gly Glu Leu Glu Arg Asp Lys Asn Gly Leu Cys Val Pro Cys Val Pro
            435                 440                 445
Gly Glu Thr Gly Glu Met Val Gly Val Ile Lys Glu Lys Asp Ile Leu
            450                 455                 460
Leu Lys Phe Glu Gly Tyr Val Ser Glu Gly Asp Thr Ala Lys Lys Ile
465                 470                 475                 480
Tyr Arg Asp Val Phe Lys His Gly Asp Lys Val Phe Ala Ser Gly Asp
                485                 490                 495
Ile Leu His Trp Asp Asp Leu Gly Tyr Leu Tyr Phe Val Asp Arg Cys
            500                 505                 510
Gly Asp Thr Phe Arg Trp Lys Gly Glu Asn Val Ser Thr Thr Glu Val
            515                 520                 525
Glu Gly Ile Leu Gln Pro Val Met Asp Val Glu Asp Ala Thr Val Tyr
            530                 535                 540
Gly Val Thr Val Gly Lys Met Glu Gly Arg Ala Gly Met Ala Gly Ile
545                 550                 555                 560
Val Val Lys Asp Gly Thr Asp Val Glu Lys Phe Ile Ala Asp Ile Thr
                565                 570                 575
Ser Arg Leu Thr Glu Asn Leu Ala Ser Tyr Ala Ile Pro Val Phe Ile
            580                 585                 590
Arg Leu Cys Lys Glu Val Asp Arg Thr Gly Thr Phe Lys Leu Lys Lys
            595                 600                 605
Thr Asp Leu Gln Lys Gln Gly Tyr Asp Leu Val Ala Cys Lys Gly Asp
            610                 615                 620
Pro Ile Tyr Tyr Trp Ser Ala Ala Glu Lys Ser Tyr Lys Pro Leu Thr
625                 630                 635                 640
Asp Lys Met Gln Gln Asp Ile Asp Thr Gly Val Tyr Asp Arg Ile
                645                 650                 655

<210> SEQ ID NO 82
<211> LENGTH: 1932
<212> TYPE: DNA
<213> ORGANISM: Cochliobolu heterostrophus

<400> SEQUENCE: 82
atggcgtgta tgcatcaggc tcagctatac aatgatctag aggaattgct aactggtcca      60
tcagtaccca tcgttgctgg agctgctgga gctgcagctc tcactgccta cattaacgcc     120
aaataccaca tagcccatga tctcaagacc ctcggtggtg gattgacaca atcgtccgaa     180
gcgattgatt tcataaaccg ccgcgtcgca caaaagcgcg tcctcacgca ccacatcttc     240
caggagcagg tccaaaaaca atcaaatcat cccttcctta tctttgaggg caagacatgg     300
tcttacaagg agttctctga ggcatacacg agggtcgcga actggctgat tgatgagctg     360
gacgtacaag taggggagat ggtcgcaatt gatggcggaa atagtgcaga gcacctgatg     420
ctttggcttg cacttgatgc aatcggtgcg gctacgagtt ttttgaactg gaacctgaca     480
ggggcagggt taattcattg cataaagcta tgcgaatgtc gattcgttat cgcagacatc     540
gatattaaag cgaacattga accgtgccgt ggcgaactgg aggagacggg catcaacatt     600
cactactatg acccatcctt catctcatcg ctaccgaata acacgccaat tcccgacagc     660
cgcactgaga acattgaatt agattcagta cgaggactga tatacacatc tggaaccact     720
```

-continued

```
ggtctaccta aaggcgtgtt tataagcact ggccgcgagc ttaggactga ctggtcgatt    780
tcaaagtatc taaatctcaa gcccacggat cgaatgtata catgtatgcc gctctaccat    840
gccgctgcac acagcctctg tacagcatca gttattcatg gtggaggtac cgtggtattg    900
agcaggaaat tctcacacaa gaagttctgg cctgaagttg tggcttcgga agcaaatatc    960
attcagtacg ttggtgaatt aggtcgatat ctcctgaatg gtccaaagag tccttacgac   1020
agggcccata aagtccagat ggcgtggggc aatggcatgc gtccagacgt gtgggaagcg   1080
tttcgtgaac gcttcaacat accaattatt catgagctct atgccgcaac cgatgggctc   1140
gggtcaatga ccaatcgtaa cgcgggccct tttacagcaa actgtattgc gctgcgaggg   1200
ctgatctggc actggaaatt tcgaaatcag gaagtgctgg tcaagatgga tctcgatact   1260
gatgagatca tgagagatcg caatgggttt gcgatacgat gcgctgtcaa tgaacctgga   1320
cagatgcttt ttcggctgac acccgaaact ctggctggtg caccaagcta ctacaacaac   1380
gaaacggcca cacagagcag gcggattaca gatgtgtttc aaaagggtga cctgtggttc   1440
aagtccggtg acatgctacg gcaagacgcc gaaggccgcg tctactttgt cgatcgacta   1500
ggcgatacgt tccgctggaa atccgaaaac gtttctacca atgaagtcgc ggacgtgatg   1560
ggcacatttc ctcagattgc tgaaacgaat gtatacggtg tccttgtgcc gggtaacgat   1620
ggtcgagtgc gcagcctcaa ttgtcatggc agacggcgtg acagagtcga cattcgcttc   1680
gctgcccttg caaagcacgc ccgagatcgg ttaccgggtt atgctgtacc actgtttctg   1740
agggtaactc cagcacttga atatacgggc acattaaaga ttcagaaagg acgcctcaag   1800
caggaaggta tagacccaga taagatttcc ggcgaagata agttatactg gctgccgcct   1860
ggtagcgata tatatttacc atttggaaag atggagtggc agggaattgt agataagcgt   1920
atacggctgt ga                                                       1932
```

<210> SEQ ID NO 83
<211> LENGTH: 643
<212> TYPE: PRT
<213> ORGANISM: Cochliobolu heterostrophus

<400> SEQUENCE: 83

```
Met Ala Cys Met His Gln Ala Gln Leu Tyr Asn Asp Leu Glu Glu Leu
  1               5                  10                  15

Leu Thr Gly Pro Ser Val Pro Ile Val Ala Gly Ala Ala Gly Ala Ala
             20                  25                  30

Ala Leu Thr Ala Tyr Ile Asn Ala Lys Tyr His Ile Ala His Asp Leu
         35                  40                  45

Lys Thr Leu Gly Gly Gly Leu Thr Gln Ser Ser Glu Ala Ile Asp Phe
     50                  55                  60

Ile Asn Arg Arg Val Ala Gln Lys Arg Val Leu Thr His His Ile Phe
 65                  70                  75                  80

Gln Glu Gln Val Gln Lys Gln Ser Asn His Pro Phe Leu Ile Phe Glu
                 85                  90                  95

Gly Lys Thr Trp Ser Tyr Lys Glu Phe Ser Glu Ala Tyr Thr Arg Val
            100                 105                 110

Ala Asn Trp Leu Ile Asp Glu Leu Asp Val Gln Val Gly Glu Met Val
        115                 120                 125

Ala Ile Asp Gly Gly Asn Ser Ala Glu His Leu Met Leu Trp Leu Ala
    130                 135                 140

Leu Asp Ala Ile Gly Ala Ala Thr Ser Phe Leu Asn Trp Asn Leu Thr
145                 150                 155                 160
```

-continued

```
Gly Ala Gly Leu Ile His Cys Ile Lys Leu Cys Glu Cys Arg Phe Val
            165                 170                 175
Ile Ala Asp Ile Asp Ile Lys Ala Asn Ile Glu Pro Cys Arg Gly Glu
            180                 185                 190
Leu Glu Glu Thr Gly Ile Asn Ile His Tyr Tyr Asp Pro Ser Phe Ile
            195                 200                 205
Ser Ser Leu Pro Asn Asn Thr Pro Ile Pro Asp Ser Arg Thr Glu Asn
    210                 215                 220
Ile Glu Leu Asp Ser Val Arg Gly Leu Ile Tyr Thr Ser Gly Thr Thr
225                 230                 235                 240
Gly Leu Pro Lys Gly Val Phe Ile Ser Thr Gly Arg Glu Leu Arg Thr
                245                 250                 255
Asp Trp Ser Ile Ser Lys Tyr Leu Asn Leu Lys Pro Thr Asp Arg Met
                260                 265                 270
Tyr Thr Cys Met Pro Leu Tyr His Ala Ala His Ser Leu Cys Thr
            275                 280                 285
Ala Ser Val Ile His Gly Gly Thr Val Val Leu Ser Arg Lys Phe
    290                 295                 300
Ser His Lys Lys Phe Trp Pro Glu Val Val Ala Ser Glu Ala Asn Ile
305                 310                 315                 320
Ile Gln Tyr Val Gly Glu Leu Gly Arg Tyr Leu Leu Asn Gly Pro Lys
                325                 330                 335
Ser Pro Tyr Asp Arg Ala His Lys Val Gln Met Ala Trp Gly Asn Gly
                340                 345                 350
Met Arg Pro Asp Val Trp Glu Ala Phe Arg Glu Arg Phe Asn Ile Pro
            355                 360                 365
Ile Ile His Glu Leu Tyr Ala Ala Thr Asp Gly Leu Gly Ser Met Thr
            370                 375                 380
Asn Arg Asn Ala Gly Pro Phe Thr Ala Asn Cys Ile Ala Leu Arg Gly
385                 390                 395                 400
Leu Ile Trp His Trp Lys Phe Arg Asn Gln Glu Val Leu Val Lys Met
                405                 410                 415
Asp Leu Asp Thr Asp Glu Ile Met Arg Asp Arg Asn Gly Phe Ala Ile
                420                 425                 430
Arg Cys Ala Val Asn Glu Pro Gly Gln Met Leu Phe Arg Leu Thr Pro
            435                 440                 445
Glu Thr Leu Ala Gly Ala Pro Ser Tyr Tyr Asn Asn Glu Thr Ala Thr
    450                 455                 460
Gln Ser Arg Arg Ile Thr Asp Val Phe Gln Lys Gly Asp Leu Trp Phe
465                 470                 475                 480
Lys Ser Gly Asp Met Leu Arg Gln Asp Ala Glu Gly Arg Val Tyr Phe
                485                 490                 495
Val Asp Arg Leu Gly Asp Thr Phe Arg Trp Lys Ser Glu Asn Val Ser
                500                 505                 510
Thr Asn Glu Val Ala Asp Val Met Gly Thr Phe Pro Gln Ile Ala Glu
            515                 520                 525
Thr Asn Val Tyr Gly Val Leu Val Pro Gly Asn Asp Gly Arg Val Arg
            530                 535                 540
Ser Leu Asn Cys His Gly Arg Arg Asp Arg Val Asp Ile Arg Phe
545                 550                 555                 560
Ala Ala Leu Ala Lys His Ala Arg Asp Arg Leu Pro Gly Tyr Ala Val
                565                 570                 575
```

```
Pro Leu Phe Leu Arg Val Thr Pro Ala Leu Glu Tyr Thr Gly Thr Leu
                580                 585                 590

Lys Ile Gln Lys Gly Arg Leu Lys Gln Glu Gly Ile Asp Pro Asp Lys
            595                 600                 605

Ile Ser Gly Glu Asp Lys Leu Tyr Trp Leu Pro Pro Gly Ser Asp Ile
        610                 615                 620

Tyr Leu Pro Phe Gly Lys Met Glu Trp Gln Gly Ile Val Asp Lys Arg
625                 630                 635                 640

Ile Arg Leu

<210> SEQ ID NO 84
<211> LENGTH: 597
<212> TYPE: DNA
<213> ORGANISM: Aspergillus nidulans

<400> SEQUENCE: 84
ctttaccatt catcagcttc attctgcatt tttagcttga cggcagccgg gtctacgctg      60
atcatcggcc gcaagttctc cgcgagaaac ttcataaagg aagcgcgcga gaacgacgcc     120
acggtcatcc agtacgtggg tgagaccttg cgatatctgc tcgccacccc cggtgaaacc     180
gatccagtta ctggcgaaga cctggacaaa agcacaata ttcgagcagt atacggcaac      240
gggctacggc cggatatctg gaaccgcttc aaggagcgct tcaacgtgcc gacggttgcc     300
gaattttatg ctgcaaccga gagcccaggc ggaacatgga actattcaac aaatgacttc     360
actgccggag ccattgggca cactggcgtg cttagtggat ggcttcttgg acgcggcctt     420
actattgtcg aggtggacca ggaatcacag gaaccatggc gcgatcccca aaccgggttc     480
tgcaagccgg tcccgcgagg cgaagcaggc gagctcctgt atgccattga tccggccgac     540
ccgggcgaga ccttccaggg ctactaccgc aactccttta gagcacactg gcggccg       597

<210> SEQ ID NO 85
<211> LENGTH: 199
<212> TYPE: PRT
<213> ORGANISM: Aspergillus nidulans

<400> SEQUENCE: 85

Leu Tyr His Ser Ser Ala Ser Phe Cys Ile Phe Ser Leu Thr Ala Ala
1               5                  10                  15

Gly Ser Thr Leu Ile Ile Gly Arg Lys Phe Ser Ala Arg Asn Phe Ile
            20                  25                  30

Lys Glu Ala Arg Glu Asn Asp Ala Thr Val Ile Gln Tyr Val Gly Glu
        35                  40                  45

Thr Leu Arg Tyr Leu Leu Ala Thr Pro Gly Glu Thr Asp Pro Val Thr
    50                  55                  60

Gly Glu Asp Leu Asp Lys Lys His Asn Ile Arg Ala Val Tyr Gly Asn
65                  70                  75                  80

Gly Leu Arg Pro Asp Ile Trp Asn Arg Phe Lys Glu Arg Phe Asn Val
                85                  90                  95

Pro Thr Val Ala Glu Phe Tyr Ala Ala Thr Glu Ser Pro Gly Gly Thr
            100                 105                 110

Trp Asn Tyr Ser Thr Asn Asp Phe Thr Ala Gly Ala Ile Gly His Thr
        115                 120                 125

Gly Val Leu Ser Gly Trp Leu Leu Gly Arg Gly Leu Thr Ile Val Glu
    130                 135                 140

Val Asp Gln Glu Ser Gln Glu Pro Trp Arg Asp Pro Gln Thr Gly Phe
145                 150                 155                 160
```

```
Cys Lys Pro Val Pro Arg Gly Glu Ala Gly Glu Leu Leu Tyr Ala Ile
            165                 170                 175

Asp Pro Ala Asp Pro Gly Glu Thr Phe Gln Gly Tyr Tyr Arg Asn Ser
        180                 185                 190

Phe Arg Ala His Trp Arg Pro
        195
```

<210> SEQ ID NO 86
<211> LENGTH: 522
<212> TYPE: DNA
<213> ORGANISM: Magnaporthe grisea
<220> FEATURE:
<221> NAME/KEY: misc_feature
<222> LOCATION: (1)...(522)
<223> OTHER INFORMATION: n = A,T,C or G

<400> SEQUENCE: 86

```
gcaaaggccg acgcgtggct gcggacgggt aacgtgatca gggcggacaa cgaagggcga      60
ctcttcttcc acgaccggat cggagacacg ttccgatgga agggagagac ngtcagcaca     120
caagaggtca gtttggtgct cggacgacac gactcaatca aggaggccaa cgtgtacggc     180
gtgacggtgc cgaaccacga cgggcgggcc ggctgcgctg cgctcacgct atcagacgct     240
ctggcgactg aaaagaagct gggcgatgag ctgctaaagg gattggctac tcactcgtcg     300
acttcgcttc ccaagtttgc ggtgccgcag ttcctacggg tggtgcgcgg cgagatgcag     360
tcaacgggca ccaacaagca acagaagcac gacctgaggg tgcagggtgt agagccgggc     420
aaggtgggcg tagacgaggt gtactggttg cggggaggga catatgtacc attcggaaca     480
gaggattggg atgggttgaa gaagggtctt gtgaagttgt ga                        522
```

<210> SEQ ID NO 87
<211> LENGTH: 173
<212> TYPE: PRT
<213> ORGANISM: Magnaporthe grisea

<400> SEQUENCE: 87

```
Ala Lys Ala Asp Ala Trp Leu Arg Thr Gly Asn Val Ile Arg Ala Asp
 1               5                  10                  15

Asn Glu Gly Arg Leu Phe Phe His Asp Arg Ile Gly Asp Thr Phe Arg
            20                  25                  30

Trp Lys Gly Glu Thr Val Ser Thr Gln Glu Val Ser Leu Val Leu Gly
        35                  40                  45

Arg His Asp Ser Ile Lys Glu Ala Asn Val Tyr Gly Val Thr Val Pro
    50                  55                  60

Asn His Asp Gly Arg Ala Gly Cys Ala Ala Leu Thr Leu Ser Asp Ala
65                  70                  75                  80

Leu Ala Thr Glu Lys Lys Leu Gly Asp Glu Leu Leu Lys Gly Leu Ala
                85                  90                  95

Thr His Ser Ser Thr Ser Leu Pro Lys Phe Ala Val Pro Gln Phe Leu
            100                 105                 110

Arg Val Val Arg Gly Glu Met Gln Ser Thr Gly Thr Asn Lys Gln Gln
        115                 120                 125

Lys His Asp Leu Arg Val Gln Gly Val Glu Pro Gly Lys Val Gly Val
    130                 135                 140

Asp Glu Val Tyr Trp Leu Arg Gly Gly Thr Tyr Val Pro Phe Gly Thr
145                 150                 155                 160

Glu Asp Trp Asp Gly Leu Lys Lys Gly Leu Val Lys Leu
                165                 170
```

-continued

<210> SEQ ID NO 88
<211> LENGTH: 1872
<212> TYPE: DNA
<213> ORGANISM: Saccharomyces cerevisiae

<400> SEQUENCE: 88

| | |
|---|---|
| atgtctccca tacaggttgt tgtctttgcc ttgtcaagga ttttcctgct attattcaga | 60 |
| cttatcaagc taattataac ccctatccag aaatcactgg gttatctatt tggtaattat | 120 |
| tttgatgaat tagaccgtaa atatagatac aaggaggatt ggtatattat tccttacttt | 180 |
| ttgaaaagcg tgttttgtta tatcattgat gtgagaagac ataggtttca aaactggtac | 240 |
| ttatttatta aacaggtcca acaaaatggt gaccatttag cgattagtta cacccgtccc | 300 |
| atggccgaaa agggagaatt tcaactcgaa acctttacgt atattgaaac ttataacata | 360 |
| gtgttgagat tgtctcatat tttgcatttt gattataacg ttcaggccgg tgactacgtg | 420 |
| gcaatcgatt gtactaataa acctcttttc gtatttttat ggctttcttt gtggaacatt | 480 |
| ggggctattc cagcttttttt aaactataat actaaaggca ctccgctggt tcactcccta | 540 |
| aagatttcca atattacgca ggtatttatt gaccctgatg ccagtaatcc gatcagagaa | 600 |
| tcggaagaag aaatcaaaaa cgcacttcct gatgttaaat aaactatct tgaagaacaa | 660 |
| gacttaatgc atgaactttt aaattcgcaa tcaccggaat tcttacaaca agacaacgtt | 720 |
| aggacaccac taggcttgac cgattttaaa ccctctatgt taatttatac atctggaacc | 780 |
| actggtttgc ctaaatccgc tattatgtct tggagaaaat cctccgtagg ttgtcaagtt | 840 |
| tttggtcatg tttacatat gactaatgaa agcactgtgt tcacagccat gccattgttc | 900 |
| cattcaactg ctgccttatt aggtgcgtgc gccattctat ctcacggtgg ttgccttgcg | 960 |
| ttatcgcata aattttctgc cagtacattt tggaagcaag tttatttaac aggagccacg | 1020 |
| cacatccaat atgtcggaga agtctgtaga tacctgttac atacgccaat ttctaagtat | 1080 |
| gaaaagatgc ataaggtgaa ggttgcttat ggtaacgggc tgagacctga catctggcag | 1140 |
| gacttcagga agaggttcaa catagaagtt attggtgaat ctatgccgc aactgaagct | 1200 |
| cctttttgcta caactacctt ccagaaaggt gactttggaa ttggcgcatg taggaactat | 1260 |
| ggtactataa ttcaatggtt tttgtcattc caacaaacat tggtaaggat ggacccaaat | 1320 |
| gacgattccg ttatatatag aaattccaag ggtttctgcg aagtggcccc tgttggcgaa | 1380 |
| ccaggagaaa tgttaatgag aatcttttc cctaaaaaac cagaaacatc ttttcaaggt | 1440 |
| tatcttggta atgccaagga aacaaagtcc aaagttgtga gggatgtctt cagacgtggc | 1500 |
| gatgcttggt atagatgtgg agattatta aaagcggacg aatatggatt atggtatttc | 1560 |
| cttgatagaa tgggtgatac tttcagatgg aaatctgaaa atgtttccac tactgaagta | 1620 |
| gaagatcagt tgacggccag taacaaagaa caatatgcac aagttctagt tgttggtatt | 1680 |
| aaagtaccta aatatgaagg tagagctggt tttgcagtta ttaaactaac tgacaactct | 1740 |
| cttgacatca ctgcaaagac caaattatta atgattcct tgagccggtt aaatctaccg | 1800 |
| tcttatgcta tgccctatt tgttaaattt gttgatgaaa ttaaaatgac agataacctc | 1860 |
| ataaaatttt ga | 1872 |

<210> SEQ ID NO 89
<211> LENGTH: 623
<212> TYPE: PRT
<213> ORGANISM: Saccharomyces cerevisiae

<400> SEQUENCE: 89

```
Met Ser Pro Ile Gln Val Val Phe Ala Leu Ser Arg Ile Phe Leu
1               5                   10                  15
Leu Leu Phe Arg Leu Ile Lys Leu Ile Thr Pro Ile Gln Lys Ser
                20                  25                  30
Leu Gly Tyr Leu Phe Gly Asn Tyr Phe Asp Glu Leu Asp Arg Lys Tyr
            35                  40                  45
Arg Tyr Lys Glu Asp Trp Tyr Ile Pro Tyr Phe Leu Lys Ser Val
        50                  55                  60
Phe Cys Tyr Ile Ile Asp Val Arg Arg His Arg Phe Gln Asn Trp Tyr
65                  70                  75                  80
Leu Phe Ile Lys Gln Val Gln Gln Asn Gly Asp His Leu Ala Ile Ser
                85                  90                  95
Tyr Thr Arg Pro Met Ala Glu Lys Gly Glu Phe Gln Leu Glu Thr Phe
                100                 105                 110
Thr Tyr Ile Glu Thr Tyr Asn Ile Val Leu Arg Leu Ser His Ile Leu
            115                 120                 125
His Phe Asp Tyr Asn Val Gln Ala Gly Asp Tyr Val Ala Ile Asp Cys
    130                 135                 140
Thr Asn Lys Pro Leu Phe Val Phe Leu Trp Leu Ser Leu Trp Asn Ile
145                 150                 155                 160
Gly Ala Ile Pro Ala Phe Leu Asn Tyr Asn Thr Lys Gly Thr Pro Leu
                165                 170                 175
Val His Ser Leu Lys Ile Ser Asn Ile Thr Gln Val Phe Ile Asp Pro
            180                 185                 190
Asp Ala Ser Asn Pro Ile Arg Glu Ser Glu Glu Ile Lys Asn Ala
        195                 200                 205
Leu Pro Asp Val Lys Leu Asn Tyr Leu Glu Glu Gln Asp Leu Met His
    210                 215                 220
Glu Leu Leu Asn Ser Gln Ser Pro Glu Phe Leu Gln Gln Asp Asn Val
225                 230                 235                 240
Arg Thr Pro Leu Gly Leu Thr Asp Phe Lys Pro Ser Met Leu Ile Tyr
                245                 250                 255
Thr Ser Gly Thr Thr Gly Leu Pro Lys Ser Ala Ile Met Ser Trp Arg
            260                 265                 270
Lys Ser Ser Val Gly Cys Gln Val Phe Gly His Val Leu His Met Thr
        275                 280                 285
Asn Glu Ser Thr Val Phe Thr Ala Met Pro Leu Phe His Ser Thr Ala
    290                 295                 300
Ala Leu Leu Gly Ala Cys Ala Ile Leu Ser His Gly Gly Cys Leu Ala
305                 310                 315                 320
Leu Ser His Lys Phe Ser Ala Ser Thr Phe Trp Lys Gln Val Tyr Leu
                325                 330                 335
Thr Gly Ala Thr His Ile Gln Tyr Val Gly Glu Val Cys Arg Tyr Leu
            340                 345                 350
Leu His Thr Pro Ile Ser Lys Tyr Glu Lys Met His Lys Val Lys Val
        355                 360                 365
Ala Tyr Gly Asn Gly Leu Arg Pro Asp Ile Trp Gln Asp Phe Arg Lys
    370                 375                 380
Arg Phe Asn Ile Glu Val Ile Gly Glu Phe Tyr Ala Ala Thr Glu Ala
385                 390                 395                 400
Pro Phe Ala Thr Thr Thr Phe Gln Lys Gly Asp Phe Gly Ile Gly Ala
```

```
                  405                 410                 415
Cys Arg Asn Tyr Gly Thr Ile Ile Gln Trp Phe Leu Ser Phe Gln Gln
            420                 425                 430

Thr Leu Val Arg Met Asp Pro Asn Asp Asp Ser Val Ile Tyr Arg Asn
            435                 440                 445

Ser Lys Gly Phe Cys Glu Val Ala Pro Val Gly Glu Pro Gly Glu Met
            450                 455                 460

Leu Met Arg Ile Phe Phe Pro Lys Lys Pro Glu Thr Ser Phe Gln Gly
465                 470                 475                 480

Tyr Leu Gly Asn Ala Lys Glu Thr Lys Ser Lys Val Val Arg Asp Val
                485                 490                 495

Phe Arg Arg Gly Asp Ala Trp Tyr Arg Cys Gly Asp Leu Leu Lys Ala
                500                 505                 510

Asp Glu Tyr Gly Leu Trp Tyr Phe Leu Asp Arg Met Gly Asp Thr Phe
            515                 520                 525

Arg Trp Lys Ser Glu Asn Val Ser Thr Thr Glu Val Glu Asp Gln Leu
            530                 535                 540

Thr Ala Ser Asn Lys Glu Gln Tyr Ala Gln Val Leu Val Val Gly Ile
545                 550                 555                 560

Lys Val Pro Lys Tyr Glu Gly Arg Ala Gly Phe Ala Val Ile Lys Leu
                565                 570                 575

Thr Asp Asn Ser Leu Asp Ile Thr Ala Lys Thr Lys Leu Leu Asn Asp
            580                 585                 590

Ser Leu Ser Arg Leu Asn Leu Pro Ser Tyr Ala Met Pro Leu Phe Val
            595                 600                 605

Lys Phe Val Asp Glu Ile Lys Met Thr Asp Asn Leu Ile Lys Phe
            610                 615                 620

<210> SEQ ID NO 90
<211> LENGTH: 1794
<212> TYPE: DNA
<213> ORGANISM: Mycobacterium tuberculosis

<400> SEQUENCE: 90
gtgtccgatt actacggcgg cgcacacaca acggtcaggc tgatcgacct ggcaactcgg      60
atgccgcgag tgttggcgga cacgccggtg attgtgcgtg gggcaatgac cgggctgctg     120
gcccggccga attccaaggc gtcgatcggc acggtgttcc aggaccgggc cgctcgctac     180
ggtgaccgag tcttcctgaa attcggcgat cagcagctga cctaccgcga cgctaacgcc     240
accgccaacc ggtacgccgc ggtgttggcc gcccgcggcg tcggccccgg cgacgtcgtt     300
ggcatcatgt tgcgtaactc acccagcaca gtcttggcga tgctggccac ggtcaagtgc     360
ggcgctatcg ccggcatgct caactaccac cagcgcggcg aggtgttggc gcacagcctg     420
ggtctgctgg acgcgaaggt actgatcgca gagtccgact tggtcagcgc cgtcgccgaa     480
tgcggcgcct cgcgcggccg ggtagcgggc gacgtgctga ccgtcgagga cgtggagcga     540
ttcgccacaa cggcgcccgc caccaacccg cgtcggcgt cggcggtgca agccaaagac     600
accgcgttct acatcttcac ctcgggcacc accggatttc ccaaggccag tgtcatgacg     660
catcatcggt ggctgcgggc gctggccgtc ttcggaggga tggggctgcg gctgaagggt     720
tccgacacgc tctacagctg cctgccgctg taccacaaca acgcgttaac ggtcgcggtg     780
tcgtcggtga tcaattctgg ggcgaccctg cgctgggta agtcgttttc ggcgtcgcgg     840
ttctgggatg aggtgattgc caaccgggcg acggcgttcg tctacatcgg cgaaatctgc     900
```

```
cgttatctgc tcaaccagcc ggccaagccg accgaccgtg cccaccaggt gcgggtgatc    960
tgcggtaacg ggctgcggcc ggagatctgg gatgagttca ccacccgctt cggggtcgcg   1020
cgggtgtgcg agttctacgc cgccagcgaa ggcaactcgg cctttatcaa catcttcaac   1080
gtgcccagga ccgccggggt atcgccgatg ccgcttgcct ttgtggaata cgacctggac   1140
accggcgatc cgctgcggga tgcgagcggg cgagtgcgtc gggtaccga cggtgaaccc    1200
ggcctgttgc ttagccgggt caaccggctg cagccgttcg acggctacac cgacccggtt   1260
gccagcgaaa agaagttggt gcgcaacgct tttcgagatg cgactgtttg gttcaacacc   1320
ggtgacgtga tgagcccgca gggcatgggc catgccgcct tcgtcgatcg gctgggcgac   1380
accttccgct ggaagggcga gaatgtcgcc accactcagg tcgaagcggc actggcctcc   1440
gaccagaccg tcgaggagtg cacggtctac ggcgtccaga ttccgcgcac cggcgggcgc   1500
gccggaatgg ccgcgatcac actgcgcgct ggcgccgaat cgacggcca ggcgctggcc    1560
cgaacggttt acggtcactt gcccggctat gcacttccgc tctttgttcg ggtagtgggg   1620
tcgctggcgc acaccacgac gttcaagagt cgcaaggtgg agttgcgcaa ccaggcctat   1680
ggcgccgaca tcgaggatcc gctgtacgta ctggccggcc cggacgaagg atatgtgccg   1740
tactacgccg aatacctga ggaggtttcg ctcggaaggc gaccgcaggg ctag           1794
```

<210> SEQ ID NO 91
<211> LENGTH: 597
<212> TYPE: PRT
<213> ORGANISM: Mycobacterium tuberculosis

<400> SEQUENCE: 91

```
Met Ser Asp Tyr Tyr Gly Gly Ala His Thr Thr Val Arg Leu Ile Asp
  1               5                  10                  15

Leu Ala Thr Arg Met Pro Arg Val Leu Ala Asp Thr Pro Val Ile Val
                 20                  25                  30

Arg Gly Ala Met Thr Gly Leu Leu Ala Arg Pro Asn Ser Lys Ala Ser
             35                  40                  45

Ile Gly Thr Val Phe Gln Asp Arg Ala Ala Arg Tyr Gly Asp Arg Val
         50                  55                  60

Phe Leu Lys Phe Gly Asp Gln Gln Leu Thr Tyr Arg Asp Ala Asn Ala
 65                  70                  75                  80

Thr Ala Asn Arg Tyr Ala Ala Val Leu Ala Ala Arg Gly Val Gly Pro
                 85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
            115                 120                 125

Tyr His Gln Arg Gly Glu Val Leu Ala His Ser Leu Gly Leu Leu Asp
        130                 135                 140

Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
                165                 170                 175

Asp Val Glu Arg Phe Ala Thr Thr Ala Pro Ala Thr Asn Pro Ala Ser
            180                 185                 190

Ala Ser Ala Val Gln Ala Lys Asp Thr Ala Phe Tyr Ile Phe Thr Ser
            195                 200                 205

Gly Thr Thr Gly Phe Pro Lys Ala Ser Val Met Thr His His Arg Trp
        210                 215                 220
```

```
Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
            245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
            275                 280                 285

Arg Ala Thr Ala Phe Val Tyr Ile Gly Glu Ile Cys Arg Tyr Leu Leu
290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
                340                 345                 350

Ser Ala Phe Ile Asn Ile Phe Asn Val Pro Arg Thr Ala Gly Val Ser
            355                 360                 365

Pro Met Pro Leu Ala Phe Val Glu Tyr Asp Leu Asp Thr Gly Asp Pro
370                 375                 380

Leu Arg Asp Ala Ser Gly Arg Val Arg Val Pro Asp Gly Glu Pro
385                 390                 395                 400

Gly Leu Leu Leu Ser Arg Val Asn Arg Leu Gln Pro Phe Asp Gly Tyr
                405                 410                 415

Thr Asp Pro Val Ala Ser Glu Lys Lys Leu Val Arg Asn Ala Phe Arg
            420                 425                 430

Asp Gly Asp Cys Trp Phe Asn Thr Gly Asp Val Met Ser Pro Gln Gly
            435                 440                 445

Met Gly His Ala Ala Phe Val Asp Arg Leu Gly Asp Thr Phe Arg Trp
450                 455                 460

Lys Gly Glu Asn Val Ala Thr Thr Gln Val Glu Ala Ala Leu Ala Ser
465                 470                 475                 480

Asp Gln Thr Val Glu Glu Cys Thr Val Tyr Gly Val Gln Ile Pro Arg
                485                 490                 495

Thr Gly Gly Arg Ala Gly Met Ala Ala Ile Thr Leu Arg Ala Gly Ala
                500                 505                 510

Glu Phe Asp Gly Gln Ala Leu Ala Arg Thr Val Tyr Gly His Leu Pro
            515                 520                 525

Gly Tyr Ala Leu Pro Leu Phe Val Arg Val Val Gly Ser Leu Ala His
530                 535                 540

Thr Thr Thr Phe Lys Ser Arg Lys Val Glu Leu Arg Asn Gln Ala Tyr
545                 550                 555                 560

Gly Ala Asp Ile Glu Asp Pro Leu Tyr Val Leu Ala Gly Pro Asp Glu
                565                 570                 575

Gly Tyr Val Pro Tyr Tyr Ala Glu Tyr Pro Glu Glu Val Ser Leu Gly
                580                 585                 590

Arg Arg Pro Gln Gly
            595

<210> SEQ ID NO 92
<211> LENGTH: 646
<212> TYPE: PRT
<213> ORGANISM: Mus musculus
```

-continued

```
<400> SEQUENCE: 92

Met Arg Ala Pro Gly Ala Gly Thr Ala Ser Val Ala Ser Leu Ala Leu
1               5                   10                  15

Leu Trp Phe Leu Gly Leu Pro Trp Thr Trp Ser Ala Ala Ala Ala Phe
            20                  25                  30

Cys Val Tyr Val Gly Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Arg Arg Ala Gly Asp Thr Ile Pro Cys
65                  70                  75                  80

Ile Phe Gln Ala Val Ala Arg Arg Gln Pro Glu Arg Leu Ala Leu Val
                85                  90                  95

Asp Ala Ser Ser Gly Ile Cys Trp Thr Phe Ala Gln Leu Asp Thr Tyr
            100                 105                 110

Ser Asn Ala Val Ala Asn Leu Phe Arg Gln Leu Gly Phe Ala Pro Gly
        115                 120                 125

Asp Val Val Ala Val Phe Leu Glu Gly Arg Pro Glu Phe Val Gly Leu
130                 135                 140

Trp Leu Gly Leu Ala Lys Ala Gly Val Val Ala Ala Leu Leu Asn Val
145                 150                 155                 160

Asn Leu Arg Arg Glu Pro Leu Ala Phe Cys Leu Gly Thr Ser Ala Ala
                165                 170                 175

Lys Ala Leu Ile Tyr Gly Gly Glu Met Ala Ala Val Ala Glu Val
            180                 185                 190

Ser Glu Gln Leu Gly Lys Ser Leu Leu Lys Phe Cys Ser Gly Asp Leu
        195                 200                 205

Gly Pro Glu Ser Ile Leu Pro Asp Thr Gln Leu Leu Asp Pro Met Leu
210                 215                 220

Ala Glu Ala Pro Thr Thr Pro Leu Ala Gln Ala Pro Gly Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Ile Ala Ala Phe
            260                 265                 270

Gly His His Ser Tyr Ser Met Arg Ala Ala Asp Val Leu Tyr Asp Cys
        275                 280                 285

Leu Pro Leu Tyr His Ser Ala Gly Asn Ile Met Gly Val Gly Gln Cys
    290                 295                 300

Val Ile Tyr Gly Leu Thr Val Val Leu Arg Lys Lys Phe Ser Ala Ser
305                 310                 315                 320

Arg Phe Trp Asp Asp Cys Val Lys Tyr Asn Cys Thr Val Val Gln Tyr
                325                 330                 335

Ile Gly Glu Ile Cys Arg Tyr Leu Leu Arg Gln Pro Val Arg Asp Val
            340                 345                 350

Glu Gln Arg His Arg Val Arg Leu Ala Val Gly Asn Gly Leu Arg Pro
        355                 360                 365

Ala Ile Trp Glu Glu Phe Thr Gln Arg Phe Gly Val Pro Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Thr His Val
                405                 410                 415
```

```
Tyr Pro Ile Arg Leu Val Lys Val Asn Glu Asp Thr Met Glu Pro Leu
            420                 425                 430

Arg Asp Ser Glu Gly Leu Cys Ile Pro Cys Gln Pro Gly Glu Pro Gly
            435                 440                 445

Leu Leu Val Gly Gln Ile Asn Gln Gln Asp Pro Leu Arg Arg Phe Asp
            450                 455                 460

Gly Tyr Val Ser Asp Ser Ala Thr Asn Lys Lys Ile Ala His Ser Val
465                 470                 475                 480

Phe Arg Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Ala Val Leu
            515                 520                 525

Ser Arg Leu Leu Gly Gln Thr Asp Val Ala Val Tyr Gly Val Ala Val
            530                 535                 540

Pro Gly Val Glu Gly Lys Ala Gly Met Ala Ala Ile Ala Asp Pro His
545                 550                 555                 560

Ser Gln Leu Asp Pro Asn Ser Met Tyr Gln Glu Leu Gln Lys Val Leu
                565                 570                 575

Ala Ser Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
            595                 600                 605

Phe Asp Pro Arg Gln Thr Ser Asp Arg Leu Phe Phe Leu Asp Leu Lys
            610                 615                 620

Gln Gly Arg Tyr Leu Pro Leu Asp Glu Arg Val His Ala Arg Ile Cys
625                 630                 635                 640

Ala Gly Asp Phe Ser Leu
                645

<210> SEQ ID NO 93
<211> LENGTH: 620
<212> TYPE: PRT
<213> ORGANISM: Mus musculus
<220> FEATURE:
<221> NAME/KEY: VARIANT
<222> LOCATION: (1)...(620)
<223> OTHER INFORMATION: Xaa = Any Amino Acid

<400> SEQUENCE: 93

Met Leu Pro Val Leu Tyr Thr Gly Leu Ala Gly Leu Leu Leu Pro
  1               5                  10                  15

Leu Leu Leu Thr Cys Cys Pro Tyr Leu Leu Gln Asp Val Arg Tyr
            20                  25                  30

Phe Leu Arg Leu Ala Asn Met Ala Arg Arg Val Arg Ser Tyr Arg Gln
            35                  40                  45

Arg Arg Pro Val Arg Thr Ile Leu Arg Ala Phe Leu Glu Gln Ala Arg
            50                  55                  60

Lys Thr Pro His Lys Pro Phe Leu Leu Phe Arg Asp Glu Thr Leu Thr
 65                 70                  75                  80

Tyr Ala Gln Val Asp Arg Arg Ser Asn Gln Val Ala Arg Ala Leu His
                85                  90                  95

Asp Gln Leu Gly Leu Arg Gln Gly Asp Cys Val Ala Leu Phe Met Gly
            100                 105                 110
```

```
Asn Glu Pro Ala Tyr Val Trp Ile Trp Leu Gly Leu Leu Lys Leu Gly
        115                 120                 125

Cys Pro Met Ala Cys Leu Asn Tyr Asn Ile Arg Ala Lys Ser Leu Leu
130                 135                 140

His Cys Phe Gln Cys Cys Gly Ala Lys Val Leu Leu Ala Ser Pro Asp
145                 150                 155                 160

Leu Gln Glu Ala Val Glu Glu Val Leu Pro Thr Leu Lys Lys Asp Ala
                165                 170                 175

Val Ser Val Phe Tyr Val Ser Arg Thr Ser Asn Thr Asn Gly Val Asp
                180                 185                 190

Thr Ile Leu Asp Lys Val Asp Gly Val Ser Ala Glu Pro Thr Pro Glu
        195                 200                 205

Ser Trp Arg Ser Glu Val Thr Phe Thr Thr Pro Ala Val Tyr Ile Tyr
        210                 215                 220

Thr Ser Gly Thr Thr Gly Leu Pro Lys Ala Ala Thr Ile Asn His His
225                 230                 235                 240

Arg Leu Arg Tyr Gly Thr Gly Leu Ala Met Ser Ser Gly Ile Thr Ala
                245                 250                 255

Gln Asp Val Ile Tyr Thr Thr Met Pro Leu Tyr His Ser Ala Ala Leu
                260                 265                 270

Met Ile Gly Leu His Gly Cys Ile Val Val Gly Ala Xaa Xaa Xaa Leu
        275                 280                 285

Cys Asp Lys Phe Ser Ala Ser Gln Phe Trp Asp Asp Cys Arg Lys Tyr
        290                 295                 300

Asn Val Thr Val Ile Gln Tyr Ile Gly Glu Leu Leu Arg Tyr Leu Cys
305                 310                 315                 320

Asn Thr Pro Gln Lys Pro Asn Asp Arg Asp His Lys Val Lys Lys Ala
                325                 330                 335

Leu Gly Asn Gly Leu Arg Gly Asp Val Trp Arg Glu Phe Ile Lys Arg
                340                 345                 350

Phe Gly Asp Ile His Val Tyr Glu Phe Tyr Ala Ser Thr Glu Gly Asn
        355                 360                 365

Ile Gly Phe Val Asn Tyr Pro Arg Lys Ile Gly Ala Val Gly Arg Ala
        370                 375                 380

Asn Tyr Leu Gln Arg Lys Val Ala Arg Tyr Glu Leu Ile Lys Tyr Asp
385                 390                 395                 400

Val Glu Lys Asp Glu Pro Val Arg Asp Ala Asn Gly Tyr Cys Ile Lys
                405                 410                 415

Val Pro Lys Gly Glu Val Gly Leu Leu Val Cys Lys Ile Thr Gln Leu
                420                 425                 430

Thr Pro Phe Ile Gly Tyr Ala Gly Gly Lys Thr Gln Thr Glu Lys Lys
        435                 440                 445

Lys Leu Arg Asp Val Phe Lys Lys Gly Asp Ile Tyr Phe Asn Ser Gly
450                 455                 460

Asp Leu Leu Met Ile Asp Arg Glu Asn Phe Val Tyr Phe His Asp Arg
465                 470                 475                 480

Val Gly Asp Thr Phe Arg Trp Lys Gly Glu Asn Val Ala Thr Thr Glu
                485                 490                 495

Val Ala Asp Ile Val Gly Leu Val Asp Phe Val Glu Glu Val Asn Val
                500                 505                 510

Tyr Gly Val Pro Val Pro Gly His Glu Gly Arg Ile Gly Met Ala Ser
        515                 520                 525

Leu Lys Ile Lys Glu Asn Tyr Glu Phe Asn Gly Lys Lys Leu Phe Gln
```

```
              530              535              540
His Ile Ala Glu Tyr Leu Pro Ser Tyr Ala Arg Pro Arg Phe Leu Arg
545                  550                  555                  560

Ile Gln Asp Thr Ile Glu Ile Thr Gly Thr Phe Lys His Arg Lys Val
                565                  570                  575

Thr Leu Met Glu Glu Gly Phe Asn Pro Thr Val Ile Lys Asp Thr Leu
            580                  585                  590

Tyr Phe Met Asp Asp Ala Glu Lys Thr Phe Val Pro Met Thr Glu Asn
        595                  600                  605

Ile Tyr Asn Ala Ile Ile Asp Lys Thr Leu Lys Leu
    610                  615                  620

<210> SEQ ID NO 94
<211> LENGTH: 613
<212> TYPE: PRT
<213> ORGANISM: Mus musculus

<400> SEQUENCE: 94

Ala Ala Asp Pro Glu Ser Ser Glu Ser Gly Cys Ser Leu Ala Trp Arg
1               5                   10                  15

Leu Ala Tyr Leu Ala Arg Glu Gln Pro Thr His Thr Phe Leu Ile His
                20                  25                  30

Gly Ala Gln Arg Phe Ser Tyr Ala Glu Ala Glu Arg Glu Ser Asn Arg
            35                  40                  45

Ile Ala Arg Ala Phe Leu Arg Ala Arg Gly Trp Thr Gly Gly Arg Arg
        50                  55                  60

Gly Ser Gly Arg Gly Ser Thr Glu Glu Gly Ala Arg Val Ala Pro Pro
65                  70                  75                  80

Ala Gly Asp Ala Ala Ala Arg Gly Thr Thr Ala Pro Pro Leu Ala Pro
                85                  90                  95

Gly Ala Thr Val Ala Leu Leu Leu Pro Ala Gly Pro Asp Phe Leu Trp
            100                 105                 110

Ile Trp Phe Gly Leu Ala Lys Ala Gly Leu Arg Thr Ala Phe Val Pro
        115                 120                 125

Thr Ala Leu Arg Arg Gly Pro Leu Leu His Cys Leu Arg Ser Cys Gly
    130                 135                 140

Ala Ser Ala Leu Val Leu Ala Thr Glu Phe Leu Glu Ser Leu Glu Pro
145                 150                 155                 160

Asp Leu Pro Ala Leu Arg Ala Met Gly Leu His Leu Trp Ala Thr Gly
                165                 170                 175

Pro Glu Thr Asn Val Ala Gly Ile Ser Asn Leu Leu Ser Glu Ala Ala
            180                 185                 190

Asp Gln Val Asp Glu Pro Val Pro Gly Tyr Leu Ser Ala Pro Gln Asn
        195                 200                 205

Ile Met Asp Thr Cys Leu Tyr Ile Phe Thr Ser Gly Thr Thr Gly Leu
    210                 215                 220

Pro Lys Ala Ala Arg Ile Ser His Leu Lys Val Leu Gln Cys Gln Gly
225                 230                 235                 240

Phe Tyr His Leu Cys Gly Val His Gln Glu Asp Val Ile Tyr Leu Ala
                245                 250                 255

Leu Pro Leu Tyr His Met Ser Gly Ser Leu Leu Gly Ile Val Gly Cys
            260                 265                 270

Leu Gly Ile Gly Ala Thr Val Val Leu Lys Pro Lys Phe Ser Ala Ser
        275                 280                 285
```

```
Gln Phe Trp Asp Asp Cys Gln Lys His Arg Val Thr Val Phe Gln Tyr
    290                 295                 300

Ile Gly Glu Leu Cys Arg Tyr Leu Val Asn Gln Pro Pro Ser Lys Ala
305                 310                 315                 320

Glu Phe Asp His Lys Val Arg Leu Ala Val Gly Ser Gly Leu Arg Pro
                325                 330                 335

Asp Thr Trp Glu Arg Phe Leu Arg Arg Phe Gly Pro Leu Gln Ile Leu
            340                 345                 350

Glu Thr Tyr Gly Met Thr Glu Gly Asn Val Ala Thr Phe Asn Tyr Thr
        355                 360                 365

Gly Arg Gln Gly Ala Val Gly Arg Ala Ser Trp Leu Tyr Lys His Ile
    370                 375                 380

Phe Pro Phe Ser Leu Ile Arg Tyr Asp Val Met Thr Gly Glu Pro Ile
385                 390                 395                 400

Arg Asn Ala Gln Gly His Cys Met Thr Thr Ser Pro Gly Glu Pro Gly
                405                 410                 415

Leu Leu Val Ala Pro Val Ser Gln Gln Ser Pro Phe Leu Gly Tyr Ala
            420                 425                 430

Gly Ala Pro Glu Leu Ala Lys Asp Lys Leu Leu Lys Asp Val Phe Trp
        435                 440                 445

Ser Gly Asp Val Phe Phe Asn Thr Gly Asp Leu Leu Val Cys Asp Glu
450                 455                 460

Gln Gly Phe Leu His Phe His Asp Arg Thr Gly Asp Thr Ile Arg Trp
465                 470                 475                 480

Lys Gly Glu Asn Val Ala Thr Thr Glu Val Ala Glu Val Leu Glu Thr
                485                 490                 495

Leu Asp Phe Leu Gln Glu Val Asn Ile Tyr Gly Val Thr Val Pro Gly
            500                 505                 510

His Glu Gly Arg Ala Gly Met Ala Ala Leu Ala Leu Arg Pro Pro Gln
        515                 520                 525

Ala Leu Asn Leu Val Gln Leu Tyr Ser His Val Ser Glu Asn Leu Pro
    530                 535                 540

Pro Tyr Ala Arg Pro Arg Phe Leu Arg Leu Gln Glu Ser Leu Ala Thr
545                 550                 555                 560

Thr Glu Thr Phe Lys Gln Gln Lys Val Arg Met Ala Asn Glu Gly Phe
                565                 570                 575

Asp Pro Ser Val Leu Ser Asp Pro Leu Tyr Val Leu Asp Gln Asp Ile
            580                 585                 590

Gly Ala Tyr Leu Pro Leu Thr Pro Ala Arg Tyr Ser Ala Leu Leu Ser
        595                 600                 605

Gly Asp Leu Arg Ile
    610

<210> SEQ ID NO 95
<211> LENGTH: 506
<212> TYPE: PRT
<213> ORGANISM: Mus musculus

<400> SEQUENCE: 95

His Ala Ser Ala His Ala Ser Gly Met Ala Lys Leu Gly Val Glu Ala
1               5                   10                  15

Ala Leu Ile Asn Thr Asn Leu Arg Arg Asp Ala Leu Arg His Cys Leu
            20                  25                  30

Asp Thr Ser Lys Ala Arg Ala Leu Ile Phe Gly Ser Glu Met Ala Ser
        35                  40                  45
```

```
Ala Ile Cys Glu Ile His Ala Ser Leu Glu Pro Thr Leu Ser Leu Phe
 50                  55                  60

Cys Ser Gly Ser Trp Glu Pro Ser Thr Val Pro Val Ser Thr Glu His
 65                  70                  75                  80

Leu Asp Pro Leu Leu Glu Asp Ala Pro Lys His Leu Pro Ser His Pro
                 85                  90                  95

Asp Lys Gly Phe Thr Asp Lys Leu Phe Tyr Ile Tyr Thr Ser Gly Thr
                100                 105                 110

Thr Gly Leu Pro Lys Ala Ala Ile Val Val His Ser Arg Tyr Tyr Arg
                115                 120                 125

Met Ala Ser Leu Val Tyr Gly Phe Arg Met Arg Pro Asp Asp Ile
    130                 135                 140

Val Tyr Asp Cys Leu Pro Leu Tyr His Ser Ser Arg Lys His Arg Gly
145                 150                 155                 160

Asp Trp Gln Cys Leu Leu His Gly Met Thr Val Ile Arg Lys Lys
                165                 170                 175

Phe Ser Ala Ser Arg Phe Trp Asp Asp Cys Ile Lys Tyr Asn Cys Thr
                180                 185                 190

Val Val Gln Tyr Ile Gly Glu Leu Cys Arg Tyr Leu Leu Asn Gln Pro
                195                 200                 205

Pro Arg Glu Ala Glu Ser Arg His Lys Val Arg Met Ala Leu Gly Asn
210                 215                 220

Gly Leu Arg Gln Ser Ile Trp Thr Asp Phe Ser Ser Arg Phe His Ile
225                 230                 235                 240

Pro Gln Val Ala Glu Phe Tyr Gly Ala Thr Glu Cys Asn Cys Ser Leu
                245                 250                 255

Gly Asn Phe Asp Ser Arg Val Gly Ala Cys Gly Phe Asn Ser Arg Ile
                260                 265                 270

Leu Ser Phe Val Tyr Pro Ile Arg Leu Val Arg Val Asn Glu Asp Thr
                275                 280                 285

Met Glu Leu Ile Arg Gly Pro Asp Gly Val Cys Ile Pro Cys Gln Pro
    290                 295                 300

Gly Gln Pro Gly Gln Leu Val Gly Arg Ile Ile Gln Gln Asp Pro Leu
305                 310                 315                 320

Arg Arg Phe Asp Gly Tyr Leu Asn Gln Gly Ala Asn Asn Lys Lys Ile
                325                 330                 335

Ala Asn Asp Val Phe Lys Lys Gly Asp Gln Ala Tyr Leu Thr Gly Asp
                340                 345                 350

Val Leu Val Met Asp Glu Leu Gly Tyr Leu Tyr Phe Arg Asp Arg Thr
    355                 360                 365

Gly Asp Thr Phe Arg Trp Lys Gly Glu Asn Val Ser Thr Thr Glu Val
    370                 375                 380

Glu Gly Thr Leu Ser Arg Leu Leu His Met Ala Asp Val Ala Val Tyr
385                 390                 395                 400

Gly Val Glu Val Pro Gly Thr Glu Gly Arg Ala Gly Met Ala Ala Val
                405                 410                 415

Ala Ser Pro Ile Ser Asn Cys Asp Leu Glu Ser Phe Ala Gln Thr Leu
                420                 425                 430

Lys Lys Glu Leu Pro Leu Tyr Ala Arg Pro Ile Phe Leu Arg Phe Leu
        435                 440                 445

Pro Glu Leu His Lys Thr Gly Thr Phe Lys Phe Gln Lys Thr Glu Leu
450                 455                 460
```

```
Arg Lys Glu Gly Phe Asp Pro Ser Val Val Lys Asp Pro Leu Phe Tyr
465                 470                 475                 480

Leu Asp Ala Arg Lys Gly Cys Tyr Val Ala Leu Asp Gln Glu Ala Tyr
            485                 490                 495

Thr Arg Ile Gln Ala Gly Glu Glu Lys Leu
        500                 505

<210> SEQ ID NO 96
<211> LENGTH: 662
<212> TYPE: PRT
<213> ORGANISM: Mus musculus

<400> SEQUENCE: 96

Met Ala Leu Ala Leu Arg Trp Phe Leu Gly Asp Pro Thr Cys Leu Val
1               5                   10                  15

Leu Leu Gly Leu Ala Leu Leu Gly Arg Pro Trp Ile Ser Ser Trp Met
            20                  25                  30

Pro His Trp Leu Ser Leu Val Gly Ala Ala Leu Thr Leu Phe Leu Leu
        35                  40                  45

Pro Leu Gln Pro Pro Pro Gly Leu Arg Trp Leu His Lys Asp Val Ala
    50                  55                  60

Phe Thr Phe Lys Met Leu Phe Tyr Gly Leu Lys Phe Arg Arg Arg Leu
65                  70                  75                  80

Asn Lys His Pro Pro Glu Thr Phe Val Asp Ala Leu Glu Arg Gln Ala
                85                  90                  95

Leu Ala Trp Pro Asp Arg Val Ala Leu Val Cys Thr Gly Ser Glu Gly
            100                 105                 110

Ser Ser Ile Thr Asn Ser Gln Leu Asp Ala Arg Ser Cys Gln Ala Ala
        115                 120                 125

Trp Val Leu Lys Ala Lys Leu Lys Asp Ala Val Ile Gln Asn Thr Arg
130                 135                 140

Asp Ala Ala Ala Ile Leu Val Leu Pro Ser Lys Thr Ile Ser Ala Leu
145                 150                 155                 160

Ser Val Phe Leu Gly Leu Ala Lys Leu Gly Cys Pro Val Ala Trp Ile
                165                 170                 175

Asn Pro His Ser Arg Gly Met Pro Leu Leu His Ser Val Arg Ser Ser
                180                 185                 190

Gly Ala Ser Val Leu Ile Val Asp Pro Asp Leu Gln Glu Asn Leu Glu
            195                 200                 205

Glu Val Leu Pro Lys Leu Ala Glu Asn Ile His Cys Phe Tyr Leu
        210                 215                 220

Gly His Ser Ser Pro Thr Pro Gly Val Glu Ala Leu Gly Ala Ser Leu
225                 230                 235                 240

Asp Ala Ala Pro Ser Asp Pro Val Pro Ala Ser Leu Arg Ala Thr Ile
                245                 250                 255

Lys Trp Lys Ser Pro Ala Ile Phe Ile Phe Thr Ser Gly Thr Thr Gly
            260                 265                 270

Leu Pro Lys Pro Ala Ile Leu Ser His Glu Arg Val Ile Gln Val Ser
        275                 280                 285

Asn Val Leu Ser Phe Cys Gly Cys Arg Ala Asp Asp Val Val Tyr Asp
    290                 295                 300

Val Leu Pro Leu Tyr His Thr Ile Gly Leu Val Leu Gly Phe Leu Gly
305                 310                 315                 320

Cys Leu Gln Val Gly Ala Thr Cys Val Leu Ala Pro Lys Phe Ser Ala
                325                 330                 335
```

-continued

```
Ser Arg Phe Trp Ala Glu Cys Arg Gln His Gly Val Thr Val Ile Leu
        340                 345                 350

Tyr Val Gly Glu Ile Leu Arg Tyr Leu Cys Asn Val Pro Glu Gln Pro
        355                 360                 365

Glu Asp Lys Ile His Thr Val Arg Leu Ala Met Gly Thr Gly Leu Arg
        370                 375                 380

Ala Asn Val Trp Lys Asn Phe Gln Gln Arg Phe Gly Pro Ile Arg Ile
385                 390                 395                 400

Trp Glu Phe Tyr Gly Ser Thr Glu Gly Asn Val Gly Leu Met Asn Tyr
                405                 410                 415

Val Gly His Cys Gly Ala Val Gly Arg Thr Ser Cys Ile Leu Arg Met
                420                 425                 430

Leu Thr Pro Phe Glu Leu Val Gln Phe Asp Ile Glu Thr Ala Glu Pro
                435                 440                 445

Leu Arg Asp Lys Gln Gly Phe Cys Ile Pro Val Glu Pro Gly Lys Pro
450                 455                 460

Gly Leu Leu Leu Thr Lys Val Arg Lys Asn Gln Pro Phe Leu Gly Tyr
465                 470                 475                 480

Arg Gly Ser Gln Ala Glu Ser Asn Arg Lys Leu Val Ala Asn Val Arg
                485                 490                 495

Arg Val Gly Asp Leu Tyr Phe Asn Thr Gly Asp Val Leu Thr Leu Asp
                500                 505                 510

Gln Glu Gly Phe Phe Tyr Phe Gln Asp Arg Leu Gly Asp Thr Phe Arg
                515                 520                 525

Trp Lys Gly Glu Asn Val Ser Thr Gly Glu Val Glu Cys Val Leu Ser
        530                 535                 540

Ser Leu Asp Phe Leu Glu Glu Val Asn Val Tyr Gly Val Pro Val Pro
545                 550                 555                 560

Gly Cys Glu Gly Lys Val Gly Met Ala Ala Val Lys Leu Ala Pro Gly
                565                 570                 575

Lys Thr Phe Asp Gly Gln Lys Leu Tyr Gln His Val Arg Ser Trp Leu
                580                 585                 590

Pro Ala Tyr Ala Thr Pro His Phe Ile Arg Ile Gln Asp Ser Leu Glu
            595                 600                 605

Ile Thr Asn Thr Tyr Lys Leu Val Lys Ser Arg Leu Val Arg Glu Gly
        610                 615                 620

Phe Asp Val Gly Ile Ile Ala Asp Pro Leu Tyr Ile Leu Asp Asn Lys
625                 630                 635                 640

Ala Gln Thr Phe Arg Ser Leu Met Pro Asp Val Tyr Gln Ala Val Cys
                645                 650                 655

Glu Gly Thr Trp Asn Leu
            660

<210> SEQ ID NO 97
<211> LENGTH: 650
<212> TYPE: PRT
<213> ORGANISM: Caenorhabditis elegans

<400> SEQUENCE: 97

Met Lys Leu Glu Glu Leu Val Thr Val Met Leu Leu Thr Val Ala Val
 1               5                  10                  15

Ile Ala Gln Asn Leu Pro Ile Gly Val Ile Leu Ala Gly Val Leu Ile
            20                  25                  30

Leu Tyr Ile Thr Val Val His Gly Asp Phe Ile Tyr Arg Ser Tyr Leu
```

-continued

```
                35                  40                  45
Thr Leu Asn Arg Asp Leu Thr Gly Leu Ala Leu Ile Ile Glu Val Lys
            50                  55                  60

Ile Asp Leu Trp Trp Arg Leu His Gln Asn Lys Gly Ile His Glu Leu
 65                  70                  75                  80

Phe Leu Asp Ile Val Lys Lys Asn Pro Asn Lys Pro Ala Met Ile Asp
                85                  90                  95

Ile Glu Thr Asn Thr Thr Glu Thr Tyr Ala Glu Phe Asn Ala His Cys
            100                 105                 110

Asn Arg Tyr Ala Asn Tyr Phe Gln Gly Leu Gly Tyr Arg Ser Gly Asp
                115                 120                 125

Val Val Ala Leu Tyr Met Glu Asn Ser Val Glu Phe Val Ala Ala Trp
            130                 135                 140

Met Gly Leu Ala Lys Ile Gly Val Val Thr Ala Trp Ile Asn Ser Asn
145                 150                 155                 160

Leu Lys Arg Glu Gln Leu Val His Cys Ile Thr Ala Ser Lys Thr Lys
                165                 170                 175

Ala Ile Ile Thr Ser Val Thr Leu Gln Asn Ile Met Leu Asp Ala Ile
                180                 185                 190

Asp Gln Lys Leu Phe Asp Val Glu Gly Ile Glu Val Tyr Ser Val Gly
            195                 200                 205

Glu Pro Lys Lys Asn Ser Gly Phe Lys Asn Leu Lys Lys Leu Asp
            210                 215                 220

Ala Gln Ile Thr Thr Glu Pro Lys Thr Leu Asp Ile Val Asp Phe Lys
225                 230                 235                 240

Ser Ile Leu Cys Phe Ile Tyr Thr Ser Gly Thr Thr Gly Met Pro Lys
                245                 250                 255

Ala Ala Val Met Lys His Phe Arg Tyr Tyr Ser Ile Ala Val Gly Ala
                260                 265                 270

Ala Lys Ser Phe Gly Ile Arg Pro Ser Asp Arg Met Tyr Val Ser Met
                275                 280                 285

Pro Ile Tyr His Thr Ala Ala Gly Ile Leu Gly Val Gly Gln Ala Leu
            290                 295                 300

Leu Gly Ser Ser Cys Val Ile Arg Lys Lys Phe Ser Ala Ser Asn
305                 310                 315                 320

Phe Trp Arg Asp Cys Val Lys Tyr Asp Cys Thr Val Ser Gln Tyr Ile
                325                 330                 335

Gly Glu Ile Cys Arg Tyr Leu Leu Ala Gln Pro Val Val Glu Glu Glu
            340                 345                 350

Ser Arg His Arg Met Arg Leu Leu Val Gly Asn Gly Leu Arg Ala Glu
            355                 360                 365

Ile Trp Gln Pro Phe Val Asp Arg Phe Arg Val Arg Ile Gly Glu Leu
370                 375                 380

Tyr Gly Ser Thr Glu Gly Thr Ser Ser Leu Val Asn Ile Asp Gly His
385                 390                 395                 400

Val Gly Ala Cys Gly Phe Leu Pro Ile Ser Pro Leu Thr Lys Lys Met
                405                 410                 415

His Pro Val Arg Leu Ile Lys Val Asp Asp Val Thr Gly Glu Ala Ile
            420                 425                 430

Arg Thr Ser Asp Gly Leu Cys Ile Ala Cys Asn Pro Gly Glu Ser Gly
            435                 440                 445

Ala Met Val Ser Thr Ile Arg Lys Asn Asn Pro Leu Leu Gln Phe Glu
450                 455                 460
```

```
Gly Tyr Leu Asn Lys Lys Glu Thr Asn Lys Lys Ile Ile Arg Asp Val
465                 470                 475                 480

Phe Ala Lys Gly Asp Ser Cys Phe Leu Thr Gly Asp Leu Leu His Trp
                485                 490                 495

Asp Arg Leu Gly Tyr Val Tyr Phe Lys Asp Arg Thr Gly Asp Thr Phe
                500                 505                 510

Arg Trp Lys Gly Glu Asn Val Ser Thr Thr Glu Val Glu Ala Ile Leu
            515                 520                 525

His Pro Ile Thr Gly Leu Ser Asp Ala Thr Val Tyr Gly Val Glu Val
            530                 535                 540

Pro Gln Arg Glu Gly Arg Val Gly Met Ala Ser Val Val Arg Val Val
545                 550                 555                 560

Ser His Glu Glu Asp Glu Thr Gln Phe Val His Arg Val Gly Ala Arg
                565                 570                 575

Leu Ala Ser Ser Leu Thr Ser Tyr Ala Ile Pro Gln Phe Met Arg Ile
                580                 585                 590

Cys Gln Asp Val Glu Lys Thr Gly Thr Phe Lys Leu Val Lys Thr Asn
            595                 600                 605

Leu Gln Arg Leu Gly Ile Met Asp Ala Pro Ser Asp Ser Ile Tyr Ile
            610                 615                 620

Tyr Asn Ser Glu Asn Arg Asn Phe Val Pro Phe Asp Asn Asp Leu Arg
625                 630                 635                 640

Cys Lys Val Ser Leu Gly Ser Tyr Pro Phe
                645                 650

<210> SEQ ID NO 98
<211> LENGTH: 623
<212> TYPE: PRT
<213> ORGANISM: Saccharomyces cerevisiae

<400> SEQUENCE: 98

Met Ser Pro Ile Gln Val Val Phe Ala Leu Ser Arg Ile Phe Leu
 1               5                  10                  15

Leu Leu Phe Arg Leu Ile Lys Leu Ile Ile Thr Pro Ile Gln Lys Ser
                20                  25                  30

Leu Gly Tyr Leu Phe Gly Asn Tyr Phe Asp Glu Leu Asp Arg Lys Tyr
            35                  40                  45

Arg Tyr Lys Glu Asp Trp Tyr Ile Pro Tyr Phe Leu Lys Ser Val
    50                  55                  60

Phe Cys Tyr Ile Ile Asp Val Arg Arg His Arg Phe Gln Asn Trp Tyr
65                  70                  75                  80

Leu Phe Ile Lys Gln Val Gln Gln Asn Gly Asp His Leu Ala Ile Ser
                85                  90                  95

Tyr Thr Arg Pro Met Ala Glu Lys Gly Glu Phe Gln Leu Glu Thr Phe
            100                 105                 110

Thr Tyr Ile Glu Thr Tyr Asn Ile Val Leu Arg Leu Ser His Ile Leu
        115                 120                 125

His Phe Asp Tyr Asn Val Gln Ala Gly Asp Tyr Val Ala Ile Asp Cys
    130                 135                 140

Thr Asn Lys Pro Leu Phe Val Phe Leu Trp Leu Ser Leu Trp Asn Ile
145                 150                 155                 160

Gly Ala Ile Pro Ala Phe Leu Asn Tyr Asn Thr Lys Gly Thr Pro Leu
                165                 170                 175

Val His Ser Leu Lys Ile Ser Asn Ile Thr Gln Val Phe Ile Asp Pro
```

-continued

```
              180                 185                 190
Asp Ala Ser Asn Pro Ile Arg Glu Ser Glu Glu Ile Lys Asn Ala
            195                 200                 205
Leu Pro Asp Val Lys Leu Asn Tyr Leu Glu Glu Gln Asp Leu Met His
210                 215                 220
Glu Leu Leu Asn Ser Gln Ser Pro Glu Phe Leu Gln Gln Asp Asn Val
225                 230                 235                 240
Arg Thr Pro Leu Gly Leu Thr Asp Phe Lys Pro Ser Met Leu Ile Tyr
            245                 250                 255
Thr Ser Gly Thr Thr Gly Leu Pro Lys Ser Ala Ile Met Ser Trp Arg
            260                 265                 270
Lys Ser Ser Val Gly Cys Gln Val Phe Gly His Val Leu His Met Thr
            275                 280                 285
Asn Glu Ser Thr Val Phe Thr Ala Met Pro Leu Phe His Ser Thr Ala
            290                 295                 300
Ala Leu Leu Gly Ala Cys Ala Ile Leu Ser His Gly Gly Cys Leu Ala
305                 310                 315                 320
Leu Ser His Lys Phe Ser Ala Ser Thr Phe Trp Lys Gln Val Tyr Leu
            325                 330                 335
Thr Gly Ala Thr His Ile Gln Tyr Val Gly Glu Val Cys Arg Tyr Leu
            340                 345                 350
Leu His Thr Pro Ile Ser Lys Tyr Glu Lys Met His Lys Val Lys Val
            355                 360                 365
Ala Tyr Gly Asn Gly Leu Arg Pro Asp Ile Trp Gln Asp Phe Arg Lys
370                 375                 380
Arg Phe Asn Ile Glu Val Ile Gly Glu Phe Tyr Ala Ala Thr Glu Ala
385                 390                 395                 400
Pro Phe Ala Thr Thr Thr Phe Gln Lys Gly Asp Phe Gly Ile Gly Ala
            405                 410                 415
Cys Arg Asn Tyr Gly Thr Ile Ile Gln Trp Phe Leu Ser Phe Gln Gln
            420                 425                 430
Thr Leu Val Arg Met Asp Pro Asn Asp Asp Ser Val Ile Tyr Arg Asn
            435                 440                 445
Ser Lys Gly Phe Cys Glu Val Ala Pro Val Gly Glu Pro Gly Glu Met
450                 455                 460
Leu Met Arg Ile Phe Phe Pro Lys Lys Pro Glu Thr Ser Phe Gln Gly
465                 470                 475                 480
Tyr Leu Gly Asn Ala Lys Glu Thr Lys Ser Lys Val Val Arg Asp Val
            485                 490                 495
Phe Arg Arg Gly Asp Ala Trp Tyr Arg Cys Gly Asp Leu Leu Lys Ala
            500                 505                 510
Asp Glu Tyr Gly Leu Trp Tyr Phe Leu Asp Arg Met Gly Asp Thr Phe
            515                 520                 525
Arg Trp Lys Ser Glu Asn Val Ser Thr Glu Val Glu Asp Gln Leu
            530                 535                 540
Thr Ala Ser Asn Lys Glu Gln Tyr Ala Gln Val Leu Val Gly Ile
545                 550                 555                 560
Lys Val Pro Lys Tyr Glu Gly Arg Ala Gly Phe Ala Val Ile Lys Leu
            565                 570                 575
Thr Asp Asn Ser Leu Asp Ile Thr Ala Lys Thr Lys Leu Leu Asn Asp
            580                 585                 590
Ser Leu Ser Arg Leu Asn Leu Pro Ser Tyr Ala Met Pro Leu Phe Val
            595                 600                 605
```

```
Lys Phe Val Asp Glu Ile Lys Met Thr Asp Asn Leu Ile Lys Phe
    610                 615                 620

<210> SEQ ID NO 99
<211> LENGTH: 597
<212> TYPE: PRT
<213> ORGANISM: Mycobacterium tuberculosis

<400> SEQUENCE: 99

Met Ser Asp Tyr Tyr Gly Gly Ala His Thr Thr Val Arg Leu Ile Asp
  1               5                  10                  15

Leu Ala Thr Arg Met Pro Arg Val Leu Ala Asp Thr Pro Val Ile Val
                 20                  25                  30

Arg Gly Ala Met Thr Gly Leu Leu Ala Arg Pro Asn Ser Lys Ala Ser
             35                  40                  45

Ile Gly Thr Val Phe Gln Asp Arg Ala Ala Arg Tyr Gly Asp Arg Val
         50                  55                  60

Phe Leu Lys Phe Gly Asp Gln Gln Leu Thr Tyr Arg Asp Ala Asn Ala
 65                  70                  75                  80

Thr Ala Asn Arg Tyr Ala Ala Val Leu Ala Ala Arg Gly Val Gly Pro
                 85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
            115                 120                 125

Tyr His Gln Arg Gly Glu Val Leu Ala His Ser Leu Gly Leu Leu Asp
        130                 135                 140

Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
                165                 170                 175

Asp Val Glu Arg Phe Ala Thr Thr Ala Pro Ala Thr Asn Pro Ala Ser
            180                 185                 190

Ala Ser Ala Val Gln Ala Lys Asp Thr Ala Phe Tyr Ile Phe Thr Ser
        195                 200                 205

Gly Thr Thr Gly Phe Pro Lys Ala Ser Val Met Thr His His Arg Trp
    210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
            340                 345                 350

Ser Ala Phe Ile Asn Ile Phe Asn Val Pro Arg Thr Ala Gly Val Ser
```

```
                    355                 360                 365
Pro Met Pro Leu Ala Phe Val Glu Tyr Asp Leu Asp Thr Gly Asp Pro
        370                 375                 380

Leu Arg Asp Ala Ser Gly Arg Val Arg Val Pro Asp Gly Glu Pro
385                 390                 395                 400

Gly Leu Leu Ser Arg Val Asn Arg Leu Gln Pro Phe Asp Gly Tyr
                405                 410                 415

Thr Asp Pro Val Ala Ser Glu Lys Lys Leu Val Arg Asn Ala Phe Arg
                420                 425                 430

Asp Gly Asp Cys Trp Phe Asn Thr Gly Asp Val Met Ser Pro Gln Gly
            435                 440                 445

Met Gly His Ala Ala Phe Val Asp Arg Leu Gly Asp Thr Phe Arg Trp
        450                 455                 460

Lys Gly Glu Asn Val Ala Thr Thr Gln Val Glu Ala Ala Leu Ala Ser
465                 470                 475                 480

Asp Gln Thr Val Glu Glu Cys Thr Val Tyr Gly Val Gln Ile Pro Arg
                485                 490                 495

Thr Gly Gly Arg Ala Gly Met Ala Ala Ile Thr Leu Arg Ala Gly Ala
            500                 505                 510

Glu Phe Asp Gly Gln Ala Leu Ala Arg Thr Val Tyr Gly His Leu Pro
        515                 520                 525

Gly Tyr Ala Leu Pro Leu Phe Val Arg Val Val Gly Ser Leu Ala His
        530                 535                 540

Thr Thr Thr Phe Lys Ser Arg Lys Val Glu Leu Arg Asn Gln Ala Tyr
545                 550                 555                 560

Gly Ala Asp Ile Glu Asp Pro Leu Tyr Val Leu Ala Gly Pro Asp Glu
                565                 570                 575

Gly Tyr Val Pro Tyr Tyr Ala Glu Tyr Pro Glu Glu Val Ser Leu Gly
                580                 585                 590

Arg Arg Pro Gln Gly
            595

<210> SEQ ID NO 100
<211> LENGTH: 304
<212> TYPE: PRT
<213> ORGANISM: concensus FATP signature sequence

<400> SEQUENCE: 100

Tyr Ile Tyr Thr Ser Gly Thr Thr Gly Leu Pro Lys Ala Ala Ile Ile
1               5                   10                  15

Val His Ser Arg Tyr Tyr Arg Gly Ala Ala Leu His Ser Gly Arg Met
                20                  25                  30

Arg Pro Asp Val Val Tyr Asp Cys Leu Pro Leu Tyr His Ser Ala Ala
            35                  40                  45

Leu Ile Leu Gly Ile Gly Gln Cys Leu Leu His Gly Ala Thr Val Val
        50                  55                  60

Leu Arg Lys Lys Phe Ser Ala Ser Arg Phe Trp Asp Asp Cys Val Lys
65                  70                  75                  80

Tyr Asn Val Thr Val Ile Gln Tyr Ile Gly Glu Leu Cys Arg Tyr Leu
                85                  90                  95

Leu Asn Gln Pro Pro Arg Pro Ala Glu Arg Arg His Lys Val Arg Leu
            100                 105                 110

Ala Val Gly Asn Gly Leu Arg Pro Asp Ile Trp Glu Glu Phe Val Ser
        115                 120                 125
```

-continued

```
Arg Phe Gly Ile Pro Gln Ile Gly Glu Phe Tyr Gly Ala Thr Glu Gly
    130                 135                 140

Asn Cys Ser Leu Met Asn Tyr Asp Gly Lys Val Gly Ala Cys Gly Ser
145                 150                 155                 160

Arg Ile Leu Lys Lys Val Tyr Pro Ile Arg Leu Val Lys Val Asp Glu
                165                 170                 175

Asp Thr Gly Glu Pro Ile Arg Asp Ala Gln Gly Leu Cys Ile Pro Cys
            180                 185                 190

Gln Pro Gly Glu Pro Gly Leu Leu Val Gly Arg Ile Asn Gln Gln Asp
        195                 200                 205

Pro Phe Arg Gly Phe Gly Tyr Gly Ser Glu Gly Ala Thr Asn Lys Lys
    210                 215                 220

Ile Ala Arg Asp Val Phe Lys Lys Gly Asp Val Ala Phe Asn Thr Gly
225                 230                 235                 240

Asp Val Leu Val Met Asp Glu Leu Gly Tyr Leu Tyr Phe Arg Asp Arg
                245                 250                 255

Thr Gly Asp Thr Phe Arg Trp Lys Gly Glu Asn Val Ser Thr Thr Glu
            260                 265                 270

Val Glu Gly Val Leu Ser Arg Leu Asp Phe Val Ala Glu Val Asn Val
        275                 280                 285

Tyr Gly Val Thr Val Pro Gly His Glu Gly Arg Ala Gly Met Ala Ala
    290                 295                 300
```

<210> SEQ ID NO 101
<211> LENGTH: 2166
<212> TYPE: DNA
<213> ORGANISM: Homo sapiens
<220> FEATURE:
<221> NAME/KEY: CDS
<222> LOCATION: (19)...(2124)

<400> SEQUENCE: 101

```
cgacccacgc gtccgggg atg ttt gcg agc ggc tgg aac cag acg gtg ccg         51
                    Met Phe Ala Ser Gly Trp Asn Gln Thr Val Pro
                     1               5                  10 ata gag gaa gcg ggc tcc atg gct gcc ctc ctg ctg ctg ccc ctg ctg         99
Ile Glu Glu Ala Gly Ser Met Ala Ala Leu Leu Leu Leu Pro Leu Leu
              15                  20                  25 ctg ttg cta ccg ctg ctg ctg ctg aag cta cac ctc tgg ccg cag            147
Leu Leu Leu Pro Leu Leu Leu Leu Lys Leu His Leu Trp Pro Gln
          30                  35                  40 ttg cgc tgg ctt ccg gcg gac ttg gcc ttt gcg gtg cga gct ctg tgc        195
Leu Arg Trp Leu Pro Ala Asp Leu Ala Phe Ala Val Arg Ala Leu Cys
 45                  50                  55 tgc aaa agg gct ctt cga gct cgc gcc ctg gcc gcg gct gcc gcc gac        243
Cys Lys Arg Ala Leu Arg Ala Arg Ala Leu Ala Ala Ala Ala Ala Asp
 60                  65                  70                  75 ccg gaa ggt ccc gag ggg ggc tgc agc ctg gcc tgg cgc ctc gcg gaa        291
Pro Glu Gly Pro Glu Gly Gly Cys Ser Leu Ala Trp Arg Leu Ala Glu
                 80                  85                  90 ctg gcc cag cag cgc gcc gcg cac acc ttt ctc att cac ggc tcg cgg        339
Leu Ala Gln Gln Arg Ala Ala His Thr Phe Leu Ile His Gly Ser Arg
             95                 100                 105 cgc ttt agc tac tca gag gcg gag cgc gag agt aac agg gct gca cgc        387
Arg Phe Ser Tyr Ser Glu Ala Glu Arg Glu Ser Asn Arg Ala Ala Arg
        110                 115                 120 gcc ttc cta cgt gcg cta ggc tgg gac tgg gga ccc gac ggc ggc gac        435
Ala Phe Leu Arg Ala Leu Gly Trp Asp Trp Gly Pro Asp Gly Gly Asp
    125                 130                 135
```

-continued

| | | | | | | | | | | | | | | | | |
|---|---|---|---|---|---|---|---|---|---|---|---|---|---|---|---|---|
| | 125 | | | | | 130 | | | | | 135 | | | | | |
| agc | ggc | gag | ggg | agc | gct | gga | gaa | ggc | gag | cgg | gca | gcg | ccg | gga | gcc | 483 |
| Ser | Gly | Glu | Gly | Ser | Ala | Gly | Glu | Gly | Glu | Arg | Ala | Ala | Pro | Gly | Ala | |
| 140 | | | | | 145 | | | | | 150 | | | | | 155 | |
| gga | gat | gca | gcg | gcc | gga | agc | ggc | gcg | gag | ttt | gcc | gga | ggg | gac | ggt | 531 |
| Gly | Asp | Ala | Ala | Ala | Gly | Ser | Gly | Ala | Glu | Phe | Ala | Gly | Gly | Asp | Gly | |
| | | | | 160 | | | | | 165 | | | | | 170 | | |
| gcc | gcc | aga | ggt | gga | gga | gag | ccc | gcc | gcc | cct | ctg | tca | cct | gga | gca | 579 |
| Ala | Ala | Arg | Gly | Gly | Gly | Glu | Pro | Ala | Ala | Pro | Leu | Ser | Pro | Gly | Ala | |
| | | | 175 | | | | | 180 | | | | | 185 | | | |
| act | gtg | gcg | ctg | ctc | ctc | ccc | gct | ggc | cca | gag | ttt | ctg | tgg | ctc | tgg | 627 |
| Thr | Val | Ala | Leu | Leu | Leu | Pro | Ala | Gly | Pro | Glu | Phe | Leu | Trp | Leu | Trp | |
| | | 190 | | | | | 195 | | | | | 200 | | | | |
| ttc | ggg | ctg | gcc | aag | gcc | ggc | ctg | cgc | act | gcc | ttt | gtg | ccc | acc | gcc | 675 |
| Phe | Gly | Leu | Ala | Lys | Ala | Gly | Leu | Arg | Thr | Ala | Phe | Val | Pro | Thr | Ala | |
| | 205 | | | | | 210 | | | | | 215 | | | | | |
| ctg | cgc | cgg | ggc | ccc | ctg | ctg | cac | tgc | ctc | cgc | agc | tgc | ggc | gcg | cgc | 723 |
| Leu | Arg | Arg | Gly | Pro | Leu | Leu | His | Cys | Leu | Arg | Ser | Cys | Gly | Ala | Arg | |
| 220 | | | | | 225 | | | | | 230 | | | | | 235 | |
| gcg | ctg | gtg | ctg | gcg | cca | gag | ttt | ctg | gag | tcc | ctg | gag | ccg | gac | ctg | 771 |
| Ala | Leu | Val | Leu | Ala | Pro | Glu | Phe | Leu | Glu | Ser | Leu | Glu | Pro | Asp | Leu | |
| | | | | 240 | | | | | 245 | | | | | 250 | | |
| ccc | gcc | ctg | aga | gcc | atg | ggg | ctc | cac | ctg | tgg | gct | gca | ggc | cca | gga | 819 |
| Pro | Ala | Leu | Arg | Ala | Met | Gly | Leu | His | Leu | Trp | Ala | Ala | Gly | Pro | Gly | |
| | | | 255 | | | | | 260 | | | | | 265 | | | |
| acc | cac | cct | gct | gga | att | agc | gat | ttg | ctg | gct | gaa | gtg | tcc | gct | gaa | 867 |
| Thr | His | Pro | Ala | Gly | Ile | Ser | Asp | Leu | Leu | Ala | Glu | Val | Ser | Ala | Glu | |
| | | 270 | | | | | 275 | | | | | 280 | | | | |
| gtg | gat | ggg | cca | gtg | cca | gga | tac | ctc | tct | tcc | ccc | cag | agc | ata | aca | 915 |
| Val | Asp | Gly | Pro | Val | Pro | Gly | Tyr | Leu | Ser | Ser | Pro | Gln | Ser | Ile | Thr | |
| | 285 | | | | | 290 | | | | | 295 | | | | | |
| gac | acg | tgc | ctg | tac | atc | ttc | acc | tct | ggc | acc | acg | ggc | ctc | ccc | aag | 963 |
| Asp | Thr | Cys | Leu | Tyr | Ile | Phe | Thr | Ser | Gly | Thr | Thr | Gly | Leu | Pro | Lys | |
| 300 | | | | | 305 | | | | | 310 | | | | | 315 | |
| gct | gct | cgg | atc | agt | cat | ctg | aag | atc | ctg | caa | tgc | cag | ggc | ttc | tat | 1011 |
| Ala | Ala | Arg | Ile | Ser | His | Leu | Lys | Ile | Leu | Gln | Cys | Gln | Gly | Phe | Tyr | |
| | | | | 320 | | | | | 325 | | | | | 330 | | |
| cag | ctg | tgt | ggt | gtc | cac | cag | gaa | gat | gtg | atc | tac | ctc | gcc | ctc | cca | 1059 |
| Gln | Leu | Cys | Gly | Val | His | Gln | Glu | Asp | Val | Ile | Tyr | Leu | Ala | Leu | Pro | |
| | | | 335 | | | | | 340 | | | | | 345 | | | |
| ctc | tac | cac | atg | tcc | ggt | tcc | ctg | ctg | ggc | atc | gtg | ggc | tgc | atg | ggc | 1107 |
| Leu | Tyr | His | Met | Ser | Gly | Ser | Leu | Leu | Gly | Ile | Val | Gly | Cys | Met | Gly | |
| | | | 350 | | | | | 355 | | | | | 360 | | | |
| att | ggg | gcc | aca | gtg | gtg | ctg | aaa | tcc | aag | ttc | tcg | gct | ggt | cag | ttc | 1155 |
| Ile | Gly | Ala | Thr | Val | Val | Leu | Lys | Ser | Lys | Phe | Ser | Ala | Gly | Gln | Phe | |
| | 365 | | | | | 370 | | | | | 375 | | | | | |
| tgg | gaa | gat | tgc | cag | cag | cac | agg | gtg | acg | gtg | ttc | cag | tac | att | ggg | 1203 |
| Trp | Glu | Asp | Cys | Gln | Gln | His | Arg | Val | Thr | Val | Phe | Gln | Tyr | Ile | Gly | |
| 380 | | | | | 385 | | | | | 390 | | | | | 395 | |
| gag | ctg | tgc | cga | tac | ctt | gtc | aac | cag | ccc | ccg | agc | aag | gca | gaa | cgt | 1251 |
| Glu | Leu | Cys | Arg | Tyr | Leu | Val | Asn | Gln | Pro | Pro | Ser | Lys | Ala | Glu | Arg | |
| | | | 400 | | | | | 405 | | | | | 410 | | | |
| ggc | cat | aag | gtc | cgg | ctg | gca | gtg | ggc | agc | ggg | ctg | cgc | cca | gat | acc | 1299 |
| Gly | His | Lys | Val | Arg | Leu | Ala | Val | Gly | Ser | Gly | Leu | Arg | Pro | Asp | Thr | |
| | | 415 | | | | | 420 | | | | | 425 | | | | |
| tgg | gag | cgt | ttt | gtg | cgg | cgc | ttc | ggg | ccc | ctg | cag | gtg | ctg | gag | aca | 1347 |
| Trp | Glu | Arg | Phe | Val | Arg | Arg | Phe | Gly | Pro | Leu | Gln | Val | Leu | Glu | Thr | |
| | | 430 | | | | | 435 | | | | | 440 | | | | |
| tat | gga | ctg | aca | gag | ggc | aac | gtg | gcc | acc | atc | aac | tac | aca | gga | cag | 1395 |

| | | | | | | | | | | | | | | |
|---|---|---|---|---|---|---|---|---|---|---|---|---|---|---|
|Tyr|Gly|Leu|Thr|Glu|Gly|Asn|Val|Ala|Thr|Ile|Asn|Tyr|Thr|Gly|Gln|
| |445| | | |450| | | |455| | | | | |

```
cgg ggc gct gtg ggg cgt gct tcc tgg ctt tac aag cat atc ttc ccc    1443
Arg Gly Ala Val Gly Arg Ala Ser Trp Leu Tyr Lys His Ile Phe Pro
460             465             470             475 ttc tcc ttg att cgc tat gat gtc acc aca gga gag cca att cgg gac    1491
Phe Ser Leu Ile Arg Tyr Asp Val Thr Thr Gly Glu Pro Ile Arg Asp
                480             485             490 ccc cag ggg cac tgt atg gcc aca tct cca ggt gag cca ggg ctg ctg    1539
Pro Gln Gly His Cys Met Ala Thr Ser Pro Gly Glu Pro Gly Leu Leu
            495             500             505 gtg gcc ccg gta agc cag cag tcc cca ttc ctg ggc tat gct ggc ggg    1587
Val Ala Pro Val Ser Gln Gln Ser Pro Phe Leu Gly Tyr Ala Gly Gly
        510             515             520 cca gag ctg gcc cag ggg aag ttg cta aag gat gtc ttc cgg cct ggg    1635
Pro Glu Leu Ala Gln Gly Lys Leu Leu Lys Asp Val Phe Arg Pro Gly
    525             530             535 gat gtt ttc ttc aac act ggg gac ctg ctg gtc tgc gat gac caa ggt    1683
Asp Val Phe Phe Asn Thr Gly Asp Leu Leu Val Cys Asp Asp Gln Gly
540             545             550             555 ttt ctc cgc ttc cat gat cgt act gga gac acc ttc agg tgg aag ggg    1731
Phe Leu Arg Phe His Asp Arg Thr Gly Asp Thr Phe Arg Trp Lys Gly
                560             565             570 gag aat gtg gcc aca acc gag gtg gca gag gtc ttc gag gcc cta gat    1779
Glu Asn Val Ala Thr Thr Glu Val Ala Glu Val Phe Glu Ala Leu Asp
            575             580             585 ttt ctt cag gag gtg aac gtc tat gga gtc act gtg cca ggg cat gaa    1827
Phe Leu Gln Glu Val Asn Val Tyr Gly Val Thr Val Pro Gly His Glu
        590             595             600 ggc agg gct gga atg gca gcc cta gtt ctg cgt ccc ccc cac gct ttg    1875
Gly Arg Ala Gly Met Ala Ala Leu Val Leu Arg Pro Pro His Ala Leu
    605             610             615 gac ctt atg cag ctc tac acc cac gtg tct gag aac ttg cca cct tat    1923
Asp Leu Met Gln Leu Tyr Thr His Val Ser Glu Asn Leu Pro Pro Tyr
620             625             630             635 gcc cgg ccc cga ttc ctc agg ctc cag gag tct ttg gcc acc aca gag    1971
Ala Arg Pro Arg Phe Leu Arg Leu Gln Glu Ser Leu Ala Thr Thr Glu
                640             645             650 acc ttc aaa cag cag aaa gtt cgg atg gca aat gag ggc ttc gac ccc    2019
Thr Phe Lys Gln Gln Lys Val Arg Met Ala Asn Glu Gly Phe Asp Pro
            655             660             665 agc acc ctg tct gac cca ctg tac gtt ctg gac cag gct gta ggt gcc    2067
Ser Thr Leu Ser Asp Pro Leu Tyr Val Leu Asp Gln Ala Val Gly Ala
        670             675             680 tac ctg ccc ctc aca act gcc cgg tac agc gcc ctc ctg gca gga aac    2115
Tyr Leu Pro Leu Thr Thr Ala Arg Tyr Ser Ala Leu Leu Ala Gly Asn
    685             690             695 ctt cga atc tgagaacttc cacacctgag gcacctgaga gaggaactct           2164
Leu Arg Ile
700 gt                                                                 2166

<210> SEQ ID NO 102
<211> LENGTH: 702
<212> TYPE: PRT
<213> ORGANISM: Homo sapiens

<400> SEQUENCE: 102

Met Phe Ala Ser Gly Trp Asn Gln Thr Val Pro Ile Glu Glu Ala Gly
1               5                   10                  15
```

```
Ser Met Ala Ala Leu Leu Leu Pro Leu Leu Leu Leu Pro Leu
         20              25              30

Leu Leu Leu Leu Lys Leu His Leu Trp Pro Gln Leu Arg Trp Leu Pro
             35              40              45

Ala Asp Leu Ala Phe Ala Val Arg Ala Leu Cys Cys Lys Arg Ala Leu
         50              55              60

Arg Ala Arg Ala Leu Ala Ala Ala Ala Asp Pro Glu Gly Pro Glu
65              70              75              80

Gly Gly Cys Ser Leu Ala Trp Arg Leu Ala Glu Leu Ala Gln Gln Arg
             85              90              95

Ala Ala His Thr Phe Leu Ile His Gly Ser Arg Arg Phe Ser Tyr Ser
         100             105             110

Glu Ala Glu Arg Glu Ser Asn Arg Ala Ala Arg Ala Phe Leu Arg Ala
         115             120             125

Leu Gly Trp Asp Trp Gly Pro Asp Gly Gly Asp Ser Gly Glu Gly Ser
         130             135             140

Ala Gly Glu Gly Glu Arg Ala Ala Pro Gly Ala Gly Asp Ala Ala Ala
145             150             155             160

Gly Ser Gly Ala Glu Phe Ala Gly Gly Asp Gly Ala Ala Arg Gly Gly
             165             170             175

Gly Glu Pro Ala Ala Pro Leu Ser Pro Gly Ala Thr Val Ala Leu Leu
         180             185             190

Leu Pro Ala Gly Pro Glu Phe Leu Trp Leu Trp Phe Gly Leu Ala Lys
         195             200             205

Ala Gly Leu Arg Thr Ala Phe Val Pro Thr Ala Leu Arg Arg Gly Pro
210             215             220

Leu Leu His Cys Leu Arg Ser Cys Gly Ala Arg Ala Leu Val Leu Ala
225             230             235             240

Pro Glu Phe Leu Glu Ser Leu Glu Pro Asp Leu Pro Ala Leu Arg Ala
             245             250             255

Met Gly Leu His Leu Trp Ala Ala Gly Pro Gly Thr His Pro Ala Gly
             260             265             270

Ile Ser Asp Leu Leu Ala Glu Val Ser Ala Glu Val Asp Gly Pro Val
         275             280             285

Pro Gly Tyr Leu Ser Ser Pro Gln Ser Ile Thr Asp Thr Cys Leu Tyr
         290             295             300

Ile Phe Thr Ser Gly Thr Thr Gly Leu Pro Lys Ala Ala Arg Ile Ser
305             310             315             320

His Leu Lys Ile Leu Gln Cys Gln Gly Phe Tyr Gln Leu Cys Gly Val
             325             330             335

His Gln Glu Asp Val Ile Tyr Leu Ala Leu Pro Leu Tyr His Met Ser
             340             345             350

Gly Ser Leu Leu Gly Ile Val Gly Cys Met Gly Ile Gly Ala Thr Val
             355             360             365

Val Leu Lys Ser Lys Phe Ser Ala Gly Gln Phe Trp Glu Asp Cys Gln
         370             375             380

Gln His Arg Val Thr Val Phe Gln Tyr Ile Gly Glu Leu Cys Arg Tyr
385             390             395             400

Leu Val Asn Gln Pro Pro Ser Lys Ala Glu Arg Gly His Lys Val Arg
             405             410             415

Leu Ala Val Gly Ser Gly Leu Arg Pro Asp Thr Trp Glu Arg Phe Val
             420             425             430
```

-continued

```
Arg Arg Phe Gly Pro Leu Gln Val Leu Glu Thr Tyr Gly Leu Thr Glu
        435                 440                 445
Gly Asn Val Ala Thr Ile Asn Tyr Thr Gly Gln Arg Gly Ala Val Gly
    450                 455                 460
Arg Ala Ser Trp Leu Tyr Lys His Ile Phe Pro Phe Ser Leu Ile Arg
465                 470                 475                 480
Tyr Asp Val Thr Thr Gly Glu Pro Ile Arg Asp Pro Gln Gly His Cys
                485                 490                 495
Met Ala Thr Ser Pro Gly Glu Pro Gly Leu Leu Val Ala Pro Val Ser
                500                 505                 510
Gln Gln Ser Pro Phe Leu Gly Tyr Ala Gly Pro Glu Leu Ala Gln
            515                 520                 525
Gly Lys Leu Leu Lys Asp Val Phe Arg Pro Gly Asp Val Phe Phe Asn
    530                 535                 540
Thr Gly Asp Leu Leu Val Cys Asp Asp Gln Gly Phe Leu Arg Phe His
545                 550                 555                 560
Asp Arg Thr Gly Asp Thr Phe Arg Trp Lys Gly Glu Asn Val Ala Thr
                565                 570                 575
Thr Glu Val Ala Glu Val Phe Glu Ala Leu Asp Phe Leu Gln Glu Val
                580                 585                 590
Asn Val Tyr Gly Val Thr Val Pro His Glu Gly Arg Ala Gly Met
    595                 600                 605
Ala Ala Leu Val Leu Arg Pro Pro His Ala Leu Asp Leu Met Gln Leu
    610                 615                 620
Tyr Thr His Val Ser Glu Asn Leu Pro Pro Tyr Ala Arg Pro Arg Phe
625                 630                 635                 640
Leu Arg Leu Gln Glu Ser Leu Ala Thr Thr Glu Thr Phe Lys Gln Gln
                645                 650                 655
Lys Val Arg Met Ala Asn Glu Gly Phe Asp Pro Ser Thr Leu Ser Asp
                660                 665                 670
Pro Leu Tyr Val Leu Asp Gln Ala Val Gly Ala Tyr Leu Pro Leu Thr
            675                 680                 685
Thr Ala Arg Tyr Ser Ala Leu Leu Ala Gly Asn Leu Arg Ile
    690                 695                 700

<210> SEQ ID NO 103
<211> LENGTH: 19
<212> TYPE: DNA
<213> ORGANISM: Artificial Sequence
<220> FEATURE:
<223> OTHER INFORMATION: Oligonucleotide

<400> SEQUENCE: 103
cccccaccag agaggctcc                                            19

<210> SEQ ID NO 104
<211> LENGTH: 19
<212> TYPE: DNA
<213> ORGANISM: Artificial Sequence
<220> FEATURE:
<223> OTHER INFORMATION: Oligonucleotide

<400> SEQUENCE: 104 ccaccccgg aaagcctgc                                             19

<210> SEQ ID NO 105
<211> LENGTH: 19
<212> TYPE: DNA
```

```
<213> ORGANISM: Artificial Sequence
<220> FEATURE:
<223> OTHER INFORMATION: Oligonucleotide

<400> SEQUENCE: 105
ggagcctctc tggtggggg                                                    19
```